United States Patent
Ambrogelly et al.

(10) Patent No.: US 11,124,582 B2
(45) Date of Patent: Sep. 21, 2021

(54) FLT3L-FC FUSION PROTEINS

(71) Applicant: Gilead Sciences, Inc., Foster City, CA (US)

(72) Inventors: Alexandre Ambrogelly, Carlsbad, CA (US); Manuel Baca, Lexington, MA (US); Brian A. Carr, Foster City, CA (US); Hon Man Hamlet Chu, El Cerrito, CA (US); Magdeleine S. Hung, Mountain View, CA (US); Manu Kanwar, San Marcos, CA (US); Michelle R. Kuhne, San Francisco, CA (US); Douglas S. Rehder, Bonsall, CA (US); Matthew R. Schenauer, Dana Point, CA (US); Nicholas S. Wilson, San Carlos, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 16/951,458

(22) Filed: Nov. 18, 2020

(65) Prior Publication Data

US 2021/0070887 A1 Mar. 11, 2021

Related U.S. Application Data

(63) Continuation of application No. 16/909,521, filed on Jun. 23, 2020, now abandoned.

(60) Provisional application No. 62/866,584, filed on Jun. 25, 2019.

(51) Int. Cl.
| | |
|---|---|
| *C07K 14/52* | (2006.01) |
| *C07K 19/00* | (2006.01) |
| *C07K 14/47* | (2006.01) |
| *A61K 45/00* | (2006.01) |
| *A61K 35/12* | (2015.01) |
| *C12N 15/64* | (2006.01) |

(52) U.S. Cl.
CPC .............. *C07K 19/00* (2013.01); *C07K 14/52* (2013.01); *A61K 45/05* (2013.01); *A61K 2035/122* (2013.01); *C07K 14/4705* (2013.01); *C07K 2317/53* (2013.01); *C07K 2317/94* (2013.01); *C07K 2319/30* (2013.01); *C12N 15/64* (2013.01)

(58) Field of Classification Search
CPC ..... C07K 14/52; C07K 19/00; C07K 2319/30
See application file for complete search history.

(56) References Cited

U.S. PATENT DOCUMENTS

| 5,554,512 A | 9/1996 | Lyman et al. |
| 5,635,388 A | 6/1997 | Bennett et al. |
| 6,291,661 B1 | 9/2001 | Graddis et al. |
| 9,486,519 B2 | 11/2016 | Sahin et al. |
| 2004/0254108 A1 | 12/2004 | Ma et al. |
| 2005/0232931 A1 | 10/2005 | Ma et al. |
| 2009/0311247 A1 | 12/2009 | Priest et al. |
| 2011/0053863 A1 | 3/2011 | Lyman et al. |
| 2011/0311584 A1 | 12/2011 | Sahin et al. |
| 2019/0328785 A1 | 10/2019 | Zhao et al. |

FOREIGN PATENT DOCUMENTS

| WO | WO-2005/001048 A2 | 1/2005 |
| WO | WO-2006/060021 A2 | 6/2006 |
| WO | WO-2016/158546 A1 | 10/2016 |
| WO | WO-2016/184882 A1 | 11/2016 |
| WO | WO-2017/223422 A1 | 12/2017 |
| WO | WO-2020/128638 A1 | 6/2020 |

OTHER PUBLICATIONS

"Fc (human):FLT3 Ligand (human)" datasheet, published Jan. 25, 2013, AdipoGen Life Sciences (no author indicated), 2 pages as published.*

Alloatti, A., et al. (2016) "Dendritic cell maturation and cross-presentation: timing matters!" Immunological Reviews, 272, 12 pages.

Anandasabapathy, N., et al. (2015) "Efficacy and safety of CDX-301, recombinant human Flt3L, at expanding dendritic cells and hematopoietic stem cells in healthy human volunteers" Bone Marrow Transplant, 50:7, 19 pages.

Anandasabapathy, N., et al. (2015) "Efficacy and safety of CDX-301, recombinant human Flt3L, at expanding dendritic cells and hematopoietic stem cells in healthy human volunteers" Bone Marrow Transplantation, 50, 7 pages.

Bhardwaj, N., et al. "A Phase II, Open-label, Multicenter, Randomized Study of CDX-1401, a Dendritic Cell Targeting NY-ESO-1 Vaccine, in Patients with Malignant Melanoma Pre-Treated with CDX-301, a Recombinant Human Flt3 Ligand" Cancer Immunotherapy Trials Network.

Brasel, K., et al. (1996) "Hematologic Effects of flt3 Ligand In Vivo in Mice" Blood, 88:6, 10 pages.

Disis, M., et al. (2002) "Flt3 ligand as a vaccine adjuvant in association with HER-2/neu peptide-based vaccines in patients with HER-2/neu-overexpressing cancers" Blood, 99:8, 7 pages.

Hegde, S., et al. (2020) "Dendritic Cell Paucity Leads to Dysfunctional Immune Surveillance in Pancreatic Cancer" Cancer Cell, 37, 29 pages.

Higano, C., et al. (2004) "Safety and Biological Activity of Repeated Doses of Recombinant Human Flt3 Ligand in Patients with Bone Scan-Negative Hormone-Refractory Prostate Cancer" Clinical Cancer Research, 10, 8 pages.

Kreiter, S., et al. (2011) "FLT3 Ligand Enhances the Cancer Therapeutic Potency of Naked RNA Vaccines" Cancer Res, 71(19), 12 pages.

Lai, J., et al. (2020) "Adoptive cellular therapy with T cells expressing the dendritic cell growth factor Flt3L drives epitope spreading and antitumor immunity" Nature Immunology, 33 pages.

Mac Keon, S., et al. (2015) "Dendritic cell-based vaccination in cancer: therapeutic implications emerging from murine models" Frontiers in Immunology, 6:243, 18 pages.

(Continued)

*Primary Examiner* — Zachary C Howard

(57) ABSTRACT

Provided are FLT3L-Fc fusion proteins, polynucleotides encoding such fusion proteins, expression cassettes, vectors, cells and kits comprising such fusion proteins, and methods of using.

1 Claim, 34 Drawing Sheets

Specification includes a Sequence Listing.

(56) References Cited

OTHER PUBLICATIONS

Maraskovsky, E., (2000) "In vivo generation of human dendritic cell subsets by Flt3 ligand" Blood, 96:3, 7 pages.

Marron, T., et al. "In SituVaccinefor Low-Grade Lymphoma: Combination of Intratumoral Flt3L and Poly-ICLC With Low-Dose Radiotherapy." Icahn School of Medicine at Mount Sinai.

Ohri, N., et al. "FLT3 Ligand (CDX-301) and Stereotactic Radiotherapy for Advanced Non-Small Cell Lung Cancer" Abs #9618, Albert Einstein College of Medicine and Montefiore Medical Center, Celldex Therapeutics.

Piloto, O., et al. (2005) "Inhibitory Anti-FLT3 Antibodies Are Capable of Mediating Antibody-Dependent Cell-Mediated Cytotoxicity and Reducing Engraftment of Acute Myelogenous Leukemia Blasts in Nonobese Diabetic/Severe Combined Immunodeficient Mice" Cancer Res, 64:4, 10 pages.

Remmele, R., et al. (1999) "Minimization of Recombinant Human Flt3 Ligand Aggregation at the Tm Plateau: A Matter of Thermal Reversibility" Biochemistry, 38:16, 7 pages.

Salmon, H., et al (2016) "Expansion and Activation of CD103+ Dendritic Cell Progenitors at the Tumor Site Enhances Tumor Responses to Therapeutic PD-L1 and BRAF Inhibition" Immunity, 44, 16 pages.

Saxena, M., et al. (2018) "Re-Emergence of Dendritic Cell Vaccines for Cancer Treatment" Trends in Cancer, 4:2, 19 pages.

Tsapogas, P., et al. (2014) "In vivo evidence for an instructive role of fms-like tyrosine kinase-3 (FLT3) ligand in hematopoietic development" Haematologica, 99:4, 9 pages.

Verstraete, K., et al. (2011) "Structural insights into the extracellular assembly of the hematopoietic Flt3 signaling complex" Blood, 118:1, 9 pages.

Wculek, S., et al. (2020) "Dendritic cells in cancer immunology and immunotherapy" Nat Rev Immunol, 20, 18 pages.

Yamamoto, Y., et al. (2012) "Isolation of human mAbs that directly modulate FMS-related tyrosine kinase 3 signaling" Cancer Sci, 103:2, 10 pages.

Durai, V. et al. (2018) "Altered compensatory cytokine signaling underlies the discrepancy between $Flt3^{-/-}$ and $Flt3l^{-/-}$ mice" *Journal of Experimental Medicine* 215(5): 1417-1435.

Graddis, T. et al. (1998) "Structure-Function Analysis of FLT3 Ligand-FLT3 Receptor Interactions Using a Rapid Functional Screen" *The Journal of Biological Chemistry* 273(28): 17626-17633.

Office Action dated Jul. 26, 2021 for Taiwanese Appl. No. 109121567.

Tu, H. et al. (2014) "Robust expansion of dendritic cells in vivo by hydronamic FLT3L-FC gene transfer" *Journal of Immunological Methods* 413:69-73.

* cited by examiner

Asterisks depict doses of immunomodulator

SFU: spot-forming unit; ns, not significant; *, p < 0.033; , p < 0.021; *, p < 0.0002; ****, p < 0.0001

SEQUENCE LISTING

```
<160> NUMBER OF SEQ ID NOS: 110

<210> SEQ ID NO 1
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Gly Gly Pro
145                 150                 155                 160
```

-continued

```
Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 2
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140
```

Pro Arg Pro Leu Glu Ala Thr Ala Gly Gly Pro Ser Val Phe Leu Phe
145                 150                 155                 160

Pro Pro Lys Pro Lys Asp Thr Leu Met Ile Ser Arg Thr Pro Glu Val
            165                 170                 175

Thr Cys Val Val Val Asp Val Ser His Glu Asp Pro Glu Val Lys Phe
        180                 185                 190

Asn Trp Tyr Val Asp Gly Val Glu Val His Asn Ala Lys Thr Lys Pro
    195                 200                 205

Arg Glu Glu Gln Tyr Asn Ser Thr Tyr Arg Val Val Ser Val Leu Thr
210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360

<210> SEQ ID NO 3
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser

```
            130                 135                 140
Pro Arg Pro Leu Glu Ala Thr Ala Pro Thr Ala Pro Gln Glu Ser Lys
145                 150                 155                 160

Tyr Gly Pro Pro Cys Pro Pro Cys Pro Ala Pro Glu Phe Glu Gly Gly
                165                 170                 175

Pro Ser Val Phe Leu Phe Pro Pro Lys Pro Lys Asp Thr Leu Met Ile
            180                 185                 190

Ser Arg Thr Pro Glu Val Thr Cys Val Val Asp Val Ser Gln Glu
        195                 200                 205

Asp Pro Glu Val Gln Phe Asn Trp Tyr Val Asp Gly Val Glu Val His
    210                 215                 220

Asn Ala Lys Thr Lys Pro Arg Glu Glu Gln Phe Asn Ser Thr Tyr Arg
225                 230                 235                 240

Val Val Ser Val Leu Thr Val Leu His Gln Asp Trp Leu Asn Gly Lys
                245                 250                 255

Glu Tyr Lys Cys Lys Val Ser Asn Lys Gly Leu Pro Ser Ser Ile Glu
                260                 265                 270

Lys Thr Ile Ser Lys Ala Lys Gly Gln Pro Arg Glu Pro Gln Val Tyr
            275                 280                 285

Thr Leu Pro Pro Ser Gln Glu Glu Met Thr Lys Asn Gln Val Ser Leu
        290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                325                 330                 335

Leu Asp Ser Asp Gly Ser Phe Phe Leu Tyr Ser Arg Leu Thr Val Asp
                340                 345                 350

Lys Ser Arg Trp Gln Glu Gly Asn Val Phe Ser Cys Ser Val Met His
            355                 360                 365

Glu Ala Leu His Asn His Tyr Thr Gln Lys Ser Leu Ser Leu Ser Leu
370                 375                 380

Gly Lys
385

<210> SEQ ID NO 4
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95
```

```
Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Glu Ser Lys
145                 150                 155                 160

Tyr Gly Pro Pro Cys Pro Pro Cys Pro Ala Pro Glu Ala Ala Gly Gly
                165                 170                 175

Pro Ser Val Phe Leu Phe Pro Pro Lys Pro Lys Asp Thr Leu Met Ile
            180                 185                 190

Ser Arg Thr Pro Glu Val Thr Cys Val Val Val Asp Val Ser Gln Glu
        195                 200                 205

Asp Pro Glu Val Gln Phe Asn Trp Tyr Val Asp Gly Val Glu Val His
    210                 215                 220

Asn Ala Lys Thr Lys Pro Arg Glu Glu Gln Phe Asn Ser Thr Tyr Arg
225                 230                 235                 240

Val Val Ser Val Leu Thr Val Leu His Gln Asp Trp Leu Asn Gly Lys
                245                 250                 255

Glu Tyr Lys Cys Lys Val Ser Asn Lys Gly Leu Pro Ser Ser Ile Glu
            260                 265                 270

Lys Thr Ile Ser Lys Ala Lys Gly Gln Pro Arg Glu Pro Gln Val Tyr
        275                 280                 285

Thr Leu Pro Pro Ser Gln Glu Glu Met Thr Lys Asn Gln Val Ser Leu
    290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                325                 330                 335

Leu Asp Ser Asp Gly Ser Phe Phe Leu Tyr Ser Arg Leu Thr Val Asp
            340                 345                 350

Lys Ser Arg Trp Gln Glu Gly Asn Val Phe Ser Cys Ser Val Met His
        355                 360                 365

Glu Ala Leu His Asn His Tyr Thr Gln Lys Ser Leu Ser Leu Ser Leu
    370                 375                 380

Gly Lys
385

<210> SEQ ID NO 5
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60
```

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
            85                  90                  95

Val Gln Thr Asn Ile Ala Arg Leu Leu Gln Glu Thr Ser Glu Gln Leu
                100                 105                 110

Val Ala Leu Lys Pro Trp Ile Thr Arg Gln Asn Phe Ala Arg Cys Leu
            115                 120                 125

Glu Leu Gln Cys Gln Pro Asp Ser Ser Thr Leu Pro Pro Pro Trp Ser
130                 135                 140

Pro Arg Pro Leu Glu Ala Thr Ala Pro Thr Ala Pro Gln Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
                180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
                260                 265                 270

Leu Pro Pro Ser Arg Glu Glu Met Thr Lys Asn Gln Val Ser Leu Thr
            275                 280                 285

Cys Leu Val Lys Gly Phe Tyr Pro Ser Asp Ile Ala Val Glu Trp Glu
            290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys

<210> SEQ ID NO 6
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
            50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

Glu Leu Gln Cys Gln Pro Asp Ser Ser Thr Leu Pro Pro Pro Trp Ser
            130                 135                 140

Pro Arg Pro Leu Glu Ala Thr Ala Glu Ser Lys Tyr Gly Pro Pro Cys
145                 150                 155                 160

Pro Pro Cys Pro Ala Pro Glu Ala Ala Gly Gly Pro Ser Val Phe Leu
                165                 170                 175

Phe Pro Pro Lys Pro Lys Asp Thr Leu Met Ile Ser Arg Thr Pro Glu
                180                 185                 190

Val Thr Cys Val Val Val Asp Val Ser Gln Glu Asp Pro Glu Val Gln
            195                 200                 205

Phe Asn Trp Tyr Val Asp Gly Val Glu Val His Asn Ala Lys Thr Lys
210                 215                 220

Pro Arg Glu Glu Gln Phe Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Gly Leu Pro Ser Ser Ile Glu Lys Thr Ile Ser Lys
            260                 265                 270

Ala Lys Gly Gln Pro Arg Glu Pro Gln Val Tyr Thr Leu Pro Pro Ser
            275                 280                 285

Gln Glu Glu Met Thr Lys Asn Gln Val Ser Leu Thr Cys Leu Val Lys
            290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Arg Leu Thr Val Asp Lys Ser Arg Trp Gln
                340                 345                 350

Glu Gly Asn Val Phe Ser Cys Ser Val Met His Glu Ala Leu His Asn
            355                 360                 365

His Tyr Thr Gln Lys Ser Leu Ser Leu Ser Leu Gly Lys
            370                 375                 380

<210> SEQ ID NO 7
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val

```
                    20                  25                  30
Thr Val Ala Ser Asn Leu Gln Asp Glu Glu Leu Cys Gly Gly Leu Trp
                35                  40                  45
Arg Leu Val Leu Ala Gln Arg Trp Met Glu Arg Leu Lys Thr Val Ala
 50                  55                  60
Gly Ser Lys Met Gln Gly Leu Leu Glu Arg Val Asn Thr Glu Ile His
 65                  70                  75                  80
Phe Val Thr Lys Cys Ala Phe Gln Pro Pro Ser Cys Leu Arg Phe
                85                  90                  95
Val Gln Thr Asn Ile Ser Arg Leu Leu Gln Glu Thr Ser Glu Gln Leu
                100                 105                 110
Val Ala Leu Lys Pro Trp Ile Thr Arg Gln Asn Phe Ser Arg Cys Leu
                115                 120                 125
Glu Leu Gln Cys Gln Pro Asp Ser Ser Thr Leu Pro Pro Pro Trp Ser
                130                 135                 140
Pro Arg Pro Gly Gly Pro Ser Val Phe Leu Phe Pro Pro Lys Pro Lys
145                 150                 155                 160
Asp Thr Leu Met Ile Ser Arg Thr Pro Glu Val Thr Cys Val Val Val
                165                 170                 175
Asp Val Ser His Glu Asp Pro Glu Val Lys Phe Asn Trp Tyr Val Asp
                180                 185                 190
Gly Val Glu Val His Asn Ala Lys Thr Lys Pro Arg Glu Glu Gln Tyr
                195                 200                 205
Asn Ser Thr Tyr Arg Val Val Ser Val Leu Thr Val Leu His Gln Asp
                210                 215                 220
Trp Leu Asn Gly Lys Glu Tyr Lys Cys Lys Val Ser Asn Lys Ala Leu
225                 230                 235                 240
Pro Ala Pro Ile Glu Lys Thr Ile Ser Lys Ala Lys Gly Gln Pro Arg
                245                 250                 255
Glu Pro Gln Val Tyr Thr Leu Pro Pro Ser Arg Glu Glu Met Thr Lys
                260                 265                 270
Asn Gln Val Ser Leu Thr Cys Leu Val Lys Gly Phe Tyr Pro Ser Asp
                275                 280                 285
Ile Ala Val Glu Trp Glu Ser Asn Gly Gln Pro Glu Asn Asn Tyr Lys
                290                 295                 300
Thr Thr Pro Pro Val Leu Asp Ser Asp Gly Ser Phe Phe Leu Tyr Ser
305                 310                 315                 320
Lys Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
                340                 345                 350
Leu Ser Leu Ser Pro Gly Lys
                355

<210> SEQ ID NO 8
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Thr Gln Asp Cys Ser Phe Gln His Ser Pro Ile Ser Ser Asp Phe Ala
1               5                   10                  15
```

```
Val Lys Ile Arg Glu Leu Ser Asp Tyr Leu Leu Gln Asp Tyr Pro Val
             20                  25                  30

Thr Val Ala Ser Asn Leu Gln Asp Glu Glu Leu Cys Gly Gly Leu Trp
         35                  40                  45

Arg Leu Val Leu Ala Gln Arg Trp Met Glu Arg Leu Lys Thr Val Ala
     50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                 85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Pro Trp Ser
        130                 135                 140

Pro Arg Pro Glu Ser Lys Tyr Gly Pro Pro Cys Pro Pro Cys Pro Ala
145                 150                 155                 160

Pro Glu Ala Ala Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
                180                 185                 190

Val Asp Val Ser Gln Glu Asp Pro Glu Val Gln Phe Asn Trp Tyr Val
            195                 200                 205

Asp Gly Val Glu Val His Asn Ala Lys Thr Lys Pro Arg Glu Glu Gln
        210                 215                 220

Phe Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Gly
                245                 250                 255

Leu Pro Ser Ser Ile Glu Lys Thr Ile Ser Lys Ala Lys Gly Gln Pro
                260                 265                 270

Arg Glu Pro Gln Val Tyr Thr Leu Pro Pro Ser Gln Glu Glu Met Thr
            275                 280                 285

Lys Asn Gln Val Ser Leu Thr Cys Leu Val Lys Gly Phe Tyr Pro Ser
        290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Arg Leu Thr Val Asp Lys Ser Arg Trp Gln Glu Gly Asn Val Phe
            340                 345                 350

Ser Cys Ser Val Met His Glu Ala Leu His Asn His Tyr Thr Gln Lys
        355                 360                 365

Ser Leu Ser Leu Ser Leu Gly Lys
    370                 375

<210> SEQ ID NO 9
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65              70                  75                  80

Phe Val Thr Lys Cys Ala Phe Gln Pro Pro Ser Cys Leu Arg Phe
            85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Trp Ser
    130                 135                 140

Pro Arg Pro Leu Glu Ala Thr Ala Pro Thr Ala Pro Gln Gly Gly Pro
145                 150                 155                 160

Ser Val Phe Leu Phe Pro Pro Lys Pro Lys Asp Thr Leu Tyr Ile Thr
                165                 170                 175

Arg Glu Pro Glu Val Thr Cys Val Val Val Asp Val Ser His Glu Asp
                180                 185                 190

Pro Glu Val Lys Phe Asn Trp Tyr Val Asp Gly Val Glu Val His Asn
                195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
                260                 265                 270

Leu Pro Pro Ser Arg Glu Glu Met Thr Lys Asn Gln Val Ser Leu Thr
            275                 280                 285

Cys Leu Val Lys Gly Phe Tyr Pro Ser Asp Ile Ala Val Glu Trp Glu
            290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys

<210> SEQ ID NO 10
<211> LENGTH: 364
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
130                 135                 140

Pro Arg Pro Leu Glu Ala Thr Ala Gly Gly Pro Ser Val Phe Leu Phe
145                 150                 155                 160

Pro Pro Lys Pro Lys Asp Thr Leu Tyr Ile Thr Arg Glu Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360
```

<210> SEQ ID NO 11
<211> LENGTH: 386
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 11

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Trp Ser
    130                 135                 140

Pro Arg Pro Leu Glu Ala Thr Ala Pro Thr Ala Pro Gln Glu Ser Lys
145                 150                 155                 160

Tyr Gly Pro Pro Cys Pro Pro Cys Pro Ala Pro Glu Phe Glu Gly Gly
                165                 170                 175

Pro Ser Val Phe Leu Phe Pro Pro Lys Pro Lys Asp Thr Leu Tyr Ile
            180                 185                 190

Thr Arg Glu Pro Glu Val Thr Cys Val Val Val Asp Val Ser Gln Glu
        195                 200                 205

Asp Pro Glu Val Gln Phe Asn Trp Tyr Val Asp Gly Val Glu Val His
    210                 215                 220

Asn Ala Lys Thr Lys Pro Arg Glu Glu Gln Phe Asn Ser Thr Tyr Arg
225                 230                 235                 240

Val Val Ser Val Leu Thr Val Leu His Gln Asp Trp Leu Asn Gly Lys
                245                 250                 255

Glu Tyr Lys Cys Lys Val Ser Asn Lys Gly Leu Pro Ser Ser Ile Glu
            260                 265                 270

Lys Thr Ile Ser Lys Ala Lys Gly Gln Pro Arg Glu Pro Gln Val Tyr
        275                 280                 285

Thr Leu Pro Pro Ser Gln Glu Glu Met Thr Lys Asn Gln Val Ser Leu
    290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                325                 330                 335

Leu Asp Ser Asp Gly Ser Phe Phe Leu Tyr Ser Arg Leu Thr Val Asp
            340                 345                 350

Lys Ser Arg Trp Gln Glu Gly Asn Val Phe Ser Cys Ser Val Met His
        355                 360                 365

Glu Ala Leu His Asn His Tyr Thr Gln Lys Ser Leu Ser Leu Ser Leu
    370                 375                 380

Gly Lys
385

```
<210> SEQ ID NO 12
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Glu Ser Lys
145                 150                 155                 160

Tyr Gly Pro Pro Cys Pro Pro Cys Pro Ala Pro Glu Ala Ala Gly Gly
                165                 170                 175

Pro Ser Val Phe Leu Phe Pro Pro Lys Pro Lys Asp Thr Leu Tyr Ile
            180                 185                 190

Thr Arg Glu Pro Glu Val Thr Cys Val Val Val Asp Val Ser Gln Glu
        195                 200                 205

Asp Pro Glu Val Gln Phe Asn Trp Tyr Val Asp Gly Val Glu Val His
    210                 215                 220

Asn Ala Lys Thr Lys Pro Arg Glu Glu Gln Phe Asn Ser Thr Tyr Arg
225                 230                 235                 240

Val Val Ser Val Leu Thr Val Leu His Gln Asp Trp Leu Asn Gly Lys
                245                 250                 255

Glu Tyr Lys Cys Lys Val Ser Asn Lys Gly Leu Pro Ser Ser Ile Glu
            260                 265                 270

Lys Thr Ile Ser Lys Ala Lys Gly Gln Pro Arg Glu Pro Gln Val Tyr
        275                 280                 285

Thr Leu Pro Pro Ser Gln Glu Glu Met Thr Lys Asn Gln Val Ser Leu
    290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                325                 330                 335

Leu Asp Ser Asp Gly Ser Phe Phe Leu Tyr Ser Arg Leu Thr Val Asp
            340                 345                 350

Lys Ser Arg Trp Gln Glu Gly Asn Val Phe Ser Cys Ser Val Met His
```

```
                    355                 360                 365
Glu Ala Leu His Asn His Tyr Thr Gln Lys Ser Leu Ser Leu Ser Leu
    370                 375                 380

Gly Lys
385

<210> SEQ ID NO 13
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ala Arg Leu Leu Gln Glu Thr Ser Glu Gln Leu
            100                 105                 110

Val Ala Leu Lys Pro Trp Ile Thr Arg Gln Asn Phe Ala Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Gly Gly Pro
145                 150                 155                 160

Ser Val Phe Leu Phe Pro Pro Lys Pro Lys Asp Thr Leu Tyr Ile Thr
                165                 170                 175

Arg Glu Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320
```

-continued

```
Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 14
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Glu Ser Lys Tyr Gly Pro Pro Cys
145                 150                 155                 160

Pro Pro Cys Pro Ala Pro Glu Ala Ala Gly Gly Pro Ser Val Phe Leu
                165                 170                 175

Phe Pro Pro Lys Pro Lys Asp Thr Leu Tyr Ile Thr Arg Glu Pro Glu
            180                 185                 190

Val Thr Cys Val Val Val Asp Val Ser Gln Glu Asp Pro Glu Val Gln
        195                 200                 205

Phe Asn Trp Tyr Val Asp Gly Val Glu Val His Asn Ala Lys Thr Lys
    210                 215                 220

Pro Arg Glu Glu Gln Phe Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Gly Leu Pro Ser Ser Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Gln Glu Glu Met Thr Lys Asn Gln Val Ser Leu Thr Cys Leu Val Lys
    290                 295                 300
```

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Val Leu Asp Ser Asp Gly
            325                 330                 335

Ser Phe Phe Leu Tyr Ser Arg Leu Thr Val Asp Lys Ser Arg Trp Gln
            340                 345                 350

Glu Gly Asn Val Phe Ser Cys Ser Val Met His Glu Ala Leu His Asn
            355                 360                 365

His Tyr Thr Gln Lys Ser Leu Ser Leu Ser Leu Gly Lys
            370                 375                 380

<210> SEQ ID NO 15
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
130                 135                 140

Pro Arg Pro Gly Gly Pro Ser Val Phe Leu Phe Pro Pro Lys Pro Lys
145                 150                 155                 160

Asp Thr Leu Tyr Ile Thr Arg Glu Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

```
Ile Ala Val Glu Trp Glu Ser Asn Gly Gln Pro Glu Asn Asn Tyr Lys
        290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
                340                 345                 350

Leu Ser Leu Ser Pro Gly Lys
                355

<210> SEQ ID NO 16
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
130                 135                 140

Pro Arg Pro Glu Ser Lys Tyr Gly Pro Pro Cys Pro Pro Cys Pro Ala
145                 150                 155                 160

Pro Glu Ala Ala Gly Gly Pro Ser Val Phe Leu Phe Pro Pro Lys Pro
                165                 170                 175

Lys Asp Thr Leu Tyr Ile Thr Arg Glu Pro Glu Val Thr Cys Val Val
            180                 185                 190

Val Asp Val Ser Gln Glu Asp Pro Glu Val Gln Phe Asn Trp Tyr Val
        195                 200                 205

Asp Gly Val Glu Val His Asn Ala Lys Thr Lys Pro Arg Glu Glu Gln
    210                 215                 220

Phe Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Gly
                245                 250                 255

Leu Pro Ser Ser Ile Glu Lys Thr Ile Ser Lys Ala Lys Gly Gln Pro
            260                 265                 270

Arg Glu Pro Gln Val Tyr Thr Leu Pro Pro Ser Gln Glu Glu Met Thr
```

```
            275                 280                 285
Lys Asn Gln Val Ser Leu Thr Cys Leu Val Lys Gly Phe Tyr Pro Ser
            290                 295                 300
Asp Ile Ala Val Glu Trp Glu Ser Asn Gly Gln Pro Glu Asn Asn Tyr
305                 310                 315                 320
Lys Thr Thr Pro Pro Val Leu Asp Ser Asp Gly Ser Phe Phe Leu Tyr
                325                 330                 335
Ser Arg Leu Thr Val Asp Lys Ser Arg Trp Gln Glu Gly Asn Val Phe
                340                 345                 350
Ser Cys Ser Val Met His Glu Ala Leu His Asn His Tyr Thr Gln Lys
                355                 360                 365
Ser Leu Ser Leu Ser Leu Gly Lys
            370                 375

<210> SEQ ID NO 17
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Thr Gln Asp Cys Ser Phe Gln His Ser Pro Ile Ser Ser Asp Phe Ala
1               5                   10                  15
Val Lys Ile Arg Glu Leu Ser Asp Tyr Leu Leu Gln Asp Tyr Pro Val
                20                  25                  30
Thr Val Ala Ser Asn Leu Gln Asp Glu Glu Leu Cys Gly Gly Leu Trp
            35                  40                  45
Arg Leu Val Leu Ala Gln Arg Trp Met Glu Arg Leu Lys Thr Val Ala
50                  55                  60
Gly Ser Lys Met Gln Gly Leu Leu Glu Arg Val Asn Thr Glu Ile His
65                  70                  75                  80
Phe Val Thr Lys Cys Ala Phe Gln Pro Pro Pro Ser Cys Leu Arg Phe
                85                  90                  95
Val Gln Thr Asn Ile Ala Arg Leu Leu Gln Glu Thr Ser Glu Gln Leu
                100                 105                 110
Val Ala Leu Lys Pro Trp Ile Thr Arg Gln Asn Phe Ala Arg Cys Leu
            115                 120                 125
Glu Leu Gln Cys Gln Pro Asp Ser Ser Thr Leu Pro Pro Pro Trp Ser
130                 135                 140
Pro Arg Pro Glu Ser Lys Tyr Gly Pro Pro Cys Pro Pro Cys Pro Ala
145                 150                 155                 160
Pro Glu Ala Ala Gly Gly Pro Ser Val Phe Leu Phe Pro Pro Lys Pro
                165                 170                 175
Lys Asp Thr Leu Met Ile Ser Arg Thr Pro Glu Val Thr Cys Val Val
                180                 185                 190
Val Asp Val Ser Gln Glu Asp Pro Glu Val Gln Phe Asn Trp Tyr Val
            195                 200                 205
Asp Gly Val Glu Val His Asn Ala Lys Thr Lys Pro Arg Glu Glu Gln
            210                 215                 220
Phe Asn Ser Thr Tyr Arg Val Val Ser Val Leu Thr Val Leu His Gln
225                 230                 235                 240
Asp Trp Leu Asn Gly Lys Glu Tyr Lys Cys Lys Val Ser Asn Lys Gly
                245                 250                 255
```

Leu Pro Ser Ser Ile Glu Lys Thr Ile Ser Lys Ala Lys Gly Gln Pro
                260                 265                 270

Arg Glu Pro Gln Val Tyr Thr Leu Pro Pro Ser Gln Glu Glu Met Thr
            275                 280                 285

Lys Asn Gln Val Ser Leu Thr Cys Leu Val Lys Gly Phe Tyr Pro Ser
        290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Arg Leu Thr Val Asp Lys Ser Arg Trp Gln Glu Gly Asn Val Phe
            340                 345                 350

Ser Cys Ser Val Met His Glu Ala Leu His Asn His Tyr Thr Gln Lys
        355                 360                 365

Ser Leu Ser Leu Ser Leu Gly Lys
    370                 375

<210> SEQ ID NO 18
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ala Arg Leu Leu Gln Glu Thr Ser Glu Gln Leu
            100                 105                 110

Val Ala Leu Lys Pro Trp Ile Thr Arg Gln Asn Phe Ala Arg Cys Leu
        115                 120                 125

Glu Leu Gln Cys Gln Pro Asp Ser Ser Thr Leu Pro Pro Pro Trp Ser
130                 135                 140

Pro Arg Pro Glu Ser Lys Tyr Gly Pro Pro Cys Pro Pro Cys Pro Ala
145                 150                 155                 160

Pro Glu Ala Ala Gly Gly Pro Ser Val Phe Leu Phe Pro Pro Lys Pro
                165                 170                 175

Lys Asp Thr Leu Tyr Ile Thr Arg Glu Pro Glu Val Thr Cys Val Val
            180                 185                 190

Val Asp Val Ser Gln Glu Asp Pro Glu Val Gln Phe Asn Trp Tyr Val
        195                 200                 205

Asp Gly Val Glu Val His Asn Ala Lys Thr Lys Pro Arg Glu Glu Gln
210                 215                 220

Phe Asn Ser Thr Tyr Arg Val Val Ser Val Leu Thr Val Leu His Gln
225                 230                 235                 240

```
Asp Trp Leu Asn Gly Lys Glu Tyr Lys Cys Lys Val Ser Asn Lys Gly
                245                 250                 255

Leu Pro Ser Ser Ile Glu Lys Thr Ile Ser Lys Ala Lys Gly Gln Pro
            260                 265                 270

Arg Glu Pro Gln Val Tyr Thr Leu Pro Pro Ser Gln Glu Glu Met Thr
        275                 280                 285

Lys Asn Gln Val Ser Leu Thr Cys Leu Val Lys Gly Phe Tyr Pro Ser
    290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Arg Leu Thr Val Asp Lys Ser Arg Trp Gln Glu Gly Asn Val Phe
            340                 345                 350

Ser Cys Ser Val Met His Glu Ala Leu His Asn His Tyr Thr Gln Lys
        355                 360                 365

Ser Leu Ser Leu Ser Leu Gly Lys
    370                 375

<210> SEQ ID NO 19
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Thr Pro Asp Cys Tyr Phe Ser His Ser Pro Ile Ser Ser Asn Phe Lys
1               5                   10                  15

Val Lys Phe Arg Glu Leu Thr Asp His Leu Leu Lys Asp Tyr Pro Val
            20                  25                  30

Thr Val Ala Val Asn Leu Gln Asp Glu Lys His Cys Lys Ala Leu Trp
        35                  40                  45

Ser Leu Phe Leu Ala Gln Arg Trp Ile Glu Gln Leu Lys Thr Val Ala
    50                  55                  60

Gly Ser Lys Met Gln Thr Leu Leu Glu Asp Val Asn Thr Glu Ile His
65                  70                  75                  80

Phe Val Thr Ser Cys Thr Phe Gln Pro Leu Pro Glu Cys Leu Arg Phe
                85                  90                  95

Val Gln Thr Asn Ile Ser His Leu Leu Lys Asp Thr Cys Thr Gln Leu
            100                 105                 110

Leu Ala Leu Lys Pro Cys Ile Gly Lys Ala Cys Gln Asn Phe Ser Arg
        115                 120                 125

Cys Leu Glu Val Gln Cys Gln Pro Asp Ser Ser Thr Leu Leu Pro Pro
    130                 135                 140

Arg Ser Pro Ile Ala Leu Glu Ala Thr Glu Leu Pro Glu Pro Arg Gly
145                 150                 155                 160

Pro Thr Ile Lys Pro Cys Pro Pro Cys Lys Cys Pro Ala Pro Asn Ala
                165                 170                 175

Ala Gly Gly Pro Ser Val Phe Ile Phe Pro Pro Lys Ile Lys Asp Val
            180                 185                 190

Leu Met Ile Ser Leu Ser Pro Ile Val Thr Cys Val Val Val Asp Val
        195                 200                 205

Ser Glu Asp Asp Pro Asp Val Gln Ile Ser Trp Phe Val Asn Asn Val
```

```
              210                 215                 220
Glu Val His Thr Ala Gln Thr Gln Thr His Arg Glu Asp Tyr Asn Ser
225                 230                 235                 240

Thr Leu Arg Val Val Ser Ala Leu Pro Ile Gln His Gln Asp Trp Met
                245                 250                 255

Ser Gly Lys Glu Phe Lys Cys Lys Val Asn Asn Lys Asp Leu Gly Ala
            260                 265                 270

Pro Ile Glu Arg Thr Ile Ser Lys Pro Lys Gly Ser Val Arg Ala Pro
        275                 280                 285

Gln Val Tyr Val Leu Pro Pro Glu Glu Met Thr Lys Lys Gln
290                 295                 300

Val Thr Leu Thr Cys Met Val Thr Asp Phe Met Pro Glu Asp Ile Tyr
305                 310                 315                 320

Val Glu Trp Thr Asn Asn Gly Lys Thr Glu Leu Asn Tyr Lys Asn Thr
                325                 330                 335

Glu Pro Val Leu Asp Ser Asp Gly Ser Tyr Phe Met Tyr Ser Lys Leu
            340                 345                 350

Arg Val Glu Lys Lys Asn Trp Val Glu Arg Asn Ser Tyr Ser Cys Ser
        355                 360                 365

Val Val His Glu Gly Leu His Asn His His Thr Thr Lys Ser Phe Ser
370                 375                 380

Arg Thr Pro Gly Lys
385

<210> SEQ ID NO 20
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Thr Pro Asp Cys Tyr Phe Ser His Ser Pro Ile Ser Ser Asn Phe Lys
1               5                   10                  15

Val Lys Phe Arg Glu Leu Thr Asp His Leu Leu Lys Asp Tyr Pro Val
                20                  25                  30

Thr Val Ala Val Asn Leu Gln Asp Glu Lys His Cys Lys Ala Leu Trp
            35                  40                  45

Ser Leu Phe Leu Ala Gln Arg Trp Ile Glu Gln Leu Lys Thr Val Ala
        50                  55                  60

Gly Ser Lys Met Gln Thr Leu Leu Glu Asp Val Asn Thr Glu Ile His
65                  70                  75                  80

Phe Val Thr Ser Cys Thr Phe Gln Pro Leu Pro Glu Cys Leu Arg Phe
                85                  90                  95

Val Gln Thr Asn Ile Ser His Leu Leu Lys Asp Thr Ser Thr Gln Leu
            100                 105                 110

Leu Ala Leu Lys Pro Cys Ile Gly Lys Ala Cys Gln Asn Phe Ser Arg
        115                 120                 125

Cys Leu Glu Val Gln Cys Gln Pro Asp Ser Ser Thr Leu Leu Pro Pro
130                 135                 140

Arg Ser Pro Ile Ala Leu Glu Ala Thr Glu Leu Pro Glu Pro Arg Gly
145                 150                 155                 160

Pro Thr Ile Lys Pro Cys Pro Pro Cys Lys Cys Pro Ala Pro Asn Ala
                165                 170                 175
```

Ala Gly Gly Pro Ser Val Phe Ile Phe Pro Lys Ile Lys Asp Val
            180                 185                 190

Leu Met Ile Ser Leu Ser Pro Ile Val Thr Cys Val Val Val Asp Val
            195                 200                 205

Ser Glu Asp Asp Pro Asp Val Gln Ile Ser Trp Phe Val Asn Asn Val
210                 215                 220

Glu Val His Thr Ala Gln Thr Gln Thr His Arg Glu Asp Tyr Asn Ser
225                 230                 235                 240

Thr Leu Arg Val Val Ser Ala Leu Pro Ile Gln His Gln Asp Trp Met
            245                 250                 255

Ser Gly Lys Glu Phe Lys Cys Lys Val Asn Asn Lys Asp Leu Gly Ala
            260                 265                 270

Pro Ile Glu Arg Thr Ile Ser Lys Pro Lys Gly Ser Val Arg Ala Pro
            275                 280                 285

Gln Val Tyr Val Leu Pro Pro Pro Glu Glu Glu Met Thr Lys Lys Gln
            290                 295                 300

Val Thr Leu Thr Cys Met Val Thr Asp Phe Met Pro Glu Asp Ile Tyr
305                 310                 315                 320

Val Glu Trp Thr Asn Asn Gly Lys Thr Glu Leu Asn Tyr Lys Asn Thr
            325                 330                 335

Glu Pro Val Leu Asp Ser Asp Gly Ser Tyr Phe Met Tyr Ser Lys Leu
            340                 345                 350

Arg Val Glu Lys Lys Asn Trp Val Glu Arg Asn Ser Tyr Ser Cys Ser
            355                 360                 365

Val Val His Glu Gly Leu His Asn His His Thr Thr Lys Ser Phe Ser
            370                 375                 380

Arg Thr Pro Gly Lys
385

<210> SEQ ID NO 21
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Ala
            50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Pro Trp Ser
130                 135                 140

Pro Arg Pro Leu Glu Ala Thr Ala Pro Thr Ala Pro Gln Gly Gly Pro
145                 150                 155                 160

Ser Val Phe Leu Phe Pro Pro Lys Pro Lys Asp Thr Leu Met Ile Ser
            165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
            245                 250                 255

Thr Ile Ser Lys Ala Lys Gly Gln Pro Arg Glu Pro Gln Val Tyr Thr
            260                 265                 270

Lys Pro Pro Ser Arg Glu Glu Met Thr Lys Asn Gln Val Ser Leu Ser
            275                 280                 285

Cys Leu Val Lys Gly Phe Tyr Pro Ser Asp Ile Ala Val Glu Trp Glu
290                 295                 300

Ser Asn Gly Gln Pro Glu Asn Asn Tyr Lys Thr Thr Val Pro Val Leu
305                 310                 315                 320

Asp Ser Asp Gly Ser Phe Arg Leu Ala Ser Tyr Leu Thr Val Asp Lys
            325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys

<210> SEQ ID NO 22
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Thr Gln Asp Cys Ser Phe Gln Tyr Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Ala
50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
            85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
            115                 120                 125

```
Glu Leu Gln Cys Gln Pro Asp Ser Ser Thr Leu Pro Pro Trp Ser
    130                 135                 140

Pro Arg Pro Leu Glu Ala Thr Ala Pro Thr Ala Pro Gln Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 23
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Glu Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110
```

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Trp Ser
    130                 135                 140

Pro Arg Pro Leu Glu Ala Thr Ala Pro Thr Ala Pro Gln Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
                180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
        210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 24
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Thr Gln Asp Cys Ser Phe Gln Tyr Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Glu Cys Ala Phe Gln Pro Pro Pro Ser Cys Leu Arg Phe
                85                  90                  95

```
Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Trp Ser
    130                 135                 140

Pro Arg Pro Leu Glu Ala Thr Ala Pro Thr Ala Pro Gln Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
                180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
        210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
                260                 265                 270

Leu Pro Pro Ser Arg Glu Glu Met Thr Lys Asn Gln Val Ser Leu Thr
            275                 280                 285

Cys Leu Val Lys Gly Phe Tyr Pro Ser Asp Ile Ala Val Glu Trp Glu
        290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 25
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80
```

Phe Val Thr Lys Cys Ala Phe Gln Pro Pro Ser Cys Leu Arg Phe
            85                  90                  95

Val Gln Thr Asn Ile Ala Arg Leu Leu Gln Glu Thr Ser Glu Gln Leu
            100                 105                 110

Val Ala Leu Lys Pro Trp Ile Thr Arg Gln Asn Phe Ala Arg Cys Leu
            115                 120                 125

Glu Leu Gln Cys Gln Pro Asp Ser Ser Thr Leu Pro Pro Pro Trp Ser
130                 135                 140

Pro Arg Pro Leu Glu Ala Thr Ala Glu Ser Lys Tyr Gly Pro Pro Cys
145                 150                 155                 160

Pro Pro Cys Pro Ala Pro Glu Ala Ala Gly Gly Pro Ser Val Phe Leu
            165                 170                 175

Phe Pro Pro Lys Pro Lys Asp Thr Leu Tyr Ile Thr Arg Glu Pro Glu
            180                 185                 190

Val Thr Cys Val Val Val Asp Val Ser Gln Glu Asp Pro Glu Val Gln
            195                 200                 205

Phe Asn Trp Tyr Val Asp Gly Val Glu Val His Asn Ala Lys Thr Lys
            210                 215                 220

Pro Arg Glu Glu Gln Phe Asn Ser Thr Tyr Arg Val Val Ser Val Leu
225                 230                 235                 240

Thr Val Leu His Gln Asp Trp Leu Asn Gly Lys Glu Tyr Lys Cys Lys
            245                 250                 255

Val Ser Asn Lys Gly Leu Pro Ser Ser Ile Glu Lys Thr Ile Ser Lys
            260                 265                 270

Ala Lys Gly Gln Pro Arg Glu Pro Gln Val Tyr Thr Leu Pro Pro Ser
            275                 280                 285

Gln Glu Glu Met Thr Lys Asn Gln Val Ser Leu Thr Cys Leu Val Lys
            290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
            325                 330                 335

Ser Phe Phe Leu Tyr Ser Arg Leu Thr Val Asp Lys Ser Arg Trp Gln
            340                 345                 350

Glu Gly Asn Val Phe Ser Cys Ser Val Met His Glu Ala Leu His Asn
            355                 360                 365

His Tyr Thr Gln Lys Ser Leu Ser Leu Ser Leu Gly Lys
            370                 375                 380

<210> SEQ ID NO 26
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Ala

```
            50                  55                  60
Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                 85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ala Ala Ala Leu Pro Pro Pro Trp Ser
        130                 135                 140

Pro Arg Pro Leu Glu Ala Thr Ala Glu Ser Lys Tyr Gly Pro Pro Cys
145                 150                 155                 160

Pro Pro Cys Pro Ala Pro Glu Ala Ala Gly Gly Pro Ser Val Phe Leu
                165                 170                 175

Phe Pro Pro Lys Pro Lys Asp Thr Leu Tyr Ile Thr Arg Glu Pro Glu
                180                 185                 190

Val Thr Cys Val Val Val Asp Val Ser Gln Glu Asp Pro Glu Val Gln
            195                 200                 205

Phe Asn Trp Tyr Val Asp Gly Val Glu Val His Asn Ala Lys Thr Lys
        210                 215                 220

Pro Arg Glu Glu Gln Phe Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Gly Leu Pro Ser Ser Ile Glu Lys Thr Ile Ser Lys
                260                 265                 270

Ala Lys Gly Gln Pro Arg Glu Pro Gln Val Tyr Thr Leu Pro Pro Ser
            275                 280                 285

Gln Glu Glu Met Thr Lys Asn Gln Val Ser Leu Thr Cys Leu Val Lys
        290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Arg Leu Thr Val Asp Lys Ser Arg Trp Gln
                340                 345                 350

Glu Gly Asn Val Phe Ser Cys Ser Val Met His Glu Ala Leu His Asn
            355                 360                 365

His Tyr Thr Gln Lys Ser Leu Ser Leu Ser Leu Gly Lys
        370                 375                 380

<210> SEQ ID NO 27
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Thr Gln Asp Cys Ser Phe Gln His Ser Pro Ile Ser Ser Asp Phe Ala
 1               5                  10                  15

Val Lys Ile Arg Glu Leu Ser Asp Tyr Leu Leu Gln Asp Tyr Pro Val
             20                  25                  30
```

```
Thr Val Ala Ser Asn Leu Gln Asp Glu Glu Leu Cys Gly Gly Leu Trp
         35                  40                  45
Arg Leu Val Leu Ala Gln Arg Trp Met Glu Arg Leu Lys Thr Val Ala
 50                  55                  60
Gly Ser Lys Met Gln Gly Leu Leu Glu Arg Val Asn Thr Glu Ile His
 65                  70                  75                  80
Phe Val Thr Lys Cys Ala Phe Gln Pro Pro Ser Cys Leu Arg Phe
                 85                  90                  95
Val Gln Thr Asn Ile Ser Arg Leu Leu Gln Thr Ser Glu Gln Leu
                100                 105                 110
Val Ala Leu Lys Pro Trp Ile Thr Arg Gln Asn Phe Ser Arg Cys Leu
                115                 120                 125
Glu Leu Gln Cys Gln Pro Asp Ala Ala Ala Leu Pro Pro Pro Trp Ala
130                 135                 140
Pro Arg Pro Leu Glu Ala Thr Ala Glu Ala Lys Tyr Gly Pro Pro Cys
145                 150                 155                 160
Pro Pro Cys Pro Ala Pro Glu Ala Ala Gly Gly Pro Ser Val Phe Leu
                165                 170                 175
Phe Pro Pro Lys Pro Lys Asp Thr Leu Tyr Ile Thr Arg Glu Pro Glu
                180                 185                 190
Val Thr Cys Val Val Val Asp Val Ser Gln Glu Asp Pro Glu Val Gln
                195                 200                 205
Phe Asn Trp Tyr Val Asp Gly Val Glu Val His Asn Ala Lys Thr Lys
                210                 215                 220
Pro Arg Glu Glu Gln Phe Asn Ser Thr Tyr Arg Val Val Ser Val Leu
225                 230                 235                 240
Thr Val Leu His Gln Asp Trp Leu Asn Gly Lys Glu Tyr Lys Cys Lys
                245                 250                 255
Val Ser Asn Lys Gly Leu Pro Ser Ser Ile Glu Lys Thr Ile Ser Lys
                260                 265                 270
Ala Lys Gly Gln Pro Arg Glu Pro Gln Val Tyr Thr Leu Pro Pro Ser
                275                 280                 285
Gln Glu Glu Met Thr Lys Asn Gln Val Ser Leu Thr Cys Leu Val Lys
290                 295                 300
Gly Phe Tyr Pro Ser Asp Ile Ala Val Glu Trp Glu Ser Asn Gly Gln
305                 310                 315                 320
Pro Glu Asn Asn Tyr Lys Thr Thr Pro Pro Val Leu Asp Ser Asp Gly
                325                 330                 335
Ser Phe Phe Leu Tyr Ser Arg Leu Thr Val Asp Lys Ser Arg Trp Gln
                340                 345                 350
Glu Gly Asn Val Phe Ser Cys Ser Val Met His Glu Ala Leu His Asn
                355                 360                 365
His Tyr Thr Gln Lys Ser Leu Ser Leu Ser Leu Gly Lys
                370                 375                 380

<210> SEQ ID NO 28
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
acacaggatt gcagcttcca gcacagcccc atcagcagcg atttcgccgt gaagatcaga      60
```

| | | |
|---|---|---|
| gagctgagcg actacctgct gcaggactac cctgtgaccg tggccagcaa tctgcaggac | 120 | |
| gaagaactgt gtggtggact gtggcgactg gtgctggctc agagatggat ggaacggctg | 180 | |
| aaaacagtgg ccggcagcaa gatgcaggga ctgctggaaa gagtgaacac cgagatccac | 240 | |
| ttcgtgacca agtgcgcctt ccagcctcct ccatcctgcc tgagattcgt gcagaccaac | 300 | |
| atcagcagac tgctgcaaga dacaagcgag cagctggtgg ccctgaagcc ttggatcacc | 360 | |
| agacagaact tcagccggtg cctggaactg cagtgtcagc ccgatagcag cacactgcct | 420 | |
| ccgccttgga gtcctagacc tctggaagcc acagctccca ccgctcctca aggcggaccg | 480 | |
| tcagtcttcc tcttcccccc aaaacccaag dacaccctca tgatctcccg gacccctgag | 540 | |
| gtcacatgcg tggtggtgga cgtgagccac gaagaccctg aggtcaagtt caactggtac | 600 | |
| gtggacggcg tggaggtgca taatgccaag acaaagccgc gggaggagca gtacaacagc | 660 | |
| acgtaccgtg tggtcagcgt cctcaccgtc ctgcaccagg actggctgaa tggcaaggag | 720 | |
| tacaagtgca aggtctccaa caaagccctc ccagccccca tcgagaaaac catctccaaa | 780 | |
| gccaaagggc agccccgaga accacaggtg tacaccctgc ccccatcccg ggaggagatg | 840 | |
| accaagaacc aggtcagcct gacctgcctg gtcaaaggct tctatcccag cgacatcgcc | 900 | |
| gtggagtggg agagcaatgg gcagccggag aacaactaca agaccacgcc tcccgtgctg | 960 | |
| gactccgacg gctccttctt cctctacagc aagctcaccg tggacaagag caggtggcag | 1020 | |
| caggggaacg tcttctcatg ctccgtgatg catgaggctc tgcacaacca ctacacgcag | 1080 | |
| aagagcctct ccctgtctcc gggtaaa | 1107 | |

<210> SEQ ID NO 29
<211> LENGTH: 1107
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 29

| | | |
|---|---|---|
| acccaggact gctccttcca gcactcccct atctcttccg acttcgccgt gaagatcaga | 60 | |
| gagctgtccg actacctgct gcaggactac cctgtgaccg tggccagcaa tctgcaggac | 120 | |
| gaagaactgt gtggtggcct gtggcgactg gtgttggctc agagatggat ggaacggctg | 180 | |
| aaaaccgtgg ccggctctaa gatgcaggga ctgctggaaa gagtgaacac cgagatccac | 240 | |
| ttcgtgacca agtgcgcctt tcagcctcct ccatcctgcc tgagattcgt gcagaccaac | 300 | |
| atctcccggc tgctgcaaga dacatccgag cagctggtgg ctctgaagcc ctggatcacc | 360 | |
| cggcagaact tctctcggtg tctggaactg cagtgtcagc ccgactcttc taccctgcct | 420 | |
| ccaccttgga gccccagacc tttgaagct accgctccaa cagctcctca aggcggccct | 480 | |
| tccgtgtttc tgttccctcc aaagcctaag dacaccctga tgatctctcg gacccctgaa | 540 | |
| gtgacctgcg tggtggtgga tgtgtctcac gaggatcccg aagtgaagtt caattggtac | 600 | |
| gtggacggcg tggaagtgca caacgccaag accaagccta gagaggaaca gtacaactcc | 660 | |
| acctacagag tggtgtccgt gctgaccgtg ctgcaccagg attggctgaa cggcaaagag | 720 | |
| tacaagtgca aggtgtccaa caaggccctg cctgctccta tcgaaaagac catctccaag | 780 | |
| gccaagggcc agcctaggga accccaggtt tacaccctgc cacctagccg ggaagagatg | 840 | |
| accaagaacc aggtgtccct gacctgcctg gtcaagggct tctacccctc tgatatcgcc | 900 | |
| gtggaatggg agagcaatgg ccagcctgag aacaactaca agaccacacc tcctgtgctg | 960 | |

```
gactccgacg gctcattctt cctgtactcc aagctgacag tggacaagtc cagatggcag   1020
cagggcaacg tgttctcctg ctccgtgatg cacgaggctc tgcacaacca ctacacccag   1080
aagtccctgt ctctgtcccc tggcaaa                                       1107

<210> SEQ ID NO 30
<211> LENGTH: 1092
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
acacaggatt gcagcttcca gcacagcccc atcagcagcg atttcgccgt gaagatcaga    60
gagctgagcg actacctgct gcaggactac cctgtgaccg tggccagcaa tctgcaggac   120
gaagaactgt gtggtggact gtggcgactg gtgctggctc agagatggat ggaacggctg   180
aaaacagtgg ccggcagcaa gatgcaggga ctgctggaaa gagtgaacac cgagatccac   240
ttcgtgacca agtgcgcctt ccagcctcct ccatcctgcc tgagattcgt gcagaccaac   300
atcagcagac tgctgcaaga gacaagcgag cagctggtgg ccctgaagcc ttggatcacc   360
agacagaact tcagccggtg cctggaactg cagtgtcagc ccgatagcag cacactgcct   420
ccgccttgga gtcctagacc tctggaagcc acagctgggg gaccgtcagt cttcctcttc   480 ccccaaaac ccaaggacac cctcatgatc tcccggaccc ctgaggtcac atgcgtggtg   540
gtggacgtga gccacgaaga ccctgaggtc aagttcaact ggtacgtgga cggcgtggag   600
gtgcataatg ccaagacaaa gccgcgggag gagcagtaca acagcacgta ccgtgtggtc   660
agcgtcctca ccgtcctgca ccaggactgg ctgaatggca aggagtacaa gtgcaaggtc   720
tccaacaaag ccctcccagc ccccatcgag aaaaccatct ccaaagccaa agggcagccc   780
cgagaaccac aggtgtacac cctgccccca tcccgggagg agatgaccaa gaaccaggtc   840
agcctgacct gcctggtcaa aggcttctat cccagcgaca tcgccgtgga gtgggagagc   900
aatgggcagc cggagaacaa ctacaagacc acgcctcccg tgctggactc cgacggctcc   960
ttcttcctct acagcaagct caccgtggac aagagcaggt ggcagcaggg gaacgtcttc   1020
tcatgctccg tgatgcatga ggctctgcac aaccactaca cgcagaagag cctctccctg   1080
tctccgggta aa                                                       1092

<210> SEQ ID NO 31
<211> LENGTH: 1092
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
acccaggact gctccttcca gcactcccct atctcttccg acttcgccgt gaagatcaga    60
gagctgtccg actacctgct gcaggactat cctgtgaccg tggccagcaa cctgcaggat   120
gaagaactgt gtggtggact gtggcgactg gtgctggctc agagatggat ggaaagactg   180
aaaaccgtgg ccggctccaa gatgcaggga ctgctggaaa gagtgaacac agagatccac   240
ttcgtgacca agtgcgcctt tcagcctcct ccatcctgcc tgagattcgt gcagaccaac   300
atctcccggc tgctgcaaga gacatctgag cagctggtgg ccctgaagcc ttggatcacc   360
cggcagaact tctctcggtg cctggaactg cagtgtcagc ctgattcttc taccctgcct   420
```

```
ccaccttgga gccctagacc tttggaagct acagctggcg gcccaagcgt gttcctgttt       480
cctccaaagc ctaaggacac cctgatgatc tctcggaccc ctgaagtgac ctgcgtggtg       540
gtggatgtgt ctcacgagga tcccgaagtg aagttcaatt ggtacgtgga cggcgtggaa       600
gtgcacaacg ccaagaccaa gcctagagag aacagtaca actccaccta cagagtggtg        660
tccgtgctga ccgtgctgca ccaggattgg ctgaacggca agagtacaa gtgcaaggtg        720 tccaacaagg ccctgcctgc tcctatcgaa aagaccatct ccaaggccaa gggccagcct       780
agggaacctc aggtttacac cctgccacct agccgggaag atgaccaa aaaccaggtg         840 tccctgacct gcctggtcaa ggcttctac ccatccgata tcgccgtgga atgggagtct        900
aacggccagc ctgagaacaa ctacaagacc acacctcctg tgctggactc cgacggctca       960
ttcttcctgt actccaagct gacagtggac aagtctcggt ggcagcaggg caacgtgttc       1020
tcctgttctg tgatgcacga ggccctgcac aaccactaca cccagaagtc cctgtctctg       1080
tcccctggca aa                                                          1092
```

<210> SEQ ID NO 32
<211> LENGTH: 1158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
acacaggatt gcagcttcca gcacagcccc atcagcagcg atttcgccgt gaagatcaga        60
gagctgagcg actacctgct gcaggactac cctgtgaccg tggccagcaa tctgcaggac       120
gaagaactgt gtggtggact gtggcgactg gtgctggctc agagatggat ggaacggctg       180
aaaacagtgg ccggcagcaa gatgcaggga ctgctggaaa gagtgaacac cgagatccac       240
ttcgtgacca agtgcgcctt ccagcctcct ccatcctgcc tgagattcgt gcagaccaac       300
atcagcagac tgctgcaaga gacaagcgag cagctggtgg ccctgaagcc ttggatcacc       360
agacagaact tcagccggtg cctggaactg cagtgtcagc ccgatagcag cacactgcct       420
ccgccttgga gtcctagacc tctggaagcc acagctccca ccgctcctca gaatctaag       480 tacgccctc cctgccctcc ttgcccagcc cctgaatttg agggcggacc ctccgtgttc       540 ctgttcccc caaagcccaa ggacaccctg atgatcagcc ggaccccga agtgacctgc       600 gtggtggtgg atgtgtccca ggaagatccc gaggtgcagt tcaattggta cgtggacggc       660
gtggaagtgc acaacgccaa gaccaagccc agagaggaac agttcaacag cacctaccgg       720
gtggtgtccg tgctgacagt gctgcaccag gactggctga acggcaaaga gtacaagtgc       780
aaggtgtcca acaaggcct gcccagctcc atcgagaaaa ccatcagcaa ggccaagggc       840
cagccccgcg aacccaggt gtacacactg cctccaagcc aggaagagat gaccaagaac       900
caggtgtccc tgacctgtct cgtgaaaggc ttcacccct ccgatatcgc cgtggaatgg       960
gagagcaacg gccagcccga gaacaactac aagaccaccc ccctgtgctg gacagcgac       1020 ggctcattct tcctgtacag cagactgacc gtggacaaga gccggtggca ggaaggcaac       1080
gtgttcagct gcagcgtgat gcacgaggcc ctgcacaacc actaccca gaagtccctg       1140 tctctgtccc tgggcaaa                                                    1158
```

<210> SEQ ID NO 33
<211> LENGTH: 1158

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
acccaggact gctccttcca gcactcccct atctcttccg acttcgccgt gaagatcaga     60
gagctgtccg actacctgct gcaggactat cctgtgaccg tggccagcaa cctgcaggat    120
gaagaactgt gtggtggact gtggcgactg gtgctggctc agagatggat ggaaagactg    180
aaaaccgtgg ccggctccaa gatgcaggga ctgctggaaa gagtgaacac agagatccac    240
ttcgtgacca agtgcgcctt tcagcctcct ccatcctgcc tgagattcgt gcagaccaac    300
atctcccggc tgctgcaaga gacatctgag cagctggtgg ccctgaagcc ttggatcacc    360
cggcagaact tctctcggtg cctggaactg cagtgtcagc tgattcttc taccctgcct    420
ccaccttgga gccctagacc tttggaggct acagctccta ccgctcctca agagtctaag    480
tacggccctc cttgtcctcc atgtcctgct ccagaatttg aaggcggccc aagcgtgttc    540
ctgtttcctc caaagcctaa ggacaccctg atgatctctc ggacccctga agtgacctgc    600
gtggtggtgg atgtgtctca agaggacccc gaggtgcagt tcaattggta cgtggacggc    660
gtggaagtgc acaacgccaa gaccaagcct agagaggaac agttcaactc cacctacaga    720
gtggtgtccg tgctgaccgt gctgcaccag gattggctga acggcaaaga gtacaagtgc    780
aaggtgtcca caagggcct gcctagctcc atcgaaaaga ccatctccaa ggccaagggc    840
cagccaagag aacctcaggt gtacacactg cctccaagcc aagaggaaat gaccaagaac    900
caggtgtccc tgacctgcct ggtcaagggc ttctacccat ccgatatcgc cgtggaatgg    960
gagtctaacg gccagcctga gaacaactac aagaccacac tcctgtgct ggactccgac    1020
ggctccttct ttctgtactc tcgcctgacc gtggacaagt ctagatggca gaggcaac    1080
gtgttctcct gctctgtgat gcacgaggcc ctgcacaacc actacaccca gaagtccctg    1140
tctctgtccc tgggcaaa                                                  1158

<210> SEQ ID NO 34
<211> LENGTH: 1158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
acacaggatt gcagcttcca gcacagcccc atcagcagcg atttcgccgt gaagatcaga     60
gagctgagcg actacctgct gcaggactac cctgtgaccg tggccagcaa tctgcaggac    120
gaagaactgt gtggtggact gtggcgactg gtgctggctc agagatggat ggaacggctg    180
aaaacagtgg ccggcagcaa gatgcaggga ctgctggaaa gagtgaacac cgagatccac    240
ttcgtgacca agtgcgcctt ccagcctcct ccatcctgcc tgagattcgt gcagaccaac    300
atcagcagac tgctgcaaga gacaagcgag cagctggtgg ccctgaagcc ttggatcacc    360
agacagaact tcagccggtg cctggaactg cagtgtcagc cgatagcag cacactgcct    420
ccgccttgga gtcctagacc tctggaagcc acagctccca ccgctcctca agagtctaag    480
tacggccctc cttgtcctcc atgtcctgct ccagaagctg ctggcggccc ttccgtgttt    540
ctgttccctc caaagcctaa ggacaccctg atgatctctc ggacccctga agtgacctgc    600
```

| | |
|---|---|
| gtggtggtgg atgtgtccca agaggatccc gaggtgcagt tcaattggta cgtggacggc | 660 |
| gtggaagtgc acaacgccaa gaccaagcct agagaggaac agttcaactc cacctacaga | 720 |
| gtggtgtccg tgctgaccgt gctgcaccag gattggctga acggcaaaga gtacaagtgc | 780 |
| aaggtgtcca acaagggcct gccttccagc atcgaaaaga ccatctccaa ggccaagggc | 840 |
| cagcctaggg aaccccaggt ttacaccctg cctccaagcc aagaggaaat gaccaagaac | 900 |
| caggtgtccc tgacctgcct ggtcaagggc ttctaccctt ccgatatcgc cgtggaatgg | 960 |
| gagagcaatg gccagcctga gaacaactac aagaccacac ctcctgtgct ggactccgac | 1020 |
| ggctccttct ttctgtactc ccgcctgacc gtggacaagt ccagatggca gagggcaac | 1080 |
| gtgttctcct gctccgtgat gcacgaggcc ctgcacaatc actacaccca gaagtccctg | 1140 |
| tctctgtccc tgggcaaa | 1158 |

<210> SEQ ID NO 35
<211> LENGTH: 1158
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

| | |
|---|---|
| acccaggact gctccttcca gcactcccct atctcttccg acttcgccgt gaagatcaga | 60 |
| gagctgtccg actacctgct gcaggactat cctgtgaccg tggccagcaa cctgcaggat | 120 |
| gaagaactgt gtggtggact gtggcgactg gtgctggctc agatggatgg aaagactg | 180 |
| aaaaccgtgg ccggctccaa gatgcaggga ctgctggaaa gagtgaacac agagatccac | 240 |
| ttcgtgacca gtgcgccctt tcagcctcct ccatcctgcc tgagattcgt gcagaccaac | 300 |
| atctcccggc tgctgcaaga gacatctgag cagctggtgg ccctgaagcc ttggatcacc | 360 |
| cggcagaact tctctcggtg cctggaactg cagtgtcagc ctgattcttc taccctgcct | 420 |
| ccaccttgga gccctagacc tttggaggct acagctccta ccgctcctca agagtctaag | 480 |
| tacggccctc cttgtcctcc atgtcctgct ccagaagctg ctggcggacc aagcgttttc | 540 |
| ctgtttcctc caaagcctaa ggacaccctg atgatctctc ggacccctga agtgacctgc | 600 |
| gtggtggtgg atgtgtctca agaggacccc gaggtgcagt tcaattggta cgtggacggc | 660 |
| gtggaagtgc acaacgccaa gaccaagcct agagaggaac agttcaactc cacctacaga | 720 |
| gtggtgtccg tgctgaccgt gctgcaccag gattggctga acggcaaaga gtacaagtgc | 780 |
| aaggtgtcca acaagggcct gcctagctcc atcgaaaaga ccatctccaa ggccaagggc | 840 |
| cagccaagag aacctcaggt gtacacactg cctccaagcc aagaggaaat gaccaagaac | 900 |
| caggtgtccc tgacctgcct ggtcaagggc ttctacccat ccgatatcgc cgtggaatgg | 960 |
| gagtctaacg gccagcctga gaacaactac aagaccacac ctcctgtgct ggactccgac | 1020 |
| ggctccttct ttctgtactc tcgcctgacc gtggacaagt ctagatggca gagggcaac | 1080 |
| gtgttctcct gctctgtgat gcacgaggcc ctgcacaacc actacaccca gaagtccctg | 1140 |
| tctctgtccc tgggcaaa | 1158 |

<210> SEQ ID NO 36
<211> LENGTH: 1185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
atgacagttt tggctccagc ttggtccect acaacctacc tgctgctgct gttgctgctc      60
tcctctggcc tgtctggcac ccaggactgt tccttccagc actccctat ctccagcgac      120
ttcgccgtga agatcagaga gctgtccgac tatctgctgc aggactaccc tgtgaccgtg      180
gccagcaatc tgcaggacga agaactgtgt ggtggcctgt ggcgactggt gttggctcag      240
agatggatgg aacggctgaa aaccgtggcc ggctctaaga tgcagggcct gctggaaaga      300
gtgaacaccg agatccactt cgtgaccaag tgcgcctttc agcctcctcc atcctgcctg      360
agattcgtgc agaccaatat cgcccggctg ctgcaagaga catccgagca gctggtggct      420
ctgaagccct ggatcaccag acagaacttc gcccggtgtc tggaactgca gtgtcagcct      480
gacagctcta ccctgcctcc accttggagc cctagacctc tggaagctac cgctccaacc      540
gctcctcaag ggggaccgtc agtcttcctc ttcccccca aacccaagga caccctcatg      600
atctcccgga cccctgaggt cacatgcgtg gtggtggacg tgagccacga agaccctgag      660
gtcaagttca actggtacgt ggacggcgtg gaggtgcata atgccaagac aaagccgcgg      720
gaggagcagt acaacagcac gtaccgtgtg gtcagcgtcc tcaccgtcct gcaccaggac      780
tggctgaatg caaggagta caagtgcaag gtctccaaca aagccctccc agcccccatc      840
gagaaaacca tctccaaagc caagggcagc cccgagaac acaggtgta caccctgccc      900
ccatcccggg aggagatgac caagaaccag gtcagcctga cctgcctggt caaaggcttc      960
tatcccagcg acatcgccgt ggagtgggag agcaatgggc agccggagaa caactacaag      1020
accacgcctc ccgtgctgga ctccgacggc tccttcttcc tctacagcaa gctcaccgtg      1080
gacaagagca ggtggcagca ggggaacgtc ttctcatgct ccgtgatgca tgaggctctg      1140
cacaaccact acacgcagaa gagcctctcc ctgtctccgg gtaaa                    1185
```

<210> SEQ ID NO 37
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
acccaggact gctccttcca gcactcccct atctcttccg acttcgccgt gaagatcaga      60
gagctgtccg actacctgct gcaggactat cctgtgaccg tggccagcaa cctgcaggat      120
gaagaactgt gtggtggact gtggcgactg gtgctggctc agagatggat ggaaagactg      180
aaaaccgtgg ccggctccaa gatgcaggga ctgctggaaa gagtgaacac agagatccac      240
ttcgtgacca gtgcgccttt cagcctcctc catcctgcc tgagattcgt gcagaccaat      300
atcgcccggc tgctgcaaga gacatctgag cagctggtgg ccctgaagcc ttggatcacc      360
agacagaact tcgcccggtg cctggaactg cagtgtcagc ctgattcttc taccctgcct      420
ccaccttgga gccctagacc tttggaggct acagctccta ctgctcctca aggcggccca      480
agcgttttcc tgtttcctcc aaagcctaag gacaccctga tctctctccg accecctgaa      540
gtgacctgcg tggtggtgga tgtgtctcac gaggatcccg aagtgaagtt caattggtac      600
gtggacggcg tggaagtgca caacgccaag accaagccta gaggaaca gtacaactcc      660
acctacagag tggtgtccgt gctgaccgtg ctgcaccagg attggctgaa cggcaaagag      720
tacaagtgca aggtgtccaa caaggccctg cctgctccta tcgaaaagac catctccaag      780
```

```
gccaagggcc agcctaggga acctcaggtt tacaccctgc cacctagccg ggaagagatg     840
accaaaaacc aggtgtccct gacctgcctg gtcaagggct tctacccatc cgatatcgcc     900
gtggaatggg agtctaacgg ccagcctgag aacaactaca agaccacacc tcctgtgctg     960
gactccgacg gctcattctt cctgtactcc aagctgacag tggacaagtc tcggtggcag    1020
cagggcaacg tgttctcctg ttctgtgatg cacgaggccc tgcacaacca ctacacccag    1080
aagtccctgt ctctgtcccc tggcaaa                                        1107
```

<210> SEQ ID NO 38
<211> LENGTH: 1143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
acacaggatt gcagcttcca gcacagcccc atcagcagcg atttcgccgt gaagatcaga      60
gagctgagcg actacctgct gcaggactac cctgtgaccg tggccagcaa tctgcaggac     120
gaagaactgt gtggtggact gtggcgactg gtgctggctc agatgatgga ggaacggctg     180
aaaacagtgg ccggcagcaa gatgcaggga ctgctggaaa gagtgaacac cgagatccac     240
ttcgtgacca agtgcgcctt ccagcctcct ccatcctgcc tgagattcgt gcagaccaac     300
atcagcagac tgctgcaaga gacaagcgag cagctggtgg ccctgaagcc ttggatcacc     360
agacagaact tcagccggtg cctggaactg cagtgtcagc ccgatagcag cacactgcct     420
ccgccttgga gtcctagacc tctggaagcc acagctgagt ctaagtacgg ccctccttgt     480
cctccatgtc ctgctccaga agctgctggc ggcccttccg tgtttctgtt ccctccaaag     540
cctaaggaca ccctgatgat ctctcggacc cctgaagtga cctgcgtggt ggtggatgtg     600
tcccaagagg atcccgaggt gcagttcaat tggtacgtgg acggcgtgga agtgcacaac     660
gccaagacca agcctagaga ggaacagttc aactccacct acagagtggt gtccgtgctg     720
accgtgctgc accaggattg gctgaacggc aaagagtaca agtgcaaggt gtccaacaag     780
ggcctgcctt ccagcatcga aaagaccatc tccaaggcca agggccagcc tagggaaccc     840
caggtttaca ccctgcctcc aagccaagag gaaatgacca gaaccaggt gtccctgacc     900 tgcctggtca agggcttcta cccttccgat atcgccgtgg aatgggagag caatggccag     960
cctgagaaca actacaagac cacacctcct gtgctggact ccgacggctc cttctttctg    1020
tactcccgcc tgaccgtgga caagtccaga tggcaagagg caacgtgtt ctcctgctcc    1080 gtgatgcacg aggccctgca caatcactac acccagaagt ccctgtctct gtccctgggc    1140
aaa                                                                 1143
```

<210> SEQ ID NO 39
<211> LENGTH: 1143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
acccaggact gctccttcca gcactcccct atctcttccg acttcgccgt gaagatcaga      60
gagctgtccg actacctgct gcaggactat cctgtgaccg tggccagcaa cctgcaggat     120
```

```
gaagaactgt gtggtggact gtggcgactg gtgctggctc agagatggat ggaaagactg    180
aaaaccgtgg ccggctccaa gatgcaggga ctgctggaaa gagtgaacac agagatccac    240
ttcgtgacca agtgcgcctt tcagcctcct ccatcctgcc tgagattcgt gcagaccaac    300
atctcccggc tgctgcaaga gacatctgag cagctggtgg ccctgaagcc ttggatcacc    360
cggcagaact tctctcggtg cctggaactg cagtgtcagc ctgattcttc taccctgcct    420
ccaccttgga gccctagacc tctgaagct accgccgagt ctaagtacgg acctccttgt    480
cctccatgtc ctgctccaga agctgctggc ggaccaagcg tttcctgtt tcctccaaag    540 cctaaggaca ccctgatgat ctctcggacc cctgaagtga cctgcgtggt ggtggatgtg    600
tctcaagagg accccgaggt gcagttcaat tggtacgtgg acggcgtgga agtgcacaac    660
gccaagacca agcctagaga ggaacagttc aactccacct acagagtggt gtccgtgctg    720
accgtgctgc accaggattg gctgaacggc aaagagtaca gtgcaaggt gtccaacaag    780 ggcctgccta gctccatcga aaagaccatc tccaaggcca agggccagcc aagagaacct    840
caggtgtaca cactgcctcc aagccaagag gaaatgacca gaaccaggt gtccctgacc    900 tgcctggtca agggcttcta cccatccgat atcgccgtgg aatgggagtc taacggccag    960
cctgagaaca actacaagac cacacctcct gtgctggact ccgacggctc cttctttctg   1020
tactctcgcc tgaccgtgga caagtctaga tggcaagagg gcaacgtgtt ctcctgctct   1080
gtgatgcacg aggccctgca caaccactac acccagaagt ccctgtctct gtccctgggc   1140
aaa                                                                  1143

<210> SEQ ID NO 40
<211> LENGTH: 1077
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
acacaggatt gcagcttcca gcacagcccc atcagcagcg atttcgccgt gaagatcaga     60
gagctgagcg actacctgct gcaggactac cctgtgaccg tggccagcaa tctgcaggac    120
gaagaactgt gtggtggact gtggcgactg gtgctggctc agagatggat ggaacggctg    180
aaaacagtgg ccggcagcaa gatgcaggga ctgctggaaa gagtgaacac cgagatccac    240
ttcgtgacca agtgcgcctt ccagcctcct ccatcctgcc tgagattcgt gcagaccaac    300
atcagcagac tgctgcaaga gacaagcgag cagctggtgg ccctgaagcc ttggatcacc    360
agacagaact tcagccggtg cctggaactg cagtgtcagc ccgatagcag cacactgcct    420
ccgccttgga gtcctagacc tggggggaccg tcagtcttcc tcttcccccc aaaacccaag    480
gacaccctca tgatctcccg gacccctgag gtcacatgcg tggtggtgga cgtgagccac    540
gaagaccctg aggtcaagtt caactggtac gtggacggcg tggaggtgca taatgccaag    600
acaaagccgc gggaggagca gtacaacagc acgtaccgtg tggtcagcgt cctcaccgtc    660
ctgcaccagg actggctgaa tggcaaggag tacaagtgca aggtctccaa caaagccctc    720
ccagccccca tcgagaaaac catctccaaa gccaaaggga gcccccgaga accacaggtg    780
tacaccctgc ccccatcccg ggaggagatg accaagaacc aggtcagcct gacctgcctg    840
gtcaaaggct tctatcccag cgacatcgcc gtggagtggg agagcaatgg gcagccggag    900
aacaactaca agaccacgcc tcccgtgctg gactccgacg gctccttctt cctctacagc    960
```

```
aagctcaccg tggacaagag caggtggcag caggggaacg tcttctcatg ctccgtgatg   1020
catgaggctc tgcacaacca ctacacgcag aagagcctct ccctgtctcc gggtaaa     1077
```

<210> SEQ ID NO 41
<211> LENGTH: 1077
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
acccaggact gctccttcca gcactcccct atctcttccg acttcgccgt gaagatcaga    60
gagctgtccg actacctgct gcaggactat cctgtgaccg tggccagcaa cctgcaggat   120
gaagaactgt gtggtggact gtggcgactg gtgctggctc agatggatgg aaagactg    180 aaaaccgtgg ccggctccaa gatgcaggga ctgctggaaa gagtgaacac agagatccac   240
ttcgtgacca gtgcgccttt cagcctcct ccatcctgcc tgagattcgt gcagaccaac   300
atctcccggc tgctgcaaga gacatctgag cagctggtgg ccctgaagcc ttggatcacc   360
cggcagaact tctctcggtg cctggaactg cagtgtcagc ctgattcttc tacctgcct    420 ccaccttgga gtcctagacc tggcggacca agcgtgttcc tgtttcctcc aaagcctaag   480
gacaccctga tgatctctcg gaccctgaa gtgacctgcg tggtggtgga tgtgtctcac    540
gaggatcccg aagtgaagtt caattggtac gtggacggcg tggaagtgca caacgccaag   600
accaagccta gagaggaaca gtacaactcc acctacagag tggtgtccgt gctgaccgtg   660
ctgcaccagg attggctgaa cggcaaagag tacaagtgca aggtgtccaa caaggccctg   720
cctgctccta tcgaaaagac catctccaag gccaagggcc agcctaggga acctcaggtt   780 tacacccgc cacctagccg ggaagagatg accaaaacc aggtgtccct gacctgcctg     840
gtcaagggct ctacccatc cgatatcgcc gtggaatggg agtctaacgg ccagcctgag   900
aacaactaca agaccacacc tcctgtgctg gactccgacg gctcattctt cctgtactcc   960
aagctgacag tggacaagtc tcggtggcag cagggcaacg tgttctcctg ttctgtgatg   1020
cacgaggccc tgcacaacca ctacacccag aagtccctgt ctctgtccc tggcaaa       1077
```

<210> SEQ ID NO 42
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
acacaggatt gcagcttcca gcacagcccc atcagcagcg atttcgccgt gaagatcaga    60
gagctgagcg actacctgct gcaggactac cctgtgaccg tggccagcaa tctgcaggac   120
gaagaactgt gtggtggact gtggcgactg gtgctggctc agatggatgg aaacggctg    180 aaaacagtgg ccggcagcaa gatgcaggga ctgctggaaa gagtgaacac cgagatccac   240
ttcgtgacca gtgcgccttt ccagcctcct ccatcctgcc tgagattcgt gcagaccaac   300
atcagcagac tgctgcaaga gacaagcgag cagctggtgg ccctgaagcc ttggatcacc   360
agacagaact tcagccggtg cctggaactg cagtgtcagc ccgatagcag cacactgcct   420
ccgccttgga gtcctagacc tgagtctaag tacggccctc cttgtcctcc atgtcctgct   480
ccagaagctg ctggcggccc ttccgtgttt ctgttccctc caaagcctaa ggacaccctg   540
```

```
atgatctctc ggacccctga agtgacctgc gtggtggtgg atgtgtccca agaggatccc      600
gaggtgcagt tcaattggta cgtggacggc gtggaagtgc acaacgccaa gaccaagcct      660
agagaggaac agttcaactc cacctacaga gtggtgtccg tgctgaccgt gctgcaccag      720
gattggctga acggcaaaga gtacaagtgc aaggtgtcca acaagggcct gccttccagc      780
atcgaaaaga ccatctccaa ggccaagggc cagcctaggg aaccccaggt ttacaccctg      840
cctccaagcc aagaggaaat gaccaagaac caggtgtccc tgacctgcct ggtcaagggc      900
ttctacccct tccgatatcg cgtggaatgg gagagcaatg gccagcctga gaacaactac      960
aagaccacac tcctgtgctg gactccgac ggctccttct ttctgtactc cgcctgacc      1020 gtggacaagt ccagatggca gagggcaac gtgttctcct gctccgtgat gcacgaggcc      1080
ctgcacaatc actcaccca gaagtccctg tctctgtccc tgggcaaa               1128
```

<210> SEQ ID NO 43
<211> LENGTH: 1128
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 43

```
acccaggact gctccttcca gcactcccct atctcttccg acttcgccgt gaagatcaga      60
gagctgtccg actacctgct gcaggactat cctgtgaccg tggccagcaa cctgcaggat      120
gaagaactgt gtggtggact gtggcgactg tgctggctc agatggatgg gaaagactg      180 aaaaccgtgg ccggctccaa gatgcaggga ctgctggaaa gagtgaacac agagatccac      240
ttcgtgacca gtgcgccctt tcagcctcct ccatcctgcc tgagattcgt gcagaccaac      300
atctcccggc tgctgcaaga gacatctgag cagctggtgg ccctgaagcc ttggatcacc      360
cggcagaact tctctcggtg cctggaactg cagtgtcagc ctgattcttc taccctgcct      420
ccaccttgga gccctcggcc tgaatctaag tatggccctc cttgtcctcc atgtcctgct      480
ccagaagctg ctggcggacc aagcgttttc ctgtttcctc caaagcctaa ggacaccctg      540
atgatctctc ggacccctga agtgacctgc gtggtggtgg atgtgtctca agaggacccc      600
gaggtgcagt tcaattggta cgtggacggc gtggaagtgc acaacgccaa gaccaagcct      660
agagaggaac agttcaactc cacctacaga gtggtgtccg tgctgaccgt gctgcaccag      720
gattggctga acggcaaaga gtacaagtgc aaggtgtcca acaagggcct gcctagctcc      780
atcgaaaaga ccatctccaa ggccaagggc cagccaagag aacctcaggt gtacacactg      840
cctccaagcc aagaggaaat gaccaagaac caggtgtccc tgacctgcct ggtcaagggc      900
ttctacccat ccgatatcgc cgtggaatgg gagtctaacg gccagcctga gaacaactac      960
aagaccacac tcctgtgctg gactccgac ggctccttct ttctgtactc tcgcctgacc      1020
gtggacaagt ctagatggca gagggcaac gtgttctcct gctctgtgat gcacgaggcc      1080
ctgcacaacc actacaccca gaagtccctg tctctgtccc tgggcaaa               1128
```

<210> SEQ ID NO 44
<211> LENGTH: 1107
<212> TYPE: DNA
<213> ORGANISM: Artificial Sequence
<220> FEATURE:
<223> OTHER INFORMATION: Description of Artificial Sequence: Synthetic
    polynucleotide

```
<400> SEQUENCE: 44
acacaggatt gcagcttcca gcacagcccc atcagcagcg atttcgccgt gaagatcaga    60
gagctgagcg actacctgct gcaggactac cctgtgaccg tggccagcaa tctgcaggac   120
gaagaactgt gtggtggact gtggcgactg gtgctggctc agatggatgg ggaacggctg   180
aaaacagtgg ccggcagcaa gatgcaggga ctgctggaaa gagtgaacac cgagatccac   240
ttcgtgacca agtgcgcctt ccagcctcct ccatcctgcc tgagattcgt gcagaccaac   300
atcagcagac tgctgcaaga gacaagcgag cagctggtgg ccctgaagcc ttggatcacc   360
agacagaact tcagccggtg cctggaactg cagtgtcagc cgatagcag cacactgcct   420
ccgccttgga gtcctagacc tctggaagcc acagctccca ccgctcctca aggcggaccg   480
tcagtcttcc tcttccccccc aaaacccaag gacacccttt acatcacccg ggaacctgag   540
gtcacatgcg tggtggtgga cgtgagccac gaagaccctg aggtcaagtt caactggtac   600
gtggacggcg tggaggtgca taatgccaag acaaagccgc gggaggagca gtacaacagc   660
acgtaccgtg tggtcagcgt cctcaccgtc ctgcaccagg actggctgaa tggcaaggag   720
tacaagtgca aggtctccaa caaagccctc ccagccccca tcgagaaaac catctccaaa   780
gccaaagggc agccccgaga accacaggtg tacaccctgc ccccatcccg ggaggagatg   840
accaagaacc aggtcagcct gacctgcctg gtcaaaggct tctatccag cgacatcgcc   900
gtggagtggg agagcaatgg gcagccggag aacaactaca agaccacgcc tcccgtgctg   960
gactccgacg gctccttctt cctctacagc aagctcaccg tggacaagag caggtggcag  1020
caggggaacg tcttctcatg ctccgtgatg catgaggctc tgcacaacca ctacacgcag  1080
aagagcctct ccctgtctcc gggtaaa                                      1107

<210> SEQ ID NO 45
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
acccaggact gctccttcca gcactcccct atctcttccg acttcgccgt gaagatcaga    60
gagctgtccg actacctgct gcaggactat cctgtgaccg tggccagcaa cctgcaggat   120
gaagaactgt gtggtggact gtggcgactg gtgctggctc agatggatgg ggaaagactg   180
aaaaccgtgg ccggctccaa gatgcaggga ctgctggaaa gagtgaacac agagatccac   240
ttcgtgacca agtgcgcctt tcagcctcct ccatcctgcc tgagattcgt gcagaccaac   300
atctcccggc tgctgcaaga gacatctgag cagctggtgg ccctgaagcc ttggatcacc   360
cggcagaact tctctcggtg cctggaactg cagtgtcagc ctgattcttc taccctgcct   420
ccaccttgga gccctagacc tttggaggct acagctccta ctgctcctca aggcggccca   480
agcgttttcc tgtttcctcc aaagcctaag gacacccgt acatcacccg cgagcctgaa   540
gtgacatgcg tggtggtgga tgtgtcccac gaggaccccg aagtgaagtt caattggtac   600
gtggacggcg tggaagtgca caacgccaag accaagccta gaggaacagt acaactcc    660
acctacagag tggtgtccgt gctgaccgtg ctgcaccagg attggctgaa cggcaaagag   720
tacaagtgca aggtgtccaa caaggccctg cctgctccta tcgaaaagac catctccaag   780
gccaagggcc agcctaggga acctcaggtt tacaccctgc cacctagccg ggaagagatg   840
```

-continued

```
accaaaaacc aggtgtccct gacctgcctg gtcaagggct tctacccatc cgatatcgcc      900
gtggaatggg agtctaacgg ccagcctgag aacaactaca agaccacacc tcctgtgctg      960
gactccgacg gctcattctt cctgtactcc aagctgacag tggacaagtc tcggtggcag     1020
cagggcaacg tgttctcctg ttctgtgatg cacgaggccc tgcacaacca ctacacccag     1080
aagtccctgt ctctgtcccc tggcaaa                                         1107
```

<210> SEQ ID NO 46
<211> LENGTH: 1092
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
acacaggatt gcagcttcca gcacagcccc atcagcagcg atttcgccgt gaagatcaga       60
gagctgagcg actacctgct gcaggactac cctgtgaccg tggccagcaa tctgcaggac      120
gaagaactgt gtggtggact gtggcgactg gtgctggctc agagatggat ggaacggctg      180
aaaacagtgg ccggcagcaa gatgcaggga ctgctggaaa gagtgaacac cgagatccac      240
ttcgtgacca gtgcgccctt ccagcctcct ccatcctgcc tgagattcgt gcagaccaac      300
atcagcagac tgctgcaaga gacaagcgag cagctggtgg ccctgaagcc ttggatcacc      360
agacagaact tcagccggtg cctggaactg cagtgtcagc ccgatagcag cacactgcct      420
ccgccttgga gtcctagacc tctggaagcc acagctgggg gaccgtcagt cttcctcttc      480
cccccaaaac ccaaggacac cctctacatc acccgggaac ctgaggtcac atgcgtggtg      540
gtggacgtga gccacgaaga ccctgaggtc aagttcaact ggtacgtgga cggcgtggag      600
gtgcataatg ccaagacaaa gccgcgggag gagcagtaca acagcacgta ccgtgtggtc      660
agcgtcctca ccgtcctgca ccaggactgg ctgaatggca aggagtacaa gtgcaaggtc      720
tccaacaaag ccctcccagc ccccatcgag aaaaccatct ccaaagccaa agggcagccc      780
cgagaaccac aggtgtacac cctgcccccca tcccgggagg agatgaccaa gaaccaggtc      840
agcctgacct gcctggtcaa aggcttctat cccagcgaca tcgccgtgga gtgggagagc      900
aatgggcagc cggagaacaa ctacaagacc acgcctcccg tgctggactc cgacggctcc      960
ttcttcctct acagcaagct caccgtggac aagagcaggt ggcagcaggg gaacgtcttc     1020
tcatgctccg tgatgcatga ggctctgcac aaccactaca cgcagaagag cctctccctg     1080
tctccgggta aa                                                         1092
```

<210> SEQ ID NO 47
<211> LENGTH: 1092
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
acccaggact gctccttcca gcactcccct atctcttccg acttcgccgt gaagatcaga       60
gagctgtccg actacctgct gcaggactat cctgtgaccg tggccagcaa cctgcaggat      120
gaagaactgt gtggtggact gtggcgactg gtgctggctc agagatggat ggaaagactg      180
aaaaccgtgg ccggctccaa gatgcaggga ctgctggaaa gagtgaacac agagatccac      240
ttcgtgacca gtgcgccctt tcagcctcct ccatcctgcc tgagattcgt gcagaccaac      300
```

| | |
|---|---|
| atctcccggc tgctgcaaga gacatctgag cagctggtgg ccctgaagcc ttggatcacc | 360 |
| cggcagaact tctctcggtg cctggaactg cagtgtcagc ctgattcttc taccctgcct | 420 |
| ccaccttgga gccctagacc tttggaagct acagctggcg gcccaagcgt gttcctgttt | 480 |
| cctccaaagc ctaaggacac cctgtacatc acccgcgagc tgaagtgac atgcgtggtg | 540 |
| gtggatgtgt cccacgagga ccccgaagtg aagttcaatt ggtacgtgga cggcgtggaa | 600 |
| gtgcacaacg ccaagaccaa gcctagagag gaacagtaca actccaccta cagagtggtg | 660 |
| tccgtgctga ccgtgctgca ccaggattgg ctgaacggca agagtacaa gtgcaaggtg | 720 |
| tccaacaagg ccctgcctgc tcctatcgaa aagaccatct ccaaggccaa gggccagcct | 780 |
| agggaacctc aggtttacac cctgccacct agccgggaag atgaccaa aaaccaggtg | 840 |
| tccctgacct gcctggtcaa gggcttctac ccatccgata tcgccgtgga atgggagtct | 900 |
| aacggccagc ctgagaacaa ctacaagacc acacctcctg tgctggactc cgacggctca | 960 |
| ttcttcctgt actccaagct gacagtggac aagtctcggt ggcagcaggg caacgtgttc | 1020 |
| tcctgttctg tgatgcacga ggccctgcac aaccactaca cccagaagtc cctgtctctg | 1080 |
| tcccctggca aa | 1092 |

<210> SEQ ID NO 48
<211> LENGTH: 1158
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

| | |
|---|---|
| acacaggatt gcagcttcca gcacagcccc atcagcagcg atttcgccgt gaagatcaga | 60 |
| gagctgagcg actacctgct gcaggactac cctgtgaccg tggccagcaa tctgcaggac | 120 |
| gaagaactgt gtggtggact gtggcgactg gtgctggctc agagatggat ggaacggctg | 180 |
| aaaacagtgg ccggcagcaa gatgcaggga ctgctggaaa gagtgaacac cgagatccac | 240 |
| ttcgtgacca gtgcgccctt ccagcctcct ccatcctgcc tgagattcgt gcagaccaac | 300 |
| atcagcagac tgctgcaaga gacaagcgag cagctggtgg ccctgaagcc ttggatcacc | 360 |
| agacagaact tcagccggtg cctggaactg cagtgtcagc ccgatagcag cacactgcct | 420 |
| ccgccttgga gtcctagacc tctggaagcc acagctccca ccgctcctca gaatctaag | 480 |
| tacgccctc cctgccctcc ttgcccagcc cctgaatttg agggcggacc ctccgtgttc | 540 |
| ctgttccccc caaagcccaa ggacaccctg tacatcaccc gggaacccga agtgacctgc | 600 |
| gtggtggtgg atgtgtccca ggaagatccc gaggtgcagt tcaattggta cgtggacggc | 660 |
| gtggaagtgc acaacgccaa gaccaagccc agagaggaac agttcaacag cacctaccgg | 720 |
| gtggtgtccg tgctgacagt gctgcaccag gactggctga acggcaaaga gtacaagtgc | 780 |
| aaggtgtcca acaagggcct gcccagctcc atcgagaaaa ccatcagcaa ggccaagggc | 840 |
| cagccccgcg aaccccaggt gtacacactg cctccaagcc aggaagagat gaccaagaac | 900 |
| caggtgtccc tgacctgtct cgtgaaaggc ttctaccct ccgatatcgc cgtggaatgg | 960 |
| gagagcaacg gccagcccga gaacaactac aagaccaccc ccctgtgct ggacagcgac | 1020 |
| ggctcattct tcctgtacag cagactgacc gtggacaaga gccggtggca ggaaggcaac | 1080 |
| gtgttcagct gcagcgtgat gcacgaggcc ctgcacaacc actacaccca gaagtccctg | 1140 |
| tctctgtccc tgggcaaa | 1158 |

<210> SEQ ID NO 49
<211> LENGTH: 1158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

| | | |
|---|---|---|
| acccaggact gctccttcca gcactcccct atctcttccg acttcgccgt gaagatcaga | 60 |
| gagctgtccg actacctgct gcaggactat cctgtgaccg tggccagcaa cctgcaggat | 120 |
| gaagaactgt gtggtggact gtggcgactg gtgctggctc agagatggat ggaaagactg | 180 |
| aaaaccgtgg ccggctccaa gatgcaggga ctgctggaaa gagtgaacac agagatccac | 240 |
| ttcgtgacca agtgcgcctt tcagcctcct ccatcctgcc tgagattcgt gcagaccaac | 300 |
| atctcccggc tgctgcaaga gacatctgag cagctggtgg ccctgaagcc ttggatcacc | 360 |
| cggcagaact tctctcggtg cctggaactg cagtgtcagc ctgattcttc taccctgcct | 420 |
| ccaccttgga gccctagacc tttggaggct acagctccta ccgctcctca agagtctaag | 480 |
| tacgcccctc cttgtcctcc atgtcctgct ccagaatttg aaggcggccc aagcgtgttc | 540 |
| ctgtttcctc caaagcctaa ggacaccctg tacatcaccc gcgagcctga agtgacatgc | 600 |
| gtggtggtgg atgtgtccca agaggacccc gaggtgcagt tcaattggta cgtggacggc | 660 |
| gtggaagtgc acaacgccaa gaccaagcct agagaggaac agttcaactc cacctacaga | 720 |
| gtggtgtccg tgctgaccgt gctgcaccag gattggctga acggcaaaga gtacaagtgc | 780 |
| aaggtgtcca caagggcct gcctagctcc atcgaaaaga ccatctccaa ggccaagggc | 840 |
| cagccaagag aacctcaggt gtacacactg cctccaagcc aagaggaaat gaccaagaac | 900 |
| caggtgtccc tgacctgcct ggtcaagggc ttctacccat ccgatatcgc cgtggaatgg | 960 |
| gagtctaacg gccagcctga gaacaactac aagaccacac tcctgtgct ggactccgac | 1020 |
| ggctccttct ttctgtactc tcgcctgacc gtggacaagt ctagatggca gaggcaac | 1080 |
| gtgttctcct gctctgtgat gcacgaggcc ctgcacaacc actacaccca gaagtccctg | 1140 |
| tctctgtccc tgggcaaa | 1158 |

<210> SEQ ID NO 50
<211> LENGTH: 1158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

| | | |
|---|---|---|
| acacaggatt gcagcttcca gcacagcccc atcagcagcg atttcgccgt gaagatcaga | 60 |
| gagctgagcg actacctgct gcaggactac cctgtgaccg tggccagcaa tctgcaggac | 120 |
| gaagaactgt gtggtggact gtggcgactg gtgctggctc agagatggat ggaacggctg | 180 |
| aaaacagtgg ccggcagcaa gatgcaggga ctgctggaaa gagtgaacac cgagatccac | 240 |
| ttcgtgacca agtgcgcctt ccagcctcct ccatcctgcc tgagattcgt gcagaccaac | 300 |
| atcagcagac tgctgcaaga gacaagcgag cagctggtgg ccctgaagcc ttggatcacc | 360 |
| agacagaact tcagccggtg cctggaactg cagtgtcagc cgatagcag cacactgcct | 420 |
| ccgccttgga gtcctagacc tctggaagcc acagctccca ccgctcctca agagtctaag | 480 |

| tacggccctc cttgtcctcc atgtcctgct ccagaagctg ctggcggccc ttccgtgttt | 540 |
| ctgttccctc caaagcctaa ggacaccctg tacatcaccc gggaacccga agtgacctgc | 600 |
| gtggtggtgg atgtgtccca ggaagatccc gaggtgcagt tcaattggta cgtggacggc | 660 |
| gtggaagtgc acaacgccaa gaccaagccc agagaggaac agttcaacag cacctaccgg | 720 |
| gtggtgtccg tgctgacagt gctgcaccag gactggctga acggcaaaga gtacaagtgc | 780 |
| aaggtgtcca acaagggcct gcccagctcc atcgagaaaa ccatcagcaa ggccaagggc | 840 |
| cagccccgcg aacccaggt gtacacactg cctccaagcc aggaagagat gaccaagaac | 900 |
| caggtgtccc tgacctgtct cgtgaaaggc ttctacccct ccgatatcgc cgtggaatgg | 960 |
| gagagcaacg gccagcccga gaacaactac aagaccaccc ccctgtgct ggacagcgac | 1020 |
| ggctcattct tcctgtacag cagactgacc gtggacaaga ccggtggca ggaaggcaac | 1080 |
| gtgttcagct gcagcgtgat gcacgaggcc ctgcacaacc actacaccca gaagtccctg | 1140 |
| tctctgtccc tgggcaaa | 1158 |

<210> SEQ ID NO 51
<211> LENGTH: 1158
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

| acccaggact gctccttcca gcactcccct atctcttccg acttcgccgt gaagatcaga | 60 |
| gagctgtccg actacctgct gcaggactat cctgtgaccg tggccagcaa cctgcaggat | 120 |
| gaagaactgt gtggtggact gtggcgactg gtgctggctc agatggat ggaaagactg | 180 |
| aaaaccgtgg ccggctccaa gatgcaggga ctgctggaaa gagtgaacac agagatccac | 240 |
| ttcgtgacca gtgcgccctt tcagcctcct ccatcctgcc tgagattcgt gcagaccaac | 300 |
| atctcccggc tgctgcaaga gacatctgag cagctggtgg ccctgaagcc ttggatcacc | 360 |
| cggcagaact tctctcggtg cctggaactg cagtgtcagc ctgattcttc taccctgcct | 420 |
| ccaccttgga gccctagacc tttggaggct acagctccta ccgctcctca agagtctaag | 480 |
| tacggccctc cttgtcctcc atgtcctgct ccagaagctg ctggcggacc aagcgttttc | 540 |
| ctgtttcctc caaagcctaa ggacaccctg tacatcaccc gcgagcctga agtgacatgc | 600 |
| gtggtggtgg atgtgtccca agaggaccc gaggtgcagt tcaattggta cgtggacggc | 660 |
| gtggaagtgc acaacgccaa gaccaagcct agagaggaac agttcaactc cacctacaga | 720 |
| gtggtgtccg tgctgaccgt gctgcaccag gattggctga acggcaaaga gtacaagtgc | 780 |
| aaggtgtcca acaagggcct gcctagctcc atcgaaaaga ccatctccaa ggccaagggc | 840 |
| cagccaagag aacctcaggt gtacacactg cctccaagcc aagaggaaat gaccaagaac | 900 |
| caggtgtccc tgacctgcct ggtcaaggc ttctacccat ccgatatcgc cgtggaatgg | 960 |
| gagtctaacg gccagcctga gaacaactac aagaccacac ctcctgtgct ggactccgac | 1020 |
| ggctccttct ttctgtactc tcgcctgacc gtggacaagt ctagatggca agagggcaac | 1080 |
| gtgttctcct gctctgtgat gcacgaggcc ctgcacaacc actacaccca gaagtccctg | 1140 |
| tctctgtccc tgggcaaa | 1158 |

<210> SEQ ID NO 52
<211> LENGTH: 1185
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 52

| | |
|---|---|
| atgacagttt tggctccagc ttggtcccct acaacctacc tgctgctgct gttgctgctc | 60 |
| tcctctggcc tgtctggcac ccaggactgt tccttccagc actccctat ctccagcgac | 120 |
| ttcgccgtga agatcagaga gctgtccgac tatctgctgc aggactaccc tgtgaccgtg | 180 |
| gccagcaatc tgcaggacga agaactgtgt ggtggcctgt ggcgactggt gttggctcag | 240 |
| agatggatgg aacggctgaa aaccgtggcc ggctctaaga tgcagggcct gctggaaaga | 300 |
| gtgaacaccg agatccactt cgtgaccaag tgcgcctttc agcctcctcc atcctgcctg | 360 |
| agattcgtgc agaccaatat cgcccggctg ctgcaagaga catccgagca gctggtggct | 420 |
| ctgaagccct ggatcaccag acagaacttc gcccgtgtc tggaactgca gtgtcagcct | 480 |
| gacagctcta ccctgcctcc accttggagc cctagacctc tggaagctac cgctccaacc | 540 |
| gctcctcaag ggggaccgtc agtcttcctc ttccccccaa acccaagga caccctctac | 600 |
| atcacccggg aacctgaggt cacatgcgtg gtggtggacg tgagccacga agaccctgag | 660 |
| gtcaagttca actggtacgt ggacggcgtg gaggtgcata atgccaagac aaagccgcgg | 720 |
| gaggagcagt acaacagcac gtaccgtgtg gtcagcgtcc tcaccgtcct gcaccaggac | 780 |
| tggctgaatg caaggagta caagtgcaag gtctccaaca aagccctccc agccccatc | 840 |
| gagaaaacca tctccaaagc caagggcag ccccgagaac cacaggtgta caccctgccc | 900 |
| ccatcccggg aggagatgac caagaaccag gtcagcctga cctgcctggt caaaggcttc | 960 |
| tatcccagcg acatcgccgt ggagtgggag agcaatgggc agccggagaa caactacaag | 1020 |
| accacgcctc ccgtgctgga ctccgacggc tccttcttcc tctacagcaa gctcaccgtg | 1080 |
| gacaagagca ggtggcagca ggggaacgtc ttctcatgct ccgtgatgca tgaggctctg | 1140 |
| cacaaccact acacgcagaa gagcctctcc ctgtctccgg gtaaa | 1185 |

<210> SEQ ID NO 53
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

| | |
|---|---|
| acccaggact gctccttcca gcactcccct atctcttccg acttcgccgt gaagatcaga | 60 |
| gagctgtccg actacctgct gcaggactat cctgtgaccg tggccagcaa cctgcaggat | 120 |
| gaagaactgt gtggtggact gtggcgactg gtgctggctc agagatggat ggaaagactg | 180 |
| aaaaccgtgg ccggctccaa gatgcaggga ctgctggaaa gagtgaacac agagatccac | 240 |
| ttcgtgacca agtgcgcctt tcagcctcct ccatcctgcc tgagattcgt gcagaccaat | 300 |
| atcgcccggc tgctgcaaga gacatctgag cagctggtgg ccctgaagcc ttggatcacc | 360 |
| agacagaact tcgcccggtg cctggaactg cagtgtcagc ctgattcttc taccctgcct | 420 |
| ccaccttgga gccctagacc tttggaggct acagctccta ctgctcctca aggcggccca | 480 |
| agcgttttcc tgtttcctcc aaagcctaag gacaccctgt acatcacccg cgagcctgaa | 540 |
| gtgacatgcg tggtggtgga tgtgtcccac gaggaccccg aagtgaagtt caattggtac | 600 |
| gtggacggcg tggaagtgca caacgccaag accaagccta gagaggaaca gtacaactcc | 660 |

```
acctacagag tggtgtccgt gctgaccgtg ctgcaccagg attggctgaa cggcaaagag    720
tacaagtgca aggtgtccaa caaggccctg cctgctccta tcgaaaagac catctccaag    780
gccaagggcc agcctaggga acctcaggtt tacaccctgc acctagccg ggaagagatg     840 accaaaaacc aggtgtccct gacctgcctg gtcaagggct tctacccatc cgatatcgcc    900
gtggaatggg agtctaacgg ccagcctgag aacaactaca agaccacacc tcctgtgctg    960
gactccgacg gctcattctt cctgtactcc aagctgacag tggacaagtc tcggtggcag   1020
cagggcaacg tgttctcctg ttctgtgatg cacgaggccc tgcacaacca ctacacccag   1080
aagtccctgt ctctgtcccc tggcaaa                                       1107
```

<210> SEQ ID NO 54
<211> LENGTH: 1143
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
acacaggatt gcagcttcca gcacagcccc atcagcagcg atttcgccgt gaagatcaga     60
gagctgagcg actacctgct gcaggactac cctgtgaccg tggccagcaa tctgcaggac    120
gaagaactgt gtggtggact gtggcgactg gtgctggctc agagatggat ggaacggctg    180
aaaacagtgg ccggcagcaa gatgcaggga ctgctggaaa gagtgaacac cgagatccac    240
ttcgtgacca agtgcgcctt ccagcctcct ccatcctgcc tgagattcgt gcagaccaac    300
atcagcagac tgctgcaaga gacaagcgag cagctggtgg ccctgaagcc ttggatcacc    360
agacagaact tcagccggtg cctggaactg cagtgtcagc ccgatagcag cacactgcct    420
ccgccttgga gtcctagacc tctggaagcc acagctgagt ctaagtacgg ccctccttgt    480
cctccatgtc ctgctccaga agctgctggc ggcccttccg tgtttctgtt ccctccaaag    540
cccaaggaca ccctgtacat cacccgggaa cccgaagtga cctgcgtggt ggtggatgtg    600
tcccaggaag atcccgaggt gcagttcaat tggtacgtgg acggcgtgga agtgcacaac    660
gccaagacca agcccagaga ggaacagttc aacagcacct accgggtggt gtccgtgctg    720
acagtgctgc accaggactg gctgaacggc aaagagtaca agtgcaaggt gtccaacaag    780
ggcctgccca gctccatcga aaaaccatc agcaaggcca agggccagcc ccgcgaaccc    840
caggtgtaca cactgcctcc aagccaggaa gagatgacca gaaccaggt gtccctgacc    900 tgtctcgtga aaggcttcta cccctccgat atcgccgtgg aatgggagag caacggccag    960
cccgagaaca actacaagac caccccccct gtgctggaca cgacggctc attcttcctg   1020 tacagcagac tgaccgtgga caagagccgg tggcaggaag caacgtgtt cagctgcagc   1080 gtgatgcacg aggccctgca caaccactac acccagaagt ccctgtctct gtccctgggc   1140
aaa                                                                 1143
```

<210> SEQ ID NO 55
<211> LENGTH: 1143
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
acccaggact gctccttcca gcactcccct atctcttccg acttcgccgt gaagatcaga      60
gagctgtccg actacctgct gcaggactat cctgtgaccg tggccagcaa cctgcaggat     120
gaagaactgt gtggtggact gtggcgactg gtgctggctc agagatggat ggaaagactg     180
aaaaccgtgg ccggctccaa gatgcaggga ctgctggaaa gagtgaacac agagatccac     240
ttcgtgacca agtgcgcctt tcagcctcct ccatcctgcc tgagattcgt gcagaccaac     300
atctcccggc tgctgcaaga gacatctgag cagctggtgg ccctgaagcc ttggatcacc     360
cggcagaact tctctcggtg cctggaactg cagtgtcagc ctgattcttc taccctgcct     420
ccaccttgga gccctagacc tctggaagct accgccgagt ctaagtacgg acctccttgt     480
cctccatgtc ctgctccaga agctgctggc ggaccaagcg ttttcctgtt tcctccaaag     540
cctaaggaca ccctgtacat cacccgcgag cctgaagtga catgcgtggt ggtggatgtg     600
tcccaagagg accccgaggt gcagttcaat tggtacgtgg acggcgtgga agtgcacaac     660
gccaagacca agcctagaga ggaacagttc aactccacct acagagtggt gtccgtgctg     720
accgtgctgc accaggattg gctgaacggc aaagagtaca gtgcaaggt gtccaacaag     780 ggcctgccta gctccatcga aaagaccatc tccaaggcca agggccagcc aagagaacct     840
caggtgtaca cactgcctcc aagccaagag gaaatgacca gaaccaggt gtccctgacc     900 tgcctggtca gggcttcta cccatccgat atcgccgtgg aatgggagtc taacggccag     960
cctgagaaca actacaagac cacacctcct gtgctggact ccgacggctc cttctttctg    1020
tactctcgcc tgaccgtgga caagtctaga tggcaagagg gcaacgtgtt ctcctgctct    1080
gtgatgcacg aggccctgca caaccactac acccagaagt ccctgtctct gtccctgggc    1140
aaa                                                                  1143

<210> SEQ ID NO 56
<211> LENGTH: 1077
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
acacaggatt gcagcttcca gcacagcccc atcagcagcg atttcgccgt gaagatcaga      60
gagctgagcg actacctgct gcaggactac cctgtgaccg tggccagcaa tctgcaggac     120
gaagaactgt gtggtggact gtggcgactg gtgctggctc agagatggat ggaacggctg     180
aaaacagtgg ccggcagcaa gatgcaggga ctgctggaaa gagtgaacac cgagatccac     240
ttcgtgacca agtgcgcctt ccagcctcct ccatcctgcc tgagattcgt gcagaccaac     300
atcagcagac tgctgcaaga gacaagcgag cagctggtgg ccctgaagcc ttggatcacc     360
agacagaact tcagccggtg cctggaactg cagtgtcagc ccgatagcag cacactgcct     420
ccgccttgga gtcctagacc tggggaccg tcagtcttcc tcttcccccc aaaacccaag     480
gacaccctct acatcacccg ggaacctgag gtcacatgcg tggtggtgga cgtgagccac     540
gaagaccctg aggtcaagtt caactggtac gtggacggcg tggaggtgca taatgccaag     600
acaaagccgc gggaggagca gtacaacagc acgtaccgtg tggtcagcgt cctcaccgtc     660
ctgcaccagg actggctgaa tggcaaggag tacaagtgca aggtctccaa caaagccctc     720
ccagccccca tcgagaaaac catctccaaa gccaagggc agccccgaga accacaggtg     780
tacaccctgc ccccatcccg ggaggagatg accaagaacc aggtcagcct gacctgcctg     840
```

```
gtcaaaggct tctatcccag cgacatcgcc gtggagtggg agagcaatgg gcagccggag    900
aacaactaca agaccacgcc tcccgtgctg gactccgacg gctccttctt cctctacagc    960
aagctcaccg tggacaagag caggtggcag caggggaacg tcttctcatg ctccgtgatg   1020
catgaggctc tgcacaacca ctacacgcag aagagcctct ccctgtctcc gggtaaa     1077
```

<210> SEQ ID NO 57
<211> LENGTH: 1077
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
acccaggact gctccttcca gcactcccct atctcttccg acttcgccgt gaagatcaga     60
gagctgtccg actacctgct gcaggactat cctgtgaccg tggccagcaa cctgcaggat    120
gaagaactgt gtggtggact gtggcgactg tgctggctc agatggat ggaaagactg       180 aaaaccgtgg ccggctccaa gatgcaggga ctgctggaaa gagtgaacac agagatccac    240
ttcgtgacca agtgcgcctt tcagcctcct ccatcctgcc tgagattcgt gcagaccaac    300
atctcccggc tgctgcaaga gacatctgag cagctggtgg ccctgaagcc ttggatcacc    360
cggcagaact tctctcggtg cctggaactg cagtgtcagc ctgattcttc taccctgcct    420
ccaccttgga gtcctagacc tggcggacca agcgtgttcc tgtttcctcc aaagcctaag    480
gacaccctgt acatcacccg cgagcctgaa gtgacatgcg tggtggtgga tgtgtcccac    540 gaggacccg aagtgaagtt caattggtac gtggacggcg tggaagtgca aacgccaag    600 accaagccta gagggaaca gtacaactcc acctacagag tggtgtccgt gctgaccgtg    660
ctgcaccagg attggctgaa cggcaaagag tacaagtgca aggtgtccaa caaggccctg    720
cctgctccta tcgaaaagac catctccaag gccaagggcc agcctaggga acctcaggtt    780
tacaccctgc cacctagccg ggaagagatg accaaaaacc aggtgtccct gacctgcctg    840
gtcaagggct tctacccatc cgatatcgcc gtggaatggg agtctaacgg ccagcctgag    900
aacaactaca agaccacacc tcctgtgctg gactccgacg gctcattctt cctgtactcc    960
aagctgacag tggacaagtc tcggtggcag cagggcaacg tgttctcctg ttctgtgatg   1020
cacgaggccc tgcacaacca ctacacccag aagtccctgt ctctgtcccc tggcaaa     1077
```

<210> SEQ ID NO 58
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
acacaggatt gcagcttcca gcacagcccc atcagcagcg atttcgccgt gaagatcaga     60
gagctgagcg actacctgct gcaggactac cctgtgaccg tggccagcaa tctgcaggac    120
gaagaactgt gtggtggact gtggcgactg tgctggctc agatggat ggaacggctg       180 aaaacagtgg ccggcagcaa gatgcaggga ctgctggaaa gagtgaacac cgagatccac    240
ttcgtgacca agtgcgcctt ccagcctcct ccatcctgcc tgagattcgt gcagaccaac    300
atcagcagac tgctgcaaga gacaagcgag cagctggtgg ccctgaagcc ttggatcacc    360
agacagaact tcagccggtg cctggaactg cagtgtcagc ccgatagcag cacactgcct    420
```

```
ccgccttgga gtcctagacc tgagtctaag tacggccctc cttgtcctcc atgtcctgct      480
ccagaagctg ctggcggccc ttccgtgttt ctgttccctc caaagcctaa ggacaccctg      540
tacatcaccc gggaacccga agtgacctgc gtggtggtgg atgtgtccca ggaagatccc      600
gaggtgcagt tcaattggta cgtggacggc gtggaagtgc acaacgccaa gaccaagccc      660
agagaggaac agttcaacag cacctaccgg gtggtgtccg tgctgacagt gctgcaccag      720
gactggctga acggcaaaga gtacaagtgc aaggtgtcca acaagggcct gcccagctcc      780
atcgagaaaa ccatcagcaa ggccaagggc agccccgcg aaccccaggt gtacacactg       840
cctccaagcc aggaagagat gaccaagaac caggtgtccc tgacctgtct cgtgaaaggc      900
ttctacccct ccgatatcgc cgtggaatgg gagagcaacg gccagcccga gaacaactac      960
aagaccaccc cccctgtgct ggacagcgac ggctcattct tcctgtacag cagactgacc     1020
gtggacaaga ccggtggca ggaaggcaac gtgttcagct gcagcgtgat gcacgaggcc      1080
ctgcacaacc actacaccca gaagtccctg tctctgtccc tgggcaaa               1128
```

<210> SEQ ID NO 59
<211> LENGTH: 1128
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 59

```
acccaggact gctccttcca gcactcccct atctcttccg acttcgccgt gaagatcaga       60
gagctgtccg actacctgct gcaggactat cctgtgaccg tggccagcaa cctgcaggat      120
gaagaactgt gtggtggact gtggcgactg gtgctggctc agatggat ggaaagactg        180 aaaaccgtgg ccggctccaa gatgcaggga ctgctggaaa gagtgaacac agagatccac      240
ttcgtgacca agtgcgcctt tcagcctcct ccatcctgcc tgagattcgt gcagaccaac      300
atctcccggc tgctgcaaga gacatctgag cagctggtgg ccctgaagcc ttggatcacc      360
cggcagaact tctctcggtg cctggaactg cagtgtcagc ctgattcttc taccctgcct      420
ccaccttgga gccctcggcc tgaatctaag tatggccctc cttgtcctcc atgtcctgct      480
ccagaagctg ctggcggacc aagcgttttc ctgtttcctc caaagcctaa ggacaccctg      540
tacatcaccc gcgagcctga agtgacatgc gtggtggtgg atgtgtccca agaggacccc      600
gaggtgcagt tcaattggta cgtggacggc gtggaagtgc acaacgccaa gaccaagcct      660
agagaggaac agttcaactc cacctacaga gtggtgtccg tgctgaccgt gctgcaccag      720
gattggctga acggcaaaga gtacaagtgc aaggtgtcca acaagggcct gcctagctcc      780
atcgaaaaga ccatctccaa ggccaagggc agccaagag aacctcaggt gtacacactg       840
cctccaagcc aagaggaaat gaccaagaac caggtgtccc tgacctgcct ggtcaagggc     900
ttctacccat ccgatatcgc cgtggaatgg gagtctaacg gccagcctga gaacaactac      960
aagaccacac ctcctgtgct ggactccgac ggctccttct ttctgtactc cgcctgacc      1020 gtggacaagt ctagatggca agagggcaac gtgttctcct gctctgtgat gcacgaggcc     1080
ctgcacaacc actacaccca gaagtccctg tctctgtccc tgggcaaa               1128
```

<210> SEQ ID NO 60
<211> LENGTH: 1128
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 60
acccaggact gttccttcca gcactcccct atctccagcg acttcgccgt gaagatcaga      60
gagctgtccg actatctgct gcaggactac cctgtgaccg tggccagcaa tctgcaggac    120
gaagaactgt gtggtggcct gtggcgactg gtgttggctc agatggat ggaacggctg     180 aaaaccgtgg ccggctctaa gatgcagggc ctgctggaaa gagtgaacac cgagatccac    240
ttcgtgacca gtgcgccctt tcagcctcct ccatcctgcc tgagattcgt gcagaccaat    300
atcgcccggc tgctgcaaga gacatccgag cagctggtgg ctctgaagcc ctggatcacc    360
agacagaact cgcccggtg tctggaactg cagtgtcagc ctgacagctc taccctgcct    420
ccaccttgga gccctagacc tgagtctaag tacggccctc cttgtcctcc atgtcctgct    480
ccagaagctg ctggcggccc ttccgtgttt ctgttccctc aaagcctaa ggacaccctg     540 atgatctctc ggaccctga agtgacctgc gtggtggtgg atgtgtccca agaggatccc    600
gaggtgcagt tcaattggta cgtggacggc gtggaagtgc acaacgccaa gaccaagcct    660
agagaggaac agttcaactc cacctacaga gtggtgtccg tgctgaccgt gctgcaccag    720
gattggctga acggcaaaga gtacaagtgc aaggtgtcca acaagggcct gccttccagc    780
atcgaaaaga ccatctccaa ggccaagggc cagcctaggg aacccaggt ttacaccctg     840 cctccaagcc aagaggaaat gaccaagaac caggtgtccc tgacctgcct ggtcaagggc    900
ttctacccct ccgatatcgc cgtggaatgg gagagcaatg ccagcctga gaacaactac     960 aagaccacac ctcctgtgct ggactccgac ggctccttct ttctgtactc ccgcctgacc   1020
gtggacaagt ccagatggca gagggcaac gtgttctcct gctccgtgat gcacgaggcc    1080
ctgcacaatc actacaccca gaagtccctg tctctgtccc tgggcaaa                 1128

<210> SEQ ID NO 61
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
acccaggact gttccttcca gcactcccct atctccagcg acttcgccgt gaagatcaga      60
gagctgtccg actatctgct gcaggactac cctgtgaccg tggccagcaa tctgcaggac    120
gaagaactgt gtggtggcct gtggcgactg gtgttggctc agatggat ggaacggctg     180 aaaaccgtgg ccggctctaa gatgcagggc ctgctggaaa gagtgaacac cgagatccac    240
ttcgtgacca gtgcgccctt tcagcctcct ccatcctgcc tgagattcgt gcagaccaat    300
atcgcccggc tgctgcaaga gacatccgag cagctggtgg ctctgaagcc ctggatcacc    360
agacagaact cgcccggtg tctggaactg cagtgtcagc ctgacagctc taccctgcct    420
ccaccttgga gccctagacc tgagtctaag tacggccctc cttgtcctcc atgtcctgct    480
ccagaagctg ctggcggccc ttccgtgttt ctgttccctc aaagcctaa ggacaccctg     540 tacatcaccc gggaacccga agtgacctgc gtggtggtgg atgtgtccca ggaagatccc    600
gaggtgcagt tcaattggta cgtggacggc gtggaagtgc acaacgccaa gaccaagccc    660
agagaggaac agttcaacag cacctaccgg gtggtgtccg tgctgacagt gctgcaccag    720
```

| | |
|---|---|
| gactggctga acggcaaaga gtacaagtgc aaggtgtcca acaagggcct gcccagctcc | 780 |
| atcgagaaaa ccatcagcaa ggccaagggc cagccccgcg aacccccaggt gtacacactg | 840 |
| cctccaagcc aggaagagat gaccaagaac caggtgtccc tgacctgtct cgtgaaaggc | 900 |
| ttctacccct ccgatatcgc cgtggaatgg gagagcaacg gccagcccga gaacaactac | 960 |
| aagaccaccc cccctgtgct ggacagcgac ggctcattct tcctgtacag cagactgacc | 1020 |
| gtggacaaga gccggtggca ggaaggcaac gtgttcagct gcagcgtgat gcacgaggcc | 1080 |
| ctgcacaacc actacaccca gaagtccctg tctctgtccc tgggcaaa | 1128 |

<210> SEQ ID NO 62
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

| | |
|---|---|
| acccctgact gctacttcag ccactctcct atctccagca acttcaaagt gaagttccgc | 60 |
| gagctgaccg accatctgct gaaggactat cctgtgaccg tggccgtgaa cctgcaggac | 120 |
| gaaaagcact gcaaggccct gtggtccctg tttctggccc agagatggat cgagcagctg | 180 |
| aaaaccgtgg ctggctccaa gatgcagacc ctgctggaag atgtgaacac cgagatccac | 240 |
| ttcgtgacca gctgcacctt ccagcctctg cctgagtgcc tgagattcgt gcagaccaac | 300 |
| atctcccacc tgttgaagga cacatgcacc cagctgctgg ccctgaagcc ttgtatcggc | 360 |
| aaggcctgcc agaacttctc ccggtgtctg gaagtgcagt gccagcctga ctcctccaca | 420 |
| ctgctgccac ctagaagccc tatcgctctg gaagctaccg agctgcctga gcctagaggc | 480 |
| cctaccatca agccttgtcc tccatgcaag tgccccgctc ctaatgctgc tggtggccct | 540 |
| tccgtgttca tcttcccacc taagatcaag gacgtgctga tgatctccct gtctcctatc | 600 |
| gtgacctgcg tggtggtgga cgtgtccgag gatgatcctg acgtgcagat cagttggttc | 660 |
| gtgaacaacg tggaagtgca caccgctcag acccagacac acagagagga ctacaacagc | 720 |
| accctgagag tggtgtctgc cctgcctatc cagcaccagg attggatgtc cggcaaagaa | 780 |
| ttcaagtgca aagtgaacaa caaggacctg ggcgctccca tcgagcggac catctctaag | 840 |
| cctaagggat ccgtcagagc ccctcaggtg tacgttctgc ctccacctga ggaagagatg | 900 |
| accaagaaac aagtgacccct gacctgcatg gtcaccgact tcatgcccga ggacatctac | 960 |
| gtggaatgga ccaacaacgg caagaccgag ctgaactaca agaacaccga gcctgtgctg | 1020 |
| gactccgacg gctcctactt catgtactcc aagctgcgcg tcgagaagaa gaactgggtc | 1080 |
| gagagaaact cctactcctg ctccgtggtg cacgagggcc tgcacaatca ccacaccacc | 1140 |
| aagtccttct ctcggacccc tggcaaa | 1167 |

<210> SEQ ID NO 63
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

| | |
|---|---|
| acccctgact gctacttcag ccactctcct atctccagca acttcaaagt gaagttccgc | 60 |
| gagctgaccg accatctgct gaaggactat cctgtgaccg tggccgtgaa cctgcaggac | 120 |

```
gaaaagcact gcaaggccct gtggtccctg tttctggccc agagatggat cgagcagctg    180
aaaaccgtgg ctggctccaa gatgcagacc ctgctggaag atgtgaacac cgagatccac    240
ttcgtgacca gctgcacctt ccagcctctg cctgagtgcc tgagattcgt gcagaccaac    300
atctcccacc tgttgaagga cacatccacc cagctgctgg ccctgaagcc ttgtatcggc    360
aaggcctgcc agaacttctc ccggtgtctg gaagtgcagt gccagcctga ctcctccaca    420
ctgctgccac ctagaagccc tatcgctctg aagctaccg agctgcctga gcctagaggc    480
cctaccatca agccttgtcc tccatgcaag tgccccgctc ctaatgctgc tggtggccct    540
tccgtgttca tcttcccacc taagatcaag acgtgctga tgatctccct gtctcctatc    600
gtgacctgcg tggtggtgga cgtgtccgag gatgatcctg acgtgcagat cagttggttc    660
gtgaacaacg tggaagtgca caccgctcag acccagacac acagagagga ctacaacagc    720
accctgagag tggtgtctgc cctgcctatc agcaccagg attggatgtc cggcaaagaa    780
ttcaagtgca aagtgaacaa caaggacctg ggcgctccca tcgagcggac catctctaag    840
cctaagggat ccgtcagagc ccctcaggtg tacgttctgc ctccacctga ggaagagatg    900
accaagaaac aagtgaccct gacctgcatg gtcaccgact tcatgcccga ggacatctac    960
gtggaatgga ccaacaacgg caagaccgag ctgaactaca agaacaccga gcctgtgctg    1020
gactccgacg gctcctactt catgtactcc aagctgcgcg tcgagaagaa gaactgggtc    1080
gagagaaact cctactcctg ctccgtggtg cacgagggcc tgcacaatca ccacaccacc    1140
aagtccttct ctcggacccc tggcaaa                                       1167
```

<210> SEQ ID NO 64
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
acacaggatt gcagcttcca gcacagcccc atcagcagcg atttcgccgt gaagatcaga    60
gagctgagcg actacctgct gcaggactac cctgtgaccg tggccagcaa tctgcaggac    120
gaagaactgt gtggtggact gtggcgactg gtgctggctc agagatggat ggaacggctg    180
aaaacagtgg ccggcagcaa gatgcaggga ctgctggaaa gagtgaacac cgagatccac    240
ttcgtgacca agtgcgcctt ccagcctcct ccatcctgcc tgagattcgt gcagaccaac    300
atcagcagac tgctgcaaga gacaagcgag cagctggtgg ccctgaagcc ttggatcacc    360
agacagaact tcagccggtg cctggaactg cagtgtcagc ccgatagcag cacactgcct    420
ccgccttgga gtcctagacc tctggaagcc acagctccca ccgctcctca aggcggaccg    480
tcagtctttc tgttccctcc aaagcctaag acaccctga tgatcagcag aaccctgaa     540 gtgacctgcg tggtggtgga tgtgtcccac gaggatcccg aagtgaagtt caattggtac    600
gtggacggcg tggaagtgca caacgccaag accaagccta gagggaaca gtacaacagc    660 acctacagag tggtgtccgt gctgaccgtg ctgcaccagg attggctgaa cggcaaagag    720
tacaagtgca aggtgtccaa caaggccctg cctgctccta tcgagaaaac catcagcaag    780
gccaagggcc agcctaggga accccaggtg tacacaaagc tccaagccg ggaagagatg     840 accaagaacc aggtgtccct gagctgcctg gtcaagggct tttaccccag cgacattgcc    900
gtggaatggg agagcaatgg ccagcctgag aacaactaca gaccaccgt gcctgtgctg     960
```

| | |
|---|---|
| gacagcgacg gctcttttag actggccagc tacctgaccg tggacaagag cagatggcag | 1020 |
| cagggcaacg tgttcagctg cagcgtgatg cacgaggccc tgcacaacca ctacacccag | 1080 |
| aagtccctgt ctctgagccc cggcaaa | 1107 |

<210> SEQ ID NO 65
<211> LENGTH: 1107
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

| | |
|---|---|
| acacaggatt gcagcttcca gtacagcccc atcagcagcg atttcgccgt gaagatcaga | 60 |
| gagctgagcg actacctgct gcaggactac cctgtgaccg tggccagcaa tctgcaggac | 120 |
| gaagaactgt gtggtggact gtggcgactg gtgctggctc agatggat ggaacggctg | 180 |
| aaaacagtgg ccggcagcaa gatgcaggga ctgctggaaa gagtgaacac cgagatccac | 240 |
| ttcgtgacca agtgcgcctt ccagcctcct ccatcctgcc tgagattcgt gcagaccaac | 300 |
| atcagcagac tgctgcaaga gacaagcgag cagctggtgg ccctgaagcc ttggatcacc | 360 |
| agacagaact tcagccggtg cctggaactg cagtgtcagc ccgatagcag cacactgcct | 420 |
| ccgccttgga gtcctagacc tctggaagcc acagctccca ccgctcctca aggcggaccg | 480 |
| tcagtcttcc tcttcccccc aaaacccaag gacaccctca tgatctcccg gacccctgag | 540 |
| gtcacatgcg tggtggtgga cgtgagccac gaagaccctg aggtcaagtt caactggtac | 600 |
| gtggacggcg tggaggtgca taatgccaag acaaagccgc gggaggagca gtacaacagc | 660 |
| acgtaccgtg tggtcagcgt cctcaccgtc ctgcaccagg actggctgaa tggcaaggag | 720 |
| tacaagtgca aggtctccaa caaagccctc ccagccccca tcgagaaaac catctccaaa | 780 |
| gccaaagggc agccccgaga accacaggtg tacaccctgc ccccatcccg ggaggagatg | 840 |
| accaagaacc aggtcagcct gacctgcctg gtcaaaggct tctatcccag cgacatcgcc | 900 |
| gtggagtggg agagcaatgg gcagccggag aacaactaca agaccacgcc tcccgtgctg | 960 |
| gactccgacg gctccttctt cctctacagc aagctcaccg tggacaagag caggtggcag | 1020 |
| caggggaacg tcttctcatg ctccgtgatg catgaggctc tgcacaacca ctacacgcag | 1080 |
| aagagcctct ccctgtctcc gggtaaa | 1107 |

<210> SEQ ID NO 66
<211> LENGTH: 1107
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

| | |
|---|---|
| acacaggatt gcagcttcca gcacagcccc atcagcagcg atttcgccgt gaagatcaga | 60 |
| gagctgagcg actacctgct gcaggactac cctgtgaccg tggccagcaa tctgcaggac | 120 |
| gaagaactgt gtggtggact gtggcgactg gtgctggctc agatggat ggaacggctg | 180 |
| aaaacagtgg ccggcagcaa gatgcaggga ctgctggaaa gagtgaacac cgagatccac | 240 |
| ttcgtgaccg agtgcgcctt ccagcctcct ccatcctgcc tgagattcgt gcagaccaac | 300 |
| atcagcagac tgctgcaaga gacaagcgag cagctggtgg ccctgaagcc ttggatcacc | 360 |

| | |
|---|---|
| agacagaact tcagccggtg cctggaactg cagtgtcagc ccgatagcag cacactgcct | 420 |
| ccgccttgga gtcctagacc tctggaagcc acagctccca ccgctcctca aggcggaccg | 480 |
| tcagtcttcc tcttcccccc aaaacccaag gacaccctca tgatctcccg gacccctgag | 540 |
| gtcacatgcg tggtggtgga cgtgagccac gaagaccctg aggtcaagtt caactggtac | 600 |
| gtggacggcg tggaggtgca taatgccaag acaaagccgc gggaggagca gtacaacagc | 660 |
| acgtaccgtg tggtcagcgt cctcaccgtc ctgcaccagg actggctgaa tggcaaggag | 720 |
| tacaagtgca aggtctccaa caaagccctc ccagccccca tcgagaaaac catctccaaa | 780 |
| gccaaagggc agccccgaga accacaggtg tacaccctgc ccccatcccg ggaggagatg | 840 |
| accaagaacc aggtcagcct gacctgcctg gtcaaaggct tctatcccag cgacatcgcc | 900 |
| gtggagtggg agagcaatgg gcagccggag aacaactaca agaccacgcc tcccgtgctg | 960 |
| gactccgacg gctccttctt cctctacagc aagctcaccg tggacaagag caggtggcag | 1020 |
| caggggaacg tcttctcatg ctccgtgatg catgaggctc tgcacaacca ctacacgcag | 1080 |
| aagagcctct ccctgtctcc gggtaaa | 1107 |

<210> SEQ ID NO 67
<211> LENGTH: 1107
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

| | |
|---|---|
| acacaggatt gcagcttcca gtacagcccc atcagcagcg atttcgccgt gaagatcaga | 60 |
| gagctgagcg actacctgct gcaggactac cctgtgaccg tggccagcaa tctgcaggac | 120 |
| gaagaactgt gtggtggact gtggcgactg gtgctggctc agagatggat ggaacggctg | 180 |
| aaaacagtgg ccggcagcaa gatgcaggga ctgctggaaa gagtgaacac cgagatccac | 240 |
| ttcgtgaccg agtgcgcctt ccagcctcct ccatcctgcc tgagattcgt gcagaccaac | 300 |
| atcagcagac tgctgcaaga gacaagcgag cagctggtgg ccctgaagcc ttggatcacc | 360 |
| agacagaact tcagccggtg cctggaactg cagtgtcagc ccgatagcag cacactgcct | 420 |
| ccgccttgga gtcctagacc tctggaagcc acagctccca ccgctcctca aggcggaccg | 480 |
| tcagtcttcc tcttcccccc aaaacccaag gacaccctca tgatctcccg gacccctgag | 540 |
| gtcacatgcg tggtggtgga cgtgagccac gaagaccctg aggtcaagtt caactggtac | 600 |
| gtggacggcg tggaggtgca taatgccaag acaaagccgc gggaggagca gtacaacagc | 660 |
| acgtaccgtg tggtcagcgt cctcaccgtc ctgcaccagg actggctgaa tggcaaggag | 720 |
| tacaagtgca aggtctccaa caaagccctc ccagccccca tcgagaaaac catctccaaa | 780 |
| gccaaagggc agccccgaga accacaggtg tacaccctgc ccccatcccg ggaggagatg | 840 |
| accaagaacc aggtcagcct gacctgcctg gtcaaaggct tctatcccag cgacatcgcc | 900 |
| gtggagtggg agagcaatgg gcagccggag aacaactaca agaccacgcc tcccgtgctg | 960 |
| gactccgacg gctccttctt cctctacagc aagctcaccg tggacaagag caggtggcag | 1020 |
| caggggaacg tcttctcatg ctccgtgatg catgaggctc tgcacaacca ctacacgcag | 1080 |
| aagagcctct ccctgtctcc gggtaaa | 1107 |

<210> SEQ ID NO 68
<211> LENGTH: 1143
<212> TYPE: DNA

<213> ORGANISM: Artificial Sequence
<220> FEATURE:
<223> OTHER INFORMATION: Description of Artificial Sequence: Synthetic
    polynucleotide

<400> SEQUENCE: 68

```
acccaggact gttccttcca gcactcccct atctccagcg acttcgccgt gaagatcaga      60
gagctgtccg actatctgct gcaggactac cctgtgaccg tggccagcaa tctgcaggac     120
gaagaactgt gtggtggcct gtggcgactg gtgttggctc agagatggat ggaacggctg     180
aaaaccgtgg ccggctctaa gatgcagggc ctgctggaaa gagtgaacac cgagatccac     240
ttcgtgacca agtgcgcctt tcagcctcct ccatcctgcc tgagattcgt gcagaccaat     300
atcgcccggc tgctgcaaga gacatccgag cagctggtgg ctctgaagcc tggatcacc     360
agacagaact cgcccggtg tctgaactg cagtgtcagc ctgacagctc taccctgcct     420
ccaccttgga gccctagacc tctggaagct accgctgagt ctaagtacgg ccctccttgt     480
cctccatgtc ctgctccaga agctgctggc ggcccttccg tgtttctgtt ccctccaaag     540
cccaaggaca ccctgtacat cacccgggaa cccgaagtga cctgcgtggt ggtggatgtg     600
tcccaggaag atcccgaggt gcagttcaat tggtacgtgg acggcgtgga agtgcacaac     660
gccaagacca agcccagaga ggaacagttc aacagcacct accgggtggt gtccgtgctg     720
acagtgctgc accaggactg gctgaacggc aaagagtaca gtgcaaggt gtccaacaag     780
ggcctgccca gctccatcga aaaaccatc agcaaggcca agggcagcc ccgcgaaccc     840
caggtgtaca cactgcctcc aagccaggaa gagatgacca gaaccaggt gtccctgacc     900
tgtctcgtga aggcttcta cccctccgat atcgccgtgg aatgggagag caacggccag     960
cccgagaaca actacaagac cacccccct gtgctggaca cgacggctc attcttcctg    1020
tacagcagac tgaccgtgga caagagccgg tggcaggaag gcaacgtgtt cagctgcagc    1080
gtgatgcacg aggccctgca caaccactac acccagaagt ccctgtctct gtccctgggc    1140
aaa                                                                  1143
```

<210> SEQ ID NO 69
<211> LENGTH: 1143
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 69

```
acccaggact gttccttcca gcactcccct atctccagcg acttcgccgt gaagatcaga      60
gagctgtccg actatctgct gcaggactac cctgtgaccg tggccagcaa tctgcaggac     120
gaagaactgt gtggtggcct gtggcgactg gtgttggctc agagatggat ggaacggctg     180
aaaaccgtgg ccggctctaa gatgcagggc ctgctggaaa gagtgaacac cgagatccac     240
ttcgtgacca agtgcgcctt tcagcctcct ccatcctgcc tgagattcgt gcagaccaac     300
atctcccggc tgctgcaaga gacatccgag cagctggtgg ctctgaagcc tggatcacc     360
cggcagaact ctctcggtg tctgaactg cagtgtcagc ctgatgctgc cgctttgcct     420
ccaccttgga gccctagacc tctggaagct accgccgagt ctaagtacgg acctccttgt     480
cctccatgtc ctgctccaga agctgctggc ggcccttccg tgtttctgtt ccctccaaag     540
cccaaggaca ccctgtacat cacccgggaa cccgaagtga cctgcgtggt ggtggatgtg     600
tcccaggaag atcccgaggt gcagttcaat tggtacgtgg acggcgtgga agtgcacaac     660
```

| | |
|---|---|
| gccaagacca agcccagaga ggaacagttc aacagcacct accgggtggt gtccgtgctg | 720 |
| acagtgctgc accaggactg gctgaacggc aaagagtaca agtgcaaggt gtccaacaag | 780 |
| ggcctgccca gctccatcga aaaaccatc agcaaggcca agggccagcc ccgcgaaccc | 840 |
| caggtgtaca cactgcctcc aagccaggaa gagatgacca agaaccaggt gtccctgacc | 900 |
| tgtctcgtga aaggcttcta ccccctccgat atcgccgtgg aatgggagag caacggccag | 960 |
| cccgagaaca actacaagac cacccccct gtgctggaca gcgacggctc attcttcctg | 1020 |
| tacagcagac tgaccgtgga caagagccgg tggcaggaag gcaacgtgtt cagctgcagc | 1080 |
| gtgatgcacg aggccctgca caaccactac acccagaagt ccctgtctct gtccctgggc | 1140 |
| aaa | 1143 |

<210> SEQ ID NO 70
<211> LENGTH: 1143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

| | |
|---|---|
| acccaggact gttccttcca gcactcccct atctccagcg acttcgccgt gaagatcaga | 60 |
| gagctgtccg actatctgct gcaggactac cctgtgaccg tggccagcaa tctgcaggac | 120 |
| gaagaactgt gtggtggcct gtggcgactg tgttggctc agagatggat ggaacggctg | 180 |
| aaaaccgtgg ccggctctaa gatgcagggc ctgctggaaa gagtgaacac cgagatccac | 240 |
| ttcgtgacca agtgcgcctt tcagcctcct ccatcctgcc tgagattcgt gcagaccaac | 300 |
| atctcccggc tgctgcaaga gacatccgag cagctggtgg ctctgaagcc ctggatcacc | 360 |
| cggcagaact tctctcggtg tctggaactg cagtgtcagc ctgatgctgc cgctttgcct | 420 |
| cctccttggg ctcctcgacc tctggaagct acagccgagg ctaagtatgg ccctccttgt | 480 |
| cctccatgtc ctgctccaga agctgctggc ggccctttccg tgtttctgtt ccctccaaag | 540 |
| cccaaggaca cctgtacat cacccgggaa cccgaagtga cctgcgtggt ggtggatgtg | 600 |
| tcccaggaag atcccgaggt gcagttcaat tggtacgtgg acggcgtgga agtgcacaac | 660 |
| gccaagacca agcccagaga ggaacagttc aacagcacct accgggtggt gtccgtgctg | 720 |
| acagtgctgc accaggactg gctgaacggc aaagagtaca agtgcaaggt gtccaacaag | 780 |
| ggcctgccca gctccatcga aaaaccatc agcaaggcca agggccagcc ccgcgaaccc | 840 |
| caggtgtaca cactgcctcc aagccaggaa gagatgacca agaaccaggt gtccctgacc | 900 |
| tgtctcgtga aaggcttcta ccccctccgat atcgccgtgg aatgggagag caacggccag | 960 |
| cccgagaaca actacaagac cacccccct gtgctggaca gcgacggctc attcttcctg | 1020 |
| tacagcagac tgaccgtgga caagagccgg tggcaggaag gcaacgtgtt cagctgcagc | 1080 |
| gtgatgcacg aggccctgca caaccactac acccagaagt ccctgtctct gtccctgggc | 1140 |
| aaa | 1143 |

<210> SEQ ID NO 71
<211> LENGTH: 147
<212> TYPE: PRT
<213> ORGANISM: Homo sapiens

<400> SEQUENCE: 71

Thr Gln Asp Cys Ser Phe Gln His Ser Pro Ile Ser Ser Asp Phe Ala

-continued

```
                1               5                  10                  15
Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
                35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

Glu Leu Gln Cys Gln Pro Asp Ser Ser Thr Leu Pro Pro Pro Trp Ser
                130                 135                 140

Pro Arg Pro
145

<210> SEQ ID NO 72
<211> LENGTH: 148
<212> TYPE: PRT
<213> ORGANISM: Homo sapiens

<400> SEQUENCE: 72

Thr Gln Asp Cys Ser Phe Gln His Ser Pro Ile Ser Ser Asp Phe Ala
1               5                  10                  15

Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
                35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

Glu Leu Gln Cys Gln Pro Asp Ser Ser Thr Leu Pro Pro Pro Trp Ser
                130                 135                 140

Pro Arg Pro Leu
145

<210> SEQ ID NO 73
<211> LENGTH: 149
<212> TYPE: PRT
<213> ORGANISM: Homo sapiens

<400> SEQUENCE: 73

Thr Gln Asp Cys Ser Phe Gln His Ser Pro Ile Ser Ser Asp Phe Ala
1               5                  10                  15

Val Lys Ile Arg Glu Leu Ser Asp Tyr Leu Leu Gln Asp Tyr Pro Val
```

```
                    20                  25                  30

Thr Val Ala Ser Asn Leu Gln Asp Glu Glu Leu Cys Gly Gly Leu Trp
                35                  40                  45

Arg Leu Val Leu Ala Gln Arg Trp Met Glu Arg Leu Lys Thr Val Ala
            50                  55                  60

Gly Ser Lys Met Gln Gly Leu Leu Glu Arg Val Asn Thr Glu Ile His
 65                 70                  75                  80

Phe Val Thr Lys Cys Ala Phe Gln Pro Pro Ser Cys Leu Arg Phe
                    85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

Glu Leu Gln Cys Gln Pro Asp Ser Ser Thr Leu Pro Pro Pro Trp Ser
                130                 135                 140

Pro Arg Pro Leu Glu
145

<210> SEQ ID NO 74
<211> LENGTH: 150
<212> TYPE: PRT
<213> ORGANISM: Homo sapiens

<400> SEQUENCE: 74

Thr Gln Asp Cys Ser Phe Gln His Ser Pro Ile Ser Ser Asp Phe Ala
 1               5                  10                  15

Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
                35                  40                  45

Arg Leu Val Leu Ala Gln Arg Trp Met Glu Arg Leu Lys Thr Val Ala
            50                  55                  60

Gly Ser Lys Met Gln Gly Leu Leu Glu Arg Val Asn Thr Glu Ile His
 65                 70                  75                  80

Phe Val Thr Lys Cys Ala Phe Gln Pro Pro Ser Cys Leu Arg Phe
                    85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

Glu Leu Gln Cys Gln Pro Asp Ser Ser Thr Leu Pro Pro Pro Trp Ser
                130                 135                 140

Pro Arg Pro Leu Glu Ala
145                 150

<210> SEQ ID NO 75
<211> LENGTH: 151
<212> TYPE: PRT
<213> ORGANISM: Homo sapiens

<400> SEQUENCE: 75

Thr Gln Asp Cys Ser Phe Gln His Ser Pro Ile Ser Ser Asp Phe Ala
 1               5                  10                  15

Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
```

```
                35                  40                  45
Arg Leu Val Leu Ala Gln Arg Trp Met Glu Arg Leu Lys Thr Val Ala
 50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                 85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

Glu Leu Gln Cys Gln Pro Asp Ser Ser Thr Leu Pro Pro Pro Trp Ser
            130                 135                 140

Pro Arg Pro Leu Glu Ala Thr
145                 150

<210> SEQ ID NO 76
<211> LENGTH: 152
<212> TYPE: PRT
<213> ORGANISM: Homo sapiens

<400> SEQUENCE: 76

Thr Gln Asp Cys Ser Phe Gln His Ser Pro Ile Ser Ser Asp Phe Ala
  1               5                  10                  15

Val Lys Ile Arg Glu Leu Ser Asp Tyr Leu Leu Gln Asp Tyr Pro Val
                 20                  25                  30

Thr Val Ala Ser Asn Leu Gln Asp Glu Glu Leu Cys Gly Gly Leu Trp
             35                  40                  45

Arg Leu Val Leu Ala Gln Arg Trp Met Glu Arg Leu Lys Thr Val Ala
 50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                 85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

Glu Leu Gln Cys Gln Pro Asp Ser Ser Thr Leu Pro Pro Pro Trp Ser
            130                 135                 140

Pro Arg Pro Leu Glu Ala Thr Ala
145                 150

<210> SEQ ID NO 77
<211> LENGTH: 153
<212> TYPE: PRT
<213> ORGANISM: Homo sapiens

<400> SEQUENCE: 77

Thr Gln Asp Cys Ser Phe Gln His Ser Pro Ile Ser Ser Asp Phe Ala
  1               5                  10                  15

Val Lys Ile Arg Glu Leu Ser Asp Tyr Leu Leu Gln Asp Tyr Pro Val
                 20                  25                  30

Thr Val Ala Ser Asn Leu Gln Asp Glu Glu Leu Cys Gly Gly Leu Trp
             35                  40                  45

Arg Leu Val Leu Ala Gln Arg Trp Met Glu Arg Leu Lys Thr Val Ala
```

```
                 50                  55                  60
Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                     85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Pro Trp Ser
       130                  135                 140

Pro Arg Pro Leu Glu Ala Thr Ala Pro
145                 150

<210> SEQ ID NO 78
<211> LENGTH: 154
<212> TYPE: PRT
<213> ORGANISM: Homo sapiens

<400> SEQUENCE: 78

Thr Gln Asp Cys Ser Phe Gln His Ser Pro Ile Ser Ser Asp Phe Ala
  1               5                  10                  15

Val Lys Ile Arg Glu Leu Ser Asp Tyr Leu Leu Gln Asp Tyr Pro Val
                 20                  25                  30

Thr Val Ala Ser Asn Leu Gln Asp Glu Glu Leu Cys Gly Gly Leu Trp
             35                  40                  45

Arg Leu Val Leu Ala Gln Arg Trp Met Glu Arg Leu Lys Thr Val Ala
 50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                     85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Pro Trp Ser
       130                  135                 140

Pro Arg Pro Leu Glu Ala Thr Ala Pro Thr
145                 150

<210> SEQ ID NO 79
<211> LENGTH: 155
<212> TYPE: PRT
<213> ORGANISM: Homo sapiens

<400> SEQUENCE: 79

Thr Gln Asp Cys Ser Phe Gln His Ser Pro Ile Ser Ser Asp Phe Ala
  1               5                  10                  15

Val Lys Ile Arg Glu Leu Ser Asp Tyr Leu Leu Gln Asp Tyr Pro Val
                 20                  25                  30

Thr Val Ala Ser Asn Leu Gln Asp Glu Glu Leu Cys Gly Gly Leu Trp
             35                  40                  45

Arg Leu Val Leu Ala Gln Arg Trp Met Glu Arg Leu Lys Thr Val Ala
 50                  55                  60

Gly Ser Lys Met Gln Gly Leu Leu Glu Arg Val Asn Thr Glu Ile His
```

```
                65                  70                  75                  80
Phe Val Thr Lys Cys Ala Phe Gln Pro Pro Ser Cys Leu Arg Phe
                    85                  90                  95
Val Gln Thr Asn Ile Ser Arg Leu Leu Gln Glu Thr Ser Glu Gln Leu
                100                 105                 110
Val Ala Leu Lys Pro Trp Ile Thr Arg Gln Asn Phe Ser Arg Cys Leu
                115                 120                 125
Glu Leu Gln Cys Gln Pro Asp Ser Ser Thr Leu Pro Pro Pro Trp Ser
            130                 135                 140
Pro Arg Pro Leu Glu Ala Thr Ala Pro Thr Ala
145                 150                 155

<210> SEQ ID NO 80
<211> LENGTH: 156
<212> TYPE: PRT
<213> ORGANISM: Homo sapiens

<400> SEQUENCE: 80

Thr Gln Asp Cys Ser Phe Gln His Ser Pro Ile Ser Ser Asp Phe Ala
1               5                   10                  15
Val Lys Ile Arg Glu Leu Ser Asp Tyr Leu Leu Gln Asp Tyr Pro Val
                20                  25                  30
Thr Val Ala Ser Asn Leu Gln Asp Glu Glu Leu Cys Gly Gly Leu Trp
            35                  40                  45
Arg Leu Val Leu Ala Gln Arg Trp Met Glu Arg Leu Lys Thr Val Ala
        50                  55                  60
Gly Ser Lys Met Gln Gly Leu Leu Glu Arg Val Asn Thr Glu Ile His
65                  70                  75                  80
Phe Val Thr Lys Cys Ala Phe Gln Pro Pro Ser Cys Leu Arg Phe
                    85                  90                  95
Val Gln Thr Asn Ile Ser Arg Leu Leu Gln Glu Thr Ser Glu Gln Leu
                100                 105                 110
Val Ala Leu Lys Pro Trp Ile Thr Arg Gln Asn Phe Ser Arg Cys Leu
                115                 120                 125
Glu Leu Gln Cys Gln Pro Asp Ser Ser Thr Leu Pro Pro Pro Trp Ser
            130                 135                 140
Pro Arg Pro Leu Glu Ala Thr Ala Pro Thr Ala Pro
145                 150                 155

<210> SEQ ID NO 81
<211> LENGTH: 157
<212> TYPE: PRT
<213> ORGANISM: Homo sapiens

<400> SEQUENCE: 81

Thr Gln Asp Cys Ser Phe Gln His Ser Pro Ile Ser Ser Asp Phe Ala
1               5                   10                  15
Val Lys Ile Arg Glu Leu Ser Asp Tyr Leu Leu Gln Asp Tyr Pro Val
                20                  25                  30
Thr Val Ala Ser Asn Leu Gln Asp Glu Glu Leu Cys Gly Gly Leu Trp
            35                  40                  45
Arg Leu Val Leu Ala Gln Arg Trp Met Glu Arg Leu Lys Thr Val Ala
        50                  55                  60
Gly Ser Lys Met Gln Gly Leu Leu Glu Arg Val Asn Thr Glu Ile His
65                  70                  75                  80
Phe Val Thr Lys Cys Ala Phe Gln Pro Pro Ser Cys Leu Arg Phe
```

```
                    85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln
145                 150                 155

<210> SEQ ID NO 82
<211> LENGTH: 17
<212> TYPE: PRT
<213> ORGANISM: Unknown
<220> FEATURE:
<223> OTHER INFORMATION: Description of Unknown:
      Serum albumin signal peptide

<400> SEQUENCE: 82

Lys Trp Val Thr Phe Ile Ser Leu Leu Phe Leu Phe Ser Ser Ala Tyr
1               5                   10                  15

Ser

<210> SEQ ID NO 83
<211> LENGTH: 26
<212> TYPE: PRT
<213> ORGANISM: Unknown
<220> FEATURE:
<223> OTHER INFORMATION: Description of Unknown:
      FLT3L signal peptide

<400> SEQUENCE: 83

Met Thr Val Leu Ala Pro Ala Trp Ser Pro Thr Thr Tyr Leu Leu Leu
1               5                   10                  15

Leu Leu Leu Leu Ser Ser Gly Leu Ser Gly
            20                  25

<210> SEQ ID NO 84
<211> LENGTH: 27
<212> TYPE: PRT
<213> ORGANISM: Unknown
<220> FEATURE:
<223> OTHER INFORMATION: Description of Unknown:
      FLT3L signal peptide

<400> SEQUENCE: 84

Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly
            20                  25

<210> SEQ ID NO 85
<211> LENGTH: 5
<212> TYPE: PRT
<213> ORGANISM: Homo sapiens

<400> SEQUENCE: 85

Pro Thr Ala Pro Gln
1               5

<210> SEQ ID NO 86
<211> LENGTH: 6
<212> TYPE: PRT
```

```
<213> ORGANISM: Homo sapiens

<400> SEQUENCE: 86

Ala Pro Thr Ala Pro Gln
1               5

<210> SEQ ID NO 87
<211> LENGTH: 7
<212> TYPE: PRT
<213> ORGANISM: Homo sapiens

<400> SEQUENCE: 87

Thr Ala Pro Thr Ala Pro Gln
1               5

<210> SEQ ID NO 88
<211> LENGTH: 8
<212> TYPE: PRT
<213> ORGANISM: Homo sapiens

<400> SEQUENCE: 88

Ala Thr Ala Pro Thr Ala Pro Gln
1               5

<210> SEQ ID NO 89
<211> LENGTH: 9
<212> TYPE: PRT
<213> ORGANISM: Homo sapiens

<400> SEQUENCE: 89

Glu Ala Thr Ala Pro Thr Ala Pro Gln
1               5

<210> SEQ ID NO 90
<211> LENGTH: 10
<212> TYPE: PRT
<213> ORGANISM: Homo sapiens

<400> SEQUENCE: 90

Leu Glu Ala Thr Ala Pro Thr Ala Pro Gln
1               5                   10

<210> SEQ ID NO 91
<211> LENGTH: 7
<212> TYPE: PRT
<213> ORGANISM: Homo sapiens

<400> SEQUENCE: 91

Pro Thr Ala Pro Gln Pro Pro
1               5

<210> SEQ ID NO 92
<211> LENGTH: 8
<212> TYPE: PRT
<213> ORGANISM: Homo sapiens

<400> SEQUENCE: 92

Ala Pro Thr Ala Pro Gln Pro Pro
1               5

<210> SEQ ID NO 93
<211> LENGTH: 9
<212> TYPE: PRT
<213> ORGANISM: Homo sapiens
```

```
<400> SEQUENCE: 93

Thr Ala Pro Thr Ala Pro Gln Pro Pro
1               5

<210> SEQ ID NO 94
<211> LENGTH: 10
<212> TYPE: PRT
<213> ORGANISM: Homo sapiens

<400> SEQUENCE: 94

Ala Thr Ala Pro Thr Ala Pro Gln Pro Pro
1               5                   10

<210> SEQ ID NO 95
<211> LENGTH: 11
<212> TYPE: PRT
<213> ORGANISM: Homo sapiens

<400> SEQUENCE: 95

Glu Ala Thr Ala Pro Thr Ala Pro Gln Pro Pro
1               5                   10

<210> SEQ ID NO 96
<211> LENGTH: 12
<212> TYPE: PRT
<213> ORGANISM: Homo sapiens

<400> SEQUENCE: 96

Leu Glu Ala Thr Ala Pro Thr Ala Pro Gln Pro Pro
1               5                   10

<210> SEQ ID NO 97
<211> LENGTH: 5
<212> TYPE: PRT
<213> ORGANISM: Homo sapiens

<400> SEQUENCE: 97

Glu Ser Lys Tyr Gly
1               5

<210> SEQ ID NO 98
<211> LENGTH: 159
<212> TYPE: PRT
<213> ORGANISM: Mus musculus

<400> SEQUENCE: 98

Thr Pro Asp Cys Tyr Phe Ser His Ser Pro Ile Ser Ser Asn Phe Lys
1               5                   10                  15

Val Lys Phe Arg Glu Leu Thr Asp His Leu Leu Lys Asp Tyr Pro Val
            20                  25                  30

Thr Val Ala Val Asn Leu Gln Asp Glu Lys His Cys Lys Ala Leu Trp
        35                  40                  45

Ser Leu Phe Leu Ala Gln Arg Trp Ile Glu Gln Leu Lys Thr Val Ala
    50                  55                  60

Gly Ser Lys Met Gln Thr Leu Leu Glu Asp Val Asn Thr Glu Ile His
65                  70                  75                  80

Phe Val Thr Ser Cys Thr Phe Gln Pro Leu Pro Glu Cys Leu Arg Phe
                85                  90                  95

Val Gln Thr Asn Ile Ser His Leu Leu Lys Asp Thr Cys Thr Gln Leu
            100                 105                 110

Leu Ala Leu Lys Pro Cys Ile Gly Lys Ala Cys Gln Asn Phe Ser Arg
```

```
                    115                 120                 125
Cys Leu Glu Val Gln Cys Gln Pro Asp Ser Ser Thr Leu Leu Pro Pro
    130                 135                 140

Arg Ser Pro Ile Ala Leu Glu Ala Thr Glu Leu Pro Glu Pro Arg
145                 150                 155

<210> SEQ ID NO 99
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 3-4 "Gly Gly Gly
      Gly Ser" repeating units

<400> SEQUENCE: 99

Gly Gly Gly Gly Ser Gly Gly Gly Gly Ser Gly Gly Gly Gly Ser Gly
1               5                   10                  15

Gly Gly Gly Ser
            20

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Glu Ser Lys Tyr Gly Pro Pro Cys Pro Pro Cys Pro
1               5                   10

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Glu Pro Lys Ser Cys Asp Lys Thr His Thr Cys Pro Pro Cys Pro
1               5                   10                  15

<210> SEQ ID NO 102
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
```

```
                50                  55                  60
Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 103
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Gly Pro Ser Val Phe Leu Phe Pro Pro Lys Pro Lys Asp Thr Leu
 1               5                  10                  15

Met Ile Ser Arg Thr Pro Glu Val Thr Cys Val Val Val Asp Val Ser
             20                  25                  30

His Glu Asp Pro Glu Val Lys Phe Asn Trp Tyr Val Asp Gly Val Glu
         35                  40                  45

Val His Asn Ala Lys Thr Lys Pro Arg Glu Glu Gln Tyr Asn Ser Thr
     50                  55                  60

Tyr Arg Val Val Ser Val Leu Thr Val Leu His Gln Asp Trp Leu Asn
 65                  70                  75                  80

Gly Lys Glu Tyr Lys Cys Lys Val Ser Asn Lys Ala Leu Pro Ala Pro
                 85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175
```

```
Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

Ser Pro Gly Lys
    210

<210> SEQ ID NO 104
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gly Gly Pro Ser Val Phe Leu Phe Pro Pro Lys Pro Lys Asp Thr Leu
1               5                   10                  15

Tyr Ile Thr Arg Glu Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

Ser Pro Gly Lys
    210

<210> SEQ ID NO 105
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30
```

```
Leu Met Ile Ser Arg Thr Pro Glu Val Thr Cys Val Val Asp Val
         35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 106
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Ser Lys Tyr Gly Pro Pro Cys Pro Pro Cys Pro Ala Pro Glu Ala
 1               5                  10                  15

Ala Gly Gly Pro Ser Val Phe Leu Phe Pro Pro Lys Pro Lys Asp Thr
             20                  25                  30

Leu Met Ile Ser Arg Thr Pro Glu Val Thr Cys Val Val Val Asp Val
         35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160
```

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Lys
225

<210> SEQ ID NO 107
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Tyr Ile Thr Arg Glu Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Lys
225

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic

```
                peptide

<400> SEQUENCE: 108

Arg Arg Cys Pro Leu Tyr Ile Ser Tyr Asp Pro Val Cys Arg Arg
1               5                   10                  15

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Arg Arg Arg Cys Pro Leu Tyr Ile Ser Tyr Asp Pro Val Cys Arg
1               5                   10                  15

Arg Arg Arg

<210> SEQ ID NO 110
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Glu Pro Lys Ser Cys Asp Lys Thr His Thr Cys Pro Pro Cys Pro Ala
1               5                   10                  15

Pro Glu Leu Leu
            20
```

US 11,124,582 B2

FLT3L-FC FUSION PROTEINS

CROSS-REFERENCE TO RELATED APPLICATIONS

This is a continuation application of U.S. patent application Ser. No. 16/909,521, filed Jun. 23, 2020, which application claims the benefit under 35 U.S.C. § 119(e) of U.S. provisional application No. 62/866,584, filed Jun. 25, 2019, each of which is hereby incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on May 27, 2020, is named 1290_PC_SL.txt and is 195,679 bytes in size.

BACKGROUND

Dendritic cells (DCs) are the most potent antigen-presenting cell in the body. DCs function to process antigen material and present it on the cell surface to the T cells. DCs act as messengers between the innate and the adaptive immune systems. Fms related tyrosine kinase 3 ligand (FLT3LG, FLT3L, NCBI Gene ID: 2323) selectively expands DCs from bone marrow precursors, as well as promotes proliferation of terminally differentiated DCs in lymphoid and tumor tissues.

Soluble recombinant human protein forms of FLT3L have a serum half-life in humans of about 12-28 hours after five consecutive subcutaneous (SC) doses, requiring daily administration to the patient over a 28-day therapeutic cycle. Daily administration is undesirable, for both the patient and clinician, and is dose scheduling that does not align with other approved immune-oncology therapeutic agents, which is usually once every 2 to 3 weeks. Longer acting antiviral therapeutic agents are also considered desirable.

SUMMARY

Provided are FLT3L-Fc fusion proteins that have an extended serum half-life in a human subject, relative to soluble FLT3L.

Accordingly, in one aspect, provided are fusion proteins comprising: a human fms related tyrosine kinase 3 ligand (FLT3L) extracellular domain operably linked to an immunoglobulin fragment crystallizable region (Fc region), wherein: at least 5 amino acids are truncated from the C-terminus of the FLT3L extracellular domain; and/or the Fc region does not comprise a hinge region. In some embodiments, the FLT3L extracellular domain is derived from a human FLT3L extracellular domain. In some embodiments, the FLT3L extracellular domain is a human FLT3L extracellular domain. In some embodiments, the fusion protein is capable of binding to human FLT3. In some embodiments, the FLT3L extracellular domain is from FLT3L isoform 1 or from FLT3L isoform 2. In some embodiments, at least 6, 7, 8, 9, 10, 11, 12, 13, 14 or 15 amino acids are truncated from the C-terminus of the FLT3L extracellular domain. In some embodiments, the FLT3L extracellular domain does not comprise (e.g., is deleted, removed or excluded) the amino acid sequence PTAPQ (SEQ ID NO:85), APTAPQ (SEQ ID NO:86), TAPTAPQ (SEQ ID NO:87), ATAPTAPQ (SEQ ID NO:88), EATAPTAPQ (SEQ ID NO:89), or LEATAPTAPQ (SEQ ID NO:90), PTAPQPP (SEQ ID NO:91), APTAPQPP (SEQ ID NO:92), TAPTAPQPP (SEQ ID NO:93), ATAPTAPQPP (SEQ ID NO:94), EATAPTAPQPP (SEQ ID NO:95), or LEATAPTAPQPP (SEQ ID NO:96). In some embodiments, the FLT3L extracellular domain comprises an N-terminal signal peptide. In some embodiments, the FLT3L extracellular domain comprises one or more of the following amino acid substitutions: H8Y; K84E; S102A; and/or S125A; wherein the amino acid residue positions are with reference to SEQ ID NOs: 1-18, 21-27 or 71-81. In some embodiments, one or both of serine residues at positions 102 and 125 are substituted to alanine, wherein the amino acid residue positions are with reference to SEQ ID NOs: 1-18, 21-27 or 71-81. In some embodiments, the Fc region is from a human IgG1, IgG2, IgG3 or IgG4. In some embodiments, the Fc region is from a human IgG1 or IgG4. In some embodiments, the Fc region comprises a human IgG1 isotype and comprises one or more amino acid substitutions in the Fc region at a residue position selected from the group consisting of: N297A, N297G, N297Q, N297G, D265A, L234A, L235A, C226S, C229S, P238S, E233P, L234V, P238A, A327Q, A327G, P329A, P329G, K322A, L234F, L235E, P331S, T394D, A330L, M252Y, S254T, T256E, M428L, N434S, T366W, T366S, L368A, Y407V, and any combination thereof, wherein the numbering of the residues is according to EU numbering. In some embodiments, the Fc region comprises a human IgG1 isotype and comprises one or more amino acid substitutions in the Fc region at a residue position selected from the group consisting of: L234A, L234V, L234F, L235A, L235E, P331S, and any combination thereof, wherein the numbering of the residues is according to EU numbering. In some embodiments, the Fc region comprises a human IgG4 isotype and comprises one or more amino acid substitutions in the Fc region at a residue position selected from the group consisting of: E233P, F234V, F234A, L235A, G237A, E318A, S228P, L235E, T394D, M252Y, S254T, T256E, N297A, N297G, N297Q, T366W, T366S, L368A, Y407V, M428L, N434S, and any combination thereof, wherein the numbering of the residues is according to EU numbering. In some embodiments, the Fc region comprises a human IgG4 isotype and comprises one or more amino acid substitutions in the Fc region at a residue position selected from the group consisting of: F234V, F234A, L235A, L235E, S228P, and any combination thereof, wherein the numbering of the residues is according to EU numbering. In some embodiments, the Fc region comprises the following amino acids at the indicated positions (EU index numbering): (i) Tyrosine at position 252, threonine at position 254 and glutamic acid at position 256 (YTE); or (ii) Leucine at position 428 and serine at position 434 (LS). In some embodiments, the FLT3L extracellular domain comprises an amino acid sequence that is at least 80%, at least 85%, at least 90%, at least 91%, at least 92%, at least 93%, at least 94%, at least 95%, at least 96%, at least 97%, at least 98%, at least 99%, or 100%, identical to an amino acid sequence selected from the group consisting of SEQ ID NOs: 71-81. In some embodiments, the Fc region comprises an amino acid sequence that is at least 80%, at least 85%, at least 90%, at least 91%, at least 92%, at least 93%, at least 94%, at least 95%, at least 96%, at least 97%, at least 98%, at least 99%, or 100%, identical to an amino acid sequence selected from the group consisting of SEQ ID NOs: 103-107. In some embodiments, the fusion protein comprises an amino acid sequence that is at least 80%, at least 85%, at least 90%, at least 91%, at least 92%, at least 93%, at least 94%, at least 95%, at least 96%, at least 97%, at least 98%, at least 99%, or 100%, identical to an amino acid sequence selected from the group consisting of SEQ ID NOs: 1-18 and 21-27. In some embodiments, the Fc region is from a human IgG1 and does not comprise a hinge region. In some embodiments, the C-terminus of the FLT3L extracellular domain is not truncated. In some embodiments, the fusion protein comprises or consists of an amino acid sequence of SEQ ID NO:1. In some embodiments, the fusion protein comprises or consists of an amino acid sequence of SEQ ID NO:9. In some embodiments, the fusion protein comprises or consists of an amino acid sequence selected from the group consisting of SEQ ID NOs: 1, 2, 5, 7, 9, 10, 13, 15, 22, 23 and 24, or comprises or consists of an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 1, 2, 5, 7, 9, 10, 13, 15, 22, 23 and 24, wherein the Fc region is derived from a human IgG1 isotype and does not comprise a hinge region, e.g., does not the amino acid sequence EPKSCDKTHTCPPCP (SEQ ID NO:101) or EPKSCDKTHTCPPCPAPELL (SEQ ID NO:110). In some embodiments, the Fc region is from a human IgG4 and at least 5 amino acids are truncated from the C-terminus of the FLT3L extracellular domain. In some embodiments, the Fc region comprises a hinge region. In some embodiments, the fusion protein comprises or consists of an amino acid sequence of SEQ ID NO:6. In some embodiments, the fusion protein comprises or consists of an amino acid sequence of SEQ ID NO:14. In some embodiments, the fusion protein comprises or consists of an amino acid sequence selected from the group consisting of SEQ ID NOs: 3, 4, 6, 8, 11, 12, 14, 16, 17, 18, 25 and 26, or comprises or consists of an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 3, 4, 6, 8, 11, 12, 14, 16, 17, 18, 25 and 26, wherein the Fc region is derived from a human IgG4 isotype and wherein at least 5 amino acids are truncated from the C-terminus of the FLT3L extracellular domain, e.g., wherein the FLT3L extracellular domain does not comprise the amino acid sequence PTAPQ (SEQ ID NO:85).

In a further aspect, provided is a fusion protein comprising an amino acid sequence that is at least 80%, at least 85%, at least 90%, at least 91%, at least 92%, at least 93%, at least 94%, at least 95%, at least 96%, at least 97%, at least 98%, at least 99%, or 100%, identical to an amino acid sequence selected from the group consisting of SEQ ID NOs: 19-20.

In a further aspect, provided are fusion proteins comprising: (i) a FLT3L-Fc fusion protein comprising an amino acid sequence that is at least 80%, at least 85%, at least 90%, at least 91%, at least 92%, at least 93%, at least 94%, at least 95%, at least 96%, at least 97%, at least 98%, at least 99%, or 100%, identical to an amino acid sequence selected from the group consisting of SEQ ID NOs: 1-27; and (ii) a second polypeptide. In some embodiments, the second polypeptide comprises a targeting moiety or domain, a growth factor, a cytokine, a chemokine or a TNF superfamily (TNFSF) member. In some embodiments, the second polypeptide is N-terminal to the FLT3L extracellular domain. In some embodiments, the second polypeptide is C-terminal to the Fc region. In some embodiments, the second polypeptide is between the FLT3L extracellular domain and the Fc region. In some embodiments, the targeting moiety domain binds to a target protein or antigen identified in Table B, below, such as without limitation CD19, MS4A1 (CD20), CD22, IL2RA (CD25), CD27, TNFRSF8 (CD30), CD33, CD37, CD38, CD40, CD44, CD48, CD52, CD70, NT5E (CD73), ENTPD1 (CD39), CD74, CD79b, CD80, CD86, IL3RA (CD123), PROM1 (CD133), CD137, SDC1 (CD138), alpha fetoprotein (AFP); c-Met; c-Kit; C-type lectin domain family 12 member A (CLEC12A, CLL1, CD371); C-type lectin domain containing 9A (CLEC9A, CD370); cadherin 3 (CDH3, p-cadherin, PCAD); carbonic anhydrase 6 (CA6); carbonic anhydrase 9 (CA9, CAIX); carcinoembryonic antigen related cell adhesion molecule 3 (CEACAM3); carcinoembryonic antigen related cell adhesion molecule 5 (CEACAM5); carcinoembryonic antigen related cell adhesion molecule 6 (CEACAM6, CD66c); chorionic somatomammotropin hormone 1 (CSH1, CS1); coagulation factor III, tissue factor (F3, TF); collectin subfamily member 10 (COLEC10); delta like canonical Notch ligand 3 (DLL3); ectonucleotide pyrophosphatase/phosphodiesterase 3 (ENPP3); ephrin A1 (EFNA1); epidermal growth factor receptor (EGFR); EGFR variant III (EGFRvIII); EPH receptor A2 (EPHA2); epithelial cell adhesion molecule (EP-CAM); erb-b2 receptor tyrosine kinase 2 (ERBB2; HER2); fibroblast activation protein alpha (FAP); fibroblast growth factor receptor 2 (FGFR2); fibroblast growth factor receptor 3 (FGFR3); folate hydrolase 1 (FOLH1, PSMA); folate receptor 1 (FOLR1, FRα); GD2 ganglioside; glycoprotein NMB (GPNMB, osteoactivin); guanylate cyclase 2C (GUCY2C, GCC); human papillomavirus (HPV) E6; HPV E7; major histocompatibility complex (MHC) class I-presented neoantigens; major histocompatibility complex (MHC) class II-presented neoantigens; major histocompatibility complex, class I, E (HLA-E); major histocompatibility complex, class I, F (HLA-F); major histocompatibility complex, class I, G (HLA-G, MHC-G); integrin subunit beta 7 (ITGB7); leukocyte immunoglobulin like receptor B1 (LILRB1, ILT2); leukocyte immunoglobulin like receptor B2 (LILRB2, ILT4); LY6/PLAUR domain containing 3 (LYPD3, C4.4A); glypican 3 (GPC3); KRAS proto-oncogene, GTPase (KRAS); MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member D1 (MAGED1); MAGE family member D2 (MAGED2); mesothelin (MSLN); mucin 1 (MUC1) and splice variants thereof (e.g., MUC1/C, D, and Z); mucin 16 (MUC16); necdin (NDN); nectin cell adhesion molecule 4 (NECTIN4); SLIT and NTRK like family member 6 (SLITRK6); promyelocytic leukemia (PML, TRIM19); protein tyrosine kinase 7 (inactive) (PTK7); SLAM family member 6 (SLAMF6, CD352); SLAM family member 7 (SLAMF7, 19A, CD319, CRACC, CS1); sialic acid binding Ig like lectin 7 (SIGLEC7); sialic acid binding Ig like lectin 9 (SIGLEC9); solute carrier family 34 (sodium phosphate), member 2 (SLC34A2); solute carrier family 39 member 6 (SLC39A6; LIV1); STEAP family member 1 (STEAP1); TNF receptor superfamily member 4 (TNFRSF4, OX40 or CD134); TNF superfamily member 9 (TNFSF9; 4-1BB-L, CD137L); TNF receptor superfamily member 10a (TNFRSF10A, DR4, CD261, TRAILR1); TNF receptor superfamily member 10b (TNFRSF10B, DR5, CD262, TRAILR2); TNF receptor superfamily member 13B (TNFRSF13B; CD267, TACI, IGAD2); TNF receptor superfamily member 17 (TNFRSF17, BCMA, CD269); TNF receptor superfamily member 18 (TNFRSF18, GITR or CD357); transferrin (TF); transforming growth factor beta 1 (TGFB1); trophoblast glycoprotein (TPBG, 5T4); trophinin (TRO, MAGED3); tumor associated calcium signal transducer 2 (TACSTD2, TROP2, EGP1); Fucosyl GM1; sialyl Lewis adhesion molecule (sLe); and Lewis Y antigen.

In a related aspect, provided is a homodimer comprising two (i.e., first and second) identical FLT3L-Fc fusion proteins, as described above and herein. In a related aspect, provided is a heterodimer comprising two (i.e., first and second) non-identical FLT3L-Fc fusion proteins, as described above and herein. In various embodiments of such heterodimers, the FLT3L domain is the same and the Fc region is different between the first and second FLT3L-Fc fusion proteins.

In a further aspect, provided are heterodimers comprising a FLT3L-Fc fusion protein, as described above and herein, and a second fusion protein comprising a targeting moiety domain fused to a second Fc region. In some embodiments, the targeting moiety domain binds to a target protein or antigen identified in Table B, below, such as without limitation CD19, MS4A1 (CD20), CD22, IL2RA (CD25), CD27, TNFRSF8 (CD30), CD33, CD37, CD38, CD40, CD44, CD48, CD52, CD70, NT5E (CD73), ENTPD1 (CD39), CD74, CD79b, CD80, CD86, IL3RA (CD123), PROM1 (CD133), CD137, SDC1 (CD138), alpha fetoprotein (AFP), c-Met; c-Kit; C-type lectin domain family 12 member A (CLEC12A, CLL1, CD371); C-type lectin domain containing 9A (CLEC9A, CD370); cadherin 3 (CDH3, p-cadherin, PCAD); carbonic anhydrase 6 (CA6); carbonic anhydrase 9 (CA9, CAIX); carcinoembryonic antigen related cell adhesion molecule 3 (CEACAM3); carcinoembryonic antigen related cell adhesion molecule 5 (CEACAM5); carcinoembryonic antigen related cell adhesion molecule 6 (CEACAM6, CD66c); chorionic somatomammotropin hormone 1 (CSH1, CS1); coagulation factor III, tissue factor (F3, TF); collectin subfamily member 10 (COLEC10); delta like canonical Notch ligand 3 (DLL3); ectonucleotide pyrophosphatase/phosphodiesterase 3 (ENPP3); ephrin A1 (EFNA1); epidermal growth factor receptor (EGFR); EGFR variant III (EGFRvIII); EPH receptor A2 (EPHA2); epithelial cell adhesion molecule (EPCAM); erb-b2 receptor tyrosine kinase 2 (ERBB2; HER2); fibroblast activation protein alpha (FAP); fibroblast growth factor receptor 2 (FGFR2); fibroblast growth factor receptor 3 (FGFR3); folate hydrolase 1 (FOLH1, PSMA); folate receptor 1 (FOLR1, FRα); GD2 ganglioside; glycoprotein NMB (GPNMB, osteoactivin); guanylate cyclase 2C (GUCY2C, GCC); human papillomavirus (HPV) E6; HPV E7; major histocompatibility complex (WIC) class I-presented neoantigens, major histocompatibility complex (MHC) class II-presented neoantigens, major histocompatibility complex, class I, E (HLA-E); major histocompatibility complex, class I, F (HLA-F); major histocompatibility complex, class I, G (HLA-G, MHC-G); integrin subunit beta 7 (ITGB7); leukocyte immunoglobulin like receptor B1 (LILRB1, ILT2); leukocyte immunoglobulin like receptor B2 (LILRB2, ILT4); LY6/PLAUR domain containing 3 (LYPD3, C4.4A); glypican 3 (GPC3); KRAS proto-oncogene, GTPase (KRAS); MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member D1 (MAGED1); MAGE family member D2 (MAGED2); mesothelin (MSLN); mucin 1 (MUC1) and splice variants thereof (e.g., MUC1/C, D, and Z); mucin 16 (MUC16); necdin (NDN); nectin cell adhesion molecule 4 (NECTIN4); SLIT and NTRK like family member 6 (SLITRK6); promyelocytic leukemia (PML, TRIM19); protein tyrosine kinase 7 (inactive) (PTK7); SLAM family member 6 (SLAMF6, CD352); SLAM family member 7 (SLAMF7, 19A, CD319, CRACC, CS1); sialic acid binding Ig like lectin 7 (SIGLEC7); sialic acid binding Ig like lectin 9 (SIGLEC9); solute carrier family 34 (sodium phosphate), member 2 (SLC34A2); solute carrier family 39 member 6 (SLC39A6; LIV1); STEAP family member 1 (STEAP1); TNF receptor superfamily member 4 (TNFRSF4, OX40 or CD134); TNF superfamily member 9 (TNFSF9; 4-1BB-L, CD137L); TNF receptor superfamily member 10a (TNFRSF10A, DR4, CD261, TRAILR1); TNF receptor superfamily member 10b (TNFRSF10B, DR5, CD262, TRAILR2); TNF receptor superfamily member 13B (TNFRSF13B; CD267, TACT, IGAD2); TNF receptor superfamily member 17 (TNFRSF17, BCMA, CD269); TNF receptor superfamily member 18 (TNFRSF18, GITR or CD357); transferrin (TF); transforming growth factor beta 1 (TGFB1); trophoblast glycoprotein (TPBG, 5T4); trophinin (TRO, MAGED3); tumor associated calcium signal transducer 2 (TACSTD2, TROP2, EGP1); Fucosyl GM1; sialyl Lewis adhesion molecule (sLe); and Lewis Y antigen.

In some embodiments, the targeting moiety domain comprises an antigen-binding antibody fragment. In some embodiments, the antibody fragment comprises a Fab or a single-chain variable fragment (scFv). In some embodiments, the targeting moiety domain comprises a non-immunoglobulin binding moiety or an antibody mimetic protein. In some embodiments, the non-immunoglobulin antigen-binding domain or antibody mimetic protein is selected from the group consisting of adnectins, affibody molecules, affilins, affimers, affitins, alphabodies, anticalins, peptide aptamers, armadillo repeat proteins (ARMs), atrimers, avimers, designed ankyrin repeat proteins (DARPins®), fynomers, knottins, Kunitz domain peptides, monobodies, and nanoCLAMPs. In some embodiments, both the first Fc region and the second Fc region do not comprise a hinge region. In some embodiments, the heterodimer is stabilized by an interaction between the first Fc region and the second Fc region. In some embodiments, the heterodimer comprises a heterodimeric human IgG1 or human IgG4. In some embodiments, the heterodimeric human IgG1 or human IgG4 comprises a first Fc region and a second Fc region, comprising the following amino acids at the indicated positions (EU numbering): (i) the first Fc region comprises a tryptophan at position 366 (T366W); and the second Fc region comprises a serine at position 366 (T366S), an alanine at position 368 (L368A) and a valine at position 407 (Y407V); (ii) the first Fc region comprises a serine at position 366 (T366S), an alanine at position 368 (L368A) and a valine at position 407 (Y407V); and the second Fc region comprises a tryptophan at position 366 (T366W); (iii) the first Fc region comprises a cysteine at position 354 (S354C), a tryptophan at position 366 (T366W); and the second Fc region comprises a cysteine at position 349 (Y349C), a serine at position 366 (T366S), an alanine at position 368 (L368A) and a valine at position 407 (Y407V); or (iv) the first Fc region comprises cysteine at position 349 (Y349C), a serine at position 366 (T366S), an alanine at position 368 (L368A) and a valine at position 407 (Y407V); and the second Fc region comprises a cysteine at position 354 (S354C), a tryptophan at position 366 (T366W).

In a further aspect, provided is a conjugate comprising: (i) a FLT3L-Fc fusion protein, as described above and herein, or a homodimer or heterodimer of such FLT3L-Fc protein; attached to a therapeutic agent or a detectable label. In some embodiments, the therapeutic agent is covalently linked. In some embodiments, the therapeutic agent is a small organic compound. In some embodiments, the therapeutic agent is an agonist or activator of a toll-like receptor (TLR) or a stimulator of interferon genes (STING) receptor. In some embodiments, the TLR agonist or activator is selected from the group consisting of a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from the group consisting of GS 9620, DS-0509, LHC-165 and TMX-101 (imiquimod), and/or wherein the TLR8 agonist is selected from the group consisting of GS-9688 and NKTR-262 (dual TLR7/TLR8 agonist). In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP. In some embodiments, the therapeutic agents is an immune checkpoint inhibitor. In some embodiments, the immune checkpoint inhibitor is a small molecule inhibitor of CD274 (PDL1, PD-L1), programmed cell death 1 (PDCD1, PD1, PD-1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 is BPI-002.

In a further aspect, provided are polynucleotides encoding a FLT3L-Fc fusion protein, as described above and herein. In some embodiments, the polynucleotide is selected from the group consisting of DNA, cDNA, RNA or mRNA. In some embodiments, the polynucleotide comprises a nucleic acid sequence that is at least 80%, at least 85%, at least 90%, at least 91%, at least 92%, at least 93%, at least 94%, at least 95%, at least 96%, at least 97%, at least 98%, at least 99%, or 100%, identical to a nucleic acid sequence selected from the group consisting of SEQ ID NOs: 28-70. Further provided are expression cassettes comprising one or more regulatory sequences operably linked to a FLT3L-Fc-encoding polynucleotide, as described herein.

In a further aspect, provided are vectors comprising a polynucleotide encoding the FLT3L-Fc fusion proteins described herein, or an expression cassette comprising such FLT3L-Fc-encoding polynucleotide. In some embodiments, the vector is a plasmid vector or a viral vector. In some embodiments, the viral vector comprises an oncolytic viral vector. In some embodiments, the viral vector comprises a DNA virus or a RNA virus. In some embodiments, the viral vector is from a viral family selected from the group consisting of: Adenoviridae (e.g., Adenovirus), Arenaviridae (e.g., lymphocytic choriomeningitis mammarenavirus, Cali mammarenavirus (a.k.a., Pichinde mammarenavirus), Poxviridae (e.g., Vaccinia virus), Herpesviridae (e.g., Herpesvirus, e.g., HSV-1), Parvoviridae (e.g., Parvovirus H1), Reoviridae (e.g., Reovirus), Picornaviridae (e.g., Coxsackievirus, Seneca Valley Virus, Poliovirus), Paramyxoviridae (e.g., Measles virus, Newcastle disease virus (NDV)), Rhabdoviridae (e.g., Vesicular stomatitis virus (VSV)), Togaviridae (e.g., Alphavirus, Sindbis virus), Enteroviridae (e.g., Echovirus).

In a further aspect, provided is a lipoplex, such as a lipid nanoparticle (LNP), comprising a polynucleotide encoding the FLT3L-Fc fusion proteins described herein, or an expression cassette or vector comprising such FLT3L-Fc-encoding polynucleotide.

In a further aspect, provided is a cell or population of cells comprising a polynucleotide encoding the FLT3L-Fc fusion proteins described herein, or an expression cassette or vector comprising such FLT3L-Fc-encoding polynucleotide, wherein the cell expresses the FLT3L-Fc fusion protein, or homodimer or heterodimer comprising such FLT3L-Fc fusion protein. In some embodiments, the cell or population of cells is a eukaryotic cell. In some embodiments, the cell or population of cells comprises a mammalian cell, an insect cell, a plant cell or a yeast cell. In some embodiments, the mammalian cell is a Chinese Hamster Ovary (CHO) cell or a human cell. In some embodiments, the human cell is a human embryonic kidney cell. In some embodiments, the cell predominantly sialylates N-linked and/or O-linked glycosylation sites in the fusion protein. In some embodiments, at least 50%, at least 60%, at least 70%, least 80%, at least 85%, at least 90%, or more, N-linked and/or O-linked glycosylation sites in the fusion protein are sialylated. In some embodiments, the sialylated N-linked and/or O-linked glycosylation sites in the fusion protein comprise from 2 to 7 sialic acid residues, e.g., from 3 to 6 sialic acid residues, e.g., from 4 to 5 sialic acid residues.

In a further aspect, provided are pharmaceutical compositions comprising a FLT3L-Fc fusion protein, as described herein, or a fusion protein, homodimer, heterodimer or conjugate comprising such FLT3L-Fc fusion protein; a polynucleotide encoding the FLT3L-Fc fusion proteins described herein, or an expression cassette, vector or lipoplex, such as an LNP, comprising such FLT3L-Fc-encoding polynucleotide, and a pharmaceutically acceptable carrier. In some embodiments, the composition comprises an aqueous formulation. In some embodiments, the composition comprises the FLT3L-Fc fusion protein, or a fusion protein, homodimer, heterodimer or conjugate comprising such FLT3L-Fc fusion protein at a concentration in the range of about 1 mg/ml to about 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml or 20 mg/ml. In some embodiments, the composition is lyophilized. In some embodiment, the composition further comprises one or more additional therapeutic agents, e.g., second, third or fourth therapeutic agents.

Further provided are methods of promoting, inducing and/or increasing the expansion and/or proliferation of a cell or a population of cells that express fms related tyrosine kinase 3 (FLT3, CD135). In some embodiments, the methods comprise contacting the cell or population of cells with an effective amount of a FLT3L-Fc fusion protein, as described herein, or a fusion protein, homodimer, heterodimer, conjugate or pharmaceutical composition comprising such FLT3L-Fc fusion protein; a polynucleotide encoding a FLT3L-Fc fusion protein described herein, or an expression cassette, vector, lipoplex, such as an LNP, or pharmaceutical composition comprising such FLT3L-Fc-encoding polynucleotide. In some embodiments, the cell or population of cells that express FLT3 comprise dendritic cells (e.g., cDC1 cells and/or cDC2 cells), monocyte-derived dendritic cells (moDCs), and/or progenitor cells thereof. In some embodiments, the cell or population of cells that express FLT3 comprise hematopoietic progenitor cells. In some embodiments, the hematopoietic progenitor cells are selected from the group consisting of: Common Lymphoid Progenitors (CLPs), Early Progenitors with Lymphoid and Myeloid potential (EPLMs), granulocyte-monocyte (GM) progenitors (GMP), monocyte-derived dendritic cells (moDCs) progenitors, and early multi-potent progenitors (MPP) within the Lineage-kit+Sca1 (LSK) compartment. In various embodiments, the cell or population of cells is contacted in vitro or in vivo. In some embodiments, the cell or population of cells proliferate or are expanded within a solid tumor. In some embodiments, conventional dendritic cells (e.g., cDC1 and/or cDC2) are expanded or induced to proliferate. In some embodiments, cDC1 dendritic cells (e.g., positive for surface expression of X-C motif chemokine receptor 1 (XCR1), thrombomodulin (THBD, CD141), and C-type lectin domain containing 9A (CLEC9A)) are expanded or induced to proliferate. In some embodiments, dendritic cells expressing C-C motif chemokine receptor 5 (CCR5, CD195) and/or X-C motif chemokine receptor 1 (XCR1) on their cell surface are expanded or induced to proliferate. In some embodiments, dendritic cells expressing one or more cell surface proteins selected from the group consisting of XCR1, cell adhesion molecule 1 (CADM1), C-type lectin domain containing 9A (CLEC9A, CD370), and thrombomodulin (THBD) on their cell surface are expanded or induced to proliferate. In some embodiments, dendritic cells expressing one or more cell surface proteins selected from the group consisting of CD1A, CD1C, CD1E, signal regulatory protein alpha (SIRPA; CD172A), CD207 and Fc fragment of IgE receptor Ia (FCER1A) on their cell surface are expanded or induced to proliferate. In some embodiments, dendritic cells expressing one or more proteins selected from the group consisting of basic leucine zipper ATF-like transcription factor 3 (BATF3) and interferon regulatory factor 8 (IRF8) on their cell surface are expanded or induced to proliferate. In some embodiments, dendritic cells expressing one or more proteins selected from the group consisting of BATF3, IRF8, THBD, CLEC9A and XCR1 on their cell surface are expanded or induced to proliferate. In some embodiments, cDC2 dendritic cells (e.g., positive for surface expression of CD1c molecule (BDCA) are expanded or induced to proliferate. In some embodiments, the FLT3L-Fc fusion protein, the homodimer, the heterodimer, the conjugate, the polynucleotide or the pharmaceutical composition is administered to a subject or patient, e.g., a mammal, e.g., a human.

Further provided are methods of expanding hematopoietic stem cells (HSCs) ex vivo, comprising culturing HSCs in vitro in the presence of mesenchymal lineage precursor or stem cells (MLPSCs) and an effective amount of a FLT3L-Fc fusion protein, as described herein, or a fusion protein, homodimer, heterodimer, conjugate or pharmaceutical composition comprising such FLT3L-Fc fusion protein; a polynucleotide encoding a FLT3L-Fc fusion protein described herein, or an expression cassette, vector, or lipoplex, such as an LNP, comprising such FLT3L-Fc-encoding polynucleotide such that HSCs having the phenotype CD34+ are expanded. In some embodiments the HSCs are further cultured in the presence of at least one histone deacetylase inhibitor (HDACi). In some embodiments, the HDACi is selected from the group consisting of valproic acid (VPA), trichostatin A (TSA), DLS3, MS275, and SAHA. In some embodiments, the HSCs have the phenotype CD34+, CD90+ or CD34+, CD45RA–, CD49f+ and are expanded at least 5-fold, at least 10-fold, at least 20-fold, or at least 40-fold. In some embodiments, the methods further comprise isolating cells having the phenotype the phenotype CD34+, CD90+ or CD34+, CD45RA–, CD49f+ to provide an enriched population of cells having the phenotype CD34+, CD90+ or CD34+, CD45RA–, CD49f+.

In a related aspect, provided are methods of preventing, reducing and/or inhibiting the recurrence, growth, proliferation, migration and/or metastasis of a cancer cell or population of cancer cells in a subject in need thereof. In another aspect, provided are methods of enhancing, promoting, and/or increasing the tumor infiltration of T-cells and/or NK cells in a subject in need thereof. Also provided are methods of enhancing, promoting, and/or accelerating the recovery from or reversing the effects of lymphopenia in a subject in need thereof. Further provided are methods of treating or preventing a viral infection. Also provided are methods for inhibiting the replication of a virus, treating a viral infection or delaying the onset of symptoms of a viral infection in a subject in need thereof. Further provided are methods of enhancing, improving, and/or increasing the response to an anticancer therapy or an antiviral therapy in a subject in need thereof. Further provided are methods of promoting, increasing, supplementing and/or boosting the immune response induced by the vaccine. Further provided are methods of enhancing, improving, and/or increasing the response to an immune checkpoint protein in a subject in need thereof. In some embodiments, the methods comprise administering to the subject effective amount of a FLT3L-Fc fusion protein, as described herein, or a fusion protein, homodimer, heterodimer, conjugate or pharmaceutical composition comprising such FLT3L-Fc fusion protein; a polynucleotide encoding a FLT3L-Fc fusion protein described herein, or an expression cassette, vector, lipoplex, such as an LNP, or pharmaceutical composition comprising such FLT3L-Fc-encoding polynucleotide. In some embodiments, one or more additional therapeutic agents, e.g., second, third and/or fourth therapeutic agents, are co-administered. In some embodiments, the one or more additional therapeutic agents comprises one or more of AGEN1884 (zalifrelimab), AGEN1181, AGEN2034 (balstilimab), AGEN1307, AGEN2373, AGEN1223 and GS-1423 (AGEN1423; see WO2019/173692). In some embodiments, the one or more additional therapeutic agents comprises a vaccine. In some embodiments, the vaccine is selected from the group consisting of an antiviral vaccine, an antibacterial vaccine and an anticancer vaccine (e.g., a neoantigen vaccine). In some embodiments, the vaccine comprises an antiviral vaccine against a virus selected from the group consisting of hepatitis A virus (HAV), hepatitis B virus (HBV), human immunodeficiency virus (HIV), cytomegalovirus (CMV), a herpes simplex virus (HSV), Epstein-Barr virus (EBV), human orthopneumovirus or human respiratory syncytial virus (RSV), human papillomavirus (HPV), varicella-zoster virus, measles virus, mumps virus, poliovirus vaccine, influenza virus, paramyxovirus, rotavirus, Zika virus, Dengue virus, Ebola virus and coronavirus. In some embodiments, the vaccine comprises an antibacterial vaccine against a bacterium selected from the group consisting of *Mycobacterium tuberculosis*, pertussis, tetanus, diphtheria, meningococcus, pneumococcus, *Haemophilus* influenza, cholera, typhoid, and anthrax. In some embodiments, the one or more additional therapeutic agents comprises an oncolytic viral vector. In some embodiments, the oncolytic viral vector comprises a DNA virus or a RNA virus. In some embodiments, the viral vector is from a viral family selected from the group consisting of: Adenoviridae (e.g., Adenovirus), Arenaviridae (e.g., lymphocytic choriomeningitis mammarenavirus, Cali mammarenavirus (a.k.a., Pichinde mammarenavirus), Poxviridae (e.g., Vaccinia virus), Herpesviridae (e.g., Herpesvirus, e.g., HSV-1), Parvoviridae (e.g., Parvovirus HD, Reoviridae (e.g., Reovirus), Picornaviridae (e.g., Coxsackievirus, Seneca Valley Virus, Poliovirus), Paramyxoviridae (e.g., Measles virus, Newcastle disease virus (NDV)), Rhabdoviridae (e.g., Vesicular stomatitis virus (VSV)), Togaviridae (e.g., Alphavirus, Sindbis virus), Enteroviridae (e.g., Echovirus). In some embodiments, the one or more additional therapeutic agents comprises an immunotherapy, an immunostimulatory therapy, a cytokine therapy, a chemokine therapy, a cellular therapy, a gene therapy, and combinations thereof. In some embodiments, the immunotherapy comprises co-administering one or more antibodies or antigen-binding antibody fragments thereof, or antibody-drug conjugates thereof, CD3-targeting multi-specific molecules, CD16-targeting multi-specific molecules, or non-immunoglobulin antigen-binding domains or antibody mimetic proteins directed against one or more targets or tumor associated antigens (TAAs) selected from the group consisting of: CD19, MS4A1 (CD20), CD22, IL2RA (CD25), CD27, TNFRSF8 (CD30), CD33, CD37, CD38, CD40, CD44, CD48, CD52, CD70, NT5E (CD73), ENTPD1 (CD39), CD74, CD79b, CD80, CD86, IL3RA (CD123), PROM1 (CD133), CD137, SDC1 (CD138), alpha fetoprotein (AFP), c-Met; c-Kit; C-type lectin domain family 12 member A (CLEC12A, CLL1, CD371); C-type lectin domain containing 9A (CLEC9A, CD370); cadherin 3 (CDH3, p-cadherin, PCAD); carbonic anhydrase 6 (CA6); carbonic anhydrase 9 (CA9, CAIX); carcinoembryonic antigen related cell adhesion molecule 3 (CEACAM3); carcinoembryonic antigen related cell adhesion molecule 5 (CEACAM5); carcinoembryonic antigen related cell adhesion molecule 6 (CEACAM6, CD66c); chorionic somatomammotropin hormone 1 (CSH1, CS1); coagulation factor III, tissue factor (F3, TF); collectin subfamily member 10 (COLEC10); delta like canonical Notch ligand 3 (DLL3); ectonucleotide pyrophosphatase/phosphodiesterase 3 (ENPP3); ephrin A1 (EFNA1); epidermal growth factor receptor (EGFR); EGFR variant III (EGFRvIII); EPH receptor A2 (EPHA2); epithelial cell adhesion molecule (EPCAM); erb-b2 receptor tyrosine kinase 2 (ERBB2, HER2); fibroblast activation protein alpha (FAP); fibroblast growth factor receptor 2 (FGFR2); fibroblast growth factor receptor 3 (FGFR3); folate hydrolase 1 (FOLH1, PSMA); folate receptor 1 (FOLR1, FRα); GD2 ganglioside; glycoprotein NMB (GPNMB, osteoactivin); guanylate cyclase 2C (GUCY2C, GCC); human papillomavirus (HPV) E6; HPV E7; major histocompatibility complex (MHC) class I-presented neoantigens, major histocompatibility complex (MHC) class II-presented neoantigens, major histocompatibility complex, class I, E (HLA-E); major histocompatibility complex, class I, F (HLA-F); major histocompatibility complex, class I, G (HLA-G, MHC-G); integrin subunit beta 7 (ITGB7); leukocyte immunoglobulin like receptor B1 (LILRB1, ILT2); leukocyte immunoglobulin like receptor B2 (LILRB2, ILT4); LY6/PLAUR domain containing 3 (LYPD3, C4.4A); glypican 3 (GPC3); KRAS proto-oncogene, GTPase (KRAS); MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member D1 (MAGED1); MAGE family member D2 (MAGED2); mesothelin (MSLN); mucin 1 (MUC1) and splice variants thereof (e.g., MUC1/C, D, and Z); mucin 16 (MUC16); necdin (NDN); nectin cell adhesion molecule 4 (NECTIN4); SLIT and NTRK like family member 6 (SLITRK6); promyelocytic leukemia (PML, TRIM19); protein tyrosine kinase 7 (inactive) (PTK7); SLAM family member 6 (SLAMF6, CD352); SLAM family member 7 (SLAMF7, 19A, CD319, CRACC, CS1); sialic acid binding Ig like lectin 7 (SIGLEC7); sialic acid binding Ig like lectin 9 (SIGLEC9); solute carrier family 34 (sodium phosphate), member 2 (SLC34A2); solute carrier family 39 member 6 (SLC39A6, LIV1); STEAP family member 1 (STEAP1); TNF receptor superfamily member 4 (TNFRSF4, OX40 or CD134); TNF superfamily member 9 (TNFSF9, 4-1BB-L, CD137L); TNF receptor superfamily member 10a (TNFRSF10A, DR4, CD261, TRAILR1); TNF receptor superfamily member 10b (TNFRSF10B, DR5, CD262, TRAILR2); TNF receptor superfamily member 13B (TNFRSF13B; CD267, TACI, IGAD2); TNF receptor superfamily member 17 (TNFRSF17, BCMA, CD269); TNF receptor superfamily member 18 (TNFRSF18, GITR, CD357); transferrin (TF); transforming growth factor beta 1 (TGFB1); trophoblast glycoprotein (TPBG, 5T4); trophinin (TRO, MAGED3); tumor associated calcium signal transducer 2 (TACSTD2, TROP2, EGP1); Fucosyl GM1; sialyl Lewis adhesion molecule (sLe); and Lewis Y antigen. In some embodiments, the one or more antibodies or antigen-binding antibody fragments thereof, or antibody-drug conjugates thereof, CD3-targeting multi-specific molecules, CD16-targeting multi-specific molecules, or non-immunoglobulin antigen-binding domains or antibody mimetic proteins binds to an epitope of a target or tumor associated antigen (TAA) presented in a major histocompatibility complex (MHC) molecule (e.g., a neoantigen). In some embodiments, the TAA is a cancer testis antigen. In some embodiments, the cancer testis antigen is selected from the group consisting of acrosin binding protein (ACRBP, CT23, OY-TES-1, SP32), alpha fetoprotein (AFP, AFPD, FETA, HPAFP); A-kinase anchoring protein 4 (AKAP4, AKAP 82, AKAP-4, AKAP82, CT99, FSC1, HI, PRKA4, hAKAP82, p82), ATPase family AAA domain containing 2 (ATAD2, ANCCA, CT137, PRO2000), kinetochore scaffold 1 (KNL1, AF15Q14, CASC5, CT29, D40, MCPH4, PPP1R55, Spc7, hKNL-1, hSpc105), centrosomal protein 55 (CEP55, ClOorf3, CT111, MARCH, URCC6), cancer/testis antigen 1A (CTAG1A, ESO1, CT6.1, LAGE-2, LAGE2A, NY-ESO-1), cancer/testis antigen 1B (CTAG1B, CT6.1, CTAG, CTAG1, ESO1, LAGE-2, LAGE2B, NY-ESO-1), cancer/testis antigen 2 (CTAG2, CAMEL, CT2, CT6.2, CT6.2a, CT6.2b, ESO2, LAGE-1, LAGE2B), CCCTC-binding factor like (CTCFL, BORIS, CT27, CTCF-T, HMGB1L1, dJ579F20.2), catenin alpha 2 (CTNNA2, CAP-R, CAPR, CDCBM9, CT114, CTNR), cancer/testis antigen 83 (CT83, CXorf61, KK-LC-1, KKLC1), cyclin A1 (CCNA1, CT146), DEAD-box helicase 43 (DDX43, CT13, HAGE), developmental pluripotency associated 2 (DPPA2, CT100, ECAT15-2, PESCRG1), fetal and adult testis expressed 1 (FATE1, CT43, FATE), FMR1 neighbor (FMR1NB, CT37, NY-SAR-35, NYSAR35), HORMA domain containing 1 (HORMAD1, CT46, NOHMA), insulin like growth factor 2 mRNA binding protein 3 (IGF2BP3, CT98, IMP-3, IMP3, KOC, KOC1, VICKZ3), leucine zipper protein 4 (LUZP4, CT-28, CT-8, CT28, HOM-TES-85), lymphocyte antigen 6 family member K (LY6K, CT97, HSJ001348, URLC10, ly-6K), maelstrom spermatogenic transposon silencer (MAEL, CT128, SPATA35), MAGE family member A1 (MAGEA1, CT1.1, MAGE1); MAGE family member A3 (MAGEA3, CT1.3, HIPS, HYPD, MAGE3, MAGEA6); MAGE family member A4 (MAGEA4, CT1.4, MAGE-41, MAGE-X2, MAGE4, MAGE4A, MAGE4B); MAGE family member A11 (MAGEA11, CT1.11, MAGE-11, MAGE11, MAGEA-11); MAGE family member C1 (MAGEC1, CT7, CT7.1); MAGE family member C2 (MAGEC2, CT10, HCA587, MAGEE1); MAGE family member D1 (MAGED1, DLXIN-1, NRAGE); MAGE family member D2 (MAGED2, 11B6, BARTS5, BCG-1, BCG1, HCA10, MAGE-D2); kinesin family member 20B (KIF20B, CT90, KRMP1, MPHOSPH1, MPP-1, MPP1); NUF2 component of NDC80 kinetochore complex (NUF2, CDCA1, CT106, NUF2R), nuclear RNA export factor 2 (NXF2, CT39, TAPL-2, TCP11X2); PAS domain containing repressor 1

(PASD1, CT63, CT64, OXTES1), PDZ binding kinase (PBK, CT84, HEL164, Nori-3, SPK, TOPK); piwi like RNA-mediated gene silencing 2 (PIWIL2, CT80, HILI, PIWIL1L, mili); preferentially expressed antigen in melanoma (PRAME, CT130, MAPE, OIP-4, OIP4); sperm associated antigen 9 (SPAG9, CT89, HLC-6, HLC4, HLC6, JIP-4, JIP4, JLP, PNET, PIG6), sperm protein associated with the nucleus, X-linked, family member A1 (SPANXA1, CT11.1, CT11.3, NAP-X, SPAN-X, SPAN-Xa, SPAN-Xb, SPANX, SPANX-A), SPANX family member A2 (SPANXA2, CT11.1, CT11.3, SPANX, SPANX-A, SPANX-C, SPANXA, SPANXC), SPANX family member C (SPANXC, CT11.3, CTp11, SPANX-C, SPANX-E, SPANXE), SPANX family member D (SPANXD, CT11.3, CT11.4, SPANX-C, SPANX-D, SPANX-E, SPANXC, SPANXE, dJ171K16.1), SSX family member 1 (SSX1, CT5.1, SSRC), SSX family member 2 (SSX2, CT5.2, CT5.2A, HD21, HOM-MEL-40, SSX), synaptonemal complex protein 3 (SYCP3, COR1, RPRGL4, SCP3, SPGF4), testis expressed 14, intercellular bridge forming factor (TEX14, CT113, SPGF23), transcription factor Dp family member 3 (TFDP3, CT30, DP4, HCA661), serine protease 50 (PRSS50, CT20, TSP50), TTK protein kinase (TTK, CT96, ESK, MPH1, MPS1, MPS1L1, PYT), and zinc finger protein 165 (ZNF165, CT53, LD65, ZSCAN7). In some embodiments, the non-immunoglobulin antigen-binding domains or antibody mimetic proteins are selected from the group consisting of adnectins, affibody molecules, affilins, affimers, affitins, alphabodies, anticalins, peptide aptamers, armadillo repeat proteins (ARMs), atrimers, avimers, designed ankyrin repeat proteins (DARPins®), fynomers, knottins, Kunitz domain peptides, monobodies, and nanoC-LAMPs. In some embodiments, the immunotherapy comprises co-administering one or more antagonists or inhibitors of an inhibitory immune checkpoint protein or receptor and/or one or more activators or agonists of a stimulatory immune checkpoint protein or receptor. In some embodiments, the one or more immune checkpoint proteins or receptors are selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments, the immunotherapy comprises co-administering one or more blockers or inhibitors of one or more T-cell inhibitory immune checkpoint proteins or receptors. In some embodiments, the T-cell inhibitory immune checkpoint proteins or receptors are selected from the group consisting of CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the immunotherapy comprises co-administering one or more agonists or activators of one or more T-cell stimulatory immune checkpoint proteins or receptors. In some embodiments, the T-cell stimulatory immune checkpoint proteins or receptors are selected from the group consisting of CD27, CD70; CD40, CD40LG; inducible T cell costimulator (ICOS, CD278); inducible T cell costimulator ligand (ICOSLG, B7H2); TNF receptor superfamily member 4

(TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the immunotherapy comprises co-administering one or more blockers or inhibitors of one or more NK-cell inhibitory immune checkpoint proteins or receptors. In some embodiments, the NK-cell inhibitory immune checkpoint proteins or receptors are selected from the group consisting of killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); killer cell lectin like receptor D1 (KLRD1, CD94); killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments, the immunotherapy comprises co-administering one or more agonists or activators of one or more NK-cell stimulatory immune checkpoint proteins or receptors. In some embodiments, the NK-cell stimulatory immune checkpoint proteins or receptors include without limitation CD16, CD226 (DNAM-1); killer cell lectin like receptor K1 (KLRK1, NKG2D, CD314); and SLAM family member 7 (SLAMF7). In some embodiments, the one or more immune checkpoint inhibitors comprises a proteinaceous inhibitor (e.g., an antibody or antigen binding fragment thereof, or a non-immunoglobulin antibody mimetic protein) of PD-L1 (CD274), PD-1 (PDCD1) or CTLA4. In some embodiments, the proteinaceous inhibitor of CTLA4 is selected from the group consisting of ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the proteinaceous inhibitor of PD-L1 (CD274) or PD-1 (PDCD1) is selected from the group consisting of pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments, the one or more immune checkpoint inhibitors comprises a small molecule inhibitor of CD274 (PDL1, PD-L1), programmed cell death 1 (PDCD1, PD1, PD-1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002. In some embodiments, the immunotherapy comprises co-administering one or more cellular therapies selected from the group consisting of: natural killer (NK) cells, NK-T cells, T cells, cytokine-induced killer (CIK) cells, macrophage (MAC) cells, tumor infiltrating lymphocytes (TILs) and dendritic cells (DCs). In some embodiments, the one or more cellular therapies comprise a T cell therapy selected from the group consisting of: alpha/beta TCR T cells, gamma/delta TCR T cells, regulatory T (Treg) cells and TRuC™ T cells. In some embodiments, the one or more cellular therapies comprise a NK cell therapy comprising NK-92 cells. In some embodiments, the one or more cellular therapies comprise cells that are autologous, syngeneic or allogeneic to the subject. In some embodiments, the one or more cellular therapies comprise cells comprising chimeric antigen receptors (CARs). In some embodiments, the cells in the cellular therapy bind to a target or tumor associated antigen (TAA) (e.g., via a chimeric antigen receptor (CAR)) selected from the group consisting of selected from the group consisting of: CD19, MS4A1 (CD20), CD22, IL2RA (CD25), CD27, TNFRSF8 (CD30), CD33, CD37, CD38, CD40, CD44, CD48, CD52, CD70, NT5E (CD73), ENTPD1 (CD39), CD74, CD79b, CD80, CD86, IL3RA (CD123), PROM1 (CD133), CD137, SDC1 (CD138), alpha fetoprotein (AFP), c-Met; c-Kit; C-type lectin domain family 12 member A (CLEC12A, CLL1, CD371); C-type lectin domain containing 9A (CLEC9A, CD370); cadherin 3 (CDH3, p-cadherin, PCAD); carbonic anhydrase 6 (CA6); carbonic anhydrase 9 (CA9, CAIX); carcinoembryonic antigen related cell adhesion molecule 3 (CEACAM3); carcinoembryonic antigen related cell adhesion molecule 5 (CEACAMS); carcinoembryonic antigen related cell adhesion molecule 6 (CEACAM6, CD66c); chorionic somatomammotropin hormone 1 (CSH1, CS1); coagulation factor III, tissue factor (F3, TF); collectin subfamily member 10 (COLEC10); delta like canonical Notch ligand 3 (DLL3); ectonucleotide pyrophosphatase/phosphodiesterase 3 (ENPP3); ephrin A1 (EFNA1); epidermal growth factor receptor (EGFR); EGFR variant III (EGFRvIII); EPH receptor A2 (EPHA2); epithelial cell adhesion molecule (EPCAM); erb-b2 receptor tyrosine kinase 2 (ERBB2; HER2); fibroblast activation protein alpha (FAP); fibroblast growth factor receptor 2 (FGFR2); fibroblast growth factor receptor 3 (FGFR3); folate hydrolase 1 (FOLH1, PSMA); folate receptor 1 (FOLR1, FRα); GD2 ganglioside; glycoprotein NMB (GPNMB, osteoactivin); guanylate cyclase 2C (GUCY2C, GCC); human papillomavirus (HPV) E6; HPV E7; major histocompatibility complex (MHC) class I-presented neoantigens, major histocompatibility complex (MHC) class II-presented neoantigens, major histocompatibility complex, class I, E (HLA-E); major histocompatibility complex, class I, F (HLA-F); major histocompatibility complex, class I, G (HLA-G, MHC-G); integrin subunit beta 7 (ITGB7); leukocyte immunoglobulin like receptor B1 (LILRB1, ILT2); leukocyte immunoglobulin like receptor B2 (LILRB2, ILT4); LY6/PLAUR domain containing 3

(LYPD3, C4.4A); glypican 3 (GPC3); KRAS proto-oncogene, GTPase (KRAS); MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member D1 (MAGED1); MAGE family member D2 (MAGED2); mesothelin (MSLN); mucin 1 (MUC1) and splice variants thereof (e.g., MUC1/C, D, and Z); mucin 16 (MUC16); necdin (NDN); nectin cell adhesion molecule 4 (NECTIN4); SLIT and NTRK like family member 6 (SLITRK6); promyelocytic leukemia (PML, TRIM19); protein tyrosine kinase 7 (inactive) (PTK7); SLAM family member 6 (SLAMF6, CD352); SLAM family member 7 (SLAMF7, 19A, CD319, CRACC, CS1); sialic acid binding Ig like lectin 7 (SIGLEC7); sialic acid binding Ig like lectin 9 (SIGLEC9); solute carrier family 34 (sodium phosphate), member 2 (SLC34A2); solute carrier family 39 member 6 (SLC39A6; LIV1); STEAP family member 1 (STEAP1); TNF receptor superfamily member 4 (TNFRSF4, OX40 or CD134); TNF superfamily member 9 (TNFSF9; 4-1BB-L, CD137L); TNF receptor superfamily member 10a (TNFRSF10A, DR4, CD261, TRAILR1); TNF receptor superfamily member 10b (TNFRSF10B, DR5, CD262, TRAILR2); TNF receptor superfamily member 13B (TNFRSF13B; CD267, TACI, IGAD2); TNF receptor superfamily member 17 (TNFRSF17, BCMA, CD269); TNF receptor superfamily member 18 (TNFRSF18, GITR or CD357); transferrin (TF); transforming growth factor beta 1 (TGFB1); trophoblast glycoprotein (TPBG, 5T4); trophinin (TRO, MAGED3); tumor associated calcium signal transducer 2 (TACSTD2, TROP2, EGP1); Fucosyl GM1; sialyl Lewis adhesion molecule (sLe); and Lewis Y antigen. In some embodiments, the cells in the cellular therapy bind to an epitope of a target or tumor associated antigen (TAA) presented in a major histocompatibility complex (MHC) molecule (e.g., a neoantigen). In some embodiments, the TAA is a cancer testis antigen. In some embodiments, the cancer testis antigen is selected from the group consisting of acrosin binding protein (ACRBP, CT23, OY-TES-1, SP32), alpha fetoprotein (AFP, AFPD, FETA, HPAFP); A-kinase anchoring protein 4 (AKAP4, AKAP 82, AKAP-4, AKAP82, CT99, FSC1, HI, PRKA4, hAKAP82, p82), ATPase family AAA domain containing 2 (ATAD2, ANCCA, CT137, PRO2000), kinetochore scaffold 1 (KNL1, AF15Q14, CASC5, CT29, D40, MCPH4, PPP1R55, Spc7, hKNL-1, hSpc105), centrosomal protein 55 (CEP55, C10orf3, CT111, MARCH, URCC6), cancer/testis antigen 1A (CTAG1A, ESO1, CT6.1, LAGE-2, LAGE2A, NY-ESO-1), cancer/testis antigen 1B (CTAG1B, CT6.1, CTAG, CTAG1, ESO1, LAGE-2, LAGE2B, NY-ESO-1), cancer/testis antigen 2 (CTAG2, CAMEL, CT2, CT6.2, CT6.2a, CT6.2b, ESO2, LAGE-1, LAGE2B), CCCTC-binding factor like (CTCFL, BORIS, CT27, CTCF-T, HMGB1L1, dJ579F20.2), catenin alpha 2 (CTNNA2, CAP-R, CAPR, CDCBM9, CT114, CTNR), cancer/testis antigen 83 (CT83, CXorf61, KK-LC-1, KKLC1), cyclin A1 (CCNA1, CT146), DEAD-box helicase 43 (DDX43, CT13, HAGE), developmental pluripotency associated 2 (DPPA2, CT100, ECAT15-2, PESCRG1), fetal and adult testis expressed 1 (FATE1, CT43, FATE), FMR1 neighbor (FMR1NB, CT37, NY-SAR-35, NYSAR35), HORMA domain containing 1 (HORMAD1, CT46, NOHMA), insulin like growth factor 2 mRNA binding protein 3 (IGF2BP3, CT98, IMP-3, IMP3, KOC, KOC1, VICKZ3), leucine zipper protein 4 (LUZP4, CT-28, CT-8, CT28, HOM-TES-85), lymphocyte antigen 6 family member K (LY6K, CT97, HSJ001348, URLC10, ly-6K), maelstrom spermatogenic transposon silencer (MAEL, CT128, SPATA35), MAGE family member A1 (MAGEA1, CT1.1, MAGE1); MAGE family member A3 (MAGEA3, CT1.3, HIPS, HYPD, MAGE3, MAGEA6); MAGE family member A4 (MAGEA4, CT1.4, MAGE-41, MAGE-X2, MAGE4, MAGE4A, MAGE4B); MAGE family member A11 (MAGEA11, CT1.11, MAGE-11, MAGE11, MAGEA-11); MAGE family member C1 (MAGEC1, CT7, CT7.1); MAGE family member C2 (MAGEC2, CT10, HCA587, MAGEE1); MAGE family member D1 (MAGED1, DLXIN-1, NRAGE); MAGE family member D2 (MAGED2, 11B6, BARTS5, BCG-1, BCG1, HCA10, MAGE-D2); kinesin family member 20B (KIF20B, CT90, KRMP1, MPHOSPH1, MPP-1, MPP1); NUF2 component of NDC80 kinetochore complex (NUF2, CDCA1, CT106, NUF2R), nuclear RNA export factor 2 (NXF2, CT39, TAPL-2, TCP11X2); PAS domain containing repressor 1 (PASD1, CT63, CT64, OXTES1), PDZ binding kinase (PBK, CT84, HEL164, Nori-3, SPK, TOPK); piwi like RNA-mediated gene silencing 2 (PIWIL2, CT80, HILI, PIWIL1L, mili); preferentially expressed antigen in melanoma (PRAME, CT130, MAPE, OIP-4, OIP4); sperm associated antigen 9 (SPAG9, CT89, HLC-6, HLC4, HLC6, JIP-4, JIP4, JLP, PNET, PIG6), sperm protein associated with the nucleus, X-linked, family member A1 (SPANXA1, CT11.1, CT11.3, NAP-X, SPAN-X, SPAN-Xa, SPAN-Xb, SPANX, SPANX-A), SPANX family member A2 (SPANXA2, CT11.1, CT11.3, SPANX, SPANX-A, SPANX-C, SPANXA, SPANXC), SPANX family member C (SPANXC, CT11.3, CTp11, SPANX-C, SPANX-E, SPANXE), SPANX family member D (SPANXD, CT11.3, CT11.4, SPANX-C, SPANX-D, SPANX-E, SPANXC, SPANXE, dJ171K16.1), SSX family member 1 (SSX1, CT5.1, SSRC), SSX family member 2 (SSX2, CT5.2, CT5.2A, HD21, HOM-MEL-40, SSX), synaptonemal complex protein 3 (SYCP3, COR1, RPRGL4, SCP3, SPGF4), testis expressed 14, intercellular bridge forming factor (TEX14, CT113, SPGF23), transcription factor Dp family member 3 (TFDP3, CT30, DP4, HCA661), serine protease 50 (PRSS50, CT20, TSP50), TTK protein kinase (TTK, CT96, ESK, MPH1, MPS1, MPS1L1, PYT), and zinc finger protein 165 (ZNF165, CT53, LD65, ZSCAN7). In some embodiments, the cytokine or chemokine therapy comprises co-administering one or more immunostimulatory cytokines or chemokines that promote or increase the proliferation or activation of T cells (including alpha/beta TCR T cells and gamma/delta TCR T cells), NK-T cells, NK cells, and/or dendritic cells. In some embodiments, the one or more immunostimulatory cytokines or chemokines are selected from the group consisting of: IL 2, IL-12, IL-15, IL-18, IL-21, interferon (IFN)-α, IFN-β, IFN-γ, CXCL9/Mig (monokine induced by interferon-γ), CXCL10/IP10 (interferon-γ-inducible 10 kDa protein) and CXCL11/I-TAC (interferon-inducible T cell a-chemoattractant), CXCL4/PF4 (platelet factor 4), monocyte chemoattractant protein 2 (MCP-2), macrophage inflammatory protein 1 alpha (MIP-1α), macrophage inflammatory protein 1 beta (MIP-1β) and regulated on activation normal T expressed and secreted protein (RANTES). In some embodiments, the one or more additional therapeutic agents comprises an activator or agonist of: a toll-like receptor (TLR); a stimulator of interferon genes (STING) receptor; inducible T cell costimulator (ICOS, CD278); and/or a TNF receptor superfamily (TNFRSF) member. In some embodiments, the TNF receptor superfamily (TNFRSF) member is selected from the group consisting of: TNFRSF1A, TNFRSF1B, TNFRSF4 (0X40), TNFRSF5 (CD40), TNFRSF6 (FAS), TNFRSF7 (CD27), TNFRSF8 (CD30), TNFRSF9 (4-1BB, CD137), TNFRSF10A (CD261, DR4, TRAILR1), TNFRSF10B (CD262, DR5, TRAILR2), TNFRSF10C (CD263, TRAILR3), TNFRSF10D (CD264, TRAILR4), TNFRSF11A (CD265, RANK), TNFRSF11B, TNFRSF12A (CD266), TNFRSF13B (CD267), TNFRSF13C (CD268), TNFRSF16 (NGFR, CD271), TNFRSF17 (BCMA, CD269), TNFRSF18 (GITR, CD357), TNFRSF19, TNFRSF21 (CD358, DR6), and TNFRSF25 (DR3). In some embodiments, the TNFRSF4 (0X40 or CD134) activator or agonist comprises INCAGN1949, tavolimab (MEDI0562), pogalizumab (MOXR0916/RG7888), MEDI6469, BMS 986178, PF-04518600, GSK3174998, IBI101, ATOR-1015, ABBV-368 or SL-279252. In some embodiments, the TNFRSF9 (4-1BB or CD137) activator or agonist comprises urelumab, BMS-663513, utomilumab (PF-05082566), CTX-471, MP-0310, ADG-106, ATOR-1017 or AGEN2373. In some embodiments, the TNFRSF18 (GITR or CD357) activator or agonist comprises GWN323, MEDI1873, MK-1248, MK-4166, TRX518, INCAGN1876, BMS-986156, BMS-986256, AMG-228, ASP1951 (PTZ 522), FPA-154 or OMP-336B11. In some embodiments, the one or more additional therapeutic agents comprises a molecule that concurrently binds to TNF receptor superfamily member 4 (TNFRSF4, OX40 or CD134) and TNF receptor superfamily member 18 (TNFRSF18, GITR or CD357). In some embodiments, the TLR agonist or activator is selected from the group consisting of a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from the group consisting of GS 9620, DS-0509, LHC-165 and TMX-101 (imiquimod), and/or wherein the TLR8 agonist is selected from the group consisting of GS-9688 and NKTR-262 (dual TLR7/TLR8 agonist). In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP. In some embodiments, the one or more additional therapeutic agents comprises an anti-CD47 antibody. In some embodiments, the anti-CD47 antibody is magrolimab. In some embodiments, the one or more additional therapeutic agents comprises an inhibitor of SIRPalpha. In some embodiments, the SIRPalpha inhibitor is selected from the group consisting of AL-008, RRx-001, CTX-5861, FSI-189 (GS-0189), ES-004, BI765063, ADU1805, and CC-95251. In some embodiments, the one or more additional therapeutic agents comprises an inhibitor or antagonist of: protein tyrosine phosphatase, non-receptor type 11 (PTPN11 or SHP2), myeloid cell leukemia sequence 1 (MCL1) apoptosis regulator, mitogen-activated protein kinase kinase kinase kinase 1 (MAP4K1) (also called Hematopoietic Progenitor Kinase 1 (HPK1)), phosphatidylinositol-4,5-bisphosphate 3-kinase, including catalytic subunit alpha (PIK3CA), catalytic subunit beta (PIK3CB), catalytic subunit gamma (PIK3CG) and catalytic subunit delta (PIK3CD), diacylglycerol kinase alpha (DGKA, DAGK, DAGK1 or DGK-alpha), 5'-nucleotidase ecto (NT5E or CD73), ectonucleoside triphosphate diphosphohydrolase 1 (ENTPD1 or CD39), transforming growth factor beta 1 (TGFB1 or TGFβ), heme oxygenase 1 (HMOX1, HO-1 or H01), heme oxygenase 2 (HMOX2, HO-2 or H02), vascular endothelial growth factor A (VEGFA or VEGF), erb-b2 receptor tyrosine kinase 2 (ERBB2, HER, HER2/neu or CD340), epidermal growth factor receptor (EGFR, ERBB, ERBB1 or HER1), ALK receptor tyrosine kinase (ALK, CD246), poly(ADP-ribose) polymerase 1 (PARP1), poly(ADP-ribose) polymerase 2 (PARP2), TCDD inducible poly(ADP-ribose) polymerase (TIPARP, PARP7), cyclin dependent kinase 4 (CDK4), cyclin dependent kinase 6 (CDK6), TNF receptor superfamily member 14 (TNFRSF14, HVEM, CD270), T cell immunoreceptor with Ig and ITIM domains (TIGIT), X-linked inhibitor of apoptosis (XIAP, BIRC4, IAP-3), baculoviral IAP repeat containing 2 (BIRC2, cIAP1), baculoviral IAP repeat containing 3 (BIRC3, cIAP2), baculoviral IAP repeat containing 5 (BIRC5, survivin), C-C motif chemokine receptor 2 (CCR2, CD192), C-C motif chemokine receptor 5 (CCR5, CD195), C-C motif chemokine receptor 8 (CCR8, CDw198), C-X-C motif chemokine receptor 2 (CXCR2, CD182), C-X-C motif chemokine receptor 3 (CXCR3, CD182, CD183), C-X-C motif chemokine receptor 4 (CXCR4, CD184), cytokine inducible SH2 containing protein (CISH), arginase (ARG1, ARG2), carbonic anhydrase (CA1, CA2, CA3, CA4, CASA, CA5B, CA6, CA7, CA8, CA9, CA10, CA11, CA12, CA13, CA14), prostaglandin-endoperoxide synthase 1 (PTGS1, COX-1), prostaglandin-endoperoxide synthase 2 (PTGS2, COX-2), secreted phospholipase A2, prostaglandin E synthase (PTGES, PGES), arachidonate 5-lipoxygenase (ALOXS, 5-LOX), soluble epoxide hydrolase 2 (EPHX2), indoleamine 2,3-dioxygenase 1 (IDO1), indoleamine 2,3-dioxygenase 2 (IDO2), hypoxia inducible factor 1 subunit alpha (HIF1A), angiopoietin 1 (ANGPT1), Endothelial TEK tyrosine kinase (TIE-2, TEK), Janus kinase 1 (JAK1), catenin beta 1 (CTNNB1), histone deacetylase 9 (HDAC9), 5'-3' exoribonuclease 1 (XRN1) and/or WRN RecQ like helicase (WRN). In some embodiments, the inhibitor comprises an antibody or an antigen-binding fragment thereof, or antibody-drug conjugate thereof, CD3-targeting multi-specific molecule, CD16-targeting multi-specific molecule, non-immunoglobulin antigen binding molecule or antibody mimetic protein. In some embodiments, the inhibitor comprises an inhibitory nucleic acid (e.g., an siRNA). In some embodiments, the inhibitor comprises a small organic molecule. In some embodiments, the inhibitor of 5'-nucleotidase ecto (NT5E or CD73) is selected from the group consisting of MEDI9447 (oleclumab), CPI-006, BMS-986179, IPH5301, TJ4309 (TJDS), NZV-930, AB-680, PSB-12379, PSB-12441, PSB-12425, CB-708, GS-1423 (AGEN1423) and PBF-1662. In some embodiments, the inhibitor of CCR2 and/or CCR5 is selected from the group consisting of BMS-813160, PF-04136309 and CCX-872. In some embodiments, the inhibitor of MCL1 is selected from the group consisting of AMG-176, AMG-397, S-64315, AZD-5991, 483-LM, A 1210477, UMI-77 and JKY-5-037. In some embodiments, the inhibitor of PTPN11 or SHP2 is selected from the group consisting of TN0155 (SHP-099), RMC-4550, JAB-3068 and RMC-4630. In some embodiments, the inhibitor of Janus kinase 1 (JAK1) is selected from the group consisting of filgotinib, tofacitinib, baricitinib and ABT-494. In some embodiments, the one or more additional therapeutic agents comprises a regulatory T cell (Treg) inhibitor. In some embodiments, the subject further receives radiation therapy. In some embodiments, the radiation therapy comprises stereotactic body radiation therapy (SBRT). In some embodiments, the one or more additional therapeutic agents comprises one or more anti-neoplastic or chemotherapeutic agents. In some embodiments, the one or more anti-neoplastic or chemotherapeutic agents are selected from the group consisting of a nucleoside analog (e.g., 5-fluorouracil, gemcitabine, cytarabine, cladribine, pentostatin, fludarabine), a taxane (e.g., paclitaxel, nab-paclitaxel, docetaxel, cabazitaxel), a platinum coordination complex (cisplatin, carboplatin, oxaliplatin, nedaplatin, triplatin tetranitrate, phenanthriplatin, picoplatin, satraplatin, dicycloplatin, eptaplatin, lobaplatin, miriplatin), a dihydrofolate reductase (DHFR) inhibitor (e.g., methotrexate, trimetrexate, pemetrexed), a topoisomerase inhibitor (e.g., doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114)), an alkylating agent (e.g., a nitrogen mustard (e.g., cyclophosphamide, chlormethine, uramustine or uracil mustard, melphalan, chlorambucil, ifosfamide, bendamustine, temozolomide, carmustine), a nitrosourea (e.g., carmustine, lomustine, streptozocin), an alkyl sulfonate (e.g., busulfan)), and mixtures thereof. In some embodiments, the one or more additional therapeutic agents comprises a FOLFOX regimen, a FOLFIRI regimen, a FOLFOXIRI regimen or a FOLFIRINOX regimen. In some embodiments, the one or more additional therapeutic agents comprises an antiviral therapy. In some embodiments, the antiviral therapy comprises co-administering a hepatitis B virus (HBV) therapeutic agent. In some embodiments, the HBV therapeutic agent is selected from an HBV vaccine, HBV polymerase inhibitor, immunomodulator, interferon alpha receptor ligand, hyaluronidase inhibitor, Hepatitis B Surface Antigen (HBsAg) inhibitor, cyclophilin inhibitor, antisense oligonucleotide, short interfering RNA (siRNA), or DNA-directed RNA interference (ddRNAi) targeting HBV viral mRNA, endonuclease modulator (e.g., PGN-514), ribonucleotide reductase inhibitor (e.g., Trimidox), HBV replication inhibitor, non-canonical RNA polymerase PAPD5 and PAPD7 inhibitor (e.g., siRNA), covalently closed circular DNA inhibitor (cccDNA), caspase 9 stimulator (e.g., ENOB-HB-01), CD3 modulator (e.g., IMC-1109V), Ffar2 and Ffar3 agonist (e.g., SFA-001), additional HBV antibody, CCR2 chemokine (e.g., propagermanium), FXR agonist, thymosine antagonist, nucleoprotein modulator, retinoic acid-inducible gene stimulator 1, arginase inhibitor (e.g., astodrimer, CB-1158, C-201, resminostat), endonuclease inhibitor (e.g., PGN-154), ribonuclease reductase inhibitor (e.g., Trimidox), non-nucleoside reverse transcriptase inhibitor (NNRTI), HBV replication inhibitor, capsid inhibitor, transcript inhibitor, CAR-T cell therapy, TCR-T cell therapy, and inhibitor of an HCV nonstructural protein (e.g., NS5A inhibitor (e.g., ledipasvir, velpatasvir), a NS5B inhibitor (e.g., sofosbuvir, mericitabine), a NS3 inhibitor (e.g., voxilaprevir)). In some embodiments, the HBV vaccine is selected from the group consisting of HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2 (HepTcell), NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), hepatitis B therapeutic DNA vaccine, AdTG-17909, AdTG-17910 AdTG-18202, ChronVac-B, TG-1050, VVX-001, GSK-3528869A (ChAd155-hli-HBV+MVA-HBV+Hbc-HBs/AS01B-4), VBI-2601, VTP-300 (ChAdOx1-SIi-HBV-CPmut-TPA-Ssh prime and MVA-SIi-HBV-CPmut-TPA-Ssh boost), MVA-BN, AVA-2100, HBV-ADV311, YS-HBV-002, and Lm HBV. In some embodiments, the HBV polymerase inhibitor is selected from the group consisting of adefovir (REPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, ATI-2173, SNC-019754, FMCA, AGX-1009, AR-II-04-26, HIP-1302, tenofovir disoproxil aspartate, tenofovir disoproxil orotate, and HS-10234. In some embodiments, the immunomodulator is selected from the group consisting of rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440, WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785, RG-7854, RO-6871765, AIC-649, and IR-103. In some embodiments, the interferon alpha receptor ligand is selected from the group consisting of interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhlFNalpha-2a), P-1101, Algeron, Alfarona, Ingaron (interferon gamma), rSIFN-co (recombinant super compound interferon), Ypeginterferon alfa-2b (YPEG-rhlFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), PEG-IFN-alpha, rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa). In some embodiments, the hyaluronidase inhibitor is astodrimer. In some embodiments, the Hepatitis B Surface Antigen (HBsAg) inhibitor is selected from the group consisting of AK-074, HBF-0259, PBHBV-001, PBHBV-2-15, PBHBV-2-1, REP-9AC, REP-9C, REP-9, REP-2139, REP-2139-Ca, REP-2055, REP-2163, REP-2165, REP-2053, REP-2031, REP-006, and REP-9AC'. In some embodiments, the HBsAg inhibitor is an HBsAg secretion inhibitor selected from the group consisting of BM601, GST-HG-131, and AB-452. In some embodiments, the cyclophilin inhibitor is selected from the group consisting of CPI-431-32, EDP-494, OCB-030, SCY-635, NVP-015, NVP-018, NVP-019, and STG-175. In some embodiments, the antisense oligonucleotide targeting viral mRNA is selected from the group consisting of ISIS-HBVRx, IONIS-HBVRx, IONIS-HBV-LRx, IONIS-GSK6-LRx, GSK-3389404, and RG-6004. In some embodiments, the short interfering RNA (siRNA) or DNA-directed RNA interference (ddRNAi) is selected from the group consisting of TKM-HBV (TKM-HepB), ALN-HBV (e.g., ALN-HBV02), SR-008, HepB-nRNA, ARC-520, ARC-521, ARB-1740, ARB-1467, AB-729, DCR-HBVS, RG-6084 (PD-L1), RG-6217, ALN-HBV-02, JNJ-3989 (ARO-HBV), STSG-0002, ALG-010133, ALG-ASO, LUNAR-HBV and DCR-HBVS (DCR-5219). In some embodiments, the ddRNAi is BB-HB-331. In some embodiments, the HBV replication inhibitor is selected from the group consisting of GP-31502, isothiafludine, IQP-HBV, RM-5038, and Xingantie. In some embodiments, the cccDNA is selected from the group consisting of BSBI-25, ccc-R08, and CHR-101. In some embodiments, the additional HBV antibody targets a surface antigen of hepatitis B virus. In some embodiments, the additional HBV antibody is selected from lenvervimab (GC-1102), XTL-17, XTL-19, KN-003, IV Hepabulin SN, VIR-3434, Omri-Hep-B, Nabi-HB, Hepatect CP, HepaGam B, igantibe, Niuliva, CT-P24, Fovepta (BT-088), and HBC-34. In some embodiments, the FXR agonist is selected from the group consisting of EYP-001, GS-9674, EDP-305, MET-409, Tropifexor, AKN-083, RDX-023, BWD-100, LMB-763, INV-3, NTX-023-1, EP-024297 and GS-8670. In some embodiments, the thymosine antagonist is selected from Thymalfasin, recombinant thymosin alpha 1 (GeneScience), NL-004 and PEGylated thymosin alpha-1. In some embodiments, the nucleoprotein modulator is selected from GS-4882, AB-423, AB-836, AT-130, ALG-001075, ALG-001024, ALG-000184, EDP-514, GLS4, NVR-1221, NVR-3778, AL-3778, BAY 41-4109, morphothiadine mesilate, ARB-168786, ARB-880, ARB-1820, GST-HG-141, JNJ-379, JNJ-632, RG-7907, GST-HG-141, HEC-72702, KL-060332, AB-506, ABI-H0731, ABI-H3733, JNJ-440, ABI-H2158, CB-HBV-001, AK-0605, SOC-10, SOC-11 and DVR-23. In some embodiments, the retinoic acid-inducible gene stimulator 1 is selected from the group consisting of inarigivir soproxil (SB-9200), SB-40, SB-44, ORI-7246, ORI-9350, ORI-7537, ORI-9020, ORI-9198, ORI-7170, and RGT-100. In some embodiments, the arginase inhibitor is selected from the group consisting of CB-1158, C-201, and resminostat. In some embodiments, the CAR-T cell therapy directed to HBV therapy includes a population of immune effector cells engineered to express a chimeric antigen receptor (CAR), wherein the CAR includes an HBV antigen-binding domain (e.g., HbsAg-CART). In some embodiments, the TCR-T cell therapy includes T cells expressing HBV-specific T cell receptors (e.g., (HBsAg)-specific TCR). In some embodiments, the HBV therapeutic agent is selected from alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, NCO-48 Fumarate, TCM-800B, reduced glutathione, RO-6864018, RG-7834, QL-007sofosbuvir, ledipasvir, UB-551, PA-1010, HPN-BV1, STSG-0002, and ZH-2N. In some embodiments, the antiviral therapy comprises co-administering a hepatitis C virus (HCV) therapeutic agent. In some embodiments, the HCV therapeutic agent is selected from daclatasvir, ledipasvir, ombitasvir, elbasvir, sofosbuvir, dasabuvir, ribavirin, asunaprevir, simeprevir, paritaprevir, ritonavir, elbasvir, and grazoprevir. In some embodiments, the antiviral therapy comprises co-administering a human immunodeficiency virus (HIV) therapeutic agent. In some embodiments, the HIV therapeutic agent comprises an HIV protease inhibitor, HIV ribonuclease H inhibitor, HIV Nef inhibitor, HIV reverse transcriptase inhibitor, HIV integrase inhibitor, HIV entry inhibitor, HIV maturation inhibitor, a latency reversing agent, HIV capsid inhibitor, HIV targeting antibody, HIV vaccine, or a birth control or contraceptive regimen. In some embodiments, the HIV protease inhibitor is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, AEBL-2, DG-17, GS-1156, TMB-657 (PPL-100), T-169, BL-008, MK-8122, TMB-607, GRL-02031, and TMC-310911. In some embodiments, the HIV ribonuclease H inhibitor is NSC-727447. In some embodiments, the HIV Nef inhibitor is FP-1. In some embodiments, the HIV reverse transcriptase inhibitor is a non-nucleoside/non-nucleotide reverse transcriptase inhibitor. In some embodiments, the non-nucleoside/non-nucleotide inhibitor is select from the group consisting of dapivirine, delavirdine, delavirdine mesylate, doravirine, efavirenz, etravirine, lentinan, nevirapine, rilpivirine, ACC-007, ACC-008, AIC-292, F-18, KM-023, PC-1005, VM-1500A-LAI, PF-3450074, elsulfavirine (sustained release oral, HIV infection), elsulfavirine (long-acting injectable nanosuspension, HIV infection), and elsulfavirine (VM-1500). In some embodiments, the HIV reverse transcriptase inhibitor is a nucleoside or nucleotide inhibitor. In some embodiments the nucleoside or nucleotide inhibitor is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir octadecyloxyethyl ester (AGX-1009), tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8591, MK-8583, VM-2500 and KP-1461. In some embodiments, the HIV integrase inhibitor is selected from the group consisting of elvitegravir, elvitegravir (extended-release microcapsules), curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, PEGylated raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, MK-0536, NSC-310217, NSC-371056, NSC-48240, NSC-642710, NSC-699171, NSC-699172, NSC-699173, NSC-699174, stilbenedisulfonic acid, T-169, STP-0404, VM-3500 and cabotegravir. In some embodiments, the HIV integrase inhibitor is an HIV non-catalytic site, or allosteric, integrase inhibitor (NCINI). In some embodiments, the NCINI is selected from the group consisting of CX-05045, CX-05168, and CX-14442. In some embodiments, the HIV an entry inhibitor is AAR-501, LBT-5001, cenicriviroc, a CCR5 inhibitor, a gp41 inhibitor, a CD4 attachment inhibitor, a gp120 inhibitor, a gp160 inhibitor a, and a CXCR4 inhibitor. In some embodiments, the CCR5 inhibitor is selected from the group consisting of aplaviroc, vicriviroc, maraviroc, maraviroc (long-acting injectable nanoemulsion), cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, thioraviroc and vMIP (Haimipu). In some embodiments, the gp41 inhibitor is selected from the group consisting of albuvirtide, enfuvirtide, griffithsin (gp41/gp120/gp160 inhibitor), BMS-986197, enfuvirtide biobetter, enfuvirtide biosimilar, HIV-1 fusion inhibitors (P26-Bapc), ITV-1, ITV-2, ITV-3, ITV-4, CPT-31, Cl3hmAb, PIE-12 trimer and sifuvirtide. In some embodiments, the a CD4 attachment inhibitor is ibalizumab or a CADA analog. In some embodiments, the gp120 inhibitor selected from the group consisting of anti-HIV microbicide, Radha-108 (receptol) 3B3-PE38, BanLec, bentonite-based nanomedicine, fostemsavir tromethamine, IQP-0831, VVX-004, and BMS-663068. In some embodiments, gp160 inhibitor is fangchinoline. In some embodiments, the CXCR4 inhibitor selected from the group consisting of plerixafor, ALT-1188, N15 peptide, and vMIP (Haimipu). In some embodiments, the HIV entry inhibitor is selected from docosanol, enfuvirtide, maraviroc, palivizumab, respiratory syncytial virus immune globulin, intravenous [RSV-IGIV], varicella-zoster immunoglobulin [VariZIG], and varicella-zoster immune globulin [VZIG]). In some embodiments, the HIV maturation inhibitor is selected from the group consisting of BMS-955176, GSK-3640254 and GSK-2838232. In some embodiments, the latency reversing agent is selected from the group consisting of toll-like receptor (TLR) agonists (including TLR7 agonists, e.g., GS-9620 (vesatolimod), vesatolimod analogs), histone deacetylase (HDAC) inhibitors, proteasome inhibitors (e.g., velcade), protein kinase C (PKC) activators (e.g., indolactam, prostratin, ingenol B, DAG-lactones), Smyd2 inhibitors, BET-bromodomain 4 (BRD4) inhibitors, ionomycin, IAP antagonists (inhibitor of apoptosis proteins; e.g., APG-1387, LBW-242), SMAC mimetics (including TL32711, LCL161, GDC-0917, HGS1029, AT-406, Debio-1143), PMA, SAHA (suberanilohydroxamic acid, or suberoyl, anilide, and hydroxamic acid), NIZ-985, IL-15 modulating antibodies, IL-15, IL-15 fusion proteins, IL-15 receptor agonists, JQ1, disulfiram, amphotericin B, and ubiquitin inhibitors (e.g., largazole analogs, APH-0812, GSK-343). In some embodiments, the HIV capsid inhibitor is selected from the group consisting of capsid polymerization inhibitors, capsid disrupting compounds, HIV nucleocapsid p7 (NCp7) inhibitors (e.g., azodicarbonamide), and HIV p24 capsid protein inhibitors (e.g., GS-6207, GS-CA1, AVI-621, AVI-101, AVI-201, AVI-301, AVI-CAN1-15 series, and PF-3450074). In some embodiments, the HIV targeting antibody is selected from bNAbs (broadly neutralizing HIV-1 antibodies), TMB-360, antibodies targeting HIV gp120 or gp41, antibody-recruiting molecules targeting HIV, anti-CD63 monoclonal antibodies, anti-GB virus C antibodies, anti-GP120/CD4, gp120 bispecific monoclonal antibodies, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), PGT121.414.LS, ibalizumab, Immuglo, MB-66, and VRC-HIVMAB091-00-AB. In some embodiments, the HIV targeting antibody is selected from the group consisting of UB-421, BF520.1, CHO1, CH59, C2F5, C4E10, C2F5+C2G12+C4E10, 3BNC117, 3BNC117-LS, 3BNC60, DH270.1, DH270.6, D1D2, 10-1074-LS, Cl3hmAb, GS-9722 (elipovimab), DH411-2, BG18, GS-9721, PGT145, PGT121, PGT-121.60, PGT-121.66, PGT122, PGT-123, PGT-124, PGT-125, PGT-126, PGT-151, PGT-130, PGT-133, PGT-134, PGT-135, PGT-128, PGT-136, PGT-137, PGT-138, PGT-139, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, VRC01, VRC-01-LS, A32, 7B2, 10E8, VRC-07-523, VRC07-523LS, VRC24, VRC41.01, 10E8VLS, 3810109, 10E8v4, IMC-HIV, iMabm36, eCD4-Ig, IOMA, CAP256-VRC26.25, DRVIA7, VRC-HIVMAB080-00-AB, VRC-HIVMAB060-00-AB, P2G12, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and VRC38.01, PGT-151, CAP248-2B, 35022, ACS202, VRC34 and VRC34.01, 10E8, 10E8v4, 10E8-5R-100cF, 4E10, DH511.11P, 2F5, 7b2, and LN01. In some embodiments, the HIV targeting antibody is a bispecific or trispecific antibody selected from the group consisting of MGD014, B12BiTe, BiIA-SG, TMB-bispecific, SAR-441236, VRC-01/PGDM-1400/10E8v4, 10E8.4/iMab, and 10E8v4/PGT121-VRC01. In some embodiments, the HIV targeting antibody is an in vivo delivered bNAbs (e.g., AAV8-VRC07; mRNA encoding anti-HIV antibody VRC01; or engineered B-cells encoding 3BNC117). In some embodiments, the HIV vaccine is selected from the group consisting of peptide vaccines, recombinant subunit protein vaccines, live vector vaccines, DNA vaccines, HIV MAG DNA vaccine, CD4-derived peptide vaccines, vaccine combinations, adenoviral vector vaccines (an adenoviral vector such as Ad5, Ad26 or Ad35), simian adenovirus (chimpanzee, gorilla, rhesus i.e., rhAd), adeno-associated virus vector vaccines, chimpanzee adenoviral vaccines (e.g., ChAdOX1, ChAd68, ChAd3, ChAd63, ChAd83, ChAd155, ChAd157, PanS, Pan6, Pan7, Pan9), Coxsackieviruses based vaccines, enteric virus based vaccines, Gorilla adenovirus vaccines, lentiviral vector based vaccine, arenavirus vaccines (e.g., LCMV, Pichinde), bi-segmented or tri-segmented arenavirus based vaccine, trimer-based HIV-1 vaccine, measles virus based vaccine, flavivirus vector based vaccines, tobacco mosaic virus vector based vaccine, Varicella-zoster virus based vaccine, human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, venezuelan equine encephalitis virus and sindbis virus; lipoplex (e.g., LNP) formulated mRNA based therapeutic vaccines; and lipoplex (e.g., LNP)-formulated self-replicating RNA/self-amplifying RNA vaccines. In some embodiments, the HIV vaccine is selected from the group consisting of anti-CD40.Env-gp140 vaccine, Ad4-EnvC150, BG505 SOSIP.664 gp140 adjuvanted vaccine, BG505 SOSIP.GT1.1 gp140 adjuvanted vaccine, Chimigen HIV vaccine, ConM SOSIP.v7 gp140, rgp120 (AIDSVAX), ALVAC HIV (vCP1521)/AIDSVAX B/E (gp120) (RV144), monomeric gp120 HIV-1 subtype C vaccine, MPER-656 liposome subunit vaccine, Remune, ITV-1, Contre Vir, Ad5-

ENVA-48, DCVax-001 (CDX-2401), Vacc-4x, Vacc-05, VAC-3 S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/ VSSP ISA-51, poly-ICLC adjuvanted vaccines, TatImmune, GTU-multiHIV (FIT-06), ChAdV63.HIVconsv, gp140 [delta]V2.TV1+MF-59, rVSVIN HIV-1 gag vaccine, SeV-EnvF, SeV-Gag vaccine, AT-20, DNK-4, ad35-Grin/ENV, TBC-M4, HIVAX, HIVAX-2, N123-VRC-34.01 inducing epitope-based HIV vaccine, NYVAC-HIV-PT1, NYVAC-HIV-PT4, DNA-HIV-PT123, rAAV1-PG9DP, GOVX-B11, GOVX-B21, GOVX-055, TVI-HIV-1, Ad-4 (Ad4-env Clade C+Ad4-mGag), Paxvax, EN41-UGR7C, EN41-FPA2, ENOB-HV-11, PreVaxTat, AE-H, MYM-V101, CombiHIVvac, ADVAX, MYM-V201, MVA-CMDR, MagaVax, DNA-Ad5 gag/pol/nef/nev (HVTN505), MVATG-17401, ETV-01, CDX-1401, DNA and Sev vectors vaccine expressing SCaVII, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, VIR-1111, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A, B, C, A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, HIV-1 iglb12 neutralizing VRC-01 antibody-stimulating anti-CD4 vaccine, arenavirus vector-based vaccines (Vaxwave, TheraT), MVA-BN HIV-1 vaccine regimen, UBI HIV gp120, mRNA based prophylactic vaccines, VPI-211, and TBL-1203HI. In some embodiments, the birth control or contraceptive regimen is selected from the group consisting of cyproterone acetate, desogestrel, dienogest, drospirenone, estradiol valerate, ethinyl estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof. In some embodiments, the antiviral therapy comprises co-administering an influenza therapeutic agent. In some embodiments, the influenza therapeutic agent is selected from a matrix 2 inhibitor (e.g., amantadine, rimantadine), neuraminidase inhibitor (e.g., zanamivir, oseltamivir, peramivir, laninamivir octanoate), and polymerase inhibitor (e.g., ribavirin, favipiravir). In some embodiments, the influenza virus inhibitor is selected from amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the influenza virus inhibitor is selected from amantadine, rimantadine, zanamivir, oseltamivir, peramivir, laninamivir octanoate, ribavirin, and favipiravir. In some embodiments, the antiviral therapy comprises co-administering a respiratory syncytial virus (RSV) therapeutic agent. In some embodiments, the RSV therapeutic agent is selected from ribavirin, ALS-8112, and presatovir. In some embodiments, the antiviral therapy comprises co-administering a picornavirus therapeutic agent. In some embodiments, the picorna therapeutic agent is selected from hydantoin, guanidine hydrochloride, L-buthionine sulfoximine, Py-11, and rupintrivir. In some embodiments, the antiviral therapy comprises co-administering an Ebola virus therapeutic agent. In some embodiments, the Ebola virus therapeutic agent is selected from ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, Ebola virus entry inhibitors (NPC1 inhibitors), rVSV-EBOV. In some embodiments, the Ebola virus therapeutic agent is selected from ZMapp, mAB114, and REGEN-EB3. In some embodiments, the antiviral therapy comprises co-administering a coronavirus therapeutic agent. In some embodiments, the coronavirus is a Severe Acute Respiratory Syndrome (SARS)-associated coronavirus. In some embodiments, the coronavirus is a Middle-East Respiratory Syndrome (MERS)—associated coronavirus. In some embodiments, the coronavirus is SARS-CoV-2. In some embodiments, the SARS-CoV-2 (COVID-19) therapeutic agent is a RNA polymerase inhibitor (e.g., remdesivir, galidesivir). In some embodiments, the SARS-CoV-2 (COVID-19) therapeutic agent is remdesivir (GS-5734). In some embodiments, the SARS-CoV-2 (COVID-19) therapeutic agent is an anti-SARS-CoV-2 hyperimmune globulin therapy (plasma from convalescent COVID-19 patients, e.g., processed into a hyperimmune globulin) (e.g., TAR-888). In some embodiments, the SARS-CoV-2 (COVID-19) therapeutic agent is selected from a COVID-19 vaccine (e.g., BN162, Ad5-nCoV, INO-4800, mRN1273), anti-IL6 receptor antibody (e.g., tocilizumab, sarilumab, TZLS-501), an anti-IL6 antibody (e.g., siltuximab), RNA dependent RNA polymerase (RdRp) inhibitor (e.g., favipravir, remdesivir), anti-CCR5 antibody (e.g., leronlimab (PRO 140)), broadly neutralizing antibody (e.g., an anti-ACE2 receptor antibody, SAB-185, COVID-HIG, COVID-EIG), ACE2 (angiotensin-converting enzyme 2)-Fc fusion protein (COVIDTRAP) or recombinant human ACE2 protein (APN1), ACE-MAB™ bi-specific fusion protein designed to bind to the spike protein of coronaviruses—including SARS-CoV-2 and SARS-CoV STI-4920, CMAB020), Janus kinase (JAK1/JAK2) inhibitor (e.g., ruxolitinib, baricitinib), an siRNA (e.g., targeting angiotensin converting enzyme-2 (ACE2) or transmembrane protease, serine 2 (TMPRSS2)), HIV-1 protease inhibitor (e.g., lopina.vir/ritonavir; darunavir alone or in combination with cobicistat), complement inhibitor (e.g., eculizumab), HCV protease inhibitor (e.g., danoprevir), stem cell therapy (e.g., MultiStem®, Remestemcel-L, CYNK-001), NK cell therapy (NKG2D-ACE2 CAR-NK cells), a neutralizing antibody against human granulocyte-macrophage colony stimulating factor (GM- CSF) (e.g., IZN-101, gimsilumab), a vasoconstrictor (e.g., angiotensin II), selective inhibitor of nuclear export (SINE), such as XPO1 inhibitor (e.g., selinexor), NSAID, including COX inhibitors (e.g., ibuprofen, aspirin, diclofenac, naxopren) and selective COX2 inhibitors (e.g., celecoxib, rofecoxib, etoricoxib, lumiracoxib, valecoxib), and other antiviral agents (e.g., ENU200, lopinavir/ritonavir combination). In some embodiments, the COVID-19 vaccine is an mRNA vaccine (e.g., BN162), including a lipoplex (e.g., lipid-nanoparticle (LNP)) encapsulated vaccine (e.g., mRNA1273). In some embodiments, the COVID-19 vaccine is a DNA vaccine (e.g., INO-4800). In some embodiments, the COVID-19 vaccine encodes for a prefusion stabilized form of the Spike (S) protein (e.g., mRNA1273). In some embodiments, the COVID-19 vaccine is a recombinant protein-based vaccine consisting of the receptor binding domain (RBD) of the spike protein of the coronavirus. In some embodiments, the COVID-19 vaccine uses a Ligand Antigen Epitope Presentation System (LEAPS) peptide including conserved regions of coronavirus proteins to stimulate protective cell mediated T cell responses and reduce viral load. In some embodiments, the COVID-19 vaccine is a microneedle array (MNA)—delivered vaccine. In some embodiments, the vaccine is based on a flu vector expressing the surface antigen of SARS-CoV-2. In some embodiments, the COVID-19 vaccine is an intranasal vaccine (e.g., AdCOVID). In some embodiments, the COVID-19 vaccine is NVX-CoV2373, INO4800, or BNT-162. In some embodiments, the SARS-CoV-2 (COVID-19) therapeutic agent is selected from a PlKfyve kinase inhibitor (e.g., apilimod), immunomodulator (e.g., rintatolimod), T-cell immunotherapy, recombinant sialidase (e.g., DAS181), CRAC channel inhibitor (e.g., CM-4620-IE), cardiac cell therapy using allogeneic cardiosphere-derived cells (e.g., CAP-1002), cardioprotective drug (e.g., aspirin, plavix, lipitor, opremazole), S11$^3$ receptor antagonist (e.g., fingolimod), a cyclooxygenase-2 (COX-2) inhibitor (e.g., celecoxib), phosphodiesterase-5 (PDE5) inhibitor (e.g., sildenafil citrate), serine protease TMPRSS2 inhibitor (camostat mesylate), anti-human complement 5a antibody (e.g., IFX-1), macrophage migration inhibitory factor (MIF) inhibitor, phosphodiesterase (PDE)-4 and -10 inhibitor (e.g., ibudilast), an eEF1A2 inhibitor (e.g., plitidepsin), sphingosine kinase 2 (SK2) inhibitor (e.g., ABC294640, RHB-107), galectin inhibitor (e.g., BXT-10), membrane fusion inhibitor (e.g., umifenovir), anti-PD1 antibody, thymosin, antimalarial (e.g., chloroquine, hydroxychloroquine), and other antiviral therapeutics (e.g., HTCC (N-(2-hydroxypropyl)-3-trimethylammonium 47 chitosan chloride, OYA1). In some embodiments, the subject has cancer. In some embodiments, the subject is in cancer remission. In some embodiment, the subject has a hematological cancer, e.g., a leukemia (e.g., Acute Myelogenous Leukemia (AML), Acute Lymphoblastic Leukemia (ALL), B-cell ALL, Myelodysplastic Syndrome (MDS), myeloproliferative disease (MPD), Chronic Myelogenous Leukemia (CML), Chronic Lymphocytic Leukemia (CLL), undifferentiated leukemia), a lymphoma (e.g., small lymphocytic lymphoma (SLL), mantle cell lymphoma (MCL), follicular lymphoma (FL), T-cell lymphoma, B-cell lymphoma, diffuse large B-cell lymphoma (DLBCL), marginal zone lymphoma (MZL), Waldestrom's macroglubulinemia (WM)) and/or a myeloma (e.g., multiple myeloma (MM)). In some embodiments, the subject has a solid tumor. In some embodiments, the tumor or cancer is malignant or metastatic. In some embodiments, the subject has a tumor infiltrated with conventional dendritic cells (cDC1). In some embodiments, the tumor infiltrating dendritic cells express C-C motif chemokine receptor 5 (CCR5, CD195) and/or X-C motif chemokine receptor 1 (XCR1) on their cell surface. In some embodiments, the tumor infiltrating dendritic cells express one or more cell surface proteins selected from the group consisting of XCR1, cell adhesion molecule 1 (CADM1), C-type lectin domain containing 9A (CLEC9A, CD370), and thrombomodulin (THBD). In some embodiments, the tumor infiltrating dendritic cells express one or more cell surface proteins selected from the group consisting of CD1A, CD1C, CD1E, signal regulatory protein alpha (SIRPA; CD172A), CD207 and Fc fragment of IgE receptor Ia (FCER1A). In some embodiments, the tumor infiltrating dendritic cells express one or more proteins selected from the group consisting of basic leucine zipper ATF-like transcription factor 3 (BATF3) and interferon regulatory factor 8 (IRF8). In some embodiments, the tumor infiltrating dendritic cells express one or more proteins selected from the group consisting of BATF3, IRF8, THBD, CLEC9A and XCR1. In some embodiments, the subject has a cancer that detectably expresses or overexpresses one or more cell surface immune checkpoint receptors. In some embodiments, the one or more cell surface immune checkpoint receptors are selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments, greater than about 50% of the cancer or tumor cells detectably express one or more cell surface immune checkpoint receptor proteins (e.g., PD1 or PD-L1; a so-called "hot" cancer or tumor). In some embodiments, greater than about 1% and less than about 50% of the cancer or tumor cells detectably express one or more cell surface immune checkpoint receptor proteins (e.g., PD1 or PD-L1; a so called "warm" cancer or tumor). In some embodiments, less than about 1% of the cancer cells detectably express one or more cell surface immune checkpoint receptor proteins (e.g., PD1 or PD-L1; a so called "cold" cancer or tumor). In some embodiments, the subject has a cancer or tumor selected from the group consisting of an epithelial tumor (e.g., a carcinoma, a squamous cell carcinoma, a basal cell carcinoma, a squamous intraepithelial neoplasia), a glandular tumor (e.g., an adenocarcinoma, an adenoma, an adenomyoma), a mesenchymal or soft tissue tumor (e.g., a sarcoma, a rhabdomyosarcoma, a leiomyosarcoma, a liposarcoma, a fibrosarcoma, a dermatofibrosarcoma, a neurofibrosarcoma, a fibrous histiocytoma, an angiosarcoma, an angiomyxoma, a leiomyoma, a chondroma, a chondrosarcoma, an alveolar soft-part sarcoma, an epithelioid hemangioendothelioma, a Spitz tumor, a synovial sarcoma), and a lymphoma. In some embodiments, the subject has a solid tumor in or arising from a tissue or organ selected from the group consisting of: bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma); lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors); esophagus (e.g., Barrett's esophagus, dysplasia and adenocarcinoma); gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus; pancreas (e.g., serous neoplasms, including microcystic or macrocystic serous cystadenoma, solid serous cystadenoma, Von Hippel-Landau (VHL)-associated serous cystic neoplasm, serous cystadenocarcinoma; mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma); gall bladder (e.g., carcinoma of the gallbladder and extrahepatic bile ducts, intrahepatic cholangiocarcinoma); neuro-endocrine (e.g., adrenal cortical carcinoma, carcinoid tumors, phaeochromocytoma, pituitary adenomas); thyroid (e.g., anaplastic (undifferentiated) carcinoma, medullary carcinoma, oncocytic tumors, papillary carcinoma, adenocarcinoma); liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma; hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor); kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma); breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma; lobular carcinoma, including without limitation, pleomorphic carcinoma, signet ring cell carcinoma, peritoneum (e.g., mesothelioma; primary peritoneal cancer); female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, Müllerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina; male sex organ tissues, including prostate, testis (e.g., germ cell tumors, spermatocytic seminoma), penis; bladder (e.g., squamous cell carcinoma, urothelial carcinoma, bladder urothelial carcinoma); brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas (NHLs), indolent non-Hodgkin's lymphoma (iNHL), refractory iNHL, pituitary tumors; eye (e.g., retinoma, retinoblastoma, ocular melanoma, posterior uveal melanoma, iris hamartoma); head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal); thymus (e.g., thymoma); heart (e.g., cardiac myxoma); lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma); lymph (e.g., lymphomas, including Hodgkin's lymphoma, non-Hodgkin's lymphoma (NHL), indolent non-Hodgkin's lymphoma (iNHL), refractory iNHL, Epstein-Barr virus (EBV)-associated lymphoproliferative diseases, including B cell lymphomas and T cell lymphomas (e.g., Burkitt lymphoma; large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis); central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, Pituitary adenomas, cranial and paraspinal nerve tumors, stellar region tumors); neurofibroma, meningioma, peripheral nerve sheath tumors, peripheral neuroblastic tumours (including without limitation neuroblastoma, ganglioneuroblastoma, ganglioneuroma), trisomy 19 ependymoma); neuroendocrine tissues (e.g., paraganglionic system including adrenal medulla (pheochromocytomas) and extra-adrenal paraganglia ((extra-adrenal) paragangliomas); skin (e.g., clear cell hidradenoma, cutaneous benign fibrous histiocytomas, cylindroma, hidradenoma, melanoma (including cutaneous melanoma, mucosal melanoma), pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, lipoblastoma, lipoma, chondroid lipoma, liposarcoma/malignant lipomatous tumors, liposarcoma, myxoid liposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non-rhabdomyosarcoma soft tissue sarcoma (NRSTS), soft tissue leiomyosarcoma, undifferentiated sarcoma, well-differentiated liposarcoma. In some embodiments, the subject has a cancer selected from the group consisting of a lung cancer, a colorectal cancer, a breast cancer, a prostate cancer, a cervical cancer and a head and neck cancer. In some embodiments, the subject has neutropenia or lymphopenia. In some embodiments, the subject has received a lymphodepleting chemotherapy regimen. In some embodiments, the subject is naïve to or has not received chemotherapy. In some embodiments, the subject has bone marrow cells, or is not depleted of bone marrow cells. In some embodiments, the subject does not have a mutation in the gene encoding the FLT3 receptor that causes or results in or is associated with cancer. In some embodiments, the subject has a viral infection. In some embodiments, the subject is at risk of contracting a viral infection. In certain embodiments, the subject may have not previously received antiviral treatment (treatment naïve). In certain embodiments, the subject may have previously received antiviral treatment (treatment experienced). In some embodiments, the viral infection is an HBV infection. In some embodiments, the viral infection is an HIV infection. In some embodiments, the viral infection is a coronavirus infection. In some embodiments, the coronavirus is MERS-associated virus. In some embodiments, the coronavirus is a SARS-associated virus. In some embodiments, the coronavirus is a COVID-19-associated virus (SARS-CoV-2). In certain embodiments, the subject may have previously received antiviral treatment and developed resistance to the previously received antiviral treatment. In some embodiments, the FLT3L-Fc fusion protein, the homodimer, the heterodimer, the conjugate, the polynucleotide, the vector, the lipoplex, such as an LNP) and/or the pharmaceutical composition are administered systemically or locally. In some embodiments, the FLT3L-Fc fusion protein, the homodimer, the heterodimer, the conjugate, the polynucleotide, the vector, the lipoplex, such as an LNP, and/or the pharmaceutical composition are administered intravenously, intratumorally, subcutaneously, intradermally, intramuscularly, intraperitoneally, intravesically, intracranially, intrathecally, intracavitary or intraventricularly. In some embodiments, the FLT3L-Fc fusion protein, the homodimer, the heterodimer, the conjugate, the polynucleotide, the vector, the lipoplex, such as an LNP, and/or the pharmaceutical composition and the one or more additional therapeutic agents are administered by the same routes or by different routes of administration. In some embodiments, the FLT3L-Fc fusion protein, the homodimer, the heterodimer, the conjugate, the polynucleotide, the vector, the lipoplex, such as an LNP, and/or the pharmaceutical composition and the one or more additional therapeutic agents are administered concurrently or sequentially. In some embodiments, the FLT3L-Fc fusion protein has a serum half-life of at least about 7 days, e.g., at least about 8, 9, 10, 12, 14, 16, 18, 20, 22, 24, 26, 28, 30 days, or longer. In some embodiments, the methods entail multiple administrations of the FLT3L-Fc fusion protein, the homodimer, the heterodimer, the conjugate, the polynucleotide, the vector, the lipoplex, such as an LNP, and/or the pharmaceutical composition, optionally with one or more additional therapeutic agents, at predetermined intervals. In some embodiments, the fusion protein, the homodimer, the heterodimer, the conjugate, the polynucleotide, the vector, the lipoplex, such as an LNP, and/or the pharmaceutical composition is administered once weekly (i.e., QW), once bi-weekly (i.e., once every other week, or once every two weeks or Q2W), once thrice-weekly (i.e., once every three weeks or Q3W), once monthly (i.e., QM) or once bi-monthly dosing (i.e., once every other month, or once every two months or Q2M), or less often. In some embodiments, the FLT3L-Fc fusion protein, the homodimer, the heterodimer, the conjugate, the polynucleotide, the vector, the lipoplex, such as an LNP, and/or the pharmaceutical composition and the one or more additional therapeutic agents are co-administered according to the same schedule (e.g., co-administered at the same time intervals). In some embodiments, the FLT3L-Fc fusion protein, the homodimer, the heterodimer, the conjugate, the polynucleotide, the vector, the lipoplex, such as an LNP, and/or the pharmaceutical composition and the one or more additional therapeutic agents are co-administered according to different schedules (e.g., co-administered at different time intervals). In some embodiments, the FLT3L fusion protein, the homodimer, the heterodimer, the conjugate, the polynucleotide, the vector, the lipoplex, such as an LNP, and/or the pharmaceutical composition is administered at a dose in the range of about 0.5 µg/kg to about 5000 µg/kg, e.g., at least about 0.5 µg/kg per dose and up to about 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 15 µg/kg, 20 µg/kg, 30 µg/kg, 50 µg/kg, 100 µg/kg, 150 µg/kg, 300 µg/kg, 400 µg/kg, 500 µg/kg, 600 µg/kg, 700 µg/kg, 800 µg/kg, 900 µg/kg, 1000 µg/kg, 1500 µg/kg, 2000 µg/kg, 2500 µg/kg, 3000 µg/kg, 3500 µg/kg, 4000 µg/kg, or 5000 µg/kg, per dose. In some embodiments, the FLT3L fusion protein, the homodimer, the heterodimer, the conjugate, the polynucleotide, the vector, the lipoplex, such as an LNP and/or the pharmaceutical composition is administered at a dose in the range of about 1 µg/kg to about 100 µg/kg, e.g., at least about 1 µg/kg per dose and up to about 100 µg/kg per dose. In some embodiments, the FLT3L fusion protein, the homodimer, the heterodimer, the conjugate, the polynucleotide, the vector, the lipoplex, such as an LNP, and/or the pharmaceutical composition is administered at a dose of 1 µg/kg per dose, 3 µg/kg per dose, 10 µg/kg per dose, 30 µg/kg per dose, 60 µg/kg per dose, or 100 µg/kg per dose. In some embodiments, the FLT3L fusion protein, the homodimer, the heterodimer, the conjugate, the polynucleotide, the vector, the lipoplex, such as an LNP, and/or the pharmaceutical composition is administered at a dose of 1 µg/kg per dose. In some embodiments, the FLT3L fusion protein, the homodimer, the heterodimer, the conjugate, the polynucleotide, the vector, the lipoplex, such as an LNP, and/or the pharmaceutical composition is administered at a dose of 3 µg/kg per dose. In some embodiments, the FLT3L fusion protein, the homodimer, the heterodimer, the conjugate, the polynucleotide, the vector, the lipoplex, such as an LNP, and/or the pharmaceutical composition is administered at a dose of 10 µg/kg per dose. In some embodiments, the FLT3L fusion protein, the homodimer, the heterodimer, the conjugate, the polynucleotide, the vector, the lipoplex, such as an LNP, and/or the pharmaceutical composition is administered at a dose of 30 µg/kg per dose. In some embodiments, the FLT3L fusion protein, the homodimer, the heterodimer, the conjugate, the polynucleotide, the vector, the lipoplex, such as an LNP, and/or the pharmaceutical composition is administered at a dose of 60 µg/kg per dose. In some embodiments, the FLT3L fusion protein, the homodimer, the heterodimer, the conjugate, the polynucleotide, the vector, the lipoplex, such as an LNP, and/or the pharmaceutical composition is administered at a dose of 100 µg/kg per dose. In some embodiments, the FLT3L-Fc fusion protein, the homodimer, the heterodimer, the conjugate, the polynucleotide, the vector, the lipoplex, such as an LNP, and/or the pharmaceutical composition is administered at a dose in the range of about 0.5 mg to about 50 mg, e.g., at least about 0.5 mg per dose and up to about 1 mg, 2 mg, 3, mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg or 50 mg per dose. In some embodiments, the FLT3L-Fc fusion protein, the homodimer, the heterodimer, the conjugate, the polynucleotide, the vector, the lipoplex, such as an LNP, and/or the pharmaceutical composition is administered at a dose of 10 mg per dose. In some embodiments, the FLT3-expressing cells (e.g., dendritic cells) are expanded by at least about 10-fold, 20-fold, 50-fold, 100-fold, 200-fold, 300-fold, 400-fold, 500-fold, or more, within 3 weeks of a single administration of the fusion protein, the homodimer, the heterodimer, the conjugate, the polynucleotide, the vector, the lipoplex, such as an LNP, and/or the pharmaceutical composition. In some embodiments, the FLT3-expressing cells (e.g., dendritic cells) are expanded in the bone marrow and/or in a solid tumor in the subject.

In another aspect, provided are kits. In various embodiments, the kits comprise one or more unitary doses of the FLT3L-Fc fusion protein, the homodimer, the heterodimer, the conjugate, the polynucleotide, the expression cassette, the vector, the lipoplex, such as an LNP, and/or the pharmaceutical composition, as described above and herein. In some embodiments, the one or more unitary doses are in a single container. In some embodiments, the one or more unitary doses are in two or more separate containers. In some embodiments, the one or more containers can comprise vials, ampules, pre-loaded syringes and combinations thereof. In some embodiments, the kits comprise one or more containers comprising the FLT3L-Fc fusion protein, the homodimer, the heterodimer, or the conjugate in an aqueous solution. In some embodiments, the aqueous solution comprises the FLT3L-Fc fusion protein, the homodimer, the heterodimer, or the conjugate at a concentration in the range of about 1-20 mg/ml, e.g., from about 1 mg/ml to about 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml or 20 mg/ml. In some embodiments, the aqueous solution comprises the FLT3L-Fc fusion protein, the homodimer, the heterodimer, or the conjugate at a concentration of about 2 mg/ml. In various embodiments, the one or more unitary doses can be the same or different. In some embodiments, each unitary dose is in the range of about 0.5 mg to about 50 mg, e.g., at least about 0.5 mg per dose and up to about 1 mg, 2 mg, 3, mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg or 50 mg per dose. In some embodiments, each unitary dose is about 10 mg per dose. In some embodiments, the kits further comprise one or more unitary doses of one or more additional therapeutic agents. In some embodiments, the kits further comprise one or more unitary doses of one or more therapeutic agents selected from the group consisting of AGEN1884 (zalifrelimab), AGEN1181, AGEN2034 (balstilimab), AGEN1307, AGEN2373, AGEN1223 and GS-1423 (AGEN1423; see WO2019/173692). In some embodiments, the kits further comprise one or more oncolytic viral vectors. In some embodiments, the viral vector is from a viral family selected from the group consisting of: Adenoviridae (e.g., Adenovirus), Arenaviridae (e.g., lymphocytic choriomeningitis mammarenavirus, Cali mammarenavirus (a.k.a., Pichinde mammarenavirus), Poxviridae (e.g., Vaccinia virus), Herpesviridae (e.g., Herpesvirus, e.g., HSV-1), Parvoviridae (e.g., Parvovirus H1), Reoviridae (e.g., Reovirus), Picornaviridae (e.g., Coxsackievirus, Seneca Valley Virus, Poliovirus), Paramyxoviridae (e.g., Measles virus, Newcastle disease virus (NDV)), Rhabdoviridae (e.g., Vesicular stomatitis virus (VSV)), Togaviridae (e.g., Alphavirus, Sindbis virus), Enteroviridae (e.g., Echovirus). In some embodiments, the kits comprise one or more antibodies or antigen-binding antibody fragments thereof, or antibody-drug conjugates thereof, CD3-targeting multi-specific molecules, CD16-targeting multi-specific molecules, or non-immunoglobulin antigen-binding domains or antibody mimetic proteins, or population of immune cells comprising a chimeric antigen receptor directed against one or more targets selected from the group consisting of: CD19, MS4A1 (CD20), CD22, IL2RA (CD25), CD27, TNFRSF8 (CD30), CD33, CD37, CD38, CD40, CD44, CD48, CD52, CD70, NT5E (CD73), ENTPD1 (CD39), CD74, CD79b, CD80, CD86, IL3RA (CD123), PROM1 (CD133), CD137, SDC1 (CD138), alpha fetoprotein (AFP), c-Met; c-Kit; C-type lectin domain family 12 member A (CLEC12A, CLL1, CD371); C-type lectin domain containing 9A (CLEC9A, CD370); cadherin 3 (CDH3, p-cadherin, PCAD); carbonic anhydrase 6 (CA6); carbonic anhydrase 9 (CA9, CAIX); carcinoembryonic antigen related cell adhesion molecule 3 (CEACAM3); carcinoembryonic antigen related cell adhesion molecule 5 (CEACAM5); carcinoembryonic antigen related cell adhesion molecule 6 (CEACAM6, CD66c); chorionic somatomammotropin hormone 1 (CSH1, CS1); coagulation factor III, tissue factor (F3, TF); collectin subfamily member 10 (COLEC10); delta like canonical Notch ligand 3 (DLL3); ectonucleotide pyrophosphatase/phosphodiesterase 3 (ENPP3); ephrin A1 (EFNA1); epidermal growth factor receptor (EGFR); EGFR variant III (EGFRvIII); EPH receptor A2 (EPHA2); epithelial cell adhesion molecule (EPCAM); erb-b2 receptor tyrosine kinase 2 (ERBB2; HER2); fibroblast activation protein alpha (FAP); fibroblast growth factor receptor 2 (FGFR2); fibroblast growth factor receptor 3 (FGFR3); folate hydrolase 1 (FOLH1, PSMA); folate receptor 1 (FOLR1, FRα); GD2 ganglioside; glycoprotein NMB (GPNMB, osteoactivin); guanylate cyclase 2C (GUCY2C, GCC); human papillomavirus (HPV) E6; HPV E7; major histocompatibility complex (MHC) class I-presented neoantigens, major histocompatibility complex (MHC) class II-presented neoantigens, major histocompatibility complex, class I, E (HLA-E); major histocompatibility complex, class I, F (HLA-F); major histocompatibility complex, class I, G (HLA-G, MHC-G); integrin subunit beta 7 (ITGB7); leukocyte immunoglobulin like receptor B1 (LILRB1, ILT2); leukocyte immunoglobulin like receptor B2 (LILRB2, ILT4); LY6/PLAUR domain containing 3 (LYPD3, C4.4A); glypican 3 (GPC3); KRAS proto-oncogene, GTPase (KRAS); MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member D1 (MAGED1); MAGE family member D2 (MAGED2); mesothelin (MSLN); mucin 1 (MUC1) and splice variants thereof (e.g., MUC1/C, D, and Z); mucin 16 (MUC16); necdin (NDN); nectin cell adhesion molecule 4 (NECTIN4); SLIT and NTRK like family member 6 (SLITRK6); promyelocytic leukemia (PML, TRIM19); protein tyrosine kinase 7 (inactive) (PTK7); SLAM family member 6 (SLAMF6, CD352); SLAM family member 7 (SLAMF7, 19A, CD319, CRACC, CS1); sialic acid binding Ig like lectin 7 (SIGLEC7); sialic acid binding Ig like lectin 9 (SIGLEC9); solute carrier family 34 (sodium phosphate), member 2 (SLC34A2); solute carrier family 39 member 6 (SLC39A6; LIV1); STEAP family member 1 (STEAP1); TNF receptor superfamily member 4 (TNFRSF4, OX40 or CD134); TNF superfamily member 9 (TNFSF9; 4-1BB-L, CD137L); TNF receptor superfamily member 10a (TNFRSF10A, DR4, CD261, TRAILR1); TNF receptor superfamily member 10b (TNFRSF10B, DR5, CD262, TRAILR2); TNF receptor superfamily member 13B (TNFRSF13B; CD267, TACI, IGAD2); TNF receptor superfamily member 17 (TNFRSF17, BCMA, CD269); TNF receptor superfamily member 18 (TNFRSF18, GITR or CD357); transferrin (TF); transforming growth factor beta 1 (TGFB1); trophoblast glycoprotein (TPBG, 5T4); trophinin (TRO, MAGED3); tumor associated calcium signal transducer 2 (TACSTD2, TROP2, EGP1); Fucosyl GM1; sialyl Lewis adhesion molecule (sLe); and Lewis Y antigen. In some embodiments, the kits further comprise one or more antagonists or inhibitors of an inhibitory immune checkpoint protein or receptor and/or one or more activators or agonists of a stimulatory immune checkpoint protein or receptor. In some embodiments, the one or more immune checkpoint proteins or receptors are selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments, the kits further comprise one or more blockers or inhibitors of one or more T-cell inhibitory immune checkpoint proteins or receptors. In some embodiments, the T-cell inhibitory immune checkpoint proteins or receptors are selected from the group consisting of CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the kits further comprise one or more agonists or activators of one or more T-cell stimulatory immune checkpoint proteins or receptors. In some embodiments, the T-cell stimulatory immune checkpoint proteins or receptors are selected from the group consisting of CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the kits further comprise one or more blockers or inhibitors of one or more NK-cell inhibitory immune checkpoint proteins or receptors. In some embodiments, the NK-cell inhibitory immune checkpoint proteins or receptors are selected from the group consisting of killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); killer cell lectin like receptor D1 (KLRD1, CD94); killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments, the kits further comprise one or more agonists or activators of one or more NK-cell stimulatory immune checkpoint proteins or receptors. In some embodiments, the NK-cell stimulatory immune checkpoint proteins or receptors include without limitation CD16, CD226 (DNAM-1); killer cell lectin like receptor K1 (KLRK1, NKG2D, CD314); and SLAM family member 7 (SLAMF7). In some embodiments, the kits further comprise one or more inhibitors of CD274, PDCD1 or CTLA4. In some embodiments, the kits further comprise one or more inhibitors of CD274, PDCD1 or CTLA4 selected from the group consisting of ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), AK-104 (CTLA4/PD-1), pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, MGD-013 (PD-1/LAG-3), FS-118 (LAG-3/PD-L1), RO-7121661 (PD-1/TIM-3), M7824 (PD-L1/TGFβ-EC domain) and CA-170 (PD-L1/VISTA), CDX-527 (CD27/PD-L1), LY-3415244 (TIM3/PDL1), INBRX-105 (4-1BB/PDL1), GS-4224, GS-4416, INCB086550, MAX10181 and BPI-002. In some embodiments, the kits further comprise one or more containers comprising one or more populations of immune cells selected from the group consisting of: natural killer (NK) cells, NK-T cells, T cells, cytokine-induced killer (CIK) cells, macrophage (MAC) cells, tumor infiltrating lymphocytes (TILs) and dendritic cell (DCs). In some embodiments, the population of T cells is selected from the group consisting of: alpha/beta TCR T cells, gamma/delta TCR T cells, regulatory T (Treg) cells and TRuC™ T cells. In some embodiments, the kits further comprise a population of NK-92 cells. In some embodiments, the one or more populations of immune cells comprise one or more chimeric antigen receptors (CARs). In some embodiments, the cells are allogeneic to an intended recipient. In some embodiments, the kits further comprises one or more cytokines or chemokines selected from the group consisting of: IL 2, IL-12, IL-15, IL-18, IL-21, interferon (IFN)-α, IFN-β, IFN-γ, CXCL9/Mig (monokine induced by interferon-γ), CXCL10/IP10 (interferon-γ-inducible 10 kDa protein) and CXCL11/I-TAC (interferon-inducible T cell a-chemoattractant), CXCL4/PF4 (platelet factor 4), monocyte chemoattractant protein 2 (MCP-2), macrophage inflammatory protein 1 alpha (MIP-1a), macrophage inflammatory protein 1 beta (MIP-1β) and regulated on activation normal T expressed and secreted protein (RANTES), IL-1β, IL-4, IL-6, IL-8, IL-10, IL-13, IL-23, transforming growth factor (TGF)-β, colony stimulating factor 3 (CSF3, GCSF), colony stimulating factor 1 (CSF1), C-C motif chemokine ligand 2 (CCL2, MCP-1), chemokine (C-X-C motif) ligand 1 (CXCL1/MGSA), stromal cell-derived factor-1, TNFα and oncostatin M (OSM). In some embodiments, the kits further comprise one or more activators or agonists of: a toll-like receptor (TLR); a stimulator of interferon genes (STING) receptor; inducible T cell costimulator (ICOS, CD278); and/or a TNF receptor superfamily (TNFRSF) member. In some embodiments, the TNF receptor superfamily (TNFRSF) member is selected from the group consisting of: TNFRSF1A, TNFRSF1B, TNFRSF4 (OX40), TNFRSF5 (CD40), TNFRSF6 (FAS), TNFRSF7 (CD27), TNFRSF8 (CD30), TNFRSF9 (4-1BB, CD137), TNFRSF10A (CD261, DR4, TRAILR1), TNFRSF10B (CD262, DRS, TRAILR2), TNFRSF10C (CD263, TRAILR3), TNFRSF10D (CD264, TRAILR4), TNFRSF11A (CD265, RANK), TNFRSF11B, TNFRSF12A (CD266), TNFRSF13B (CD267), TNFRSF13C (CD268), TNFRSF16 (NGFR, CD271), TNFRSF17 (BCMA, CD269), TNFRSF18 (GITR, CD357), TNFRSF19, TNFRSF21 (CD358, DR6), and TNFRSF25 (DR3). In some embodiments, the TNFRSF4 activator or agonist comprises INCAGN1949, tavolimab (MEDI0562), pogalizumab (MOXR0916/RG7888), MEDI6469, BMS 986178, PF-04518600, GSK3174998, IBI101, ATOR-1015, ABBV-368 or SL-279252. In some embodiments, the TNFRSF9 (4-1BB or CD137) activator or agonist comprises urelumab, BMS-663513, utomilumab (PF-05082566), CTX-471, MP-0310, ADG-106, ATOR-1017 or AGEN2373. In some embodiments, the TNFRSF18 (GITR or CD357) agonist comprises GWN323, MEDI1873, MK-1248, MK-4166, TRX518, INCAGN1876, BMS-986156, BMS-986256, AMG-228, ASP1951 (PTZ 522), FPA-154 or OMP-336B11. In some embodiments, the kits comprise a molecule that concurrently binds to TNF receptor superfamily member 4 (TNFRSF4, OX40 or CD134) and TNF receptor superfamily member 18 (TNFRSF18, GITR or CD357). In some embodiments, the TLR agonist or activator is selected from the group consisting of a TLR2 agonist, a TLR3 agonist, a TLR4 agonist, a TLR5 agonist, a TLR7 agonist, a TLR8 agonist and a TLR9 agonist. In some embodiments, the TLR7 activator or agonist is selected from the group consisting of GS 9620, DS-0509, LHC-165, and TMX-101 (imiquimod), and/or wherein the TLR8 agonist is selected from the group consisting of GS-9688 and NKTR-262 (dual TLR7/TLR8 agonist). In some embodiments, the STING receptor activator or agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP. In some embodiments, the kit comprises an anti-CD47 antibody. In some embodiments, the anti-CD47 antibody is magrolimab. In some embodiments, the kit comprises a SIRPalpha inhibitor. In some embodiments, the SIRPalpha inhibitor is selected from the group consisting of AL-008, RRx-001, CTX-5861, FSI-189 (GS-0189), ES-004, BI765063, ADU1805, and CC-95251. In some embodiments, the kits comprise one or more inhibitors or antagonists of: protein tyrosine phosphatase, non-receptor type 11 (PTPN11 or SHP2), myeloid cell leukemia sequence 1 (MCL1) apoptosis regulator, mitogen-activated protein kinase kinase kinase kinase 1 (MAP4K1) (also called Hematopoietic Progenitor Kinase 1 (HPK1)), phosphatidylinositol-4,5-bisphosphate 3-kinase, including catalytic subunit alpha (PIK3CA), catalytic subunit beta (PIK3CB), catalytic subunit gamma (PIK3CG) and catalytic subunit delta (PIK3CD), diacylglycerol kinase alpha (DGKA, DAGK, DAGK1 or DGK-alpha), 5'-nucleotidase ecto (NTSE or CD73), ectonucleoside triphosphate diphosphohydrolase 1 (ENTPD1 or CD39), transforming growth factor beta 1 (TGFB1 or TGFβ), heme oxygenase 1 (HMOX1, HO-1 or HO1), heme oxygenase 2 (HMOX2, HO-2 or HO2), vascular endothelial growth factor A (VEGFA or VEGF), erb-b2 receptor tyrosine kinase 2 (ERBB2, HER2, HER2/neu or CD340), epidermal growth factor receptor (EGFR, ERBB, ERBB1 or HER1), ALK receptor tyrosine kinase (ALK, CD246), poly(ADP-ribose) polymerase 1 (PARP1), poly (ADP-ribose) polymerase 2 (PARP2), TCDD inducible poly (ADP-ribose) polymerase (TIPARP, PARP7), cyclin dependent kinase 4 (CDK4), cyclin dependent kinase 6 (CDK6), TNF receptor superfamily member 14 (TNFRSF14, HVEM, CD270), T cell immunoreceptor with Ig and ITIM domains (TIGIT), X-linked inhibitor of apoptosis (XIAP, BIRC4, IAP-3), baculoviral IAP repeat containing 2 (BIRC2, cIAP1), baculoviral IAP repeat containing 3 (BIRC3, cIAP2), baculoviral IAP repeat containing 5 (BIRC5, survivin), C-C motif chemokine receptor 2 (CCR2, CD192), C-C motif chemokine receptor 5 (CCR5, CD195), C-C motif chemokine receptor 8 (CCR8, CDw198), C-X-C motif chemokine receptor 2 (CXCR2, CD182), C-X-C motif chemokine receptor 3 (CXCR3, CD182, CD183), C-X-C motif chemokine receptor 4 (CXCR4, CD184), cytokine inducible SH2 containing protein (CISH), arginase (ARG1, ARG2), carbonic anhydrase (CA1, CA2, CA3, CA4, CASA, CA5B, CA6, CA7, CA8, CA9, CA10, CA11, CA12, CA13, CA14), prostaglandin-endoperoxide synthase 1 (PTGS1, COX-1), prostaglandin-endoperoxide synthase 2 (PTGS2, COX-2), secreted phospholipase A2, prostaglandin E synthase (PTGES, PGES), arachidonate 5-lipoxygenase (ALOXS, 5-LOX), soluble epoxide hydrolase 2 (EPHX2), indoleamine 2,3-dioxygenase 1 (IDO1), indoleamine 2,3-dioxygenase 2 (IDO2), hypoxia inducible factor 1 subunit alpha (HIF1A), angiopoietin 1 (ANGPT1), Endothelial TEK tyrosine kinase (TIE-2, TEK), Janus kinase 1 (JAK1), catenin beta 1 (CTNNB1), histone deacetylase 9 (HDAC9), 5'-3' exoribonuclease 1 (XRN1) and/or WRN RecQ like helicase (WRN). In some embodiments, the activator/agonist or the blocker/inhibitor comprises an antibody or an antigen-binding fragment thereof, or antibody-drug conjugate thereof, CD3-targeting multi-specific molecule, CD16-targeting multi-specific molecule, non-immunoglobulin antigen binding molecule or antibody mimetic protein. In some embodiments, the activator/agonist or the blocker/inhibitor comprises a small organic molecule. In some embodiments, the inhibitor of 5'-nucleotidase ecto (NT5E or CD73) is selected from the group consisting of MEDI9447 (oleclumab), CPI-006, BMS-986179, IPH5301, TJ4309 (TJDS), NZV-930, AB-680, PSB-12379, PSB-12441, PSB-12425, CB-708, GS-1423 (AGEN1423) and PBF-1662. In some embodiments, the inhibitor of CCR2 and/or CCR5 is selected from the group consisting of BMS-813160, PF-04136309 and CCX-872. In some embodiments, the inhibitor of MCL1 is selected from the group consisting of AMG-176, AMG-397, S-64315, AZD-5991, 483-LM, A 1210477, UMI-77 and JKY-5-037. In some embodiments, the inhibitor of PTPN11 or SHP2 is selected from the group consisting of TN0155 (SHP-099), RMC-4550, JAB-3068 and RMC-4630. In some embodiments, the kits further comprise an inhibitor or antagonist of a regulatory T cell (Treg). In some embodiments, the kits further comprise one or more anti-neoplastic or chemotherapeutic agents. In some embodiments, the one or more anti-neoplastic or chemotherapeutic agents are selected from the group consisting of a nucleoside analog (e.g., 5-fluorouracil, gemcitabine, cytarabine, cladribine, pentostatin, fludarabine), a taxane (e.g., paclitaxel, nab-paclitaxel, docetaxel, cabazitaxel), a platinum coordination complex (cisplatin, carboplatin, oxaliplatin, nedaplatin, triplatin tetranitrate, phenanthriplatin, picoplatin, satraplatin, dicycloplatin, eptaplatin, lobaplatin, miriplatin), a dihydrofolate reductase (DHFR) inhibitor (e.g., methotrexate, trimetrexate, pemetrexed), a topoisomerase inhibitor (e.g., doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114)), an alkylating agent (e.g., a nitrogen mustard (e.g., cyclophosphamide, chlormethine, uramustine or uracil mustard, melphalan, chlorambucil, ifosfamide, bendamustine), a nitrosourea (e.g., carmustine, lomustine, streptozocin), an alkyl sulfonate (e.g., busulfan)), and mixtures thereof.

DETAILED DESCRIPTION

1. Introduction

Figure 1:
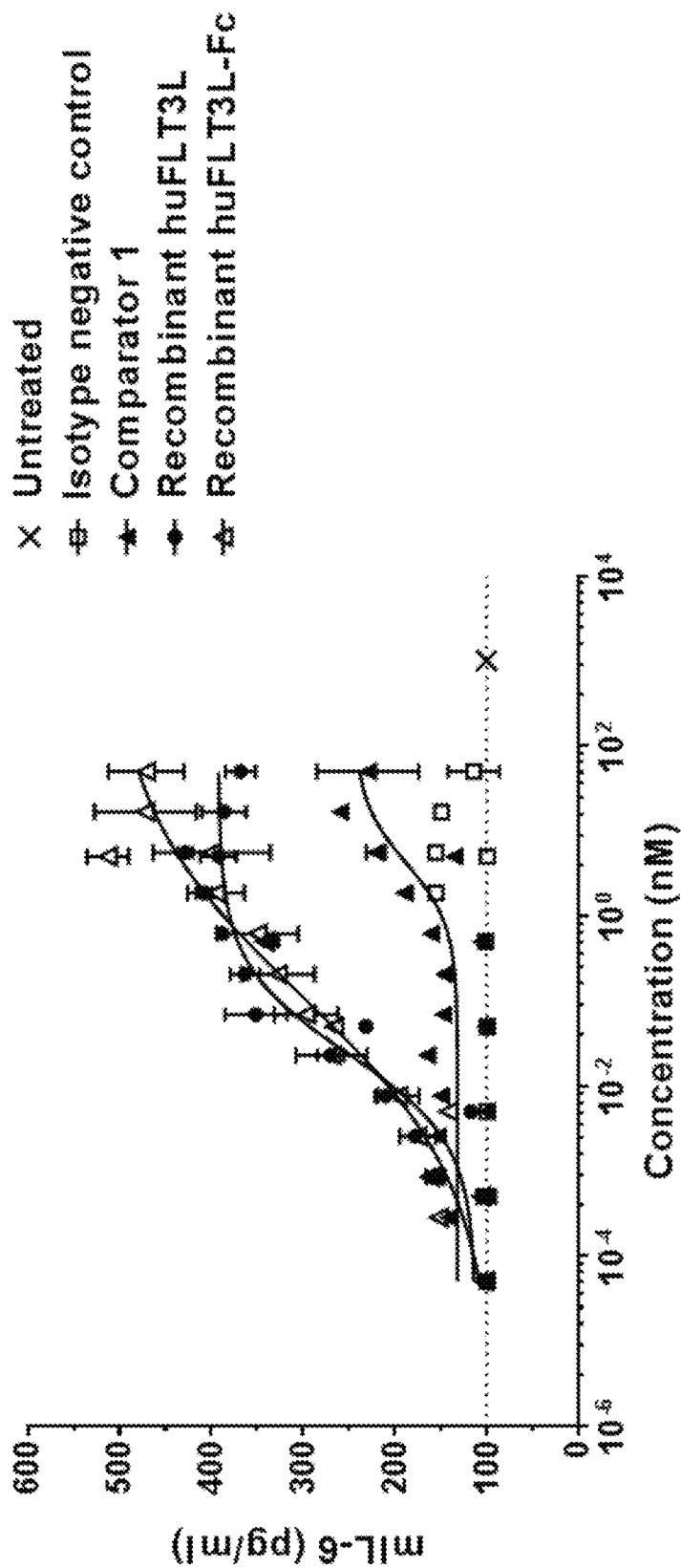
FIG. 1 illustrates induction of mouse IL-6 in a mouse FLT3-expressing M1 cell line by a titration (50-0.00005 nM) of recombinant human FLT3-ligand (Recombinant huFLT3L, closed circle), recombinant human FLT3-ligand human IgG1 fusion protein (Recombinant huFLT3L-Fc, open triangle), anti-mouse FLT3 agonist antibody (Comparator 1, closed triangle) or human IgG1 isotype antibody (Isotype negative control, open square). The x-axis shows the protein concentration (nM) and the y-axis shows mouse IL-6 concentration (pg/mL). The cross symbol indicates the IL-6 baseline level in untreated cells. Graph is a combination of two independent experiments. Experiments were performed in duplicate. Error bars represent standard deviation of the mean values. EC50 values are shown in Table 1.

Provided are fms related tyrosine kinase 3 ligand (FLT3L) extracellular domain—immunoglobulin fragment crystallizable region (Fc region) fusion proteins that have a serum half-life allowing for administration intervals that coordinates with other approved immuno-oncology therapeutic agents, e.g., about once every 1, 2, 3 or 4 weeks, or longer intervals. The FLT3L-Fc fusion proteins demonstrate favorable expression yields in in vitro culture, have structural properties that allow for efficient large-scale purification and long-term storage. The FLT3L-Fc fusion proteins described herein have an increased serum half-life in comparison to soluble FLT3L. Whereas soluble FLT3L must be administered on a daily basis, the herein described FLT3L-Fc fusion proteins can be administered about once every 1 to 8 weeks, or longer intervals.

The FLT3L-Fc fusion proteins described herein are differentiated from commercially available FLT3L-Fc fusion proteins (e.g., available from BioXCell or described in Kreiter, et al., Cancer Research (2011) 71(19):6132-42) by several structural modifications that result in improved functionality and the feasibility for administration to and functional efficacy in mammalian subjects. For example, the FLT3L-Fc fusion proteins described herein have been engineered and formulated for an improved glycosylation profile, allowing for a predictable and consistent serum half-life or pharmacokinetics (PK). The linker region between the ligand and the Fc fusion partner has reduced or eliminated glycosylation sites. In certain FLT3L-Fc fusion variants described herein, the IgG hinge region is truncated or eliminated. For example, in FLT3L-Fc fusion variants comprising a human IgG4 Fc, the N-terminal five amino acid residues of the IgG4 hinge (i.e., ESKYG (SEQ ID NO:97) are truncated or removed. Also, mutations have been incorporated to stabilize retained amino acids in a whole or truncated hinge region (e.g., S228P in a human IgG4 hinge), thereby eliminating Fab arm exchange or IgG half chain exchange, and allowing favorable chemical manufacturing controls. In addition, mutations have been introduced to reduce or eliminate Fc gamma receptor (FcRγ) binding (e.g., 234A/235A substitutions in a human IgG4), effectively reducing or eliminating antibody-dependent cell-mediated cytotoxicity (ADCC) or complement-dependent cytotoxicity (CDC). Further, alterations were made to enhance FcRn binding (e.g., 252Y/254T/256E substitutions in a human IgG4), resulting in a prolonged serum half-life of the FLT3L-Fc fusion protein (e.g., in comparison to a wild-type Fc).

In certain embodiments, the FLT3L-Fc fusion proteins described herein are not in an antibody format, and therefore only bind to the Flt3 and FcRn receptors. In such embodiments, the FLT3L-Fc fusion proteins described herein are structurally differentiated from WO 2005/001048 and WO 2006/060021, describing FLT3L fused to HER2, CD20, TRAIL, CD3 or SM5-1. In such embodiments, the lack of antigen directed binding allows systemic exposure of FLT3L-Fc which results in a systemic increase in cDC1 cells allowing the pharmacodynamics of the FLT3L-Fc to be monitored by liquid biopsy.

2. FLT3L-Fc Fusion Protein Compositions

Provided are fusion proteins comprising a fms related tyrosine kinase 3 ligand (FLT3L) extracellular domain operably linked to an immunoglobulin fragment crystallizable region (Fc region), wherein at least 5 amino acids are truncated from the C-terminus of the FLT3L extracellular domain; and/or wherein the Fc region does not comprise a hinge region.

In some embodiments, the FLT3L fusion proteins provided herein are capable of binding to human fms related tyrosine kinase 3 ligand (FLT3). Human fms related tyrosine kinase 3 is identified as NCBI Gene ID 2322 and is also known as human CD135, FLK-2, FLK2, or STK1. Binding of FLT3L fusion proteins to FLT3L can be analyzed, for example, by FACS, SPR, ELISA, immunoprecipitation-western blot, and other assay formats known in the art.

Fusion Proteins and Homodimers Thereof

FLT3L Extracellular Domain

In certain embodiments, the FLT3L extracellular domain comprises or is derived from a human FLT3L sequence. Human fms related tyrosine kinase 3 ligand is identified as NCBI Gene ID 2323 and the alternative symbols of FLT3LG, FLT3L, FL and FLG3L. NCBI identifies two isoforms and five transcriptional variants. Exemplary polynucleotide and polypeptide sequences of FLT3L include Ref Seq Nos. NM_001204502.1→NP_001191431.1 (isoform 1, transcript variant 1); NM_001204503.1→NP_001191432.1 (isoform 1, transcript variant 2); NM_001459.4→NP_001450.2 (isoform 1, transcript variant 3); NM_001278637.1→NP_001265566.1 (isoform 2, transcript variant 4); and NM_001278638.1→NP_001265567.1 (isoform 2, transcript variant 5). In some embodiments, the FLT3L extracellular domain comprises an amino acid sequence having at least 80%, at least 85%, at least 90%, at least 91%, at least 92%, at least 93%, at least 94%, at least 95%, at least 96%, at least 97%, at least 98%, at least 99%, or at least 100% identical to an amino acid sequence of NP_001191431.1, NP_001191432.1, NP_001450.2, NP_001265566.1 or NP_001265567.1, wherein the FLT3L extracellular domain binds to and activates signaling through fms related tyrosine kinase 3 (FLT3, CD135, FLK2, STK1). In some embodiments, the FLT3L extracellular domain comprises or is derived from human FLT3L isoform 1. In some embodiments, the FLT3L extracellular domain comprises or is derived from human FLT3L isoform 2.

In some embodiments, the FLT3L portion of the fusion protein comprises an amino acid sequence having at least 80%, at least 85%, at least 90%, at least 91%, at least 92%, at least 93%, at least 94%, at least 95%, at least 96%, at least 97%, at least 98%, at least 99%, or at least 100% identical to an amino acid sequence of
TQDCSFQHSPISSDFAVKIRELSDYLLQDYPVTVASN LQDEELCGGLWRLVLAQRWMERLKTVA GSKMQGLLERVNTEIHFVTKCAFQPPPSCLRFVQTNI SRLLQETSEQLVALKPWITRQNFSRCL ELQCQPDSSTLPPPWSPRP (SEQ ID NO:71); TQDCSFQHSPISSDFAVKIRELSDYLLQDYPV TVASNLQDEELCGGLWRLVLAQRWMERLKTVA GSKMQGLLERVNTEIHFVTKCAFQPPPSCLRFVQTNI SRLLQETSEQLVALKPWITRQNFSRCL ELQCQPDSSTLPPPWSPRPL (SEQ ID NO:72); TQDCSFQHSPISSDFAVKIRELSDYLLQDYPVTV ASNLQDEELCGGLWRLVLAQRWMERLKTVA GSKMQGLLERVNTEIHFVTKCAFQPPPSCLRFVQTNI SRLLQETSEQLVALKPWITRQNFSRCL ELQCQPDSSTLPPPWSPRPLE (SEQ ID NO:73); TQDCSFQHSPISSDFAVKIRELSDYLLQDYPVTVAS NLQDEELCGGLWRLVLAQRWMERLKTVA GSKMQGLLERVNTEIHFVTKCAFQPPPSCLRFVQTNI SRLLQETSEQLVALKPWITRQNFSRCL ELQCQPDSSTLPPPWSPRPLEA (SEQ ID NO:74); TQDCSFQHSPISSDFAVKIRELSDYLLQDYPVTVA SNLQDEELCGGLWRLVLAQRWMERLKTVA GSKMQGLLERVNTEIHFVTKCAFQPPPSCLRFVQTNI SRLLQETSEQLVALKPWITRQNFSRCL ELQCQPDSSTLPPPWSPRPLEAT (SEQ ID NO:75); TQDCSFQHSPISSDFAVKIRELSDYLLQDYPVTVASN LQDEELCGGLWRLVLAQRWMERLKTVA GSKMQGLLERVNTEIHFVTKCAFQPPPSCLRFVQTNI SRLLQETSEQLVALKPWITRQNFSRCL ELQCQPDSSTLPPPWSPRPLEATA (SEQ ID NO:76);

TQDCSFQHSPISSDFAVKIRELSDYLLQDYPVTVAS
NLQDEELCGGLWRLVLAQRWMERLKTVA
GSKMQGLLERVNTEIHFVTKCAFQPPPSCLRFVQTNI
SRLLQETSEQLVALKPWITRQNFSRCL
ELQCQPDSSTLPPPWSPRPLEATAP (SEQ ID NO:77);
TQDCSFQHSPISSDFAVKIRELSDYLLQDYPVTVASN
LQDEELCGGLWRLVLAQRWMERLKTVA
GSKMQGLLERVNTEIHFVTKCAFQPPPSCLRFVQTNI
SRLLQETSEQLVALKPWITRQNFSRCL
ELQCQPDSSTLPPPWSPRPLEATAPT (SEQ ID NO:78);
TQDCSFQHSPISSDFAVKIRELSDYLLQDYPVTVA
SNLQDEELCGGLWRLVLAQRWMERLKTVA
GSKMQGLLERVNTEIHFVTKCAFQPPPSCLRFVQTNI
SRLLQETSEQLVALKPWITRQNFSRCL
ELQCQPDSSTLPPPWSPRPLEATAPTA (SEQ ID NO:79);
TQDCSFQHSPISSDFAVKIRELSDYLLQDYPVTVASN
LQDEELCGGLWRLVLAQRWMERLKTVA
GSKMQGLLERVNTEIHFVTKCAFQPPPSCLRFVQTNI
SRLLQETSEQLVALKPWITRQNFSRCL
ELQCQPDSSTLPPPWSPRPLEATAPTAP (SEQ ID NO:80); or
TQDCSFQHSPISSDFAVKIRELSDYLLQDYPVTVAS
NLQDEELCGGLWRLVLAQRWMERLKTVA
GSKMQGLLERVNTEIHFVTKCAFQPPPSCLRFVQTNI
SRLLQETSEQLVALKPWITRQNFSRCL
ELQCQPDSSTLPPPWSPRPLEATAPTAPQ (SEQ ID NO: 81); wherein the FLT3L extracellular domain binds to and activates signaling through fms related tyrosine kinase 3 (Gene ID: 2322; FLT3, CD135, FLK2, STK1), and promotes or increases the proliferation of cells expressing FLT3 on their cell surface. In some embodiments, one or more FLT3L domain amino acid residues N100, S102, N123 and S125 are substituted, e.g., to remove the N-X-S/T motifs, and potential N-linked and/or O-linked glycosylation sites, e.g., to an amino acid residue selected from the group consisting of glycine (G), alanine (A), or valine (V), wherein the amino acid residue positions are with reference to SEQ ID NOs: 1-18, 21-27 or 71-81. In some embodiments, one or both of the serine residues at positions 102 and 125 are substituted to alanine (A), wherein the amino acid residue positions are with reference to SEQ ID NOs: 1-18, 21-27 or 71-81. In some embodiments, the FLT3L extracellular domain comprises one or more amino acid substitutions at the following positions: H8, K84, S102 and/or S125, wherein the amino acid residue positions are with reference to SEQ ID NOs: 1-18, 21-27 or 71-81. In some embodiments, the FLT3L extracellular domain comprises one or more of the following amino acid substitutions: H8Y, K84E; S102A; and/or S125A; wherein the amino acid residue positions are with reference to SEQ ID NOs: 1-18, 21-27 or 71-81.

Modifications may be made in the structure of the FLT3L-Fc polynucleotides and polypeptides described herein and still obtain a functional molecule that encodes a variant or derivative polypeptide with desirable characteristics. When it is desired to alter the amino acid sequence of a polypeptide to create an equivalent, or even an improved, variant or portion of a polypeptide described herein, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed antibodies and antigen-binding fragments thereof, or corresponding DNA sequences that encode said polypeptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, or over the full length of a sequence, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5: 151-153; Myers, E. W. and Muller W. (1988) CABIOS 4:11-17; Robinson, E. D. (1971) Comb. Theor 77: 105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides described herein. Software for performing BLAST analyses is publicly available through the National Center for Biotechnology Information (blast.ncbi.nlm.nih.gov/Blast.cgi).

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff (1989) Proc. Natl. Acad. Sci. USA 89: 10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

In some embodiments, the FLT3L extracellular domain does not comprise a signal peptide. In some embodiments, the FLT3L extracellular domain comprises an N-terminal signal peptide. The signal peptide can be an endogenous signal peptide (e.g., from a native or wild-type FLT3L protein), or from a heterologous polypeptide. In some embodiments, the heterologous signal peptide is from a secreted protein, e.g., a serum protein, an immunoglobulin or a cytokine. In some embodiments, the signal peptide is from a serum albumin signal peptide (e.g., having the amino acid sequence KWVTFISLLFLFSSAYS (SEQ ID NO:82). In some embodiments, the signal peptide is from a FLT3L protein (e.g., having the amino acid sequence MTVLAPAWSPTTYLLLLLLLSSGLSG (SEQ ID NO:83) or MTVLAPAWSPNSSLLLLLLLLSPCLRG (SEQ ID NO:84). The signal peptide can be designed to be cleaved off, e.g., after secretion from the cell, to form a mature fusion protein. A modified human serum albumin signal peptide to secrete proteins in cells that can find use in expressing the present fusion proteins is described, e.g., in Attallah, et al., *Protein Expr. Purif.* (2017) 132:27-33. Additional signal peptide sequences for use in expressing the herein described fusion proteins are described, e.g., in Kober, et al., *Biotechnol Bioeng.* (2013) 110(4):1164-73.

In some embodiments, at least five amino acids are truncated from the C-terminus of the FLT3L extracellular domain. For example, in various embodiments, at least 5, 6, 7, 8, 9, 10, 11, 12, 13, 14 or 15 amino acid residues are truncated or removed from the C-terminus of the FLT3L extracellular domain. In some embodiments, the FLT3L extracellular domain in the fusion protein is no longer than 147, 148, 149, 150, 151, 152, 153, 154, 155, 156 or 157 amino acid residues in length. In some embodiments, the FLT3L extracellular domain does not comprise the amino acid sequence PTAPQ (SEQ ID NO:85), APTAPQ (SEQ ID NO:86), TAPTAPQ (SEQ ID NO:87), ATAPTAPQ (SEQ ID NO:88), EATAPTAPQ (SEQ ID NO:89), or LEATAPTAPQ (SEQ ID NO:90). In some embodiments, the FLT3L extracellular domain does not comprise the amino acid sequence PTAPQPP (SEQ ID NO:91), APTAPQPP (SEQ ID NO:92), TAPTAPQPP (SEQ ID NO:93), ATAPTAPQPP (SEQ ID NO:94), EATAPTAPQPP (SEQ ID NO:95), or LEATAPTAPQPP (SEQ ID NO:96).

In certain embodiments, the FLT3L extracellular domain comprises or is derived from a mouse or murine FLT3L sequence. *Mus musculus* fms related tyrosine kinase 3 ligand is identified as NCBI Gene ID 14256 and the alternative symbols of Flt3l, Ly72L and Flt3lg. NCBI identifies one validated isoform and three unvalidated isoforms (X1, X2 and X3). Exemplary polynucleotide and polypeptide sequences of FLT3L include RefSeq Nos. NM_013520.3→NP_038548.3 (validated isoform 1); XM_006540607.3→XP_006540670.1 (isoform X1); XM_006540608.3→XP_006540671.1 (isoform X1); XM_006540606.2→XP_006540669.1 (isoform X1); XM_011250793.1→XP_011249095.1 (isoform X1); XM_006540609.3→XP_006540672.1 (isoform X2); XM_006540610.3→XP_006540673.1 (isoform X2); XM_006540612.3→XP_006540675.1 (isoform X3); and XM_011250794.2→XP_011249096.1 (isoform X3). In some embodiments, the FLT3L extracellular domain comprises an amino acid sequence having at least 80%, at least 85%, at least 90%, at least 91%, at least 92%, at least 93%, at least 94%, at least 95%, at least 96%, at least 97%, at least 98%, at least 99%, or at least 100% identical to an amino acid sequence of NP_038548.3, XP_006540670.1, XP_006540671.1, XP_006540669.1, XP_011249095.1, XP_006540672.1, XP_006540673.1, XP_006540675.1, XP_011249096.1, wherein the FLT3L extracellular domain binds to and activates signaling through fms related tyrosine kinase 3 (FLT3, CD135, FLK2, STK1), and promotes or increases the proliferation of cells expressing FLT3 on their cell surface. In some embodiments, the FLT3L extracellular domain comprises or is derived from murine FLT3L isoforms 1, X1, X2 or X3. In some embodiments, at least five amino acids are truncated from the C-terminus of the mouse FLT3L extracellular domain. For example, in various embodiments, at least 5, 6, 7, 8, 9, 10, 11, 12, 13, 14 or 15 amino acid residues are truncated or removed from the C-terminus of the mouse FLT3L extracellular domain. In some embodiments, the FLT3L extracellular domain in the fusion protein is no longer than 149, 150, 151, 152, 153, 154, 155, 156, 157, 158 or 159 amino acid residues in length.

In some embodiments, the mouse FLT3L portion of the fusion protein comprises an amino acid sequence having at least 80%, at least 85%, at least 90%, at least 91%, at least 92%, at least 93%, at least 94%, at least 95%, at least 96%, at least 97%, at least 98%, at least 99%, or at least 100% identical to an amino acid sequence of:

TPDCYFSHSPISSNFKVKFRELTDHLLKDYPVTVA-
VNLQDEKHCKALWSLFLAQRWIEQ LKTVAG-
SKMQTLLEDVNTEIHFVTSCTFQPLPECLRFVQT-
NISHLLKDTCTQLLALKPCI
GKACQNFSRCLEVQCQPDSSTLLPPRSPIALEATEL-
PEPR (SEQ ID NO:98), wherein the mouse FLT3L extracellular domain binds to and activates signaling through mouse fms related tyrosine kinase 3 (NCBI Human Gene ID: 14255; Flt3, Flk2; Ly72; wmfl; CD135; Flk-2; Flt-3; B230315G04). In some embodiments, cysteine at position 109 is substituted to an amino acid residue selected from the group consisting of glycine (G), alanine (A), serine (S), threonine (T) or valine (V), wherein the amino acid residue positions are with reference to SEQ ID NOs: 19, 20 and 42.

In certain embodiments, the FLT3L extracellular domain comprises or is derived from a macaque or *Macaca* FLT3L sequence. *Macaca mulatta* (Rhesus monkey) fms related tyrosine kinase 3 ligand is identified as NCBI Gene ID 719239 and the alternative symbols of FLT3L and FLT3LG. NCBI identifies five unvalidated isoforms (X1, X2, X3, X4, X5). Exemplary polynucleotide and polypeptide sequences of FLT3L include RefSeq Nos. XM_015124576.1→XP_014980062.1 (isoform X1), XM_015124578.1→XP_014980064.1 (isoform X2), XM_015124579.1→XP_014980065.1 (isoform X3), XM_015124580.1→XP_014980066.1 (isoform X4) and XM_015124581.1→XP_014980067.1 (isoform X5). In some embodiments, the FLT3L extracellular domain comprises an amino acid sequence having at least 80%, at least 85%, at least 90%, at least 91%, at least 92%, at least 93%, at least 94%, at least 95%, at least 96%, at least 97%, at least 98%, at least 99%, or at least 100% identical to an amino acid sequence of XP_014980062.1, XP_014980064.1, XP_014980065.1, XP_014980066.1 or XP_014980067.1, wherein the FLT3L extracellular domain binds to and activates signaling through fms related tyrosine kinase 3 (FLT3, CD135, FLK2, STK1), and promotes or increases the proliferation of cells expressing FLT3 on their cell surface. In some embodiments, the FLT3L extracellular domain comprises or is derived from macaque FLT3L isoforms X1, X2, X3, X4 or X5. In some embodiments, at least five amino acids are truncated from the C-terminus of the macaque FLT3L extracellular domain. For example, in various embodiments, at least 5, 6, 7, 8, 9, 10, 11, 12, 13, 14 or 15 amino acid residues are truncated or removed from the C-terminus of the macaque FLT3L extracellular domain. In some embodiments, the FLT3L extracellular domain in the fusion protein is no longer than 145, 146, 147, 148, 149, 150, 151, 152, 153, 154, 155, 156, 157, 158, 159, 160, 161, 162, 163, 164 or 165 amino acid residues in length.

As appropriate, in certain embodiments, the FLT3L extracellular domain is comprised of or derived from a canine or a feline FLT3L extracellular domain. In some embodiments, the dog or *Canis lupus* FLT3L portion of the fusion protein comprises an amino acid sequence having at least 80%, at least 85%, at least 90%, at least 91%, at least 92%, at least 93%, at least 94%, at least 95%, at least 96%, at least 97%, at least 98%, at least 99%, or at least 100% identical to an amino acid sequence of: NP_001003350.1, XP_005615795.1 or XP_022273164.1. In some embodiments, the cat or *Felis catus* FLT3L portion of the fusion protein comprises an amino acid sequence having at least 80%, at least 85%, at least 90%, at least 91%, at least 92%, at least 93%, at least 94%, at least 95%, at least 96%, at least 97%, at least 98%, at least 99%, or at least 100% identical to an amino acid sequence of: NP_001009842.1 or XP_011287950.1.

A "polypeptide variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences described herein and evaluating one or more biological activities of the polypeptide as described herein and/or using any of a number of techniques well known in the art.

The term "variant" may also refer to any naturally occurring or engineered molecule comprising one or more nucleotide or amino acid mutations. In one embodiment, the multi-specific antigen binding molecule is a bispecific antigen binding molecule. In one embodiment, the multi-specific antigen binding molecule is a bispecific antibody. For example, somatic variants may encompass all related naturally occurring antibodies that are part of or derived from the same B-cell lineage. Engineered variants may encompass all single mutations or combinatorial mutations made to an antibody.

Fc Region

The FLT3L extracellular domain, or truncated fragment thereof, is operably linked to an Fc domain. Generally, the Fc domain is comprised of or derived from the same species as the FLT3L extracellular domain (e.g., human, dog, cat, mouse or monkey). In some embodiments, the FLT3L extracellular domain, or truncated fragment thereof, is directly linked or contiguously linked or abutted to the Fc domain. In some embodiments, the FLT3L extracellular domain, or truncated fragment thereof, is operably linked to the Fc domain via a linker. As appropriate, the linker can be a flexible linker, e.g., a sequence comprising 3 or 4 repeats of a GGGGS motif or "G-S linker" (SEQ ID NO:99) (Desplancq et al. 1994, *Protein Engineering* 7:1027-1033).

In some embodiments, the Fc region is from a human IgG1, IgG2, IgG3 or IgG4. In some embodiments, the Fc region is from a human IgG1 or IgG4.

In certain embodiments the FLT3L extracellular domain, or truncated fragment thereof, is directly linked to, or linked via an intervening amino acid sequence (e.g., a G-S linker), to a human IgG1 (e.g., mutant IgG1m3 sequence), IgG2, IgG3 or IgG4 with 1 to 10 (e.g., 1, 2, 3, 4, 5, 6, 7, 8, 9, 10) amino acid substitutions. In some embodiments, the Fc modifications can promote one or more of increased serum half-life or decreased antibody effector function of the molecule. In other embodiments, certain of these modifications, decrease antibody effector function and increase half-life of the antibody. In some embodiments, the FLT3L-Fc fusion proteins described herein comprise two or more, three or more, four or more, five or more, six or more, six or fewer, five or fewer, four or fewer, three or fewer, two or fewer, or one modified Fc amino acid residue(s). Exemplary amino acid substitutions are described below.

In some embodiments, the Fc domain of the fusion protein does not comprise a hinge region; it is truncated or deleted, in whole or in part. The structural hinge region of human IgG1, IgG2 and IgG4 antibodies is a peptide linker of about 19 to 23 amino acids containing two to four cysteine residues, is genetically encoded on the hinge exon together with the 5'-end of the CH2 exon, and allows for disulfide bridges between first and second Fc domains (Roux, et al., *J. Immunol.* (1998) 161:4083). The structural hinge region is comprised of amino acid residue positions 216-238 (EU numbering) or 226-251 (Kabat numbering) (identified on imgt.org). In some embodiments, the Fc region comprises or is derived from a human IgG4 isotype and does not comprise the amino acid sequence ESKYGPPCPPCP (SEQ ID NO:100). In some embodiments, the Fc region comprises or is derived from a human IgG1 isotype and does not comprise the amino acid sequence EPKSCDKTHTCPPCP (SEQ ID NO:101) or EPKSCDKTHTCPPCPAPELL (SEQ ID NO:110).

Fc Mutations that Increase Serum Half-Life

In some embodiments, the Fc region comprises amino acid modifications that promote an increased serum half-life of the fusion protein. Mutations that increase the half-life of an antibody have been described. In one embodiment, the constant region of a FLT3L-Fc fusion proteins described herein comprise a methionine to tyrosine substitution at position 252 (EU numbering), a serine to threonine substitution at position 254 (EU numbering), and a threonine to glutamic acid substitution at position 256 (EU numbering). See, e.g., U.S. Pat. No. 7,658,921. This type of mutant, designated as a "YTE mutant" exhibits a four-fold increased half-life relative to wild-type versions of the same antibody (Dall'Acqua, et al., J Biol Chem, 281: 23514-24 (2006); Robbie, et al., Antimicrob Agents Chemotherap., 57(12): 6147-6153 (2013)). In certain embodiments, the FLT3L-Fc fusion proteins described herein comprise an IgG constant domain comprising one, two, three or more amino acid substitutions of amino acid residues at positions 251-257, 285-290, 308-314, 385-389, and 428-436 (EU numbering). Alternatively, M428L and N434S ("LS") substitutions can increase the pharmacokinetic half-life of the fusion protein. In other embodiments, the FLT3L-Fc fusion proteins described herein comprise a M428L and N434S substitution (EU numbering). In other embodiments, the FLT3L-Fc fusion proteins described herein comprise T250Q and M428L (EU numbering) mutations. In other embodiments, the FLT3L-Fc fusion proteins described herein comprise H433K and N434F (EU numbering) mutations.

Fc Mutations that Reduce or Eliminate Effector Activity

In some embodiments, the FLT3L-Fc fusion proteins described herein can have an Fc domain with amino acid substitutions that reduce or eliminate Fc effector function (including, e.g., antibody-dependent cellular cytotoxicity (ADCC), antibody-dependent cellular phagocytosis (ADCP), and complement-dependent cytotoxicity (CDC)).

In some embodiments, the Fc region is altered by replacing at least one amino acid residue with a different amino acid residue to reduce or eliminate effector function(s) of the antibody. For example, one or more amino acids selected from amino acid residues 234, 235, 236, 237, 297, 318, 320 and 322 (EU numbering) can be replaced with a different amino acid residue such that the fusion protein has decreased affinity for an effector ligand. The effector ligand to which affinity is altered can be, for example, an Fc receptor (e.g., at residue positions 234, 235, 236, 237, 297 (EU numbering)) or the C1 component of complement (e.g., at residue positions 297, 318, 320, 322 (EU numbering)). U.S. Pat. Nos. 5,624,821 and 5,648,260, both by Winter et al.

Fc modifications reducing or eliminating effector function include substitutions, insertions, and deletions, e.g., at one or more positions including 234, 235, 236, 237, 267, 269, 325, and 328, e.g., 234G, 235G, 236R, 237K, 267R, 269R, 325L, and 328R (EU numbering). Further, an Fc variant may comprise 236R/328R. Other modifications for reducing FcγR and complement interactions include substitutions at positions 297A, 234A, 235A, 318A, 228P, 236E, 268Q, 309L, 330S, 331S, 220S, 226S, 229S, 238S, 233P, and 234V (EU numbering). These and other modifications are reviewed in Strohl (2009) Current Opinion in Biotechnology 20:685-691. Effector functions (both ADCC and complement activation) can be reduced, while maintaining neonatal FcR binding (maintaining half-life), by mutating IgG residues at one or more of positions 233-236 and 327-331, such as E233P, L234V, L235A, optionally G236A, A327G, A330S and P331S in IgG1; E233P, F234V, L235A, optionally G236A, in IgG4; and A330S and P331S in IgG2 (EU numbering). See Armour et al. (1999) Eur. J. Immunol. 29:2613; WO 99/58572. Other mutations that reduce effector function include L234A and L235A in IgG1 (Alegre et al. (1994) Transplantation 57:1537); V234A and G237A in IgG2 (Cole et al. (1997) J. Immunol. 159:3613; see also U.S. Pat. No. 5,834,597); and S228P and L235E for IgG4 (Reddy et al. (2000) J. Immunol. 164:1925). Another combination of mutations for reducing effector function in a human IgG1 include L234F, L235E and P331S. Oganesyan et al. (2008) Acta Crystallogr. D. Biol. Crystallogr. 64:700. See generally Labrijn et gal. (2008) Curr. Op. Immunol. 20:479. Additional mutations found to decrease effector function in the context of an Fc (IgG1) fusion protein (abatacept) include C226S, C229S and P238S (EU numbering). Davis et al. (2007) J. Immunol. 34:2204.

ADCC activity may be reduced by modifying the Fc region. In certain embodiments, sites that affect binding to Fc receptors may be removed, e.g., sites other than salvage receptor binding sites. In other embodiments, an Fc region may be modified to remove an ADCC site. Exemplary ADCC sites have been described with respect to ADCC sites in IgG1 (Sarmay, et al, (1992) Molec. Immunol. 29 (5): 633-9). In one embodiment, the G236R and L328R variant of human IgG1 effectively eliminates FcγR binding (Horton, et al. (2011) J. Immunol. 186:4223 and Chu, et al. (2008) Mol. Immunol. 45:3926). In other embodiments, the Fc having reduced binding to FcγRs comprises the amino acid substitutions L234A, L235E and G237A. Gross, et al. (2001) Immunity 15:289. Modifications in the IgG Fc region to decrease binding to FcγRI to decrease ADCC (e.g., 234A; 235E; 236A; G237A) identified in WO 88/007089 can be used in the present fusion proteins. See also Duncan & Winter (1988) Nature 332:563; Chappel et al. (1991) Proc. Nat'l Acad. Sci. (USA) 88:9036; and Sondermann et al. (2000) Nature 406:267 (discussing the effects of these mutations on FcγRIII binding).

CDC activity may also be reduced by modifying the Fc region. Mutations at IgG1 positions D270, K322, P329 and P331, specifically alanine mutations D270A, K322A, P329A and P331A, significantly reduce the ability of the corresponding antibody to bind C1q and activate complement (Idusogie et al. (2000) J. Immunol. 164:4178; WO 99/51642. Modification of position 331 of IgG1 (e.g., P331S) has been shown to reduce complement binding (Tao et al. (1993) J. Exp. Med. 178:661; Xu Y, et al. J Biol Chem. 1994. 269:3469-74; and Canfield & Morrison (1991) J. Exp. Med. 173:1483). In another example, one or more amino acid residues within amino acid positions 231 to 239 are altered to thereby reduce the ability of the antibody to fix complement (WO 94/29351). Modifications in the IgG Fc region identified in WO 88/007089 that reduce or eliminate binding to complement component C1q, and therefore reduce or eliminate CDC (e.g., E318A or V/K320A and K322A/Q) can be used in the present fusion proteins.

In some embodiments, the Fc with reduced complement fixation has the amino acid substitutions A330S and P331S. Gross et al. (2001) Immunity 15:289.

Other Fc variants having reduced ADCC and/or CDC are disclosed at Glaesner et al. (2010) Diabetes Metab. Res. Rev. 26:287 (F234A and L235A to decrease ADCC and ADCP in an IgG4); Hutchins et al. (1995) Proc. Nat'l Acad. Sci. (USA) 92:11980 (F234A, G237A and E318A in an IgG4); An et al. (2009) MAbs 1:572 and U.S. Pat. App. Pub. 2007/0148167 (H268Q, V309L, A330S and P331S in an IgG2); McEarchern et al. (2007) Blood 109:1185 (C226S, C229S, E233P, L234V, L235A in an IgG1); Vafa et al. (2014) Methods 65:114 (V234A, G237A, P238S, H268A, V309L, A330S, P331S in an IgG2) (EU numbering).

In certain embodiments, the fusion protein has an Fc having essentially no effector function, e.g., the Fc has reduced or eliminated binding to FcγRs and reduced or eliminated complement fixation, e.g., is effectorless. An exemplary IgG1 Fc that is effectorless comprises the following five mutations: L234A, L235E, G237A, A330S and P331S (EU numbering) (Gross et al. (2001) Immunity 15:289). These five substitutions may be combined with N297A to eliminate glycosylation as well.

IgG1 Isotype Fc

In one embodiment, the Fc region comprises or is derived from a human IgG1. In some embodiments, the antibody has a chimeric heavy chain constant region (e.g., having the CH1, hinge, CH2 regions of IgG4 and CH3 region of IgG1).

IgG1 antibodies exist in various allotypes and isoallotypes. In particular embodiments, the FLT3L-Fc fusion proteins described herein include an IgG1 heavy chain having an allotype of G1m1; nG1m2; G1m3; G1m17,1; G1m17,1,2; G1m3,1; or G1m17. Each of these allotypes or isoallotypes is characterized by the following amino acid residues at the indicated positions within the IgG1 heavy chain constant region (Fc) (EU numbering):

G1m1: D356, L358;
nG1m1: E356, M358;
G1m3: R214, E356, M358, A431;
G1m17,1: K214, D356, L358, A431;
G1m17,1,2: K214, D356, L358, G431;
G1m3,1: R214, D356, L358, A431; and
G1m17: K214, E356, M358, A431.

In a specific embodiment, the FLT3L extracellular domain, or truncated fragment thereof, is directly linked to, or linked via an intervening amino acid sequence (e.g., a G-S linker), to a wild type IgG1m3 sequence, or fragment thereof, provided below.

(SEQ ID NO: 102)
EPKSCDKTHTCPPCPAPELLGGPSVFLFPPKP

KDTLMISRTPEVICVVVDVSHEDPEVKFNWYV

DGVEVHNAKTKPREEQYNSTYRVVSVLTVLHQ

DWLNGKEYKCKVSNKALPAPIEKTISKAKGQP

REPQVYTLPPSREEMTKNQVSLTCLVKGFYPS

DIAVEWESNGQPENNYKTTPPVLDSDGSFFLY

SKLTVDKSRWQQGNVFSCSVMHEALHNHYTQK

SLSLSPGK.

In certain embodiments, the FLT3L-Fc fusion protein has an IgG1 isotype. In some embodiments, the FLT3L-Fc fusion protein contains a human IgG1 constant region. In some embodiments, the human IgG1 Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A, N297Q (Bolt S et al. (1993) Eur J Immunol 23:403-411), D265A, L234A, L235A (McEarchem et al., (2007) Blood, 109:1185-1192), C226S, C229S (McEarchern et al., (2007) Blood. 109:1185-1192), P238S (Davis et al., (2007) J Rheumatol, 34:2204-2210), E233P, L234V (McEarchern et al., (2007) Blood, 109:1185-1192), P238A, A327Q, A327G, P329A (Shields R L. et al., (2001) J Biol Chem. 276(9):6591-604), K322A, L234F, L235E (Hezareh, et al., (2001) J Virol 75, 12161-12168; Oganesyan et al., (2008). Acta Crystallographica 64, 700-704), P331S (Oganesyan et al., (2008) Acta Crystallographica 64, 700-704), T394D (Wilkinson et al. (2013) MAbs 5(3): 406-417), A330L, M252Y, S254T, and/or T256E, where the amino acid position is according to the EU numbering convention. In certain embodiments, the Fc region further includes an amino acid deletion at a position corresponding to glycine 236 according to the EU numbering convention. As used herein, numbering of a given amino acid polymer or nucleic acid polymer "corresponds to", is "corresponding to" or is "relative to" the numbering of a selected or reference amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer.

In some embodiments, the FLT3L-Fc fusion protein has an IgG1 isotype with a heavy chain constant region that contains a C220S amino acid substitution according to the EU numbering convention.

In some embodiments, the Fc region comprises a human IgG1 isotype and comprises one or more amino acid substitutions in the Fc region at a residue position selected from the group consisting of: N297A, N297G, N297Q, N297G, D265A, L234A, L235A, C226S, C229S, P238S, E233P, L234V, P238A, A327Q, A327G, P329A, P329G, K322A, L234F, L235E, P331S, T394D, A330L, M252Y, S254T, T256E, M428L, N434S, T366W, T366S, L368A, Y407V and any combination thereof, wherein the numbering of the residues is according to EU numbering. In some embodiments, the Fc region comprises a human IgG1 isotype and comprises one or more amino acid substitutions in the Fc region at a residue position selected from the group consisting of: L234A, L234V, L234F, L235A, L235E, A330L, P331S, and any combination thereof, wherein the numbering of the residues is according to EU numbering.

IgG4 Isotype Fc

For uses where effector function is to be avoided altogether, e.g., when antigen binding alone is sufficient to generate the desired therapeutic benefit, and effector function only leads to (or increases the risk of) undesired side effects, IgG4 antibodies may be used, or antibodies or fragments lacking the Fc region or a substantial portion thereof can be devised, or the Fc may be mutated to eliminate glycosylation altogether (e.g., N297A). Alternatively, a hybrid construct of human IgG2 (CH1 domain and hinge region) and human IgG4 (CH2 and CH3 domains) has been generated that is devoid of effector function, lacking the ability to bind the FcγRs (like IgG2) and unable to activate complement (like IgG4). (see, Rother et al. (2007) Nat. Biotechnol. 25:1256; Mueller et al. (1997) Mol. Immunol. 34:441; and Labrijn et al. (2008) Curr. Op. Immunol. 20:479, discussing Fc modifications to reduce effector function generally).

In one embodiment, the Fc region comprises or is derived from a human IgG4. In certain embodiments, the FLT3L-Fc fusion protein has an IgG4 isotype. In some embodiments, the FLT3L-Fc fusion protein contains a human IgG4 constant region. In some embodiments, the human IgG4 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from E233P, F234V, F234A, L235A, G237A, E318A, S228P, L235E, T394D, M252Y, S254T, T256E, N297A, N297G, N297Q, T366W, T366S, L368A, Y407V, M428L, N434S, and any combination thereof, where the amino acid position is according to the EU numbering convention. See, e.g., Hutchins et al. (1995) *Proc Natl Acad Sci USA*, 92:11980-11984; Reddy et al., (2000) *J Immunol*, 164:1925-1933; Angal et al., (1993) *Mol Immunol*. 30(1):105-8; U.S. Pat. No. 8,614,299 B2; Vafa O. et al., (2014) *Methods* 65:114-126; and Jacobsen et. al., *J. Biol. Chem.* (2017) 292(5):1865-1875. In some embodiments, the Fc region comprises a human IgG4 isotype and comprises one or more amino acid substitutions in the Fc region at a residue position selected from the group consisting of: F234V, F234A, L235A, L235E, S228P, L234F, and any combination thereof, wherein the numbering of the residues is according to EU numbering.

In some embodiments, an IgG4 variant of the present disclosure may be combined with an S228P mutation according to the EU numbering convention (Angal et al., (1993) Mol Immunol, 30:105-108) and/or with one or more mutations described in Peters et al., (2012) J Biol Chem. 13; 287(29):24525-33) to enhance antibody stabilization.

IgG2 Isotype Fc

In certain embodiments, the FLT3L-Fc fusion protein has an IgG2 isotype. In some embodiments, the FLT3L-Fc fusion protein contains a human IgG2 constant region. In some embodiments, the human IgG2 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from P238S, V234A, G237A, H268A, H268Q, H268E, V309L, N297A, N297G, N297Q, V309L, A330S, P331 S, C232S, C233S, M252Y, S254T, and/or T256E, where the amino acid position is according to the EU numbering convention (Vafa, et al., (2014) Methods 65:114-126).

In certain embodiments, the FLT3L-Fc fusion proteins described herein comprise the L234F, L235E, D265A mutations, which are collectively referred to as "FEA." The FEA mutations decrease or abrogate effector function. In certain embodiments, the FLT3L-Fc fusion proteins described herein comprise the L234F, L235E, D265A, and F405L mutations, which are collectively referred to as "FEAL." In certain embodiments, the FLT3L-Fc fusion proteins described herein comprise the L234F, L235E, D265A, and a mutation selected from the group consisting of F405L, F405A, F405D, F405E, F405H, F405I, F405K, F405M, F405N, F405Q, F405S, F405T, F405V, F405W, and F405Y. In certain embodiments, the FLT3L-Fc fusion proteins described herein comprise the L234F, L235E, D265A, and K409R mutations, which are collectively referred to as "FEAR." In certain embodiments, FEAL and FEAR are comprised in a fusion protein described herein. In certain embodiments, the FLT3L-Fc fusion proteins described herein additionally comprise the M428L and N434S mutations, which are collectively referred to as LS. In certain embodiments, the FLT3L-Fc fusion proteins described herein comprise the L234F, L235E, D265A, F405L, M428L, and N434S mutations, which are collectively referred to as "FEALLS." In certain embodiments, the FLT3L-Fc fusion proteins described herein comprise the L234F, L235E, D265A, M428L, and N434S mutations along with one further mutation selected from the group consisting of F405L, F405A, F405D, F405E, F405H, F405I, F405K, F405M, F405N, F405Q, F405S, F405T, F405V, F405W, and F405Y. In certain embodiments, the FLT3L-Fc fusion proteins described herein comprise the L234F, L235E, D265A, K409R, M428L, and N434S mutations which are collectively referred to as "FEARLS." In certain embodiments, FEALLS and FEARLS are comprised in a fusion protein described herein. By reducing or abrogating effector function on the Fc domains of the FLT3L-Fc fusion protein, cells bound by the molecule are not killed by innate effector cells e.g., NK cells, macrophages.

In certain embodiments, the one or more modifications are selected from the following Fc amino acid substitutions (EU numbering) or combinations thereof: L234F; L235E; G236A; S239D; F243L; D265E; D265A; S267E; H268F; R292P; N297Q; N297G; N297A; S298A; S324T; I332E; S239D; A330L; L234F; L235E; P331S; F243L; Y300L; V305I; P396L; S298A; E333A; K334A; E345R; L235V; F243L; R292P; Y300L; P396L; M428L; E430G; N434S; G236A, S267E, H268F, S324T, and I332E; G236A, S239D, and I332E; S239D, A330L, I332E; L234F, L235E, and P331S; F243L, R292P, Y300L, V305I, and P396L; G236A, H268F, S324T, and I332E; S239D, H268F, S324T, and I332E; S298A, E333A, and K334A; L235V, F243L, R292P, Y300L, and P396L; S239D, I332E; S239D, S298A, and I332E; G236A, S239D, I332E, M428L, and N434S; G236A, S239D, A330L, I332E, M428L, and N434S; S239D, I332E, G236A and A330L; M428L and N4343S; M428L, N434S; G236A, S239D, A330L, and I332E; and G236A and I332E. In certain embodiments, the one or more modifications is selected from the group consisting of: D265A, L234F, L235E, N297A, N297G, N297Q, and P331S. In certain embodiments, the one or more modifications are selected from N297A and D265A. In certain embodiments, the one or more modifications are selected from L234F and L235E. In certain embodiments, the one or more modifications are selected from L234F, L234E, and D265A. In certain embodiments, the one or more modifications are selected from L234F, L234E, and N297Q. In certain embodiments, the one or more modifications are selected from L234F, L235E, and P331S. In certain embodiments, the one or more modifications are selected from D265A and N297Q. In certain embodiments, the one or more modifications are selected from L234F, L235E, D265A, N297A, N297G, N297Q, and P331S.

Mutations that reduce Fc-receptor binding and find use in the herein described fusion proteins include, for example, N297A; N297G; N297Q; D265A; L234F/L235E; L234F/L235E/N297Q; L234F/L235E/P331S; D265A/N297Q; and L234F/L235E/D265A/N297Q/P331S (all EU numbering). In certain embodiments the FLT3L-Fc fusion proteins described herein described herein comprise L234F and L235E mutations. In certain embodiments the FLT3L-Fc fusion proteins described herein described herein comprise L234F, L235E, and D265A mutations. In certain embodiments the FLT3L-Fc fusion proteins described herein described herein comprise L234F, L235E, and N297Q mutations. In certain embodiments the FLT3L-Fc fusion proteins described herein described herein comprise an N297A or N297Q mutation. In certain embodiments the FLT3L-Fc fusion proteins described herein described herein comprise an N297A, N297G or N297Q mutation as well as L234F, L235E, and D265A mutations. In certain embodiments, one, two, three, four, or more amino acid substitutions are introduced into a Fc region to alter the effector function of the antigen binding molecule. For example, these substitutions are located at positions selected from the group consisting of amino acid residues 234, 235, 236, 237, 265, 297, 318, 320, and 322, (according to EU numbering). These positions can be replaced with a different amino acid residue such that the antigen binding molecule has an altered (e.g., reduced) affinity for an effector ligand (e.g., an Fc receptor or the C1 component of complement), but retains the antigen binding ability of the parent antibody. In certain embodiments, the FLT3L-Fc fusion proteins described herein described herein comprise E233P, L234V, L235A, and/or G236A mutations (EU numbering). In some embodiments, the FLT3L-Fc fusion proteins described herein comprise A327G, A330S, and/or P331S mutations (EU numbering). In some embodiments, the FLT3L-Fc fusion proteins described herein comprise K322A mutations (EU numbering). In some embodiments the FLT3L-Fc fusion proteins described herein comprise E318A, K320A, and K322A (EU numbering) mutations. In certain embodiments, the FLT3L-Fc fusion proteins described herein comprise a L235E (EU numbering) mutation.

In some embodiments, the Fc portion of the fusion protein comprises an amino acid sequence having at least 80%, at least 85%, at least 90%, at least 91%, at least 92%, at least 93%, at least 94%, at least 95%, at least 96%, at least 97%, at least 98%, at least 99%, or at least 100% identical to an amino acid sequence of

```
                                    (SEQ ID NO: 103)
GGPSVFLFPPKPKDTLMISRTPEVTCVVVDVS

HEDPEVKFNWYVDGVEVHNAKTKPREEQYNST

YRVVSVLTVLHQDWLNGKEYKCKVSNKALPAP

IEKTISKAKGQPREPQVYTLPPSREEMTKNQV

SLTCLVKGFYPSDIAVEWESNGQPENNYKTTP

PVLDSDGSFFLYSKLTVDKSRWQQGNVFSCSV

MHEALHNHYTQKSLSLSPGK;

(SEQ ID NO:104)
GGPSVFLFPPKPKDTLYITREPEVTCVVVDVS

HEDPEVKFNWYVDGVEVHNAKTKPREEQYNST

YRVVSVLTVLHQDWLNGKEYKCKVSNKALPAP

IEKTISKAKGQPREPQVYTLPPSREEMTKNQV

SLTCLVKGFYPSDIAVEWESNGQPENNYKTTP

PVLDSDGSFFLYSKLTVDKSRWQQGNVFSCSV

MHEALHNHYTQKSLSLSPGK;

(SEQ ID NO: 105)
ESKYGPPCPPCPAPEFEGGPSVFLFPPKPKDT

LMISRTPEVTCVVVDVSQEDPEVQFNWYVDGV

EVHNAKTKPREEQFNSTYRVVSVLTVLHQDWL

NGKEYKCKVSNKGLPSSIEKTISKAKGQPREP

QVYTLPPSQEEMTKNQVSLTCLVKGFYPSDIA

VEWESNGQPENNYKTTPPVLDSDGSFFLYSRL

TVDKSRWQEGNVFSCSVMHEALHNHYTQKSLS

LSLGK;

(SEQ ID NO: 106)
ESKYGPPCPPCPAPEAAGGPSVFLFPPKPKDT

LMISRTPEVTCVVVDVSQEDPEVQFNWYVDGV

EVHNAKTKPREEQFNSTYRVVSVLTVLHQDWL

NGKEYKCKVSNKGLPSSIEKTISKAKGQPREP

QVYTLPPSQEEMTKNQVSLTCLVKGFYPSDIA

VEWESNGQPENNYKTTPPVLDSDGSFFLYSRL

TVDKSRWQEGNVFSCSVMHEALHNHYTQKSLS

LSLGK;
or
                                    (SEQ ID NO: 107)
ESKYGPPCPPCPAPEFEGGPSVFLFPPKPKDT

LYITREPEVTCVVVDVSQEDPEVQFNWYVDGV

EVHNAKTKPREEQFNSTYRVVSVLTVLHQDWL

NGKEYKCKVSNKGLPSSIEKTISKAKGQPREP

QVYTLPPSQEEMTKNQVSLTCLVKGFYPSDIA

VEWESNGQPENNYKTTPPVLDSDGSFFLYSRL

TVDKSRWQEGNVFSCSVMHEALHNHYTQKSLS

LSLGK.
```

Illustrative polypeptide sequences of the FLT3L-Fc fusion proteins described herein are provided in Table A. In some embodiments, FLT3-Fc fusion protein comprises an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 1-18 and 21-27. In some embodiments, FLT3-Fc fusion protein comprises an amino acid sequence selected from the group consisting of SEQ ID NOs: 1-18 and 21-27. In some embodiments, FLT3-Fc fusion protein comprises an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 19-20. In some embodiments, FLT3-Fc fusion protein comprises an amino acid sequence selected from the group consisting of SEQ ID NOs: 19-20.

In various embodiments, the FLT3L-Fc fusion proteins may be glycosylated or aglycosylated. In certain embodiments where the FLT3L-Fc fusion protein is glycosylated, at least 50%, at least 60%, at least 70%, least 80%, at least 85%, at least 90%, or more, N-linked and/or O-linked glycosylation sites in the fusion protein are sialylated. In certain embodiments where the FLT3L-Fc fusion protein is sialylated, the sialylated N-linked and/or O-linked glycosylation sites in the fusion protein comprise from 2 to 7 sialic acid residues, e.g., from 3 to 6 sialic acid residues, e.g., from 4 to 5 sialic acid residues.

In some embodiments, the FLT3L-Fc fusion proteins have a serum half-life of at least about 7 days, e.g., in a mammal, e.g., in a human, monkey, mouse, cat or dog. In some embodiments, the FLT3L-Fc fusion proteins have a serum half-life of at least about 7 days, e.g., at least about 8, 9, 10, 12, 14, 16, 18, 20, 22, 24, 26, 28, 30 days, or longer, e.g., in a mammal, e.g., in a human, monkey, mouse, cat or dog. Generally, a shorter serum half-life is observed with relatively lower doses. A longer serum half-life is observed with relatively higher doses.

Functionally, the FLT3L-Fc fusion proteins described herein induce, promote and/or increase the growth, proliferation and/or expansion of cells or populations of cells that express or overexpress FLT3 on their cell surface. Illustrative cells or populations of cells that express or overexpress FLT3 include dendritic cells (e.g., cDC1 cells and/or cDC2 cells), monocyte-derived dendritic cells (moDCs), and/or progenitor cells thereof. In some embodiments, the cell or population of cells that express FLT3 comprise hematopoietic progenitor cells, e.g., Common Lymphoid Progenitors (CLPs), Early Progenitors with Lymphoid and Myeloid potential (EPLMs), granulocyte-monocyte (GM) progenitors (GMP), monocyte-derived dendritic cells (moDCs) progenitors, and early multi-potent progenitors (MPP) within the Lineage-kit+Sca1 (LSK) compartment.

TABLE A

FLT3L-Fc fusion proteins

| PROTEIN NO: SEQ ID NO: | Features | Polypeptide Sequence (Fc domain is underlined) |
|---|---|---|
| 1 | FLT3L ECD-hingeless hG1 | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPLEATAPTAPQGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAPIEKTISK AKGQPREPQVYTLPPSREEMTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 2 | FLT3L ECD (Δ C-term 5aa (PTAPQ; SEQ ID NO: 85))-hingeless hG1 | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPLEATAGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIEKTISKAKGQP REPQVYTLPPSREEMTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 3 | FLT3L ECD-hG4 S228P/L235E | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPLEATAPTAPQESKYGPPCPPCPAPEFEGGPSVFLFPPKPKDTLMISRT PEVTCVVVDVSQEDPEVQFNWYVDGVEVHNAKTKPREEQFNSTYRVVSVLTVLHQDWLNGKEYKC KVSNKGLPSSIEKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQKSLSLSLGK |
| 4 | FLT3L ECD-hG4 S228P/F234A/L235A | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPLEATAPTAPQESKYGPPCPPCPAPEAAGGPSVFLFPPKPKDTLMISRT PEVTCVVVDVSQEDPEVQFNWYVDGVEVHNAKTKPREEQFNSTYRVVSVLTVLHQDWLNGKEYKC KVSNKGLPSSIEKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQKSLSLSLGK |
| 5 | Aglyco-FLT3L ECD (S128A/S151A) hingeless hG1 | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNIARLLQETSEQLVALKPWITRQNFARCLEL QCQPDSSTLPPPWSPRPLEATAPTAPQGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAPIEKTISK AKGQPREPQVYTLPPSREEMTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 6 | FLT3L (Δ C-term 5aa (TTAPQ; SEQ ID NO: 85))-hG4 S228P/F234A/L235A | TQDCSFQHSPISSDFAVKIRELSDYLLQDYPVTVASNLQDEELCGGLWRLVLAQRWMERLKTVAG SKMQGLLERVNTEIHFVTKCAFQrrrSCLRFVQTNISRLLQETSEQLVALKPWITRQNFSRCLEL QCQPDSSTLPPPWSPRPLEATAESKYGPPCPPCPAPEAAGGPSVFLFPPKPKDTLMISRTPEVTC VVVDVSQEDPEVQFNWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQKSLSLSLGK |
| 7 | FLT3L ECD (Δ C-term 10aa (LEATAPTAPQ; SEQ ID NO: 90))-hingeless hG1 | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPGGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVLDSDGSFFLYSKLTVD KSRWQQGNVFSCSVMHEALHNHYTQKSLSLSPGK |
| 8 | FLT3L ECD (Δ C-term 10aa (LEATAPTAPQ; SEQ ID NO: 90))-hG4 S228P/F234A/L235A | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPESKYGPPCPPCPAPEAAGGPSVFLFPPKPKDTLMISRTPEVTCVVVDV SQEDPEVQFNWYVDGVEVHNAKTKPREEQFNSTYRVVSVLTVLHQDWLNGKEYKCKVSNKGLPSS IEKTISKAKGQPREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLGK |

TABLE A-continued

FLT3L-Fc fusion proteins

| PROTEIN NO: SEQ ID NO: | Features | Polypeptide Sequence (Fc domain is underlined) |
|---|---|---|
| 9 | FLT3L ECD-hingeless hG1 (M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPLEATAPTAPQGGPSVFLFPPKPKDTLYITREPEVTCVVVDVSHEDPEV KFNWYVDGVEVHNAKTKPREEQYNSTYRVVSVLTVLHQDWLNGKEYKCKVSNKALPAPIEKTISK AKGQPREPQVYTLPPSREEMTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 10 | FLT3L ECD (Δ C-term 5aa (PTAPQ; SEQ ID NO: 85))-hingeless hG1 (M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPLEATAGGPSVFLFPPKPKDTLYITREPEVTCVVVDVSHEDPEVKFNWY VDGVEVHNAKTKPREEQYNSTYRVVSVLTVLHQDWLNGKEYKCKVSNKALPAPIEKTISKAKGQP REPQVYTLPPSREEMTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 11 | FLT3L ECD-hG4 S228P/L235E/ M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPLEATAPTAPQESKYGPPCPPCPAPEFEGGPSVFLFPPKPKDTLYITRE PEVTCVVVDVSQEDPEVQFNWYVDGVEVHNAKTKPREEQFNSTYRVVSVLTVLHQDWLNGKEYKC KVSNKGLPSSIEKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQKSLSLSLGK |
| 12 | FLT3L ECD-hG4 (S228P/F234A/L235A/ M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPLEATAPTAPQESKYGPPCPPCPAPEAAGGPSVFLFPPKPKDTLYITRE PEVTCVVVDVSQEDPEVQFNWYVDGVEVHNAKTKPREEQFNSTYRVVSVLTVLHQDWLNGKEYKC KVSNKGLPSSIEKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQKSLSLSLGK |
| 13 | Aglyco-FLT3L ECD (S128A/S151A) hingeless hG1 (M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNIARLLQETSEQLVALKPWITRQNFARCLEL QCQPDSSTLPPPWSPRPLEATAPTAPQGGPSVFLFPPKPKDTLYITREPEVTCVVVDVSHEDPEV KFNWYVDGVEVHNAKTKPREEQYNSTYRVVSVLTVLHQDWLNGKEYKCKVSNKALPAPIEKTISK AKGQPREPQVYTLPPSREEMTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 14 | FLT3L ECD (Δ C-term 5aa (PTAPQ; SEQ ID NO: 85))-hG4 (S228P/F234A/L235A/ M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPLEATAESKYGPPCPPCPAPEAAGGPSVFLFPPKPKDTLYITREPEVTC VVVDVSQEDPEVQFNWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQKSLSLSLGK |
| 15 | FLT3L ECD (Δ C-term 10aa (LEATAPTAPQ; SEQ ID NO: 90))-hG1 (M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPGGPSVFLFPPKPKDTLYITREPEVTCVVVDVSHEDPEVKFNWYVDGVE VHNAKTKPREEQYNSTYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVLDSDGSFFLYSKLTVD KSRWQQGNVFSCSVMHEALHNHYTQKSLSLSPGK |
| 16 | FLT3L ECD (Δ C-term 10aa (LEATAPTAPQ; SEQ ID NO: 90))-hG4 (S228P/F234A/L235A/ M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDSSTLPPPWSPRPESKYGPPCPPCPAPEAAGGPSVFLFPPKPKDTLYITREPEVTCVVVDV SQEDPEVQFNWYVDGVEVHNAKTKPREEQFNSTYRVVSVLTVLHQDWLNGKEYKCKVSNKGLPSS IEKTISKAKGQPREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLGK |
| 17 | Aglyco-FLT3L ECD (Δ C-term 10aa (LEATAPTAPQ; SEQ ID NO: 90)) (S128A/S151A)-hG4 S228P/F234A/L235A | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNIARLLQETSEQLVALKPWITRQNFARCLEL QCQPDSSTLPPPWSPRPESKYGPPCPPCPAPEAAGGPSVFLFPPKPKDTLMISRTPEVTCVVVDV SQEDPEVQFNWYVDGVEVHNAKTKPREEQFNSTYRVVSVLTVLHQDWLNGKEYKCKVSNKGLPSS IEKTISKAKGQPREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLGK |
| 18 | Aglyco-FLT3L ECD (Δ C-term 10aa (LEATAPTAPQ; SEQ ID NO: 90)) (S128A/S151A)-hG4 (S228P/F234A/L235A/ M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNIARLLQETSEQLVALKPWITRQNFARCLEL QCQPDSSTLPPPWSPRPESKYGPPCPPCPAPEAAGGPSVFLFPPKPKDTLYITREPEVTCVVVDV SQEDPEVQFNWYVDGVEVHNAKTKPREEQFNSTYRVVSVLTVLHQDWLNGKEYKCKVSNKGLPSS IEKTISKAKGQPREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLGK |

TABLE A-continued

FLT3L-Fc fusion proteins

| PROTEIN NO: SEQ ID NO: | Features | Polypeptide Sequence (Fc domain is underlined) |
|---|---|---|
| 19 | Murine surrogate mFLT3L ECD-mG2a Fc (L234A/L235A/P329G) | TPDCYFSHSPISSNFKVKFRELTDHLLKDYPVTVAVNLQDEKHCKALWSLFLAQRWIEQLKTVAG SKMQTLLEDVNTEIHFVTSCTFQPLPECLRFVQTNISHLLKDTCTQLLALKPCIGKACQNFSRCL EVQCQPDSSTLLPPRSPIALEATELPEPR<u>GPTIKPCPPCKCPAPNAAGGPSVFIFPPKIKDVLMI SLSPIVTCVVVDVSEDDPDVQISWFVNNVEVHTAQTQTHREDYNSTLRVVSALPIQHQDWMSGKE FKCKVNNKDLGAPIERTISKPKGSVRAPQVYVLPPPEEEMTKKQVTLTCMVTDFMPEDIYVEWTN NGKTELNYKNTEPVLDSDGSYFMYSKLRVEKKNWVERNSYSCSWHEGLHNHHTTKSFSRTPGK</u> |
| 20 | Murine surrogate mFLT3L ECD (C136S) mG2a Fc (L234A/L235A/P329G) | TPDCYFSHSPISSNFKVKFRELTDHLLKDYPVTVAVNLQDEKHCKALWSLFLAQRWIEQLKTVAG SKMQTLLEDVNTEIHFVTSCTFQPLPECLRFVQTNISHLLKDTSTQLLALKPCIGKACQNFSRCL EVQCQPDSSTLLPPRSPIALEATELPEPR<u>GPTIKPCPPCKCPAPNAAGGPSVFIFPPKIKDVLMI SLSPIVTCVVVDVSEDDPDVQISWFVNNVEVHTAQTQTHREDYNSTLRVVSALPIQHQDWMSGKE FKCKVNNKDLGAPIERTISKPKGSVRAPQVYVLPPPEEEMTKKQVTLTCMVTDFMPEDIYVEWTN NCKTELNYKNTEPVLDSDCSYFMYSKLRVEKKNWVERNSYSCSWHECLHNHHTTKSFSRTPCK</u> |
| 21 | FLT3L ECD-hingeless monoFc | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL <u>QCQPDSSTLPPPWSPRPLEATAPTAPQGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAPIEKTISK AKGQPREPQVYTKPPSREEMTKNQVSLSCLVKGFYPSDIAVEWESNGQPENNYKTTVPVLDSDGS FRLASYLTVDKSRWQQGNVFSCSVMHEALHNHYTQKSLSLSPGK</u> |
| 22 | FLT3L ECD (H8Y)- hingeless hG1 Fc | TQDCSFQYSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL <u>QCQPDSSTLPPPWSPRPLEATAPTAPQGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAPIEKTISK AKGQPREPQVYTLPPSREEMTKNQVSLTCLVKGFYPSDIAVEWESNGQPENNYKTTPPVLDSDGS FFLYSKLTVDKSRWQQGNVFSCSVMHEALHNHYTQKSLSLSPGK</u> |
| 23 | FLT3L ECD (K84E)- hingeless hG1 Fc | TQDCSFQHSPISSDFAVKIRELSDYLLQDYPVTVASNLQDEELCGGLWRLVLAQRWMERLKTVAG SKMQGLLERVNTEIHFVTECAFQPPPSCLRFVQTNISRLLQETSEQLVALKPWITRQNFSRCLEL <u>QCQPDSSTLPPPWSPRPLEATAPTAPQGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAPIEKTISK AKGQPREPQVYTLPPSREEMTKNQVSLTCLVKGFYPSDIAVEWESNGQPENNYKTTPPVLDSDGS FFLYSKLTVDKSRWQQGNVFSCSVMHEALHNHYTQKSLSLSPGK</u> |
| 24 | FLT3L ECD (H8Y/K84E) hingeless hG1 Fc | TQDCSFQYSPISSDFAVKIRELSDYLLQDYPVTVASNLQDEELCGGLWRLVLAQRWMERLKTVAG SKMQGLLERVNTEIHFVTECAFQPPPSCLRFVQTNISRLLQETSEQLVALKPWITRQNFSRCLEL <u>QCQPDSSTLPPPWSPRPLEATAPTAPQGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAPIEKTISK AKGQPREPQVYTLPPSREEMTKNQVSLTCLVKGFYPSDIAVEWESNGQPENNYKTTPPVLDSDGS FFLYSKLTVDKSRWQQGNVFSCSVMHEALHNHYTQKSLSLSPGK</u> |
| 25 | Aglyco-FLT3L ECD (Δ C-term 5aa (PTAPQ; SEQ ID NO: 85)) (S128A/S151A)-hG4 (S228P/F234A/L235A/ M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNIARLLQETSEQLVALKPWITRQNFARCLEL <u>QCQPDSSTLPPPWSPRPLEATAESKYGPPCPPCPAPEAAGGPSVFLFPPKPKDTLYITREPEVTC VVVDVSQEDPEVQFNWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQKSLSLSLGK</u> |
| 26 | FLT3L ECD (Δ C-term 5aa (PTAPQ; SEQ ID NO: 85))-linker SST/AAA-hG4 (S228P/F234A/L235A/ M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDAAALPPPWSPRPLEATA<u>ESKYGPPCPPCPAPEAAGGPSVFLFPPKPKDTLYITREPEVTC VVVDVSQEDPEVQFNWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQKSLSLSLGK</u> |
| 27 | FLT3L ECD (Δ C-term 5aa (PTAPQ; SEQ ID NO: 85))-linker SST/AAA; S170A/S180A-hG4 (S228P/F234A/L235A/ M252Y/S254T/T256E) | TQDCSFQHSPISSDFAVKIRELSDYLLQDYPVTVASNLQDEELCGGLWRLVLAQRWMERLKTVAG SKMQGLLERVNTEIHFVTKCAFQPPPSCLRFVQTNISRLLQETSEQLVALKPWITRQNFSRCLEL QCQPDAAALPPPWAPRPLEATA<u>EAKYGPPCPPCPAPEAAGGPSVFLFPPKPKDTLYITREPEVTC VVVDVSQEDPEVQFNWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQKSLSLSLGK</u> |

Heterodimers and Fusion Proteins Comprising a FLT3L-Fc Fusion Protein and a Second Polypeptide Further provided are fusion proteins comprising (i) a FLT3L-Fc fusion protein described herein, e.g., having an amino acid sequence that is at least 80%, at least 85%, at least 90%, at least 91%, at least 92%, at least 93%, at least 94%, at least 95%, at least 96%, at least 97%, at least 98%, at least 99%, or 100%, identical to an amino acid sequence selected from the group consisting of SEQ ID NOs: 19-20, and (ii) a second polypeptide. In some embodiments, the second polypeptide comprises a targeting moiety or domain, a growth factor, a cytokine, a chemokine or a TNF superfamily (TNFSF) member. In some embodiments, the second polypeptide is N-terminal to the FLT3L extracellular domain. In some embodiments, the second polypeptide is C-terminal to the Fc region. In some embodiments, the second polypeptide is between the FLT3L extracellular domain and the Fc region. In various embodiments, the targeting moiety binds to a protein target in Table B.

Further provided are heterodimeric molecules comprising (i) a FLT3L-Fc fusion protein described herein, e.g., having an amino acid sequence that is at least 80%, at least 85%, at least 90%, at least 91%, at least 92%, at least 93%, at least 94%, at least 95%, at least 96%, at least 97%, at least 98%, at least 99%, or 100%, identical to an amino acid sequence selected from the group consisting of SEQ ID NOs: 19-20, and (ii) a second polypeptide fused to a second Fc region. In certain embodiments, the first and second Fc regions of the heterodimeric molecules are different, e.g., having complementary "knob (W)-and-hole (S)" amino acid substitutions at position 366 (EU numbering). In some embodiments, the second polypeptide comprises a targeting moiety or domain, a growth factor, a cytokine, a chemokine or a TNF superfamily (TNFSF) member. In various embodiments, the targeting moiety binds to a protein target in Table B.

In some embodiments, the targeting moiety or domain comprises an antibody fragment (e.g., scFv, sc(Fv)$_2$, Fab, F(ab)$_2$, Fab', F(ab')$_2$, Facb, and Fv). In some embodiments, the antibody fragment comprises a Fab or a single-chain variable fragment (scFv). In some embodiments, both the first Fc region and the second Fc region do not comprise a hinge region. In some embodiments, the heterodimer is stabilized by an interaction between the first Fc region and the second Fc region. Illustrative interactions that can stabilize the heterodimer through the Fc region include without limitation disulfide bonds and complementary amino acid substitutions in the first and second Fc regions (e.g., knob-in-hole mutations).

In some embodiments, the targeting moiety or domain comprises a non-immunoglobulin or antibody mimetic protein. Examples of non-immunoglobulin or antibody mimetic protein targeting moieties or domains include without limitation adnectins, affibody molecules, affilins, affimers, affitins, alphabodies, anticalins, peptide aptamers, armadillo repeat proteins (ARMs), atrimers, avimers, designed ankyrin repeat proteins (DARPins®), fynomers, knottins, Kunitz domain peptides, monobodies, and nanoCLAMPs. Non-immunoglobulin or antibody mimetic protein targeting moieties or domains of use in the herein described FLT3L-Fc fusion protein heterodimers are described, e.g., in Zhang, et al., Methods Mol Biol. 2017; 1575:3-13; Ta, et al., Future Med Chem. 2017 August; 9(12):1301-1304; Yu, et al., Annu Rev Anal Chem (Palo Alto Calif.). 2017 Jun. 12; 10(1):293-320; Baloch, et al., Crit Rev Biotechnol. 2016; 36(2):268-75; and Bruce, et al., Chembiochem. 2016 Oct. 17; 17(20): 1892-1899.

In some embodiments, the targeting moiety or domain has T-cell receptor (TCR)-like binding properties, and binds to the epitope of a target or tumor-associated antigen (TAA) presented in a major histocompatibility complex (MHC) molecule.

In some embodiments, the targeting moiety or domain comprises a binding partner domain, e.g., a soluble or extracellular domain of the binding partner or ligand of the protein target or antigen. For example, in some embodiments, the targeting moiety or domain comprises a binding partner or ligand of any of the protein or antigen targets listed in Table B. In one embodiment, the targeting moiety or domain comprises the extracellular domain of a TGFB1 receptor (e.g., a "TGF beta trap").

In homodimers or heterodimer formats of the FLT3L-Fc fusion proteins, the dimeric molecule comprises first and second Fc domains. In certain embodiments, amino acid substitutions may be in one or both of the first and second Fc domains. In certain embodiments, the one or both of the first and second Fc domains have one or more (1, 2, 3, 4, or 5) of the following mutations (EU numbering). In some embodiments, Fc region heterodimerization of the two different immunoadhesins (Fc fusion proteins) can be facilitated by so-called 'knobs-into-holes' mutations (Atwell et al. 1997. JMB 270:26-35). The 'hole' mutations (T366S, L368A and Y407V) are incorporated into one Fc-containing chain, the T366W 'knob' mutation is incorporated into the other chain. Knob-and-hole amino acid substitutions can be incorporated into human IgG1 or human IgG4 Fc domains. In addition, a C220S mutation can be incorporated into an IgG1 hinge region of a scFv-containing arm to eliminate a free cysteine that otherwise forms a disulfide bond with a corresponding cysteine in the light chain in a wild-type IgG1. Co-transfection of such constructs leads to preferential formation of a heterodimeric Fc, with low levels of homodimer contaminants. Additionally, incorporating a S354C mutation can be incorporated into the Fc containing the 'knob' mutations and a Y349C mutation into the Fc containing the 'hole' mutations can optionally be used to generate a covalent bond between the two halves of the heterodimeric Fc if additional thermodynamic stability is desired (Merchant et al. 1998. Nat. Biotechnol. 16: 677-81). In certain embodiments, R409D, K370E mutations are introduced in the "knobs chain" and D399K, E357K mutations in the "hole chain." In other embodiments, Y349C, T366W mutations are introduced in one of the chains and E356C, T366S, L368A, Y407V mutations in the counterpart chain. In some embodiments. Y349C, T366W mutations are introduced in one chain and S354C, T366S, L368A, Y407V mutations in the counterpart chain. In some embodiments, Y349C, T366W mutations are introduced in one chain and S354C, T366S, L368A, Y407V mutations in the counterpart chain. In yet other embodiments, Y349C, T366W mutations are introduced in one chain and S354C, T366S, L368A, Y407V mutations in the counterpart chain (all EU numbering).

To facilitate purification of the heterodimeric molecule away from contaminating homodimeric products, the H435R or H435R+Y436F mutations to reduce or eliminate protein A binding can be introduced into one but not both of the Fc-containing chains (Jendeberg, L. et al. 1997 J. Immunol. Methods 201:25-34). This reduces or eliminates protein A binding of the homodimer contaminant containing these mutations, and greatly simplifies purification of the desired heterodimer away from remaining homodimer contaminant via additional chromatography steps (e.g., ion exchange). In embodiments incorporating H435R (or H435R+Y436F) mutations in the first or second Fc region of a heavy chain, if the VH region in the same heavy chain is from a VH3 family variable region, this VH region can also include amino acid substitutions, as described herein, to reduce or eliminate Protein A binding of the entire heavy chain.

Yet another exemplary method of making bispecific antibodies is by using the Trifunctional Hybrid Antibodies platform—Triomab®. This platform employs a chimeric construction made up of half of two full-length antibodies of different isotypes, mouse IgG2a and rat IgG2b. This technology relies on species-preferential heavy/light chain pairing associations. See, Lindhofer et al., J Immunol., 155:219-225 (1995).

Yet another method for making bispecific antibodies is the CrossMab technology. CrossMab are chimeric antibodies constituted by the halves of two full-length antibodies. For correct chain pairing, it combines two technologies: (i) the knob-into-hole which favors a correct pairing between the two heavy chains; and (ii) an exchange between the heavy and light chains of one of the two Fabs to introduce an asymmetry which avoids light-chain mispairing. See, Ridgway et al., Protein Eng., 9:617-621 (1996); Schaefer et al., PNAS, 108:11187-11192 (2011). CrossMabs can combine two or more antigen binding domains for targeting two or more targets or for introducing bivalency towards one target such as the 2:1 format.

In some embodiments, the targeting moiety or domain targets or binds to an effector cell, e.g., engaging or activating a T-cell or an NK cell. In certain embodiments, the targeting moiety or domains binds to CD3. In some embodiments, the targeting moiety binds to CD16. Illustrative proteins and antigens, including tumor-associated antigens, immune checkpoint proteins and dendritic cell surface proteins, that can be targeted or bound by the targeting moiety or domain, include without limitation those listed in Table B. Target names, symbols (official and alternative) and Gene IDs identified in Table B are from ncbi.nlm.nih.gov/gene.

TABLE B

Illustrative Antigen/Protein Targets

| Target Name | NCBI Official Symbol | NCBI Human Gene ID No. | Alternative Symbols (also known as) |
|---|---|---|---|
| 5'-nucleotidase ecto | NT5E | 4907 | NT; eN; NT5; NTE; eNT; CD73; E5NT; CALJA |
| ALK receptor tyrosine kinase | ALK | 238 | CD246; NBLST3 |
| Alpha fetoprotein | AFP | 174 | AFPD, FETA, HPAFP |
| B and T lymphocyte associated | BTLA | 151888 | BTLA1, CD272 |
| cadherin 3 | CDH3 | 1001 | CDHP; HJMD; p-cadherin; PCAD |
| carbonic anhydrase 6 | CA6 | 765 | CA-VI; GUSTIN |
| carbonic anhydrase 9 | CA9 | 768 | MN; CAIX |
| carcinoembryonic antigen related cell adhesion molecule 3 | CEACAM3 | 1084 | CEA; CGM1; W264; W282; CD66D |
| carcinoembryonic antigen related cell adhesion molecule 5 | CEACAM5 | 1048 | CEA; CD66e |
| carcinoembryonic antigen related cell adhesion molecule 6 | CEACAM6 | 4680 | NCA; CEAL; CD66c |
| C-C motif chemokine receptor 2 | CCR2 | 729230 | CC-CKR-2, CCR-2, CCR2A, CCR2B, CD192, CKR2, CKR2A, CKR2B, CMKBR2, MCP-1-R |
| C-C motif chemokine receptor 4 | CCR4 | 1233 | CC-CKR-4, CD194, CKR4, CMKBR4, ChemR13, HGCN: 14099, K5-5 |
| C-C motif chemokine receptor 5 | CCR5 | 1234 | CC-CKR-5, CCCKR5, CCR-5, CD195, CKR-5, CKR5, CMKBR5, IDDM22 |
| C-C motif chemokine receptor 8 | CCR8 | 1237 | CC-CKR-8, CCR-8, CDw198, CKRL1, CMKBR8, CMKBRL2, CY6, GPRCY6, TER1 |
| CD160 molecule | CD160 | 11126 | BY55, NK1, NK28 |
| CD19 molecule | CD19 | 930 | B4; CVID3 |
| CD1a molecule | CD1A | 909 | CD1, FCB6, HTA1, R4, T6 |
| CD1c molecule | CD1C | 911 | R7; CD1; CD1A; BDCA1 |
| CD1d molecule | CD1D | 912 | CD1A, R3, R3G1 |
| CD1e molecule | CD1E | 913 | CD1A, R2 |
| CD22 molecule | CD22 | 933 | SIGLEC2; SIGLEC-2 |
| CD226 molecule | CD226 | 10666 | DNAM-1, DNAM1, PTA1, TLiSA1 |
| CD24 molecule | CD24 | 100133941 | CD24A |
| CD244 molecule | CD244 | 51744 | 2B4, NAIL, NKR2B4, Nmrk, SLAMF4 |
| CD27 molecule | CD27 | 939 | T14; S152; Tp55; TNFRSF7; S152. LPFS2 |
| CD207 molecule | CD207 | 50489 | CLEC4K |
| CD274 molecule | CD274 | 29126 | B7-H; B7H1; PDL1; PD-L1; hPD-L1; PDCD1L1; PDCD1LG1 |
| CD276 molecule | CD276 | 80381 | 4Ig-B7-H3, B7-H3, B7H3, B7RP-2 |
| CD28 molecule | CD28 | 940 | Tp44 |
| CD33 molecule | CD33 | 945 | p67; SIGLEC3; SIGLEC-3 |
| CD37 molecule | CD37 | 951 | GP52-40; TSPAN26 |
| CD38 molecule | CD38 | 952 | ADPRC1; ADPRC 1 |
| CD40 ligand | CD40LG | 959 | IGM; IMD3; TRAP; gp39; CD154; CD40L; HIGM1; T-BAM; TNFSF5; hCD40L |
| CD40 molecule | CD40 | 958 | p50; Bp50; CDW40; TNFRSF5 |
| CD44 molecule | CD44 | 960 | IN; LHR; MC56; MDU2; MDU3; MIC4; Pgp1; CDW44; CSPG8; HCELL; HUTCH-I; ECMR-III |
| CD47 molecule | CD47 | 961 | IAP, MER6, OA3 |
| CD48 molecule | CD48 | 962 | BCM1; BLAST; hCD48; mCD48; BLAST1; SLAMF2; MEM-102 |
| CD52 molecule | CD52 | 1043 | HE5; CDW52; EDDM5 |
| CD70 molecule | CD70 | 970 | CD27L; LPFS3; CD27-L; CD27LG; TNFSF7; TNLG8A |
| CD74 molecule | CD74 | 972 | II; p33; DHLAG; HLADG; Ia-GAMMA |
| CD79a molecule | CD79A | 973 | IGA; MB-1 |
| CD79b molecule | CD79B | 974 | B29; IGB; AGM6 |
| CD80 molecule | CD80 | 941 | B7; BB1; B7-1; B7.1; LAB7; CD28LG; CD28LG1 |
| CD84 molecule | CD84 | 8832 | LY9B; hCD84; mCD84; SLAMF5 |
| CD86 molecule | CD86 | 942 | B70; B7-2; B7.2; LAB72; CD28LG2 |

TABLE B-continued

Illustrative Antigen/Protein Targets

| Target Name | NCBI Official Symbol | NCBI Human Gene ID No. | Alternative Symbols (also known as) |
|---|---|---|---|
| CD96 molecule | CD96 | 10225 | TACTILE |
| cell adhesion molecule 1 | CADM1 | 23705 | BL2, IGSF4, IGSF4A, NECL2, Necl-2, RA175, ST17, SYNCAM, TSLC1, sTSLC-1, sgIGSF, synCAM1 |
| chorionic somatomammotropin hormone 1 | CSH1 | 1442 | PL; CSA; CS-1; CSMT; GHB3; hCS-1; hCS-A |
| coagulation factor III, tissue factor | F3 | 2152 | TF; TFA; CD142 |
| collagen type IV alpha 1 chain | COL4A1 | 1282 | BSVD, BSVD1, RATOR |
| collagen type IV alpha 2 chain | COL4A2 | 1284 | BSVD2, ICH, POREN2 |
| collagen type IV alpha 3 chain | COL4A3 | 1285 | ATS2, ATS3 |
| collagen type IV alpha 4 chain | COL4A4 | 1286 | ATS2, BFH, CA44 |
| collagen type IV alpha 5 chain | COL4A5 | 1287 | ASLN, ATS, ATS1, CA54 |
| collectin subfamily member 10 | COLEC10 | 10584 | 3MC3; CLL1; CL-34 |
| C-type lectin domain containing 9A | CLEC9A | 283420 | CD370; DNGR1; DNGR-1; UNQ9341 |
| C-type lectin domain family 12 member A | CLEC12A | 160364 | CLL1; MICL; CD371; CLL-1; DCAL-2 |
| C-type lectin domain family 4 member C | CLEC4C | 170482 | DLEC; HECL; BDCA2; CD303; CLECSF7; CLECSF11; PRO34150 |
| C-X-C motif chemokine receptor 1 | CXCR1 | 3577 | C-C, C-C-CKR-1, CD128, CD181, CDw128a, CKR-1, CMKAR1, IL8R1, IL8RA, IL8RBA |
| C-X-C motif chemokine receptor 2 | CXCR2 | 3579 | CD182, CDw128b, CMKAR2, IL8R2, IL8RA, IL8RB |
| C-X-C motif chemokine receptor 3 | CXCR3 | 2833 | CD182, CD183, CKR-L2, CMKAR3, GPR9, IP10-R, Mig-R, MigR |
| C-X-C motif chemokine receptor 4 | CXCR4 | 7852 | CD184, D2S201E, FB22, HM89, HSY3RR, LAP-3, LAP3, LCR1, LESTR, NPY3R, NPYR, NPYRL, NPYY3R, WHIM, WHIMS |
| cytokine inducible SH2 containing protein | CISH | 1154 | CIS; G18; SOCS; CIS-1; BACTS2 |
| cytotoxic T-lymphocyte associated protein 4 | CTLA4 | 1493 | ALPS5, CD, CD152, CELIAC3, CTLA-4, GRD4, GSE, IDDM12 |
| delta like canonical Notch ligand 3 | DLL3 | 10683 | SCDO1 |
| ectonucleotide pyrophosphatase/ phosphodiesterase 3 | ENPP3 | 5169 | B10; NPP3; PDNP3; CD203c; PD-IBETA |
| ectonucleoside triphosphate diphosphohydrolase 1 | ENTPD1 | 953 | CD39; SPG64; ATPDase; NTPDase-1 |
| EPH receptor A1 | EPHA1 | 2041 | EPH; EPHT; EPHT1 |
| EPH receptor A2 | EPHA2 | 1969 | ECK; CTPA; ARCC2; CTPP1; CTRCT6 |
| EPH receptor A4 | EPHA4 | 2043 | EK8; SEK; HEK8; TYRO1 |
| EPH receptor A5 | EPHA5 | 2044 | EK7; CEK7; EHK1; HEK7; EHK-1; TYRO4 |
| EPH receptor A7 | EPHA7 | 2045 | EHK3; EK11; EHK-3; HEK11 |
| ephrin A1 | EFNA1 | 1942 | B61; EFL1; ECKLG; EPLG1; LERK1; LERK-1; TNFAIP4 |
| epidermal growth factor receptor, including variant III | EGFR (e.g., EGFRvIII) | 1956 | ERBB; HER1; mENA; ERBB1; PIG61; NISBD2 |
| epithelial cell adhesion molecule | EPCAM | 4072 | ESA; KSA; M4S1; MK-1; DIAR5; EGP-2; EGP40; KS1/4; MIC18; TROP1; EGP314; HNPCC8; TACSTD1 |
| erb-b2 receptor tyrosine kinase 2 | ERBB2 | 2064 | NEU; NGL; HER2; TKR1; CD340; HER-2; MLN 19; HER-2/neu |
| erb-b2 receptor tyrosine kinase 3 | ERBB3 | 2065 | ErbB-3, FERLK, HER3, LCCS2, MDA-BF-1, c-erbB-3, c-erbB3, erbB3-S, p180-ErbB3, p45-sErbB3, p85-sErbB3 |
| erb-b2 receptor tyrosine kinase 4 | ERBB4 | 2066 | ALS19, HER4, p180erbB4 |
| Fc fragment of IgE receptor Ia | FCER1A | 2205 | FCE1A, FcERI |
| Fc fragment of IgG receptor IIIa | FCGR3A | 2214 | CD16; FCG3; CD16A; FCGR3; IGFR3; IMD20; FCR-10; FCRIII; FCGRIII; FCRIIIA |
| fibroblast activation protein alpha | FAP | 2191 | DPPIV, FAPA, FAPalpha, SIMP |
| fibroblast growth factor receptor 1 | FGFR1 | 2260 | BFGFR, CD331, CEK, ECCL, FGFBR, FGFR-1, FLG, FLT-2, FLT2, HBGFR, HH2, HRTFDS, KAL2, N-SAM, OGD, bFGF-R-1 |
| fibroblast growth factor receptor 2 | FGFR2 | 2263 | BEK; JWS; BBDS; CEK3; CFD1; ECT1; KGFR; TK14; TK25; BFR-1; CD332; K-SAM |
| fibroblast growth factor receptor 3 | FGFR3 | 2261 | ACH, CD333, CEK2, HSFGFR3EX, JTK4 |
| fms related tyrosine kinase 1 | FLT1 | 2321 | FLT, FLT-1, VEGFR-1, VEGFR1 |
| fms related tyrosine kinase 4 | FLT4 | 2324 | FLT-4, FLT41, LMPH1A, LMPHM1, PCL, VEGFR-3, VEGFR3 |
| folate hydrolase 1 | FOLH1 | 2346 | PSM; FGCP; FOLH; GCP2; PSMA; mGCP; GCPII; NAALAD1; NAALAdase, carboxypeptidase II |
| folate receptor 1 | FOLR1 | 2348 | FBP; FOLR; FRα |
| galectin 9 | LGALS9 | 3965 | HUAT, LGALS9A |
| glypican 3 | GPC3 | 2719 | SGB; DGSX; MXR7; SDYS; SGBS; OCI-5; SGBS1; GTR2-2 |
| GPNMB glycoprotein nmb | GPNMB | 10457 | NMB; HGFIN; PLCA3; osteoactivin |
| guanylate cyclase 2C | GUCY2C | 2984 | GC-C; STAR; DIAR6; GUC2C; MECIL; MUCIL |
| hepatitis A virus cellular receptor 2 | HAVCR2 | 84868 | TIM3; CD366; KIM-3; SPTCL; TIMD3; Tim-3; TIMD-3; HAVcr-2 |
| HERV-H LTR-associating 2 | HHLA2 | 11148 | B7-H5, B7-H7, B7H7, B7y |
| immunoglobulin superfamily member 11 | IGSF11 | 152404 | CT119; VSIG3; Igsf13; BT-IgSF; CXADRL1 |

TABLE B-continued

Illustrative Antigen/Protein Targets

| Target Name | NCBI Official Symbol | NCBI Human Gene ID No. | Alternative Symbols (also known as) |
|---|---|---|---|
| inducible T cell costimulator | ICOS | 29851 | AILIM, CD278, CVID1 |
| inducible T cell costimulator ligand | ICOSLG | 23308 | B7-H2, B7H2, B7RP-1, B7RP1, B7h, CD275, GL50, ICOS-L, ICOSL, LICOS |
| integrin subunit alpha 5 | ITGA5 | 3678 | CD49e, FNRA, VLA-5, VLA5A |
| integrin subunit alpha V | ITGAV | 3685 | CD51, MSK8, VNRA, VTNR |
| integrin subunit beta 7 | ITGB7 | 3695 | |
| interleukin 2 receptor subunit alpha | IL2RA | 3559 | p55; CD25; IL2R; IMD41; TCGFR; IDDM10 |
| interleukin 3 receptor subunit alpha | IL3RA | 3563 | IL3R; CD123; IL3RX; IL3RY; IL3RAY; hIL-3Ra |
| killer cell immunoglobulin like receptor, three Ig domains and long cytoplasmic tail 1 | KIR3DL1 | 3811 | CD158E1, KIR, KIR3DL1/S1, NKAT-3, NKAT3, NKB1, NKB1B |
| killer cell immunoglobulin like receptor, two Ig domains and long cytoplasmic tail 1 | KIR2DL1 | 3802 | CD158A, KIR-K64, KIR221, KIR2DL3, NKAT, NKAT-1, NKAT1, p58.1 |
| killer cell immunoglobulin like receptor, two Ig domains and long cytoplasmic tail 2 | KIR2DL2 | 3803 | CD158B1, CD158b, NKAT-6, NKAT6, p58.2 |
| killer cell immunoglobulin like receptor, two Ig domains and long cytoplasmic tail 3 | KIR2DL3 | 3804 | p58; NKAT; GL183; NKAT2; CD158b; KIR2DL; NKAT2A; NKAT2B; CD158B2; KIR-K7b; KIR-K7c; KIR2DS5; KIRCL23; KIR-023GB |
| killer cell lectin like receptor C1 | KLRC1 | 3821 | CD159A, NKG2, NKG2A |
| killer cell lectin like receptor C2 | KLRC2 | 3822 | CD159c, NKG2-C, NKG2C |
| killer cell lectin like receptor C3 | KLRC3 | 3823 | NKG2E; NKG2-E |
| killer cell lectin like receptor C4 | KLRC4 | 8302 | NKG2-F, NKG2F |
| killer cell lectin like receptor D1 | KLRD1 | 3824 | CD94 |
| killer cell lectin like receptor G1 | KLRG1 | 10219 | 2F1, CLEC15A, MAFA, MAFA-2F1, MAFA-L, MAFA-LIKE |
| killer cell lectin like receptor K1 | KLRK1 | 22914 | CD314, D12S2489E, KLR, NKG2-D, NKG2D |
| kinase insert domain receptor | KDR | 3791 | CD309, FLK1, VEGFR, VEGFR2 |
| KIT proto-oncogene, receptor tyrosine kinase | KIT | 3815 | PBT; SCFR; C-Kit; CD117; MASTC |
| KRAS proto-oncogene, GTPase | KRAS | 3845 | NS; NS3; CFC2; RALD; K-Ras; KRAS1; KRAS2; RASK2; KI-RAS; C-K-RAS; K-RAS2A; K-RAS2B; K-RAS4A; K-RAS4B; c-Ki-ras2 |
| leukocyte immunoglobulin like receptor B1 | LILRB1 | 10859 | ILT2; LIR1; MIR7; PIRB; CD85J; ILT-2; LIR-1; MIR-7; PIR-B |
| leukocyte immunoglobulin like receptor B2 | LILRB2 | 10288 | ILT4; LIR2; CD85D; ILT-4; LIR-2; MIR10; MIR-10 |
| LY6/PLAUR domain containing 3 | LYPD3 | 27076 | C4.4A |
| lymphocyte activating 3 | LAG3 | 3902 | CD223 |
| lymphocyte antigen 9 | LY9 | 4063 | CD229, SLAMF3, hly9, mLY9 |
| MAGE family member A1 | MAGEA1 | 4100 | CT1.1; MAGE1 |
| MAGE family member A11 | MAGEA11 | 4110 | CT1.11; MAGE11; MAGE-11; MAGEA-11 |
| MAGE family member A3 | MAGEA3 | 4102 | HIP8; HYPD; CT1.3; MAGE3; MAGEA6 |
| MAGE family member A4 | MAGEA4 | 4103 | CT1.4; MAGE4; MAGE4A; MAGE4B; MAGE-41; MAGE-X2 |
| MAGE family member C1 | MAGEC1 | 9947 | CT7; CT7.1 |
| MAGE family member D1 | MAGED1 | 9500 | NRAGE; DLXIN-1 |
| MAGE family member D2 | MAGED2 | 10916 | 11B6; BCG1; BCG-1; HCA10; BARTS5; MAGE-D2 |
| major histocompatibility complex, class I, E | HLA-E | 3133 | QA1; HLA-6.2 |
| major histocompatibility complex, class I, F | HLA-F | 3134 | HLAF; CDA12; HLA-5.4; HLA-CDA12 |
| major histocompatibility complex, class I, G | HLA-G | 3135 | MHC-G |
| membrane spanning 4-domains A1 | MS4A1 | 931 | B1; S7; Bp35; CD20; CVID5; MS4A2; LEU-16 |
| Mesothelin | MSLN | 10232 | MPF, SMRP |
| MET proto-oncogene, receptor tyrosine kinase | MET | 4233 | HGFR; AUTS9; RCCP2; c-Met; DFNB97 |
| MHC class I polypeptide-related sequence A | MICA | 100507436 | MIC-A, PERB11.1 |
| MHC class I polypeptide-related sequence B | MICB | 4277 | PERB11.2 |
| mucin 1, cell surface associated, and splice variants thereof (e.g, including MUC1/A, C, D, X, Y, Z and REP) | MUC1 | 4582 | ADMCKD, ADMCKD1, CA 15-3, CD227, EMA, H23AG, KL-6, MAM6, MCD, MCKD, MCKD1, MUC-1, MUC-1/SEC, MUC-1/X, MUC1/ZD, PEM, PEMT, PUM |
| mucin 16, cell surface associated | MUC16 | 94025 | CA125 |
| natural killer cell cytotoxicity receptor 3 ligand 1 | NCR3LG1 | 374383 | B7-H6, B7H6, DKFZp686O24166 |
| necdin, MAGE family member | NDN | 4692 | PWCR; HsT16328 |
| nectin cell adhesion molecule 2 | NECTIN2 | 5819 | CD112, HVEB, PRR2, PVRL2, PVRR2 |
| nectin cell adhesion molecule 4 | NECTIN4 | 81607 | EDSS1, LNIR, PRR4, PVRL4, nectin-4 |
| neural cell adhesion molecule 1 | NCAM1 | 4684 | CD56, MSK39, NCAM |
| neuropilin 1 | NRP1 | 8829 | NP1; NRP; BDCA4; CD304; VEGF165R |
| Periostin | POSTN | 10631 | OSF-2, OSF2, PDLPOSTN, PN |
| Poliovirus receptor (PVR) cell adhesion molecule | PVR | 5817 | CD155, HVED, NECL5, Necl-5, PVS, TAGE4 |

TABLE B-continued

Illustrative Antigen/Protein Targets

| Target Name | NCBI Official Symbol | NCBI Human Gene ID No. | Alternative Symbols (also known as) |
|---|---|---|---|
| programmed cell death 1 | PDCD1 | 5133 | PD1; PD-1; CD279; SLEB2; hPD-1; hPD-l; hSLE1 |
| programmed cell death 1 ligand 2 | PDCD1LG2 | 80380 | B7DC, Btdc, CD273, PD-L2, PDCD1L2, PDL2, bA574F11.2 |
| prominin 1 | PROM1 | 8842 | RP41; AC133; CD133; MCDR2; STGD4; CORD12; PROML1; MSTP061 |
| promyelocytic leukemia | PML | 5371 | MYL, PP8675, RNF71, TRIM19 |
| protein tyrosine kinase 7 (inactive) | PTK7 | 5754 | CCK-4, CCK4 |
| PVR related immunoglobulin domain containing | PVRIG | 79037 | C7orf15, CD112R |
| retinoic acid early transcript 1E | RAET1E | 135250 | LETAL, N2DL-4, NKG2DL4, RAET1E2, RL-4, ULBP4, bA350J20.7 |
| retinoic acid early transcript 1G | RAET1G | 353091 | ULPB5 |
| retinoic acid early transcript 1L | RAET1L | 154064 | ULPB6 |
| roundabout guidance receptor 4 | ROBO4 | 54538 | ECSM4, MRB |
| sialic acid binding Ig like lectin 9 | SIGLEC9 | 27180 | CD329; CDw329; FOAP-9; siglec-9; OBBP-LIKE |
| sialic acid binding Ig like lectin 10 | SIGLEC10 | 89790 | SLG2; PRO940; SIGLEC-10 |
| sialic acid binding Ig like lectin 10 | SIGLEC10 | 89790 | SLG2; PRO940; SIGLEC-10 |
| signal regulatory protein alpha | SIRPA | 140885 | BIT; MFR; P84; SIRP; MYD-1; SHPS1; CD172A; PTPNS1 |
| signaling lymphocytic activation molecule family member 1 | SLAMF1 | 6504 | SLAM; CD150; CDw150 |
| SLAM family member 6 | SLAMF6 | 114836 | CD352, KALI, KALIb, Ly108, NTB-A, NTBA, SF2000 |
| SLAM family member 7 | SLAMF7 | 57823 | 19A, CD319, CRACC, CS1 |
| SLIT and NTRK like family member 6 | SLITRK6 | 84189 | DFNMYP |
| solute carrier family 34 (sodium phosphate), member 2 | SLC34A2 | 10568 | NPTIIb; NAPI-3B; NAPI-IIb |
| solute carrier family 39 member 6 | SLC39A6 | 25800 | LIV-1, ZIP6 |
| solute carrier family 44 member 4 | SLC44A4 | 80736 | C6orf29, CTL4, DFNA72, NG22, TPPT, hTPPT1 |
| STEAP family member 1 | STEAP1 | 26872 | PRSS24, STEAP |
| syndecan 1 | SDC1 | 6382 | SDC; CD138; SYND1; syndecan |
| T cell immunoglobulin and mucin domain containing 4 | TIMD4 | 91937 | SMUCKLER, TIM4 |
| T cell immunoreceptor with Ig and ITIM domains | TIGIT | 201633 | VSIG9, VSTM3, WUCAM |
| tenascin C | TNC | 3371 | 150-225, DFNA56, GMEM, GP, HXB, JI, TN, TN-C |
| thrombomodulin | THBD | 7056 | AHUS6, BDCA3, CD141, THPH12, THRM, TM |
| TNF receptor superfamily member 10a | TNFRSF10A | 8797 | APO2, CD261, DR4, TRAILR-1, TRAILR1 |
| TNF receptor superfamily member 10b | TNFRSF10B | 8795 | CD262, DR5, KILLER, KILLER/DR5, TRAIL-R2, TRAILR2, TRICK2, TRICK2A, TRICK2B, TRICKB, ZTNFR9 |
| TNF receptor superfamily member 14 | TNFRSF14 | 8764 | ATAR, CD270, HVEA, HVEM, LIGHTR, TR2 |
| TNF receptor superfamily member 17 | TNFRSF17 | 608 | BCM, BCMA, CD269, TNFRSF13A |
| TNF receptor superfamily member 18 | TNFRSF18 | 8784 | AITR, CD357, GITR, GITR-D |
| TNF receptor superfamily member 4 | TNFRSF4 | 7293 | OX40; ACT35; CD134; IMD16; TXGP1L |
| TNF receptor superfamily member 8 | TNFRSF8 | 943 | CD30; Ki-1; D1S166E |
| TNF receptor superfamily member 9 | TNFRSF9 | 3604 | 4-1BB, CD137, CDw137, ILA |
| TNF superfamily member 10 | TNFSF10 | 8743 | APO2L, Apo-2L, CD253, TL2, TNLG6A, TRAIL |
| TNF superfamily member 13b | TNFSF13B | 10673 | BAFF, BLYS, CD257, DTL, TALL-1, TALL1, THANK, TNFSF20, TNLG7A, ZTNF4 |
| TNF superfamily member 14 | TNFSF14 | 8740 | CD258, HVEML, LIGHT, LTg |
| TNF superfamily member 18 | TNFSF18 | 8995 | AITRL, GITRL, TL6, TNLG2A, hGITRL |
| TNF superfamily member 4 | TNFSF4 | 7292 | CD134L, CD252, GP34, OX-40L, OX4OL, TNLG2B, TXGP1 |
| TNF superfamily member 8 | TNFSF8 | 944 | CD153, CD30L, CD30LG, TNLG3A |
| TNF superfamily member 9 | TNFSF9 | 8744 | 4-1BB-L, CD137L, TNLG5A |
| transferrin | TF | 7018 | HEL-S-71p, PRO1557, PRO2086, TFQTL1 |
| transforming growth factor beta 1 and isoforms thereof | TGFB1 | 7040 | CED, DPD1, IBDIMDE, LAP, TGFB, TGFbeta |
| transmembrane and immunoglobulin domain containing 2 | TMIGD2 | 126259 | CD28H, IGPR-1, IGPR1 |
| trophinin | TRO | 7216 | MAGE-d3, MAGED3 |
| trophoblast glycoprotein | TPBG | 7162 | 5T4, 5T4AG, M6P1, WAIF1 |
| tumor associated calcium signal transducer 2 | TACSTD2 | 4070 | EGP-1, EGP1, GA733-1, GA7331, GP50, M1S1, TROP2 |
| UL16 binding protein 1 | ULBP1 | 80329 | N2DL-1, NKG2DL1, RAET1I |
| UL16 binding protein 2 | ULBP2 | 80328 | ALCAN-alpha, N2DL2, NKG2DL2, RAET1H, RAET1L |
| UL16 binding protein 3 | ULBP3 | 79465 | N2DL-3, NKG2DL3, RAET1N |
| V-set domain containing T cell activation inhibitor 1 | VTCN1 | 79679 | B7-H4, B7H4, B7S1, B7X, B7h.5, PRO1291, VCTN1 |
| V-set immunoregulatory receptor | VSIR | 64115 | B7-H5, B7H5, C10orf54, DD1alpha, Dies1, GI24, PD-1H, PP2135, SISP1, VISTA |
| X-C motif chemokine receptor 1 | XCR1 | 2829 | GPR5; CCXCR1 |

In some embodiments, the target antigen comprises a tumor-associated carbohydrate antigen (TACA). Illustrative carbohydrate antigen targets include, e.g., mucin TACAs, including truncated glycans Thomsen-nouveau (Tn) (GalNAcα1-Ser/Thr) and STn (Neu5Acα2,6GalNAcα1-Ser/Thr), R1\42 antigen hexasaccharide, carbasugars, C-glycosides, gangliosides GM2, GD2 and GD3; globo-H, sialyl Lewis(a), sialyl Lewis(x) and sialyl Lewis(y) antigens. TACAs are described, e.g., in Sadraei, et al., *Adv Carbohydr Chem Biochem.* (2017) 74:137-237; Sletmoen, et al., *Glycobiology.* (2018) 28(7):437-442; Chuang, et al., *J Am Chem Soc.* (2013) 135(30):11140-50; Ragupathi, *Cancer. Immunol Immunother.* (1996) 43(3):152-7; Ugorski, et al., *Acta Biochim Pol.* 2002; 49(2):303-11; Takada, et al., *Cancer Res.* 1993 Jan. 15; 53(2):354-61.

In some embodiments, the target antigen comprises a neoantigen presented within a major histocompatibility complex (MHC) class I or class II molecule. See, e.g., Ott, et al., *Nature.* (2017) 547(7662):217-221; Capietto, et al., *Curr Opin Immunol.* (2017) 46:58-65; Sun, et al., *Cancer Lett.* (2017) 392:17-25; Khodadoust, et al., *Nature.* (2017) 543(7647):723-727; Kreiter, et al., *Nature.* (2015) 520 (7549):692-6; Marty, et al., *Cell.* (2017) 171(6):1272-1283; and Kochin, et al., *Oncoimmunology.* (2017) 6(4):e1293214 (describing SUV39H2 peptide presented in HLA-A24).

Conjugated FLT3L-Fc Fusion Proteins

Any of the FLT3L-Fc fusion proteins, or homodimers or heterodimers thereof, disclosed herein may be conjugated. FLT3L-Fc fusion proteins which are bound to various molecules (e.g., labels) including without limitation macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), hyaluronic acid, radioactive materials (e.g., $^{90}$Y, $^{131}$I, $^{125}$I, $^{35}$S, $^{3}$H, $^{121}$In, $^{99}$Tc), fluorescent substances (e.g., fluorescein and rhodamine), fluorescent proteins, luminescent substances (e.g., luminol), Qdots, haptens, enzymes (e.g., glucose oxidase), metal chelates, biotin, avidin, and drugs.

The above-described conjugated FLT3L-Fc fusion proteins can be prepared according to known methods, e.g., performing chemical modifications on the FLT3L-Fc fusion proteins described herein. In certain embodiments, the labelling moiety or therapeutic moiety is conjugated to the Fc portion of the fusion protein. Methods for modifying antibody Fc regions are well known in the art (e.g., U.S. Pat. Nos. 5,057,313 and 5,156,840).

In some embodiments, the FLT3L-Fc fusion protein, or homodimer or heterodimer thereof, is conjugated to a drug or therapeutic agent. In various embodiments, the drug is a small organic compound or an inhibitory nucleic acid, e.g., a short-inhibitory RNA (siRNA), a microRNA (miRNA). In some embodiments, the drug or therapeutic agent is an anti-neoplastic agent or a chemotherapeutic agent, as known in the art and described herein. In a particular embodiment, the drug or therapeutic agent is selected from the group consisting of monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracycline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a vinca alkaloid, an epothilone), a pyrrolobenzodiazepine (PBD) or dimer thereof, and a duocarmycin (A, B1, B2, C1, C2, D, SA, CC-1065).

3. Polynucleotides Encoding FLT3L-Fc Fusion Proteins

Provided are polynucleotides encoding the FLT3L-Fc fusion proteins, described herein, vectors comprising such polynucleotides, and host cells (e.g., human cells, mammalian cells, yeast cells, plant cells, insect cells, bacterial cells, e.g., *E. coli*) comprising such polynucleotides or expression vectors. Provided herein are polynucleotides comprising nucleotide sequence(s) encoding any of the FLT3L-Fc fusion proteins provided herein, as well as expression cassettes and vector(s) comprising such polynucleotide sequences, e.g., expression vectors for their efficient expression in host cells, e.g., mammalian cells. In various embodiments, the polynucleotide is a DNA, a cDNA, or an mRNA.

The terms "polynucleotide" and "nucleic acid molecule" interchangeably refer to a polymeric form of nucleotides and includes both sense and anti-sense strands of RNA, cDNA, genomic DNA, and synthetic forms and mixed polymers of the above. As used herein, the term nucleic acid molecule may be interchangeable with the term polynucleotide. In some embodiments, a nucleotide refers to a ribonucleotide, deoxynucleotide or a modified form of either type of nucleotide, and combinations thereof. The terms also include without limitation, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-biased polynucleotides for improved expression in a desired host cell.

A "substitution," as used herein, denotes the replacement of one or more amino acids or nucleotides by different amino acids or nucleotides, respectively.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location. "Isolated nucleic acid encoding an FLT3L-Fc fusion protein" refers to one or more nucleic acid molecules encoding first antigen binding domain, and optionally second antigen binding domain, antibody heavy and light chains (or fragments thereof), including such nucleic acid molecule(s) in a single vector or separate vectors, and such nucleic acid molecule(s) present at one or more locations in a host cell.

An "isolated" polypeptide, such as an isolated FLT3L-Fc fusion protein provided herein, is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In some embodiments, the isolated polypeptide will be purified (1) to greater than 95% by weight of polypeptide as determined by the Lowry method, for example, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated polypeptide includes the polypeptide in situ within recombinant cells since at least one component of the antibody's natural environment will not be present. Ordinarily, however, isolated polypeptide will be prepared by at least one purification step.

A "polynucleotide variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences described herein and evaluating one or more biological activities of the encoded polypeptide as described herein and/or using any of a number of techniques well known in the art.

In some embodiments, the nucleic acid molecule is codon-biased to enhance expression in a desired host cell, e.g., in human cells, mammalian cells, yeast cells, plant cells, insect cells, or bacterial cells, e.g., *E. coli* cells. Accordingly, provided are polynucleotides encoding a FLT3L-Fc fusion protein wherein the polynucleotides are codon-biased, comprise replacement heterologous signal sequences, and/or have mRNA instability elements eliminated. Methods to generate codon-biased nucleic acids can be carried out by adapting the methods described in, e.g., U.S. Pat. Nos. 5,965,726; 6,174,666; 6,291,664; 6,414,132; and 6,794,498. Preferred codon usage for expression of the FLT3L-Fc fusion proteins in desired host cells is provided, e.g., at kazusa.or.jp/codon/; and genscript.com/tools/codon-frequency-table.

In some embodiments, the polynucleotide encoding a FLT3L-Fc fusion protein, as described herein, has at least 80%, at least 85%, at least 90%, at least 91%, at least 92%, at least 93%, at least 94%, at least 95%, at least 96%, at least 97%, at least 98%, at least 99% identical, or 100% identical to an nucleic acid sequence selected from the group consisting of SEQ ID NOs: 28-70, as provided in Table C.

As appropriate, in certain embodiments, the 3'-end of the polynucleotide encoding the FLT3L-Fc fusion protein comprises multiple tandem stop codons, e.g., two or more tandem TAG ("amber"), TAA ("ochre") or TGA ("opal" or "umber") stop codons. The multiple tandem stop codons can be the same or different.

TABLE C

Polynucleotides encoding FLT3L-Fc fusion proteins

| POLYNUCL. NO. SEQ ID NO:Features | | Polynucleotide Sequence |
|---|---|---|
| 28 | FLT3L ECD-hingeless hG1 | ACACAGGATTGCAGCTTCCAGCACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCAAGTGCGCCTTCCAGCC TCCTCCATCCTGCCTGAGATTCGTGCAGACCAACATCA GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTCTGGAAGCCACAGCT CCCACCGCTCCTCAAGGCGGACCGTCAGTCTTCCTCTT CCCCCCAAAACCCAAGGACACCCTCATGATCTCCCGGA CCCCTGAGGTCACATGCGTGGTGGTGGACGTGAGCCAC GAAGACCCTGAGGTCAAGTTCAACTGGTACGTGGACGG CGTGGAGGTGCATAATGCCAAGACAAAGCCGCGGGAGG AGCAGTACAACAGCACGTACCGTGTGGTCAGCGTCCTC ACCGTCCTGCACCAGGACTGGCTGAATGGCAAGGAGTA CAAGTGCAAGGTCTCCAACAAAGCCCTCCCAGCCCCCA TCGAGAAAACCATCTCCAAAGCCAAAGGGCAGCCCCGA GAACCACAGGTGTACACCCTGCCCCCATCCCGGGAGGA GATGACCAAGAACCAGGTCAGCCTGACCTGCCTGGTCA AAGGCTTCTATCCCAGCGACATCGCCGTGGAGTGGGAG AGCAATGGGCAGCCGGAGAACAACTACAAGACCACGCC TCCCGTGCTGGACTCCGACGGCTCTTCTTCCTCTACA GCAAGCTCACCGTGGACAAGAGCAGGTGGCAGCAGGGG AACGTCTTCTCATGCTCCGTGATGCATGAGGCTCTGCA CAACCACTACACGCAGAAGAGCCTCTCCCTGTCTCCGG GTAAA |
| 29 | FLT3L ECD-hingeless hG1 | ACCCAGGACTGCTCCTTCCAGCACTCCCCTATCTCTTC CGACTTCGCCGTGAAGATCAGAGAGCTGTCCGACTACC TGCTGCAGGACTACCCTGTGACCGTGGCCAGCAATCTG CAGGACGAAGAACTGTGTGGTGGCCTGTGGCGACTGGT GTTGGCTCAGAGATGGATGGAACGGCTGAAAACCGTGG CCGGCTCTAAGATGCAGGGCCTGCTGGAAAGAGTGAAC ACCGAGATCCACTTCGTGACCAAGTGCGCCTTTCAGCC |

TABLE C-continued

Polynucleotides encoding FLT3L-Fc fusion proteins

| POLYNUCL. NO. SEQ ID NO: | Features | Polynucleotide Sequence |
|---|---|---|
| | | TCCTCCATCCTGCCTGAGATTCGTGCAGACCAACATCT CCCGGCTGCTGCAAGAGACATCCGAGCAGCTGGTGGCT CTGAAGCCCTGGATCACCCGGCAGAACTTCTCTCGGTG TCTGGAACTGCAGTGTCAGCCCGACTCTTCTACCCTGC CTCCACCTTGGAGCCCCAGACCTTTGGAAGCTACCGCT CCAACAGCTCCTCAAGGCGGCCCTTCCGTGTTTCTGTT CCCTCCAAAGCCTAAGGACACCCTGATGATCTCTCGGA CCCCTGAAGTGACCTGCGTGGTGGTGGATGTGTCTCAC GAGGATCCCGAAGTGAAGTTCAATTGGTACGTGGACGG CGTGGAAGTGCACAACGCCAAGACCAAGCCTAGAGAGG AACAGTACAACTCCACCTACAGAGTGGTGTCCGTGCTG ACCGTGCTGCACCAGGATTGGCTGAACGGCAAAGAGTA CAAGTGCAAGGTGTCCAACAAGGCCCTGCCTGCTCCTA TCGAAAAGACCATCTCCAAGGCCAAGGGCCAGCCTAGG GAACCCCAGGTTTACACCCTGCCACCTAGCCGGGAAGA GATGACCAAGAACCAGGTGTCCCTGACCTGCCTGGTCA AGGGCTTCTACCCCTCTGATATCGCCGTGGAATGGGAG AGCAATGGCCAGCCTGAGAACAACTACAAGACCACACC TCCTGTGCTGGACTCCGACGGCTCATTCTTCCTGTACT CCAAGCTGACAGTGGACAAGTCCAGATGGCAGCAGGGC AACGTGTTCTCCTGCTCCGTGATGCACGAGGCTCTGCA CAACCACTACACCCAGAAGTCCCTGTCTCTGTCCCCTG GCAAA |
| 30 | FLT3L ECD (Δ C-term 5aa (PTAPQ; SEQ ID NO: 85)- hingeless hG1 | ACACAGGATTGCAGCTTCCAGCACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCAAGTGCGCCTTCCAGCC TCCTCCATCCTGCCTGAGATTCGTGCAGACCAACATCA GCAGCTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTCTGGAAGCCACAGCT GGGGGACCGTCAGTCTTCCTCTTCCCCCCAAAACCCAA GGACACCCTCATGATCTCCCGGACCCCTGAGGTCACAT GCGTGGTGGTGGACGTGAGCCACGAAGACCCTGAGGTC AAGTTCAACTGGTACGTGGACGGCGTGGAGGTGCATAA TGCCAAGACAAAGCCGCGGGAGGAGCAGTACAACAGCA CGTACCGTGTGGTCAGCGTCCTCACCGTCCTGCACCAG GACTGGCTGAATGGCAAGGAGTACAAGTGCAAGGTCTC CAACAAAGCCCTCCCAGCCCCCATCGAGAAAACCATCT CCAAAGCCAAAGGGCAGCCCCGAGAACCACAGGTGTAC ACCCTGCCCCCATCCCGGGAGGAGATGACCAAGAACCA GGTCAGCCTGACCTGCCTGGTCAAAGGCTTCTATCCCA GCGACATCGCCGTGGAGTGGGAGAGCAATGGGCAGCCG GAGAACAACTACAAGACCACGCCTCCCGTGCTGGACTC CGACGGCTCCTTCTTCCTCTACAGCAAGCTCACCGTGG ACAAGAGCAGGTGGCAGCAGGGGAACGTCTTCTCATGC TCCGTGATGCATGAGGCTCTGCACAACCACTACACGCA GAAGAGCCTCTCCCTGTCTCCGGGTAAA |
| 31 | FLT3L ECD (Δ C-term 5aa (PTAPQ; SEQ ID NO: 85)- hingeless hG1 | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC CTCCACCTTGGAGCCCTAGACCTTTGGAAGCTACAGCT GGCGGCCCAAGCGTGTTCCTGTTTCCTCCAAAGCCTAA GGACACCCTGATGATCTCTCGGACCCCTGAAGTGACCT GCGTGGTGGTGGATGTGTCTCACGAGGATCCCGAAGTG AAGTTCAATTGGTACGTGGACGGCGTGGAAGTGCACAA CGCCAAGACCAAGCCTAGAGAGGAACAGTACAACTCCA CCTACAGAGTGGTGTCCGTGCTGACCGTGCTGCACCAG GATTGGCTGAACGGCAAAGAGTACAAGTGCAAGGTGTC CAACAAGGCCCTGCCTGCTCCTATCGAAAAGACCATCT |

TABLE C-continued

Polynucleotides encoding FLT3L-Fc fusion proteins

| POLYNUCL. NO. SEQ ID NO: | Features | Polynucleotide Sequence |
|---|---|---|
| | | CCAAGGCCAAGGGCCAGCCTAGGGAACCTCAGGTTTAC ACCCTGCCACCTAGCCGGGAAGAGATGACCAAAAACCA GGTGTCCCTGACCTGCCTGGTCAAGGGCTTCTACCCAT CCGATATCGCCGTGGAATGGGAGTCTAACGGCCAGCCT GAGAACAACTACAAGACCACACCTCCTGTGCTGGACTC CGACGGCTCATTCTTCCTGTACTCCAAGCTGACAGTGG ACAAGTCTCGGTGGCAGCAGGGCAACGTGTTCTCCTGT TCTGTGATGCACGAGGCCCTGCACAACCACTACACCCA GAAGTCCCTGTCTCTGTCCCCTGGCAAA |
| 32 | FLT3L ECD-hG4 S228P/L235E | ACACAGGATTGCAGCTTCCAGCACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCAAGTGCGCCTTCCAGCC TCCTCCATCCTGCCTGAGATTCGTGCAGACCAACATCA GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTCTGGAAGCCACAGCT CCCACCGCTCCTCAAGAATCTAAGTACGGGCCCTCCCTG CCCTCCTTGCCCAGCCCCTGAATTTGAGGGCGGACCCT CCGTGTTCCTGTTCCCCCCAAAGCCCAAGGACACCCTG ATGATCAGCCGGACCCCCGAAGTGACCTGCGTGGTGGT GGATGTGTCCCAGGAAGATCCCGAGGTGCAGTTCAATT GGTACGTGGACGGCGTGGAAGTGCACAACGCCAAGACC AAGCCCAGAGAGGAACAGTTCAACAGCACCTACCGGGT GGTGTCCGTGCTGACAGTGCTGCACCAGGACTGGCTGA ACGGCAAAGAGTACAAGTGCAAGGTGTCCAACAAGGGC CTGCCCAGCTCCATCGAGAAAACCATCAGCAAGGCCAA GGGCCAGCCCCGCGAACCCCAGGTGTACACACTGCCTC CAAGCCAGGAAGAGATGACCAAGAACCAGGTGTCCCTG ACCTGTCTCGTGAAAGGCTTCTACCCCTCCGATATCGC CGTGGAATGGGAGAGCAACGGCCAGCCCGAGAACAACT ACAAGACCACCCCCCTGTGCTGGACAGCGACGGCTCA TTCTTCCTGTACAGCAGACTGACCGTGGACAAGAGCCG GTGGCAGGAAGGCAACGTGTTCAGCTGCAGCGTGATGC ACGAGGCCCTGCACAACCACTACACCCAGAAGTCCCTG TCTCTGTCCCTGGGCAAA |
| 33 | FLT3L ECD-hG4 S228P/L235E | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC CTCCACCTTGGAGCCCTAGACCTTTGGAGGCTACAGCT CCTACCGCTCCTCAAGAGTCTAAGTACGGCCCTCCTTG TCCTCCATGTCCTGCTCCAGAATTTGAAGGCGGCCCCAA GCGTGTTCCTGTTTCCTCCAAAGCCTAAGGACACCCTG ATGATCTCTCGGACCCCTGAAGTGACCTGCGTGGTGGT GGATGTGTCTCAAGAGGACCCCGAGGTGCAGTTCAATT GGTACGTGGACGGCGTGGAAGTGCACAACGCCAAGACC AAGCCTAGAGAGGAACAGTTCAACTCCACCTACAGAGT GGTGTCCGTGCTGACCGTGCTGCACCAGGATTGGCTGA ACGGCAAAGAGTACAAGTGCAAGGTGTCCAACAAGGGC CTGCCTAGCTCCATCGAAAAGACCATCTCCAAGGCCAA GGGCCAGCCAAGAGAACCTCAGGTGTACACACTGCCTC CAAGCCAAGAGGAAATGACCAAGAACCAGGTGTCCCTG ACCTGCCTGGTCAAGGGCTTCTACCCATCCGATATCGC CGTGGAATGGGAGTCTAACGGCCAGCCTGAGAACAACT ACAAGACCACACCTCCTGTGCTGGACTCCGACGGCTCC TTCTTTCTGTACTCTCGCCTGACCGTGGACAAGTCTAG ATGGCAAGAGGGCAACGTGTTCTCCTGCTCTGTGATGC ACGAGGCCCTGCACAACCACTACACCCAGAAGTCCCTG TCTCTGTCCCTGGGCAAA |

TABLE C-continued

Polynucleotides encoding FLT3L-Fc fusion proteins

| SEQ ID NO: | Features | Polynucleotide Sequence |
|---|---|---|
| 34 | FLT3L ECD-hG4 S228P/F234A/ L235A | ACACAGGATTGCAGCTTCCAGCACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCAAGTGCGCCTTCCAGCC TCCTCCATCCTGCCTGAGATTCGTGCAGACCAACATCA GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTCTGGAAGCCACAGCT CCCACCGCTCCTCAAGAGTCTAAGTACGGCCCTCCTTG TCCTCCATGTCCTGCTCCAGAAGCTGCTGGCGGCCCTT CCGTGTTTCTGTTCCCTCCAAAGCCTAAGGACACCCTG ATGATCTCTCGGACCCCTGAAGTGACCTGCGTGGTGGT GGATGTGTCCCAAGAGGATCCCGAGGTGCAGTTCAATT GGTACGTGGACGGCGTGGAAGTGCACAACGCCAAGACC AAGCCTAGAGAGGAACAGTTCAACTCCACCTACAGAGT GGTGTCCGTGCTGACCGTGCTGCACCAGGATTGGCTGA ACGGCAAAGAGTACAAGTGCAAGGTGTCCAACAAGGGC CTGCCTTCCAGCATCGAAAAGACCATCTCCAAGGCCAA GGGCCAGCCTAGGGAACCCCAGGTTTACACCCTGCCTC CAAGCCAAGAGGAAATGACCAAGAACCAGGTGTCCCTG ACCTGCCTGGTCAAGGGCTTCTACCCTTCCGATATCGC CGTGGAATGGGAGAGCAATGGCCAGCCTGAGAACAACT ACAAGACCACACCTCCTGTGCTGGACTCCGACGGCTCC TTCTTTCTGTACTCCCGCCTGACCGTGGACAAGTCCAG ATGGCAAGAGGGCAACGTGTTCTCCTGCTCCGTGATGC ACGAGGCCCTGCACAATCACTACACCCAGAAGTCCCTG TCTCTGTCCCTGGGCAAA |
| 35 | FLT3L ECD-hG4 S228P/F234A/ L235A | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC CTCCACCTTGGAGCCCTAGACCTTTGGAGGCTACAGCT CCTACCGCTCCTAAGAGTCTAAGTACGGCCCTCCTTG TCCTCCATGTCCTGCTCCAGAAGCTGCTGGCGGACCAA GCGTTTTCCTGTTTCCTCCAAAGCCTAAGGACACCCTG ATGATCTCTCGGACCCCTGAAGTGACCTGCGTGGTGGT GGATGTGTCTCAAGAGGACCCCGAGGTGCAGTTCAATT GGTACGTGGACGGCGTGGAAGTGCACAACGCCAAGACC AAGCCTAGAGAGGAACAGTTCAACTCCACCTACAGAGT GGTGTCCGTGCTGACCGTGCTGCACCAGGATTGGCTGA ACGGCAAAGAGTACAAGTGCAAGGTGTCCAACAAGGGC CTGCCTAGCTCCATCGAAAAGACCATCTCCAAGGCCAA GGGCCAGCCAAGAGAACCTCAGGTGTACACACTGCCTC CAAGCCAAGAGGAAATGACCAAGAACCAGGTGTCCCTG ACCTGCCTGGTCAAGGGCTTCTACCCATCCGATATCGC CGTGGAATGGGAGTCTAACGGCCAGCCTGAGAACAACT ACAAGACCACACCTCCTGTGCTGGACTCCGACGGCTCC TTCTTTCTGTACTCTCGCCTGACCGTGGACAAGTCTAG ATGGCAAGAGGGCAACGTGTTCTCCTGCTCTGTGATGC ACGAGGCCCTGCACAACCACTACACCCAGAAGTCCCTG TCTCTGTCCCTGGGCAAA |
| 36 | Aglyco-FLT3L (S128A/S151A) hingeless hG1 | ATGACAGTTTTGGCTCCAGCTTGGTCCCCTACAACCTA CCTGCTGCTGCTGTTGCTGCTCTCCTCTGGCCTGTCTG GCACCCAGGACTGTTCCTTCCAGCACTCCCCTATCTCC AGCGACTTCGCCGTGAAGATCAGAGAGCTGTCCGACTA TCTGCTGCAGGACTACCCTGTGACCGTGGCCAGCAATC TGCAGGACGAAGAACTGTGTGGTGGCCTGTGGCGACTG GTGTTGGCTCAGAGATGGATGGAACGGCTGAAAACCGT GGCCGGCTCTAAGATGCAGGGCCTGCTGGAAAGAGTGA ACACCGAGATCCACTTCGTGACCAAGTGCGCCTTTCAG CCTCCTCCATCCTGCCTGAGATTCGTGCAGACCAATAT |

TABLE C-continued

Polynucleotides encoding FLT3L-Fc fusion proteins

| POLYNUCL. NO. SEQ ID NO: | Features | Polynucleotide Sequence |
|---|---|---|
| | | CGCCCGGCTGCTGCAAGAGACATCCGAGCAGCTGGTGG<br>CTCTGAAGCCCTGGATCACCAGACAGAACTTCGCCCGG<br>TGTCTGGAACTGCAGTGTCAGCCTGACAGCTCTACCCT<br>GCCTCCACCTTGGAGCCCTAGACCTCTGGAAGCTACCG<br>CTCCAACCGCTCCTCAAGGGGGACCGTCAGTCTTCCTC<br>TTCCCCCCAAAACCCAAGGACACCCTCATGATCTCCCG<br>GACCCCTGAGGTCACATGCGTGGTGGTGGACGTGAGCC<br>ACGAAGACCCTGAGGTCAAGTTCAACTGGTACGTGGAC<br>GGCGTGGAGGTGCATAATGCCAAGACAAAGCCGCGGGA<br>GGAGCAGTACAACAGCACGTACCGTGTGGTCAGCGTCC<br>TCACCGTCCTGCACCAGGACTGGCTGAATGGCAAGGAG<br>TACAAGTGCAAGGTCTCCAACAAAGCCCTCCCAGCCCC<br>CATCGAGAAAACCATCTCCAAAGCCAAAGGGCAGCCCC<br>GAGAACCACAGGTGTACACCCTGCCCCCATCCCGGGAG<br>GAGATGACCAAGAACCAGGTCAGCCTGACCTGCCTGGT<br>CAAAGGCTTCTATCCCAGCGACATCGCCGTGGAGTGGG<br>AGAGCAATGGGCAGCCGGAGAACAACTACAAGACCACG<br>CCTCCCGTGCTGGACTCCGACGGCTCCTTCTTCCTCTA<br>CAGCAAGCTCACCGTGGACAAGAGCAGGTGGCAGCAGG<br>GGAACGTCTTCTCATGCTCCGTGATGCATGAGGCTCTG<br>CACAACCACTACACGCAGAAGAGCCTCTCCCTGTCTCC<br>GGGTAAA |
| 37 | Aglyco-FLT3L (S128A/S151A) hingeless hG1 | ACCCAGGACTGCTCCTTCCAGCACTCCCCTATCTCTTC<br>CGACTTCGCCGTGAAGATCAGAGAGCTGTCCGACTACC<br>TGCTGCAGGACTATCCTGTGACCGTGGCCAGCAACCTG<br>CAGGATGAAGAACTGTGTGGTGGACTGTGGCGACTGGT<br>GCTGGCTCAGAGATGGATGGAAAGACTGAAAACCGTGG<br>CCGGCTCCAAGATGCAGGGACTGCTGGAAAGAGTGAAC<br>ACAGAGATCCACTTCGTGACCAAGTGCGCCTTTCAGCC<br>TCCTCCATCCTGCCTGAGATTCGTGCAGACCAATATCG<br>CCCGGCTGCTGCAAGAGACATCTGAGCAGCTGGTGCC<br>CTGAAGCCTTGGATCACCAGACAGAACTTCGCCCGGTG<br>CCTGGAACTGCAGTGTCAGCCTGATTCTTCTACCCTGC<br>CTCCACCTTGGAGCCCTAGACCTTTGGAGGCTACAGCT<br>CCTACTGCTCCTCAAGGCGGCCCAAGCGTTTTCCTGTT<br>TCCTCCAAAGCCTAAGGACACCCTGATGATCTCTCGGA<br>CCCCTGAAGTGACCTGCGTGGTGGTGGATGTGTCTCAC<br>GAGGATCCCGAAGTGAAGTTCAATTGGTACGTGGACGG<br>CGTGGAAGTGCACAACGCCAAGACCAAGCCTAGAGAGG<br>AACAGTACAACTCCACCTACAGAGTGGTGTCCGTGCTG<br>ACCGTGCTGCACCAGGATTGGCTGAACGGCAAAGAGTA<br>CAAGTGCAAGGTGTCCAACAAGGCCCTGCCTGCTCCTA<br>TCGAAAAGACCATCTCCAAGGCCAAGGGCCAGCCTAGG<br>GAACCTCAGGTTTACACCCTGCCACCTAGCCGGGAAGA<br>GATGACCAAAAACCAGGTGTCCCTGACCTGCCTGGTCA<br>AGGGCTTCTACCCATCCGATATCGCCGTGGAATGGGAG<br>TCTAACGGCCAGCCTGAGAACAACTACAAGACCACACC<br>TCCTGTGCTGGACTCCGACGGCTCATTCTTCCTGTACT<br>CCAAGCTGACAGTGGACAAGTCTCGGTGGCAGCAGGGC<br>AACGTGTTCTCCTGTTCTGTGATGCACGAGGCCCTGCA<br>CAACCACTACACCCAGAAGTCCCTGTCTCTGTCCCCTG<br>GCAAA |
| 38 | FLT3L (Δ C-term 5aa (PTAPQ; SEQ ID NO: 85))-hG4 S228P/F234A/ L235A | ACACAGGATTGCAGCTTCCAGCACAGCCCCATCAGCAG<br>CGATTTCGCCGTGAAGATCAGAGAGCTGAGCGACTACC<br>TGCTGCAGGACTACCCTGTGACCGTGGCCAGCAATCTG<br>CAGGACGAAGAACTGTGTGGTGGACTGTGGCGACTGGT<br>GCTGGCTCAGAGATGGATGGAACGGCTGAAAACAGTGG<br>CCGGCAGCAAGATGCAGGGACTGCTGGAAAGAGTGAAC<br>ACCGAGATCCACTTCGTGACCAAGTGCGCCTTCCAGCC<br>TCCTCCATCCTGCCTGAGATTCGTGCAGACCAACATCA<br>GCAGACTGCTGCAAGAGACAAGCGAGCAGCTGGTGGCC<br>CTGAAGCCTTGGATCACCAGACAGAACTTCAGCCGGTG<br>CCTGGAACTGCAGTGTCAGCCCGATAGCAGCACACTGC<br>CTCCGCCTTGGAGTCCTAGACCTCTGGAAGCCACAGCT<br>GAGTCTAAGTACGGCCCTCCTTGTCCTCCATGTCCTGC<br>TCCAGAAGCTGCTGGCGGCCCTTCCGTGTTTCTGTTCC<br>CTCCAAAGCCTAAGGACACCCTGATGATCTCTCGGACC<br>CCTGAAGTGACCTGCGTGGTGGTGGATGTGTCCCAAGA<br>GGATCCCGAGGTGCAGTTCAATTGGTACGTGGACGGCG<br>TGGAAGTGCACAACGCCAAGACCAAGCCTAGAGAGGAA<br>CAGTTCAACTCCACCTACAGAGTGGTGTCCGTGCTGAC<br>CGTGCTGCACCAGGATTGGCTGAACGGCAAAGAGTACA |

TABLE C-continued

Polynucleotides encoding FLT3L-Fc fusion proteins

| POLYNUCL. NO. SEQ ID NO: | Features | Polynucleotide Sequence |
|---|---|---|
| | | AGTGCAAGGTGTCCAACAAGGGCCTGCCTTCCAGCATC GAAAAGACCATCTCCAAGGCCAAGGGCCAGCCTAGGGA ACCCCAGGTTTACACCCTGCCTCCAAGCCAAGAGGAAA TGACCAAGAACCAGGTGTCCCTGACCTGCCTGGTCAAG GGCTTCTACCCTTCCGATATCGCCGTGGAATGGGAGAG CAATGGCCAGCCTGAGAACAACTACAAGACCACACCTC CTGTGCTGGACTCCGACGGCTCCTTCTTTCTGTACTCC CGCCTGACCGTGGACAAGTCCAGATGGCAAGAGGGCAA CGTGTTCTCCTGCTCCGTGATGCACGAGGCCCTGCACA ATCACTACACCCAGAAGTCCCTGTCTCTGTCCCTGGGC AAA |
| 39 | FLT3L (Δ C-term 5aa (PTAPQ; SEQ ID NO: 85))-hG4 S228P/F234A/ L235A | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC CTCCACCTTGGAGCCCTAGACCTCTGGAAGCTACCGCC GAGTCTAAGTACGGACCTCCTTGTCCTCCATGTCCTGC TCCAGAAGCTGCTGGCGGACCAAGCGTTTTCCTGTTTC CTCCAAAGCCTAAGGACACCCTGATGATCTCTCGGACC CCTGAAGTGACCTGCGTGGTGGTGGATGTGTCTCAAGA GGACCCCGAGGTGCAGTTCAATTGGTACGTGGACGGCG TGGAAGTGCACAACGCCAAGACCAAGCCTAGAGAGGAA CAGTTCAACTCCACCTACAGAGTGGTGTCCGTGCTGAC CGTGCTGCACCAGGATTGGCTGAACGGCAAAGAGTACA AGTGCAAGGTGTCCAACAAGGGCCTGCCTAGCTCCATC GAAAAGACCATCTCCAAGGCCAAGGGCCAGCCAAGAGA ACCTCAGGTGTACACACTGCCTCCAAGCCAAGAGGAAA TGACCAAGAACCAGGTGTCCCTGACCTGCCTGGTCAAG GGCTTCTACCCATCCGATATCGCCGTGGAATGGGAGTC TAACGGCCAGCCTGAGAACAACTACAAGACCACACCTC CTGTGCTGGACTCCGACGGCTCCTTCTTTCTGTACTCT CGCCTGACCGTGGACAAGTCTAGATGGCAAGAGGGCAA CGTGTTCTCCTGCTCTGTGATGCACGAGGCCCTGCACA ACCACTACACCCAGAAGTCCCTGTCTCTGTCCCTGGGC AAA |
| 40 | FLT3L ECD (Δ C-term 10aa (LEATAPTAPQ; SEQ ID NO: 90))- hingeless hG1 | ACACAGGATTGCAGCTTCCAGCACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCAAGTGCGCCTTCCAGCC TCCTCCATCCTGCCTGAGATTCGTGCAGACCAACATCA GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTGGGGGACCGTCAGTC TTCCTCTTCCCCCCAAAACCCAAGGACACCCTCATGAT CTCCCGGACCCCTGAGGTCACATGCGTGGTGGTGGACG TGAGCCACGAAGACCCTGAGGTCAAGTTCAACTGGTAC GTGGACGGCGTGGAGGTGCATAATGCCAAGACAAAGCC GCGGGAGGAGCAGTACAACAGCACGTACCGTGTGGTCA GCGTCCTCACCGTCCTGCACCAGGACTGGCTGAATGGC AAGGAGTACAAGTGCAAGGTCTCCAACAAAGCCCTCCC AGCCCCCATCGAGAAAACCATCTCCAAAGCCAAAGGGC AGCCCCGAGAACCACAGGTGTACACCCTGCCCCCATCC CGGGAGGAGATGACCAAGAACCAGGTCAGCCTGACCTG CCTGGTCAAAGGCTTCTATCCCAGCGACATCGCCGTGG AGTGGGAGAGCAATGGGCAGCCGGAGAACAACTACAAG ACCACGCCTCCCGTGCTGGACTCCGACGGCTCCTTCTT CCTCTACAGCAAGCTCACCGTGGACAAGAGCAGGTGGC AGCAGGGGAACGTCTTCTCATGCTCCGTGATGCATGAG GCTCTGCACAACCACTACACGCAGAAGAGCCTCTCCCT GTCTCCGGGTAAA |

TABLE C-continued

Polynucleotides encoding FLT3L-Fc fusion proteins

| POLYNUCL. NO. SEQ ID NO: | Features | Polynucleotide Sequence |
|---|---|---|
| 41 | FLT3L ECD (Δ C-term 10aa (LEATAPTAPQ; SEQ ID NO: 90))- hingeless hG1 | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC CTCCACCTTGGAGTCCTAGACCTGGCGGACCAAGCGTG TTCCTGTTTCCTCCAAAGCCTAAGGACACCCTGATGAT CTCTCGGACCCCTGAAGTGACCTGCGTGGTGGTGGATG TGTCTCACGAGGATCCCGAAGTGAAGTTCAATTGGTAC GTGGACGGCGTGGAAGTGCACAACGCCAAGACCAAGCC TAGAGAGGAACAGTACAACTCCACCTACAGAGTGGTGT CCGTGCTGACCGTGCTGCACCAGGATTGGCTGAACGGC AAAGAGTACAAGTGCAAGGTGTCCAACAAGGCCCTGCC TGCTCCTATCGAAAAGACCATCTCCAAGGCCAAGGGCC AGCCTAGGGAACCTCAGGTTTACACCCTGCCACCTAGC CGGGAAGAGATGACCAAAAACCAGGTGTCCCTGACCTG CCTGGTCAAGGGCTTCTACCCATCCGATATCGCCGTGG AATGGGAGTCTAACGGCCAGCCTGAGAACAACTACAAG ACCACACCTCCTGTGCTGGACTCCGACGGCTCATTCTT CCTGTACTCCAAGCTGACAGTGGACAAGTCTCGGTGGC AGCAGGGCAACGTGTTCTCCTGTTCTGTGATGCACGAG GCCCTGCACAACCACTACACCCAGAAGTCCCTGTCTCT GTCCCCTGGCAAA |
| 42 | FLT3L ECD (Δ C-term 10aa (LEATAPTAPQ; SEQ ID NO: 90))- hG4 S228P/F234A/ L235A | ACACAGGATTGCAGCTTCCAGCACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCAAGTGCGCCTTCCAGCC TCCTCCATCCTGCCTGAGATTCGTGCAGACCAACATCA GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTGAGTCTAAGTACGGC CCTCCTTGTCCTCCATGTCCTGCTCCAGAAGCTGCTGG CGGCCCTTCCGTGTTTCTGTTCCCTCCAAAGCCTAAGG ACACCCTGATGATCTCTCGGACCCCTGAAGTGACCTGC GTGGTGGTGGATGTGTCCCAAGAGGATCCCGAGGTGCA GTTCAATTGGTACGTGGACGGCGTGGAAGTGCACAACG CCAAGACCAAGCCTAGAGAGGAACAGTTCAACTCCACC TACAGAGTGGTGTCCGTGCTGACCGTGCTGCACCAGGA TTGGCTGAACGGCAAAGAGTACAAGTGCAAGGTGTCCA ACAAGGGCCTGCCTTCCAGCATCGAAAAGACCATCTCC AAGGCCAAGGGCCAGCCTAGGGAACCCCAGGTTTACAC CCTGCCTCCAAGCCAAGAGGAAATGACCAAGAACCAGG TGTCCCTGACCTGCCTGGTCAAGGGCTTCTACCCTTCC GATATCGCCGTGGAATGGGAGAGCAATGGCCAGCCTGA GAACAACTACAAGACCACACCTCCTGTGCTGGACTCCG ACGGCTCCTTCTTTCTGTACTCCCGCCTGACCGTGGAC AAGTCCAGATGGCAAGAGGGCAACGTGTTCTCCTGCTC CGTGATGCACGAGGCCCTGCACAATCACTACACCCAGA AGTCCCTGTCTCTGTCCCTGGGCAAA |
| 43 | FLT3L ECD (Δ C-term 10aa (LEATAPTAPQ; SEQ ID NO: 90))- hG4 S228P/F234A/ L235A | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC CTCCACCTTGGAGTCCTCGGCCTGAATCTAAGTATGGC CCTCCTTGTCCTCCATGTCCTGCTCCAGAAGCTGCTGG |

TABLE C-continued

Polynucleotides encoding FLT3L-Fc fusion proteins

| POLYNUCL. NO. SEQ ID NO: | Features | Polynucleotide Sequence |
|---|---|---|
| | | CGGACCAAGCGTTTTCCTGTTTCCTCCAAAGCCTAAGG ACACCCTGATGATCTCTCGGACCCCTGAAGTGACCTGC GTGGTGGTGGATGTGTCTCAAGAGGACCCCGAGGTGCA GTTCAATTGGTACGTGGACGGCGTGGAAGTGCACAACG CCAAGACCAAGCCTAGAGAGGAACAGTTCAACTCCACC TACAGAGTGGTGTCCGTGCTGACCGTGCTGCACCAGGA TTGGCTGAACGGCAAAGAGTACAAGTGCAAGGTGTCCA ACAAGGGCCTGCCTAGCTCCATCGAAAAGACCATCTCC AAGGCCAAGGGCCAGCCAAGAGAACCTCAGGTGTACAC ACTGCCTCCAAGCCAAGAGGAAATGACCAAGAACCAGG TGTCCCTGACCTGCCTGGTCAAGGGCTTCTACCCATCC GATATCGCCGTGGAATGGGAGTCTAACGGCCAGCCTGA GAACAACTACAAGACCACACCTCCTGTGCTGGACTCCG ACGGCTCCTTCTTTCTGTACTCTCGCCTGACCGTGGAC AAGTCTAGATGGCAAGAGGGCAACGTGTTCTCCTGCTC TGTGATGCACGAGGCCCTGCACAACCACTACACCCAGA AGTCCCTGTCTCTGTCCCTGGGCAAA |
| 44 | FLT3L ECD-hingeless hG1 (M252Y/S254T/T256E) | ACACAGGATTGCAGCTTCCAGCACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCAAGTGCGCCTTCCAGCC TCCTCCATCCTGCCTGAGATTCGTGCAGACCAACATCA GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTCTGGAAGCCACAGCT CCCACCGCTCCTCAAGGCGGACCGTCAGTCTTCCTCTT CCCCCCAAAACCCAAGGACACCCTCTACATCACCCGGG AACCTGAGGTCACATGCGTGGTGGTGGACGTGAGCCAC GAAGACCCTGAGGTCAAGTTCAACTGGTACGTGGACGG CGTGGAGGTGCATAATGCCAAGACAAAGCCGCGGGAGG AGCAGTACAACAGCACGTACCGTGTGGTCAGCGTCCTC ACCGTCCTGCACCAGGACTGGCTGAATGGCAAGGAGTA CAAGTGCAAGGTCTCCAACAAAGCCCTCCCAGCCCCCA TCGAGAAAACCATCTCCAAAGCCAAAGGGCAGCCCCGA GAACCACAGGTGTACACCCTGCCCCCATCCCGGGAGGA TGATGACCAAGAACCAGGTCAGCCTGACCTGCCTGGTCA AAGGCTTCTATCCCAGCGACATCGCCGTGGAGTGGGAG AGCAATGGGCAGCCGGAGAACAACTACAAGACCACGCC TCCCGTGCTGGACTCCGACGGCTCCTTCTTCCTCTACA GCAAGCTCACCGTGGACAAGAGCAGGTGGCAGCAGGGG AACGTCTTCTCATGCTCCGTGATGCATGAGGCTCTGCA CAACCACTACACGCAGAAGAGCCTCTCCCTGTCTCCGG GTAAA |
| 45 | FLT3L ECD-hingeless hG1 (M252Y/S254T/T256E) | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC CTCCACCTTGGAGCCCTAGACCTTTGGAGGCTACAGCT CCTACTGCTCCTCAAGGCGGCCCAAGCGTTTTCCTGTT TCCTCCAAAGCCTAAGGACACCCTGTACATCACCCGCG AGCCTGAAGTGACATGCGTGGTGGTGGATGTGTCCCAC GAGGACCCCGAAGTGAAGTTCAATTGGTACGTGGACGG CGTGGAAGTGCACAACGCCAAGACCAAGCCTAGAGAGG AACAGTACAACTCCACCTACAGAGTGGTGTCCGTGCTG ACCGTGCTGCACCAGGATTGGCTGAACGGCAAAGAGTA CAAGTGCAAGGTGTCCAACAAGGCCCTGCCTGCTCCTA TCGAAAAGACCATCTCCAAGGCCAAGGGCCAGCCTAGG GAACCTCAGGTTTACACCCTGCCACCTAGCCGGGAAGA GATGACCAAAAACCAGGTGTCCCTGACCTGCCTGGTCA AGGGCTTCTACCCATCCGATATCGCCGTGGAATGGGAG TCTAACGGCCAGCCTGAGAACAACTACAAGACCACACC |

TABLE C-continued

Polynucleotides encoding FLT3L-Fc fusion proteins

| POLYNUCL. NO. SEQ ID NO: | Features | Polynucleotide Sequence |
|---|---|---|
| | | TCCTGTGCTGGACTCCGACGGCTCATTCTTCCTGTACT<br>CCAAGCTGACAGTGGACAAGTCTCGGTGGCAGCAGGGC<br>AACGTGTTCTCCTGTTCTGTGATGCACGAGGCCCTGCA<br>CAACCACTACACCCAGAAGTCCCTGTCTCTGTCCCCTG<br>GCAAA |
| 46 | FLT3L ECD (Δ C-term 5aa (PTAPQ; SEQ ID NO: 85)) - hingeless hG1 (M252Y/S254T/T256E) | ACACAGGATTGCAGCTTCCAGCACAGCCCCATCAGCAG<br>CGATTTCGCCGTGAAGATCAGAGAGCTGAGCGACTACC<br>TGCTGCAGGACTACCCTGTGACCGTGGCCAGCAATCTG<br>CAGGACGAAGAACTGTGTGGTGGACTGTGGCGACTGGT<br>GCTGGCTCAGAGATGGATGGAACGGCTGAAAACAGTGG<br>CCGGCAGCAAGATGCAGGGACTGCTGGAAAGAGTGAAC<br>ACCGAGATCCACTTCGTGACCAAGTGCGCCTTCCAGCC<br>TCCTCCATCCTGCCTGAGATTCGTGCAGACCAACATCA<br>GCAGACTGCTGCAAGAGACAAGCGAGCAGCTGGTGCC<br>CTGAAGCCTTGGATCACCAGACAGAACTTCAGCCGGTG<br>CCTGGAACTGCAGTGTCAGCCCGATAGCAGCACACTGC<br>CTCCGCCTTGGAGTCCTAGACCTCTGGAAGCCACAGCT<br>GGGGGACCGTCAGTCTTCCTCTTCCCCCCAAAACCCAA<br>GGACACCCTCTACATCACCCGGGAACCTGAGGTCACAT<br>GCGTGGTGGTGGACGTGAGCCACGAAGACCCTGAGGTC<br>AAGTTCAACTGGTACGTGGACGGCGTGGAGGTGCATAA<br>TGCCAAGACAAAGCCGCGGGAGGAGCAGTACAACAGCA<br>CGTACCGTGTGGTCAGCGTCCTCACCGTCCTGCACCAG<br>GACTGGCTGAATGGCAAGGAGTACAAGTGCAAGGTCTC<br>CAACAAAGCCCTCCCAGCCCCCATCGAGAAAACCATCT<br>CCAAAGCCAAAGGGCAGCCCCGAGAACCACAGGTGTAC<br>ACCCTGCCCCCATCCCGGGAGGAGATGACCAAGAACCA<br>GGTCAGCCTGACCTGCCTGGTCAAAGGCTTCTATCCCA<br>GCGACATCGCCGTGGAGTGGGAGAGCAATGGGCAGCCG<br>GAGAACAACTACAAGACCACGCCTCCCGTGCTGGACTC<br>CGACGGCTCCTTCTTCCTCTACAGCAAGCTCACCGTGG<br>ACAAGAGCAGGTGGCAGCAGGGGAACGTCTTCTCATGC<br>TCCGTGATGCATGAGGCTCTGCACAACCACTACACGCA<br>GAAGAGCCTCTCCCTGTCTCCGGGTAAA |
| 47 | FLT3L ECD (Δ C-term 5aa (PTAPQ; SEQ ID NO: 85)) - hingeless hG1 (M252Y/S254T/T256E) | ACCCAGGACTGCTCCTTCCAGCACTCCCCTATCTCTTC<br>CGACTTCGCCGTGAAGATCAGAGAGCTGTCCGACTACC<br>TGCTGCAGGACTATCCTGTGACCGTGGCCAGCAACCTG<br>CAGGATGAAGAACTGTGTGGTGGACTGTGGCGACTGGT<br>GCTGGCTCAGAGATGGATGGAAAGACTGAAAACCGTGG<br>CCGGCTCCAAGATGCAGGGACTGCTGGAAAGAGTGAAC<br>ACAGAGATCCACTTCGTGACCAAGTGCGCCTTTCAGCC<br>TCCTCCATCCTGCCTGAGATTCGTGCAGACCAACATCT<br>CCCGGCTGCTGCAAGAGACATCTGAGCAGCTGGTGGCC<br>CTGAAGCCTTGGATCACCCGGCAGAACTTCTCTCGGTG<br>CCTGGAACTGCAGTGTCAGCCTGATTCTTCTACCCTGC<br>CTCCACCTTGGAGCCCTAGACCTTTGGAAGCTACAGCT<br>GGCGGCCCAAGCGTGTTCCTGTTTCCTCCAAAGCCTAA<br>GGACACCCTGTACATCACCCGCGAGCCTGAAGTGACAT<br>GCGTGGTGGTGGATGTGTCCCACGAGGACCCCGAAGTG<br>AAGTTCAATTGGTACGTGGACGGCGTGGAAGTGCACAA<br>CGCCAAGACCAAGCCTAGAGAGGAACAGTACAACTCCA<br>CCTACAGAGTGGTGTCCGTGCTGACCGTGCTGCACCAG<br>GATTGGCTGAACGGCAAAGAGTACAAGTGCAAGGTGTC<br>CAACAAGGCCCTGCCTGCTCCTATCGAAAAGACCATCT<br>CCAAGGCCAAGGGCCAGCCTAGGGAACCTCAGGTTTAC<br>ACCCTGCCACCTAGCCGGGAAGAGATGACCAAAAACCA<br>GGTGTCCCTGACCTGCCTGGTCAAGGGCTTCTACCCAT<br>CCGATATCGCCGTGGAATGGGAGTCTAACGGCCAGCCT<br>GAGAACAACTACAAGACCACACCTCCTGTGCTGGACTC<br>CGACGGCTCATTCTTCCTGTACTCCAAGCTGACAGTGG<br>ACAAGTCTCGGTGGCAGCAGGGCAACGTGTTCTCCTGT<br>TCTGTGATGCACGAGGCCCTGCACAACCACTACACCCA<br>GAAGTCCCTGTCTCTGTCCCCTGGCAAA |
| 48 | FLT3L ECD-hG4 S228P/L235E/ M252Y/ S254T/T256E) | ACACAGGATTGCAGCTTCCAGCACAGCCCCATCAGCAG<br>CGATTTCGCCGTGAAGATCAGAGAGCTGAGCGACTACC<br>TGCTGCAGGACTACCCTGTGACCGTGGCCAGCAATCTG<br>CAGGACGAAGAACTGTGTGGTGGACTGTGGCGACTGGT<br>GCTGGCTCAGAGATGGATGGAACGGCTGAAAACAGTGG<br>CCGGCAGCAAGATGCAGGGACTGCTGGAAAGAGTGAAC<br>ACCGAGATCCACTTCGTGACCAAGTGCGCCTTCCAGCC<br>TCCTCCATCCTGCCTGAGATTCGTGCAGACCAACATCA |

TABLE C-continued

Polynucleotides encoding FLT3L-Fc fusion proteins

| POLYNUCL. NO. SEQ ID NO: | Features | Polynucleotide Sequence |
|---|---|---|
| | | GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTCTGGAAGCCACAGCT CCCACCGCTCCTCAAGAATCTAAGTACGGCCCTCCCTG CCCTCCTTGCCCAGCCCCTGAATTTGAGGGCGGACCCT CCGTGTTCCTGTTCCCCCCAAAGCCCAAGGACACCCTG TACATCACCCGGGAACCCGAAGTGACCTGCGTGGTGGT GGATGTGTCCCAGGAAGATCCCGAGGTGCAGTTCAATT GGTACGTGGACGGCGTGGAAGTGCACAACGCCAAGACC AAGCCCAGAGAGGAACAGTTCAACAGCACCTACCGGGT GGTGTCCGTGCTGACAGTGCTGCACCAGGACTGGCTGA ACGGCAAAGAGTACAAGTGCAAGGTGTCCAACAAGGGC CTGCCCAGCTCCATCGAGAAAACCATCAGCAAGGCCAA GGGCCAGCCCCGCGAACCCCAGGTGTACACACTGCCTC CAAGCCAGGAAGAGATGACCAAGAACCAGGTGTCCCTG ACCTGTCTCGTGAAAGGCTTCTACCCCTCCGATATCGC CGTGGAATGGGAGAGCAACGGCCAGCCCGAGAACAACT ACAAGACCACCCCCCCTGTGCTGGACAGCGACGGCTCA TTCTTCCTGTACAGCAGACTGACCGTGGACAAGAGCCG GTGGCAGGAAGGCAACGTGTTCAGCTGCAGCGTGATGC ACGAGGCCCTGCACAACCACTACACCCAGAAGTCCCTG TCTCTGTCCCTGGGCAAA |
| 49 | FLT3L ECD-hG4 S228P/L235E/ M252Y/ S254T/T256E) | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC CTCCACCTTGGAGCCCTAGACCTTTTGGAGGCTACAGCT CCTACCGCTCCTCAAGAGTCTAAGTACGGCCCTCCTTG TCCTCCATGTCCTGCTCCAGAATTTGAAGGCGGCCCAA GCGTGTTCCTGTTTCCTCCAAAGCCTAAGGACACCCTG TACATCACCCGCGAGCCTGAAGTGACATGCGTGGTGGT GGATGTGTCCCAAGAGGACCCCGAGGTGCAGTTCAATT GGTACGTGGACGGCGTGGAAGTGCACAACGCCAAGACC AAGCCTAGAGAGGAACAGTTCAACTCCACCTACAGAGT GGTGTCCGTGCTGACCGTGCTGCACCAGGATTGGCTGA ACGGCAAAGAGTACAAGTGCAAGGTGTCCAACAAGGGC CTGCCTAGCTCCATCGAAAAGACCATCTCCAAGGCCAA GGGCCAGCCAAGAGAACCTCAGGTGTACACACTGCCTC CAAGCCAAGAGGAAATGACCAAGAACCAGGTGTCCCTG ACCTGCCTGGTCAAGGGCTTCTACCCATCCGATATCGC CGTGGAATGGGAGTCTAACGGCCAGCCTGAGAACAACT ACAAGACCACACCTCCTGTGCTGGACTCCGACGGCTCC TTCTTTCTGTACTCTCGCCTGACCGTGGACAAGTCTAG ATGGCAAGAGGGCAACGTGTTCTCCTGCTCTGTGATGC ACGAGGCCCTGCACAACCACTACACCCAGAAGTCCCTG TCTCTGTCCCTGGGCAAA |
| 50 | FLT3L ECD-hG4 (S228P/F234A/L2 35A/M252Y/ S254T/T256E) | ACACAGGATTGCAGCTTCCAGCACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCAAGTGCGCCTTCAGCC TCCTCCATCCTGCCTGAGATTCGTGCAGACCAACATCA GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTCTGGAAGCCACAGCT CCCACCGCTCCTCAAGAGTCTAAGTACGGCCCTCCTTG TCCTCCATGTCCTGCTCCAGAAGCTGCTGGCGGCCCTT CCGTGTTTCTGTTCCCTCCAAAGCCTAAGGACACCCTG TACATCACCCGGGAACCCGAAGTGACCTGCGTGGTGGT GGATGTGTCCCAGGAAGATCCCGAGGTGCAGTTCAATT GGTACGTGGACGGCGTGGAAGTGCACAACGCCAAGACC |

TABLE C-continued

Polynucleotides encoding FLT3L-Fc fusion proteins

| POLYNUCL. NO. SEQ ID NO: | Features | Polynucleotide Sequence |
|---|---|---|
| | | AAGCCCAGAGAGGAACAGTTCAACAGCACCTACCGGGT GGTGTCCGTGCTGACAGTGCTGCACCAGGACTGGCTGA ACGGCAAAGAGTACAAGTGCAAGGTGTCCAACAAGGGC CTGCCCAGCTCCATCGAGAAAACCATCAGCAAGGCCAA GGGCCAGCCCCGCGAACCCCAGGTGTACACACTGCCTC CAAGCCAGGAAGAGATGACCAAGAACCAGGTGTCCCTG ACCTGTCTCGTGAAAGGCTTCTACCCCTCCGATATCGC CGTGGAATGGGAGAGCAACGGCCAGCCCGAGAACAACT ACAAGACCACCCCCCCTGTGCTGGACAGCGACGGCTCA TTCTTCCTGTACAGCAGACTGACCGTGGACAAGAGCCG GTGGCAGGAAGGCAACGTGTTCAGCTGCAGCGTGATGC ACGAGGCCCTGCACAACCACTACACCCAGAAGTCCCTG TCTCTGTCCCTGGGCAAA |
| 51 | FLT3L ECD-hG4 (S228P/F234A/L2 35A/M252Y/ S254T/T256E) | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC CTCCACCTTGGAGCCCTAGACCTTTGGAGGCTACAGCT CCTACCGCTCCTCAAGAGTCTAAGTACGCCCTCCTTG TCCTCCATGTCCTGCTCCAGAAGCTGCTGGCGGACCAA GCGTTTTCCTGTTTCCTCCAAAGCCTAAGGACACCCTG TACATCACCCGCGAGCCTGAAGTGACATGCGTGGTGGT GGATGTGTCCAAGAGGACCCCGAGGTGCAGTTCAATT GGTACGTGGACGGCGTGGAAGTGCACAACGCCAAGACC AAGCCTAGAGAGGAACAGTTCAACTCCACCTACAGAGT GGTGTCCGTGCTGACCGTGCTGCACCAGGATTGGCTGA ACGGCAAAGAGTACAAGTGCAAGGTGTCCAACAAGGGC CTGCCTAGCTCCATCGAAAAGACCATCTCCAAGGCCAA GGGCCAGCCAAGAGAACCTCAGGTGTACACACTGCCTC CAAGCCAAGAGGAAATGACCAAGAACCAGGTGTCCCTG ACCTGCCTGGTCAAGGGCTTCTACCCATCCGATATCGC CGTGGAATGGGAGTCTAACGGCCAGCCTGAGAACAACT ACAAGACCACACCTCCTGTGCTGGACTCCGACGGCTCC TTCTTTCTGTACTCTCGCCTGACCGTGGACAAGTCTAG ATGGCAAGAGGGCAACGTGTTCTCCTGCTCTGTGATGC ACGAGGCCCTGCACAACCACTACACCCAGAAGTCCCTG TCTCTGTCCCTGGGCAAA |
| 52 | Aglyco-FLT3L ECD (S128A/S151A) hingeless hG1 (M252Y/S254T/T2 56E) | ATGACAGTTTTGGCTCCAGCTTGGTCCCCTACAACCTA CCTGCTGCTGCTGTTGCTGCTCCTCTGGCCTGTCTG GCACCCAGGACTGTTCCTTCCAGCACTCCCCTATCTCC AGCGACTTCGCCGTGAAGATCAGAGAGCTGTCCGACTA TCTGCTGCAGGACTACCCTGTGACCGTGGCCAGCAATC TGCAGGACGAAGAACTGTGTGGTGGCCTGTGGCGACTG GTGTTGGCTCAGAGATGGATGGAACGGCTGAAAACCGT GGCCGGCTCTAAGATGCAGGGCCTGCTGGAAAGAGTGA ACACCGAGATCCACTTCGTGACCAAGTGCGCCTTTCAG CCTCCTCCATCCTGCCTGAGATTCGTGCAGACCAATAT CGCCCGGCTGCTGCAAGAGACATCCGAGCAGCTGGTGG CTCTGAAGCCCTGGATCACCAGACAGAACTTCGCCCGG TGTCTGGAACTGCAGTGTCAGCCTGACAGCTCTACCCT GCCTCCACCTTGGAGCCCTAGACCTCTGGAAGCTACCG CTCCAACCGCTCCTCAAGGGGGACCGTCAGTCTTCCTC TTCCCCCCAAAACCCAAGGACACCCTCTACATCACCCG GGAACCTGAGGTCACATGCGTGGTGGACGTGAGCC ACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCC TCACCGTCCTGCACCAGGACTGGCTGAATGGCAAGGAG TACAAGTGCAAGGTCTCCAACAAAGCCCTCCCAGCCCC CATCGAGAAAACCATCTCCAAAGCCAAAGGGCAGCCCC GAGAACCACAGGTGTACACCCTGCCCCCATCCCGGGAG GAGATGACCAAGAACCAGGTCAGCCTGACCTGCCTGGT CAAAGGCTTCTATCCCAGCGACATCGCCGTGGAGTGGG AGAGCAATGGGCAGCCGGAGAACAACTACAAGACCACG CCTCCCGTGCTGGACTCCGACGGCTCCTTCTTCCTCTA |

TABLE C-continued

Polynucleotides encoding FLT3L-Fc fusion proteins

| POLYNUCL. NO. SEQ ID NO: | Features | Polynucleotide Sequence |
|---|---|---|
| | | CAGCAAGCTCACCGTGGACAAGAGCAGGTGGCAGCAGG GGAACGTCTTCTCATGCTCCGTGATGCATGAGGCTCTG CACAACCACTACACGCAGAAGAGCCTCTCCCTGTCTCC GGGTAAA |
| 53 | Aglyco-FLT3L ECD (S128A/S151A) hingeless hG1 (M252Y/S254T/T256E) | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAATATCG CCCGGCTGCTGCAAGAGACATCTGAGCAGCTGGTGGCC CTGAAGCCTTGGATCACCAGACAGAACTTCAGCCGGTG CCTGGAACTGCAGTGTCAGCCTGATTCTTCTACCCTGC CTCCACCTTGGAGCCCTAGACCTTTGGAGGCTACAGCT CCTACTGCTCCTCAAGGCGGCCCAAGCGTTTTCCTGTT TCCTCCAAAGCCTAAGGACACCCTGTACATCACCCGCG AGCCTGAAGTGACATGCGTGGTGGTGGATGTGTCCCAC GAGGACCCCGAAGTGAAGTTCAATTGGTACGTGGACGG CGTGGAAGTGCACAACGCCAAGACCAAGCCTAGAGAGG AACAGTACAACTCCACCTACAGAGTGGTGTCCGTGCTG ACCGTGCTGCACCAGGATTGGCTGAACGGCAAAGAGTA CAAGTGCAAGGTGTCCAACAAGGCCCTGCCTGCTCCTA TCGAAAAGACCATCTCCAAGGCCAAGGGCCAGCCTAGG GAACCTCAGGTTTACACCCTGCCACCTAGCCGGGAAGA GATGACCAAAAACCAGGTGTCCCTGACCTGCCTGGTCA AGGGCTTCTACCCATCCGATATCGCCGTGGAATGGGAG TCTAACGGCCAGCCTGAGAACAACTACAAGACCACACC TCCTGTGCTGGACTCCGACGGCTCATTCTTCCTGTACT CCAAGCTGACAGTGGACAAGTCTCGGTGGCAGCAGGGC AACGTGTTCTCCTGTTCTGTGATGCACGAGGCCCTGCA CAACCACTACACCCAGAAGTCCCTGTCTCTGTCCCCTG GCAAA |
| 54 | FLT3L ECD (Δ C-term 5aa (PTAPQ; SEQ ID NO: 85))-hG4 (S228P/F234A/L235A/M252Y/S254T/T256E) | ACACAGGATTGCAGCTTCCAGCACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCAAGTGCGCCTTCCAGCC TCCTCCATCCTGCCTGAGATTCGTGCAGACCAACATCA GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTCTGGAAGCCACAGCT GAGTCTAAGTACGGCCCTCCTTGTCCTCCATGTCCTGC TCCAGAAGCTGCTGGCGGCCCTTCCGTGTTTCTGTTCC CTCCAAAGCCCAAGGACACCCTGTACATCACCCGGGAA CCCGAAGTGACCTGCGTGGTGGTGGATGTGTCCCAGGA AGATCCCGAGGTGCAGTTCAATTGGTACGTGGACGGCG TGGAAGTGCACAACGCCAAGACCAAGCCCAGAGAGGAA CAGTTCAACAGCACCTACCGGGTGGTGTCCGTGCTGAC AGTGCTGCACCAGGACTGGCTGAACGGCAAAGAGTACA AGTGCAAGGTGTCCAACAAGGGCCTGCCCAGCTCCATC GAGAAACCATCAGCAAGGCCAAGGGCCAGCCCCGCGA ACCCCAGGTGTACACACTGCCTCCAAGCCAGGAAGAGA TGACCAAGAACCAGGTGTCCCTGACCTGTCTCGTGAAA GGCTTCTACCCCTCCGATATCGCCGTGGAATGGGAGAG CAACGGCCAGCCCGAGAACAACTACAAGACCACCCCCC CTGTGCTGGACAGCGACGGCTCATTCTTCCTGTACAGC AGACTGACCGTGGACAAGAGCCGGTGGCAGGAAGGCAA CGTGTTCAGCTGCAGCGTGATGCACGAGGCCCTGCACA ACCACTACACCCAGAAGTCCCTGTCTCTGTCCCTGGGC AAA |

TABLE C-continued

Polynucleotides encoding FLT3L-Fc fusion proteins

| POLYNUCL. NO. SEQ ID NO: | Features | Polynucleotide Sequence |
|---|---|---|
| 55 | FLT3L ECD (Δ C-term 5aa (PTAPQ; SEQ ID NO: 85))-hG4 (S228P/F234A/L235A/M252Y/S254T/T256E) | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC CTCCACCTTGGAGCCCTAGACCTCTGGAAGCTACCGCC GAGTCTAAGTACGGACCTCCTTGTCCTCCATGTCCTGC TCCAGAAGCTGCTGGCGGACCAAGCGTTTTCCTGTTTC CTCCAAAGCCTAAGGACACCCTGTACATCACCCGCGAG CCTGAAGTGACATGCGTGGTGGTGGATGTGTCCCAAGA GGACCCCGAGGTGCAGTTCAATTGGTACGTGGACGGCG TGGAAGTGCACAACGCCAAGACCAAGCCTAGAGAGGAA CAGTTCAACTCCACCTACAGAGTGGTGTCCGTGCTGAC CGTGCTGCACCAGGATTGGCTGAACGGCAAAGAGTACA AGTGCAAGGTGTCCAACAAGGGCCTGCCTAGCTCCATC GAAAAGACCATCTCCAAGGCCAAGGGCCAGCCAAGAGA ACCTCAGGTGTACACACTGCCTCCAAGCCAAGAGGAAA TGACCAAGAACCAGGTGTCCCTGACCTGCCTGGTCAAG GGCTTCTACCCATCCGATATCGCCGTGGAATGGGAGTC TAACGGCCAGCCTGAGAACAACTACAAGACCACACCTC CTGTGCTGGACTCCGACGGCTCCTTCTTTCTGTACTCT CGCCTGACCGTGGACAAGTCTAGATGGCAAGAGGGCAA CGTGTTCTCCTGCTCTGTGATGCACGAGGCCCTGCACA ACCACTACACCCAGAAGTCCCTGTCTCTGTCCCTGGGC AAA |
| 56 | FLT3L ECD (Δ C-term 10aa (LEATAPTAPQ; SEQ ID NO: 90))-hG1 (M252Y/S254T/T256E) | ACACAGGATTGCAGCTTCCAGCACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCAAGTGCGCCTTCCAGCC TCCTCCATCCTGCCTGAGATTCGTGCAGACCAACATCA GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTGGGGGACCGTCAGTC TTCCTCTTCCCCCCAAAACCCAAGGACACCCTCTACAT CACCCGGGAACCTGAGGTCACATGCGTGGTGGTGGACG TGAGCCACGAAGACCCTGAGGTCAAGTTCAACTGGTAC GTGGACGGCGTGGAGGTGCATAATGCCAAGACAAAGCC GCGGGAGGAGCAGTACAACAGCACGTACCGTGTGGTCA GCGTCCTCACCGTCCTGCACCAGGACTGGCTGAATGGC AAGGAGTACAAGTGCAAGGTCTCCAACAAAGCCCTCCC AGCCCCCATCGAGAAAACCATCTCCAAAGCCAAAGGGC AGCCCCGAGAACCACAGGTGTACACCCTGCCCCCATCC CGGGAGGAGATGACCAAGAACCAGGTCAGCCTGACCTG CCTGGTCAAAGGCTTCTATCCCAGCGACATCGCCGTGG AGTGGGAGAGCAATGGGCAGCCGGAGAACAACTACAAG ACCACGCCTCCCGTGCTGGACTCCGACGGCTCCTTCTT CCTCTACAGCAAGCTCACCGTGGACAAGAGCAGGTGGC AGCAGGGGAACGTCTTCTCATGCTCCGTGATGCATGAG GCTCTGCACAACCACTACACGCAGAAGAGCCTCTCCCT GTCTCCGGGTAAA |
| 57 | FLT3L ECD (Δ C-term 10aa (LEATAPTAPQ; SEQ ID NO: 90))-hG1 (M252Y/S254T/T256E) | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC |

TABLE C-continued

Polynucleotides encoding FLT3L-Fc fusion proteins

| POLYNUCL. NO. SEQ ID NO:Features | | Polynucleotide Sequence |
|---|---|---|
| | | CTCCACCTTGGAGTCCTAGACCTGGCGGACCAAGCGTG TTCCTGTTTCCTCCAAAGCCTAAGGACACCCTGTACAT CACCCGCGAGCCTGAAGTGACATGCGTGGTGGTGGATG TGTCCCACGAGGACCCCGAAGTGAAGTTCAATTGGTAC GTGGACGGCGTGGAAGTGCACAACGCCAAGACCAAGCC TAGAGAGGAACAGTACAACTCCACCTACAGAGTGGTGT CCGTGCTGACCGTGCTGCACCAGGATTGGCTGAACGGC AAAGAGTACAAGTGCAAGGTGTCCAACAAGGCCCTGCC TGCTCCTATCGAAAAGACCATCTCCAAGGCCAAGGGCC AGCCTAGGGAACCTCAGGTTTACACCCTGCCACCTAGC CGGGAAGAGATGACCAAAAACCAGGTGTCCCTGACCTG CCTGGTCAAGGGCTTCTACCCATCCGATATCGCCGTGG AATGGGAGTCTAACGGCCAGCCTGAGAACAACTACAAG ACCACACCTCCTGTGCTGGACTCCGACGGCTCATTCTT CCTGTACTCCAAGCTGACAGTGGACAAGTCTCGGTGGC AGCAGGGCAACGTGTTCTCCTGTTCTGTGATGCACGAG GCCCTGCACAACCACTACACCCAGAAGTCCCTGTCTCT GTCCCCTGGCAAA |
| 58 | FLT3L ECD (Δ C-term 10aa (LEATAPTAPQ; SEQ ID NO: 90))- hG4 (3228P/F234A/L2 35A/M252Y/ S254T/T256E) | ACACAGGATTGCAGCTTCCAGCACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCAAGTGCGCCTTCCAGCC TCCTCCATCCTGCCTGAGATTCGTGCAGACCAACATCA GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTGAGTCTAAGTACGGC CCTCCTTGTCCTCCATGTCCTGCTCCAGAAGCTGCTGG CGGCCCCTTCCGTGTTTCTGTTCCCTCCAAAGCCTAAGG ACACCCTGTACATCACCCGGGAACCCGAAGTGACCTGC GTGGTGGTGGATGTGTCCCAGGAAGATCCCGAGGTGCA GTTCAATTGGTACGTGGACGGCGTGGAAGTGCACAACG CCAAGACCAAGCCCAGAGAGGAACAGTTCAACAGCACC TACCGGGTGGTGTCCGTGCTGACAGTGCTGCACCAGGA CTGGCTGAACGGCAAAGAGTACAAGTGCAAGGTGTCCA ACAAGGGCCTGCCCAGCTCCATCGAGAAAACCATCAGC AAGGCCAAGGGCCAGCCCCGCGAACCCCAGGTGTACAC ACTGCCTCCAAGCCAGGAAGAGATGACCAAGAACCAGG TGTCCCTGACCTGTCTCGTGAAAGGCTTCTACCCCTCC GATATCGCCGTGGAATGGGAGAGCAACGGCCAGCCCGA GAACAACTACAAGACCACCCCCCCTGTGCTGGACAGCG ACGGCTCATTCTTCCTGTACAGCAGACTGACCGTGGAC AAGAGCCGGTGGCAGGAAGGCAACGTGTTCAGCTGCAG CGTGATGCACGAGGCCCTGCACAACCACTACACCCAGA AGTCCCTGTCTCTGTCCCCTGGCAAA |
| 59 | FLT3L ECD (Δ C-term 10aa (LEATAPTAPQ; SEQ ID NO: 90))- hG4 (S228P/F234A/L2 35A/M252Y/ S254T/T256E) | ACCCAGGACTGCTCCTTCCAGCACTCCCCTATCTCTTC CGACTTCGCCGTGAAGATCAGAGAGCTGTCCGACTACC TGCTGCAGGACTATCCTGTGACCGTGGCCAGCAACCTG CAGGATGAAGAACTGTGTGGTGGACTGTGGCGACTGGT GCTGGCTCAGAGATGGATGGAAAGACTGAAAACCGTGG CCGGCTCCAAGATGCAGGGACTGCTGGAAAGAGTGAAC ACAGAGATCCACTTCGTGACCAAGTGCGCCTTTCAGCC TCCTCCATCCTGCCTGAGATTCGTGCAGACCAACATCT CCCGGCTGCTGCAAGAGACATCTGAGCAGCTGGTGGCC CTGAAGCCTTGGATCACCCGGCAGAACTTCTCTCGGTG CCTGGAACTGCAGTGTCAGCCTGATTCTTCTACCCTGC CTCCACCTTGGAGCCCTCGGCCTGAATCTAAGTATGGC CCTCCTTGTCCTCCATGTCCTGCTCCAGAAGCTGCTGG CGGACCAAGCGTTTTCCTGTTTCCTCCAAAGCCTAAGG ACACCCTGTACATCACCCGCGAGCCTGAAGTGACATGC GTGGTGGTGGATGTGTCCCAAGAGGACCCCGAGGTGCA GTTCAATTGGTACGTGGACGGCGTGGAAGTGCACAACG CCAAGACCAAGCCTAGAGAGGAACAGTTCAACTCCACC TACAGAGTGGTGTCCGTGCTGACCGTGCTGCACCAGGA TTGGCTGAACGGCAAAGAGTACAAGTGCAAGGTGTCCA ACAAGGGCCTGCCTAGCTCCATCGAAAAGACCATCTCC AAGGCCAAGGGCCAGCCAAGAGAACCTCAGGTGTACAC ACTGCCTCCAAGCCAAGAGGAAATGACCAAGAACCAGG TGTCCCTGACCTGCCTGGTCAAGGGCTTCTACCCATCC |

TABLE C-continued

Polynucleotides encoding FLT3L-Fc fusion proteins

| POLYNUCL. NO. SEQ ID NO: | Features | Polynucleotide Sequence |
|---|---|---|
| | | GATATCGCCGTGGAATGGGAGTCTAACGGCCAGCCTGA<br>GAACAACTACAAGACCACACCTCCTGTGCTGGACTCCG<br>ACGGCTCCTTCTTTCTGTACTCTCGCCTGACCGTGGAC<br>AAGTCTAGATGGCAAGAGGGCAACGTGTTCTCCTGCTC<br>TGTGATGCACGAGGCCCTGCACAACCACTACACCCAGA<br>AGTCCCTGTCTCTGTCCCTGGGCAAA |
| 60 | Aglyco-FLT3L ECD (Δ C-term 10aa (LEATAPTAPQ; SEQ ID NO:90)) (S128A/S151A) - hG4 S228P/F234A/ L235A | ACCCAGGACTGTTCCTTCCAGCACTCCCCTATCTCCAG<br>CGACTTCGCCGTGAAGATCAGAGAGCTGTCCGACTATC<br>TGCTGCAGGACTACCCTGTGACCGTGGCCAGCAATCTG<br>CAGGACGAAGAACTGTGTGGTGGCCTGTGGCGACTGGT<br>GTTGGCTCAGAGATGGATGGAACGGCTGAAAACCGTGG<br>CCGGCTCTAAGATGCAGGGCCTGCTGGAAAGAGTGAAC<br>ACCGAGATCCACTTCGTGACCAAGTGCGCCTTTCAGCC<br>TCCTCCATCCTGCCTGAGATTCGTGCAGACCAATATCG<br>CCCGGCTGCTGCAAGAGACATCCGAGCAGCTGGTGGCT<br>CTGAAGCCCTGGATCACCAGACAGAACTTCGCCCGGTG<br>TCTGGAACTGCAGTGTCAGCCTGACAGCTCTACCCTGC<br>CTCCACCTTGGAGCCCTAGACCTGAGTCTAAGTACGGC<br>CCTCCTTGTCCTCCATGTCCTGCTCCAGAAGCTGCTGG<br>CGGCCCTTCCGTGTTTCTGTTCCCTCCAAAGCCTAAGG<br>ACACCCTGATGATCTCTCGGACCCCTGAAGTGACCTGC<br>GTGGTGGTGGATGTGTCCCAAGAGGATCCCGAGGTGCA<br>GTTCAATTGGTACGTGGACGGCGTGGAAGTGCACAACG<br>CCAAGACCAAGCCTAGAGAGGAACAGTTCAACTCCACC<br>TACAGAGTGGTGTCCGTGCTGACCGTGCTGCACCAGGA<br>TTGGCTGAACGGCAAAGAGTACAAGTGCAAGGTGTCCA<br>ACAAGGGCCTGCCTTCCAGCATCGAAAAGACCATCTCC<br>AAGGCCAAGGGCCAGCCTAGGGAACCCCAGGTTTACAC<br>CCTGCCTCCAAGCCAAGAGGGAAATGACCAAGAACCAGG<br>TGTCCCTGACCTGCCTGGTCAAGGGCTTCTACCCTTCC<br>GATATCGCCGTGGAATGGGAGAGCAATGGCCAGCCTGA<br>GAACAACTACAAGACCACACCTCCTGTGCTGGACTCCG<br>ACGGCTCCTTCTTTCTGTACTCCCGCCTGACCGTGGAC<br>AAGTCCAGATGGCAAGAGGGCAACGTGTTCTCCTGCTC<br>CGTGATGCACGAGGCCCTGCACAATCACTACACCCAGA<br>AGTCCCTGTCTCTGTCCCTGGGCAAA |
| 61 | Aglyco-FLT3L ECD (Δ C-term 10aa (LEATAPTAPQ; SEQ ID NO: 90)) (S128A/S151A) - hG4 (S228P/F234A/L2 35A/M252Y/ S254T/T256E) | ACCCAGGACTGTTCCTTCCAGCACTCCCCTATCTCCAG<br>CGACTTCGCCGTGAAGATCAGAGAGCTGTCCGACTATC<br>TGCTGCAGGACTACCCTGTGACCGTGGCCAGCAATCTG<br>CAGGACGAAGAACTGTGTGGTGGCCTGTGGCGACTGGT<br>GTTGGCTCAGAGATGGATGGAACGGCTGAAAACCGTGG<br>CCGGCTCTAAGATGCAGGGCCTGCTGGAAAGAGTGAAC<br>ACCGAGATCCACTTCGTGACCAAGTGCGCCTTTCAGCC<br>TCCTCCATCCTGCCTGAGATTCGTGCAGACCAATATCG<br>CCCGGCTGCTGCAAGAGACATCCGAGCAGCTGGTGGCT<br>CTGAAGCCCTGGATCACCAGACAGAACTTCGCCCGGTG<br>TCTGGAACTGCAGTGTCAGCCTGACAGCTCTACCCTGC<br>CTCCACCTTGGAGCCCTAGACCTGAGTCTAAGTACGGC<br>CCTCCTTGTCCTCCATGTCCTGCTCCAGAAGCTGCTGG<br>CGGCCCTTCCGTGTTTCTGTTCCCTCCAAAGCCCAAGG<br>ACACCCTGTACATCACCCGGGAACCCGAAGTGACCTGC<br>GTGGTGGTGGATGTGTCCCAGGAAGATCCCGAGGTGCA<br>GTTCAATTGGTACGTGGACGGCGTGGAAGTGCACAACG<br>CCAAGACCAAGCCCAGAGAGGAACAGTTCAACAGCACC<br>TACCGGGTGGTGTCCGTGCTGACAGTGCTGCACCAGGA<br>CTGGCTGAACGGCAAAGAGTACAAGTGCAAGGTGTCCA<br>ACAAGGGCCTGCCCAGCTCCATCGAGAAAACCATCAGC<br>AAGGCCAAGGGCCAGCCCCGCGAACCCCAGGTGTACAC<br>ACTGCCTCCAAGCCAGGAAGAGATGACCAAGAACCAGG<br>TGTCCCTGACCTGTCTCGTGAAAGGCTTCTACCCCTCC<br>GATATCGCCGTGGAATGGGAGAGCAACGGCCAGCCCGA<br>GAACAACTACAAGACCACCCCCCTGTGCTGGACAGCG<br>ACGGCTCATTCTTCCTGTACAGCAGACTGACCGTGGAC<br>AAGAGCCGGTGGCAGGAAGGCAACGTGTTCAGCTGCAG<br>CGTGATGCACGAGGCCCTGCACAACCACTACACCCAGA<br>AGTCCCTGTCTCTGTCCCTGGGCAAA |

TABLE C-continued

Polynucleotides encoding FLT3L-Fc fusion proteins

| POLYNUCL. NO. SEQ ID NO: | Features | Polynucleotide Sequence |
|---|---|---|
| 62 | Murine surrogate mFLT3L ECD-mG2a Fc (L234A/L235A/P329G) | ACCCCTGACTGCTACTTCAGCCACTCTCCTATCTCCAG<br>CAACTTCAAAGTGAAGTTCCGCGAGCTGACCGACCATC<br>TGCTGAAGGACTATCCTGTGACCGTGGCCGTGAACCTG<br>CAGGACGAAAAGCACTGCAAGGCCCTGTGGTCCCTGTT<br>TCTGGCCCAGAGATGGATCGAGCAGCTGAAAACCGTGG<br>CTGGCTCCAAGATGCAGACCCTGCTGGAAGATGTGAAC<br>ACCGAGATCCACTTCGTGACCAGCTGCACCTTCCAGCC<br>TCTGCCTGAGTGCCTGAGATTCGTGCAGACCAACATCT<br>CCCACCTGTTGAAGGACACATGCACCCAGCTGCTGGCC<br>CTGAAGCCTTGTATCGGCAAGGCCTGCCAGAACTTCTC<br>CCGGTGTCTGGAAGTGCAGTGCCAGCCTGACTCCTCCA<br>CACTGCTGCCACCTAGAAGCCCTATCGCTCTGGAAGCT<br>ACCGAGCTGCCTGAGCCTAGAGGCCCTACCATCAAGCC<br>TTGTCCTCCATGCAAGTGCCCCGCTCCTAATGCTGCTG<br>GTGGCCCTTCCGTGTTCATCTTCCCACCTAAGATCAAG<br>GACGTGCTGATGATCTCCCTGTCTCCTATCGTGACCTG<br>CGTGGTGGTGGACGTGTCCGAGGATGATCCTGACGTGC<br>AGATCAGTTGGTTCGTGAACAACGTGGAAGTGCACACC<br>GCTCAGACCCAGACACACAGAGAGGACTACAACAGCAC<br>CCTGAGAGTGGTGTCTGCCCTGCCTATCCAGCACCAGG<br>ATTGGATGTCCGGCAAAGAATTCAAGTGCAAAGTGAAC<br>AACAAGGACCTGGGCGCTCCCATCGAGCGGACCATCTC<br>TAAGCCTAAGGGATCCGTCAGAGCCCCTCAGGTGTACG<br>TTCTGCCTCCACCTGAGGAAGAGATGACCAAGAAACAA<br>GTGACCCTGACCTGCATGGTCACCGACTTCATGCCCGA<br>GGACATCTACGTGGAATGGACCAACAACGGCAAGACCG<br>AGCTGAACTACAAGAACACCGAGCCTGTGCTGGACTCC<br>GACGGCTCCTACTTCATGTACTCCAAGCTGCGCGTCGA<br>GAAGAAGAACTGGGTCGAGAGAAACTCCTACTCCTGCT<br>CCGTGGTGCACGAGGGCCTGCACAATCACCACACCACC<br>AAGTCCTTCTCTCGGACCCCTGGCAAA |
| 63 | Murine surrogate mFLT3L ECD (C136S) mG2a Fc (L234A/L235A/P329G) | ACCCCTGACTGCTACTTCAGCCACTCTCCTATCTCCAG<br>CAACTTCAAAGTGAAGTTCCGCGAGCTGACCGACCATC<br>TGCTGAAGGACTATCCTGTGACCGTGGCCGTGAACCTG<br>CAGGACGAAAAGCACTGCAAGGCCCTGTGGTCCCTGTT<br>TCTGGCCCAGAGATGGATCGAGCAGCTGAAAACCGTGG<br>CTGGCTCCAAGATGCAGACCCTGCTGGAAGATGTGAAC<br>ACCGAGATCCACTTCGTGACCAGCTGCACCTTCCAGCC<br>TCTGCCTGAGTGCCTGAGATTCGTGCAGACCAACATCT<br>CCCACCTGTTGAAGGACACATCCACCCAGCTGCTGGCC<br>CTGAAGCCTTGTATCGGCAAGGCCTGCCAGAACTTCTC<br>CCGGTGTCTGGAAGTGCAGTGCCAGCCTGACTCCTCCA<br>CACTGCTGCCACCTAGAAGCCCTATCGCTCTGGAAGCT<br>ACCGAGCTGCCTGAGCCTAGAGGCCCTACCATCAAGCC<br>TTGTCCTCCATGCAAGTGCCCCGCTCCTAATGCTGCTG<br>GTGGCCCTTCCGTGTTCATCTTCCCACCTAAGATCAAG<br>GACGTGCTGATGATCTCCCTGTCTCCTATCGTGACCTG<br>CGTGGTGGTGGACGTGTCCGAGGATGATCCTGACGTGC<br>AGATCAGTTGGTTCGTGAACAACGTGGAAGTGCACACC<br>GCTCAGACCCAGACACACAGAGAGGACTACAACAGCAC<br>CCTGAGAGTGGTGTCTGCCCTGCCTATCCAGCACCAGG<br>ATTGGATGTCCGGCAAAGAATTCAAGTGCAAAGTGAAC<br>AACAAGGACCTGGGCGCTCCCATCGAGCGGACCATCTC<br>TAAGCCTAAGGGATCCGTCAGAGCCCCTCAGGTGTACG<br>TTCTGCCTCCACCTGAGGAAGAGATGACCAAGAAACAA<br>GTGACCCTGACCTGCATGGTCACCGACTTCATGCCCGA<br>GGACATCTACGTGGAATGGACCAACAACGGCAAGACCG<br>AGCTGAACTACAAGAACACCGAGCCTGTGCTGGACTCC<br>GACGGCTCCTACTTCATGTACTCCAAGCTGCGCGTCGA<br>GAAGAAGAACTGGGTCGAGAGAAACTCCTACTCCTGCT<br>CCGTGGTGCACGAGGGCCTGCACAATCACCACACCACC<br>AAGTCCTTCTCTCGGACCCCTGGCAAA |
| 64 | FLT3L ECD-hingeless monoFc | ACACAGGATTGCAGCTTCCAGCACAGCCCCATCAGCAG<br>CGATTTCGCCGTGAAGATCAGAGAGCTGAGCGACTACC<br>TGCTGCAGGACTACCCTGTGACCGTGGCCAGCAATCTG<br>CAGGACGAAGAACTGTGTGGTGGACTGTGGCGACTGGT<br>GCTGGCTCAGAGATGGATGGAACGGCTGAAAACAGTGG<br>CCGGCAGCAAGATGCAGGGACTGCTGGAAAAGAGTGAA<br>ACCGAGATCCACTTCGTGACCAAGTGCGCCTTCCAGCC<br>TCCTCCATCCTGCCTGAGATTCGTGCAGACCAACATCA<br>GCAGACTGCTGCAAGAGACAAGCGAGCAGCTGGTGGCC |

TABLE C-continued

Polynucleotides encoding FLT3L-Fc fusion proteins

| POLYNUCL. NO. SEQ ID NO: | Features | Polynucleotide Sequence |
|---|---|---|
| | | CTGAAGCCTTGGATCACCAGACAGAACTTCAGCCGGTG<br>CCTGGAACTGCAGTGTCAGCCCGATAGCAGCACACTGC<br>CTCCGCCTTGGAGTCCTAGACCTCTGGAAGCCACAGCT<br>CCCACCGCTCCTCAAGGCGGACCGTCAGTCTTTCTGTT<br>CCCTCCAAAGCCTAAGGACACCCTGATGATCAGCAGAA<br>CCCCTGAAGTGACCTGCGTGGTGGTGGATGTGTCCCAC<br>GAGGATCCCGAAGTGAAGTTCAATTGGTACGTGGACGG<br>CGTGGAAGTGCACAACGCCAAGACCAAGCCTAGAGAGG<br>AACAGTACAACAGCACCTACAGAGTGGTGTCCGTGCTG<br>ACCGTGCTGCACCAGGATTGGCTGAACGGCAAAGAGTA<br>CAAGTGCAAGGTGTCCAACAAGGCCCTGCCTGCTCCTA<br>TCGAGAAAACCATCAGCAAGGCCAAGGGCCAGCCTAGG<br>GAACCCCAGGTGTACACAAAGCCTCCAAGCCGGGAAGA<br>GATGACCAAGAACCAGGTGTCCCTGAGCTGCCTGGTCA<br>AGGGCTTTTACCCCAGCGACATTGCCGTGGAATGGGAG<br>AGCAATGGCCAGCCTGAGAACAACTACAAGACCACCGT<br>GCCTGTGCTGGACAGCGACGGCTCTTTTAGACTGGCCA<br>GCTACCTGACCGTGGACAAGAGCAGATGGCAGCAGGGC<br>AACGTGTTCAGCTGCAGCGTGATGCACGAGGCCCTGCA<br>CAACCACTACACCCAGAAGTCCCTGTCTCTGAGCCCCG<br>GCAAA |
| 65 | FLT3L ECD (H8Y)-<br>hingeless hG1<br>Fc | ACACAGGATTGCAGCTTCCAGTACAGCCCCATCAGCAG<br>CGATTTCGCCGTGAAGATCAGAGAGCTGAGCGACTACC<br>TGCTGCAGGACTACCCTGTGACCGTGGCCAGCAATCTG<br>CAGGACGAAGAACTGTGTGGTGGACTGTGGCGACTGGT<br>GCTGGCTCAGAGATGGATGGAACGGCTGAAAACAGTGG<br>CCGGCAGCAAGATGCAGGGACTGCTGGAAAGAGTGAAC<br>ACCGAGATCCACTTCGTGACCAAGTGCGCCTTCCAGCC<br>TCCTCCATCCTGCCTGAGATTCGTGCAGACCAACATCA<br>GCAGACTGCTGCAAGAGACAAGCGAGCAGCTGGTGGCC<br>CTGAAGCCTTGGATCACCAGACAGAACTTCAGCCGGTG<br>CCTGGAACTGCAGTGTCAGCCCGATAGCAGCACACTGC<br>CTCCGCCTTGGAGTCCTAGACCTCTGGAAGCCACAGCT<br>CCCACCGCTCCTCAAGGCGGACCGTCAGTCTTCCTCTT<br>CCCCCCAAAACCCAAGGACACCCTCATGATCTCCCGGA<br>CCCCTGAGGTCACATGCGTGGTGGTGGACGTGAGCCAC<br>GAAGACCCTGAGGTCAAGTTCAACTGGTACGTGGACGG<br>CGTGGAGGTGCATAATGCCAAGACAAAGCCGCGGGAGG<br>AGCAGTACAACAGCACGTACCGTGTGGTCAGCGTCCTC<br>ACCGTCCTGCACCAGGACTGGCTGAATGGCAAGGAGTA<br>CAAGTGCAAGGTCTCCAACAAAGCCCTCCCAGCCCCCA<br>TCGAGAAAACCATCTCCAAAGCCAAAGGGCAGCCCCGA<br>GAACCACAGGTGTACACCCTGCCCCCATCCCGGGAGGA<br>GATGACCAAGAACCAGGTCAGCCTGACCTGCCTGGTCA<br>AAGGCTTCTATCCCAGCGACATCGCCGTGGAGTGGGAG<br>AGCAATGGGCAGCCGGAGAACAACTACAAGACCACGCC<br>TCCCGTGCTGGACTCCGACGGCTCCTTCTTCCTCTACA<br>GCAAGCTCACCGTGGACAAGAGCAGGTGGCAGCAGGGG<br>AACGTCTTCTCATGCTCCGTGATGCATGAGGCTCTGCA<br>CAACCACTACACGCAGAAGAGCCTCTCCCTGTCTCCGG<br>GTAAA |
| 66 | FLT3L ECD<br>(K84E)-<br>hingeless hG1<br>Fc | ACACAGGATTGCAGCTTCCAGCACAGCCCCATCAGCAG<br>CGATTTCGCCGTGAAGATCAGAGAGCTGAGCGACTACC<br>TGCTGCAGGACTACCCTGTGACCGTGGCCAGCAATCTG<br>CAGGACGAAGAACTGTGTGGTGGACTGTGGCGACTGGT<br>GCTGGCTCAGAGATGGATGGAACGGCTGAAAACAGTGG<br>CCGGCAGCAAGATGCAGGGACTGCTGGAAAGAGTGAAC<br>ACCGAGATCCACTTCGTGACCGAGTGCGCCTTCCAGCC<br>TCCTCCATCCTGCCTGAGATTCGTGCAGACCAACATCA<br>GCAGACTGCTGCAAGAGACAAGCGAGCAGCTGGTGGCC<br>CTGAAGCCTTGGATCACCAGACAGAACTTCAGCCGGTG<br>CCTGGAACTGCAGTGTCAGCCCGATAGCAGCACACTGC<br>CTCCGCCTTGGAGTCCTAGACCTCTGGAAGCCACAGCT<br>CCCACCGCTCCTCAAGGCGGACCGTCAGTCTTCCTCTT<br>CCCCCCAAAACCCAAGGACACCCTCATGATCTCCCGGA<br>CCCCTGAGGTCACATGCGTGGTGGTGGACGTGAGCCAC<br>GAAGACCCTGAGGTCAAGTTCAACTGGTACGTGGACGG<br>CGTGGAGGTGCATAATGCCAAGACAAAGCCGCGGGAGG<br>AGCAGTACAACAGCACGTACCGTGTGGTCAGCGTCCTC<br>ACCGTCCTGCACCAGGACTGGCTGAATGGCAAGGAGTA<br>CAAGTGCAAGGTCTCCAACAAAGCCCTCCCAGCCCCCA<br>TCGAGAAAACCATCTCCAAAGCCAAAGGGCAGCCCCGA |

TABLE C-continued

Polynucleotides encoding FLT3L-Fc fusion proteins

| POLYNUCL. NO. SEQ ID NO | Features | Polynucleotide Sequence |
|---|---|---|
| | | GAACCACAGGTGTACACCCTGCCCCCATCCCGGGAGGA GATGACCAAGAACCAGGTCAGCCTGACCTGCCTGGTCA AAGGCTTCTATCCCAGCGACATCGCCGTGGAGTGGGAG AGCAATGGGCAGCCGGAGAACAACTACAAGACCACGCC TCCCGTGCTGGACTCCGACGGCTCCTTCTTCCTCTACA GCAAGCTCACCGTGGACAAGAGCAGGTGGCAGCAGGGG AACGTCTTCTCATGCTCCGTGATGCATGAGGCTCTGCA CAACCACTACACGCAGAAGAGCCTCTCCCTGTCTCCGG GTAAA |
| 67 | FLT3L ECD (H8Y/K84E) hingeless hG1 Fc | ACACAGGATTGCAGCTTCCAGTACAGCCCCATCAGCAG CGATTTCGCCGTGAAGATCAGAGAGCTGAGCGACTACC TGCTGCAGGACTACCCTGTGACCGTGGCCAGCAATCTG CAGGACGAAGAACTGTGTGGTGGACTGTGGCGACTGGT GCTGGCTCAGAGATGGATGGAACGGCTGAAAACAGTGG CCGGCAGCAAGATGCAGGGACTGCTGGAAAGAGTGAAC ACCGAGATCCACTTCGTGACCGAGTGCGCCTTCCAGCC TCCTCCATCCTGCCTGAGATTCGTGCAGACCAACATCA GCAGACTGCTGCAAGAGACAAGCGAGCAGCTGGTGGCC CTGAAGCCTTGGATCACCAGACAGAACTTCAGCCGGTG CCTGGAACTGCAGTGTCAGCCCGATAGCAGCACACTGC CTCCGCCTTGGAGTCCTAGACCTCTGGAAGCCACAGCT CCCACCGCTCCTCAAGGCGGACCGTCAGTCTTCCTCTT CCCCCCAAAACCCAAGGACACCCTCATGATCTCCCGGA CCCCTGAGGTCACATGCGTGGTGGTGGACGTGAGCCAC GAAGACCCTGAGGTCAAGTTCAACTGGTACGTGGACGG CGTGGAGGTGCATAATGCCAAGACAAAGCCGCGGGAGG AGCAGTACAACAGCACGTACCGTGTGGTCAGCGTCCTC ACCGTCCTGCACCAGGACTGGCTGAATGGCAAGGAGTA CAAGTGCAAGGTCTCCAACAAAGCCCTCCCAGCCCCCA TCGAGAAAACCATCTCCAAAGCCAAAGGGCAGCCCCGA GAACCACAGGTGTACACCCTGCCCCCATCCCGGGAGGA GATGACCAAGAACCAGGTCAGCCTGACCTGCCTGGTCA AAGGCTTCTATCCCAGCGACATCGCCGTGGAGTGGGAG AGCAATGGGCAGCCGGAGAACAACTACAAGACCACGCC TCCCGTGCTGGACTCCGACGGCTCCTTCTTCCTCTACA GCAAGCTCACCGTGGACAAGAGCAGGTGGCAGCAGGGG AACGTCTTCTCATGCTCCGTGATGCATGAGGCTCTGCA CAACCACTACACGCAGAAGAGCCTCTCCCTGTCTCCGG GTAAA |
| 68 | Aglyco-FLT3L ECD (Δ C-term 5aa (PTAPQ; SEQ ID NO: 85)) (S128A/S151A)- hG4 (S228P/F234A/ L235A/M252Y/ S254T/T256E) | ACCCAGGACTGTTCCTTCCAGCACTCCCCTATCTCCAG CGACTTCGCCGTGAAGATCAGAGAGCTGTCCGACTATC TGCTGCAGGACTACCCTGTGACCGTGGCCAGCAATCTG CAGGACGAAGAACTGTGTGGTGGCCTGTGGCGACTGGT GTTGGCTCAGAGATGGATGGAACGGCTGAAAACCGTGG CCGGCTCTAAGATGCAGGGCCTGCTGGAAAGAGTGAAC ACCGAGATCCACTTCGTGACCAAGTGCGCCTTTCAGCC TCCTCCATCCTGCCTGAGATTCGTGCAGACCAATATCG CCCGGCTGCTGCAAGAGACATCCGAGCAGCTGGTGGCT CTGAAGCCCTGGATCACCAGACAGAACTTCGCCCGGTG TCTGGAACTGCAGTGTCAGCCTGACAGCTCTACCCTGC CTCCACCTTGGAGCCCTAGACCTCTGGAAGCTACCGCT GAGTCTAAGTACGGCCCTCCTTGTCCTCCATGTCCTGC TCCAGAAGCTGCTGGCGGCCCTTCCGTGTTTCTGTTCC CTCCAAAGCCCAAGGACACCCTGtacATCaccCGGgaa CCCGAAGTGACCTGCGTGGTGGTGGATGTGTCCCAGGA AGATCCCGAGGTGCAGTTCAATTGGTACGTGGACGGCG TGGAAGTGCACAACGCCAAGACCAAGCCCAGAGAGGAA CAGTTCAACAGCACCTACCGGGTGGTGTCCGTGCTGAC AGTGCTGCACCAGGACTGGCTGAACGGCAAAGAGTACA AGTGCAAGGTGTCCAACAAGGGCCTGCCCAGCTCCATC GAGAAAACCATCAGCAAGGCCAAGGGCCAGCCCCGCGA ACCCCAGGTGTACACACTGCCTCCAAGCCAGGAAGAGA TGACCAAGAACCAGGTGTCCCTGACCTGTCTCGTGAAA GGCTTCTACCCCTCCGATATCGCCGTGGAATGGGAGAG CAACGGCCAGCCCGAGAACAACTACAAGACCACCCCCC CTGTGCTGGACAGCGACGGCTCATTCTTCCTGTACAGC AGACTGACCGTGGACAAGAGCCGGTGGCAGGAAGGCAA CGTGTTCAGCTGCAGCGTGATGCACGAGGCCCTGCACA ACCACTACACCCAGAAGTCCCTGTCTCTGTCCCTGGGC AAA |

TABLE C-continued

Polynucleotides encoding FLT3L-Fc fusion proteins

| POLYNUCL. NO. SEQ ID NO: | Features | Polynucleotide Sequence |
|---|---|---|
| 69 | FLT3L ECD (Δ C-term 5aa (PTAPQ; SEQ ID NO: 85))-linker SST/AAA-hG4 (S228P/F234A/ L235A/M252Y/ S254T/T256E) | ACCCAGGACTGTTCCTTCCAGCACTCCCCTATCTCCAG CGACTTCGCCGTGAAGATCAGAGAGCTGTCCGACTATC TGCTGCAGGACTACCCTGTGACCGTGGCCAGCAATCTG CAGGACGAAGAACTGTGTGGTGGCCTGTGGCGACTGGT GTTGGCTCAGAGATGGATGGAACGGCTGAAAACCGTGG CCGGCTCTAAGATGCAGGGCCTGCTGGAAAGAGTGAAC ACCGAGATCCACTTCGTGACCAAGTGCGCCTTTCAGCC TCCTCCATCCTGCCTGAGATTCGTGCAGACCAACATCT CCCGGCTGCTGCAAGAGACATCCGAGCAGCTGGTGGCT CTGAAGCCCTGGATCACCCGGCAGAACTTCTCTCGGTG TCTGGAACTGCAGTGTCAGCCTGATGCTGCCGCTTTGC CTCCACCTTGGAGCCCTAGACCTCTGGAAGCTACCGCC GAGTCTAAGTACGGACCTCCTTGTCCTCCATGTCCTGC TCCAGAAGCTGCTGGCGGCCCTTCCGTGTTTCTGTTCC CTCCAAAGCCCAAGGACACCCTGTACATCACCCGGGAA CCCGAAGTGACCTGCGTGGTGGTGGATGTGTCCCAGGA AGATCCCGAGGTGCAGTTCAATTGGTACGTGGACGGCG TGGAAGTGCACAACGCCAAGACCAAGCCCAGAGAGGAA CAGTTCAACAGCACCTACCGGGTGGTGTCCGTGCTGAC AGTGCTGCACCAGGACTGGCTGAACGGCAAAGAGTACA AGTGCAAGGTGTCCAACAAGGGCCTGCCCAGCTCCATC GAGAAAACCATCAGCAAGGCCAAGGGCCAGCCCCGCGA ACCCCAGGTGTACACACTGCCTCCAAGCCAGGAAGAGA TGACCAAGAACCAGGTGTCCCTGACCTGTCTCGTGAAA GGCTTCTACCCCTCCGATATCGCCGTGGAATGGGAGAG CAACGGCCAGCCCGAGAACAACTACAAGACCACCCCC CTGTGCTGGACAGCGACGGCTCATTCTTCCTGTACAGC AGACTGACCGTGGACAAGAGCCGGTGGCAGGAAGGCAA CGTGTTCAGCTGCAGCGTGATGCACGAGGCCCTGCACA ACCACTACACCCAGAAGTCCCTGTCTCTGTCCCTGGGC AAA |
| 70 | FLT3L ECD (Δ C-term 5aa (PTAPQ; SEQ ID NO: 85))-linker SST/AAA; S170A/S180A-hG4 (S228P/F234A/ L235A/M252Y/ S254T/T256E) | ACCCAGGACTGTTCCTTCCAGCACTCCCCTATCTCCAG CGACTTCGCCGTGAAGATCAGAGAGCTGTCCGACTATC TGCTGCAGGACTACCCTGTGACCGTGGCCAGCAATCTG CAGGACGAAGAACTGTGTGGTGGCCTGTGGCGACTGGT GTTGGCTCAGAGATGGATGGAACGGCTGAAAACCGTGG CCGGCTCTAAGATGCAGGGCCTGCTGGAAAGAGTGAAC ACCGAGATCCACTTCGTGACCAAGTGCGCCTTTCAGCC TCCTCCATCCTGCCTGAGATTCGTGCAGACCAACATCT CCCGGCTGCTGCAAGAGACATCCGAGCAGCTGGTGGCT CTGAAGCCCTGGATCACCCGGCAGAACTTCTCTCGGTG TCTGGAACTGCAGTGTCAGCCTGATGCTGCCGCTTTGC CTCCTCCTTGGGCTCCTGACCTCTGGAAGCTACAGCC GAGGCTAAGTATGGCCCTCCTTGTCCTCCATGTCCTGC TCCAGAAGCTGCTGGCGGCCCTTCCGTGTTTCTGTTCC CTCCAAAGCCCAAGGACACCCTGTACATCACCCGGGAA CCCGAAGTGACCTGCGTGGTGGTGGATGTGTCCCAGGA AGATCCCGAGGTGCAGTTCAATTGGTACGTGGACGGCG TGGAAGTGCACAACGCCAAGACCAAGCCCAGAGAGGAA CAGTTCAACAGCACCTACCGGGTGGTGTCCGTGCTGAC AGTGCTGCACCAGGACTGGCTGAACGGCAAAGAGTACA AGTGCAAGGTGTCCAACAAGGGCCTGCCCAGCTCCATC GAGAAAACCATCAGCAAGGCCAAGGGCCAGCCCCGCGA ACCCCAGGTGTACACACTGCCTCCAAGCCAGGAAGAGA TGACCAAGAACCAGGTGTCCCTGACCTGTCTCGTGAAA GGCTTCTACCCCTCCGATATCGCCGTGGAATGGGAGAG CAACGGCCAGCCCGAGAACAACTACAAGACCACCCCC CTGTGCTGGACAGCGACGGCTCATTCTTCCTGTACAGC AGACTGACCGTGGACAAGAGCCGGTGGCAGGAAGGCAA CGTGTTCAGCTGCAGCGTGATGCACGAGGCCCTGCACA ACCACTACACCCAGAAGTCCCTGTCTCTGTCCCTGGGC AAA |

4. Vectors and Host Cells

Further provided are vectors comprising one or more polynucleotides encoding one or more of the FLT3L-Fc fusion proteins, described herein. A vector can be of any type, for example, a recombinant vector such as an expression vector. Vectors include without limitation, plasmids, cosmids, bacterial artificial chromosomes (BAC) and yeast artificial chromosomes (YAC) and vectors derived from bacteriophages or plant or animal (including human) viruses. Vectors can comprise an origin of replication recognized by the proposed host cell and in the case of expression vectors, promoter and other regulatory regions recognized by the host cell. In additional embodiments, a vector comprises a polynucleotide encoding an antibody of the disclosure operably linked to a promoter and optionally additional regulatory elements. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome. Vectors include without limitation, those suitable for recombinant production of the antibodies disclosed herein.

The choice of the vector is dependent on the recombinant procedures followed and the host used. Introduction of vectors into host cells can be affected by inter alia calcium phosphate transfection, virus infection, DEAE-dextran-mediated transfection, lipofectamine transfection or electroporation. Vectors may be autonomously replicating or may replicate together with the chromosome into which they have been integrated. In certain embodiments, the vectors contain one or more selection markers. The choice of the markers may depend on the host cells of choice. These include without limitation, kanamycin, neomycin, puromycin, hygromycin, zeocin, thymidine kinase gene from Herpes simplex virus (HSV-TK), and dihydrofolate reductase gene from mouse (dhfr). Vectors comprising one or more nucleic acid molecules encoding the FLT3L-Fc fusion proteins described herein, operably linked to one or more nucleic acid molecules encoding proteins or peptides that can be used to isolate the FLT3L-Fc fusion proteins, are also covered by the disclosure. These proteins or peptides include without limitation, glutathione-S-transferase, maltose binding protein, metal-binding polyhistidine, green fluorescent protein, luciferase and beta-galactosidase.

In other embodiments, the vector that is used is pcDNA™3.1+(ThermoFisher, MA).

In some embodiments, the viral vector comprises an oncolytic viral vector. As appropriate, the oncolytic viral vector can be a DNA virus or a RNA virus. In some embodiments, the viral vector is from a viral family selected from the group consisting of: Adenoviridae (e.g., Adenovirus), Arenaviridae (e.g., lymphocytic choriomeningitis mammarenavirus, Cali mammarenavirus (a.k.a., Pichinde mammarenavirus), Poxviridae (e.g., Vaccinia virus), Herpesviridae (e.g., Herpesvirus, e.g., HSV-1), Parvoviridae (e.g., Parvovirus H1), Reoviridae (e.g., Reovirus), Picornaviridae (e.g., Coxsackievirus, Seneca Valley Virus, Poliovirus), Paramyxoviridae (e.g., Measles virus, Newcastle disease virus (NDV)), Rhabdoviridae (e.g., Vesicular stomatitis virus (VSV)), Togaviridae (e.g., Alphavirus, Sindbis virus), Enteroviridae (e.g., Echovirus). The use of oncolytic viruses in cancer therapy is described e.g., Fukuhara, et al., *Cancer Sci.* (2016) 107(10):1373-1379; Kaufman, et al., *Nat Rev Drug Discov.* (2015) 14(9):642-62; Hamid, et al., *Cancer Immunol Immunother.* (2017) 66(10):1249-1264; Taguchi, et al., *Int J Urol.* (2017) 24(5):342-351; and Buij s, et al., *Hum Vaccin Immunother.* (2015) 11(7):1573-84.

The disclosure also provides host cells comprising a nucleic acid or a vector described herein. Any of a variety of host cells can be used. In one embodiment, a host cell is a prokaryotic cell, for example, *E. coli*. In another embodiment, a host cell is a eukaryotic cell, for example, a yeast cell, a plant cell, an insect cell, a mammalian cell, such as a Chinese Hamster Ovary (CHO)-based or CHO-origin cell line (e.g., CHO-S, CHO DG44, ExpiCHO™, CHOZN® ZEN-modified GS−/− CHO cell line, CHO-K1, CHO-K1a), COS cells, BHK cells, NS0 cells or Bowes melanoma cells. Examples of human host cells are, inter alia, HeLa, 911, AT1080, A549 and HEK293 (e.g., HEK293E, HEK293T, Expi293™). In addition, the FLT3L-Fc fusion proteins can be expressed in a yeast cell such as *Pichia* (see, e.g., Powers et al., *J Immunol Methods.* 251:123-35 (2001)), Hanseula, or *Saccharomyces*.

In some embodiments, the host cell predominantly sialylates N-linked glycosylation sites of the fusion protein. In some embodiments, the polynucleotides encoding a FLT3L-Fc fusion protein, as described herein, are expressed in a host cell that sialylates at least 50%, at least 55%, at least 60%, at least 65%, at least 70%, at least 75%, at least 80%, at least 85%, at least 90%, at least 91%, at least 92%, at least 93%, at least 94%, at least 95%, or more, N-linked glycosylation sites in the expressed FLT3L-Fc fusion proteins.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Some vectors are suitable for delivering the nucleic acid molecule or polynucleotide of the present application. Certain vectors are capable of directing the expression of nucleic acids to which they are operatively linked. Such vectors are referred to herein as expression vectors.

The term "operably linked" refers to two or more nucleic acid sequence or polypeptide elements that are usually physically linked and are in a functional relationship with each other. For instance, a promoter is operably linked to a coding sequence if the promoter is able to initiate or regulate the transcription or expression of a coding sequence, in which case, the coding sequence should be understood as being "under the control of" the promoter.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As appropriate, the host cells can be stably or transiently transfected with a polynucleotide encoding a FLT3L-Fc fusion protein, as described herein.

5. Methods of Producing FLT3L-Fc Fusion Proteins

The FLT3L-Fc fusion proteins described herein can be produced by any method known in the art for the synthesis of fusion proteins, for example, by chemical synthesis or by recombinant expression techniques.

Methods of recombinant expression of fusion proteins are known and can be applied to the recombinant production and isolation/purification of the FLT3L-Fc fusion proteins. Methods of recombinantly expressing proteins, including fusion proteins, are described, for example, in Green and Sambrook, "Molecular Cloning: A Laboratory Manual," 4$^{th}$ Edition, 2012, Cold Spring Harbor Laboratory Press; Current Protocols in Protein Science, Wiley, 1995-2109 (currentprotocols.onlinelibrary.wiley.com/journal/19343663/); and Current Protocols in Molecular Biology, Wiley, 1987-2019 (currentprotocols.onlinelibrary.wiley.com/journal/19343647/). In addition, other publications relating to producing recombinantly expressed fusion proteins include, e.g., Argelia Lorence (Editor), "Recombinant Gene Expression" (Methods in Molecular Biology) 2012, Humana Press; James L Hartley (Editor), "Protein Expression in Mammalian Cells: Methods and Protocols" (Methods in Molecular Biology) 2012, Humana Press; Roslyn M. Bill (Editor), "Recombinant Protein Production in Yeast: Methods and Protocols" (Methods in Molecular Biology) 2012, Humana Press; and MacDonald, Kolotilin and Menassa (Editors) "Recombinant Proteins from Plants: Methods and Protocols" (Methods in Molecular Biology), 2n$^d$ Edition, 2016, Humana Press.

In various embodiments, the FLT3L-Fc fusion proteins described herein may be produced in bacterial or eukaryotic cells. The FLT3L-Fc fusion proteins can also be produced in eukaryotic cells such as transformed cell lines (e.g., CHO, CHO-S, CHO DG44, ExpiCHO™, CHOZN®, CHO-K1, CHO-Kla, 293E, 293T, COS, NIH3T3). In addition, the FLT3L-Fc fusion proteins described herein can be expressed in a yeast cell such as Pichia (see, e.g., Powers et al., J Immunol Methods. 251:123-35 (2001)), Hanseula, or Saccharomyces. In one embodiment, the FLT3L-Fc fusion proteins described herein are produced in a CHO cell line, e.g., a CHO-S, CHO DG44, ExpiCHO™, CHOZN®, CHO-K1, CHO-K1a cell line, or a HEK293 (e.g., HEK293E, HEK293T, Expi293TM) cell line. To produce the FLT3L-Fc fusion proteins of interest (including a heterodimer comprising the FLT3-Fc fusion protein), one or more polynucleotides encoding the FLT3L-Fc fusion proteins is constructed, introduced into an expression vector, and then expressed in one or more suitable host cells. In some embodiments, three polynucleotides encoding a FLT3L-Fc fusion, a Fab heavy chain and a Fab light chain comprising a second antigen binding domain are co-expressed in a single host cell. Standard molecular biology techniques are used to prepare the recombinant expression vector, transfect the host cells, select for transformants, culture the host cells, and recover the FLT3L-Fc fusion proteins.

In some embodiments, the host cell predominantly sialylates N-linked glycosylation sites of the fusion protein. In some embodiments, the polynucleotides encoding a FLT3L-Fc fusion protein, as described herein, are expressed in a host cell that sialylates at least 50%, at least 55%, at least 60%, at least 65%, at least 70%, at least 75%, at least 80%, at least 85%, at least 90%, at least 91%, at least 92%, at least 93%, at least 94%, at least 95%, or more, N-linked glycosylation sites in the expressed FLT3L-Fc fusion proteins.

If the FLT3L-Fc fusion proteins are to be expressed in bacterial cells (e.g., E. coli), the expression vector should have characteristics that permit amplification of the vector in the bacterial cells. Additionally, when E. coli such as JM109, DH5α, HB101, or XL1-Blue is used as a host, the vector must have a promoter, for example, a lacZ promoter (Ward et al., 341:544-546 (1989), araB promoter (Better et al., Science, 240:1041-1043 (1988)), or T7 promoter that can allow efficient expression in E. coli. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for secretion of the FLT3L-Fc fusion proteins. For production into the periplasm of E. coli, the pelB signal sequence (Lei et al., J. Bacteriol., 169: 4379 (1987)) may be used as the signal sequence for secretion of the FLT3L-Fc fusion proteins. For bacterial expression, calcium chloride methods or electroporation methods may be used to introduce the expression vector into the bacterial cell.

If the FLT3L-Fc fusion proteins are to be expressed in mammalian cells (e.g., such as CHO-S, CHO DG44, ExpiCHO™, CHOZN®, CHO-K1, CHO-K1a, 293E, 293T, Expi293™, COS, NIH3T3 cells), the expression vector includes a promoter to promote expression in these cells, for example, an SV40 promoter (Mulligan et al., Nature, 277: 108 (1979)), MMLV-LTR promoter, EF1α promoter (Mizushima et al., Nucleic Acids Res., 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, the FLT3L-Fc fusion proteins are produced in mammalian cells. Exemplary mammalian host cells for expressing FLT3L-Fc fusion proteins include Chinese Hamster Ovary (e.g., CHO, CHO-S, CHO DG44, ExpiCHO™, CHOZN®, CHO-K1, CHO-K1a) (including dhfr-CHO cells, described in Urlaub and Chasin (1980) Proc. Natl. Acad. Sci. USA 77: 4216-4220, used with a DHFR selectable marker, e.g., as described in Kaufman and Sharp (1982) Mol. Biol. 159:601 621), human embryonic kidney 293 cells (e.g., 293, 293E, 293T, Expi293™), COS cells, NIH3T3 cells, lymphocytic cell lines, e.g., NSO myeloma cells and SP2 cells, and a cell from a transgenic animal, e.g., a transgenic mammal. For example, in some embodiments, the cell is a mammary epithelial cell.

In an exemplary system for expression of the FLT3L-Fc fusion proteins, recombinant expression vectors encoding the FLT3L-Fc fusion protein are introduced into dhfr-CHO cells by calcium phosphate-mediated transfection. In a specific embodiment, the dhfr-CHO cells are cells of the DG44 cell line, such as DG44i (see, e.g., Derouaz et al., Biochem Biophys Res Commun., 340(4):1069-77 (2006)). Within the recombinant expression vectors, the polynucleotide encoding the FLT3L-Fc fusion protein, and optionally a second polynucleotide encoding a second Fc fusion protein for forming a heterodimer, are operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vectors also carry a DHFR gene, which allows for selection of CHO cells that have been transfected with the vector using methotrexate selection/amplification. The selected transformant host cells are cultured to allow for expression and secretion of the FLT3L-Fc fusion protein, and the fusion protein is recovered from the culture medium.

The FLT3L-Fc fusion proteins can also be produced by a transgenic animal. For example, U.S. Pat. No. 5,849,992 describes a method of expressing an antibody in the mammary gland of a transgenic mammal. A transgene is constructed that includes a milk-specific promoter and one or more polynucleotides encoding the FLT3L-Fc fusion protein of interest and a signal sequence for secretion. The milk produced by females of such transgenic mammals includes, secreted-therein, the FLT3L-Fc fusion protein of interest. The FLT3L-Fc fusion protein can be purified from the milk, or for some applications, used directly. Animals are also provided comprising one or more of the FLT3L-Fc-encoding nucleic acids described herein.

The FLT3L-Fc fusion proteins can be isolated from inside or outside (such as medium) of the host cell and purified as substantially pure and homogenous, non-aggregated FLT3L-Fc fusion proteins (e.g, including monomeric, homodimeric and/or heterodimeric bispecific FLT3L-Fc fusion proteins). Methods for isolation and purification commonly used for protein purification, including antibody purification, may be used for the isolation and purification of herein described FLT3L-Fc fusion proteins, and are not limited to any particular method. Applicable protein purification techniques are described, e.g., in Labrou, Chronopoulou and Ataya (Editors), "Handbook on Protein Purification: Industry Challenges and Technological Developments, 2018, Nova Science Pub Inc; Gottschalk (Editor), "Process Scale Purification of Antibodies," 2nd Edition, 2017, Wiley; Staby, Rathore and Ahuja (Editors), "Preparative Chromatography for Separation of Proteins, 2017, Wiley; and Labrou (Editor), "Protein Downstream Processing: Design, Development and Application of High and Low-Resolution Methods, 2014, Human Press. The FLT3L-Fc fusion proteins may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes FLT3L-Fc fusion proteins that are highly purified using these purification methods.

6. Pharmaceutical Compositions

Provided are pharmaceutical compositions comprising a FLT3L-Fc fusion protein, as described herein, or a polynucleotide encoding a FLT3L-Fc fusion protein, as described herein, and a pharmaceutically acceptable diluent, carrier or excipient. In certain embodiments, the pharmaceutical composition comprises a therapeutically effective amount of the FLT3L-Fc fusion protein, or polynucleotide encoding such FLT3L-Fc fusion protein.

Various pharmaceutically acceptable diluents, carriers, and excipients, and techniques for the preparation and use of pharmaceutical compositions will be known to those of skill in the art in light of the present disclosure. Illustrative pharmaceutical compositions and pharmaceutically acceptable diluents, carriers, and excipients are also described in, e.g., Loyd V. Allen Jr (Editor), "Remington: The Science and Practice of Pharmacy," $22^{nd}$ Edition, 2012, Pharmaceutical Press; Brunton, Knollman and Hilal-Dandan, "Goodman and Gilman's The Pharmacological Basis of Therapeutics," 13th Edition, 2017, McGraw-Hill Education/Medical; McNally and Hastedt (Editors), "Protein Formulation and Delivery," 2nd Edition, 2007, CRC Press; Banga, "Therapeutic Peptides and Proteins: Formulation, Processing, and Delivery Systems," 3rd Edition, 2015, CRC Press; Lars Hovgaard, Frokjaer and van de Weert (Editors), "Pharmaceutical Formulation Development of Peptides and Proteins," 2nd Edition, 2012, CRC Press; Carpenter and Manning (Editors), "Rational Design of Stable Protein Formulations: Theory and Practice," 2002, Springer (Pharmaceutical Biotechnology (Book 13)); Meyer (Editor), "Therapeutic Protein Drug Products: Practical Approaches to Formulation in the Laboratory, Manufacturing, and the Clinic," 2012, Woodhead Publishing; and Shire, "Monoclonal Antibodies: Meeting the Challenges in Manufacturing, Formulation, Delivery and Stability of Final Drug Product," 2015, Woodhead Publishing.

In some embodiments, each carrier, diluent or excipient is "acceptable" in the sense of being compatible with the other ingredients of the pharmaceutical composition and not injurious to the subject. Often, the pharmaceutically acceptable carrier is an aqueous pH-buffered solution. Some examples of materials which can serve as pharmaceutically-acceptable carriers, diluents or excipients include: water; buffers, e.g., phosphate-buffered saline; sugars, such as lactose, trehalose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; amino acids (e.g., charged amino acids, including without limitation, aspartate, asparagine, glutamate, glutamine, histidine, lysine); and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The formulation of and delivery methods of pharmaceutical compositions will generally be adapted according to the site and the disease to be treated. Exemplary formulations include without limitation, those suitable for parenteral administration, e.g., intratumoral, intravenous, intra-arterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. In some embodiments, the pharmaceutical compositions are formulated for parenteral, e.g., intravenous, subcutaneous, or oral administration. In some embodiments, the pharmaceutical compositions are formulated for intratumoral administration.

In certain embodiments, pharmaceutical compositions are sterile. In certain embodiments, the pharmaceutical composition has a pH in the range of 4.5 to 8.5, 4.5 to 6.5, 6.5 to 8.5, or a pH of about 5.0, about 5.5, about 6.0, about 6.5, about 7.0, about 7.5, about 8.0 or about 8.5. In some embodiments, the pharmaceutical composition has a pH of 5.9. In one embodiment, the pharmaceutical composition has an osmolarity in the range of 240-260 or 250-330 mOsmol/L. In certain embodiments, the pharmaceutical composition is isotonic or near isotonic.

In some embodiments, the pharmaceutical compositions are liquids or solids. In some embodiments, the pharmaceutical composition comprises an aqueous solution, e.g., at a concentration in the range of about 1 mg/ml to about 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml or 20 mg/ml. In some embodiments, the pharmaceutical composition comprises an aqueous solution of FLT3L-Fc fusion protein at a concentration of about 2 mg/ml. In some embodiments, the pharmaceutical composition comprises an aqueous solution of FLT3L-Fc fusion protein at a concentration of 2 mg/ml. In some embodiments, the pharmaceutical composition is lyophilized. In certain embodiments, the pharmaceutical composition is formulated for intravenous administration and has a concentration of FLT3L-Fc fusion protein of about 1-100 mg/ml, 1-10 mg/ml, 2-20 mg/ml or about 1, 2, 3, 4, 5, 6, 7, 8, 9 or 10 mg/ml. In certain embodiments, the pharmaceutical composition is formulated for intravenous administration and has a concentration of FLT3L-Fc fusion protein of about 2 mg/ml. In certain embodiments, the pharmaceutical composition is formulated for intravenous administration and has a concentration of FLT3L-Fc fusion protein of 2 mg/ml. In some embodiments, the pharmaceutical composition is formulated for subcutaneous injection and has a concentration of FLT3L-Fc fusion protein of 1-100 mg/ml, 1-10 mg/ml, 2-20 mg/ml or about 1, 2, 3, 4, 5, 6, 7, 8, 9 or 10 mg/ml, and a viscosity less than 50 cP, less than 30 cP, less than 20 cP, or about 10 cP.

In some embodiments, the pharmaceutical composition is an aqueous solution containing 2 mg/mL FLT3L-Fc fusion protein in 20 mM histidine, 90 g/L sucrose, 0.2 g/L polysorbate 80, pH 5.9.

In some embodiments, the pharmaceutical composition further comprises one or more additional therapeutic agents, e.g., a second therapeutic agent, or second and third therapeutic agents.

7. Methods of Treatment

The FLT3L-Fc fusion proteins described herein find use for treating cancer or another proliferative disorder. In some embodiments, the methods entail administering a FLT3L-Fc fusion protein, homodimer or heterodimer comprising such fusion protein, polynucleotide encoding such fusion protein, or pharmaceutical composition comprising such fusion protein or polynucleotide, to a patient with cancer or another proliferative disorder. In certain embodiments, the method of treating cancer or another proliferative disorder comprises administering a provided compound or composition thereof to a mammal.

In another aspect, provided herein are methods for inducing the immune system in a subject in need thereof comprising administering an FLT3L-Fc fusion protein or lipoplex, such as an LNP, provided herein or a polynucleotide or vector encoding an FLT3L-Fc fusion protein provided herein to the subject.

In another aspect, provided herein are compounds for use in treating cancer comprising an FLT3L-Fc fusion protein provided herein, or a polynucleotide or vector encoding an FLT3L-Fc fusion protein provided herein.

In another aspect, the FLT3L-Fc fusion proteins described herein find use for treating or preventing a viral infection. In some embodiments, the viral infection is an infection caused by HIV. In some embodiments the viral infection is an infection caused by HBV. In some embodiments, the viral infection is caused by a coronavirus. In some embodiments, the coronavirus infection is caused by the SARS virus, the MERS virus, or the 2019-nCoV (COVID-19) virus. In some embodiments, the methods entail administering a FLT3L-Fc fusion protein, homodimer or heterodimer comprising such fusion protein, polynucleotide encoding such fusion protein, or pharmaceutical composition comprising such fusion protein or polynucleotide, to a patient having or at risk of having an infection caused by a virus. In some embodiments, the patient has or is at risk of having an infection caused by HIV, HBV, or coronavirus (e.g., SARS virus, MERS, virus, or COVID-19 virus). In certain embodiments, the method of treating or preventing a viral infection, such as an infection caused by a virus such as HIV, HBV, or coronavirus (e.g., SARS virus, MERS, virus, or COVID-19 virus), comprises administering a provided compound or composition thereof to a mammal.

As used herein, the terms "inhibition of cancer" and "inhibition of cancer cell proliferation" refer to the inhibition of the growth, division, maturation or viability of cancer cells, and/or causing the death of cancer cells, individually or in aggregate with other cancer cells, by cytotoxicity, nutrient depletion, or the induction of apoptosis.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, "delaying" development of a disease or disorder, or one or more symptoms thereof, means to defer, hinder, slow, retard, stabilize and/or postpone development of the disease, disorder, or symptom thereof. This delay can be of varying lengths of time, depending on the history of the disease and/or subject being treated. As is evident to one skilled in the art, a sufficient or significant delay can, in effect, encompass prevention, in that the subject does not develop the disease, disorder, or symptom thereof. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming a subject's HIV$^+$ status and assessing the subject's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in subjects with functioning immune systems but does occur in AIDS patients). Development may also refer to disease progression that may be initially undetectable and includes occurrence, recurrence and onset.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. For example, the term "preventing HIV infection" refers to administering to a subject who does not have a detectable HIV infection an anti-HIV therapeutic substance. It is understood that the subject for anti-HIV preventative therapy may be an individual at risk of contracting the HIV virus. Further, it is understood that prevention may not result in complete protection against onset of the disease or disorder. In some instances, prevention includes reducing the risk of developing the disease or disorder. The reduction of the risk may not result in complete elimination of the risk of developing the disease or disorder.

With respect to subjects, in some embodiments, the methods of treatment provided herein may be used to treat a subject (e.g., human, monkey, dog, cat, mouse) who has been diagnosed with or is suspected of having cancer. In some embodiments, the methods of treatment provided herein can be used to treat a subject (e.g., human, monkey, dog, cat, mouse) who has been diagnosed with or is suspected of having a viral infection. As used herein, a subject refers to a mammal, including, for example, a human.

In some embodiments, the subject may be a human who exhibits one or more symptoms associated with cancer or hyperproliferative disease (e.g., a tumor). In some embodiments, the subject may be a human who exhibits one or more symptoms associated with cancer. Any of the methods of cancer treatment provided herein may be used to treat cancer at various stages. By way of example, the cancer stage includes but is not limited to early, advanced, locally advanced, remission, refractory, reoccurred after remission and progressive. In some embodiments, the subject is at an early stage of a cancer. In other embodiments, the subject is at an advanced stage of cancer. In various embodiments, the subject has a stage I, stage II, stage III or stage IV cancer. One or more administrations of the FLT3L-Fc fusion protein, optionally with one or more additional therapeutic agents, can promote reduction or retraction of a tumor, decrease or inhibit tumor growth or cancer cell proliferation, and/or induce, increase or promote tumor cell killing. In some embodiments, the subject is in cancer remission. One or more administrations of the FLT3L-Fc fusion protein, optionally with one or more additional therapeutic agents, can prevent or delay metastasis or recurrence of cancer.

In some embodiments, the subject may be a human who exhibits one or more symptoms associated with a viral infection (e.g., a detectable viral titer). In some embodiments, the subject may be a human who exhibits one or more symptoms associated with a viral infection. Any of the methods of antiviral treatment provided herein may be used to treat a viral infection at various stages. In some embodiments, the subject is at an early stage of a viral infection. In other embodiments, the subject is at an advanced stage of a viral infection. In some embodiments, one or more administrations of the FLT3L-Fc fusion protein, optionally with one or more additional therapeutic agents, can promote the reduction of a viral titer in a subject.

In some embodiments, the subject may be a human who is at risk, or genetically or otherwise predisposed (e.g., risk factor) to developing cancer or hyperproliferative disease who has or has not been diagnosed. In some embodiments, the subject may be a human who is at risk, or genetically or otherwise predisposed (e.g., risk factor) to a disease, disorder, or symptoms thereof, caused by a viral infection who has or has not been diagnosed.

As used herein, an "at risk" individual is an individual who is at risk of developing a condition to be treated. In some embodiments, an "at risk" subject is a subject who is at risk of developing cancer. Generally, an "at risk" subject may or may not have detectable disease, and may or may not have displayed detectable disease prior to the treatment methods described herein. "At risk" denotes that an individual has one or more so-called risk factors, which are measurable parameters that correlate with development of a disease or condition and are known in the art. For example, an at risk subject may have one or more risk factors, which are measurable parameters that correlate with development of cancer, which are described herein. A subject having one or more of these risk factors has a higher probability of developing cancer than an individual without these risk factor(s). In general, risk factors may include, for example, age, sex, race, diet, history of previous disease, presence of precursor disease, genetic (e.g., hereditary) considerations, and environmental exposure. In some embodiments, the subjects at risk for cancer include, for example, those having relatives who have experienced the disease, and those whose risk is determined by analysis of genetic or biochemical markers. In some embodiments, the at risk subject is at risk of developing symptoms of a viral infection. For example, individuals at risk for AIDS are those infected with HIV.

In addition, the subject may be a human who is undergoing one or more standard therapies, such as chemotherapy, radiotherapy, immunotherapy, surgery, or combination thereof. Accordingly, one or more kinase inhibitors may be administered before, during, or after administration of chemotherapy, radiotherapy, immunotherapy, surgery or combination thereof.

In certain embodiments, the subject may be a human who is (i) substantially refractory to at least one chemotherapy treatment, or (ii) is in relapse after treatment with chemotherapy, or both (i) and (ii). In some of embodiments, the subject is refractory to at least two, at least three, or at least four chemotherapy treatments (including standard or experimental chemotherapies).

The FLT3L-Fc fusion proteins described herein find use as a vaccine adjuvant, promoting, increasing, supplementing and/or boosting the immune response induced by the vaccine. In various embodiments, the vaccine can be an anticancer vaccine, antiviral vaccine, or antibacterial vaccine. In some embodiments, the anticancer vaccine is a neoantigen vaccine, wherein a neoantigen refers to a class of HLA-bound peptides that arise from tumor-specific mutations. Illustrative neoantigen anticancer vaccines are described, e.g., in Ott, et al., *Nature.* 2017 Jul. 13; 547(7662):217-221; Li, et al., *Ann Oncol.* 2017 Dec. 1; 28(suppl_12):xii11-xii17; Aldous, et al., *Bioorg Med Chem.* 2018 Jun. 1; 26(10):2842-2849; and Linette, et al, *Trends Mol Med.* 2017 October; 23(10):869-871. In various embodiments, the vaccine comprises an antiviral vaccine against a virus selected from the group consisting of hepatitis A virus (HAV), hepatitis B virus (HBV), human immunodeficiency virus (HIV), cytomegalovirus (CMV), a herpes simplex virus (HSV), Epstein-Barr virus (EBV), human orthopneumovirus or human respiratory syncytial virus (RSV), human papillomavirus (HPV), varicella-zoster virus, measles virus, mumps virus, poliovirus vaccine, influenza virus, paramyxovirus, rotavirus, Zika virus, Dengue virus and Ebola virus. In some embodiments, the vaccine comprises an antibacterial vaccine against a bacterium selected from the group consisting of *Mycobacterium tuberculosis*, pertussis, tetanus, diphtheria, meningococcus, pneumococcus, *Haemophilus* influenza, cholera, typhoid, and anthrax. Illustrative anticancer vaccines include without limitation *Bacillus* Calmettle-Guerin (TheraCys®)—a live attenuated strain of *Mycobacterium bovis* for non-muscle invasive bladder carcinoma; Sipuleucel-T (Provenge®)—a dendritic cell (DC) vaccine for metastatic castration resistant prostate cancer (mCRPC); talimogene laherparepvec (T-VEC or Imlygic®)—an oncolytic viral-based vaccine for advanced melanoma; and recombinant viral prostate cancer vaccine PROSTVAC®-VF/TRI-COM™. In some embodiments, the anticancer vaccine is an antiviral vaccine. In some embodiments the anticancer vaccine is an HPV vaccine. In some embodiments, the HPV vaccine is PRGN-2009 (Precigen; PGEN Therapeutics). In some embodiments the HPV vaccine is Gardasil or Gardasil-9 (Merck&Co). In some embodiments, the HPV vaccine is Cervarix (GlaxoSmithKline Biologicals). In some embodiments the HSV vaccine is HSV529 (Sanofi Pasteur).

Accordingly, in one embodiment, provided are methods for promoting, inducing and/or increasing the expansion and/or proliferation of a cell or a population of cells that express fms related tyrosine kinase 3 (FLT3, CD135). In some embodiments, the methods comprise contacting the cell or population of cells with an effective amount of a FLT3L-Fc fusion protein, as described herein, a homodimer or heterodimer comprising such fusion protein, a polynucleotide encoding such fusion protein, a vector or lipoplex, such as a lipid nanoparticle (LNP), comprising such polynucleotide, or pharmaceutical composition comprising such fusion protein or polynucleotide. As used herein, a "lipoplex" refers to cationic liposomes that are nonviral (synthetic) lipid carriers of DNA. In some embodiments the lipoplex is a lipid nanoparticle (LNP). As used herein, the term "lipid nanoparticle" refers to one or more spherical nanoparticles with an average diameter of between about 10 to about 1000 nanometers, and which comprise a solid lipid core matrix that can solubilize lipophilic molecules. In certain embodiments, the lipid core is stabilized by surfactants (e.g., emulsifiers), and can comprise one or more of triglycerides (e.g., tristearin), diglycerides (e.g., glycerol bahenate), monoglycerides (e.g., glycerol monostearate), fatty acids (e.g., stearic acid), steroids (e.g., cholesterol), and waxes (e.g., cetyl palmitate), including combinations thereof. Lipid nanoparticles are described, for example, in Petrilli et al., *Curr Pharm Biotechnol.* 15:847-55, 2014; and U.S. Pat. Nos. 6,217,912; 6,881,421; 7,402,573; 7,404,969; 7,550,441; 7,727,969; 8,003,621; 8,691,750; 8,871,509; 9,017,726; 9,173,853; 9,220,779; 9,227,917; and 9,278,130, each of which is incorporated by reference in its entirety.

In some embodiments, the cell or population of cells that express FLT3 comprise dendritic cells (e.g., cDC1 cells and/or cDC2 cells), monocyte-derived dendritic cells (moDCs), and/or progenitor cells thereof. In some embodiments, the cell or population of cells that express FLT3 comprise hematopoietic progenitor cells. In some embodiments, the hematopoietic progenitor cells comprise Common Lymphoid Progenitors (CLPs), Early Progenitors with Lymphoid and Myeloid potential (EPLMs), granulocyte-monocyte (GM) progenitors (GMP), monocyte-derived dendritic cells (moDCs) progenitors, and/or early multi-potent progenitors (MPP) within the Lineage-kit+Scal (LSK) compartment. As appropriate, the cell can be contacted in vitro or in vivo. In some embodiments, conventional dendritic cells (e.g., cDC1 and/or cDC2) are expanded. In some embodiments, cDC1 dendritic cells (e.g., positive for surface expression of X-C motif chemokine receptor 1 (XCR1), thrombomodulin (THBD, CD141), and C-type lectin domain containing 9A (CLEC9A)) are expanded or induced to proliferate. In some embodiments, cDC2 dendritic cells (e.g., positive for surface expression of CD1c molecule (BDCA1)) are expanded or induced to proliferate. In some embodiments, dendritic cells positive for surface expression of BDCA1 (cDC1), BDCA2 (CLEC4c), BDCA3 (THBD) and/or BDCA4 (NRP1) are expanded or induced to proliferate. In some embodiments, the FLT3-expressing cells (e.g., dendritic cells) are expanded by at least about 10-fold, 20-fold, 50-fold, 100-fold, 200-fold, 300-fold, 400-fold, 500-fold, or more, e.g., in the tumor, in the lymph nodes, within 3 weeks of a single administration of the fusion protein, the homodimer, the heterodimer, the conjugate, the polynucleotide, the vector, the lipoplex (e.g., LNP) and/or the pharmaceutical composition.

In a further embodiment, provided are methods of expanding hematopoietic stem cells (HSCs) ex vivo, comprising culturing HSCs in vitro, in the presence of mesenchymal lineage precursor or stem cells (MLPSCs) and an effective amount of a FLT3L-Fc fusion protein, as described herein, a homodimer or heterodimer comprising such fusion protein, a polynucleotide encoding such fusion protein, or a vector or lipoplex, such as an lipid nanoparticle (LNP), comprising such polynucleotide such that HSCs having the phenotype CD34+ are expanded. In some embodiments, the HSC are derived from bone marrow, umbilical cord, peripheral blood, liver, thymus, lymph, or spleen. In some embodiments, the HSCs are further cultured in the presence of one or more hi stone deacetylase inhibitors (HDACi), such as valproic acid (VPA), trichostatin A (TSA), DLS3, MS275, or SAHA. In some embodiments, the HSCs have the phenotype CD34+, CD90+ or CD34+, CD45RA−, CD49f+. In some embodiments, the HSC are expanded at least 5-fold, at least 10-fold, at least 20-fold, or at least 40-fold. In some embodiments, the HSCs are further cultured in the presence of one or more factors selected from the group consisting of stem cell factor (SCF), thrombopoietin (TPO), interleukin 3 (IL3), and interleukin 6 (IL6). In some embodiments, the methods further comprise isolating cells having the phenotype the phenotype CD34+, CD90+ or CD34+, CD45RA−, CD49f+ to provide an enriched population of cells having the phenotype CD34+, CD90+ or CD34+, CD45RA−, CD49f+. In a further embodiment, provided are compositions comprising HSCs having of the phenotype CD34+, CD90+ or CD34+, CD45RA−, CD49f+ obtained using a method described herein. Illustrative examples of methods of HSC ex vivo expansion in which a FLT3L-Fc fusion protein described herein, a homodimer or heterodimer comprising such fusion protein, a polynucleotide encoding such fusion protein, or a vector or lipoplex, such as a lipid nanoparticle (LNP), comprising such polynucleotide could be applied are described for example, without limitation, in WO 2020/089411.

In a further embodiment, provided are methods of preventing, reducing and/or inhibiting the recurrence, growth, proliferation, migration and/or metastasis of a cancer cell or population of cancer cells in a subject in need thereof. Further provided are methods of enhancing, improving, and/or increasing the response to an anticancer therapy in a subject in need thereof. In some embodiments, the methods entail administering to the subject an effective amount of a FLT3L-Fc fusion protein, as described herein, a homodimer or heterodimer comprising such fusion protein, a polynucleotide encoding such fusion protein, a vector or lipoplex, such as a lipid nanoparticle (LNP), comprising such polynucleotide, or pharmaceutical composition comprising such fusion protein or polynucleotide.

In a further embodiment, provided are methods of treating or preventing a virus infection, comprising administering to a subject in need thereof an effective amount of a FLT3L-Fc fusion protein, as described herein, a homodimer or heterodimer comprising such fusion protein, a polynucleotide encoding such fusion protein, a vector or lipoplex, such as an lipid nanoparticle (LNP), comprising such polynucleotide. Further provided are methods of enhancing, improving, and/or increasing the response to an antiviral therapy in a subject in need thereof comprising administering to the subject an effective amount of a FLT3L-Fc fusion protein, as described herein, a homodimer or heterodimer comprising such fusion protein, a polynucleotide encoding such fusion protein, a vector or lipoplex, such as a lipid nanoparticle (LNP), comprising such polynucleotide. In some embodiments, the virus infection is a human hepatitis B virus (HBV) infection. In some embodiments, the virus infection is a human immunodeficiency virus (HIV) infection. In some embodiments, the virus infection is a coronavirus infection. In some embodiments the coronavirus is a Severe Acute Respiratory Syndrome (SARS)-associated virus. In some embodiments the coronavirus is a MERS-associated virus. In some embodiments, the coronavirus is a COVID-19-associated virus (e.g., SARS-CoV-2).

As used herein, "HBV" refers to a virus described by NCBI Taxonomy ID: NCBI:txid10407.

As used herein, "HIV" refers to a virus described by NCBI Taxonomy ID: NCBI:txid11676.

As used herein, "SARS"-associated virus refers to a virus described by NCBI Taxonomy ID: NCBI:txid694009.

As used herein, "MFRS"-associated virus refers to a virus described by NCBI Taxonomy ID: NCBI:txid1335626.

As used herein, "COVID-19-associated virus" or "SARS-CoV-2" refers to a virus described by NCBI Taxonomy ID: NCBI:txid2697049.

In a further embodiment, provided are methods of treating or preventing a human hepatitis B virus (HBV) infection comprising administering to a subject in need thereof an effective amount of a FLT3L-Fc fusion protein, as described herein, a homodimer or heterodimer comprising such fusion protein, a polynucleotide encoding such fusion protein, a vector or lipoplex, such as an lipid nanoparticle (LNP), comprising such polynucleotide. In certain embodiments, provided are methods of treating an HBV infection comprising administering to a subject in need thereof an effective amount of a FLT3L-Fc fusion protein, as described herein, a homodimer or heterodimer comprising such fusion protein, a polynucleotide encoding such fusion protein, a vector or lipoplex, such as a lipid nanoparticle (LNP), comprising such polynucleotide. In certain embodiments, the method comprises administering a FLT3L-Fc fusion protein, as described herein, a homodimer or heterodimer comprising such fusion protein, a polynucleotide encoding such fusion protein, a vector or lipoplex, such as a lipid nanoparticle (LNP), comprising such polynucleotide, in combination with one or more (e.g., one, two, three, one or two, or one to three) additional therapeutic agents. In certain embodiments, the subject is at risk of contracting the HBV virus, such as a subject who has one or more risk factors known to be associated with contracting the HBV virus. In certain embodiments, the subject may have not previously received antiviral treatment (treatment naïve). In certain embodiments, the subject may have previously received antiviral treatment (treatment experienced). In certain embodiments, the subject may have previously received antiviral treatment and developed resistance to the previously received antiviral treatment. In some embodiments, a method for inhibiting the replication of the HBV virus, treating an HBV infection or delaying the onset of symptoms of an HBV infection in a subject (e.g., a human), comprising administering an effective amount of a FLT3L-Fc fusion protein, as described herein to the subject is disclosed.

In a further embodiment, provided are methods of treating or preventing a human immunodeficiency virus (HIV) infection comprising administering to a subject in need thereof an effective amount of a FLT3L-Fc fusion protein, as described herein, a homodimer or heterodimer comprising such fusion protein, a polynucleotide encoding such fusion protein, a vector or lipoplex, such as an lipid nanoparticle (LNP), comprising such polynucleotide. In certain embodiments, provided are methods of treating an HIV infection comprising administering to a subject in need thereof an effective amount of a FLT3L-Fc fusion protein, as described herein, a homodimer or heterodimer comprising such fusion protein, a polynucleotide encoding such fusion protein, a vector or lipoplex, such as a lipid nanoparticle (LNP), comprising such polynucleotide. In certain embodiments, the method comprises administering a FLT3L-Fc fusion protein, as described herein, a homodimer or heterodimer comprising such fusion protein, a polynucleotide encoding such fusion protein, a vector or lipoplex, such as a lipid nanoparticle (LNP), comprising such polynucleotide, in combination with one or more (e.g., one, two, three, one or two, or one to three) additional therapeutic agents. In certain embodiments, the subject is at risk of contracting the HIV virus, such as a subject who has one or more risk factors known to be associated with contracting the HIV virus. In certain embodiments, the subject may have not previously received antiviral treatment (treatment naïve). In certain embodiments, the subject may have previously received antiviral treatment (treatment experienced). In certain embodiments, the subject may have previously received antiviral treatment and developed resistance to the previously received antiviral treatment. In some embodiments, a method for inhibiting the replication of the HIV virus, treating AIDS or delaying the onset of AIDS in a subject (e.g., a human), comprising administering an effective amount of a FLT3L-Fc fusion protein, as described herein, to the subject is disclosed.

In a further embodiment, provided are methods of treating or preventing a coronavirus infection comprising administering to a subject in need thereof an effective amount of a FLT3L-Fc fusion protein, as described herein, a homodimer or heterodimer comprising such fusion protein, a polynucleotide encoding such fusion protein, a vector or lipoplex, such as an lipid nanoparticle (LNP), comprising such polynucleotide. In certain embodiments, provided herein are methods of treating a coronavirus infection comprising administering to a subject in need thereof an effective amount of a FLT3L-Fc fusion protein, as described herein, a homodimer or heterodimer comprising such fusion protein, a polynucleotide encoding such fusion protein, a vector or lipoplex, such as a lipid nanoparticle (LNP) comprising such polynucleotide. In certain embodiments, the method comprises administering a compound disclosed herein, or a pharmaceutically acceptable salt thereof, in combination with one or more (e.g., one, two, three, one or two, or one to three) additional therapeutic agents. In certain embodiments, the subject is at risk of contracting the coronavirus. In certain embodiments, the subject may have not previously received antiviral treatment (treatment naïve). In certain embodiments, the subject may have previously received antiviral treatment (treatment experienced). In certain embodiments, the subject may have previously received antiviral treatment and developed resistance to the previously received antiviral treatment. In some embodiments, a method for inhibiting the replication of a coronavirus, treating a coronavirus or delaying the onset of symptoms of a coronavirus infection in a subject (e.g., a human), comprising administering an effective amount of a FLT3L-Fc fusion protein, as described herein, to the subject is disclosed. In certain embodiments, the coronavirus infection is an infection caused by the SARS virus, the MERS virus, or the 2019-nCoV (COVID-19) virus. In certain embodiments, the coronavirus infection is an infection caused by the SARS virus. In certain embodiments, the coronavirus infection is an infection caused by the MERS virus. In certain embodiments, the coronavirus infection is an infection caused by the 2019-nCoV (COVID-19) virus.

With respect to route of administration, in various embodiments, the FLT3L-Fc fusion protein, the homodimer, the heterodimer, the conjugate, the polynucleotide, the vector, the lipoplex, such as an LNP, and/or the pharmaceutical composition are administered systemically or locally. In some embodiments, the FLT3L-Fc fusion protein, the homodimer, the heterodimer, the conjugate, the polynucleotide, the vector, the lipoplex, such as an LNP, and/or the pharmaceutical composition can be administered intravenously, intratumorally, subcutaneously, intradermally, intramuscularly, intraperitoneally, intravesically, intracranially, intrathecally, intracavitary or intraventricularly. In embodiments involving combination therapies, as appropriate, the FLT3L-Fc fusion protein, the homodimer, the heterodimer, the conjugate, the polynucleotide, the vector, the lipoplex, such as an LNP, and/or the pharmaceutical composition and the one or more additional therapeutic agents can be administered by the same or different routes of administration. As appropriate, in certain embodiments, administration is via injection or infusion.

With respect to dosing, a therapeutically effective amount of FLT3L-Fc fusion protein, the homodimer, the heterodimer, the conjugate, the polynucleotide, the vector, the lipoplex, such as an LNP, and/or the pharmaceutical composition is administered to the subject. As used herein, a "therapeutically effective amount" means an amount sufficient to induce, promote and/or increase expansion and/or proliferation of FLT3$^+$ cells, and thereby treat a subject (such as a human) suffering an indication, or to alleviate the existing symptoms of the indication (e.g., cancer, viral infection, bacterial infection). Determination of a therapeutically effective amount is within the capability of those skilled in the art, especially in light of the detailed disclosure provided herein.

In some embodiments, a therapeutically effective amount of a FLT3L-Fc fusion protein, homodimer, heterodimer, conjugate, polynucleotide, vector, lipoplex, such as an LNP, and/or pharmaceutical composition, as described herein, optionally, with one or more additional therapeutic agents, as described herein, can (i) reduce the number of diseased cells; (ii) reduce tumor size; (iii) inhibit, retard, slow to some extent, and preferably stop the diseased cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with cancer or myeloproliferative disease. In some embodiments, a therapeutically effective amount of a FLT3L-Fc fusion protein, homodimer, heterodimer, conjugate, polynucleotide, vector, lipoplex, such as an LNP, and/or pharmaceutical composition, as described herein, optionally, with one or more additional therapeutic agents, as described herein, can (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

In some embodiments, a therapeutically effective amount of a FLT3L-Fc fusion protein, homodimer, heterodimer, conjugate, polynucleotide, vector, lipoplex, such as an LNP, and/or pharmaceutical composition, as described herein, optionally, with one or more additional therapeutic agents, as described herein, can inhibit the proliferation of a virus in a subject and/or delay to some extent one or more of the symptoms associated with viral infection (e.g., AIDS, SARS, MERS, liver disease caused by HBV). In various embodiments, the amount is sufficient to ameliorate, palliate, lessen, and/or delay one or more of symptoms of a viral infection.

An "increased" or "enhanced" amount (e.g., with respect to FLT3L+ cell expansion, antitumor response, cancer cell metastasis) refers to an increase that is 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 2.1, 2.2, 2.3, 2.4, etc.) an amount or level described herein. It may also include an increase of at least 10%, at least 20%, at least 30%, at least 40%, at least 50%, at least 60%, at least 70%, at least 80%, at least 90%, at least 100%, at least 150%, at least 200%, at least 500%, or at least 1000% of an amount or level described herein.

A "decreased" or "reduced" or "lesser" amount (e.g., with respect to tumor size, cancer cell proliferation or growth) refers to a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein. It may also include a decrease of at least 10%, at least 20%, at least 30%, at least 40%, at least 50%, at least 60%, at least 70%, at least 80%, or at least 90%, at least 100%, at least 150%, at least 200%, at least 500%, or at least 1000% of an amount or level described herein.

In some embodiments, the FLT3L-Fc fusion protein, homodimer, heterodimer, conjugate, polynucleotide, vector, lipoplex, such as an LNP, and/or pharmaceutical composition, as described herein, is administered at a dose in the range of about 0.5 µg/kg to about 5000 µg/kg, e.g., at least about 0.5 µg/kg per dose and up to about 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 15 µg/kg, 20 µg/kg, 30 µg/kg, 50 µg/kg, 100 µg/kg, 150 µg/kg, 300 µg/kg, 400 µg/kg, 500 µg/kg, 600 µg/kg, 700 µg/kg, 800 µg/kg, 900 µg/kg, 1000 µg/kg, 1500 µg/kg, 2000 µg/kg, 2500 µg/kg, 3000 µg/kg, 3500 µg/kg, 4000 µg/kg, or 5000 µg/kg, per dose. In some embodiments, the FLT3L-Fc fusion protein, homodimer, heterodimer, conjugate, polynucleotide, vector, lipoplex, such as an LNP, and/or pharmaceutical composition, as described herein, is administered at a dose in the range of about 1 µg/kg to about 100 µg/kg, per dose. In some embodiments, the FLT3L-Fc fusion protein, homodimer, heterodimer, conjugate, polynucleotide, vector, lipoplex, such as an LNP, and/or pharmaceutical composition, as described herein, is administered at a dose of 1 µg/kg, per dose. In some embodiments, the FLT3L-Fc fusion protein, homodimer, heterodimer, conjugate, polynucleotide, vector, lipoplex, such as an LNP, and/or pharmaceutical composition, as described herein, is administered at a dose of 3 µg/kg, per dose. In some embodiments, the FLT3L-Fc fusion protein, homodimer, heterodimer, conjugate, polynucleotide, vector, lipoplex, such as an LNP, and/or pharmaceutical composition, as described herein, is administered at a dose of 10 µg/kg, per dose. In some embodiments, the FLT3L-Fc fusion protein, homodimer, heterodimer, conjugate, polynucleotide, vector, lipoplex, such as an LNP, and/or pharmaceutical composition, as described herein, is administered at a dose of 30 µg/kg, per dose. In some embodiments, the FLT3L-Fc fusion protein, homodimer, heterodimer, conjugate, polynucleotide, vector, lipoplex, such as an LNP, and/or pharmaceutical composition, as described herein, is administered at a dose of 60 µg/kg, per dose. In some embodiments, the FLT3L-Fc fusion protein, homodimer, heterodimer, conjugate, polynucleotide, vector, lipoplex, such as an LNP, and/or pharmaceutical composition, as described herein, is administered at a dose of 100 µg/kg, per dose. In some embodiments, the FLT3L-Fc fusion protein, homodimer, heterodimer, conjugate, polynucleotide, vector, lipoplex, such as an LNP, and/or pharmaceutical composition, as described herein, is administered at a dose in the range of about 0.5 mg to about 50 mg, e.g., at least about 0.5 mg per dose and up to about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg or 50 mg per dose. In some embodiments, the FLT3L-Fc fusion protein, homodimer, heterodimer, conjugate, polynucleotide, vector, lipoplex, such as an LNP, and/or pharmaceutical composition, as described herein, is administered at a dose of dose about 10 mg, per dose. In some embodiments, the FLT3L-Fc fusion protein, homodimer, heterodimer, conjugate, polynucleotide, vector, lipoplex, such as an LNP, and/or pharmaceutical composition, as described herein, is administered at a dose that saturates FLT3 receptors in the tumor. In some embodiments, the FLT3L-Fc fusion protein, homodimer, heterodimer, conjugate, polynucleotide, vector, lipoplex, such as an LNP, and/or pharmaceutical composition, as described herein, is administered at a dose that saturates FLT3 receptors in the subject.

With respect to scheduling of administrations, in various embodiments, the methods comprise administering multiple administrations or doses of the fusion protein, the homodimer, the heterodimer, the conjugate, the polynucleotide, the vector, the lipoplex, such as an LNP, and/or the pharmaceutical composition, optionally with one or more additional therapeutic agents, at predetermined intervals. As appropriate, in various embodiments, the FLT3L-Fc fusion protein, the homodimer, the heterodimer, the conjugate, the polynucleotide, the vector, the lipoplex, such as an LNP, and/or the pharmaceutical composition can be administered once weekly (i.e., QW), once bi-weekly (i.e., once every other week, or once every two weeks or Q2W), once thrice-weekly (i.e., once every three weeks or Q3W), once monthly (i.e., QM) or once bi-monthly dosing (i.e., once every other month, or once every two months or Q2M), or less often. As appropriate, the fusion protein, the homodimer, the heterodimer, the conjugate, the polynucleotide, the vector, the lipoplex, such as an LNP, and/or the pharmaceutical composition and the one or more additional therapeutic agents can be co-administered according to the same schedule (e.g., co-administered at the same time intervals) or different schedules (e.g., co-administered at different time intervals). in various embodiments, the FLT3L-Fc fusion protein, the homodimer, the heterodimer, the conjugate, the polynucleotide, the vector, the lipoplex, such as an LNP, and/or the pharmaceutical composition can be administered first, followed by administration of the one or more additional therapeutic agents, e.g., 1, 2 or 3 weeks later, e.g., after detectable or sufficient expansion of FLT3-expressing cells, e.g., cDC1 dendritic cells.

Examples of tissues containing cancerous cells whose proliferation is inhibited by the FLT3L-Fc fusion proteins described herein and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the subject has a solid tumor. In various embodiments, the cancer or tumor is malignant and/or a metastatic. In various embodiments, the subject has a cancer selected from the group consisting of an epithelial tumor (e.g., a carcinoma, a squamous cell carcinoma, a basal cell carcinoma, a squamous intraepithelial neoplasia), a glandular tumor (e.g., an adenocarcinoma, an adenoma, an adenomyoma), a mesenchymal or soft tissue tumor (e.g., a sarcoma, a rhabdomyosarcoma, a leiomyosarcoma, a liposarcoma, a fibrosarcoma, a dermatofibrosarcoma, a neurofibrosarcoma, a fibrous histiocytoma, an angiosarcoma, an angiomyxoma, a leiomyoma, a chondroma, a chondrosarcoma, an alveolar soft-part sarcoma, an epithelioid hemangioendothelioma, a Spitz tumor, a synovial sarcoma), and a lymphoma.

In various embodiments, the subject has a solid tumor in or arising from a tissue or organ selected from the group consisting of:

bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma);

lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors);

esophagus (e.g., Barrett's esophagus, dysplasia and adenocarcinoma);

gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus;

pancreas (e.g., serous neoplasms, including microcystic or macrocystic serous cystadenoma, solid serous cystadenoma, Von Hippel-Landau (VHL)-associated serous cystic neoplasm, serous cystadenocarcinoma; mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma);

gall bladder (e.g., carcinoma of the gallbladder and extrahepatic bile ducts, intrahepatic cholangiocarcinoma);

neuro-endocrine (e.g., adrenal cortical carcinoma, carcinoid tumors, phaeochromocytoma, pituitary adenomas);

thyroid (e.g., anaplastic (undifferentiated) carcinoma, medullary carcinoma, oncocytic tumors, papillary carcinoma, adenocarcinoma);

liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma; hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor);

kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma);

breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma; lobular carcinoma, including without limitation, pleomorphic carcinoma, signet ring cell carcinoma);

peritoneum (e.g., mesothelioma; primary peritoneal cancer);

female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, mullerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma-MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina;

male sex organ tissues, including prostate, testis (e.g., germ cell tumors, spermatocytic seminoma), penis;

bladder (e.g., squamous cell carcinoma, urothelial carcinoma, bladder urothelial carcinoma);

brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas (NHLs), indolent non-Hodgkin's lymphoma (iNHL), refractory iNHL, pituitary tumors;

eye (e.g., retinoma, retinoblastoma, ocular melanoma, posterior uveal melanoma, iris hamartoma);

head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal);

thymus (e.g., thymoma);

heart (e.g., cardiac myxoma);

lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma);

lymph (e.g., lymphomas, including Hodgkin's lymphoma, non-Hodgkin's lymphoma (NHL), indolent non-Hodgkin's lymphoma (iNHL), refractory iNHL, Epstein-Barr virus (EBV)-associated lymphoproliferative diseases, including B cell lymphomas and T cell lymphomas (e.g., Burkitt lymphoma; large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis);

central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., sub ependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, Pituitary adenomas, cranial and paraspinal nerve tumors, stellar region tumors); neurofibroma, meningioma, peripheral nerve sheath tumors, peripheral neuroblastic tumours (including without limitation neuroblastoma, ganglioneuroblastoma, ganglioneuroma), trisomy 19 ependymoma);

neuroendocrine tissues (e.g., paraganglionic system including adrenal medulla (pheochromocytomas) and extra-adrenal paraganglia ((extra-adrenal) paragangliomas);

skin (e.g., clear cell hidradenoma, cutaneous benign fibrous histiocytomas, cylindroma, hidradenoma, melanoma (including cutaneous melanoma, mucosal melanoma), basal cell carcinoma, pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, lipoblastoma, lipoma, chondroid lipoma, liposarcoma/malignant lipomatous tumors, liposarcoma, myxoid liposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non-rhabdomyosarcoma soft tissue sarcoma (NRSTS), soft tissue leiomyosarcoma, undifferentiated sarcoma, well-differentiated liposarcoma.

In some embodiments, the subject has a hematological cancer, e.g., a leukemia (e.g., Acute Myelogenous Leukemia (AML), Acute Lymphoblastic Leukemia (ALL), B-cell ALL, Myelodysplastic Syndrome (MDS), myeloproliferative disease (MPD), Chronic Myelogenous Leukemia (CML), Chronic Lymphocytic Leukemia (CLL), undifferentiated leukemia), a lymphoma (e.g., small lymphocytic lymphoma (SLL), mantle cell lymphoma (MCL), follicular lymphoma (FL), T-cell lymphoma, B-cell lymphoma, diffuse large B-cell lymphoma (DLBCL), marginal zone lymphoma (MZL), Waldestrom's macroglobulinemia (WM)) and/or a myeloma (e.g., multiple myeloma (MM)).

In some embodiments, the subject has a tumor that is infiltrated with conventional dendritic cells (cDCs). In some embodiments, the tumor infiltrating dendritic cells express C-C motif chemokine receptor 5 (CCR5, CD195) and/or X-C motif chemokine receptor 1 (XCR1) on their cell surface and/or produce CXCL9/10. Expression of XCR1 and CCR5 by cDC1 enables local recruitment by cytotoxic lymphocytes producing the ligands for these chemokine receptors, XCL1 and CCL4/5. cDC1 ability to produce CXCL9/10 promotes local recruitment of effector and memory CTLs expressing CXCR3. Cancel, et al., Front Immunol. (2019) 10:9. In some embodiments, the tumor infiltrating dendritic cells express one or more cell surface proteins selected from the group consisting of XCR1, interferon regulatory factor 8 (IRF8), cell adhesion molecule 1 (CADM1), C-type lectin domain containing 9A (CLEC9A, CD370), and thrombomodulin (THBD), which identify a cDC1 subtype. In some embodiments, the tumor infiltrating dendritic cells express one or more proteins selected from the group consisting of XCR1, IRF8, CADM1, CLEC9A, THBD, copine 3 (CPNE3), carboxypeptidase vitellogenic like (CPVL), N-acylethanolamine acid amidase (NAAA), cystatin C (CST3), WDFY family member 4 (WDFY4) and galectin 2 (LGALS2), which identify a cDC1 subtype. cDC1 cells are efficient antigen cross-presenters to CD8+ T cells. In some embodiments, the tumor infiltrating dendritic cells express one or more cell surface proteins selected from the group consisting of CD1A, CD1C, CD1E, signal regulatory protein alpha (SIRPA; CD172A), CD207 and Fc fragment of IgE receptor Ia (FCER1A), which identify a cDC2 subtype. In some embodiments, the tumor infiltrating dendritic cells express one or more cell surface proteins selected from the group consisting of CD1A, CD1C, CD1E, SIRPA, FCER1A, CD207, HLA-DQA2, HLA-DQB2, Fc fragment of IgG binding protein (FCGBP), S100 calcium binding protein B (S100B), NDRG family member 2 (NDRG2), interleukin 22 receptor subunit alpha 2 (IL22RA2), and chondroadherin (CHAD), which identify a cDC2 subtype. cDC2 cells preferentially interact with CD4+ T cells. In some embodiments, the tumor infiltrating dendritic cells expresses one or more proteins selected from the group consisting of basic leucine zipper ATF-like transcription factor 3 (BATF3) and interferon regulatory factor 8 (IRF8), identifying an "activated" DC phenotype or hDC3 subtype. In some embodiments, the tumor infiltrating dendritic cells expresses one or more proteins selected from the group consisting of BATF3, IRF8, C-C motif chemokine ligand 22 (CCL22), lymphocyte antigen 75 (LY75), C-C motif chemokine receptor 7 (CCR7), protein 0-glucosyltransferase 1 (POGLUT1), lysine demethylase 2B (KDM2B), INSM transcriptional repressor 1 (INSM1), and UV radiation resistance associated (UVRAG), identifying an "activated" DC phenotype or hDC3 subtype. Expression signatures of various dendritic cell subtypes are described in Zilionis et al., Immunity (2019) 50, 1317-1334. In some embodiments, the tumor infiltrating dendritic cells express one or more cell surface proteins selected from the group consisting of XCR1, BATF3, IRF8, CLEC9A and THBD.

Administration of the FLT3L-Fc proteins described herein can promote or increase expansion and/or infiltration of myeloid cells (e.g., T-cells, NK cells and dendritic cells) into a tumor. Further, administration of the FLT3L-Fc proteins described herein can improve, increase, enhance and/or promote the antitumor effects or efficacy of an immune checkpoint inhibitor. In some embodiments, the subject has a cancer that detectably expresses or overexpresses one or more cell surface immune checkpoint receptors. In certain embodiments, greater than about 50% of the cells within the tumor (e.g., tumor cells, T cells and/or NK cells within the tumor) detectably express one or more cell surface immune checkpoint proteins (e.g., the subject has a so-called "hot" cancer or tumor). In some embodiments, greater than about 1% and less than about 50% of the cells within the tumor (e.g., tumor cells, T cells and/or NK cells within the tumor) detectably express one or more cell surface immune checkpoint proteins (e.g., the subject has a so called "warm"

cancer or tumor). In some embodiments, the one or more cell surface immune checkpoint receptors are selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9).

The FLT3L-Fc variants described herein can be used to promote or accelerate the recovery from or reverse the effects of lymphopenia or neutropenia. Accordingly, in some embodiments, the subject has neutropenia or lymphopenia, e.g., as a result of having received or undergone a lymphodepleting chemotherapy regimen, e.g., an alkylating agent such as chlorambucil or cyclophosphamide, or a nucleoside analog, including pyrimidine nucleosides such as cytarabine and purine nucleosides such as cladribine, pentostatin and fludarabine. See, e.g., Lowe, et al., *Gene Therapy* (2018) 25:176-191. In certain embodiments, the methods comprise (a) subjecting a patient to a lymphodepleting chemotherapy regimen; (b) administering a FLT3L-Fc fusion protein, homodimer, heterodimer, conjugate, polynucleotide, vector, lipoplex, such as an LNP, and/or pharmaceutical composition, as described herein; and (c) administering to the patient a cellular therapy, as described herein. Illustrative lymphodepleting chemotherapy regimens, along with correlative beneficial biomarkers, are described in WO 2016/191756 and WO 2019/079564, incorporated herein by reference in their entireties for all purposes. In certain embodiments, the lymphodepleting chemotherapy regimen comprises administering to the patient doses of cyclophosphamide (between 200 mg/m$^2$/day and 2000 mg/m$^2$/day) and doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days, e.g., prior to administration of a therapeutically effective amount of a cellular therapy (e.g., an effector cell having a chimeric antigen receptor) to the patient. In another example, in some embodiments, a lymphodepleting chemotherapy regimen of cyclophosphamide 500 mg/m$^2$ IV and fludarabine 30 mg/m$^2$ IV on the fifth, fourth, and third day e.g., prior to administration of a therapeutically effective amount of a cellular therapy (e.g., an effector cell having a chimeric antigen receptor) to the patient. In some embodiments, the subject is naïve to or has not received chemotherapy. In some embodiments, the subject has bone marrow cells (e.g., is not depleted of bone marrow cells).

In some embodiments, the subject does not have a mutation in the gene encoding the FLT3 receptor that causes or results in or is associated with cancer, e.g., FLT3 mutations associated with constitutive signaling of the FLT3 receptor, e.g., FLT3 mutations associated with Acute Myeloid Leukemia (AML). For example, in certain embodiments, the subject does not have internal tandem duplication (ITD) of the FMS-related tyrosine kinase 3 (FLT3) gene, which occurs in exons 14 and 15, and is one of the most prevalent somatic mutations in adult acute myeloid leukemia (AML). In some embodiments, the subject does not have a mutation in the FLT3 gene in exon 20 that affects codon 835, encoding the tyrosine kinase domain (TKD) mutation, which occurs relatively frequently in adult AML. In some embodiments, the subject does not have point mutations affecting amino acid positions D835 (e.g., resulting in D835Y, D835V, and D835H amino acid substitutions) and/or 1836 in the TKD. See, e.g., Azari-Yam, et al., *Clin Lab.* (2016) 62(10):2011-2017; Han, et al., *Zhongguo Shi Yan Xue Ye Xue Za Zhi.* (2009) 17(5):1135-9; Shoji, et al., *Rinsho Byori.* (2017) 65(1):44-5; and Liang, et al., *Leukemia.* (2003) 17(5):883-6.

8. Combination Therapies

In various embodiments, the FLT3L-Fc fusion proteins, homodimers, heterodimers, polynucleotides, vectors, lipoplex, such as an LNPs, and/or pharmaceutical compositions, as described herein, are combined with one or more additional therapeutic agents, e.g., an inhibitory immune checkpoint blocker or inhibitor, a stimulatory immune checkpoint stimulator, agonist or activator, a chemotherapeutic agent, an anticancer agent, an antiviral agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (mono- and multi-specific antibodies and fragments thereof in any format (e.g., including without limitation DARTs®, Duobodies®, BiTEs®, BiKEs, TriKEs, XmAbs®, TandAbs®, scFvs, Fabs, Fab derivatives), bi-specific antibodies, non-immunoglobulin antibody mimetics (e.g., including without limitation adnectins, affibody molecules, affilins, affimers, affitins, alphabodies, anticalins, peptide aptamers, armadillo repeat proteins (ARMs), atrimers, avimers, designed ankyrin repeat proteins (DARPins®), fynomers, knottins, Kunitz domain peptides, monobodies, and nanoCLAMPs), antibody-drug conjugates (ADC)), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, without limitation, an inhibitor, agonist, antagonist, ligand, modulator, stimulator, blocker, activator or suppressor of a target (e.g., polypeptide or polynucleotide) including without limitation: Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, 4-1BB ligand (CD137L), Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C-C motif) receptor (such as CCR2, CCR4, CCR5, CCR5), chemokine (C-X-C motif) receptor (such as CXCR1, CXCR2, CXCR3 and CXCR4), Chemokine CC21 ligand, Cholecystokinin CCK2 receptor, Chorionic gonadotropin, c-Kit (tyrosine-protein kinase Kit or CD117), CISH (Cytokine-inducible SH2-containing protein), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e (CEACAM6), CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COPS signalosome subunit 5, CSF-1 (colony-stimulating factor 1 receptor), CSF2 gene, CTLA-4 (cytotoxic T-lymphocyte protein 4) receptor, C-type lectin domain protein 9A (CLEC9A), Cyclin D1, Cyclin G1, Cyclin-dependent kinases (CDK, such as CDK1, CDK1B, CDK2-9), cyclooxygenase (such as COX1, COX2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Death receptor 5 (DR5, TRAILR2), Death receptor 4 (DR4, TRAILR1), Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropinreleaseing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heme oxygenase 1 (H01), Heme oxygenase 2 (H02), Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, HLA class I antigen alpha G (HLA-G), Non-classical HLA, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIF1a), Imprinted Maternally Expressed Transcript (H19) gene, mitogen-activated protein kinase kinase kinase kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1 and IDO2), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukocyte immunoglobulin-like receptor subfamily B member 1 (ILT2), Leukocyte immunoglobulin-like receptor subfamily B member 2 (ILT4), Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), 5-Lipoxygenase (5-LOX), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mc1-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyl-transferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, NLRP3 (NACHT LRR PYD domain protein 3) modulators, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methyl-guanine DNA methyltransferase, Opioid receptor (such as delta), Ornithine decarboxylase, Orotate phosphoribosyl-transferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly (ADP-ribose) polymerase (PARP, such as PARP1, PARP2 and PARP3, PARP7, and mono-PARPs), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), Prostaglandin E2 synthase, prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase)gene, Ros1 tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Secreted phospholipase A2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Suppressor of cytokine signaling modulators (SOCS), Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, transferrin (TF); transforming growth factor beta 1 (TGFB1) and isoforms thereof, TGF beta 2 ligand, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tumor specific neoantigens, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E2I (UBE2I, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase, Mer (Mer tyrosine kinase receptor modulators), YAP (Yes-associated protein modulators)es, Wee-1 protein kinase, Wilms' tumor antigen 1, Wilms' tumor protein, WW domain containing transcription regulator protein 1 (TAZ), X-linked inhibitor of apoptosis protein, Zinc finger protein transcription factor or any combination thereof.

In some embodiments, the one or more additional therapeutic agents include without limitation an HBV DNA polymerase inhibitor, immunomodulator, TLR modulator, HBsAg inhibitor, HBsAg secretion or assembly inhibitor, HBV therapeutic vaccine, HBV antibody, such as HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitor, stimulator of retinoic acid-inducible gene 1, stimulator of RIG-I like receptor, PD-1 inhibitor, PD-L1 inhibitor, arginase inhibitor, PI3K inhibitor, IDO inhibitor, stimulator of NOD2, HBV viral entry inhibitors, NTCP inhibitor, HBx inhibitor, cccDNA inhibitor, HBV antibody targeting the surface antigens of the hepatitis B virus, siRNA, miRNA gene therapy agents, sshRNAs, KDM5 inhibitors, or nucleoprotein modulator (HBV core or capsid protein modulator).

In some embodiments, the one or more additional therapeutic agents include without limitation an HBV DNA polymerase inhibitor, immunomodulator, TLR modulator, HBsAg inhibitor, HBV therapeutic vaccine, HBV antibody, such as an HBV antibody targeting a surface antigens of the hepatitis B virus, bispecific antibody and "antibody-like" therapeutic protein (such as DARPins®, anti-pMHC TCR-like antibodies, DARTs®, DUOBODIES®, BITES®, XmAbs®, TandAbs®, Fab derivatives, or TCR-like antibodies), cyclophilin inhibitor, stimulator of retinoic acid-inducible gene 1, stimulator of RIG-I like receptor, PD-1 inhibitor, PD-L1 inhibitor, arginase inhibitor, PI3K inhibitor, IDO inhibitor, and stimulator of NOD2.

In some embodiments, the one or more additional therapeutic agents include without limitation an HBV DNA polymerase inhibitor, HBV viral entry inhibitor, NTCP inhibitor, HBx inhibitor, cccDNA inhibitor, an HBV antibody targeting a surface antigen of the hepatitis B virus, siRNA, miRNA gene therapy agent, sshRNA, KDM5 inhibitor, and nucleoprotein modulator (HBV core or capsid protein inhibitors).

In some embodiments, the one or more additional therapeutic agents include without limitation an inhibitor of certain HCV nonstructural proteins, such as a NS5A inhibitor, a NS5B inhibitor, a NS3 inhibitor, or combinations thereof.

In some embodiments, the one or more additional therapeutic agents include without limitation a combination drug for HIV, another drug for treating HIV, HIV protease inhibitor, HIV non-nucleoside or non-nucleotide inhibitor of reverse transcriptase, HIV nucleoside or nucleotide inhibitor of reverse transcriptase, HIV integrase inhibitor, HIV non-catalytic site (or allosteric) integrase inhibitor, HIV entry inhibitor, HIV maturation inhibitor, immunomodulator, immunotherapeutic agent, antibody-drug conjugate, gene modifier, gene editor (such as CRISPR/Cas9, zinc finger nuclease, homing nuclease, synthetic nuclease, TALEN), cell therapy (such as chimeric antigen receptor T-cell, CAR-T, and engineered T cell receptor, TCR-T, autologous T cell therapy), latency reversing agent, compound that targets the HIV capsid, immune-based therapy, phosphatidylinositol 3-kinase (PI3K) inhibitor, HIV antibody, bispecific antibody and "antibody-like" therapeutic protein, HIV p17 matrix protein inhibitor, IL-13 antagonist, peptidyl-prolyl cis-trans isomerase A modulator, protein disulfide isomerase inhibitor, complement C5a receptor antagonist, DNA methyltransferase inhibitor, HIV vif gene modulator, Vif dimerization antagonist, HIV-1 viral infectivity factor inhibitor, TAT protein inhibitor, HIV-1 Nef modulator, Hck tyrosine kinase modulator, mixed lineage kinase-3 (MLK-3) inhibitor, HIV-1 splicing inhibitor, Rev protein inhibitor, integrin antagonist, nucleoprotein inhibitor, splicing factor modulator, COMM domain containing protein 1 modulator, CD4 modulator, CD4 antagonist, HIV ribonuclease H inhibitor, retrocyclin modulator, CDK-9 inhibitor, CCR5 chemokine antagonist, CCR5 gene modulator, dendritic ICAM-3 grabbing nonintegrin 1 inhibitor, HIV GAG protein inhibitor, HIV POL protein inhibitor, hyaluronidase inhibitor, Nef antagonist, Nef inhibitor, protease-activated receptor-1 antagonist, TNF alpha ligand inhibitor, PDE4 inhibitor, Complement Factor H modulator, ubiquitin ligase inhibitor, deoxycytidine kinase inhibitor, cyclin dependent kinase inhibitor, proprotein convertase PC9 stimulator, ATP dependent RNA helicase DDX3X inhibitor, reverse transcriptase priming complex inhibitor, G6PD and NADH-oxidase inhibitor, pharmacokinetic enhancer, HIV gene therapy, and HIV vaccines, a long-acting HIV regimen, and a contraceptive agent, or any combination thereof. In certain embodiments, the one or more additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or any combinations thereof. In certain embodiments, the one or more additional therapeutic agents do not include a pharmacokinetic enhancer.

In some embodiments, the one or more additional therapeutic agents include without limitation an HIV protease inhibitor, HIV reverse transcriptase inhibitor, HIV integrase inhibitor, HIV non-catalytic site (or allosteric) integrase inhibitor, HIV entry (fusion) inhibitor, HIV maturation inhibitor, HIV latency reversing agent, HIV capsid inhibitor, anti-HIV antibody, or combination thereof.

In some embodiments, the one or more additional therapeutic agents include an HIV nucleoside or nucleotide inhibitor of reverse transcriptase and an HIV non-nucleoside inhibitor of reverse transcriptase. In some embodiments, the one or more additional therapeutic agents include an HIV nucleoside or nucleotide inhibitor of reverse transcriptase, and an HIV protease inhibiting compound. In some embodiments, the one or more additional therapeutic agents include an HIV nucleoside or nucleotide inhibitor of reverse transcriptase, an HIV non-nucleoside inhibitor of reverse transcriptase, and a pharmacokinetic enhancer. In some embodiments, the one or more additional therapeutic agents include at least one HIV nucleoside inhibitor of reverse transcriptase, an integrase inhibitor, and a pharmacokinetic enhancer. In some embodiments, the one or more additional therapeutic agents include two HIV nucleoside or nucleotide inhibitors of reverse transcriptase.

In some embodiments, the one or more additional therapeutic agents include one or more antiviral agents. Any suitable antiviral agent can be used in the methods described herein. In some embodiments, the one or more antiviral agents include without limitation a 5-substituted 2'-deoxyuridine analogue, a nucleoside analogue, a pyrophosphate analogue, a nucleoside reverse transcriptase inhibitor, a non-nucleoside reverse transcriptase inhibitor, a protease inhibitor, an integrase inhibitor, an entry inhibitor, an acyclic guanosine analogue, an acyclic nucleoside phosphonate analogue, a HCV NS5A/NS5B inhibitor, an influenza virus inhibitors, an interferon, an immunostimulator, an oligonucleotide, an antimitotic inhibitor, and combinations thereof. In some embodiments the one or more therapeutic agents include an RNA polymerase inhibitor.

Illustrative Mechanisms of Action

In various embodiments, the one or more additional therapeutic agents may be categorized by their mechanism of action into, for example, the following groups:

anti-metabolites/anticancer agents, such as pyrimidine analogs floxuridine, capecitabine, cytarabine, CPX-351 (liposomal cytarabine, daunorubicin), and TAS-118;

purine analogs, folate antagonists (such as pralatrexate), cladribine, pentostatin, fludarabine and related inhibitors;

antiproliferative/antimitotic agents including natural products, such as vinca alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);

DNA damaging agents, such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide;

DNA-hypomethylating agents, such as guadecitabine (SGI-110), ASTX727;

antibiotics such as dactinomycin, daunorubicin, doxorubicin, idarubicin, anthracyclines, mitoxantrone, bleomycins, plicamycin (mithramycin);

enzymes such as L-asparaginase which systemically metabolizes L-asparagine and deprives cells which do not have the capacity to synthesize their own asparagine;

DNAi oligonucleotides targeting Bcl-2, such as PNT2258; agents that activate or reactivate latent human immunodeficiency virus (HIV), such as panobinostat and romidepsin;

asparaginase stimulators, such as crisantaspase (Erwinase®) and GRASPA (ERY-001, ERY-ASP), calaspargase pegol;

pan-Trk, ROS1 and ALK inhibitors, such as entrectinib, TPX-0005; anaplastic lymphoma kinase (ALK) inhibitors, such as alectinib, ceritinib;

antiproliferative/antimitotic alkylating agents, such as nitrogen mustard cyclophosphamide and analogs (e.g., melphalan, chlorambucil, hexamethylmelamine, thiotepa), alkyl nitrosoureas (e.g., carmustine) and analogs, streptozocin, and triazenes (e.g., dacarbazine);

antiproliferative/antimitotic antimetabolites, such as folic acid analogs (methotrexate);

platinum coordination complexes (e.g., cisplatin, oxiloplatinim, and carboplatin), procarbazine, hydroxyurea, mitotane, and aminoglutethimide;

hormones, hormone analogs (e.g., estrogen, tamoxifen, goserelin, bicalutamide, and nilutamide), and aromatase inhibitors (e.g., letrozole and anastrozole);

antiplatelet agents; anticoagulants such as heparin, synthetic heparin salts, and other inhibitors of thrombin;
fibrinolytic agents such as tissue plasminogen activator, streptokinase, urokinase, aspirin, dipyridamole, ticlopidine, and clopidogrel;
antimigratory agents; antisecretory agents (e.g., breveldin);
immunosuppressives, such as tacrolimus, sirolimus, azathioprine, and mycophenolate;
growth factor inhibitors, and vascular endothelial growth factor inhibitors;
fibroblast growth factor inhibitors, such as FPA14;
anti-VEGFR antibodies, such as IMC-3C5, GNR-011, tanibirumab, LYN-00101;
anti-VEGF/DDL4 antibodies, such as ABT-165;
anti-cadherin antibodies, such as HKT-288;
anti-CD52 antibodies, such as alemtuzumab;
anti-CD70 antibodies, such as AMG-172;
anti-leucine-rich repeat containing 15 (LRRC15) antibodies, such as ABBV-085, ARGX-110;
angiotensin receptor blockers, nitric oxide donors;
antisense oligonucleotides, such as AEG35156, IONIS-KRAS-2.5Rx, EZN-3042, RX-0201, IONIS-AR-2.5Rx, BP-100 (prexigebersen), IONIS-STAT3-2.5Rx;
DNA interference oligonucleotides, such as PNT2258, AZD-9150;
anti-angiopoietin (ANG)-2 antibodies, such as MEDI3617, and LY3127804;
anti-ANG-1/ANG-2 antibodies, such as AMG-780;
anti-CSF1R antibodies, such as emactuzumab, LY3022855, AMG-820, FPA-008 (cabiralizumab);
anti-CD40 antibodies, such as RG7876, SEA-CD40, APX-005M, ABBV-428;
anti-endoglin antibodies, such as TRC105 (carotuximab);
anti-CD45 antibodies, such as 131I-BC8 (lomab-B); anti-HER3 antibodies, such as LJM716, GSK2849330;
anti-MET/EGFR antibodies, such as LY3164530;
anti-EGFR antibodies, such as ABT-414, AMG-595, necitumumab, ABBV-221, depatuxizumab mafodotin (ABT-414), tomuzotuximab, ABT-806, vectibix, modotuximab, RM-1929;
anti-HER2 antibodies, such as HERCEPTIN® (trastuzumab), margetuximab, MEDI4276, BAT-8001, Pertuzumab (Perjeta), ZW25 (a bispecific HER2-directed antibody targeting the extracellular domains 2 and 4; Cancer Discov. 2019 January; 9(1):8; PMID: 30504239);
HER2 inhibitors, such as neratinib, tucatinib (ONT-380);
EGFR/ErbB2/Ephb4 inhibitors, such as tesevatinib;
anti-ERBB antibodies, such as CDX-3379, HLX-02, seribantumab;
EGFR/ErbB-2 inhibitors, such as varlitinib;
Mutant selective EGFR inhibitors, such as PF-06747775, EGF816 (nazartinib), ASP8273, ACEA-0010, BI-1482694;
anti-HLA-DR antibodies, such as IMMU-114;
anti-IL-3 antibodies, such as JNJ-56022473;
anti-TNF receptor superfamily member 4 (TNFRSF4, OX40; NCBI Gene ID: 7293) antibodies, such as MEDI6469, MEDI6383, MEDI0562 (tavolixizumab), MOXR0916, PF-04518600, RG-7888, GSK-3174998, INCAGN1949, BMS-986178, GBR-8383, ABBV-368; and those described in Intl. Patent Publ. Nos. WO 2016/179517, WO 2017/096179, WO 2017/096182, WO 2017/096281 and WO 2018/089628;
anti-TNF receptor superfamily member 18 (TNFRSF18, GITR; NCBI Gene ID: 8784) antibodies, such as MEDI1873, FPA-154, INCAGN-1876, TRX-518, BMS-986156, MK-1248, GWN-323; and those described, e.g., in Intl. Patent Publ. Nos. WO 2017/096179, WO 2017/096276, WO 2017/096189; and WO 2018/089628;
anti-TNFRSF4 (OX40)/TNFRSF18(GITR) bi-specific antibodies, such as those described in Intl. Patent Publ. Nos. WO 2017/096179 and WO 2018/089628;
anti-EphA3 antibodies, such as KB-004;
anti-CD20 antibodies, such as obinutuzumab, IGN-002;
anti-CD37 antibodies, such as AGS67E, otlertuzumab (TRU-016);
anti-ENPP3 antibodies, such as AGS-16C3F;
anti-FGFR-3 antibodies, such as LY3076226, B-701;
anti-FGFR-2 antibodies, such as GAL-F2;
anti-05 antibodies, such as ALXN-1210;
anti-CD27 antibodies, such as varlilumab (CDX-1127);
anti-TROP-2 antibodies, such as IMMU-132;
anti-NKG2a antibodies, such as monalizumab;
anti-VISTA antibodies, such as HMBD-002;
anti-PVRIG antibodies, such as COM-701;
anti-EpCAM antibodies, such as VB4-845;
antibodies against TNF receptor superfamily member 17 (TNFRSF17, BCMA), such as GSK-2857916;
anti-CEA antibodies, such as RG-7813;
anti-cluster of differentiation 3 (CD3) antibodies, such as MGD015; anti-folate receptor alpha antibodies, such as IMGN853;
epha2 inhibitors, such as MM-310;
anti LAG-3 (Lymphocyte-activation) antibodies, such as relatlimab (ONO-4482), LAG-525, MK-4280, REGN-3767, INCAGN2385;
raf kinase/VEGFR inhibitors, such as RAF-265;
polycomb protein (EED) inhibitors, such as MAK683;
anti-fibroblast activation protein (FAP)/IL-2R antibodies, such as RG7461;
anti-fibroblast activation protein (FAP)/TRAIL-R2 antibodies, such as RG7386;
anti-fucosyl-GM1 antibodies, such as BMS-986012;
p38 MAP kinase inhibitors, such as ralimetinib;
PRMT1 inhibitors, such as MS203;
Sphingosine kinase 2 (SK2) inhibitors, such as opaganib;
Nuclear erythroid 2-related factor 2 stimulators, such as omaveloxolone (RTA-408);
Tropomyosin receptor kinase (TRK) inhibitors, such as LOXO-195, ONO-7579;
anti-ICOS antibodies, such as JTX-2011, GSK3359609;
ICOS agonists, such as ICOS-L.COMP (Gariepy, J. et al. 106th Annu Meet Am Assoc Immunologists (AAI) (May 9-13, San Diego) 2019, Abst 71.5);
anti-TNF receptor superfamily member 10b (TNFRSF10B, DR5, TRAILR2) antibodies, such as DS-8273, CTB-006, INBRX-109, GEN-1029;
anti-Carcinoembryonic-antigen-related-cell-adhesion-molecule-6 (CEACAM6, CD66C) antibodies, such as BAY-1834942, NEO-201 (CEACAM 5/6);
anti-GD2 antibodies, such as APN-301;
anti-interleukin-17 (IL-17) antibodies, such as CJM-112;
anti-carbonic anhydrase 9 (CA9, CAIX) antibodies, such as TX-250;
anti-CD38 antibodies, such as isatuximab, MOR-202;
anti-CD38-attenukine, such as TAK573;
anti-Mucin 1 (MUC1) antibodies, such as gatipotuzumab, Mab-AR-20.5;
Mucin 1 inhibitors, such as GO-203-2C;
MARCKS protein inhibitors, such as BIO-11006;
Folate antagonists, such as arfolitixorin;

Galectin-3 inhibitors, such as GR-MD-02;
Phosphorylated P68 inhibitors, such as RX-5902;
CD95/TNF modulators, such as ofranergene obadenovec;
PI3K/Akt/mTOR inhibitors, such as ABTL-0812;
pan-PIM kinase inhibitors, such as INCB-053914;
IL-12 gene stimulators, such as EGEN-001, tavokinogene telseplasmid;
Heat shock protein HSP90 inhibitors, such as TAS-116, PEN-866;
VEGF/HGF antagonists, such as MP-0250;
SYK tyrosine kinase/JAK tyrosine kinase inhibitors, such as ASN-002;
JAK3/JAK1/TBK1 kinase inhibitors, such as CS-12912;
IL-24 antagonist, such as AD-IL24;
NLRP3 (NACHT LRR PYD domain protein 3) modulators, such as BMS-986299;
RIG-I agonists, such as RGT-100;
Aerolysin stimulators, such as topsalysin;
P-Glycoprotein 1 inhibitors, such as HM-30181A;
CSF-1 antagonists, such as ARRY-382, BLZ-945;
CCR8 inhibitors, such as 1-309, SB-649701, HG-1013, RAP-310;
anti-CCR8 antibodies, such as neutralizing anti-CCR8 antibodies, or anti-CCR8 antibodies having ADCC activity;
anti-Mesothelin antibodies, such as SEL-403;
Thymidine kinase stimulators, such as aglatimagene besadenovec;
Polo-like kinase 1 inhibitors, such as PCM-075;
NEDD8 inhibitors, such as pevonedistat (MLN-4924), TAS-4464;
Pleiotropic pathway modulators, such as avadomide (CC-122);
FoxM1 inhibitors, such as thiostrepton;
UBA1 inhibitors, such as TAK-243;
Src tyrosine kinase inhibitors, such as VAL-201;
VDAC/HK inhibitors, such as VDA-1102;
BRAF/PI3K inhibitors, such as ASN-003;
Elf4a inhibitors, such as rohinitib, eFT226;
TP53 gene stimulators, such as ad-p53;
Retinoic acid receptor alpha (RARa) inhibitors, such as SY-1425;
SIRT3 inhibitors, such as YC8-02;
Stromal cell-derived factor 1 ligand inhibitors, such as olaptesed pegol (NOX-A12);
IL-4 receptor modulators, such as MDNA-55;
Arginase-I stimulators, such as pegzilarginase;
Topoisomerase I inhibitor/hypoxia inducible factor-1 alpha inhibitors, such as PEG-SN38 (firtecan pegol);
Hypoxia inducible factor-1 alpha inhibitors, such as PT-2977, PT-2385;
CD122 agonists, such as NKTR-214;
TLR7/TLR8 agonist, such as NKTR-262;
TLR7 agonists, such as DS-0509, GS-9620 (versatolimod), LHC-165, TMX-101 (imiquimod);
p53 tumor suppressor protein stimulators such as kevetrin;
Mdm4/Mdm2 p53-binding protein inhibitors, such as ALRN-6924;
kinesin spindle protein (KSP) inhibitors, such as filanesib (ARRY-520);
CD80-fc fusion protein inhibitors, such as FPT-155;
Menin and mixed lineage leukemia (MLL) inhibitors such as KO-539;
Liver x receptor agonists, such as RGX-104;
IL-10 agonists, such as AM-0010;
VEGFR/PDGFR inhibitors, such as vorolanib;
IRAK4 inhibitors, such as CA-4948;
anti-TLR-2 antibodies, such as OPN-305;
Calmodulin modulators, such as CBP-501;
Glucocorticoid receptor antagonists, such as relacorilant (CORT-125134);
Second mitochondria-derived activator of caspases (SMAC) protein inhibitors, such as BI-891065;
Lactoferrin modulators, such as LTX-315;
KIT proto-oncogene, receptor tyrosine kinase (KIT) inhibitors, such as PLX-9486;
platelet derived growth factor receptor alpha (PDGFRA)/ KIT proto-oncogene, receptor tyrosine kinase (KIT) mutant-specific antagonists/inhibitors such as BLU-285, DCC-2618;
Exportin 1 inhibitors, such as eltanexor;
anti-CD33 antibodies, such as IMGN-779;
anti-KMA antibodies, such as MDX-1097;
anti-TIM-3 antibodies, such as TSR-022, LY-3321367, MBG-453;
anti-CD55 antibodies, such as PAT-SC1;
anti-PSMA antibodies, such as ATL-101;
anti-CD100 antibodies, such as VX-15;
anti-EPHA3 antibodies, such as fibatuzumab;
anti-APRIL antibodies, such as BION-1301;
anti-TIGIT antibodies, such as BMS-986207, RG-6058, AGEN-1307, AGEN-1327, AGEN-1777, AB154;
anti-TIM-3 antibodies, such as INCAGN-2390;
CHST15 gene inhibitors, such as STNM-01;
RAS inhibitors, such as NEO-100;
Somatostatin receptor antagonist, such as OPS-201;
CEBPA gene stimulators, such as MTL-501;
DKK3 gene modulators, such as MTG-201;
Chemokine (CXCR1/CXCR2) inhibitors, such as SX-682;
p70s6k inhibitors, such as MSC2363318A;
methionine aminopeptidase 2 (MetAP2) inhibitors, such as M8891, APL-1202;
arginine N-methyltransferase 5 inhibitors, such as GSK-3326595;
anti-programmed cell death protein 1 (anti-PD-1) antibodies, such as nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317 (tislelizumab), GLS-010 (WBP-3055), AK-103 (HX-008), CS-1003, HLX-10, MGA-012, BI-754091, REGN-2810 (cemiplimab), AGEN-2034 (balstilimab), JS-001 (toripalimab), JNJ-63723283, genolimzumab (CBT-501), LZM-009, BCD-100, LY-3300054, SHR-1201, SHR-1210 (camrelizumab), Sym-021, ABBV-181, AK-105, PD1-PIK, BAT-1306, zimberelimab, and anti-programmed death-ligand 1 (anti-PD-L1) antibodies such as BMS-936559, atezolizumab (MPDL3280A), durvalumab (MEDI-4736), avelumab, CK-301 (MSB0010718C), MEDI-0680, CX-072, CBT-502, PDR-001 (spartalizumab), TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, and MDX1105-01;
PD-L1/VISTA antagonists such as CA-170;
PD-1/PD-L1 inhibitors, such as INCB086550, GS-4224, GS-4416;
anti-PD-L1/TGFβ antibodies, such as M-7824;
PD-L1/EGFR inhibitors, such as GNS-1480 (lazertinib);
PD-1/CTLA-4 inhibitors, such as PF-06936308;

anti-CD73/TGFβ inhibitors, such as GS-1423 (AGEN1423; published in WO2019/173692);
anti-CTLA-4 (cytotoxic T-lymphocyte protein-4) antibodies, such as tremelimumab, ipilimumab (BMS-734016), AGEN-1884, BMS-986218, AGEN1181, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BA-3071;
CTLA-4 (cytotoxic T-lymphocyte protein-4) inhibitors, such as BPI-002; TLR-3 agonist/interferon inducers, such as Poly-ICLC (NSC-301463);
anti-transferrin antibodies, such as CX-2029;
anti-IL-8 (Interleukin-8) antibodies, such as HuMax-Inflam;
ATM (ataxia telangiectasia) inhibitors, such as AZD0156;
CHK1 inhibitors, such as GDC-0575, LY2606368 (prexasertib), SRA737, RG7741 (CHK1/2);
CXCR4 antagonists, such as BL-8040, LY2510924, burixafor (TG-0054), X4P-002, X4P-00140, Plerixafor;
EXH2 inhibitors, such as GSK2816126;
KDM1 inhibitors, such as ORY-1001, IMG-7289, INCB-59872, GSK-2879552;
CXCR2 antagonists, such as AZD-5069;
GM-CSF antibodies, such as lenzilumab;
DNA dependent protein kinase inhibitors, such as MSC2490484A (nedisertib), VX-984, AsiDNA (DT-01); protein kinase C (PKC) inhibitors, such as LXS-196, sotrastaurin;
Selective estrogen receptor downregulators (SERD), such as fulvestrant (Faslodex®), RG6046, RG6047, elacestrant (RAD-1901) and AZD9496;
Selective estrogen receptor covalent antagonists (SERCAs), such as H3B-6545;
selective androgen receptor modulator (SARM), such as GTX-024, darolutamide;
transforming growth factor-beta (TGF-beta) kinase antagonists, such as galunisertib; TGF-beta inhibitors described in WO 2019/103203;
anti-transforming growth factor-beta (TGF-beta) antibodies, such as LY3022859, NIS793, XOMA 089, SRK-181;
bispecific antibodies, such as MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), FS-118 (LAG-3/PD-L1) MGD-019 (PD-1/CTLA-4), KN-046 (PD-1/CTLA-4), MEDI-5752 (CTLA-4/PD-1), RO-7121661 (PD-1/TIM-3), XmAb-20717 (PD-1/CTLA-4), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), MGD-009 (CD3/B7H3), AGEN1223, IMCgp100 (CD3/gp100), AGEN-1423 (GS-1423; CD73/TGF-beta), ATOR-1015 (CTLA-4/0X40), LY-3415244 (TIM3/PDL1), INHIBRX-105 (4-1BB/PDL1), faricimab (VEGF-A/ANG-2), FAP-4-IBBL (4-1BB/FAP), XmAb-13676 (CD3/CD20), TG-1801 (CD19/CD47), XmAb-18087 (SSTR2/CD3), catumaxomab (CD3/EpCAM), SAR-156597 (IL4/IL13), EMB-01 (EGFR/cMET), REGN-4018 (MUC16/CD3), RG-7828 (CD20/CD3), CC-93269 (CD3/BCMA), REGN-5458 (CD3/BCMA), navicixizumab (DLL4/VEGF), GRB-1302 (CD3/Erbb2), vanucizumab (VEGF-A/ANG-2), GRB-1342 (CD38/CD3), GEM-333 (CD3/CD33), IMM-0306 (CD47/CD20);
anti-delta-like protein ligand 3 (DDL3) antibodies, such as rovalpituzumab tesirine;
anti-clusterin antibodies, such as AB-16B5;
anti-Ephrin-A4 (EFNA4) antibodies, such as PF-06647263;
anti-RANKL antibodies, such as denosumab;
anti-mesothelin antibodies, such as BMS-986148, Anti-MSLN-MMAE;
anti-sodium phosphate cotransporter 2B (NaP2B) antibodies, such as lifastuzumab;
anti-c-Met antibodies, such as ABBV-399;
Adenosine A2A receptor antagonists, such as CPI-444, AZD-4635, preladenant, PBF-509;
Dual adenosine A2A/A2B receptor antagonists, such as AB-928:
Alpha-ketoglutarate dehydrogenase (KGDH) inhibitors, such as CPI-613;
XPO1 inhibitors, such as selinexor (KPT-330);
Isocitrate dehydrogenase 2 (IDH2) inhibitors, such as enasidenib (AG-221);
IDH1 inhibitors such as AG-120, and AG-881 (IDH1 and IDH2), IDH-305, BAY-1436032; interleukin-3 receptor (IL-3R) modulators, such as SL-401;
Arginine deiminase stimulators, such as pegargiminase (ADI-PEG-20);
antibody-drug conjugates, such as MLN0264 (anti-GCC, guanylyl cyclase C), T-DM1 (trastuzumab emtansine, Kadcycla); SYD985 (anti-HER2, Duocarmycin), milatuzumab-doxorubicin (hCD74-DOX), brentuximab vedotin, DCDT2980S, polatuzumab vedotin (RG-7596), SGN-CD70A, SGN-CD19A, inotuzumab ozogamicin (CMC-544), lorvotuzumab mertansine, SAR3419, isactuzumab govitecan, enfortumab vedotin (ASG-22ME), ASG-15ME, DS-8201 ((trastuzumab deruxtecan), 225Ac-lintuzumab, U3-1402, 177Lu-tet-raxetan-tetuloma, tisotumab vedotin, anetumab ravtansine, CX-2009, SAR-566658, W-0101, polatuzumab vedotin, ABBV-085, gemtuzumab ozogamicin, ABT-414, glembatumumab vedotin (CDX-011), labetuzumab govitecan (IMMU-130), sacituzumab govitecan (IMMU-132), lifastuzumab vedotin, (RG-7599), milatuzumab-doxorubicin (IMMU-110), indatuximab ravtansine (BT-062), pinatuzumab vedotin (RG-7593), SGN-LIV1A, SGN-CD33A, SAR566658, MLN2704, SAR408701, rovalpituzumab tesirine, ABBV-399, AGS-16C3F, ASG-22ME, AGS67E, AMG 172, AMG 595, AGS-15E, BAY1129980, BAY1187982, BAY94-934 (anetumab ravtansine), GSK2857916, Humax-TF-ADC (tisotumab vedotin), IMGN289, IMGN529, IMGN853 (mirvetuximab soravtansine), LOP628, PCA062, MDX-1203, MEDI-547, PF-06263507, PF-06647020, PF-06647263, PF-06664178, RG7450, RG7458, RG7598, SAR566658, SGN-CD33A, DS-1602 and DS-7300, DS-6157, DS-6000;
claudin-18 inhibitors, such as claudiximab;
β-catenin inhibitors, such as CWP-291;
anti-CD73 antibodies, such as MEDI-9447 (oleclumab), CPX-006, IPH-53, BMS-986179, NZV-930, GS-1423 (AGEN-1423);

CD73 inhibitors, such as AB-680, PSB-12379, PSB-12441, PSB-12425, CB-708, GS-1423 (AGEN-1423);

CD39/CD73 inhibitors, such as PBF-1662;

anti-CD39 antibodies, such as TTX-030;

chemokine receptor 2 (CCR) inhibitors, such as PF-04136309, CCX-872, BMS-813160 (CCR2/CCR5);

thymidylate synthase inhibitors, such as ONX-0801;

ALK/ROS1 inhibtors, such as lorlatinib;

tankyrase inhibitors, such as G007-LK;

Mdm2 p53-binding protein inhibitors, such as CMG-097, HDM-201;

c-PIM inhibitors, such as PIM447;

BRAF inhibitors, such as dabrafenib, vemurafenib, encorafenib (LGX818), PLX8394;

sphingosine kinase-2 (SK2) inhibitors, such as Yeliva® (ABC294640);

cell cycle inhibitors, such as selumetinib (MEK1/2), and sapacitabine;

AKT inhibitors such as MK-2206, ipatasertib, afuresertib, AZD5363, and ARQ-092, capivasertib, triciribine;

c-MET inhibitors, such as AMG-337, savolitinib, tivantinib (ARQ-197), capmatinib, and tepotinib, ABT-700, AG213, AMG-208, JNJ-38877618 (OMO-1), merestinib, HQP-8361;

c-Met/VEGFR inhibitors, such as BMS-817378, TAS-115;

c-Met/RON inhibitors, such as BMS-777607;

BRAF/EGFR inhibitors, such as BGB-283;

bcr/abl inhibitors, such as rebastinib, asciminib;

MNK1/MNK2 inhibitors, such as eFT-508;

mTOR inhibitor/cytochrome P450 3A4 stimulators, such as TYME-88;

lysine-specific demethylase-1 (LSD1) inhibitors, such as CC-90011;

Pan-RAF inhibitors, such as LY3009120, LXH254, TAK-580;

Raf/MEK inhibitors, such as RG7304;

CSF1R/KIT and FLT3 inhibitors, such as pexidartinib (PLX3397);

kinase inhibitors, such as vandetanib;

E selectin antagonists, such as GMI-1271;

differentiation inducers, such as tretinoin;

epidermal growth factor receptor (EGFR) inhibitors, such as osimertinib (AZD-9291);

topoisomerase inhibitors, such as doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114);

corticosteroids, such as cortisone, dexamethasone, hydrocortisone, methylprednisolone, prednisone, prednisolone;

growth factor signal transduction kinase inhibitors;

nucleoside analogs, such as DFP-10917;

Axl inhibitors, such as BGB-324 (bemcentinib), SLC-0211;

Inhibitors of bromodomain and extraterminal motif (BET) proteins, including BRD2 (NCBI Gene ID: 6046), BRD3 (NCBI Gene ID: 8019), BRD4 (NCBI Gene ID: 23476), and bromodomain testis-specific protein (BRDT; NCBI Gene ID: 676), such as INCB-054329, INCB057643, TEN-010, AZD-5153, ABT-767, BMS-986158, CC-90010, GSK525762 (molibresib), NHWD-870, ODM-207, GSK-2820151, GSK-1210151A, ZBC246, ZBC260, ZEN3694, FT-1101, RG-6146, CC-90010, mivebresib, BI-894999, PLX-2853, PLX-51107, CPI-0610, GS-5829;

PARP inhibitors, such as olaparib, rucaparib, veliparib, talazoparib, ABT-767, BGB-290, fluzolepali (SHR-3162), niraparib (JNJ-64091742), bendamustine hydrochloride;

PARP/Tankyrase inhibitors such as 2X-121 (e-7499);

IMP-4297, SC-10914, IDX-1197, HWH-340, CK-102, simmiparib;

Proteasome inhibitors, such as ixazomib, carfilzomib (Kyprolis®), marizomib;

Glutaminase inhibitors, such as CB-839 (telaglenastat), bis-2-(5-phenylacetamido-1,3,4-thiadiazol-2-yl)ethyl sulfide (BPTES);

mitochondrial complex I inhibitors, such as metformin, phenformin;

Vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131; bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, tapuldencel-T, eltrapuldencel-T, SL-701, BSKO1TM, rocapuldencel-T (AGS-003), DCVAC, CVactm, stapuldencel-T, eltrapuldencel-T, SL-701, BSKO1TM, ADXS31-142; oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, CreaVax-BC, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; GI-4000; 10-103; Neoantigen peptide vaccines, such as AGEN-2017, GEN-010, NeoVax, RG-6180, GEN-009, PGV-001 (TLR-3 agonist), GRANITE-001, NEO-PV-01; Peptide vaccines that target heat shock proteins, such as PhosphoSynVax™; Vitespen (HSPPC-96-C);

anti-DLL4 (delta like ligand 4) antibodies, such as demcizumab;

STAT-3 inhibitors, such as napabucasin (BBI-608);

ATPase p97 inhibitors, such as CB-5083;

smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;

interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-nl (Humoferon, SM-10500, Sumiferon);

interferon gamma ligand modulators, such as interferon gamma (OH-6000, Ogamma 100);

IL-6 receptor modulators, such as tocilizumab, siltuximab, AS-101 (CB-06-02, IVX-Q-101);

Telomerase modulators, such as, tertomotide (GV-1001, HR-2802, Riavax) and imetelstat (GRN-163, JNJ-63935937);

DNA methyltransferases inhibitors, such as temozolomide (CCRG-81045), decitabine, guadecitabine (S-110, SGI-110), KRX-0402, RX-3117, RRx-001, and azacitidine;

DNA gyrase inhibitors, such as pixantrone and sobuzoxane;

Bc1-2 family protein inhibitors, such as ABT-263, venetoclax (ABT-199), ABT-737, and AT-101;

Notch inhibitors, such as LY3039478 (crenigacestat), tarextumab (anti-Notch2/3), BMS-906024;

anti-myostatin inhibitors, such as landogrozumab;

hyaluronidase stimulators, such as PEGPH-20;

Wnt pathway inhibitors, such as SM-04755, PRI-724, WNT-974;

gamma-secretase inhibitors, such as PF-03084014, MK-0752, RO-4929097;

Grb-2 (growth factor receptor bound protein-2) inhibitors, such as BP1001;

TRAIL pathway-inducing compounds, such as ONC201, ABBV-621;

Focal adhesion kinase inhibitors, such as VS-4718, defactinib, GSK2256098;

hedgehog inhibitors, such as saridegib, sonidegib (LDE225), glasdegib and vismodegib;

Aurora kinase inhibitors, such as alisertib (MLN-8237), and AZD-2811, AMG-900, barasertib, ENMD-2076;

HSPB1 modulators (heat shock protein 27, HSP27), such as brivudine, apatorsen;

ATR inhibitors, such as BAY-937, AZD6738, AZD6783, VX-803, VX-970 (berzosertib) and VX-970;

mTOR inhibitors, such as sapanisertib and vistusertib (AZD2014), ME-344;

mTOR/PI3K inhibitors, such as gedatolisib, GSK2141795, omipalisib, RG6114;

Hsp90 inhibitors, such as AUY922, onalespib (AT13387), SNX-2112, SNX5422;

Murine double minute (mdm2) oncogene inhibitors, such as DS-3032b, RG7775, AMG-232, HDM201, and idasanutlin (RG7388);

CD137 agonists, such as urelumab, utomilumab (PF-05082566), AGEN2373, ADG-106; STING agonists, such as ADU-S100 (MIW-815), SB-11285, MK-1454, SR-8291, AdVCA0848, GSK-532, SYN-STING, MSA-1, SR-8291;

FGFR inhibitors, such as FGF-401, INCB-054828, BAY-1163877, AZD4547, JNJ-42756493, LY2874455, Debio-1347;

fatty acid synthase (FASN) inhibitors, such as TVB-2640;

Anti-killer cell immunoglobulin like receptor, three Ig domains and long cytoplasmic tail 1 (KIR3DL1; KIR; NCBI Gene ID: 3811) monoclonal antibodies, such as lirilumab (IPH-2102), IPH-4102;

Antigen CD19 inhibitors, such as MOR208, MEDI-551, AFM-11, inebilizumab;

CD44 binders, such as A6;

protein phosphatease 2A (PP2A) inhibitors, such as LB-100;

CYP17 inhibitors, such as seviteronel (VT-464), ASN-001, ODM-204, CFG920, abiraterone acetate;

RXR agonists, such as IRX4204;

hedgehog/smoothened (hh/Smo) antagonists, such as taladegib, patidegib;

complement C3 modulators, such as Imprime PGG;

IL-15 agonists, such as ALT-803, NKTR-255, and hetIL-15;

EZH2 (enhancer of zeste homolog 2) inhibitors, such as tazemetostat, CPI-1205, GSK-2816126;

Oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, OBP-301;

DOT1L (histone methyltransferase) inhibitors, such as pinometostat (EPZ-5676);

toxins such as Cholera toxin, ricin, *Pseudomonas* exotoxin, *Bordetella pertussis* adenylate cyclase toxin, diphtheria toxin, and caspase activators;

DNA plasmids, such as BC-819;

PLK inhibitors of PLK 1, 2, and 3, such as volasertib (PLK1);

WEE1 inhibitors, such as AZD-1775 (adavosertib); Rho kinase (ROCK) inhibitors, such as AT13148, KD025;

ERK inhibitors, such as GDC-0994, LY3214996, MK-8353;

Inhibition of Apoptosis Protein (IAP) inhibitors, such as ASTX660, debio-1143, birinapant, APG-1387, LCL-161;

RNA polymerase inhibitors, such has lurbinectedin (PM-1183), CX-5461;

Tubulin inhibitors, such as PM-184, BAL-101553 (lisavanbulin), and OXI-4503, fluorapacin (AC-0001), plinabulin;

Toll-like receptor 4 (TL4) agonists, such as G100, GSK1795091, and PEPA-10;

Elongation factor 1 alpha 2 inhibitors, such as plitidepsin;

CD95 inhibitors, such as APG-101, APO-010, asunercept;

WT1 inhibitors, such as DSP-7888;

splicing factor 3B subunit1 (SF3B1) inhibitors, such as H3B-8800;

retinoid Z receptor gamma (RORγ) agonists, such as LYC-55716; and

Microbiome modulators, such as SER-401, EDP-1503, MRx-0518.

In some embodiments, the fusion protein, the homodimer, the heterodimer, the conjugate, the polynucleotide, the vector, the lipoplex, such as an LNP, and/or the pharmaceutical composition is co-administered with one or more additional therapeutic agents comprising an inhibitor or antagonist of: protein tyrosine phosphatase, non-receptor type 11 (PTPN11 or SHP2; NCBI Gene ID: 5781); myeloid cell leukemia sequence 1 (MCL1) apoptosis regulator (NCBI Gene ID: 4170); mitogen-activated protein kinase kinase kinase kinase 1 (MAP4K1) (also called Hematopoietic Progenitor Kinase 1 (HPK1), NCBI Gene ID: 11184); phosphatidylinositol-4,5-bisphosphate 3-kinase, including catalytic subunit alpha (PIK3CA; NCBI Gene ID: 5290), catalytic subunit beta (PIK3CB; NCBI Gene ID: 5291), catalytic subunit gamma (PIK3CG; NCBI Gene ID: 5294) and catalytic subunit delta (PIK3CD; NCBI Gene ID: 5293), diacylglycerol kinase alpha (DGKA, DAGK, DAGK1 or DGK-alpha; NCBI Gene ID: 1606); 5'-nucleotidase ecto (NTSE or CD73; NCBI Gene ID: 4907); ectonucleoside triphosphate diphosphohydrolase 1 (ENTPD1 or CD39; NCBI Gene ID: 593); transforming growth factor beta 1 (TGFB1 or TGFβ; NCBI Gene ID: 7040); heme oxygenase 1 (HMOX1, HO-1 or H01; NCBI Gene ID: 3162); heme oxygenase 2 (HMOX2, HO-2 or H02; NCBI Gene ID: 3163); vascular endothelial growth factor A (VEGFA or VEGF; NCBI Gene ID: 7422); erb-b2 receptor tyrosine kinase 2 (ERBB2, HER2, HER2/neu or CD340; NCBI Gene ID: 2064), epidermal growth factor receptor (EGFR, ERBB, ERBB1 or HER1; NCBI Gene ID: 1956); ALK receptor tyrosine kinase (ALK, CD246; NCBI Gene ID: 238); poly(ADP-ribose) polymerase 1 (PARP1; NCBI Gene ID: 142); poly(ADP-ribose) polymerase 2 (PARP2; NCBI Gene ID: 10038); TCDD inducible poly(ADP-ribose) polymerase (TIPARP, PARP7; NCBI Gene ID: 25976); cyclin dependent kinase 4 (CDK4; NCBI Gene ID: 1019); cyclin dependent kinase 6 (CDK6; NCBI Gene ID: 1021); TNF receptor superfamily member 14 (TNFRSF14, HVEM, CD270; NCBI Gene ID: 8764); T cell immunoreceptor with Ig and ITIM domains (TIGIT; NCBI Gene ID: 201633); X-linked inhibitor of apoptosis (XIAP, BIRC4, IAP-3; NCBI Gene ID: 331); baculoviral IAP repeat containing 2 (BIRC2, cIAP1; NCBI Gene ID: 329); baculoviral IAP repeat containing 3 (BIRC3, cIAP2; NCBI Gene ID: 330); baculoviral IAP repeat containing 5 (BIRC5, surviving; NCBI Gene ID: 332); C-C motif chemokine receptor 2 (CCR2, CD192; NCBI Gene ID: 729230); C-C motif chemokine receptor 5 (CCR5, CD195; NCBI Gene ID: 1234); C-C motif chemokine receptor 8 (CCR8, CDw198; NCBI Gene ID: 1237); C-X-C motif chemokine receptor 2 (CXCR2, CD182; NCBI Gene ID: 3579); C-X-C motif chemokine receptor 3 (CXCR3, CD182, CD183; NCBI Gene ID: 2833); C-X-C motif chemokine receptor 4 (CXCR4, CD184; NCBI Gene ID: 7852); cytokine inducible SH2 containing protein (CISH; NCBI Gene ID: 1154); arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CASA (NCBI Gene ID: 763), CASB (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOXS, 5-LOX; NCBI Gene ID: 240) and/or soluble epoxide hydrolase 2 (EPHX2, SEH; NCBI Gene ID: 2053); a secreted phospholipase A2 (e.g., PLA2G1B (NCBI Gene ID: 5319); PLA2G7 (NCBI Gene ID: 7941), PLA2G3 (NCBI Gene ID: 50487), PLA2G2A (NCBI Gene ID: 5320); PLA2G4A (NCBI Gene ID: 5321); PLA2G12A (NCBI Gene ID: 81579); PLA2G12B (NCBI Gene ID: 84647); PLA2G10 (NCBI Gene ID: 8399); PLA2G5 (NCBI Gene ID: 5322); PLA2G2D (NCBI Gene ID: 26279); PLA2G15 (NCBI Gene ID: 23659)); indoleamine 2,3-dioxygenase 1 (IDO1; NCBI Gene ID: 3620); indoleamine 2,3-dioxygenase 2 (IDO2; NCBI Gene ID: 169355); hypoxia inducible factor 1 subunit alpha (HIF1A; NCBI Gene ID: 3091); angiopoietin 1 (ANGPT1; NCBI Gene ID: 284); Endothelial TEK tyrosine kinase (TIE-2, TEK, CD202B; NCBI Gene ID: 7010); Janus kinase 1 (JAK1; NCBI Gene ID: 3716); catenin beta 1 (CTNNB1; NCBI Gene ID: 1499); histone deacetylase 9 (HDAC9; NCBI Gene ID: 9734), 5'-3' exoribonuclease 1 (XRN1; NCBI Gene ID: 54464); and/or WRN RecQ like helicase (WRN; NCBI Gene ID: 7486).

Immune Checkpoint Modulators

In various embodiments, the FLT3L-Fc fusion proteins, homodimers, heterodimers, polynucleotides, vectors, lipoplexes, such as LNPs, and/or pharmaceutical compositions, as described herein, are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In various embodiments, the immune checkpoint proteins or receptors regulate T cell responses (e.g., reviewed in Xu, et al., *J Exp Clin Cancer Res.* (2018) 37:110). In various embodiments, the immune checkpoint proteins or receptors regulate NK cell responses (e.g., reviewed in Davis, et al., *Semin Immunol.* (2017) 31:64-75 and Chiossone, et al., *Nat Rev Immunol.* (2018) 18(11):671-688).

Examples of immune checkpoint proteins or receptors include without limitation CD27 (NCBI Gene ID: 939), CD70 (NCBI Gene ID: 970); CD40 (NCBI Gene ID: 958), CD40LG (NCBI Gene ID: 959); CD47 (NCBI Gene ID: 961), SIRPA (NCBI Gene ID: 140885); CD48 (SLAMF2; NCBI Gene ID: 962), transmembrane and immunoglobulin domain containing 2 (TMIGD2, CD28H; NCBI Gene ID: 126259), CD84 (LY9B, SLAMFS; NCBI Gene ID: 8832), CD96 (NCBI Gene ID: 10225), CD160 (NCBI Gene ID: 11126), MS4A1 (CD20; NCBI Gene ID: 931), CD244 (SLAMF4; NCBI Gene ID: 51744); CD276 (B7H3; NCBI Gene ID: 80381); V-set domain containing T cell activation inhibitor 1 (VTCN1, B7H4); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943), TNFSF8 (CD30L; NCBI Gene ID: 944); TNFRSF10A (CD261, DR4, TRAILR1; NCBI Gene ID: 8797), TNFRSF9 (CD137; NCBI Gene ID: 3604), TNFSF9 (CD137L; NCBI Gene ID: 8744); TNFRSF10B (CD262, DR5, TRAILR2; NCBI Gene ID: 8795), TNFRSF10 (TRAIL; NCBI Gene ID: 8743); TNFRSF14 (HVEM, CD270; NCBI Gene ID: 8764), TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608), TNFSF13B (BAFF; NCBI Gene ID: 10673); TNFRSF18 (GITR; NCBI Gene ID: 8784), TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941), CD28

(NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAET1E; ULBP4; NCBI Gene ID: 135250); retinoic acid early transcript 1G (RAET1G; ULBPS; NCBI Gene ID: 353091); retinoic acid early transcript 1L (RAET1L; ULBP6; NCBI Gene ID: 154064); killer cell immunoglobulin like receptor, three Ig domains and long cytoplasmic tail 1 (KIR, CD158E1; NCBI Gene ID: 3811, e.g., lirilumab (IPH-2102, IPH-4102)); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1); killer cell lectin like receptor D1 (KLRD1; NCBI Gene ID: 3824); killer cell lectin like receptor G1 (KLRG1; CLEC15A, MAFA, 2F1; NCBI Gene ID: 10219); sialic acid binding Ig like lectin 7 (SIGLEC7; NCBI Gene ID: 27036); and sialic acid binding Ig like lectin 9 (SIGLEC9; NCBI Gene ID: 27180).

In various embodiments, the FLT3L-Fc fusion proteins, homodimers, heterodimers, polynucleotides, vectors, lipoplexes, such as LNPs, and/or pharmaceutical compositions, as described herein, are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, the FLT3L-Fc fusion proteins, homodimers, heterodimers, polynucleotides, vectors, lipoplexes, such as LNPs, and/or pharmaceutical compositions, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res*. (2018) 37:110.

In various embodiments, the FLT3L-Fc fusion proteins, homodimers, heterodimers, polynucleotides, vectors, lipoplexes, such as LNPs, and/or pharmaceutical compositions, as described herein, are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); killer cell lectin like receptor D1 (KLRD1, CD94), killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In various embodiments, the FLT3L-Fc fusion proteins, homodimers, heterodimers, polynucleotides, vectors, lipoplexes, such as LNPs, and/or pharmaceutical compositions, as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol*. (2017) 31:64-75; Fang, et al., *Semin Immunol*. (2017) 31:37-54; and Chiossone, et al., *Nat Rev Immunol*. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4.

Examples of inhibitors of CTLA4 that can be co-administered include without limitation ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, AGEN2034 (balstilimab), zimberelimab, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

TNF Receptor Superfamily (TNFRSF) Member Agonists or Activators

In various embodiments, the FLT3L-Fc fusion proteins, homodimers, heterodimers, polynucleotides, vectors, lipoplexes, such as LNPs, and/or pharmaceutical compositions, as described herein, are combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

In some embodiments, the anti-TNFRSF17 (BCMA) antibody GSK-2857916 is co-administered.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi-specific antibodies targeting TNFRSF family members that can be co-administered include without limitation PRS-343 (CD-137/HER2), AFM26 (BCMA/CD16A), AFM-13 (CD16/CD30), REGN-1979 (CD20/CD3), AMG-420 (BCMA/CD3), INHIBRX-105 (4-1BB/PDL1), FAP-4-IBBL (4-1BB/FAP), XmAb-13676 (CD3/CD20), RG-7828 (CD20/CD3), CC-93269 (CD3/BCMA), REGN-5458 (CD3/BCMA), and IMM-0306 (CD47/CD20).

Bi-Specific T-Cell Engagers

In various embodiments, the FLT3L-Fc fusion proteins, homodimers, heterodimers, polynucleotides, vectors, lipoplexes, such as LNPs, and/or pharmaceutical compositions, as described herein, are combined with a bi-specific T-cell engager (e.g., not having an Fc) or an anti-CD3 bi-specific antibody (e.g., having an Fc). Illustrative anti-CD3 bi-specific antibodies or BiTEs that can be co-administered include JNJ-64052781 (CD19/CD3), AMG-211 (CEA/CD3), RG7802 (CEA/CD3), ERY-974 (CD3/GPC3), PF-06671008 (Cadherins/CD3), APV0436 (CD123/CD3), flotetuzumab (CD123/CD3), REGN-1979 (CD20/CD3), MCLA-117 (CD3/CLEC12A), JNJ-0819, JNJ-7564 (CD3/heme), AMG-757 (DLL3-CD3), AMG-330 (CD33/CD3), AMG-420 (BCMA/CD3), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), XmAb-18087 (SSTR2/CD3), catumaxomab (CD3/EpCAM), REGN-4018 (MUC16/CD3), RG-7828 (CD20/CD3), CC-93269 (CD3/BCMA), REGN-5458 (CD3/BCMA), GRB-1302 (CD3/Erbb2), GRB-1342 (CD38/CD3), GEM-333 (CD3/CD33). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., *Oncoimmunology*. (2017) May 17; 6(7):e1326437); PD-L1 (Horn, et al., *Oncotarget*. 2017 Aug.

3; 8(35):57964-57980); and EGFRvIII (Yang, et al., *Cancer Lett.* 2017 Sep. 10; 403:224-230).

Bi- and Tri-Specific Natural Killer (NK)-Cell Engagers

In various embodiments, the FLT3L-Fc fusion proteins, homodimers, heterodimers, polynucleotides, vectors, lipoplexes, such as LNPs, and/or pharmaceutical compositions, as described herein, are combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol.* (2016) 1441:333-346; Fang, et al., *Semin Immunol.* (2017) 31:37-54.

MCL1 Apoptosis Regulator, BCL2 Family Member (MCL1) Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of MCL1 apoptosis regulator, BCL2 family member (MCL1, TM; EAT; MCL1L; MCL1S; Mc1-1; BCL2L3; MCL1-ES; bc12-L-3; mcll/EAT; NCBI Gene ID: 4170). Examples of MCL1 inhibitors include AMG-176, AMG-397, S-64315, and AZD-5991, 483-LM, A-1210477, UMI-77, JKY-5-037, and those described in WO2018183418, WO2016033486, and WO2017147410.

SHP2 Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TN0155 (SHP-099), RMC-4550, JAB-3068, RMC-4630, and those described in WO2018172984 and WO2017211303.

Hematopoietic Progenitor Kinase 1 (HPK1) Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO-2018183956, WO-2018183964, WO-2018167147, WO-2018183964, WO-2016205942, WO-2018049214, WO-2018049200, WO-2018049191, WO-2018102366, WO-2018049152 and WO-2016090300;

Apoptosis Signal-Regulating Kinase (ASK) Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of an ASK inhibitor, e.g., mitogen-activated protein kinase kinase kinase 5 (MAP3K5; ASK1, MAPKKKS, MEKKS; NCBI Gene ID: 4217). Examples of ASK1 inhibitors include without limitation, those described in WO 2011/008709 (Gilead Sciences) and WO 2013/112741 (Gilead Sciences).

Bruton Tyrosine Kinase (BTK) Inhibitors

In various embodiments, the FLT3L-Fc fusion proteins, homodimers, heterodimers, polynucleotides, vectors, lipoplex, such as LNPs, and/or pharmaceutical compositions, as described herein, are combined with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include without limitation, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315.

Cluster of Differentiation 47 (CD47) Inhibitors

In various embodiments, the FLT3L-Fc fusion proteins, homodimers, heterodimers, polynucleotides, vectors, lipoplex, such as LNPs, and/or pharmaceutical compositions, as described herein, are combined with an inhibitor of CD47 (IAP, MER6, 0A3; NCBI Gene ID: 961). Examples of CD47 inhibitors include without limitation anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621. In some embodiments, the CD47 inhibitor is magrolimab.

SIRPα Targeting Agents

In various embodiments, the FLT3L-Fc fusion proteins, homodimers, heterodimers, polynucleotides, vectors, lipoplexes, such as LNPs, and/or pharmaceutical compositions, as described herein, are combined with a SIRPa targeting agent (NCBI Gene ID: 140885; UniProt P78324). Examples of SIRPa targeting agents include without limitation SIRPa inhibitors, such as AL-008, RRx-001, and CTX-5861, and anti-SIRPa antibodies, such as FSI-189 (GS-0189), ES-004, BI765063, ADU1805, and CC-95251. Additional SIRPa-targeting agents of use are described, for example, in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170 and WO2020068752.

Cyclin-Dependent Kinase (CDK) Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of cyclin dependent kinase 1 (CDK1, CDC$l_2$; CDC$l_2$8A; P34CDC$l_2$; NCBI Gene ID: 983); cyclin dependent kinase 2 (CDK2, CDKN2; p33(CDK2); NCBI Gene ID: 1017); cyclin dependent kinase 3 (CDK3; NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; M15; STK1; CDKN7; p39MO15; NCBI Gene ID: 1022); cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include without limitation abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, and TG-02.

Discoidin Domain Receptor (DDR) Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include without limitation, dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Targeted E3 Ligase Ligand Conjugates

In various embodiments, the FLT3L-Fc fusion proteins, homodimers, heterodimers, polynucleotides, vectors, lipoplexes, such as LNPs, and/or pharmaceutical compositions, as described herein, are combined with a targeted E3 ligase ligand conjugate. Such conjugates have a target protein binding moiety and an E3 ligase binding moiety (e.g., an inhibitor of apoptosis protein (IAP) (e.g., XIAP, c-IAP1, c-IAP2, NIL-IAP, Bruce, and surviving) E3 ubiquitin ligase binding moiety, Von Hippel-Lindau E3 ubiquitin ligase (VHL) binding moiety, a cereblon E3 ubiquitin ligase binding moiety, mouse double minute 2 homolog (MDM2) E3 ubiquitin ligase binding moiety), and can be used to promote or increase the degradation of targeted proteins, e.g., via the ubiquitin pathway. In one embodiment, the targeted E3 ligase ligand conjugates comprise a targeting or binding moiety that targets or binds a protein identified in Table B, and an E3 ligase ligand or binding moiety. In one embodiment, the targeted E3 ligase ligand conjugates comprise a targeting or binding moiety that targets or binds a protein selected from Cbl proto-oncogene B (CBLB; Cbl-b, Nbla00127, RNF56; NCBI Gene ID: 868) and hypoxia inducible factor 1 subunit alpha (HIF1A; NCBI Gene ID: 3091). In one embodiment, the targeted E3 ligase ligand conjugates comprise a kinase inhibitor (e.g., a small molecule kinase inhibitor, e.g., of BTK and an E3 ligase ligand or binding moiety. See, e.g., WO2018098280. In another embodiment, the targeted E3 ligase ligand conjugates comprise a binding moiety targeting or binding to Interleukin-1 (IL-1) Receptor-Associated Kinase-4 (IRAK-4); Rapidly Accelerated Fibrosarcoma (RAF, such as c-RAF, A-RAF and/or B-RAF), c-Met/p38, or a BRD protein; and an E3 ligase ligand or binding moiety. See, e.g., WO2019099926, WO2018226542, WO2018119448, WO2018223909, WO2019079701. Additional targeted E3 ligase ligand conjugates that can be co-administered are described, e.g., in WO2018237026, WO2019084026, WO2019084030, WO2019067733, WO2019043217, WO2019043208 and WO2018144649.

Histone Deacetylase (HDAC) Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, entinostat.

Indoleamine-pyrrole-2,3-dioxygenase (IDO1) inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Janus Kinase (JAK) Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3 HUMAN, JAKL, L-JAK, LJAK; NCBI Gene ID: 3718). Examples of JAK inhibitors include without limitation, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019.

Lysyl Oxidase-Like Protein (LOXL) Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of a LOXL protein, e.g., LOXL1 (NCBI Gene ID: 4016), LOXL2 (NCBI Gene ID: 4017), LOXL3 (NCBI Gene ID: 84695), LOXL4 (NCBI Gene ID: 84171), and/or LOX (NCBI Gene ID: 4015). Examples of LOXL inhibitors include without limitation, the antibodies described in WO 2009/017833 (Arresto Biosciences). Examples of LOXL2 inhibitors include without limitation, the antibodies described in WO 2009/017833 (Arresto Biosciences), WO 2009/035791 (Arresto Biosciences), and WO 2011/097513 (Gilead Biologics).

Matrix Metalloprotease (MMP) Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMPI (NCBI Gene ID: 4316), MMP8 (NCBI Gene ID: 4317), MMP9 (NCBI Gene ID: 4318); MMP10 (NCBI Gene ID: 4319); MMP11

(NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include without limitation, marimastat (BB-2516), cipemastat (Ro 32-3555), GS-5745 (andecaliximab) and those described in WO 2012/027721 (Gilead Biologics).

RAS and RAS Pathway Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of KRAS proto-oncogene, GTPase (KRAS; a.k.a., NS; NS3; CFC2; RALD; K-Ras; KRAS1; KRAS2; RASK2; KI-RAS; C—K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893); HRas proto-oncogene, GTPase (HRAS; a.k.a., CTLO; KRAS; HAMSV; HRAS1; KRAS2; RASH1; RASK2; Ki-Ras; p2lras; CH-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR. Illustrative K-Ras inhibitors that can be co-administered include ARS-1620 (G12C), SML-8-73-1 (G12C), Compound 3144 (G12D), Kobe0065/2602 (Ras GTP), RT11, MRTX-849 (G12C) and K-Ras (G12D)-selective inhibitory peptides, including KRpep-2 (Ac-RRCPLYISYDPVCRR-NH$_2$) (SEQ ID NO:108) and KRpep-2d (Ac-RRRRCPLYISYDPVCRRRR-NH$_2$) (SEQ ID NO:109). Illustrative KRAS mRNA inhibitors include anti-KRAS U1 adaptor, AZD-4785, siG12D-LODER™, and siG12D exosomes. Illustrative MEK inhibitors that can be co-administered include binimetinib, cobimetinib, PD-0325901, pimasertib, RG-7304, selumetinib, trametinib, and those described below and herein. Illustrative Raf dimer inhibitors that can be co-administered BGB-283, HM-95573, LXH-254, LY-3009120, RG7304 and TAK-580. Illustrative ERK inhibitors that can be co-administered include LTT-462, LY-3214996, MK-8353, ravoxertinib and ulixertinib. Illustrative Ras GTPase inhibitors that can be co-administered include rigosertib. Illustrative PI3K inhibitors that can be co-administered include idelalisib (Zydelig®), alpelisib, buparlisib, pictilisib, and those described below and herein. Illustrative PI3K/mTOR inhibitors that can be co-administered include dactolisib, omipalisib and voxtalisib. In certain embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., Cancer Biol Ther. 2018 Feb. 1; 19(2):132-137.

Mitogen-Activated Protein Kinase (MEK) Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib.

Phosphatidylinositol 3-Kinase (PI3K) Inhibitors

In various embodiments, the FLT3L-Fc fusion proteins, homodimers, heterodimers, polynucleotides, vectors, lipoplexes, such as an LNPs, and/or pharmaceutical compositions, as described herein, are combined with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWSS, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments, the PI3K inhibitor is a pan-PI3K inhibitor. Examples of PI3K inhibitors include without limitation, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Spleen Tyrosine Kinase (SYK) Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an inhibitor of spleen associated tyrosine kinase (SYK, p72-Syk, Gene ID: 6850). Examples of SYK inhibitors include without limitation, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Connecticut) and those described in U.S. 2015/0175616.

Toll-Like Receptor (TLR) Agonists

In various embodiments, the FLT3L-Fc fusion proteins, homodimers, heterodimers, polynucleotides, vectors, lipoplexes, such as LNPs, and/or pharmaceutical compositions, as described herein, are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation DS-0509, GS-9620 (vesatolimod), vesatolimod analogs, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include without limitation AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Tyrosine-Kinase Inhibitors (TKIs)

In various embodiments, the FLT3L-Fc fusion proteins, homodimers, heterodimers, polynucleotides, vectors, lipoplexes, such as LNPs, and/or pharmaceutical compositions, as described herein, are combined with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rocile- tinib, sulfatinib (HMPL-012), sunitinib, famitinib L-malate, (MAC-4), tivoanib, TH-4000, and MEDI-575 (anti-PDGFR antibody).

Chemotherapeutic Agents

In various embodiments, the FLT3L-Fc fusion proteins, homodimers, heterodimers, polynucleotides, vectors, lipoplexes, such as LNPs, and/or pharmaceutical compositions, as described herein, are combined with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiII), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

An example progesterone receptor antagonist includes onapristone.

Anti-Angiogenic Agents

In various embodiments, the FLT3L-Fc fusion proteins, homodimers, heterodimers, polynucleotides, vectors, lipoplexes, such as LNPs, and/or pharmaceutical compositions, as described herein, are combined with an anti-angiogenic agent. Anti-angiogenic agents that can be co-administered include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, a,a'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carb oxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

In various embodiments, the FLT3L-Fc fusion proteins, homodimers, heterodimers, polynucleotides, vectors, lipoplexes, such as LNPs, and/or pharmaceutical compositions, as described herein, are combined with an anti-fibrotic agent. Anti-fibrotic agents that can be co-administered include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethyl amine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-l-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In various embodiments, the FLT3L-Fc fusion proteins, homodimers, heterodimers, polynucleotides, vectors, lipoplexes, such as LNPs, and/or pharmaceutical compositions, as described herein, are combined with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CASA (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CAl 1 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOXS, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include without limitation mofezolac, GLY-230, and TRK-700.

Examples of inhibitors of prostaglandin-endoperoxide synthase 2 (PTGS2, COX-2; NCBI Gene ID: 5743) that can be co-administered include without limitation diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, Anitrazafen, Apricoxib, Cimicoxib, Deracoxib, Flumizole, Firocoxib, Mavacoxib, NS-398, Pamicogrel, Parecoxib, Robenacoxib, Rofecoxib, Rutecarpine, Tilmacoxib, and Zaltoprofen. Examples of dual COX1/COX2 inhibitors that can be co-administered include without limitation, HP-5000, lornoxicam, ketorolac tromethamine, bromfenac sodium, ATB-346, HP-5000. Examples of dual COX-2/carbonic anhydrase (CA) inhibitors that can be co-administered include without limitation polmacoxib and imrecoxib.

Examples of inhibitors of secreted phospholipase A2, prostaglandin E synthase (PTGES, PGES; Gene ID: 9536) that can be co-administered include without limitation LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett.* (2017) 389:23-32; and Liu, et al., Oncotarget. (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CASA (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CAl 1 (NCBI Gene ID: 770), CA12 (NCBI Gene ID: 771), CA13 (NCBI Gene ID: 377677), CA14 (NCBI Gene ID: 23632)) that can be co-administered include without limitation acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOXS, 5-LOX; NCBI Gene ID: 240) that can be co-administered include without limitation meclofenamate sodium, zileuton.

Examples of inhibitors of soluble epoxide hydrolase 2 (EPHX2, SEH; NCBI Gene ID: 2053) that can be co-administered include without limitation compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include without limitation GS-4875, GS-5290, BHM-078 and those described, e.g., in WO2006124944, WO2006124692, WO2014064215, WO2018005435, Teli, et al., *J Enzyme Inhib Med Chem.* (2012) 27(4):558-70; Gangwall, et al., *Curr Top Med Chem.* (2013) 13(9):1015-35; Wu, et al., *Bioorg Med Chem Lett.* (2009) 19(13):3485-8; Kaila, et al., *Bioorg Med Chem.* (2007) 15(19):6425-42; and Hu, et al., *Bioorg Med Chem Lett.* (2011) 21(16):4758-61.

Tumor Oxygenation Agents

In various embodiments, the FLT3L-Fc fusion proteins, homodimers, heterodimers, polynucleotides, vectors, lipoplexes, such as LNPs, and/or pharmaceutical compositions, as described herein, are combined with an agent that promotes or increases tumor oxygenation or reoxygenation, or prevents or reduces tumor hypoxia. Illustrative agents that can be co-administered include, e.g., Hypoxia inducible factor-1 alpha (HIF-1a) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO 2007/137767, WO 2007/139791, WO 2014/107171, and WO 2016/149562.

Immunotherapeutic Agents

In various embodiments, the FLT3L-Fc fusion proteins, homodimers, heterodimers, polynucleotides, vectors, lipoplexes, such as LNPs, and/or pharmaceutical compositions, as described herein, are combined with an immunotherapeutic agent. Example immunotherapeutic agents that can be co-administered include without limitation abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

In some embodiments, the immunotherapeutic agent is an antibody-drug conjugate (ADC). Illustrative ADCs that can be co-administered include without limitation drug-conjugated antibodies, fragments thereof, or antibody mimetics targeting the proteins or antigens listed above and herein (e.g., in Table B). Example ADCs that can be co-administered include without limitation gemtuzumab, brentuximab, trastuzumab, inotuzumab, glembatumumab, anetumab, mirvetuximab, depatuxizumab, rovalpituzumab, vadastuximab, labetuzumab, sacituzumab, lifastuzumab, indusatumab, polatzumab, pinatuzumab, coltuximab, indatuximab, milatuzumab, rovalpituzumab, ABBV-399, AGS-16C3F, ASG-22ME, AGS67E, AMG172, AMG575, BAY1129980, BAY1187982, BAY94-9343, GSK2857916, Humax-TF-ADC, IMGN289, IMGN529, IMGN853, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A and SYD985. ADCs that can be co-administered are described, e.g., in Lambert, et al., *Adv Ther* (2017) 34:1015-1035 and in de Goeij, *Current Opinion in Immunology* (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracycline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a vinca alkaloid, an epothilone), a pyrrolobenzodiazepine (PBD) or dimer thereof, a duocarmycin (A, B1, B2, C1, C2, D, SA, CC-1065), and other anticancer or anti-neoplastic agents described herein. In some embodiments, the therapeutic agents (e.g., anticancer or antineoplastic agents) that can be conjugated to the drug-conjugated antibodies, fragments thereof, or antibody mimetics include an immune checkpoint inhibitor. In some embodiments, the conjugated immune checkpoint inhibitor is a conjugated small molecule inhibitor of CD274 (PDL1, PD-L1), programmed cell death 1 (PDCD1, PD1, PD-1) or CTLA4. In some embodiments, the conjugated small molecule inhibitor of CD274 or PDCD1 is selected from the group consisting of GS-4224, GS-4416, INCB086550 and MAX10181. In some embodiments, the conjugated small molecule inhibitor of CTLA4 comprises BPI-002.

Cancer Gene Therapy and Cell Therapy

In various embodiments, the FLT3L-Fc fusion proteins, homodimers, heterodimers, polynucleotides, vectors, lipoplexes, such as LNPs, and/or pharmaceutical compositions, as described herein, are combined with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In various embodiments, the FLT3L-Fc fusion proteins, homodimers, heterodimers, polynucleotides, vectors, lipoplexes, such as LNPs, and/or pharmaceutical compositions, as described herein, are combined with one or more cellular therapies. Illustrative cellular therapies include without limitation co-administration of one or more of a population of natural killer (NK) cells, NK-T cells, T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments, the cellular therapy entails co-administering cells comprising chimeric antigen receptors (CARs). In such therapies, a population of immune effector cells engineered to express a CAR, wherein the CAR comprises a tumor antigen-binding domain. In T cell therapies, the T cell receptors (TCRs) are engineered to target tumor derived peptides presented on the surface of tumor cells.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CD1E (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD160, CD19, IL2R beta, IL2R gamma, IL7R, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, CD29, ITGB2 (LFA-1, CD18), ITGB7, TNFR2, DNAM1 (CD226), SLAMF4 (CD244, 2B4), CD84, CD96 (TACTILE), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRv111); ganglioside G2 (GD2); ganglioside GD3 ($\alpha$NeuSAc(2-8)$\alpha$NeuSAc(2-3)$\beta$DGaip(1-4)bDGIcp(1-1) Cer); ganglioside GM3 ($\alpha$NeuSAc(2-3)$\beta$DGalp(1-4) $\beta$DGlcp(1-1)Cer); TNF receptor superfamily member 17 (TNFRSF17, BCMA); Tn antigen ((Tn Ag) or (GalNAcu-Ser/Thr)); prostate-specific membrane antigen (PSMA); Receptor tyrosine kinase-like orphan receptor 1 (RORI); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y)antigen; CD24; Platelet-derived growth factor receptor beta (PDGFR-beta); Stage-specificembryonic antigen-4 (SSEA-4); CD20; delta like 3 (DLL3); Folate receptor alpha; Receptor tyrosine-protein kinase, ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2(EphA2); Fucosyl GM1; sialyl Lewis adhesion molecule (sLe); transglutaminase 5 (TGS5); high molecular weight-melanomaassociatedantigen (HMW-MAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CX-ORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS 1E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1(CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CDS, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

In some embodiments, the antigen binding domain binds to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP; CT23, OY-TES-1, SP32; NCBI Gene ID: 84519), alpha fetoprotein (AFP; AFPD, FETA, HPAFP; NCBI Gene ID: 174); A-kinase anchoring protein 4 (AKAP4; AKAP 82, AKAP-4, AKAP82, CT99, FSC1, HI, PRKA4, hAKAP82, p82; NCBI Gene ID: 8852), ATPase family AAA domain containing 2 (ATAD2; ANCCA, CT137, PRO2000; NCBI Gene ID: 29028), kinetochore scaffold 1 (KNL1; AF15Q14, CASCS, CT29, D40, MCPH4, PPP1R55, Spc7, hKNL-1, hSpc105; NCBI Gene ID: 57082), centrosomal protein 55 (CEP55; C10orf3, CT111, MARCH, URCC6; NCBI Gene ID: 55165), cancer/testis antigen 1A (CTAG1A; ESO1; CT6.1; LAGE-2; LAGE2A; NY-ESO-1; NCBI Gene ID: 246100), cancer/testis antigen 1B (CTAG1B; CT6.1, CTAG, CTAG1, ESO1, LAGE-2, LAGE2B, NY-ESO-1; NCBI Gene ID: 1485), cancer/testis antigen 2 (CTAG2; CAMEL, CT2, CT6.2, CT6.2a, CT6.2b, ESO2, LAGE-1, LAGE2B; NCBI Gene ID: 30848), CCCTC-binding factor like (CTCFL; BORIS, CT27, CTCF-T, HMGB1L1, dJ579F20.2; NCBI Gene ID: 140690), catenin alpha 2 (CTNNA2; CAP-R, CAPR, CDCBM9, CT114, CTNR; NCBI Gene ID: 1496), cancer/testis antigen 83 (CT83; CXorf61, KK-LC-1, KKLC1; NCBI Gene ID: 203413), cyclin A1 (CCNA1; CT146; NCBI Gene ID: 8900), DEAD-box helicase 43 (DDX43; CT13, HAGE; NCBI Gene ID: 55510), developmental pluripotency associated 2 (DPPA2; CT100, ECAT15-2, PESCRG1; NCBI Gene ID: 151871), fetal and adult testis expressed 1 (FATE1; CT43, FATE; NCBI Gene ID: 89885), FMR1 neighbor (FMR1NB; CT37, NY-SAR-35, NYSAR35; NCBI Gene ID: 158521), HORMA domain containing 1 (HORMAD1; CT46, NOHMA; NCBI Gene ID: 84072), insulin like growth factor 2 mRNA binding protein 3 (IGF2BP3; CT98, IMP-3, IMP3, KOC, KOC1, VICKZ3; NCBI Gene ID: 10643), leucine zipper protein 4 (LUZP4; CT-28, CT-8, CT28, HOM-TES-85; NCBI Gene ID: 51213), lymphocyte antigen 6 family member K (LY6K; CT97, HSJ001348, URLC10, ly-6K; NCBI Gene ID: 54742), maelstrom spermatogenic transposon silencer (MAEL; CT128, SPATA35; NCBI Gene ID: 84944), MAGE family member A1 (MAGEA1; CT1.1, MAGE1; NCBI Gene ID: 4100); MAGE family member A3 (MAGEA3; CT1.3, HIP8, HYPD, MAGE3, MAGEA6; NCBI Gene ID: 4102); MAGE family member A4 (MAGEA4; CT1.4, MAGE-41, MAGE-X2, MAGE4, MAGE4A, MAGE4B; NCBI Gene ID: 4103); MAGE family member A11 (MAGEA11; CT1.11, MAGE-11, MAGE11, MAGEA-11; NCBI Gene ID: 4110); MAGE family member C1 (MAGEC1; CT7, CT7.1; NCBI Gene ID: 9947); MAGE family member C2 (MAGEC2; CT10, HCA587, MAGEE1; NCBI Gene ID: 51438); MAGE family member D1 (MAGED1; DLXIN-1, NRAGE; NCBI Gene ID: 9500); MAGE family member D2 (MAGED2; 11B6, BARTSS, BCG-1, BCG1, HCA10, MAGE-D2; NCBI Gene ID: 10916), kinesin family member 20B (KIF20B; CT90, KRMP1, MPHOSPH1, MPP-1, MPP1; NCBI Gene ID: 9585), NUF2 component of NDC80 kinetochore complex (NUF2; CDCA1, CT106, NUF2R; NCBI Gene ID: 83540), nuclear RNA export factor 2 (NXF2; CT39, TAPL-2, TCP11X2; NCBI Gene ID: 56001), PAS domain containing repressor 1 (PASD1; CT63, CT64, OXTES1; NCBI Gene ID: 139135), PDZ binding kinase (PBK; CT84, HEL164, Nori-3, SPK, TOPK; NCBI Gene ID: 55872), piwi like RNA-mediated gene silencing 2 (PIWIL2; CT80, HILI, PIWIL1L, mili; NCBI Gene ID: 55124), preferentially expressed antigen in melanoma (PRAME; CT130, MAPE, OIP-4, OIP4; NCBI Gene ID: 23532), sperm associated antigen 9 (SPAG9; CT89, HLC-6, HLC4, HLC6, JIP-4, JIP4, JLP, PNET, PIG6; NCBI Gene ID: 9043), sperm protein associated with the nucleus, X-linked, family member A1 (SPANXA1; CT11.1, CT11.3, NAP-X, SPAN-X, SPAN-Xa, SPAN-Xb, SPANX, SPANX-A; NCBI Gene ID: 30014), SPANX family member A2 (SPANXA2; CT11.1, CT11.3, SPANX, SPANX-A, SPANX-C, SPANXA, SPANXC; NCBI Gene ID: 728712), SPANX family member C (SPANXC; CT11.3, CTp11, SPANX-C, SPANX-E, SPANXE; NCBI Gene ID: 64663), SPANX family member D (SPANXD; CT11.3, CT11.4, SPANX-C, SPANX-D, SPANX-E, SPANXC, SPANXE, dJ171K16.1; NCBI Gene ID: 64648), SSX family member 1 (SSX1; CT5.1, SSRC; NCBI Gene ID: 6756), SSX family member 2 (SSX2; CT5.2, CT5.2A, HD21, HOM-MEL-40, SSX; NCBI Gene ID: 6757), synaptonemal complex protein 3 (SYCP3; COR1, RPRGL4, SCP3, SPGF4; NCBI Gene ID: 50511), testis expressed 14, intercellular bridge forming factor (TEX14; CT113, SPGF23; NCBI Gene ID: 56155), transcription factor Dp family member 3 (TFDP3; CT30, DP4, HCA661; NCBI Gene ID: 51270), serine protease 50 (PRSS50; CT20, TSP50; NCBI Gene ID: 29122), TTK protein kinase (TTK; CT96, ESK, MPH1, MPS1, MPS1L1, PYT; NCBI Gene ID: 7272) and zinc finger protein 165 (ZNF165; CT53, LD65, ZSCAN7; NCBI Gene ID: 7718). T cell receptors (TCRs) and TCR-like antibodies that bind to an epitope of a cancer testis antigen presented in a major histocompatibility complex (MHC) molecule are known in the art and can be used in the herein described heterodimers. Cancer testis antigens associated with neoplasia are summarized, e.g., in Gibbs, et al., *Trends Cancer* 2018 October; 4(10):701-712 and the CT database website at cta.lncc.br/index.php. Illustrative TCRs and TCR-like antibodies that bind to an epitope of NY-ESO-1 presented in an MHC are described, e.g., in Stewart-Jones, et al., *Proc Natl Acad Sci USA*. 2009 Apr. 7; 106(14):5784-8; WO2005113595, WO2006031221, WO2010106431, WO2016177339, WO2016210365, WO2017044661, WO2017076308, WO2017109496, WO2018132739, WO2019084538, WO2019162043, WO2020086158 and WO2020086647. Illustrative TCRs and TCR-like antibodies that bind to an epitope of PRAME presented in an MEW are described, e.g., in WO2011062634, WO2016142783, WO2016191246, WO2018172533, WO2018234319 and WO2019109821. Illustrative TCRs and TCR-like antibodies that bind to an epitope of a MAGE variant presented in an MEW are described, e.g., in WO2007032255, WO2012054825, WO2013039889, WO2013041865, WO2014118236, WO2016055785, WO2017174822, WO2017174823, WO2017174824, WO2017175006, WO2018097951, WO2018170338, WO2018225732 and WO2019204683. Illustrative TCRs and TCR-like antibodies that bind to an epitope of alpha fetoprotein (AFP) presented in an MHC are described, e.g., in WO2015011450. Illustrative TCRs and TCR-like antibodies that bind to an epitope of SSX2 presented in an MEW are described, e.g., in WO2020063488. Illustrative TCRs and TCR-like antibodies that bind to an epitope of KK-LC-1 (CT83) presented in an MEW are described, e.g., in WO2017189254.

Examples of cell therapies include without limitation: Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCRS-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502,CMD-601, CMD-602, CSG-005.

Additional agents for targeting tumors include without limitation:

Alpha-fetoprotein, such as ET-1402, and AFP-TCR;
Anthrax toxin receptor 1, such as anti-TEM8 CAR T-cell therapy;
TNF receptor superfamily member 17 (TNFRSF17, BCMA), such as bb-2121, UCART-BCMA, ET-140, KITE-585, MCM-998, LCAR-B38M, CART-BCMA, SEA-BCMA, BB212, UCART-BCMA, ET-140, P-BCMA-101, AUTO-2 (APRIL-CAR);
Anti-CLL-1 antibodies, such as KITE-796;
Anti-PD-L1-CAR tank cell therapy, such as KD-045;
B7 homolog 6, such as CAR-NKp30 and CAR-B7H6;
B-lymphocyte antigen CD19, such as TBI-1501, CTL-119 huCART-19 T cells, JCAR-015 U.S. Pat. No. 7,446,190, JCAR-014, JCAR-017, (WO2016196388, WO2016033570, WO2015157386), axicabtagene ciloleucel (KTE-C19, Yescarta®), KTE-X19, U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T, TC-110;
B-lymphocyte antigen CD20, such as ACTR707 ATTCK-20;
B-lymphocyte antigen CD19/B-lymphocyte antigen 22, such as TC-310;
B-lymphocyte antigen 22 cell adhesion, such as UCART-22, JCAR-018 WO2016090190;
NY-ESO-1, such as GSK-3377794, TBI-1301;
Carbonic anhydrase, such as DC-Ad-GMCAIX;
Caspase 9 suicide gene, such as CaspaCIDe DLI, BPX-501;
CCR5, such as SB-728;
CDw123, such as MB-102, UCART-123;
CD4, such as ICG-122;
CD33, such as CIK-CAR.CD33;
CD38, such as T-007, UCART-38;
CD40 ligand, such as BPX-201;
CEACAM protein 5 modulators, such as MG7-CART;
Claudin 6, such as CSG-002;
EBV targeted, such as CMD-003;
MUC16EGFR, such as autologous 4H11-28z/fIL-12/EFGRt T cell;
Endonuclease, such as PGN-514, PGN-201;
Epstein-Barr virus specific T-lymphocytes, such as TT-10;
Erbb2, such as CST-102, CIDeCAR;
Ganglioside (GD2), such as 4SCAR-GD2;
folate hydrolase 1 (FOLH1, Glutamate carboxypeptidase II, PSMA; NCBI Gene ID: 2346), such as CIK-CAR.PSMA, CART-PSMA-TGFβRDN, P-PSMA-101;
Glypican-3(GPC3), such as TT-16, GLYCAR;
Hemoglobin, such as PGN-236;
Hepatocyte growth factor receptor, such as anti-cMet RNA CAR T;
Human papillomavirus E7 protein, such as KITE-439;
Immunoglobulin gamma Fc receptor III, such as ACTR087;
IL-12, such as DC-RTS-IL-12;
IL-12 agonist/mucin 16, such as JCAR-020;
IL-13 alpha 2, such as MB-101;
IL-2, such as CST-101;
K-Ras GTPase, such as anti-KRAS G12V mTCR cell therapy;
Neural cell adhesion molecule L1 L1CAM (CD171), such as JCAR-023;
Latent membrane protein 1/Latent membrane protein 2, such as Ad5f35-LMPd1-2-transduced autologous dendritic cells;
Melanoma associated antigen 10, such as MAGE-A10C796T MAGE-A10 TCR;
Melanoma associated antigen 3/Melanoma associated antigen 6 (MAGE A3/A6) such as KITE-718;
Mesothelin, such as CSG-MESO, TC-210;
NKG2D, such as NKR-2;
Ntrkr1 tyrosine kinase receptor, such as JCAR-024;
PRAMET cell receptor, such as BPX-701;
T-lymphocyte, such as TT-12;

Tumor infiltrating lymphocytes, such as LN-144, LN-145; and/or

Wilms tumor protein, such as JTCR-016, WT1-CTL.

In various embodiments, the FLT3L-Fc fusion proteins, homodimers, heterodimers, polynucleotides, vectors, lipoplexes, such as LNPs, and/or pharmaceutical compositions, as described herein, are combined with a gene or cell therapy regimen that can target a cell infected with a virus (e.g., HIV). A gene or cell therapy that can be combined with an agent disclosed herein includes without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Illustrative examples of a cell therapy that can be combined with an agent disclosed herein include LB-1903, ENOB-HV-01, GOVX-B01, and SupT1 cell-based therapy. Illustrative examples of a dendritic cell therapy that can be combined with an agent disclosed herein include AGS-004. An illustrative example of a CCR5 gene editing agent that can be used in combination with an agent disclosed herein is SB-728T. An illustrative example of a CCR5 gene inhibitor that can be used in combination with an agent disclosed herein is Cal-1. In some embodiments, C34-CCR5/C34-CXCR4 expressing CD4-positive T-cells are co-administered with an agent disclosed herein. In some embodiments, the agents described herein are co-administered with AGT-103-transduced autologous T-cell therapy or AAV-eCD4-Ig gene therapy.

In various embodiments, the FLT3L-Fc fusion proteins, homodimers, heterodimers, polynucleotides, vectors, lipoplexes, such as LNPs, and/or pharmaceutical compositions, as described herein, can be co-administered with a population of immune effector cells engineered to express a chimeric antigen receptor (CAR), wherein the CAR comprises an HIV antigen binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include convertibleCAR-T, VC-CAR-T, CMV-N6-CART, anti-CD4 CART-cell therapy, CD4 CAR+C34-CXCR4+CCR5 ZFN T-cells, autologous hematopoietic stem cells genetically engineered to express a CD4 CAR and the C46 peptide.

In various embodiments, the FLT3L-Fc fusion proteins, homodimers, heterodimers, polynucleotides, vectors, lipoplexes, such as LNPs, and/or pharmaceutical compositions, as described herein, are combined with a population of TCR-T-cells. TCR-T-cells are engineered to target HIV derived peptides present on the surface of virus-infected cells, for example ImmTAV.

In various embodiments, the FLT3L-Fc fusion proteins, homodimers, heterodimers, polynucleotides, vectors, lipoplexes, such as LNPs, and/or pharmaceutical compositions, as described herein, are combined with a population of B cells genetically modified to express broadly neutralizing antibodies, such as 3BNC117 (Hartweger et al., J. Exp. Med. 2019, 1301; Moffett et al., Sci. Immunol. 4, eaax0644 (2019) 17 May 2019).

Gene Editors

In various embodiments, the FLT3L-Fc fusion proteins, homodimers, heterodimers, polynucleotides, vectors, lipoplexes, such as LNPs, and/or pharmaceutical compositions, as described herein, are combined with gene editor. Illustrative gene editing system that can be co-administered include without limitation a CRISPR/Cas9 system, a zinc finger nuclease system, a TALEN system, a homing endonucleases system (e.g., an ARCUS), and a homing meganuclease system.

In some embodiments, the FLT3L-Fc fusion proteins, homodimers, heterodimers, polynucleotides, vectors, lipoplexes, such as LNPs, and/or pharmaceutical compositions, as described herein described herein are combined with an HIV targeted gene editor. An illustrative HIV targeted gene editor includes without limitation the CRISPR/Cas9 system EBT-101.

HIV Therapeutic Agents

In various embodiments, the FLT3L-Fc fusion proteins, homodimers, heterodimers, polynucleotides, vectors, lipoplexes, such as LNPs, and/or pharmaceutical compositions, as described herein, are combined with an HIV therapeutic agent.

In some embodiments, the HIV therapeutic agents that can be combined with an agent disclosed herein include an HIV protease inhibitor. Illustrative HIV protease inhibitors that can be co-administered include without limitation amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, AEBL-2, DG-17, GS-1156, TMB-657 (PPL-100), T-169, BL-008, MK-8122, TMB-607, GRL-02031, and TMC-310911.

In some embodiments, the HIV therapeutic agents that can be combined with an agent disclosed herein include an HIV ribonuclease H inhibitor. Examples of HIV ribonuclease H inhibitors that can be combined with an agent of this disclosure include NSC-727447.

In some embodiments, the HIV therapeutic agents that can be combined with an agent disclosed herein include an HIV Nef inhibitor. Examples of HIV Nef inhibitors that can be combined with an agent of this disclosure include FP-1.

In some embodiments, the HIV therapeutic agents that can be combined with an agent disclosed herein include a reverse transcriptase inhibitor. In some embodiments the reverse transcriptase inhibitor is a non-nucleoside/non-nucleotide inhibitor. Illustrative examples of non-nucleoside/non-nucleotide inhibitors that can be co-administered include without limitation dapivirine, delavirdine, delavirdine mesylate, doravirine, efavirenz, etravirine, lentinan, nevirapine, rilpivirine, ACC-007, ACC-008, AIC-292, F-18, KM-023, PC-1005, VM-1500A-LAI, PF-3450074, elsulfavirine (sustained release oral, HIV infection), elsulfavirine (long-acting injectable nanosuspension, HIV infection), and elsulfavirine (VM-1500). In some embodiments, the non-nucleoside/non-nucleotide inhibitor is selected from nevirapine, delavirdine, efavirenz, etravirine, and rilpivirine. In some embodiments the reverse transcriptase inhibitor that can be combined with an agent of this disclosure is a nucleoside or nucleotide inhibitor. Illustrative examples of nucleoside or nucleotide inhibitors of reverse transcriptase inhibitor that can be co-administered include without limitation adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir octadecyloxyethyl ester (AGX-1009), tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8591, MK-8583, VM-2500 and KP-1461. In some embodiments the nucleoside or nucleotide inhibitors of reverse transcriptase inhibitor is selected from zidovudine, didanosine, zalcitabine, stavudine, lamivudine, abacavir, and emtricitabine.

In some embodiments, the HIV therapeutic agents that can be combined with an agent disclosed herein include an HIV integrase inhibitor. In some embodiments, the HIV integrase inhibitor that can be combined with an agent of this disclosure is selected from the group consisting of: elvitegravir, elvitegravir (extended-release microcapsules), curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, PEGylated raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, MK-0536, NSC-310217, NSC-371056, NSC-48240, NSC-642710, NSC-699171, NSC-699172, NSC-699173, NSC-699174, stilbenedisulfonic acid, T-169, STP-0404, VM-3500 and cabotegravir. In some embodiments, the HIV integrase inhibitor that can be combined with an agent of this disclosure is an HIV non-catalytic site, or allosteric, integrase inhibitor (NCINI). Illustrative examples of such HIV non-catalytic site, or allosteric, integrase inhibitors (NCINI) include CX-05045, CX-05168, and CX-14442.

In some embodiments, the HIV therapeutic agents that can be combined with an agent disclosed herein include HIV an entry inhibitor. In some embodiments, the entry inhibitor is an HBV entry inhibitor (e.g., Myrcludex B). Illustrative examples of entry inhibitors that can be combined with an agent of this disclosure include without limitation AAR-501, LBT-5001, cenicriviroc, a CCR5 inhibitor, a gp41 inhibitor, a CD4 attachment inhibitor, a gp120 inhibitor, a gp160 inhibitor a, and a CXCR4 inhibitor.

In some embodiments the entry inhibitor that can be combined with an agent of this disclosure is a CCR5 inhibitor selected from the group consisting of: aplaviroc, vicriviroc, maraviroc, maraviroc (long-acting injectable nanoemulsion), cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, thioraviroc and vMIP (Haimipu).

In some embodiments the entry inhibitor that can be combined with an agent of this disclosure is a gp41 inhibitor selected from the group consisting of: albuvirtide, enfuvirtide, griffithsin (gp41/gp120/gp160 inhibitor), BMS-986197, enfuvirtide biobetter, enfuvirtide biosimilar, HIV-1 fusion inhibitors (P26-Bapc), ITV-1, ITV-2, ITV-3, ITV-4, CPT-31, Cl3hmAb, PIE-12 trimer and sifuvirtide.

In some embodiments the entry inhibitor that can be combined with an agent of this disclosure is a CD4 attachment inhibitor selected from ibalizumab and a CADA analog.

In some embodiments the entry inhibitor that can be combined with an agent of this disclosure is a gp120 inhibitor selected from anti-HIV microbicide, Radha-108 (receptol) 3B3-PE38, BanLec, bentonite-based nanomedicine, fostemsavir tromethamine, IQP-0831, VVX-004, and BMS-663068.

In some embodiments the entry inhibitor that can be co-administered is a gp160 inhibitor such as fangchinoline.

In some embodiments the entry inhibitor that can be combined with an agent of this disclosure is a CXCR4 inhibitor selected from plerixafor, ALT-1188, N15 peptide, and vMIP (Haimipu).

In some embodiments the entry inhibitor that can be combined with an agent of this disclosure is selected from docosanol, enfuvirtide, maraviroc, palivizumab, respiratory syncytial virus immune globulin, intravenous [RSV-IGIV], varicella-zoster immunoglobulin [VariZIG], and varicella-zoster immune globulin [VZIG]).

In some embodiments, the HIV therapeutic agents that can be combined with an agent disclosed herein include an HIV maturation inhibitor. In some embodiments, the HIV maturation inhibitor that can be co-administered is selected from BMS-955176, GSK-3640254 and GSK-2838232.

In some embodiments, the HIV therapeutic agents that can be combined with an agent disclosed herein include a latency reversing agent. Illustrative examples of latency reversing agent that can be combined with an agent of this disclosure include without limitation toll-like receptor (TLR) agonists (including TLR7 agonists, e.g., GS-9620 (vesatolimod), vesatolimod analogs), histone deacetylase (HDAC) inhibitors, proteasome inhibitors such as velcade, protein kinase C (PKC) activators, Smyd2 inhibitors, BET-bromodomain 4 (BRD4) inhibitors, ionomycin, IAP antagonists (inhibitor of apoptosis proteins, such as APG-1387, li3W-242), SMAC mimetics (including TL32711, LCL161, GDC-0917, HGS1029, AT-406, Debio-1143), PMA, SAHA (suberanilohydroxamic acid, or suberoyl, anilide, and hydroxamic acid), NIZ-985, IL-15 modulating antibodies (including IL-15, IL-15 fusion proteins and IL-15 receptor agonists), JQ1, disulfiram, amphotericin B, and ubiquitin inhibitors such as largazole analogs, APH-0812, and GSK-343. Examples of PKC activators that can be co-administered include without limitation indolactam, prostratin, ingenol B, and DAG-lactones.

In some embodiments, the HIV therapeutic agents that can be combined with an agent disclosed herein include a capsid inhibitor. Illustrative examples of capsid inhibitors that can be combined with an agent of this disclosure include without limitation capsid polymerization inhibitors, capsid disrupting compounds, HIV nucleocapsid p7 (NCp7) inhibitors (e.g., azodicarbonamide), HIV p24 capsid protein inhibitors (e.g., GS-6207, GS-CA1, AVI-621, AVI-101, AVI-201, AVI-301, AVI-CAN1-15 series, and PF-3450074), and compounds described in the International Patent Publication No. WO2019/087016.

In some embodiments, the HIV therapeutic agents that can be combined with an agent disclosed herein include an HIV targeting antibody. HIV targeting antibodies that can be combined with an agent of this disclosure include bispecific antibodies, trispecific antibodies, and "antibody-like" therapeutic proteins. In some embodiments, the HIV targeting antibodies that can be co-administered with an agent of this disclosrue are selected from DARTs®, DUOBODIES®, BITES®, XmAbs®, TandAbs®, Fab derivatives, bNAbs (broadly neutralizing HIV-1 antibodies), TMB-360, antibodies targeting HIV gp120 or gp41, antibody-recruiting molecules targeting HIV, anti-CD63 monoclonal antibodies, anti-GB virus C antibodies, anti-GP120/CD4, gp120 bispecific monoclonal antibodies, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), PGT121.414.LS, ibalizumab, Immuglo, MB-66, and VRC-HIVMAB091-00-AB.

In some embodiments the HIV targeting antibody that can be combined with an agent of this disclosure is a bNAb, including without limitation those described in U.S. Pat. Nos. 8,673,307, 9,493,549, and 9,783,594, and in International Patent Publication Nos. WO2014/063059, WO2012/158948, WO2015/117008, WO/2016/014484, and WO2017/09622. In some embodiments the bNAb that can be combined with an agent of this disclosure is selected from 12A12, 12A21, NIH45-46, bANC131, 8ANC134, IB2530, INC9, 8ANC195. 8ANC196, 10-259, 10-303, 10-410, 10-847, 10-996, 10-1074, 10-1121, 10-1130, 10-1146, 10-1341, 10-1369, and 10-1074GM. Additional examples of bNAbs that can be co-administered with an agent of this disclosure include those described in Klein et al., Nature, 492(7427): 118-22 (2012), Horwitz et al., Proc Natl Acad Sci USA, 110(41): 16538-43 (2013), Scheid, et al., Science, 333: 1633-1637 (2011), Scheid, et al., Nature, 458:636-640 (2009), Eroshkin et al, Nucleic Acids Res., 42 (Database issue):D1 133-9 (2014), Mascola et al., Immunol Rev., 254(0:225-44 (2013), such as 2F5, 4E10, M66.6, CAP206-CH12, 10E81 (all of which bind the MPER of gp41); PG9, PG16, CH01-04 (all of which bind V1V2-glycan), 2G12 (which binds to outer domain glycan); b12, HJ16, CH103-106, VRC01-03, VRC-PG04, 04b, VRC-CH30-34, 3BNC62, 3BNC89, 3BNC91, 3BNC95, 3BNC104, 3BNC176, and 8ANC131 (all of which bind to the CD4 binding site). Additional illustrative examples of bNAbs that can be co-administered with an agent of this disclosure are described, e.g., in U.S. Pat. Nos. 8,673,307; 9,493,549; 9,783,594; and in International Patent Publication Nos. WO 2012/154312; WO2012/158948; WO 2013/086533; WO 2013/142324; WO2014/063059; WO 2014/089152, WO 2015/048462; WO 2015/103549; WO 2015/117008; WO2016/014484; WO 2016/154003; WO 2016/196975; WO 2016/149710; WO2017/096221; WO 2017/133639; and WO 2017/133640. Additional examples of bNAbs that can be combined with an agent of this disclosure are described, e.g., in Sajadi, et al., Cell. (2018) 173(7):1783-1795; Sajadi, et al., J Infect Dis. (2016) 213(1):156-64; Klein et al., Nature, 492(7427): 118-22 (2012), Horwitz et al., Proc Natl Acad Sci USA, 110(41): 16538-43 (2013), Scheid, et al., Science, 333: 1633-1637 (2011), Scheid, et al., Nature, 458:636-640 (2009), Eroshkin et al, Nucleic Acids Res., 42 (Database issue):D1 133-9 (2014), Mascola et al., Immunol Rev., 254(1):225-44 (2013), such as 2F5, 4E10, M66.6, CAP206-CH12, 10E8, 10E8v4, 10E8-5R-100cF, DH511.11P, 7b2, and LN01 (all of which bind the MPER of gp41).

In some embodiments, the HIV targeting antibody that can be combined with an agent of this disclosure is selected from the group consisting of: UB-421, BF520.1, CHO1, CH59, C2F5, C4E10, C2F5+C2G12+C4E10, 3BNC117, 3BNC117-LS, 3BNC60, DH270.1, DH270.6, D1D2, 10-1074-LS, Cl3hmAb, GS-9722 (elipovimab), DH411-2, BG18, GS-9721, PGT145, PGT121, PGT-121.60, PGT-121.66, PGT122, PGT-123, PGT-124, PGT-125, PGT-126, PGT-151, PGT-130, PGT-133, PGT-134, PGT-135, PGT-128, PGT-136, PGT-137, PGT-138, PGT-139, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, MDX010 (ipilimumab), VRC01, VRC-01-LS, A32, 7B2, 10E8, VRC-07-523, VRC07-523LS, VRC24, VRC41.01, 10E8VLS, 3810109, 10E8v4, IMC-HIV, iMabm36, eCD4-Ig, IOMA, CAP256-VRC26.25, DRVIA7, VRC-HIVMAB080-00-AB, VRC-HIVMAB060-00-AB, P2G12, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and VRC38.01, PGT-151, CAP248-2B, 35022, ACS202, VRC34 and VRC34.01, 10E8, 10E8v4, 10E8-5R-100cF, 4E10, DH511.11P, 2F5, 7b2, and LN01.

In some embodiments, the HIV targeting antibody that can be co-administered with an agent of this disclosure is a bispecific or trispecific antibody such as MGD014, B12BiTe, BiIA-SG, TMB-bispecific, SAR-441236, VRC-01/PGDM-1400/10E8v4, 10E8.4/iMab, or 10E8v4/PGT121-VRC01.

In some embodiments, an agent of this disclosure can be combined with in vivo delivered bNAbs such as AAV8-VRC07; mRNA encoding anti-HIV antibody VRC01; or engineered B-cells encoding 3BNC117 (Hartweger et al, J. Exp. Med. 2019, 1301).

In some embodiments, the HIV therapeutic agents that can be combined with an agent disclosed herein include an HIV vaccine. Illustrative examples of HIV vaccines that can be combined with an agent of this disclosure include without limitation peptide vaccines, recombinant subunit protein vaccines, live vector vaccines, DNA vaccines, HIV MAG DNA vaccine, CD4-derived peptide vaccines, vaccine combinations, adenoviral vector vaccines (an adenoviral vector such as Ad5, Ad26 or Ad35), simian adenovirus (chimpanzee, gorilla, rhesus i.e., rhAd), adeno-associated virus vector vaccines, Chimpanzee adenoviral vaccines (e.g., ChAdOX1, ChAd68, ChAd3, ChAd63, ChAd83, ChAd155, ChAd157, Pan5, Pan6, Pan7, Pan9), Coxsackieviruses based vaccines, enteric virus based vaccines, Gorilla adenovirus vaccines, lentiviral vector based vaccine, arenavirus vaccines (such as LCMV, Pichinde), bi-segmented or tri-segmented arenavirus based vaccine, trimer-based HIV-1 vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, venezuelan equine encephalitis virus and sindbis virus; (see Lauer, Clinical and Vaccine Immunology, 2017, DOI: 10.1128/CVI.00298-16); a lipoplex, such as an LNP, formulated mRNA based therapeutic vaccines; and LNP-formulated self-replicating RNA/self-amplifying RNA vaccines.

Additional illustrative examples of HIV vaccines that can be combined with an agent of this disclosure include without limitation anti-CD40.Env-gp140 vaccine, Ad4-EnvC150, BG505 SOSIP.664 gp140 adjuvanted vaccine, BG505 SOSIP.GT1.1 gp140 adjuvanted vaccine, Chimigen HIV vaccine, ConM SOSIP.v7 gp140, rgp120 (AIDSVAX), ALVAC HIV (vCP1521)/AIDSVAX B/E (gp120) (RV144), monomeric gp120 HIV-1 subtype C vaccine, MPER-656 liposome subunit vaccine, Remune, ITV-1, Contre Vir, Ad5-ENVA-48, DCVax-001 (CDX-2401), Vacc-4x, Vacc-05, VAC-3 S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/ VSSP ISA-51, poly-ICLC adjuvanted vaccines, TatImmune, GTU-multiHIV (FIT-06), ChAdV63.HIVconsv, gp140 [delta]V2.TV1+MF-59, rVSVIN HIV-1 gag vaccine, SeV-EnvF, SeV-Gag vaccine, AT-20, DNK-4, ad35-Grin/ENV, TBC-M4, HIVAX, HIVAX-2, N123-VRC-34.01 inducing epitope-based HIV vaccine, NYVAC-HIV-PT1, NYVAC-HIV-PT4, DNA-HIV-PT123, rAAV1-PG9DP, GOVX-B11, GOVX-B21, GOVX-055, TVI-HIV-1, Ad-4 (Ad4-env Clade C+Ad4-mGag), Paxvax, EN41-UGR7C, EN41-FPA2, ENOB-HV-11, PreVaxTat, AE-H, MYM-V101, CombiHIV-vac, ADVAX, MYM-V201, MVA-CMDR, MagaVax, DNA-Ad5 gag/pol/nef/nev (HVTN505), MVATG-17401, ETV-01, CDX-1401, DNA and Sev vectors vaccine expressing SCaVII, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, VIR-1111, IHV-001, and virus-like particle vaccines such as pseudovirion vaccine, CombiV-ICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, HIV-1 iglb12 neutralizing VRC-01 antibody-stimulating anti-CD4 vaccine, arenavirus vector-based vaccines (Vaxwave, TheraT), MVA-BN HIV-1 vaccine regimen, UBI HIV gp120, mRNA based prophylactic vaccines, VPI-211, or TBL-1203HI.

In some embodiments, the HIV therapeutic agents that can be combined with an agent disclosed herein include a birth control or contraceptive regimen. Illustrative examples of birth control or contraceptive regimens that can be combined with an agent of this disclosure include without limitation cyproterone acetate, desogestrel, dienogest, drospirenone, estradiol valerate, ethinyl estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

HBV Therapeutic Agents

In various embodiments, the FLT3L-Fc fusion proteins, homodimers, heterodimers, polynucleotides, vectors, lipoplexes, such as LNPs, and/or pharmaceutical compositions, as described herein, are combined with an HBV therapeutic agent.

In some embodiments, the HBV therapeutic agents that can be combined with an agent disclosed herein are selected from alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, NCO-48 Fumarate, TCM-800B, reduced glutathione, RO-6864018, RG-7834, QL-007sofosbuvir, ledipasvir, UB-551, PA-1010, HPN-BV1, STSG-0002, and ZH-2N, and the compounds disclosed in US20150210682, (Roche), US 2016/0122344 (Roche), WO2015173164 (Roche), WO2016023877 (Roche), US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

In some embodiments, the HBV therapeutic agents that can be combined with an agent disclosed herein are selected from include an HBV vaccine. In some embodiments, the HBV vaccine is selected from HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2 (HepTcell), NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), hepatitis B therapeutic DNA vaccine, AdTG-17909, AdTG-17910, AdTG-18202, ChronVac-B, TG-1050, VVX-001, GSK-3528869A (ChAd155-hli-HBV+MVA-HBV+Hbc-HBs/ASO1B-4), VBI-2601, VTP-300 (ChAdOx1-SIi-HBV-CPmut-TPA-Ssh prime and MVA-SIi-HBV-CPmut-TPA-Ssh boost), MVA-BN, AVA-2100, HBV-ADV311, YS-HBV-002, and Lm HBV. HBV Arenavirus vaccines are described, e.g., in WO2017076988 and WO2017198726.

In some embodiments, the HBV therapeutic agents that can be combined with an agent disclosed herein include an HBV polymerase inhibitor. In some embodiments, the HBV polymerase inhibitor is selected from adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, ATI-2173, SNC-019754, FMCA, AGX-1009, AR-II-04-26, HIP-1302, tenofovir disoproxil aspartate, tenofovir disoproxil orotate, and HS-10234.

In some embodiments, the HBV therapeutic agents that can be combined with an agent disclosed herein include an immunomodulator. In some embodiments, the immunomodulator is selected from rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440, WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785, RG-7854, RO-6871765, AIC-649, and IR-103.

In some embodiments, the HBV therapeutic agents that can be combined with an agent disclosed herein include an interferon alpha receptor ligand. In some embodiments the interferon alpha receptor ligand is selected from interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1(HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), PEG-IFN-alpha, rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

In some embodiments, the HBV therapeutic agents that can be combined with an agent disclosed herein include a hyaluronidase inhibitor. In some embodiments the hyaluronidase inhibitor is astodrimer.

In some embodiments, the HBV therapeutic agents that can be combined with an agent disclosed herein include a Hepatitis B Surface Antigen (HBsAg) inhibitor. In some embodiments the HBsAg inhibitor is selected from AK-074, HBF-0259, PBHBV-001, PBHBV-2-15, PBHBV-2-1, REP-9AC, REP-9C, REP-9, REP-2139, REP-2139-Ca, REP-2055, REP-2163, REP-2165, REP-2053, REP-2031, REP-006, and REP-9AC'. In some embodiments, the HBsAg inhibitor is an HBsAg secretion inhibitor such as BM601, GST-HG-131, AB-452.

In some embodiments, the HBV therapeutic agents that can be combined with an agent disclosed herein include a cyclophilin inhibitor. In some embodiments, the cyclophilin inhibitor is selected from CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

In some embodiments, the HBV therapeutic agents that can be combined with an agent disclosed herein include an antisense oligonucleotide targeting viral mRNA. In some embodiments, the antisense oligonucleotide is selected from ISIS-HBVRx, IONIS-HBVRx, IONIS-HBV-LRx, IONIS-GSK6-LRx, GSK-3389404, and RG-6004.

In some embodiments, the HBV therapeutic agents that can be combined with an agent disclosed herein include a short interfering RNA (siRNA) or DNA-directed RNA interference (ddRNAi). In some embodiments, the siRNA is selected from TKM-HBV (TKM-HepB), ALN-HBV (e.g., ALN-HBV02), SR-008, HepB-nRNA, ARC-520, ARC-521, ARB-1740, ARB-1467, AB-729, DCR-HBVS, RG-6084 (PD-L1), RG-6217, ALN-HBV-02, JNJ-3989 (ARO-HBV), STSG-0002, ALG-010133, ALG-ASO, LUNAR-HBV and DCR-HBVS (DCR-5219). An illustrative example of ddRNAi is BB-HB-331.

In some embodiments, the HBV therapeutic agents that can be combined with an agent disclosed herein include an endonuclease modulator (e.g., PGN-514).

In some embodiments, the HBV therapeutic agents that can be combined with an agent disclosed herein include a ribonucleotide reductase inhibitor (e.g., Trimidox).

In some embodiments, the HBV therapeutic agents that can be combined with an agent disclosed herein include a non-nucleoside reverse transcriptase inhibitor (NNRTI). In some embodiments, the NNRTI is selected from the compounds disclosed in WO2018118826 (Merck), WO2018080903 (Merck), WO2018119013 (Merck), WO2017100108 (Idenix), WO2017027434 (Merck), WO2017007701 (Merck), and WO2008005555 (Gilead).

In some embodiments, the HBV therapeutic agents that can be combined with an agent disclosed herein include an HBV replication inhibitor. In some embodiments, the HVB replication inhibitor is selected from GP-31502, isothiafludine, IQP-HBV, RM-5038, and Xingantie.

In some embodiments, the HBV therapeutic agents that can be combined with an agent disclosed herein include a non-canonical RNA polymerase PAPD5 and PAPD7 inhibitor. Illustrative examples of non-canonical RNA polymerase PAPD5 and PAPD7 inhibitors include PAPD5 and PAPD7 targeting locked nucleic acid antisense oligonucleotides.

In some embodiments, the HBV therapeutic agents that can be combined with an agent disclosed herein include a covalently closed circular DNA inhibitor (cccDNA), such as BSBI-25, ccc-R08, and CHR-101.

In some embodiments, the HBV therapeutic agents that can be combined with an agent disclosed herein include a caspase 9 stimulator such as ENOB-HB-01.

In some embodiments, the HBV therapeutic agents that can be combined with an agent disclosed herein include a CD3 modulator such as IMC-I109V.

In some embodiments, the HBV therapeutic agents that can be combined with an agent disclosed herein include a Ffar2 and Ffar3 agonist, such as SFA-001.

In some embodiments, the HBV therapeutic agents that can be combined with an agent disclosed herein include an additional HBV antibody. In some embodiments, the additional HBV antibody targets a surface antigen of hepatitis B virus. The additional HBV antibody can include monoclonal and polyclonal antibodies. In some embodiments, the additional HBV antibody is selected from lenvervimab (GC-1102), XTL-17, XTL-19, KN-003, IV Hepabulin SN, VIR-3434, and fully human monoclonal antibody therapy (hepatitis B virus infection, Humabs BioMed). In some embodiments, the additional HBV antibody is selected from Zutectra, Shang Sheng Gan Di, Uman Big (Hepatitis B Hyperimmune), Omri-Hep-B, Nabi-HB, Hepatect CP, Hepa-Gam B, igantibe, Niuliva, CT-P24, hepatitis B immunoglobulin (intravenous, pH4, HBV infection, Shanghai RAAS Blood Products), and Fovepta (BT-088). In some embodiments, the additional HBV antibody is a fully human monoclonal antibody such as HBC-34. In some embodiments, the additional HBV antibody is an antibody against HBV viral peptide/major histocompatibility complex (MHC) class I (pMHC) complexes, e.g., as are described in Sastry, et al., J Virol. 2011 March; 85(5):1935-42 or in WO2011062562.

In some embodiments, the HBV therapeutic agents that can be combined with an agent disclosed herein include a CCR2 chemokine antagonist such as propagermanium.

In some embodiments, the HBV therapeutic agents that can be combined with an agent disclosed herein include a farnesoid x receptor (FXR) agonists. In some embodiments, the FXR agonist is selected from EYP-001, GS-9674, EDP-305, MET-409, Tropifexor, AKN-083, RDX-023, BWD-100, LMB-763, INV-3, NTX-023-1, EP-024297 and GS-8670.

In some embodiments, the HBV therapeutic agents that can be combined with an agent disclosed herein include a thymosine antagonist such as Thymalfasin, recombinant thymosin alpha 1 (GeneScience), NL-004 or PEGylated thymosin alpha-1.

In some embodiments, the HBV therapeutic agents that can be combined with an agent disclosed herein include a nucleoprotein modulator. In some embodiments, the nucleoprotein modulator is selected from GS-4882, AB-423, AB-836, AT-130, ALG-001075, ALG-001024, ALG-000184, EDP-514, GLS4, NVR-1221, NVR-3778, AL-3778, BAY 41-4109, morphothiadine mesilate, ARB-168786, ARB-880, ARB-1820, GST-HG-141, JNJ-379, JNJ-632, RG-7907, GST-HG-141, HEC-72702, KL-060332, AB-506, ABI-H0731, ABI-H3733, JNJ-440, ABI-H2158, CB-HBV-001, AK-0605, SOC-10, SOC-11 and DVR-23.

In some embodiments, the HBV therapeutic agents that can be combined with an agent disclosed herein include a capsid inhibitor. In some embodiments, the capsid inhibitor is selected from the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), and US20170121329 (Novira).

In some embodiments, the HBV therapeutic agents that can be combined with an agent disclosed herein include a transcript inhibitor. In some embodiments, the transcript inhibitor is selected from the compounds disclosed in WO2017013046 (Roche), WO2017016960 (Roche), WO2017017042 (Roche), WO2017017043 (Roche), WO2017061466 (Toyoma Chemicals), WO2016177655 (Roche), WO2016161268 (Enanta), WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), and WO2018045911 (Zhejiang Pharma).

In some embodiments, the HBV therapeutic agents that can be combined with an agent disclosed herein include a retinoic acid-inducible gene stimulator 1. In some embodiments, the retinoic acid-inducible gene stimulator 1 is selected from inarigivir soproxil (SB-9200), SB-40, SB-44, ORI-7246, ORI-9350, ORI-7537, ORI-9020, ORI-9198, ORI-7170, and RGT-100.

In some embodiments, the HBV therapeutic agents that can be combined with an agent disclosed herein include an arginase inhibitor. In some embodiments, the arginase inhibitor is selected from CB-1158, C-201, and resminostat.

In some embodiments, the HBV therapeutic agents that can be combined with an agent disclosed herein include a CAR-T cell therapy. CAR-T cell therapy includes a population of immune effector cells engineered to express a chimeric antigen receptor (CAR), wherein the CAR includes an HBV antigen-binding domain. In certain embodiments, the antigen-binding domain is a domain disclosed herein. In certain embodiments, the antigen-binding domain is other than a domain disclosed herein. In certain embodiments, the antigen is HBsAg (HbsAg-CART). The immune effector cell is a T-cell or an NK cell. In certain embodiments, the T-cell is a CD4+ T-cell, a CD8+ T-cell, a NK cell or a combination thereof. Cells can be autologous or allogeneic. An example of a CART directed to HBV is described in Cytotherapy. 2018 May; 20(5):697-705. doi: 10.1016/j.jcyt.2018.02.

In some embodiments, the HBV therapeutic agents that can be combined with an agent disclosed herein include a TCR-T cell therapy. TCR-T cell therapy includes T cells expressing HBV-specific T cell receptors. TCR-T cells are engineered to target HBV derived peptides presented on the surface of virus-infected cells. An example of a TCR directed to HBV is described in Wisskirchen, K. et al. T cell receptor grafting allows virological control of hepatitis B virus infection. *J Clin Invest.* 2019; 129(7):2932-2945. In some embodiments, the TCR-T cell therapy includes T-Cells expressing HBV surface antigen (HBsAg)-specific TCR. In some embodiments, the TCR-T cell therapy includes TCR-T therapy directed to treatment of HBV, such as LTCR-H2-1.

In some embodiments, the HBV therapeutic agents that can be combined with an agent disclosed herein include an inhibitor of certain HCV nonstructural proteins, such as a NS5A inhibitor, a NS5B inhibitor, a NS3 inhibitor, or combinations thereof. In some embodiments. In one embodiment, the NS5A inhibitor is ledipasvir or velpatasvir. In one embodiment, the NS5B inhibitor is sofosbuvir or mericitabine. In one embodiment, the NS5A inhibitor is ledipasvir and the NS5B inhibitor is sofosbuvir. In one embodiment, the NS3 inhibitor is voxilaprevir.

HCV Therapeutic Agents

In various embodiments, the FLT3L-Fc fusion proteins, homodimers, heterodimers, polynucleotides, vectors, lipoplexes, such as LNPs, and/or pharmaceutical compositions, as described herein, are combined with an HCV therapeutic agent such as an HCV NS5A/NS5B inhibitor, HCV NS3/4A protease inhibitor, HCV NS5A protein inhibitor, HCV NS5B polymerase inhibitor of the nucleoside/nucleotide type, or HCV NS5B polymerase inhibitor of the nonnucleoside type. In various embodiments, the FLT3L-Fc fusion proteins, homodimers, heterodimers, polynucleotides, vectors, lipoplexes, such as LNPs, and/or pharmaceutical compositions, as described herein, are combined with an additional therapeutic agent selected from the group consisting of daclatasvir, ledipasvir, ombitasvir, elbasvir, sofosbuvir, dasabuvir, ribavirin, asunaprevir, simeprevir, paritaprevir, ritonavir, elbasvir, and grazoprevir. In some embodiments, an additional therapeutic agent is selected from the group consisting of daclatasvir, ledipasvir, ombitasvir, elbasvir, sofosbuvir, and dasabuvir.

Influenza Virus Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with an influenza virus inhibitor. In some embodiments the influenza virus inhibitor that can be combined with an agent of this disclosure includes a matrix 2 inhibitor (e.g., amantadine, rimantadine), a neuraminidase inhibitor (e.g., zanamivir, oseltamivir, peramivir, laninamivir octanoate), or a polymerase inhibitor (e.g., ribavirin, favipiravir), or combinations thereof. In some embodiments, the influenza virus inhibitor is selected from amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the influenza virus inhibitor is selected from amantadine, rimantadine, zanamivir, oseltamivir, peramivir, laninamivir octanoate, ribavirin, favipiravir, and combinations thereof.

RSV Therapeutic Agents

In various embodiments, the FLT3L-Fc fusion proteins, homodimers, heterodimers, polynucleotides, vectors, lipoplexes, such as LNPs, and/or pharmaceutical compositions, as described herein, are combined with an RSV therapeutic agent, such as ribavirin, ALS-8112, presatovir, or combinations thereof.

Picornavirus Therapeutic Agents

In various embodiments, the FLT3L-Fc fusion proteins, homodimers, heterodimers, polynucleotides, vectors, lipoplexes, such as LNPs, and/or pharmaceutical compositions, as described herein, are combined with a picornavirus therapeutic agent, such as hydantoin, guanidine hydrochloride, L-buthionine sulfoximine, Py-11, rupintrivir, or combinations thereof.

Ebola Virus Therapeutic Agents

In various embodiments, the FLT3L-Fc fusion proteins, homodimers, heterodimers, polynucleotides, vectors, lipoplexes, such as LNPs, and/or pharmaceutical compositions, as described herein, are combined with an ebola virus therapeutic agent. In some embodiments the ebola virus therapeutic agent that can be combined with an agent of this disclosure is selected from ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan),T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof.

In some embodiments, the ebola virus therapeutic agent is selected from ZMapp, mAB114, REGEN-EB3, and combinations thereof.

Coronavirus Therapeutic Agents

In various embodiments, the FLT3L-Fc fusion proteins, homodimers, heterodimers, polynucleotides, vectors, lipoplexes, such as LNPs, and/or pharmaceutical compositions, as described herein, are combined with a coronavirus therapeutic agent. In some embodiments, the coronavirus therapeutic agent is a SARS therapeutic agent. In some embodiments, the coronavirus therapeutic agent is a MERS therapeutic agent. In some embodiments, the coronavirus therapeutic agent is a COVID-19 therapeutic agent.

In some embodiments, the FLT3L-Fc fusion proteins, homodimers, heterodimers, polynucleotides, vectors, lipoplexes, such as LNPs, and/or pharmaceutical compositions, as described herein, are combined with a COVID-19 therapeutic agent. Illustrative examples of COVID-19 therapeutic agents that can be combined with an agent disclosed herein include without limitation, an adjuvant, antiangiogenic, antibiotic, antiemetic, antifibrotic, antioxidant, antiparasitic, antiproliferative, antithrombotic, antiviral, convalescent plasma, epigenetic mofifier, immunomodulator, immunostimulant, immunosuppressant, metabolic modifier, mucolytic, neuromodulatory, neutralizing antibody, oxygen delivery, proapoptotic, surfactant, thyromimetic, vaccine, vasoconstrictor, or vasodilator.

In various embodiments, the FLT3L-Fc fusion proteins, homodimers, heterodimers, polynucleotides, vectors, lipoplexes, such as LNPs, and/or pharmaceutical compositions, as described herein, are combined with an adjuvant. Illustrative examples of adjuvants that can be combined with an agent disclosed herein include without limitation a TLR9 agonist (e.g., CpG 1018 (Dynavax)), Matrix-M (Novavax), CoVaccine HT (Boston Scientific), 7HP349 (7 Hills Pharma), FirmaVacc (PCI Biotech).

In various embodiments, the FLT3L-Fc fusion proteins, homodimers, heterodimers, polynucleotides, vectors, lipoplexes, such as LNPs, and/or pharmaceutical compositions, as described herein, are combined with an antiangiogenic, such as an integrin alpha 4 modulator (e.g., LY3127804 (Eli Lilly)).

In various embodiments, the FLT3L-Fc fusion proteins, homodimers, heterodimers, polynucleotides, vectors, lipoplexes, such as LNPs, and/or pharmaceutical compositions, as described herein, are combined with an antibiotic. Illustrative examples of antibiotics that can be combined with an agent disclosed herein include without limitation azithromycin, olumiant baricitinib, chloramphenicol, dactinomycin, linezolid, tigecycline, carrimycin, incyclinide.

In various embodiments, the FLT3L-Fc fusion proteins, homodimers, heterodimers, polynucleotides, vectors, lipoplexes, such as LNPs, and/or pharmaceutical compositions, as described herein, are combined with an antiemetic, such as a neurokinin 1 receptor (NK1R) modulator (e.g., tradipitant (Vanda Pharmaceuticals)).

In various embodiments, the FLT3L-Fc fusion proteins, homodimers, heterodimers, polynucleotides, vectors, lipoplexes, such as LNPs, and/or pharmaceutical compositions, as described herein, are combined with an antifibrotic. Illustrative examples of antifibrotics that can be combined with an agent disclosed herein include without limitation a platelet derived growth factor receptor (PDGFR) modulator (e.g., nintedanib), tight junction protein 1 modulator (e.g., aCT1), FK506 binding protein 4 (FKBP4) modulator (e.g., RT1840), amphiregulin (AREG) modulator (e.g., amphisiran (siRNAgen Therapeutics), and angiotensin II receptor type 2 (AGTR2) modulator (e.g., VP01 (Vicore Pharma)).

In various embodiments, the FLT3L-Fc fusion proteins, homodimers, heterodimers, polynucleotides, vectors, lipoplexes, such as LNPs, and/or pharmaceutical compositions, as described herein, are combined with an antifungal, such as inhaled pentamidine or oral amphotericin B (e.g., ICO-019, iCo Therapeutics).

In various embodiments, the FLT3L-Fc fusion proteins, homodimers, heterodimers, polynucleotides, vectors, lipoplexes, such as LNPs, and/or pharmaceutical compositions, as described herein, are combined with an antimicrobial, such as NORS (Nitric Oxide Releasing Solution) or brilacidin (PMX-30063).

In various embodiments, the FLT3L-Fc fusion proteins, homodimers, heterodimers, polynucleotides, vectors, lipoplexes, such as LNPs, and/or pharmaceutical compositions, as described herein, are combined with an antioxidant, such as a sirtuin 1 (SIRT1) agonist (e.g., resveratrol, JOTROL (high oral bioavailability resveratrol)), transglutaminase 2 modulator (e.g., TTI-0102 (cysteamine prodrug, Thiogenesis)), or bucillamine (Revive).

In various embodiments, the FLT3L-Fc fusion proteins, homodimers, heterodimers, polynucleotides, vectors, lipoplexes, such as LNPs, and/or pharmaceutical compositions, as described herein, are combined with an antiparasitic. Illustrative examples of antiparasitics that can be combined with an agent disclosed herein include without limitation chloraquine phosphate, hydroxychloroquine, plasmodium cytochrome bc1 modulator (e.g., atovaquone), Glutamate decarboxylase 2 (GAD2; GAD65) modulator (e.g., LAI ivermectin), pyruvate ferredoxin oxidoreductase modulator (e.g., nitazoxanide, NT-300 (nitazoxanide extended-release tablets, Romark Pharmaceuticals)), nicotinic acetylcholine receptor (nAchR) modulator (e.g., levamisole), FW-1022 (oral niclosamide; First Wave), emetine (Acer Therapeutics), or UNI911 (niclosamide) (Union Therapeutics).

In various embodiments, the FLT3L-Fc fusion proteins, homodimers, heterodimers, polynucleotides, vectors, lipoplexes, such as LNPs, and/or pharmaceutical compositions, as described herein, are combined with an antiproliferative. Illustrative examples of antiproliferatives that can be combined with an agent disclosed herein include without limitation estrogen receptor 1 (ER1) modulator (e.g., toremifene), BRAF inhibitor (e.g., trafinlar dabrafenib), Bruton's tyrosine kinase (Btk) inhibitor (e.g., brukinsa zanubrutinib (Beigene), acalabrutinib), eukaryotic translation elongation factor 1 alpha 2 (EEF1A2) modulator (e.g., aplidin plitidepsin (PharmaMar)) NEDD8 activating enzyme (NAE) modulator (e.g., pevonedistat), RAS inhibitor (e.g., rigosertib), vimentin modulator (e.g., pritumumab), Mammalian target of rapamycin (mTOR; FRAP; RAFT1) inhibitor (e.g., sapanisertib (TAK-228); Dactolisib (RTB101)), MAP kinase interacting serine-threonine kinase 1 (MKNK1; MNK1) or MKNK2 inhibitor (e.g., tomivosertib), Urokinase-type plasminogen activator (PLAU; uPA) inhibitor (e.g., upamostat (RHB-107, WX-671)), tubulin inhibitor (e.g., VERU-111), eukaryotic translation initiation factor 4A1 (EIF4A1; EIF4A) inhibitor (e.g., zotatifin), MAP kinase inhibitor (e.g., KTH-222 (Kalos Oncology)), MAP kinase interacting serine-threonine kinase 1 (MKNK1; MNK1)inhibitor, p53 (TP53); mitogen-activated protein kinase kinase kinase kinase 1 (HPK1; MAP4K1) inhibitor, c-jun N-terminal kinase (JNK) inhibitor (e.g., Satcon), vascular endothelial growth factor (VEGF) inhibitor (e.g., avastin bevacizumab), or exportin 1 (X001; CRM1) inhibitor (e.g., selinexor).

In various embodiments, the FLT3L-Fc fusion proteins, homodimers, heterodimers, polynucleotides, vectors, lipoplexes, such as LNPs, and/or pharmaceutical compositions, as described herein, are combined with an antithrombotic. Illustrative examples of antithrombotics that can be combined with an agent disclosed herein include without limitation plasmin inhibitor (e.g., tranexamic acid), Purinergic receptor P2Y G protein-coupled 12 (P2RY12; P2Y12) inhibitor (e.g., clopidogrel), factor Xa (e.g., rivaroxaban), fibrin inhibitor (e.g., alteplase), cathepsin G inhibitor (e.g., defibrotide), or serine protease inhibitor (e.g., nafamostat).

In various embodiments, the FLT3L-Fc fusion proteins, homodimers, heterodimers, polynucleotides, vectors, lipoplexes, such as LNPs, and/or pharmaceutical compositions, as described herein, are combined with an antiviral. Illustrative examples of antivirals that can be combined with an agent disclosed herein include without limitation HIV protease inhibitor (e.g., lopinavir/ritonavir, atazanavir, ritonavir), HIV reverse transcriptase inhibitor (e.g., Emtricitabine/tenofovir disoproxil), neuraminidase inhibitor (e.g., oseltamivir), HIV protease/cytochrome P450 (e.g., darunavir/cobicistat), amantadine, viral RNA polymerase PA subunit inhibitor (e.g., baloxavir marboxil), RNA-dependent RNA polymerase inhibitor (e.g., ribavirin, galidesivir, remdesivir), omega 3 viruxide, serine protease inhibitor (e.g., camostat), viral RNA polymerase inhibitor (e.g., avigan favipiravir), arbidol umifenovir, HCV protease+HIV protease inhibitors (e.g., Ganovo danoprevir+ritonavir), SARS-CoV-2 3C-like protease (SARS-CoV-2 3CLpro; SARS-CoV-2 NSP5; SARS-CoV-2 Mpro; SARS-CoV-2 main protease) inhibitor, AT-H201 (Atossa Therapeutics), xylometazoline hydrochloride and iota-carrageenan, sialic acid, berdazimer sodium, dihydroorotate dehydrogenase (DHODH) inhibitor (e.g., IMU-838), Inosine monophosphate dehydrogenase (IMPDH) inhibitor (e.g., merimepodib), viral reverse transcriptase inhibitor (e.g., azvudine), checkpoint kinase 1 (Chkl; CHEK1) inhibitor (e.g., prexasertib), heat shock 70 kDa protein 5 (glucose-regulated protein, 78 kDa; GRP78; HspA5) inhibitor (e.g., BOLD-100), exportin 1 (XPO1; CRM1) inhibitor (e.g., verdinexor), CD147 inhibitor (e.g., meplzumab), bacterial 30S ribosomal subunit protein S5 (RpsE) inhibitor (e.g., eravacycline), or Calpain 1 (CAPN1), CAPN2 or CAPN9 inhibitor (e.g., BLD-2660, Blade Therapeutics).

In various embodiments, the FLT3L-Fc fusion proteins, homodimers, heterodimers, polynucleotides, vectors, lipoplexes, such as LNPs, and/or pharmaceutical compositions, as described herein, are combined with convalescent plasma, including without limitation intravenous immunoglobulin (Grifols) or hyperimmune plasma.

In various embodiments, the FLT3L-Fc fusion proteins, homodimers, heterodimers, polynucleotides, vectors, lipoplexes, such as LNPs, and/or pharmaceutical compositions, as described herein, are combined with an epigenetic modifier, such as a BET bromodomain protein inhibitor (e.g., apabetalone, CPI-0610, ABBV-744).

In various embodiments, the FLT3L-Fc fusion proteins, homodimers, heterodimers, polynucleotides, vectors, lipoplexes, such as LNPs, and/or pharmaceutical compositions, as described herein, are combined with an immunomodulator. Illustrative examples of immunomodulators that can be combined with an agent disclosed herein include without limitation BCR-ABL tyrosine kinase (BCR-ABL) inhibitor, stem cell factor (SCF) receptor tyrosine kinase (c-Kit; KIT; CD117) inhibitor (e.g., imatinib, masitinib), spleen tyrosine kinase (SYK) inhibitor (e.g., fostamatinib), Toll-like receptor 3 (TLR3) agonist (e.g., rintatolimod, polyIC), signal transducer and activator of transcription 3 (STAT3) or STATE inhibitor 9 (e.g., mosedipimod), neuropilin 2 (NRP2) inhibitor (e.g., ATYR1923 (aTyr Pharma)), natural killer (NK) cell (e.g., ex vivo expanded allogeneic MRx-4DP0004, 4D Pharma), or type I interferon (IFN) receptor agonist (e.g., interferon beta-1a, novaferon, pegylated interferon alpha-2b, interferon-β1a, interferon (IFN) lambda receptor (IL28RA; IFNLR1) agonist (e.g., peginterferon lambda-1a, interferon-a). Programmed cell death 1 (PD-1; PDCD1; CD279) inhibitor (e.g., pembrolizumab, camrelizumab), granulocyte macrophage colony-stimulating factor (GM-CSF) receptor (CSF2RA) (GMR) (CD116) (GMCSFR) agonist (e.g., sargramostim), LAG-3Ig fusion protein (e.g., eftilagimod alpha), interleukin-15 (IL-15) receptor alpha chain (IL-15RA) agonist (e.g., IL-15 mutant (IL-15N72D) bound to an IL-15 receptor a/IgG1 Fc fusion protein (N-803, ImmunityBio)), Toll-like receptor (TLR) 2 (TLR2), TLR6, or TLR9 agonist, humanized virus suppressing factor variant 13 (e.g., hzVSF-v13 (ImmuneMed)), intercellular adhesion molecule-3 (ICAM-3; CD50) modulator (e.g., AVM0703 (AVM Biotechnology)), glucocorticoid receptor modulator (e.g., dexamethasone, methylprednisolone, hydrocortisone, fluasterone), histamine H1 receptor (HRH1), interleukin-6 (IL-6) receptor (CD126) antagonist (e.g., tocilizumab, sarilumab), tubulin inhibitor (e.g., colchicine), interleukin-1 (IL-1) beta antagonist (e.g., canakinumab), Janus kinase-1 (JAK-1), JAK-2 or JAK-3 inhibitor (e.g., ruxolitinib, tofacitinib, pacritinib), cyclooxygenase (COX) inhibitor (e.g., naproxen, aspirin, ibuprofen), FK506 binding protein 1A 12 kDa (FKBP12; FKBP1A) modulator (e.g., tacrolimus, rapamycin), sphingosine 1-phosphate receptor 1 (S1PR1; S1P1; EDG1), S1PR3, S1PR4, or S1PR5 modulator (e.g., fingolimod), complement 5 antagonist (eculizumab, ravulizumab-cwvz, avdoralimab), neutophil elastase inhibitor (e.g., alpha-1 antitrypsin), phosphodiesterase-4 (PDE-4) inhibitor (e.g., apremilast, ibudilast), IL-6 antagonist (e.g., siltuximab, olokizumab), interleukin-1 (IL-1) receptor 1 (IL1R1) antagonist (e.g., anakinra), interferon gamma antagonist (e.g., emapalumab), vasoactive intestinal peptide receptor 1 (VPAC1) or VPAC2 agonist (e.g., Aviptadil (NeuroRx)), telomerase reverse transcriptase (TERT) inhibitor (e.g., tertomotide), stem cell therapy (e.g., mesenchymal stem cells (MSC), human amniotic fluid, PLX cells (Pluristem)), granulocyte macrophage colony-stimulating factor (GM-CSF; CSF2) antagonist (e.g., otilimab, lenzilumab, namilumab, gimsilumab), CC chemokine receptor 5 (CCRS) antagonist (e.g., leronlimab (PRO 140)), CD24-Fc fusion protein, adenosine A3 receptor (ADORA3) antagonist (e.g., piclidenoson), transforming growth factor (TGF) beta 2 (TGFB2) antagonist (e.g., OT-101 (siRNA)), CD14 antagonist (OT-101), matrix metalloproteinase 12 (MMP12) inhibitor, VE-cadherin (CD144; cadherin-5) modulator (FX06), dipeptidyl peptidase-1 (DPP-1; CTSC) (e.g., brensocatib), Chemokine CXC motif ligand 10 (CXCL10; IP-10) inhibitor (e.g., NI-0101), Galectin-3 (LGALS3) modulator, Microsomal prostaglandin E synthase-1 (PTGES; mPGES-1) inhibitor (e.g., Sonlicromanol), neutrophil elastase (ELANE; NE; HLE) inhibitor (e.g., lonodelestat), complement receptor 5A (C5AR1; CSAR; CD88) antagonist (avdoralimab), cyclin dependent kinase 2 (CDK2) or CDK9 inhibitor (e.g., fadraciclib, seliciclib), Transient receptor potential vanilloid 1 (TRPV1; VR1) modulator (Ser-014 (e.g., Serentrix)), pirfenidone, docisparstat, or Sphingosine kinase 2 (SPHK2) inhibitor (e.g., opaganib).

In various embodiments, the FLT3L-Fc fusion proteins, homodimers, heterodimers, polynucleotides, vectors, lipoplexes, such as LNPs, and/or pharmaceutical compositions, as described herein, are combined with a metabolic agent. Illustrative examples of metabolic agents that can be combined with an agent disclosed herein include without limitation Dipeptidyl peptidase-4 (DPP-4; CD26) inhibitor (linagliptin), sodium-glucose cotransporter 2 (SGLT2) inhibitor (dapagliflozin), H+/K ATPase pump inhibitor (e.g., omeprazole), aldose reductase inhibitor (AT-100), a-glucosidase inhibitor (e.g., IHVR-19029), or protein tyrosine phosphatase 1B (PTP-1B; PTPN1) inhibitor (e.g., trodusquemine).

In various embodiments, the FLT3L-Fc fusion proteins, homodimers, heterodimers, polynucleotides, vectors, lipoplexes, such as LNPs, and/or pharmaceutical compositions, as described herein, are combined with a vaccine. Illustrative examples of metabolic agents that can be combined with an agent disclosed herein include without limitation BCG vaccine, MMR vaccine, SARS-CoV-2 spike protein (SARS-CoV-2 S) vaccine (e.g., Ad5-nCoV (CanSino Biologics), ChAdOxl nCoV-19 (e.g., ChAdOxl Consortium), INO-4800 (Inovio Pharmaceuticals), bacTRL-Spike (Symvivo Corporation), mRNA-1273 (Moderna Therapeutics), NVX-CoV2373 (Novavax; Emergent BioSolutions)), SARS-CoV-2 3C-like protease (SARS-CoV-2 3CLpro; SARS-CoV-2 NSP5; SARS-CoV-2 Mpro; SARS-CoV-2 main protease)(e.g., BNT162 (BioNTech; Pfizer; Fosun Pharma)); or new coronavirus inactivated vaccine (Vero cells; Sinopharm). In some embodiments the vaccine is Ad-nCoV (CanSino Biologics). In some embodiments, the vaccine is mRNA-1273 (Moderna Therapeutics). In some embodiments, the vaccine is BNT-162 (CanSino Biologics, Biontech). In some embodiments, the vaccine is AZD-1222 (ChAdOxl nCoV-19, AstraZeneca). In some embodiments the vaccine is INO-4800 (Inovio Pharmaceuticals). In some embodiments, the vaccine is NVX-CoV2373 (Novavax).

In various embodiments, the FLT3L-Fc fusion proteins, homodimers, heterodimers, polynucleotides, vectors, lipoplexes, such as LNPs, and/or pharmaceutical compositions, as described herein, are combined with a vasoconstrictor or vasodilator. Illustrative examples of vasoconstrictors or vasodilators that can be combined with an agent disclosed herein include without limitation angiotensin II type 1 (AT1) receptor (AGTR1) agonist (e.g., angiotensin II); angiotensin II type 1 (AT1) receptor (AGTR1) antagonist (e.g., valsartan, losartan); cGMP specific phosphodiesterase type 5 (PDE5) inhibitor (e.g., sildenafil), Angiotensin-converting enzyme (ACE) inhibitor (e.g., captopril, lisonopril), endothelin receptor antagonist (e.g., iloprost), calcitonin gene-related peptide (CGRP) receptor antagonist (e.g., vazegepant), or MAS receptor agonist (e.g., angiotensin-(1-7)).

In various embodiments, the FLT3L-Fc fusion proteins, homodimers, heterodimers, polynucleotides, vectors, lipoplexes, such as LNPs, and/or pharmaceutical compositions, as described herein, are combined with a 2019-nCoV virus antibody. Illustrative examples of a 2019-nCoV virus antibody that can be combined with an agent disclosed herein include without limitation LY-CoV555, 5309, SAB-185, CB6, STI-1499, JS016, VNAR, VIR-7832, VIR-7831, REGN-COV2, BAT2020, BAT2019, 47D11, or COVI-SHIELD.

In some embodiments, the FLT3L-Fc fusion proteins, homodimers, heterodimers, polynucleotides, vectors, lipoplexes, such as LNPs, and/or pharmaceutical compositions, as described herein, are combined with a COVID-19 therapeutic agent. Illustrative examples of COVID-19 therapeutic agents that can be combined with an agent disclosed herein include without limitation, a COVID-19 vaccine (e.g., BN162, Ad5-nCoV, INO-4800, mRN1273), an anti-IL6 antibody, an anti-IL6 receptor antibody (e.g., tocilizumab, sarilumab, TILS-501), an anti-IL6 antibody (e.g., siltuximab), an RNA dependent RNA polymerase (RdRp) inhibitor (e.g., favipravir, remdesivir), an anti-CCR5 antibody (e.g., leronlimab (PRO 140)), a broadly neutralizing antibody (e.g., an anti-ACE2 receptor antibody, SAB-185, COVID-HIG, COVID-EIG), including monoclonal or polyclonal neutralizing antibodies, an ACE2 (angiotensin-converting enzyme 2)-Fc fusion protein (COVIDTRAP) or recombinant human ACE2 protein (APN1), ACE-MAB™ bi-specific fusion protein designed to bind to the spike protein of coronaviruses—including SARS-CoV-2 and SARS-CoV (STI-4920, CMAB020), a Janus kinase (JAK1/JAK2) inhibitor (e.g., ruxolitinib, baricitinib), an siRNA (e.g., targeting angiotensin converting enzyme-2 (ACE2) or transmembrane protease, serine 2 (TMPRSS2)), HIV-1 protease inhibitor (e.g., lopinavir/ritonavir), a complement inhibitor (e.g., eculizumab), a recombinant human angiotensin-converting enzyme 2 (rhACE2; e.g., APN01), an HCV protease inhibitor (e.g., danoprevir), a stem cell therapy (e.g., MultiStem®, Remestemcel-L, CYNK-001) or NK cell therapy (INKG21)-ACE2 CAR-NK cells), a neutralizing antibody against human granulocyte-macrophage colony stimulating factor (GM-CSF) (e.g., IZN-101, gimsilumab), a vasoconstrictor (e.g., angiotensin II), or a selective inhibitor of nuclear export (SINE), such as XPO1 inhibitor (e.g., selinexor), NSAID, including COX inhibitors (e.g., ibuprofen, aspirin (acetylsalicylate), diclofenac, and naproxen) and selective COX2 inhibitors (e.g., celecoxib, rofecoxib, etoricoxib, lumiracoxib, and valecoxib), or other antiviral agents (e.g., ENU200, lopinavir/ritonavir combination). In some embodiments, the COVID-19 vaccine is an mRNA vaccine (e.g., BN162), including a lipid-nanoparticle (LNP) encapsulated vaccine (e.g., mRNA1273). In some embodiments, the COVID-19 vaccine is a DNA vaccine (e.g., INO-4800). In some embodiments, the COVID-19 vaccine encodes for a prefusion stabilized form of the Spike (S) protein (e.g., mRNA1273). In some embodiments, the COVID-19 vaccine is a recombinant protein-based vaccine consisting of the receptor binding domain (RBD) of the spike protein of the coronavirus. In some embodiments, the COVID-19 vaccine uses a Ligand Antigen Epitope Presentation System (LEAPS) peptide including conserved regions of coronavirus proteins to stimulate protective cell mediated T cell responses and reduce viral load. In some embodiments, the COVID-19 vaccine is a microneedle array (MNA)—delivered recombinant protein subunit delivered vaccine. In some embodiments, the vaccine is based on a flu vector expressing the surface antigen of SARS-CoV-2. In some embodiments, the COVID-19 vaccine is an intranasal vaccine (e.g., AdCOVID). In some embodiments, the COVID-19 vaccine is NVX-CoV2373, INO4800, or BNT-162. Additional illustrative examples of COVID-19 therapeutic agents that can be combined with an agent disclosed herein include without limitation a PIKfyve kinase inhibitor (e.g., apilimod), an immunemodulator (e.g., rintatolimod), a T-cell immunotherapy, a recombinant sialidase (e.g., DAS181), a CRAC channel inhibitor (e.g., CM-4620-IE), a cardiac cell therapy using allogeneic cardiosphere-derived cells (e.g., CAP-1002), a cardioprotective drug (e.g., aspirin, plavix, lipitor, opremazole), an S1P receptor antagonist (e.g., fingolimod), a cyclooxygenase-2 (COX-2) inhibitor (e.g., celecoxib), a phosphodiesterase-5 (PDE5) inhibitor (e.g., sildenafil citrate), a serine protease TMPRSS2 inhibitor (camostat mesylate), an anti-human complement 5a antibody (e.g., IFX-1), a macrophage migration inhibitory factor (MIF) inhibitor and phosphodiesterase (PDE)-4 and -10 inhibitor (e.g., ibudilast), an eEF1A2 inhibitor (e.g., plitidepsin), a sphingosine kinase 2 (SK2) inhibitor (e.g., ABC294640, RHB-107), a galectin inhibitor (e.g., BXT-10), an HIV-1 protease inhibitor (e.g., darunavir alone or in combination with cobicistat), a membrane fusion inhibitor (e.g., umifenovir), an anti-PDI antibody, thymosine, or other antiviral therapeutics (e.g., HTCC (N-(2-hydroxypropyl)-3-trimethylammonium 47 chitosan chloride, OYA1). Additional illustrative examples of COVID-19 therapeutic agents that can be combined with an agent disclosed herein include without limitation chloroquine or hydroxychloroquine. In some embodiments, the COVID-19 therapeutic agent is selected from ifenprodil (Algernon Therapeutics), recombinant sialidase (DAS-181, Ansun Biopharma), ruxolitinib, angiotensin II, and lenzilumab. In some embodiments the COVID-19 therapeutic agent is tocilizumab (Actemra).

In various embodiments, the FLT3L-Fc fusion proteins, homodimers, heterodimers, polynucleotides, vectors, lipoplexes, such as LNPs, and/or pharmaceutical compositions, as described herein, are combined with an anti-SARS-CoV-2 hyperimmune globulin therapy (plasma from convalescent COVID-19 patients, e.g., processed into a hyperimmune globulin) (e.g., TAK-888).

In various embodiments, the FLT3L-Fc fusion proteins, homodimers, heterodimers, polynucleotides, vectors, lipoplexes, such as LNPs, and/or pharmaceutical compositions, as described herein, are combined with and RNA polymerase inhibitor (e.g., remdesivir, galidesivir). In various embodiments, the FLT3L-Fc fusion proteins, homodimers, heterodimers, polynucleotides, vectors, lipoplexes, such as LNPs, and/or pharmaceutical compositions, as described herein, are combined with remdesivir (GS-5734).

Antimalarial Agents

In various embodiments, the FLT3L-Fc fusion proteins, homodimers, heterodimers, polynucleotides, vectors, lipoplexes, such as LNPs, and/or pharmaceutical compositions, as described herein, are combined with an antimalarial agent. In some embodiments, the antimalarial agent that can be combined with an agent disclosed herein is selected from hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

CDK Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with a CDK inhibitor such as VS2-370.

STING Agonists, RIG-I and NOD2 Modulators

In various embodiments, the FLT3L-Fc fusion proteins, homodimers, heterodimers, polynucleotides, vectors, lipoplexes, such as LNPs, and/or pharmaceutical compositions, as described herein, are combined with a stimulator of interferon genes (STING) agonist or activator, a RIG-I modulator (e.g., RGT-100), or a NOD2 modulator (e.g., SB-9200, IR-103). In some embodiments, the STING receptor agonist or activator that can be co-administered with an agent of this disclosure is selected from ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP. In some embodiments, the STING agonist is selected from the compounds disclosed in WO 2018065360 ("Biolog Life Science Institute Forschungslabor and Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkiline), WO 2017075477 (Aduro Biotech), US 20170044206 (Merck), WO 2014179760 (University of California), WO2018098203 (Janssn), WO2018118665 (Merck), WO2018118664 (Merck), WO2018100558 (Takeda), WO2018067423 (Merck), and WO2018060323 (Boehringer).

LAG-3 and TIM-3 Inhibitors

In various embodiments, the FLT3L-Fc fusion proteins, homodimers, heterodimers, polynucleotides, vectors, lipoplexes, such as LNPs, and/or pharmaceutical compositions, as described herein, are combined with a LAG-3 inhibitor or a TIM-3 inhibitor. In some embodiments, the LAG-3 inhibitor that can be co-administered with an agent of this disclosure is selected from relatlimab (ONO-4482), LAG-525, MK-4280, REGN-3767, and INCAGN2385. In some embodiments, the TIM-3 inhibitor that can be co-administered with an agent of this disclosure is an anti-TIM-3 antibody, such as TSR-022, LY-3321367, MBG-453, or INCAGN-23 90.

Interleukine Agonists

In various embodiments, the FLT3L-Fc fusion proteins, homodimers, heterodimers, polynucleotides, vectors, lipoplexes, such as LNPs, and/or pharmaceutical compositions, as described herein, are combined with an interleukin agonist, such as an IL-2, IL-7, IL-15, IL-10, or IL-12 agonist. Illustrative examples of IL-2 agonists that can be combined with an agent of this disclosure include without limitation proleukin (aldesleukin, IL-2); pegylated IL-2 (e.g., NKTR-214); modified variants of IL-2 (e.g., THOR-707), bempegaldesleukin, AIC-284, ALKS-4230, CUI-101, and Neo-2/15. Illustrative examples of IL-15 agonists that can be combined with an agent of this disclosure include without limitation ALT-803, NKTR-255, hetIL-15, interleukin-15/Fc fusion protein, AM-0015, NIZ-985, SO-C101, IL-15 Synthorin (pegylated 11-15), P-22339, and IL-15-PD-1 fusion protein N-809. An illustrative example of an IL-7 agonist that can be combined with an agent of this disclosure is CYT-107.

Pharmacokinetic Enhancers

In various embodiments, the FLT3L-Fc fusion proteins, homodimers, heterodimers, polynucleotides, vectors, lipoplexes, such as LNPs, and/or pharmaceutical compositions, as described herein, are combined with a pharmacokinetic enhancer such as cobicistat and ritonavir.

5-Substituted 2'-Deoxyuridine Analogues

In various embodiments, the FLT3L-Fc fusion proteins, homodimers, heterodimers, polynucleotides, vectors, lipoplexes, such as LNPs, and/or pharmaceutical compositions, as described herein, are combined with a 5-substituted 2'-deoxyuridine analogue. Illustrative examples of 5-substituted 2'-deoxyuridine analogues that can be combined with an agent disclosed herein include without limitation idoxuridine, trifluridine, brivudine [BVDU], and combinations thereof.

Nucleoside Analogue

In various embodiments, the FLT3L-Fc fusion proteins, homodimers, heterodimers, polynucleotides, vectors, lipoplexes, such as LNPs, and/or pharmaceutical compositions, as described herein, are combined with a nucleoside analogue. Illustrative examples of nucleoside analogues that can be combined with an agent disclosed herein include without limitation vidarabine, entecavir (ETV), telbivudine, lamivudine, adefovir dipivoxil, tenofovir disoproxil fumarate (TDF), and combinations thereof.

Pyrophosphate Analogue

In various embodiments, the FLT3L-Fc fusion proteins, homodimers, heterodimers, polynucleotides, vectors, lipoplexes, such as LNPs, and/or pharmaceutical compositions, as described herein, are combined with a pyrophosphate analogue. Illustrative examples of pyrophosphate analogues that can be combined with an agent disclosed herein include without limitation foscarnet or phosphonoacetic acid. In some embodiments, the pyrophosphate analogue includes foscarnet.

Acyclic Guanosine Analogue

In various embodiments, the FLT3L-Fc fusion proteins, homodimers, heterodimers, polynucleotides, vectors, lipoplexes, such as LNPs, and/or pharmaceutical compositions, as described herein, are combined with an acyclic guanosine analogue. Illustrative examples of acyclic guanosine analogue that can be combined with an agent disclosed herein include without limitation acyclovir, ganciclovir, valacyclovir (also known as valaciclovir), valganciclovir, penciclovir, and famciclovir.

Acyclic Nucleoside Phosphonate Analogue

In various embodiments, the FLT3L-Fc fusion proteins, homodimers, heterodimers, polynucleotides, vectors, lipoplexes, such as LNPs, and/or pharmaceutical compositions, as described herein, are combined with an acyclic nucleoside phosphonate analogue. Illustrative examples of acyclic nucleoside phosphonate analogue that can be combined with an agent disclosed herein include without limitation cidofovir, adefovir, adefovir dipivoxil, tenofovir, TDF, emtricitabine, efavirenz, rilpivirine, and elvitegravir. In some embodiments, the acyclic nucleoside phosphonate analogue is selected from cidofovir, adefovir, adefovir dipivoxil, tenofovir, TDF, emtricitabine, efavirenz, rilpivirine, and elvitegravir. In some embodiments, the acyclic nucleoside phosphonate analogue is selected from cidofovir, adefovir, adefovir dipivoxil, tenofovir, TDF. In some embodiments, the acyclic nucleoside phosphonate analogue is selected from cidofovir, adefovir dipivoxil, TDF.

Interferons

In various embodiments, the FLT3L-Fc fusion proteins, homodimers, heterodimers, polynucleotides, vectors, lipoplexes, such as LNPs, and/or pharmaceutical compositions, as described herein, are combined with an interferon. In some embodiments, the interferon that can be combined with an agent of this disclosure is selected from interferon alfacon 1, interferon alfa 1b, interferon alfa 2a, interferon alfa 2b, pegylated interferon alfacon 1, pegylated interferon alfa 1b, pegylated interferon alfa 2a (PegIFNα-2a), and PegIFNα-2b, and combinations thereof. In some embodiments, the interferon that can be combined with an agent of this disclosure is selected from interferon alfacon 1, pegylated interferon alfa 2a (PegIFNα-2a), PegIFNα-2b, ribavirin, and combinations thereof. In some embodiments, the interferon that can be combined with an agent of this disclosure is selected from pegylated interferon alfa-2a, pegylated interferon alfa-2b, and combinations thereof.

Immunostimulatory Agents

In various embodiments, the FLT3L-Fc fusion proteins, homodimers, heterodimers, polynucleotides, vectors, lipoplexes, such as LNPs, and/or pharmaceutical compositions, as described herein, are combined with an immunostimulatory agent, such as an oligonucleotide or an antimitotic inhibitor. In some embodiments, the immunostimulatory agent that can be combined with an agent of this disclosure is selected from fomivirsen, podofilox, imiquimod, sinecatechins, and combinations thereof.

Additional Therapeutic Agents

In various embodiments, the FLT3L-Fc fusion proteins, homodimers, heterodimers, polynucleotides, vectors, lipoplexes, such as LNPs, and/or pharmaceutical compositions, as described herein, are combined with an additional therapeutic agent selected from the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

In various embodiments, the FLT3L-Fc fusion proteins, homodimers, heterodimers, polynucleotides, vectors, lipoplexes, such as LNPs, and/or pharmaceutical compositions, as described herein, are combined with an additional therapeutic agent selected from besifovir, nitazoxanide, REGN2222, doravirine, sofosbuvir, velpatasvir, daclatasvir, asunaprevir, beclabuvir, FV100, and letermovir, and combinations thereof.

In various embodiments, the FLT3L-Fc fusion proteins, homodimers, heterodimers, polynucleotides, vectors, lipoplexes, such as LNPs, and/or pharmaceutical compositions, as described herein, are combined with an additional therapeutic agent selected from IFX-1, FM-201, CYNK-001, DPP4-Fc, ranpirnase, nafamostat, LB-2, AM-1, antiviroporins, and combinations thereof.

Exemplified Combination Therapies

Lymphoma or Leukemia Combination Therapy

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WHIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CC1-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CC1-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and R ICE.

Chronic Lymphocytic Leukemia Combination Therapy

Examples of therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy

Myelofibrosis inhibiting agents include, but are not limited to, hedgehog inhibitors, histone deacetylase (HDAC) inhibitors, and tyrosine kinase inhibitors. Non-limiting examples of hedgehog inhibitors are saridegib and vismodegib. Examples of HDAC inhibitors include, but are not limited to, pracinostat and panobinostat. Non-limiting examples of tyrosine kinase inhibitors are lestaurtinib, bosutinib, imatinib, gilteritinib, radotinib, and cabozantinib.

Hyperproliferative Disorder Combination Therapy

Gemcitabine, nab-paclitaxel, and gemcitabine/nab-paclitaxel may be used with a JAK inhibitor and/or PI3Kδ inhibitor to treat hyperproliferative disorders.

Bladder Cancer Combination Therapy

Therapeutic agents used to treat bladder cancer include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combination thereof.

Breast Cancer Combination Therapy

Therapeutic agents used to treat breast cancer include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy

Therapeutic agents used to treat triple negative breast cancer include cyclophosphamide, docetaxel, doxorubicin, epirubicin, fluorouracil, paclitaxel, and combinations thereof.

Colorectal Cancer Combination Therapy

Therapeutic agents used to treat colorectal cancer include bevacizumab, capecitabine, cetuximab, fluorouracil, irinotecan, leucovorin, oxaliplatin, panitumumab, ziv-aflibercept, and any combinations thereof.

Castration-Resistant Prostate Cancer Combination Therapy

Therapeutic agents used to treat castration-resistant prostate cancer include abiraterone, cabazitaxel, docetaxel, enzalutamide, prednisone, sipuleucel-T, and any combinations thereof.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary Cancer Combination Therapy

Therapeutic agents used to treat hepatobiliary cancer include capecitabine, cisplatin, fluoropyrimidine, 5-fluorourcil, gemcitabine, oxaliplatin, sorafenib, and any combinations thereof Hepatocellular Carcinoma Combination Therapy Therapeutic agents used to treat hepatocellular carcinoma include capecitabine, doxorubicin, gemcitabine, sorafenib, and any combinations thereof.

Non-Small Cell Lung Cancer Combination Therapy

Therapeutic agents used to treat non-small cell lung cancer (NSCLC) include afatinib, albumin-bound paclitaxel, alectinib, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy

Therapeutic agents used to treat small cell lung cancer (SCLC) include bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof.

Melanoma Combination Therapy

Therapeutic agents used to treat melanoma cancer include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic Cancer Combination Therapy

Therapeutic agents used to treat pancreatic cancer include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof Renal Cell Carcinoma Combination Therapy Therapeutic agents used to treat renal cell carcinoma include axitinib, bevacizumab, cabozantinib, erlotinib, everolimus, levantinib, nivolumab, pazopanib, sorafenib, sunitinib, temsirolimus, and any combinations thereof.

HBV Combination Therapy

Therapeutic agents used to treat an infection caused by HBV include compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics),U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085(Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In certain embodiments, an agent disclosed herein is combined with 5 mg-30 mg tenofovir alafenamide fumarate, tenofovir alafenamide hemifumarate, or tenofovir alafenamide. In certain embodiments, an agent disclosed herein, or a pharmaceutically acceptable salt thereof, is combined with 5 mg-10 mg; 5 mg-15 mg; 5 mg-20 mg; 5 mg-25 mg; 25 mg-30 mg; 20 mg-30 mg; 15 mg-30 mg; or 10 mg-30 mg tenofovir alafenamide fumarate, tenofovir alafenamide hemifumarate, or tenofovir alafenamide. In certain embodiments, an agent disclosed herein, or a pharmaceutically acceptable salt thereof, is combined with 10 mg tenofovir alafenamide fumarate, tenofovir alafenamide hemifumarate, or tenofovir alafenamide. In certain embodiments, an agent disclosed herein, or a pharmaceutically acceptable salt thereof, is combined with 25 mg tenofovir alafenamide fumarate, tenofovir alafenamide hemifumarate, or tenofovir alafenamide. An agent as disclosed herein may be combined with the agents provided herein in any dosage amount of the compound (e.g., from 50 mg to 500 mg of compound) the same as if each combination of dosages were specifically and individually listed.

In certain embodiments, an agent disclosed herein is combined with a combination of either ledipasvir or velpatasvir, together with sofosbuvir and voxilaprevir. In certain embodiments, an agent disclosed herein is combined with a combination of either ledipasvir or velpatasvir, together with sofosbuvir and tenofovir.

HIV Combination Therapy

Therapeutic agents used to treat an infection caused by HIV include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY (bictegravir+emtricitabine+tenofovir alafenamide), adefovir; adefovir dipivoxil; cobicistat; emtricitabine; tenofovir; tenofovir alafenamide and elvitegravir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; PEGylated raltegravir; raltegravir and lamivudine; maraviroc; tenofovir+emtricitabine+maraviroc, enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

Additional examples of therapeutic agents treating an infection caused by HIV include aspernigrin C, acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, bevirimat derivatives, ABX-464, AG-1105, APH-0812, bryostatin analogs, BIT-225, CYT-107, CS-TATI-1, fluoro-beta-D-arabinose nucleic acid (FANA)-modified antisense oligonucleotides, FX-101, griffithsin, HGTV-43, HPH-116, HS-10234, hydroxychloroquine, IMB-10035, IMO-3100, IND-02, JL-18008, LADAVRU, MK-1376, MK-2048, MK-4250, MK-8507, MK-8558, MK-8591 (islatravir), NOV-205, OB-002H, ODE-Bn-TFV, M1-TFV, PA-1050040 (PA-040), PC-707, PGN-007, QF-036, S-648414, SCY-635, SB-9200, SCB-719, TR-452, TEV-90110, TEV-90112, TEV-90111, TEV-90113, RN-18, DIACC-1010, Fasnall, Immuglo, 2-CLIPS peptide, HRF-4467, thrombospondin analogs, TBL-1004HI, VG-1177, x1-081, rfhSP-D, [18F]-MC-225, URMC-099-C, RES-529, VIR-576, and any combinations thereof.

In various embodiments, the FLT3L-Fc fusion proteins, homodimers, heterodimers, polynucleotides, vectors, lipoplexes, such as LNPs, and/or pharmaceutical compositions, as described herein, are combined with a an HIV nucleoside or nucleotide inhibitor of reverse transcriptase and an HIV non-nucleoside inhibitor of reverse transcriptase. In another specific embodiment, an agent disclosed herein, or a pharmaceutical composition thereof, is combined with an HIV nucleoside or nucleotide inhibitor of reverse transcriptase, and an HIV protease inhibiting compound. In an additional embodiment, an agent disclosed herein, or a pharmaceutical composition thereof, is combined with an HIV nucleoside or nucleotide inhibitor of reverse transcriptase, an HIV non-nucleoside inhibitor of reverse transcriptase, and a pharmacokinetic enhancer. In certain embodiments, an agent disclosed herein, or a pharmaceutical composition thereof, is combined with at least one HIV nucleoside inhibitor of reverse transcriptase, an integrase inhibitor, and a pharmacokinetic enhancer. In another embodiment, an agent disclosed herein, or a pharmaceutical composition thereof, is combined with two HIV nucleoside or nucleotide inhibitors of reverse transcriptase.

In some embodiments, the FLT3L-Fc fusion proteins, homodimers, heterodimers, polynucleotides, vectors, lipoplexes, such as LNPs, and/or pharmaceutical compositions, as described herein, are combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In some embodiments, the FLT3L-Fc fusion proteins, homodimers, heterodimers, polynucleotides, vectors, lipoplexes, such as LNPs, and/or pharmaceutical compositions, as described herein, are combined with tenofovir, tenofovir disoproxil, tenofovir disoproxil fumarate, tenofovir alafenamide, or tenofovir alafenamide hemifumarate.

In some embodiments, the FLT3L-Fc fusion proteins, homodimers, heterodimers, polynucleotides, vectors, lipoplexes, such as LNPs, and/or pharmaceutical compositions, as described herein, are combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In some embodiments, the FLT3L-Fc fusion proteins, homodimers, heterodimers, polynucleotides, vectors, lipoplexes, such as LNPs, and/or pharmaceutical compositions, as described herein, are combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

In some embodiments, the FLT3L-Fc fusion proteins, homodimers, heterodimers, polynucleotides, vectors, lipoplexes, such as LNPs, and/or pharmaceutical compositions, as described herein, are combined with a first additional therapeutic agent (a contraceptive) selected from the group consisting of cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segesterone acetate, ulipristal acetate, and any combinations thereof.

In some embodiments, the FLT3L-Fc fusion proteins, homodimers, heterodimers, polynucleotides, vectors, lipoplexes, such as LNPs, and/or pharmaceutical compositions, as described herein, are combined with one or more additional therapeutic agents selected from compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono Pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432 (Quanticel), US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

Coronavirus Combination Therapy

In some embodiments, the FLT3L-Fc fusion proteins, homodimers, heterodimers, polynucleotides, vectors, lipoplexes, such as LNPs, and/or pharmaceutical compositions, as described herein, are combined with remdesivir.

9. Kits

Further provided are kits comprising one or more containers comprising one or more unitary doses of a FLT3L-Fc fusion protein, as described herein, a homodimer or heterodimer comprising such fusion protein, a polynucleotide encoding such fusion protein, a vector or lipoplex, such as a lipid nanoparticle (LNP) comprising such polynucleotide, or pharmaceutical composition comprising such fusion protein or polynucleotide. In some embodiments, the kits comprise two or more unitary doses of the FLT3L-Fc fusion protein, the homodimer or heterodimer comprising such fusion protein, the polynucleotide encoding such fusion protein, the vector or lipoplex, such as a lipid nanoparticle (LNP) comprising such polynucleotide, or pharmaceutical composition comprising such fusion protein or polynucleotide, in two or more containers. In some embodiments, the kit comprises one or more unitary doses of the FLT3L-Fc fusion protein, the homodimer or heterodimer comprising such fusion protein, the polynucleotide encoding such fusion protein, the vector or lipoplex, such as a lipid nanoparticle (LNP) comprising such polynucleotide, or pharmaceutical composition comprising such fusion protein or polynucleotide and one or more (e.g., one, two, three, one or two, or one to three) additional therapeutic agents in separate containers. The one or more additional therapeutic agents (e.g., for vaccination and/or for treating cancer or a viral infection) are as described above and herein. In some embodiments, the kits comprise two or more unitary doses wherein the unitary doses are the same. In some embodiments, the kits comprise two or more unitary doses, wherein the unitary doses are different.

In one embodiment, the kit comprises one or more pharmaceutical packs comprising one or more containers (e.g., vials, ampules, pre-loaded syringes) containing one or more of the ingredients of the pharmaceutical compositions described herein, such as the FLT3L-Fc fusion protein, the homodimer or heterodimer comprising such fusion protein, the polynucleotide encoding such fusion protein, the vector or lipoplex, such as a lipid nanoparticle (LNP), comprising such polynucleotide, or pharmaceutical composition comprising such fusion protein or polynucleotide, as provided herein. In some instances, the kits contain a pharmaceutical composition described herein. In some embodiments, the kit comprises one or more containers comprising the FLT3L-Fc fusion protein, the homodimer or heterodimer comprising such fusion protein, the polynucleotide encoding such fusion protein, the vector or lipoplex, such as a lipid nanoparticle (LNP), comprising such polynucleotide, or pharmaceutical composition comprising such fusion protein or polynucleotide, in an aqueous solution. In some embodiments, the aqueous solution comprises the FLT3L-Fc fusion protein, the homodimer or heterodimer comprising such fusion protein, or pharmaceutical composition comprising such fusion protein, at a concentration in the range of about 1 mg/ml to about 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml or 20 mg/ml. In some embodiments, the kit comprises one or more containers comprising the FLT3L-Fc fusion protein, the homodimer or heterodimer comprising such fusion protein, the polynucleotide encoding such fusion protein, the vector or lipoplex, such as a lipid nanoparticle (LNP), comprising such polynucleotide, or pharmaceutical composition comprising such fusion protein or polynucleotide, in lyophilized form.

Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

The following examples are offered to illustrate, but not to limit the claimed invention.

Example 1

In Vitro Potency of Different FLT3 Agonist Modalities

In this example, we compared the in vitro potency of FLT3 agonists of different modalities, including recombinant ligand, FLT3 ligand-Fc fusion protein, and anti-mouse FLT3 agonist antibody (comparator 1). We tested in vitro potency employing a M1 IL-6 Secretion Assay.

Methods

M1 IL-6 Secretion Assay: Murine myeloid leukemic M1 cells (American Type Culture Collection (ATCC), TIB-192) were collected from culture, counted, and resuspended to $0.5\times10^6$ cells/ml with serum-free RPMI1640. In a 96-well U-bottom tissue culture plate, 100 μl of resuspended cells (50,000 cells) was added to each well, then 50 μl of 4× test article was added to each well and 50 μl of serum-free RPMI was added into the wells for a final volume of 200 μl per well. Cells were incubated overnight at 37° C. The next day, cells were spun down at 500 g for 5 min at ambient temperatures. Supernatants were then collected for mouse IL-6 quantification (Meso Scale Discovery (MSD), Cat: K152AKB-1) which was performed by following the manufacturer's protocol. EC50 and Emax values of each sample were determined by plotting the concentration of the FLT3 agonist compound against the IL-6 supernatant concentration (pg/mL) and fit to a four parameter logistic (4PL) regression curve.

Results

The data demonstrated that recombinant FLT3-ligand and recombinant FLT3-ligand Fc fusion protein were superior to FLT3 agonist antibody (comparator 1) in activating M1 cells to produce IL-6 in a dose dependent manner. These data also demonstrated that human FLT3-ligand proteins can potently activate murine FLT3. These results are summarized in Table 1 and depicted in FIG. 1.

TABLE 1

EC50 and Emax values for Recombinant huFlt3L, Recombinant huFLT3L-Fc and Comparator 1 in the M1 IL-6 release assay

|  | anti-mouse FLT3 agonist antibody (Comparator 1) | Recombinant huFlt3L-Fc | Recombinant huFLT3L |
| --- | --- | --- | --- |
| EC50(nM) | 4.188 | 0.117 | 0.024 |
| Emax(pg/ml) | 244.1 | 516.6 | 392.3 |

The results guided us to further pursue a FLT3-ligand Fc fusion protein as a FLT3 agonist.

Example 2

In Vitro Potency of FLT3L-Fc Fusion Proteins Having Different IgG Backbones In this example, we compared the in vitro potency of different FLT3-Ligand Fc fusion protein variants: one having a hingeless human IgG1 backbone (SEQ ID NO:1) and a second having a human IgG1 backbone (SEQ ID N0:21). For this comparison, we tested the in vitro potency employing an AML5 Proliferation Assay.

Methods

AML5 Proliferation Assay: AML5 cells (Deutsche Sammlung von Mikroorganismen and Zellkulturen (DSMZ), ACC247) were starved 0/N (18-24h) with serum free MEM-a. The next day, using a 96-well white opaque half area flat bottom TC plates (Costar, 3688), 25,000 cells per well were stimulated with the various compounds for 72h. Plates were sealed with a breathable plate sealer (Sigma, Z380059-1PAK) during the incubation. After incubation, proliferation was assessed through CellTiter Glo assay (Promega, G7571) using manufacturer's recommendations. Luminescence signals were measured using a SpectraMax plate reader. EC50 value of each sample was determined by plotting the concentration of the compound against the luminescence signal and fit to a 4PL curve.

Results

Figure 2:
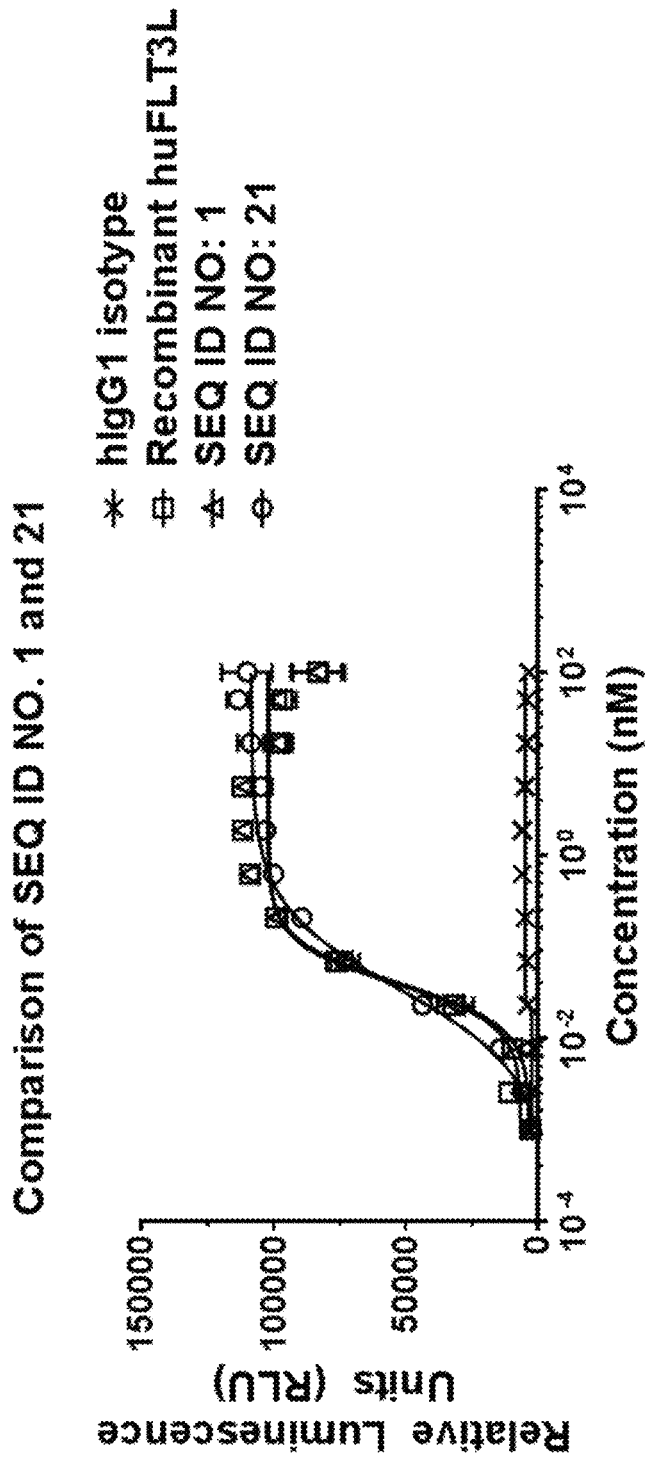
FIG. 2 illustrates proliferation of a human FLT3-expressing AML5 cell line in response to a titration (100-0.0025 nM) of recombinant human FLT3-ligand (Recombinant huFLT3L, open square), human FLT3-ligand human hingeless IgG1 fusion protein (SEQ ID NO:1, open triangle), human FLT3-ligand human IgG1 fusion protein (SEQ ID NO:21, open circle) or human IgG1 isotype antibody (hIgG1 Isotype, cross). The x-axis shows the protein concentration (nM) and the y-axis shows the relative luminescence units (RLU). Graph is a result of one experiment. Experiments were performed in triplicate. Error bars represent standard deviation of the mean values. EC50 values are shown in Table 2.

The data demonstrated that the potency of FLT3-ligand Fc fusion with hingeless IgG1 (SEQ ID NO:1) and FLT3-ligand Fc fusion with IgG1 (SEQ ID NO:21) was similar to that of recombinant human FLT3 ligand in inducing FLT3-dependent proliferation in AML5 cells, with EC50 values ranging between 0.035-0.04 nM. The results are summarized in Table 2 and depicted in FIG. 2.

TABLE 2

EC50 values for Inducing Proliferation of AML5
Cells by FLT3L-Fc Variants Having Different IgG Backbones
EC50 (nM)

| recombinant huFLT3L | hingeless IgG1 SEQ ID NO: 1 | IgG1 SEQ ID NO: 21 |
|---|---|---|
| 0.039 | 0.040 | 0.035 |

Example 3

In Vitro Potency of FLT3L-Fc Variants Having Mutations in the FLT3L EC Domain

In this example, we compared the in vitro potency of human FLT3-ligand hingeless human IgG1 fusion proteins containing different FLT3-ligand gain-of-fusion mutations. We tested the in vitro potency FLT3L-Fc fusion protein variants having mutations in the FLT3L extracellular (EC) domain (H8Y and/or K84E) by employing an AML5 Proliferation Assay. The methods are as described above in Example 2.

Results

Figure 3:
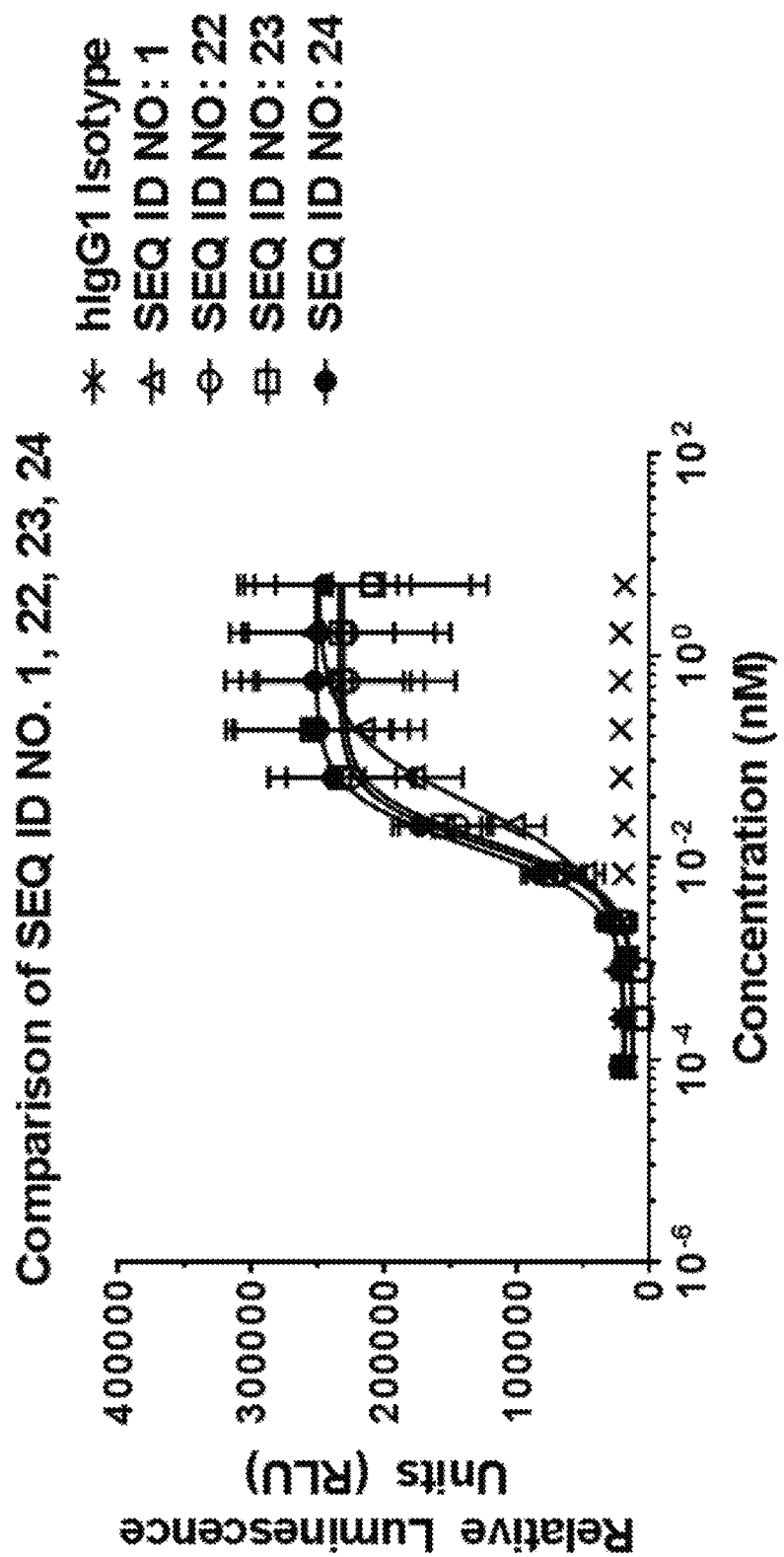
FIG. 3 illustrates proliferation of a human FLT3-expressing AML5 cell line induced by a titration (5-0.00008 nM) of human wildtype FLT3-ligand human hingeless IgG1 fusion protein (SEQ ID NO:1, open triangle), human FLT3-ligand (H8Y) human hingeless IgG1 fusion protein (SEQ ID NO:22, open circle), human FLT3-ligand (K84E) human hingeless IgG1 fusion protein (SEQ ID NO:23, open square), human FLT3-ligand (H8Y+K84E) human hingeless IgG1 fusion protein (SEQ ID NO:24, closed circle), or human IgG1 isotype antibody (hIgG1 Isotype, cross). The x-axis shows the protein concentration (nM) and the y-axis shows the relative luminescence units (RLU). Graph is a combination of two independent experiments. Experiments were performed in triplicate. Error bars represent standard deviation of the mean values. EC50 values are shown in Table 3.

The data demonstrated that the potency of FLT3-ligand Fc fusion protein variants with gain-of-function mutations in the FLT3L extracellular domain (H8Y and/or K84E; SEQ ID NOs: 22, 23 and 24) in inducing FLT3-dependent proliferation in AML5 cells was approximately 2.5× fold higher than that of human FLT3-ligand Fc fusion protein (SEQ ID NO:1). The results are summarized in Table 3 and depicted in FIG. 3.

TABLE 3

EC50 values for Inducing Proliferation of AML5 Cells by
FLT3L-Fc Variants Having Mutations in the FLT3L EC Domain
EC50 (nM)

| hFLT3L ECD SEQ ID NO: 1 | hFLT3L ECD (H8Y) SEQ ID NO: 22 | hFLT3L ECD (K84E) SEQ ID NO: 23 | hFLT3L ECD (H8Y/K84E) SEQ ID NO: 24 |
|---|---|---|---|
| 0.034 | 0.014 | 0.013 | 0.013 |

Example 4

In Vitro Potency of Murine Surrogate FLT3-Ligand Fc Fusion Variants

In this example, we compared the in vitro potency of human FLT3-ligand hingeless human IgG1 fusion protein with two murine surrogate FLT3-ligand Fc fusion proteins. These murine surrogate proteins contained the wild type murine FLT3-ligand extracellular region fused to a L234A/L235A/P329G variant of murine IgG2a Fc region (IgG2a-LALA-PG), or, a C136S variant of murine FLT3-ligand extracellular region fused to the same Fc, where the C136S mutation was incorporated to eliminate an unpaired cysteine liability. We tested the in vitro potency employing an AML5 Proliferation Assay. The methods are as described above in Example 2.

Results

Figure 4:
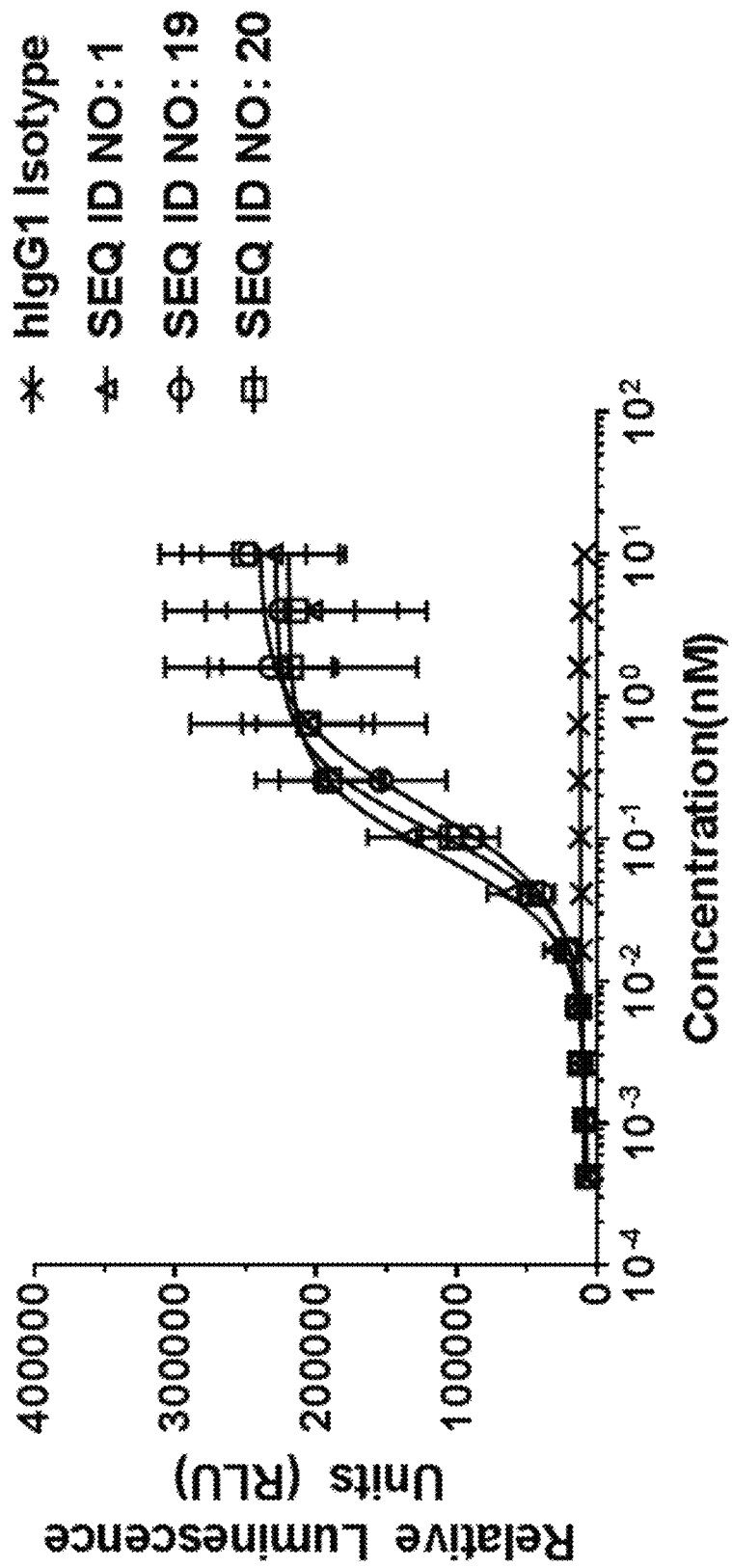
FIG. 4 illustrates proliferation of a human FLT3-expressing AML5 cell line induced by a titration (10-0.0004 nM) of human FLT3-ligand human hingeless IgG1 fusion protein (SEQ ID NO:1, open triangle), mouse FLT3-ligand mouse IgG2a (LALA-PG) fusion protein (SEQ ID NO:19, open circle), mouse FLT3-ligand mouse IgG2a (C136S LALA-PG) fusion protein (SEQ ID NO:20, open square), or human IgG1 isotype antibody (hIgG1 Isotype, cross). The x-axis shows the protein concentration (nM) and the y-axis shows the relative luminescence units (RLU). Graph is a result of one experiment of Experiment was performed in triplicate. Error bars represent standard deviation of the mean values. EC50 values are shown in Table 4.

The data demonstrated that the potency of murine surrogate FLT3-ligand Fc fusion proteins (SEQ ID NOs: 19 and 20) in inducing human FLT3-dependent proliferation in AML5 cells is similar to that of human FLT3-ligand Fc fusion protein (SEQ ID NO:1), with EC50 values ranging between 0.171-0.078 nM. The results are summarized in Table 4 and depicted in FIG. 4.

TABLE 4

EC50 values for Inducing Proliferation of AML5 Cells
by Murine Surrogate FLT3-Ligand Fc Fusion Variants
EC50 (nM)

| SEQ ID NO: 1 | SEQ ID NO: 19 | SEQ ID NO: 20 |
|---|---|---|
| 0.078 | 0.171 | 0.115 |

Based on these assay results and reduced risk of disulfide-mediated aggregation, we proceeded with using the murine surrogate FLT3-ligand Fc fusion variant of SEQ ID NO:20 in mouse preclinical models.

Example 5

In Vitro Potency of Different FLT3L-Fc Proteins

In this example, we compared the in vitro potency of eight different human FLT3-ligand human Fc fusion proteins. We tested the in vitro potency employing an AML5 Proliferation Assay. The methods are as described above in Example 2.

Results

Figure 5:
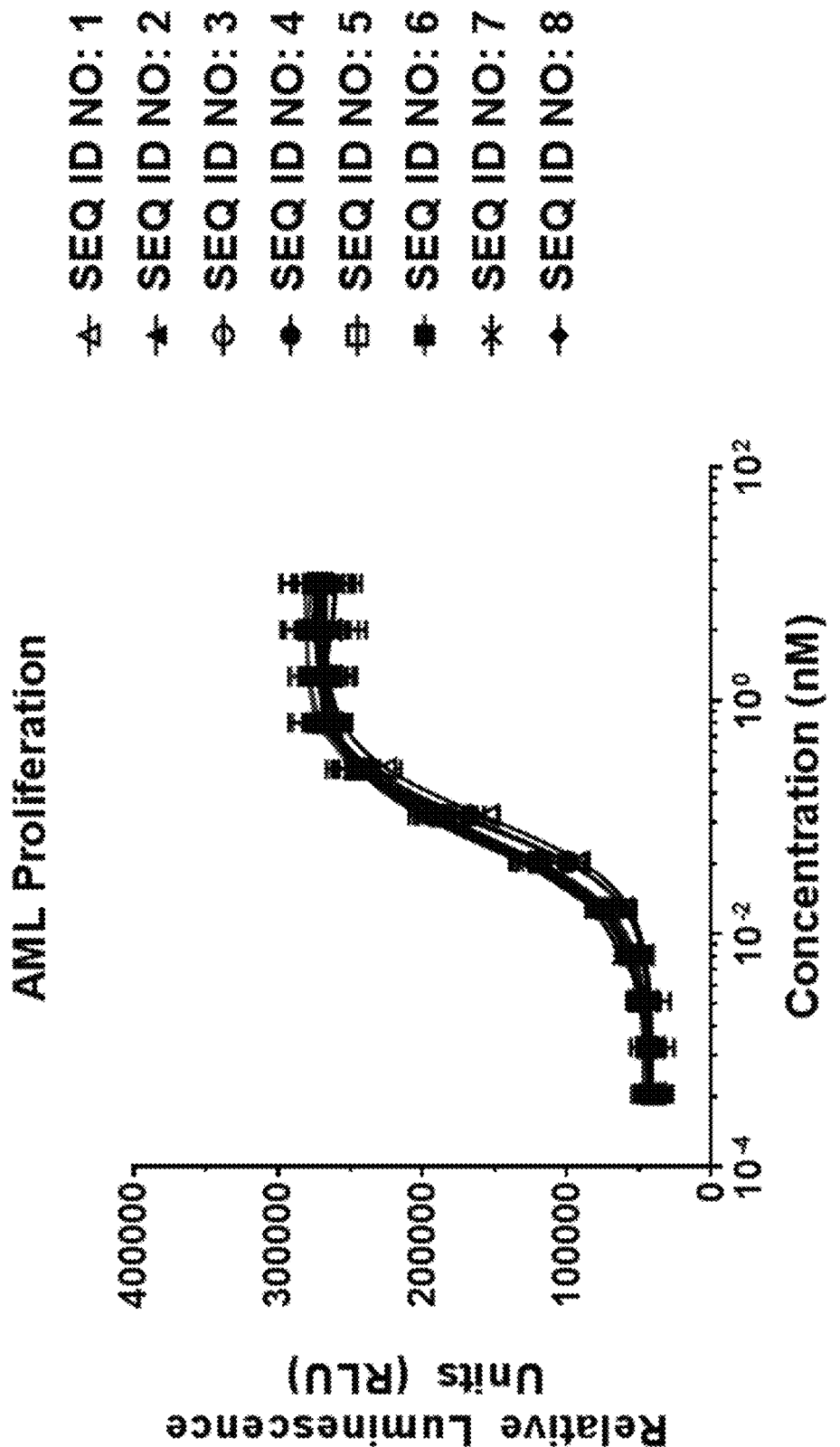
FIG. 5 illustrates proliferation of a human FLT3-expressing AML5 cell line induced by a titration (10-0.0004 nM) of human FLT3-ligand human hingeless IgG1 fusion protein (SEQ ID NO:1, open triangle), human FLT3-ligand (Δ5 amino acid) human hingeless IgG1 fusion protein (SEQ ID NO:2, closed triangle), human FLT3-ligand human IgG4 (S228P/L235E) fusion protein (SEQ ID NO:3, open circle), human FLT3-ligand human IgG4 (S228P/F234A/L235A) fusion protein (SEQ ID NO:4, closed circle), human FLT3-ligand (S128A/S151A) human hingeless IgG1 fusion protein (SEQ ID NO:5, open square), human FLT3-ligand (Δ5 amino acid) human IgG4 (S228P/F234A/L235A) fusion protein (SEQ ID NO:6, closed square), human FLT3-ligand (Δ10 amino acid) human hingeless IgG1 fusion protein (SEQ ID NO:7, cross), or human FLT3-ligand (Δ10 amino acid) human IgG4 (S228P/F234A/L235A) fusion protein (SEQ ID NO:8, closed diamond). The x-axis shows the protein concentration (nM) and the y-axis shows the relative luminescence units (RLU). Graph is a combination of two independent experiments. Experiment was performed in triplicate. Error bars represent standard deviation of the mean values. EC50 values are shown in Table 5.

We tested the potency in inducing FLT3-dependent proliferation in AML5 cells of the eight human FLT3-ligand Fc fusion protein variants with different Fc regions, or containing modifications in the FLT3-ligand derived sequence (SEQ ID NOs: 1-8). The eight FLT3L-Fc variants tested are as follows: human FLT3-ligand human hingeless IgG1 fusion protein (SEQ ID NO:1), human FLT3-ligand (Δ5 amino acid) human hingeless IgG1 fusion protein (SEQ ID NO:2), human FLT3-ligand human IgG4 (S228P/L235E) fusion protein (SEQ ID NO:3), human FLT3-ligand human IgG4 (S228P/F234A/L235A) fusion protein (SEQ ID NO:4), human FLT3-ligand (S128A/S151A) human hingeless IgG1 fusion protein (SEQ ID NO:5), human FLT3-ligand (Δ5 amino acid) human IgG4 (S228P/F234A/L235A) fusion protein (SEQ ID NO:6), human FLT3-ligand (Δ10 amino acid) human hingeless IgG1 fusion protein (SEQ ID NO:7), or human FLT3-ligand (Δ10 amino acid) human IgG4 (S228P/F234A/L235A) fusion protein (SEQ ID NO:8). The resulting EC50 values ranged between 0.071-0.088 nM. The results are summarized in Table 5 and depicted in FIG. 5.

TABLE 5

EC50 Values for SEQ ID NOs: 1-8
in an AML5 Proliferation Assay

| FLT3L-Fc Variant SEQ ID NO: | EC50 (nM) |
|---|---|
| 1 | 0.080 |
| 2 | 0.083 |
| 3 | 0.088 |
| 4 | 0.073 |
| 5 | 0.078 |
| 6 | 0.078 |

TABLE 5-continued

EC50 Values for SEQ ID NOs: 1-8
in an AML5 Proliferation Assay

| FLT3L-Fc Variant SEQ ID NO: | EC50 (nM) |
|---|---|
| 7 | 0.071 |
| 8 | 0.075 |

Example 6

In Vitro FLT3 Binding of Different FLT3L-Fc Fusion Proteins

In this example, we compared the in vitro binding to human recombinant FLT3 of eight different human FLT3-ligand human Fc fusion protein variants. We tested the in vitro FLT3 binding employing an enzyme-linked immunosorbent assay (ELISA).

Methods

Flt3L-Fc fusion protein constructs were serially diluted and added to 96-well nickel plates (Pierce) coated with his-tagged recombinant human Flt3 receptor (Sino Biologicals). Bound Flt3L-Fc was detected using a goat anti-human (H+L) polyclonal antibody conjugated to horseradish peroxidase (Jackson Immunoresearch). Signal was developed using TMB substrate then quenched prior to reading absorbance at 450 nm on a SpectraMax plate reader. Flt3L-Fc concentration was plotted against signal and fit to a 4PL curve to determine the EC50 value of each construct.

Results

Figure 6:
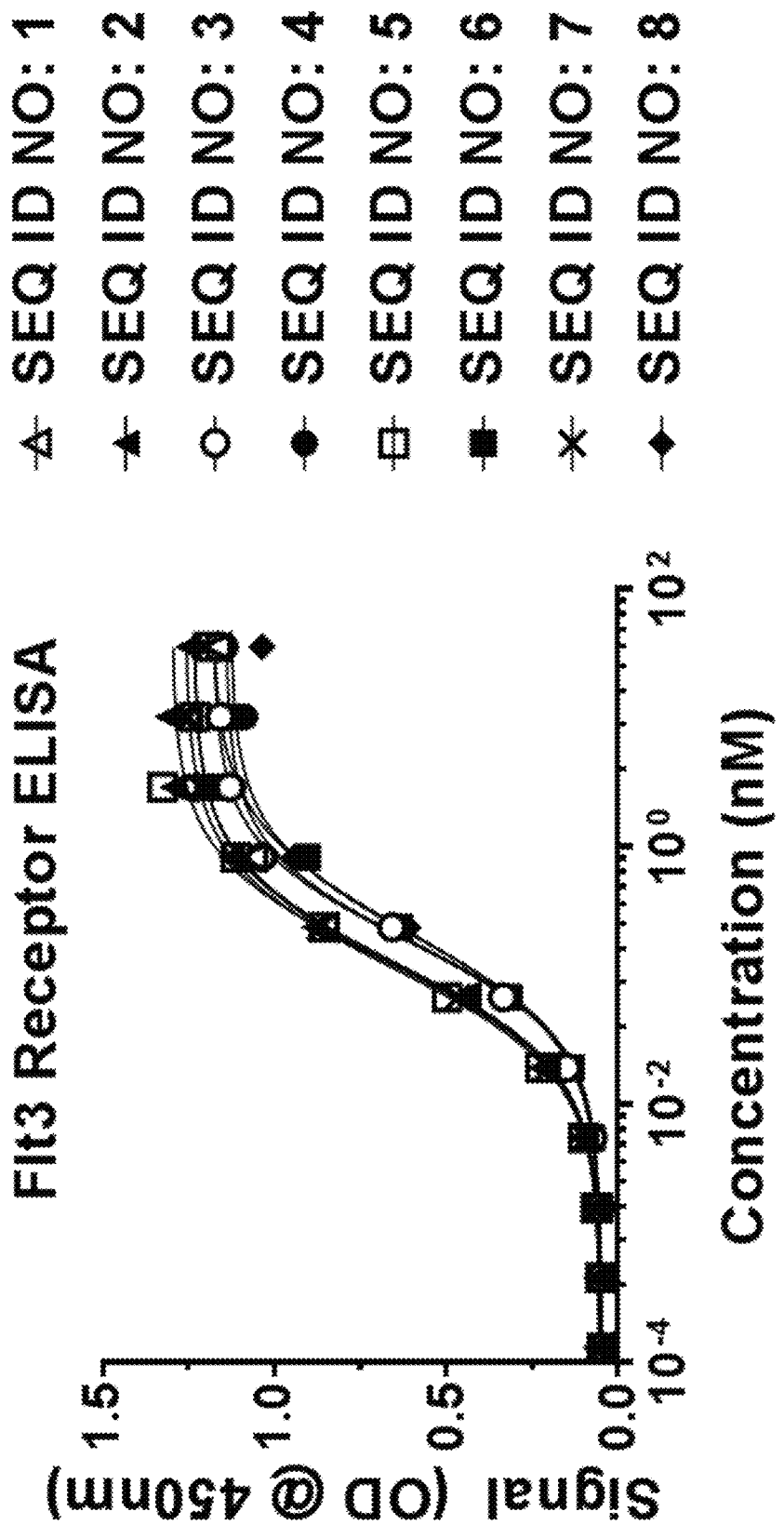
FIG. 6 illustrates binding to recombinant human FLT3 of a titration (35-0.0001 nM) of human FLT3-ligand human hingeless IgG1 fusion protein (SEQ ID NO:1, open triangle), human FLT3-ligand (Δ5 amino acid) human hingeless IgG1 fusion protein (SEQ ID NO:2, closed triangle), human FLT3-ligand human IgG4 (S228P/L235E) fusion protein (SEQ ID NO:3, open circle), human FLT3-ligand human IgG4 (S228P/F234A/L235A) fusion protein (SEQ ID NO:4, closed circle), human FLT3-ligand (S128A/S151A) human hingeless IgG1 fusion protein (SEQ ID NO:5, open square), human FLT3-ligand (Δ5 amino acid) human IgG4 (S228P/F234A/L235A) fusion protein (SEQ ID NO:6, closed square), human FLT3-ligand (Δ10 amino acid) human hingeless IgG1 fusion protein (SEQ ID NO:7, cross), or human FLT3-ligand (Δ10 amino acid) human IgG4 (S228P/F234A/L235A) fusion protein (SEQ ID NO:8, closed diamond). The x-axis shows the protein concentration (nM) and the y-axis shows the optical density (OD) at 450 nm. Graph is a result of one experiment. EC50 values are shown in Table 6.

These data demonstrated that binding to human FLT3 receptor was similar for FLT3-ligand Fc fusion proteins of the same Fc isotype (IgG1, SEQ ID NOs: 1, 2, 5, 7; or IgG4, SEQ ID NOs: 3, 4, 6, 8). EC50 values ranged between 0.11-0.13 nM for IgG1 constructs, 0.18-0.22 nM for IgG4 constructs. These data also demonstrated that short truncations at the C-terminus of the FLT3-ligand portion (SEQ ID NOs: 2, 6, 7, 8) or mutations that eliminate N-linked glycans in FLT3-ligand (SEQ ID NO: 5) also had negligible effect on binding to FLT3. The results are summarized in Table 6 and depicted in FIG. 6.

TABLE 6

EC50 Values for FLT3L-Fc SEQ ID NOs:
1-8 Binding to Human Recombinant FLT3

| FLT3L-Fc Variant SEQ ID NO: | EC50 (nM) |
|---|---|
| 1 | 0.12 |
| 2 | 0.13 |
| 3 | 0.18 |
| 4 | 0.18 |
| 5 | 0.11 |
| 6 | 0.22 |
| 7 | 0.12 |
| 8 | 0.20 |

Example 7

In Vitro FcRn Binding of Different FLT3L-Fc Fusion Proteins

In this example, we compared the in vitro binding of eight different human FLT3-ligand human Fc fusion proteins to human recombinant FcRn. We tested the in vitro FLT3 binding employing an enzyme-linked immunosorbent assay (ELISA).

Methods

Flt3L-Fc constructs were serially diluted and added to 96-well plates coated with recombinant human FcRn. The bound Flt3L-Fc was detected using a donkey anti-human (H+L) antibody conjugated to horseradish peroxidase (Jackson Immunoresearch). Signal was developed using TMB substrate then quenched prior to reading absorbance at 450-650 nm on a SpectraMax plate reader. Flt3L-Fc concentration was plotted against signal and fit to a 4PL curve. A full length IgG1 and IgG4 isotype was included in the initial experiment as Fc isotype controls.

Results

Figure 7:
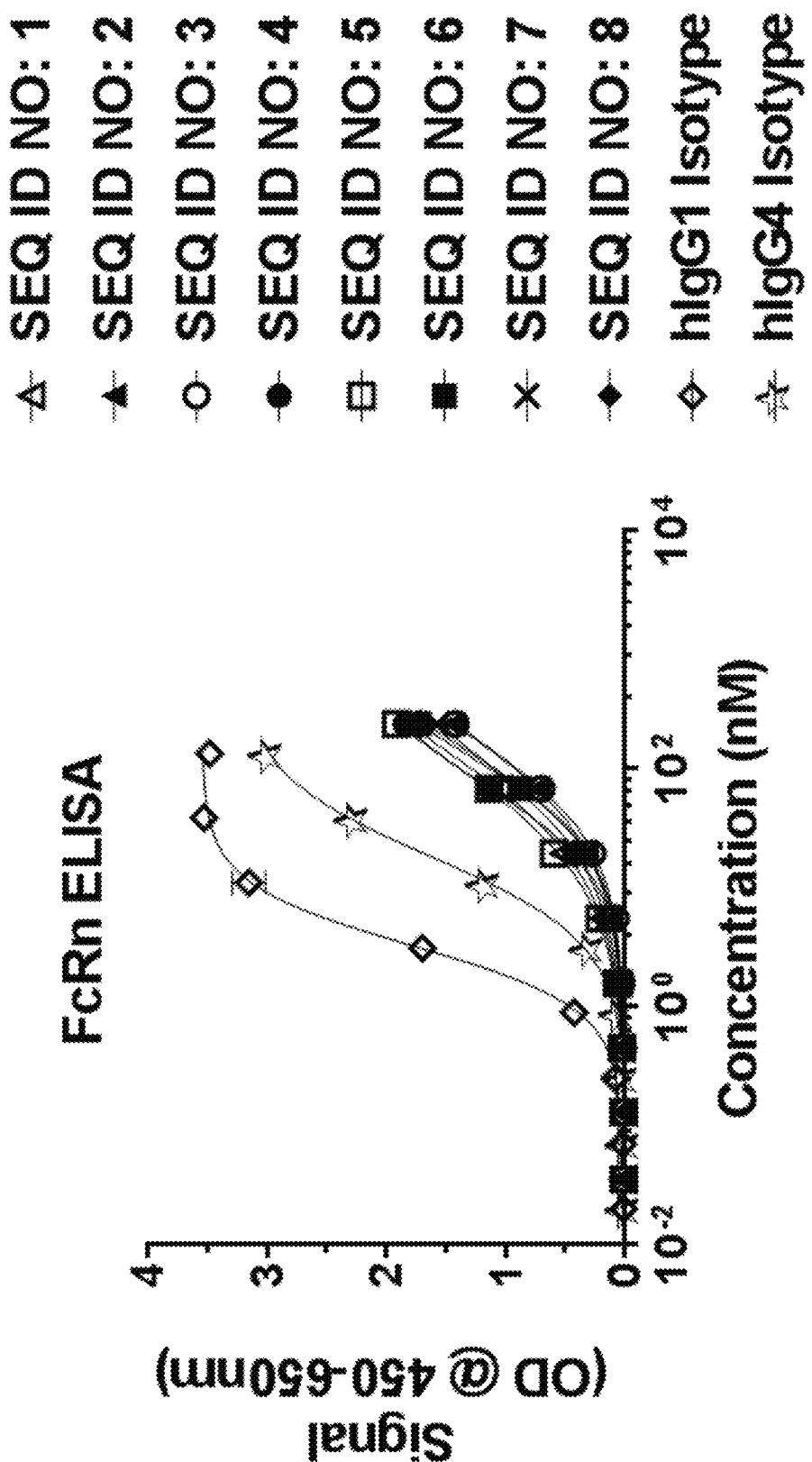
FIG. 7 illustrates binding of recombinant human FcRn with a dose titration (235-0.035 nM) of human FLT3-ligand human hingeless IgG1 fusion protein (SEQ ID NO:1, open triangle), human FLT3-ligand (Δ5 amino acid) human hingeless IgG1 fusion protein (SEQ ID NO:2, closed triangle), human FLT3-ligand human IgG4 (S228P/L235E) fusion protein (SEQ ID NO:3, open circle), human FLT3-ligand human IgG4 (S228P/F234A/L235A) fusion protein (SEQ ID NO:4, closed circle), human FLT3-ligand (S128A/S151A) human hingeless IgG1 fusion protein (SEQ ID NO:5, open square), human FLT3-ligand (Δ5 amino acid) human IgG4 (S228P/F234A/L235A) fusion protein (SEQ ID NO:6, closed square), human FLT3-ligand (Δ10 amino acid) human hingeless IgG1 fusion protein (SEQ ID NO:7, cross), human FLT3-ligand (Δ10 amino acid) human IgG4 (S228P/F234A/L235A) fusion protein (SEQ ID NO:8, closed diamond), human IgG1 isotype antibody (open diamond), or human IgG4 isotype antibody (open star). The x-axis shows the protein concentration (nM) and the y-axis shows the optical density (OD) at 450-650 nm. Graph is a result of one experiment. Experiment was performed in duplicate. Error bars represent standard deviation of the mean values. Estimated EC50 values are shown in Table 7.

These data demonstrated that binding to human FcRn in this assay was weaker for the eight human FLT3-ligand Fc fusion proteins with different Fc variants (SEQ ID NOs: 1-8) compared to the human IgG1 and IgG4 isotype antibody controls, but relatively similar to each other. EC50 values for the FLT3L-Fc protein variant samples summarized in Table 7 are only estimates, as none of the FLT3L-Fc variants of SEQ ID NOs: 1-8 demonstrated saturating signal at the highest concentration tested. The results are also depicted in FIG. 7.

TABLE 7

Estimated EC50 values for FLT3L-Fc Variants SEQ
ID NOs: 1-8 Binding to Human Recombinant FcRn

| FLT3L-Fc Variant SEQ ID NO: | EC50 (nM) |
|---|---|
| 1 | 150.70 |
| 2 | 300.40 |
| 3 | 183.30 |
| 4 | 68.76 |
| 5 | 132.70 |
| 6 | 136.50 |
| 7 | 157.90 |
| 8 | 139.90 |
| hIgG1 Isotype | 4.46 |
| hIgG4 Isotype | 25.86 |

Example 8

Ability of FLT3L-Fc Variants to Compete for Binding to Human FcγRI

In this example, we compared the in vitro ability of eight different human FLT3-ligand human Fc fusion proteins to compete with a human IgG molecule for binding to human recombinant FcγRI. To evaluate the ability to compete for binding to FcγRI, we employed an amplified luminescent proximity homogeneous assay (AlphaScreen® by Perkin Elmer).

Methods

Serial dilutions of the Flt3L-Fc constructs were added to 96-well plates containing biotinylated FcγRI protein (Sino Biological). Human IgG acceptor beads (Perkin Elmer) were added to the plate, followed by streptavidin donor beads (Perkin Elmer). Acceptor beads contain thioxene derivatives. Donor beads contain a photosensitizer, phthalocyanine, which converts ambient oxygen to an excited and reactive form of O2, singlet oxygen (molecular oxygen with a single excited electron), upon illumination at 680 nm. If an acceptor bead is within 200 nm of a donor bead, energy is transferred from the singlet oxygen to thioxene derivatives within the acceptor bead, subsequently culminating in light production at 520-620 nm. Signal was measured on an EnVision™ plate reader (Perkin Elmer). Flt3L-Fc concentration was plotted against signal and fit to a 4PL curve. Full length IgG1 and IgG4 molecules were included on each plate as Fc isotype controls.

Results

Figure 8:
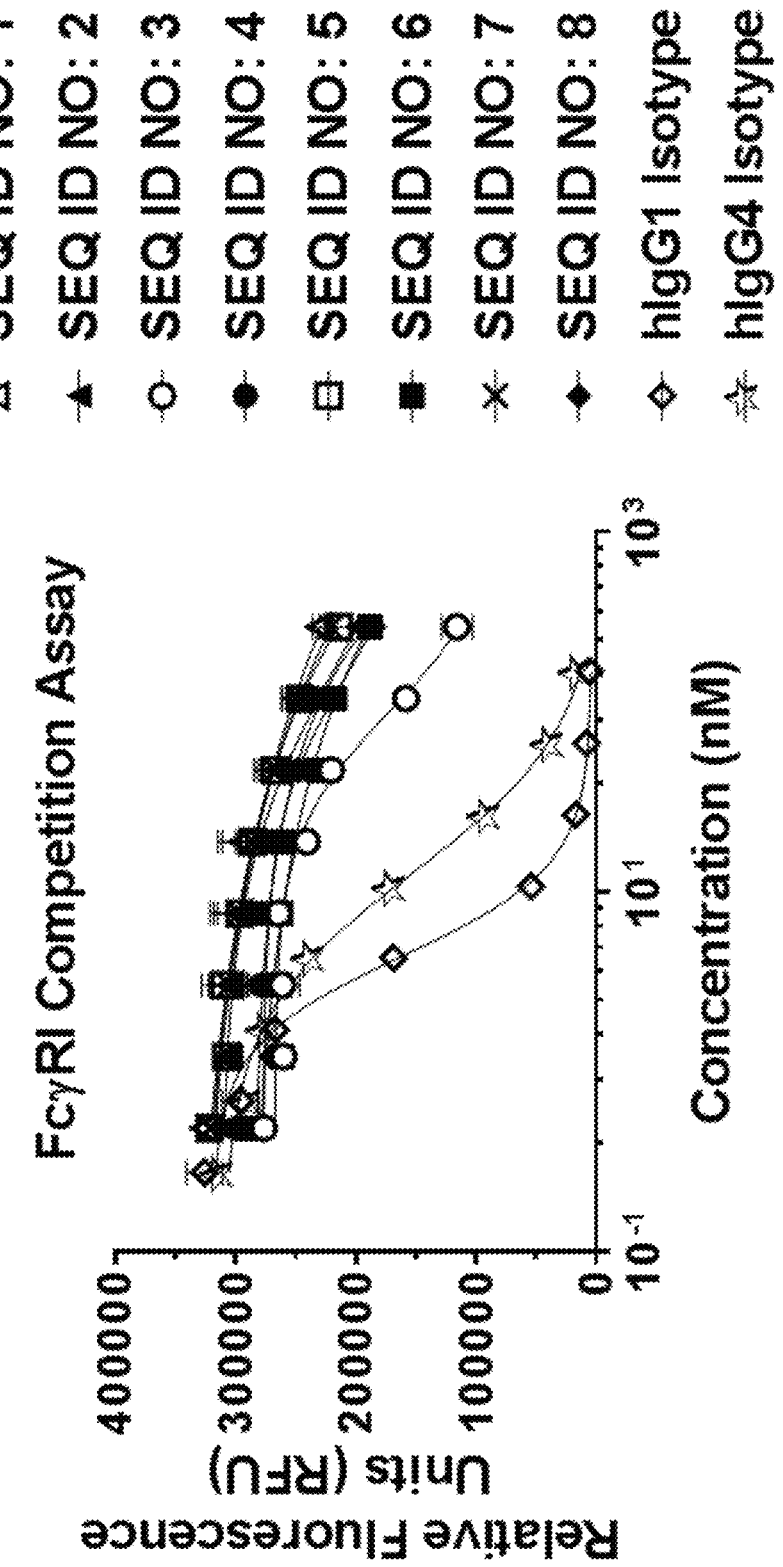
FIG. 8 illustrates binding of human IgG to recombinant human FcγRI competed with a titration (294-0.48 nM) of human FLT3-ligand human hingeless IgG1 fusion protein (SEQ ID NO:1, open triangle), human FLT3-ligand (Δ5 amino acid) human hingeless IgG1 fusion protein (SEQ ID NO:2, closed triangle), human FLT3-ligand human IgG4 (S228P/L235E) fusion protein (SEQ ID NO:3, open circle), human FLT3-ligand human IgG4 (S228P/F234A/L235A) fusion protein (SEQ ID NO:4, closed circle), human FLT3-ligand (S128A/S151A) human hingeless IgG1 fusion protein (SEQ ID NO:5, open square), human FLT3-ligand (Δ5 amino acid) human IgG4 (S228P/F234A/L235A) fusion protein (SEQ ID NO:6, closed square), human FLT3-ligand (Δ10 amino acid) human hingeless IgG1 fusion protein (SEQ ID NO:7, cross), human FLT3-ligand (Δ10 amino acid) human IgG4 (S228P/F234A/L235A) fusion protein (SEQ ID NO:8, closed diamond), human IgG1 isotype antibody (open diamond), or human IgG4 isotype antibody (open star). The x-axis shows the protein concentration (nM) and the y-axis shows the relative fluorescence units (RFU). Graph is a result of one experiment. Experiment was performed in duplicate. Error bars represent standard deviation of the mean values. EC50 values are shown in Table 8.

These data demonstrated that none of the eight human FLT3-ligand Fc fusion proteins with different Fc variants (SEQ ID NOs: 1-8) could fully compete with human IgG for binding to FcγRI at the highest concentrations tested. Both the human IgG1 and IgG4 isotype antibody controls demonstrated complete dose-response curves, with the IgG4 isotype showing reduced competition compared to the IgG1. The results are summarized in Table 8 and depicted in FIG. 8.

TABLE 8

EC50 Values for the Ability of FLT3L-Fc Variants to Compete for Binding to FcγRI

| FLT3L-Fc Variant SEQ ID NO: | EC50 (nM) |
|---|---|
| 1 | NA |
| 2 | NA |
| 3 | NA |
| 4 | NA |
| 5 | NA |
| 6 | NA |
| 7 | NA |
| 8 | NA |
| hIgG1 Isotype | 4.44 |
| hIgG4 Isotype | 13.62 |

Example 9

Ability of FLT3L-Fc Variants to Compete for Binding to Human FcγRIIIa

In this example, we compared the in vitro ability of eight different human FLT3-ligand human Fc fusion proteins to compete for binding of human recombinant FcγRIIIa (V-variant) with a human IgG molecule. To evaluate the ability to compete for binding to FcγRIIIa, we employed an AlphaScreen® by Perkin Elmer. The methods are analogous to those described in Example 8.

Methods

Serial dilutions of the Flt3L-Fc constructs were added to 96-well plates containing biotinylated FcγRIIIa (Val 176 variant) protein (Sino Biological). Human IgG acceptor beads (Perkin Elmer) were added to the plate, followed by streptavidin donor beads (Perkin Elmer), and signal was measured on an EnVision™ plate reader. Flt3L-Fc concentration was plotted against signal and fit to a 4PL curve. Full length IgG1 and IgG4 molecules were included on each plate as Fc isotype controls.

Results

Figure 9:
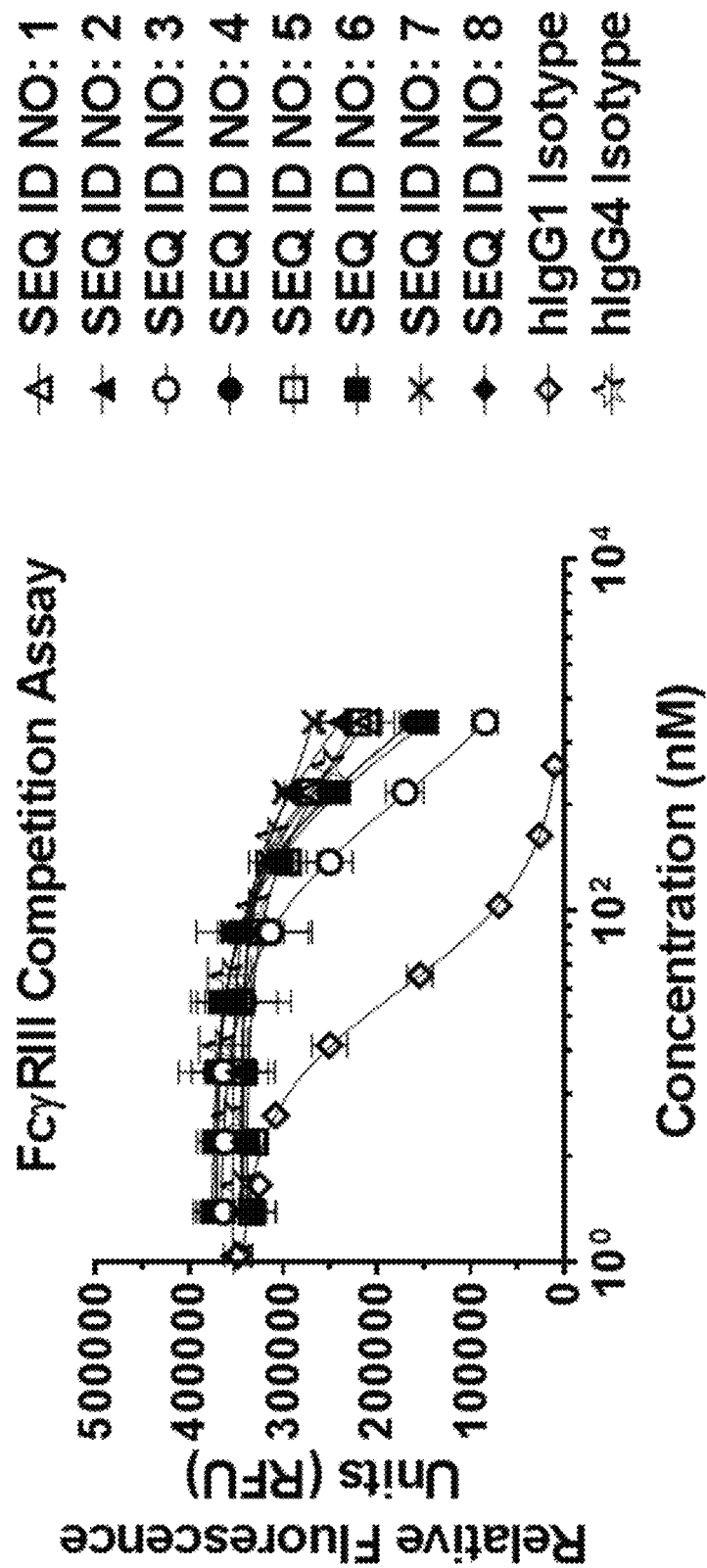
FIG. 9 illustrates binding of human IgG to recombinant human FcγRIIIa (V-variant) competed with a dose titration (1176-1.92 nM) of human FLT3-ligand human hingeless IgG1 fusion protein (SEQ ID NO:1, open triangle), human FLT3-ligand (Δ5 amino acid) human hingeless IgG1 fusion protein (SEQ ID NO:2, closed triangle), human FLT3-ligand human IgG4 (S228P/L235E) fusion protein (SEQ ID NO:3, open circle), human FLT3-ligand human IgG4 (S228P/F234A/L235A) fusion protein (SEQ ID NO:4, closed circle), human FLT3-ligand (S128A/S151A) human hingeless IgG1 fusion protein (SEQ ID NO:5, open square), human FLT3-ligand (Δ5 amino acid) human IgG4 (S228P/F234A/L235A) fusion protein (SEQ ID NO:6, closed square)), human FLT3-ligand (Δ10 amino acid) human hingeless IgG1 fusion protein (SEQ ID NO:7, cross), human FLT3-ligand (Δ10 amino acid) human IgG4 (S228P/F234A/L235A) fusion protein (SEQ ID NO:8, closed diamond), human IgG1 isotype antibody (open diamond), or human IgG4 isotype antibody (open star). The x-axis shows the protein concentration (nM) and the y-axis shows the relative fluorescence units (RFU). Graph is a result of one experiment. Experiment was performed in duplicate. Error bars represent standard deviation of the mean values. EC50 values are shown in Table 9.

These data demonstrated that none of the eight human FLT3-ligand Fc fusion proteins with different Fc variants (SEQ ID NOs: 1-8) could fully compete with human IgG for binding to FcγRIIIa (Val176 variant) at the highest concentrations tested. Only human IgG1 isotype control demonstrated a complete dose-response curve. The results are summarized in Table 9 and depicted in FIG. 9.

TABLE 9

EC50 Values for the Ability of FLT3L-Fc Variants to Compete for Binding to FcγRIIIa

| FLT3L-Fc Variant SEQ ID NO: | EC50 (nM) |
|---|---|
| 1 | NA |
| 2 | NA |
| 3 | NA |
| 4 | NA |
| 5 | NA |
| 6 | NA |
| 7 | NA |
| 8 | NA |
| hIgG1 Isotype | 32.09 |
| hIgG4 Isotype | 325.90 |

Example 10

In Vitro Binding of FLT3L-Fc Variants to Human C1q

In this example, we compared the in vitro binding of eight different human FLT3-ligand human Fc fusion proteins to human recombinant complement protein, C1q. To evaluate binding to C1q, we employed an ELISA.

Methods

Serial dilutions of the Flt3L-Fc constructs were immobilized onto 96-well plates, followed by incubation with the recombinant human C1q protein (Fitzgerald). Binding was detected using a sheep anti-C1q antibody conjugated to horseradish peroxidase (BioRad). Signal was developed using TMB substrate then quenched prior to reading absorbance at 450-650 nm on a SpectraMax plate reader. Flt3L-Fc concentration was plotted against signal and fit to a 4PL curve. Full length IgG1 and IgG4 molecules were included on each plate as Fc isotype controls.

Results

Figure 10:
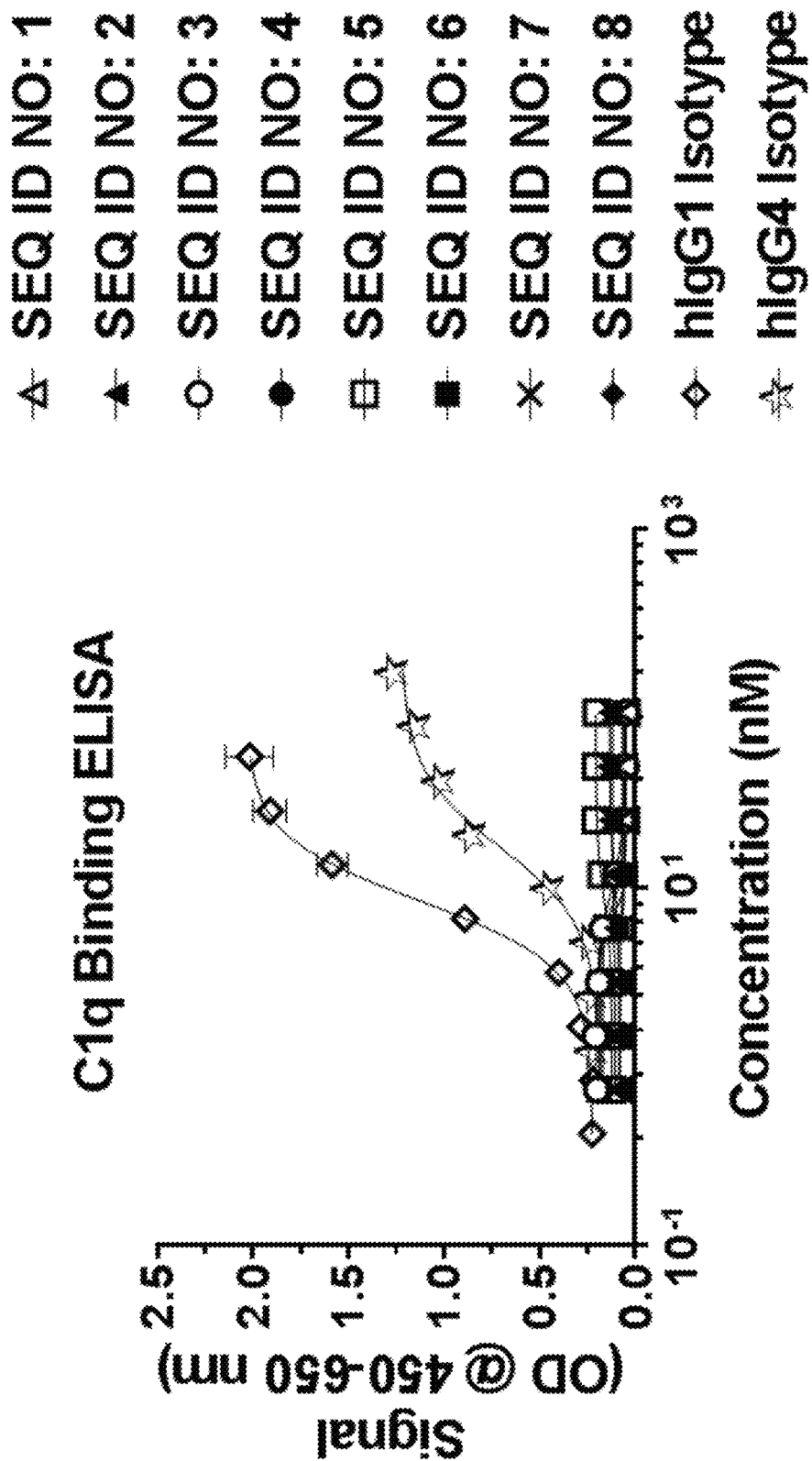
FIG. 10 illustrates binding of recombinant human C1q to a titration (94-0.74 nM) of human FLT3-ligand human hingeless IgG1 fusion protein (SEQ ID NO:1, open triangle), human FLT3-ligand (Δ5 amino acid) human hingeless IgG1 fusion protein (SEQ ID NO:2, closed triangle), human FLT3-ligand human IgG4 (S228P/L235E) fusion protein (SEQ ID NO:3, open circle), human FLT3-ligand human IgG4 (S228P/F234A/L235A) fusion protein (SEQ ID NO:4, closed circle), human FLT3-ligand (S128A/S151A) human hingeless IgG1 fusion protein (SEQ ID NO:5, open square), human FLT3-ligand (Δ5 amino acid) human IgG4 (S228P/F234A/L235A) fusion protein (SEQ ID NO:6, closed square)), human FLT3-ligand (Δ10 amino acid) human hingeless IgG1 fusion protein (SEQ ID NO:7, cross), human FLT3-ligand (Δ10 amino acid) human IgG4 (S228P/F234A/L235A) fusion protein (SEQ ID NO:8, closed diamond), human IgG1 isotype antibody (open diamond), or human IgG4 isotype antibody (open star). The x-axis shows the protein concentration (nM) and the y-axis shows the optical density (OD) at 450-650 nm. Graph is a result of one experiment. Experiment was performed in duplicate. Error bars represent standard deviation of the mean values. EC50 values are shown in Table 10.

These data demonstrated that the eight human FLT3-ligand Fc fusion proteins with different Fc variants (SEQ ID NOs: 1-8) were devoid of C1q binding ability. Both the human IgG1 and IgG4 isotype controls demonstrated binding to C1q, with the IgG4 isotype showing reduced binding compared to the IgG1. The results are summarized in Table 10 and depicted in FIG. 10.

TABLE 10

EC50 Values for FLT3L-Fc Variants Binding to Human C1q

| FLT3L-Fc Variant SEQ ID NO: | EC50 (nM) |
|---|---|
| 1 | NA |
| 2 | NA |
| 3 | NA |
| 4 | NA |
| 5 | NA |
| 6 | NA |
| 7 | NA |
| 8 | NA |
| hIgG1 Isotype | 8.40 |
| hIgG4 Isotype | 16.69 |

Example 11

In Vivo Pharmacokinetics of FLT3L-Fc Variants in Mice

In this example, we compared the single dose pharmacokinetics of eight different human FLT3-ligand human Fc fusion proteins in C57Bl/6 mice.

Methods

FLT3L-Fc Variants (SEQ ID NOs:1-8) were administered to male C57Bl/6 mice n=4/group (Covance, Wis.) at 5 mg/kg via a single intraperitoneal (IP) injection to characterize their basic pharmacokinetic (PK) profiles. Serial serum samples collected from mice were analyzed using U-PLEX FLT3L assay (Mesos Scale Discovery, MSD) according to the manufacturer's instructions. The calibration curve used the respective individual FLT3-ligand fusion proteins as reference standards in spiked mouse matrix fit to a 4-parameter logistic model with 1/Y2 weighting. Analyte concentrations were determined from the electrochemiluminescence signals back-fitted to the calibration curve. Serum concentration-time profiles were used to calculate the mean±SD serum PK parameters by non-compartmental PK analysis. Area under the curve (AUC0-7d) was determined through day 7 due to development of immunogenicity. Clearance (Cl/F) and half-life values reported in Table 11 are considered estimates due to the incomplete terminal extrapolation.

Results

Figure 11A:
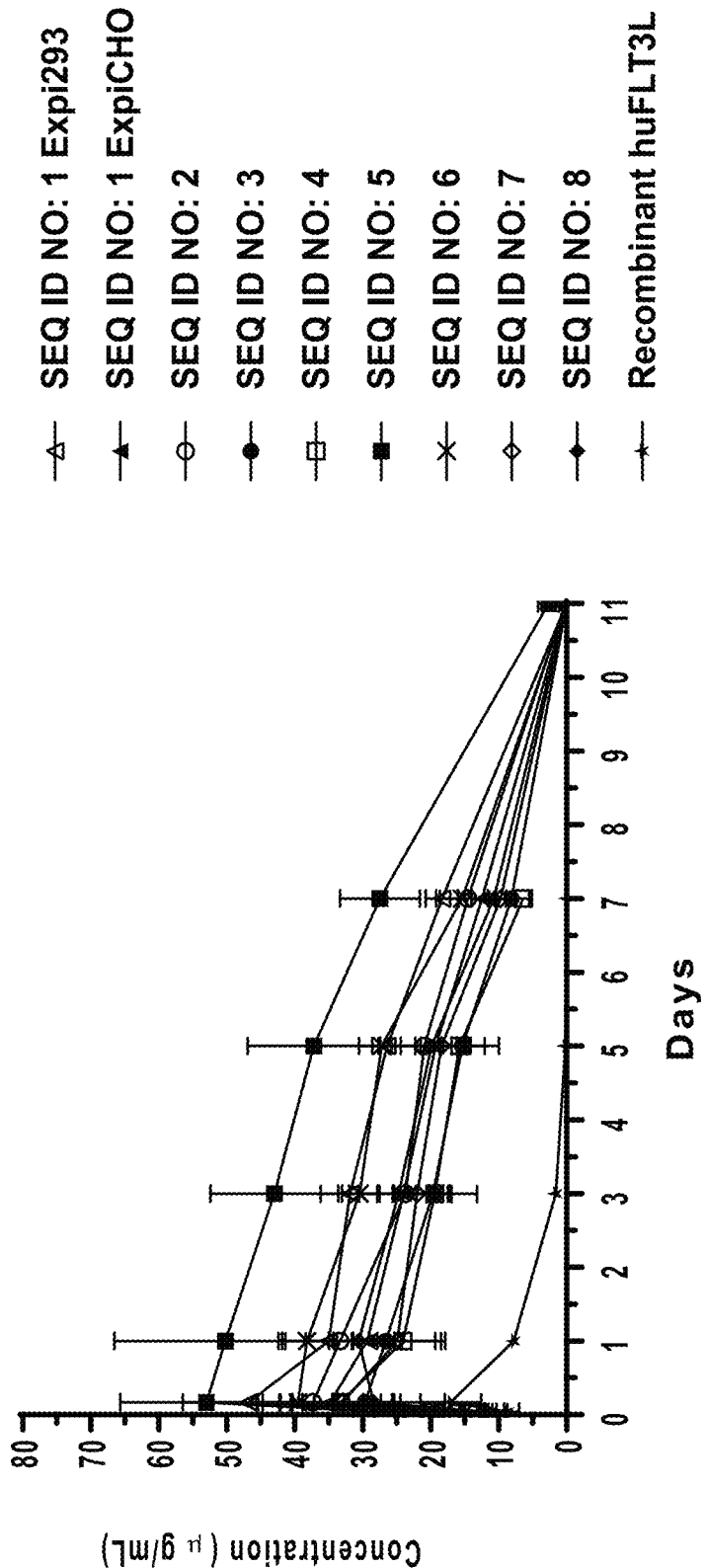
FIGS. 11A-11B illustrate a mouse serum concentration-time profile following 5 mg/kg intraperitoneal dosing of 8 FLT3-ligand fusion proteins relative to recombinant FLT3-ligand. Panel A: linear scale; Panel B: Log10 scale after a single dose intravenous administration (5 mg/kg) of human FLT3-ligand human hingeless IgG1 fusion protein produced in Expi293 expression system (SEQ ID NO:1 Expi293, open triangle), human FLT3-ligand human hingeless IgG1 fusion protein produced in ExpiCHO expression system (SEQ ID NO:1 ExpiCHO, closed triangle), human FLT3-ligand (Δ5 amino acid) human hingeless IgG1 fusion protein (SEQ ID NO:2, open circle), human FLT3-ligand human IgG4 (S228P/L235E) fusion protein (SEQ ID NO:3, closed circle), human FLT3-ligand human IgG4 (S228P/F234A/L235A) fusion protein (SEQ ID NO:4, open square), human FLT3-ligand (S128A/S151A) human hingeless IgG1 fusion protein (SEQ ID NO:5, closed square), human FLT3-ligand (Δ5 amino acid) human IgG4 (S228P/F234A/L235A) fusion protein (SEQ ID NO:6, cross), human FLT3-ligand (Δ10 amino acid) human hingeless IgG1 fusion protein (SEQ ID NO:7, open diamond), human FLT3-ligand (Δ10 amino acid) human IgG4 (S228P/F234A/L235A) fusion protein (SEQ ID NO:8, closed diamond), or recombinant human FLT3-ligand (Recombinant huFLT3L, closed star). Graph is a result of one experiment. The x-axis shows days post injection and the y-axis shows protein concentration in serum (μg/mL). Each data point represents the mean value of 4 animals. Error bars represent standard deviation (SD) of the mean values. Mean pharmacokinetic values±SD are shown in Table 11.
Figure 11B:
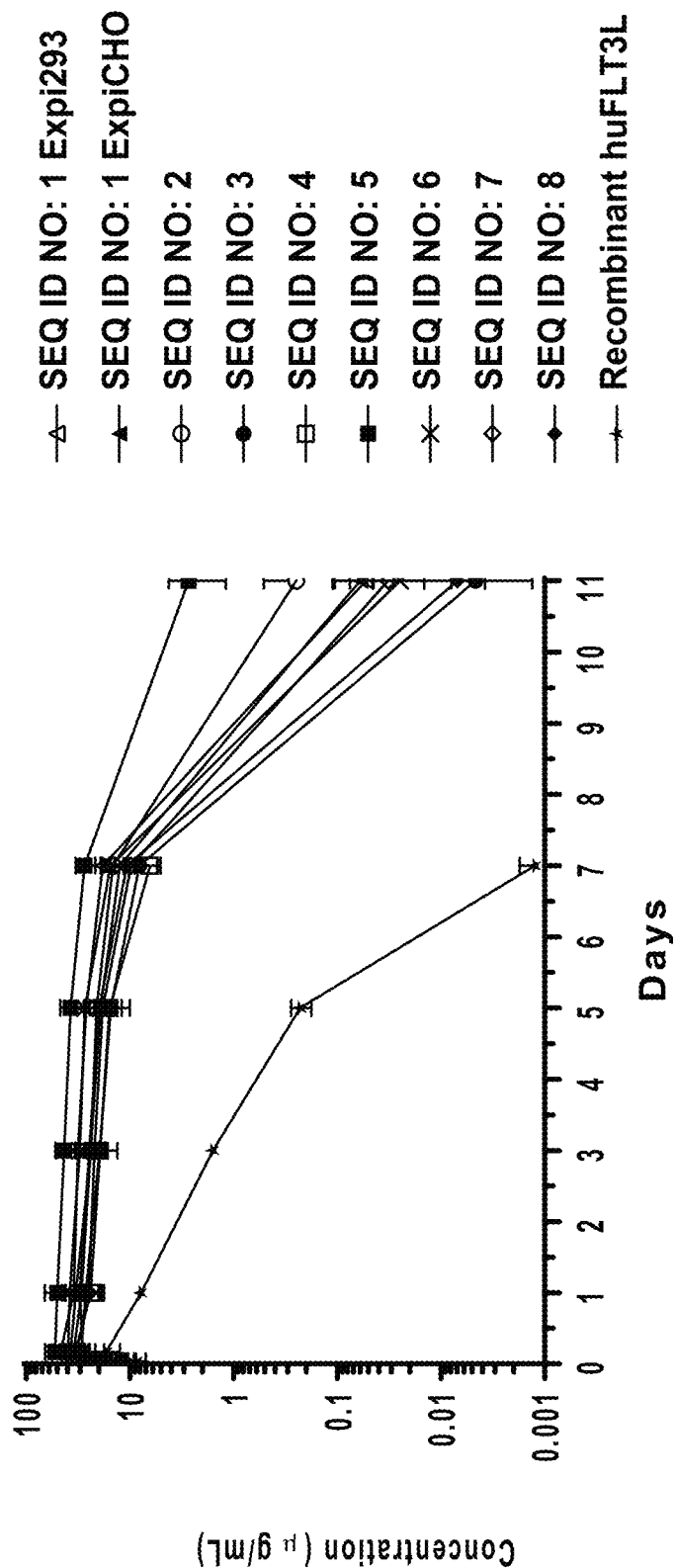

Pharmacokinetic analysis demonstrated that all eight Fc-fusions significantly enhanced the AUC exposure by approximately 5-12-fold in comparison to native human Flt3L, resulting in reduced FLT3-ligand clearance and prolonging the half-life (Table 11). We further observed a potential role of N-linked glycosylation on the pharmacokinetics because the aglycosylated FLT3L-Fc variant (SEQ ID NO: 5) had the highest AUC exposure. Additionally, we observed cell line dependent differences in PK evident by comparing data for samples corresponding to SEQ ID NO:1 produced in either Expi293 or ExpiCHO cells. The results are summarized in Table 11 and depicted in FIGS. 11A-11B.

TABLE 11

Single-Dose Pharmacokinetic Values for SEQ ID NOs: 1-8 in C57Bl/6 mice.

| SEQ ID NO | $AUC_{0-7d}$ (µg*d/mL) | Cl/F* (mL/d/kg) | $C_{max}$ (µg/mL) | Half-life* (d) |
|---|---|---|---|---|
| 1 - Expi293 | 209 ± 28.2 | 13.3 ± 2.26 | 46.8 ± 9.72 | 6.54 ± 0.653 |
| 1 - ExpiCHO | 159 ± 29.6 | 20.9 ± 7.07 | 34.8 ± 7.45 | 5.15 ± 1.40 |
| 2 | 171 ± 45.7 | 18.9 ± 6.11 | 38.9 ± 8.13 | 5.34 ± 0.795 |
| 3 | 131 ± 9.60 | 28.9 ± 2.83 | 29.7 ± 4.00 | 3.64 ± 0.313 |
| 4 | 128 ± 37.4 | 33.3 ± 9.38 | 33.3 ± 8.80 | 3.34 ± 0.162 |
| 5 | 287 ± 71.4 | 8.72 ± 2.38 | 54.1 ± 13.4 | 8.02 ± 3.24 |
| 6 | 205 ± 8.77 | 15.9 ± 3.10 | 42.3 ± 1.57 | 5.10 ± 1.54 |
| 7 | 143 ± 26.1 | 25.1 ± 6.38 | 33.0 ± 7.63 | 4.63 ± 1.00 |
| 8 | 158 ± 52.3 | 24.4 ± 8.02 | 31.9 ± 11.4 | 4.16 ± 0.238 |
| Recombinant huFLT3L | 23.5 ± 3.84 | 215 ± 35.4 | 17.1 ± 4.51 | 0.785 ± 0.0441 |

*CL/F and Half-life are estimates for Fc-fusions due to incomplete terminal extrapolation.

Example 12

Ability of FLT3L-Fc Variants to Promote Proliferation and Expansion of cDC1

In this example, we compared the ability of eight different human FLT3-ligand human Fc fusion proteins (SEQ ID NOs: 1-8) to induce proliferation of and expand conventional dendritic cell subtype 1 (cDC1) in C57Bl/6.

Methods

Spleens were harvested from C57BL/6 mice from FIG. 11 at Day 11 post injection at 4° C. in HypoThermosol solution (BioLife Solutions). Spleens were then dissociated by using the gentleMACS Dissociator (Miltenyi Biotec) with heaters, following manufacturer's protocol. After enzymatic digestion, cell suspension was filtered through a 70 µm cell strainer. The remaining tube and strainer were rinsed 1× with 15-20 ml of RPMI and collected with the rest of the sample. Cells were centrifuged at 500 g for 5 min at room temperature. Supernatant was discarded and cells were washed 1× with PBS. Residual red blood cells were lysed by adding 2 ml of ACK lysis to each sample for 1-2 min at room temperature. FACS staining Buffer (BD Bioscience) was added to the samples to stop the ACK lysis activity. Cells were spun down and washed additionally with PBS. Samples were then stained with Live/Dead Fixable Aqua Dead Cell Stain Kit (ThermoFisher) at 1:750 dilution for 15 min at 4° C. Cells were washed 2× with FACS staining buffer, then Fc blocked for 30 min at 4° C. FACS antibodies (Biolegend) were directly added to the blocked samples and incubated at 4° C. for 30 min without spinning down or washing out the Fc block. Cells were washed 2x, resuspended in Staining Buffer, and analyzed by LSR Fortessa FACS analyzer. Raw data were analyzed by FlowJo X (BD Bioscience).

Results

Figure 12:
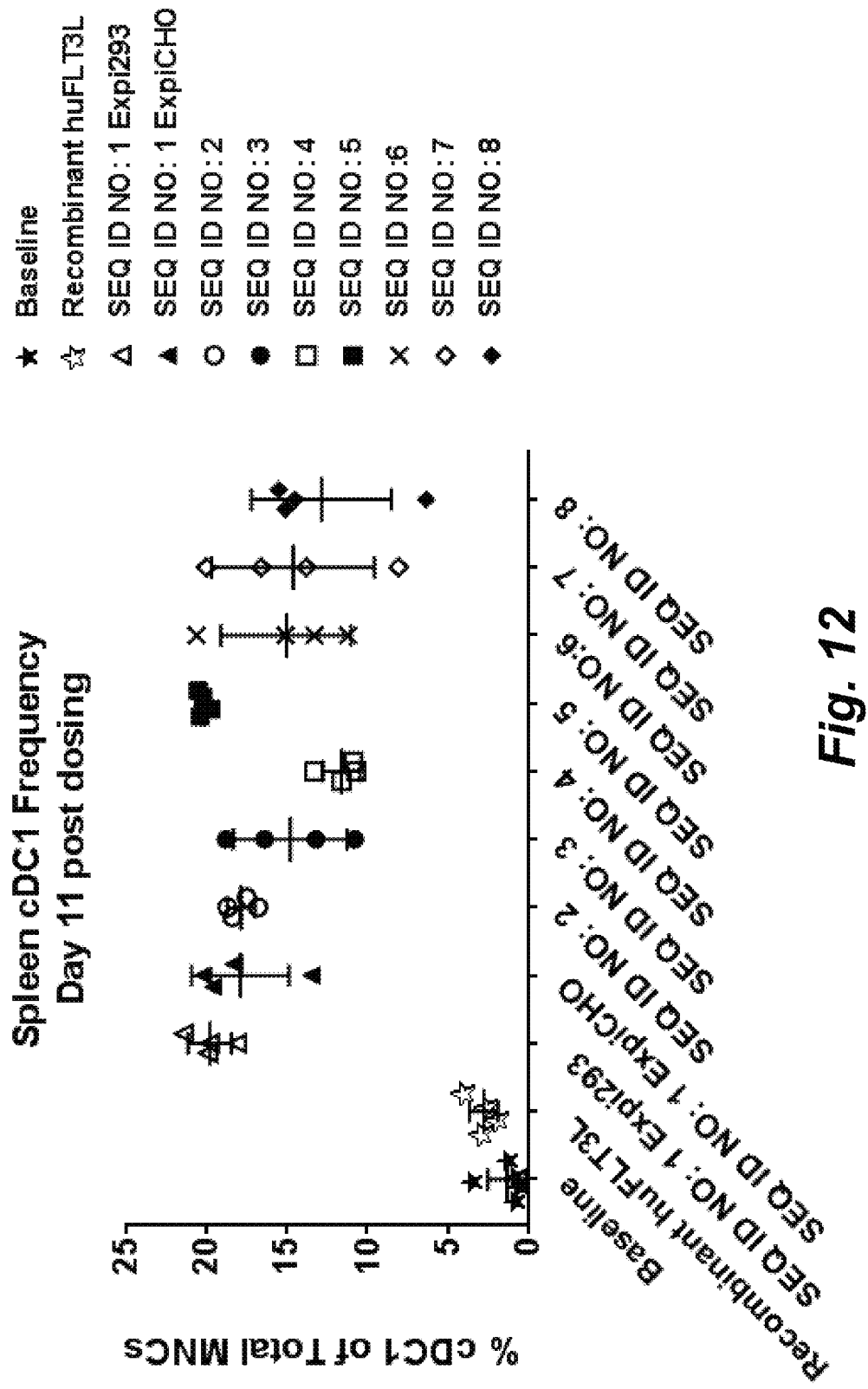
FIG. 12 illustrates day 11 frequency of conventional dendritic cell subtype 1 (cDC1) in spleens of C57BL/6 mice administrated intravenously with 5 mg/kg of human FLT3-ligand human hingeless IgG1 fusion protein produced in Expi293 expression system (SEQ ID NO:1 Expi293, open triangle), human FLT3-ligand human hingeless IgG1 fusion protein produced in ExpiCHO expression system (SEQ ID NO:1 ExpiCHO, closed triangle), human FLT3-ligand (Δ5 amino acid) human hingeless IgG1 fusion protein (SEQ ID NO:2, open circle), human FLT3-ligand human IgG4 (S228P/L235E) fusion protein (SEQ ID NO:3, closed circle), human FLT3-ligand human IgG4 (S228P/F234A/L235A) fusion protein (SEQ ID NO:4, open square), human FLT3-ligand (S128A/S151A) human hingeless IgG1 fusion protein (SEQ ID NO:5, closed square), human FLT3-ligand (Δ5 amino acid) human IgG4 (S228P/F234A/L235A) fusion protein (SEQ ID NO:6, cross), human FLT3-ligand (Δ10 amino acid) human hingeless IgG1 fusion protein (SEQ ID NO:7, open diamond), human FLT3-ligand (Δ10 amino acid) human IgG4 (S228P/F234A/L235A) fusion protein (SEQ ID NO:8, closed diamond), or recombinant human FLT3-ligand (Recombinant huFLT3L, open star) at day 0. Baseline cDC1 frequency is indicated (closed star). The x-axis shows the percentage of splenic cDC1 in total mononuclear cells (MNCs). Graph is a result of one experiment. Each individual symbol represents the data point of a single mouse. Horizontal bars represent the mean values and the error bars represent standard deviation of the mean values. Mean frequency of each group is shown in Table 12.

The data demonstrated that the ability of the eight human FLT3-ligand Fc fusion proteins with different Fc variants (SEQ ID NOs: 1-8) to expand splenic conventional dendritic cell subtype 1 (cDC1) in vivo at day 11 in mice was greater than that of the recombinant FLT3-ligand after a single dose administration at day 0. The results are summarized in Table 12 and depicted in FIG. 12.

TABLE 12

Average Frequency of Splenic cDC1 at day 11 in C57Bl/6 Mice Injected with FLT3L-Fc Variants SEQ ID NO: 1-8 at Day 0

| FLT3L-Fc Variant SEQ ID NO: | % cDC1 in total MNCs |
|---|---|
| 1 - Expi293 | 19.8 |
| 1 - ExpiCHO | 17.9 |
| 2 | 17.85 |
| 3 | 14.8 |
| 4 | 11.62 |
| 5 | 20.2 |
| 6 | 15.05 |
| 7 | 14.62 |
| 8 | 12.87 |
| Recombinant huFLT3L | 2.8 |
| Baseline | 1.36 |

Example 13

In Vitro Potency of FLT3L-Fc Variants in Cell Proliferation Assay

In this example, we compared the in vitro potency of four different human FLT3-ligand human Fc fusion proteins: human FLT3-ligand human hingeless IgG1 fusion protein (SEQ ID NO:1), human FLT3-ligand (Δ5 amino acid) human IgG4 (S228P/F234A/L235A) fusion protein (SEQ ID NO:6), human FLT3-ligand human hingeless IgG1 (M252Y/S254T/T256E) fusion protein (SEQ ID NO:9), or human FLT3-ligand (Δ5 amino acid) human IgG4 (S228P/F234A/L235A/M252Y/S254T/T256E) fusion protein (SEQ ID NO:14). To evaluate the in vitro potency, we employed an AML5 cell proliferation assay. The methods are as described above in Example 5.

Results

Figure 13:
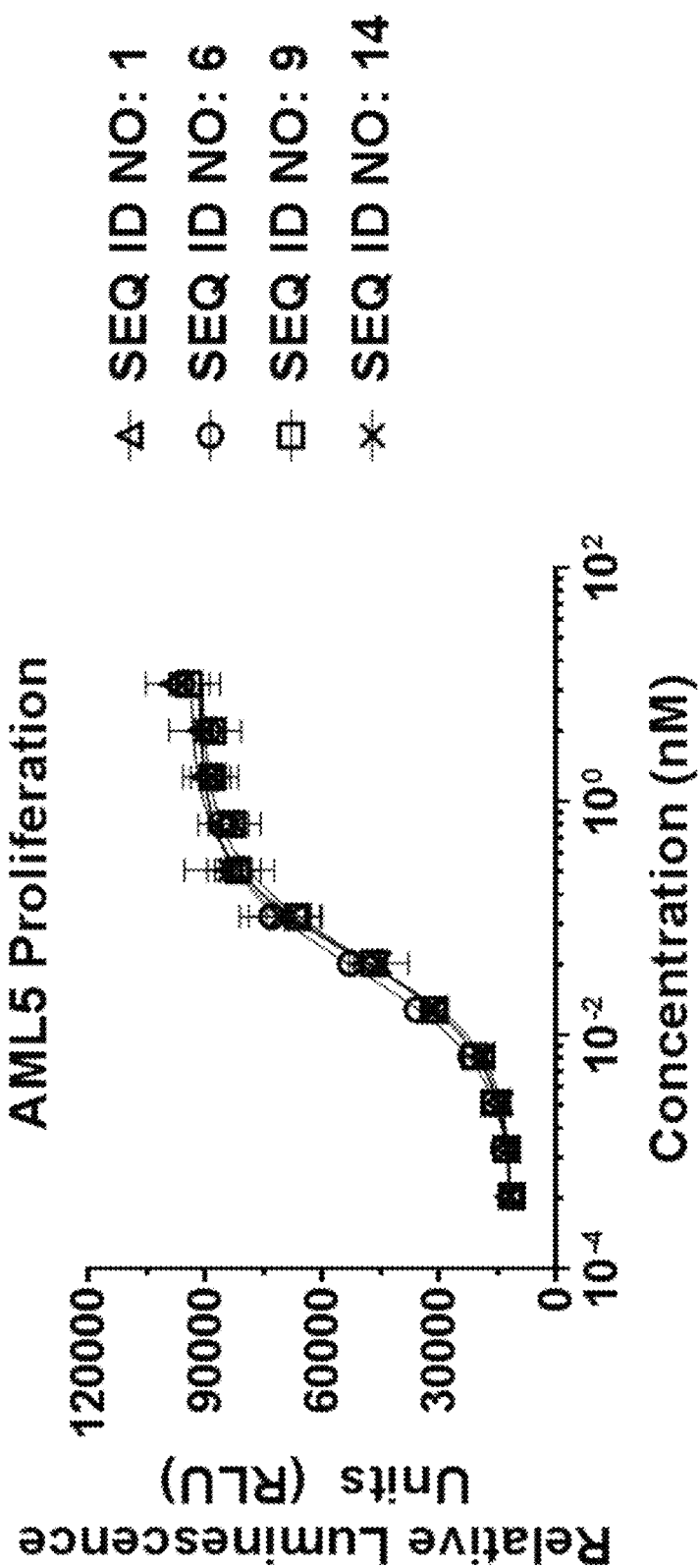
FIG. 13 illustrates proliferation of a human FLT3-expressing AML5 cell line stimulated by a dose titration (10-0.0004 nM) of human FLT3-ligand human hingeless IgG1 fusion protein (SEQ ID NO:1, open triangle), human FLT3-ligand (Δ5 amino acid) human IgG4 (S228P/F234A/L235A) fusion protein (SEQ ID NO:6, open circle), human FLT3-ligand human hingeless IgG1 (M252Y/S254T/T256E) fusion protein (SEQ ID NO:9, open square), or human FLT3-ligand (Δ5 amino acid) human IgG4 (S228P/F234A/L235A/M252Y/S254T/T256E) fusion protein (SEQ ID NO:14, cross). The x-axis shows the protein concentration (nM) and the y-axis shows the relative luminescence units (RLU). Graph is a result of one experiment. Experiment was performed in duplicate. Error bars represent standard deviation of the mean values. EC50 values are shown in Table 13.

These data demonstrated that the potency of the four human FLT3-ligand Fc fusion proteins with different Fc variants (SEQ ID NOs: 1, 6, 9 and 14) in inducing FLT3-dependent proliferation in AML5 cells was similar, with EC50 values ranging between 0.037-0.050 nM. The results are summarized in Table 13 and depicted in FIG. 13.

TABLE 13

EC50 values for FLT3L-Fc Variant SEQ ID NOs: 1, 6, 9 and 14 in AML5 Proliferation Assay

| FLT3L-Fc Variant SEQ ID NO: | EC50 (nM) |
|---|---|
| 1 | 0.050 |
| 6 | 0.048 |
| 9 | 0.037 |
| 14 | 0.046 |

Example 14

In Vitro Potency of FLT3L-Fc Variants in cDC1 Differentiation Assay

In this example, we compared the in vitro potency of four different human FLT3-ligand human Fc fusion proteins to differentiate human bone marrow CD34+ stem cells into conventional dendritic cell subtype 1 (cDC1).

Methods 96-well flat-bottom tissue culture plates (Falcon, 353072) were coated with recombinant DLL1 (R&D Systems, 1818-DL-050) as follows. DLL1 was reconstituted in PBS to create a stock solution of 500 µg/ml. The stock solution was diluted in DPBS (Corning, 21-030-CV) to a final working concentration of 5 µg/ml, and 100 µl of this was plated into each well. Plates were sealed and placed on a flat surface at 4° C. overnight.

Bone marrow CD34+ stem cells from 13 healthy donors were thawed in a 37° C. water bath and transferred into complete media (Alpha-Mem (Gibco, 12561056), 10% heat-inactivated FCS, 1x Pen/Strep). To recover the cells, 20,000 cells per well were plated into a 96-well round bottom tissue culture plate.

The next day, the DLL1 coated plates were washed 3× with DBPS, then 10,000 recovered cells per well were cultured with 20 ng/ml human GM-CSF, 20 ng/ml human SCF, 2.5 ng/ml human IL-4 and various test articles. On day 6, half the media was removed and fresh cytokines and compounds were added to the cells. On day 14, cells were collected. Staining antibodies were then added to the cells and incubated for 30 min at 4° C. Cells were then washed twice with FACS staining buffer and analyzed LSR Fortessa FACS analyzer (BD Bioscience). Raw data were analyzed by FlowJo X (BD Bioscience).

Results

Figure 14:
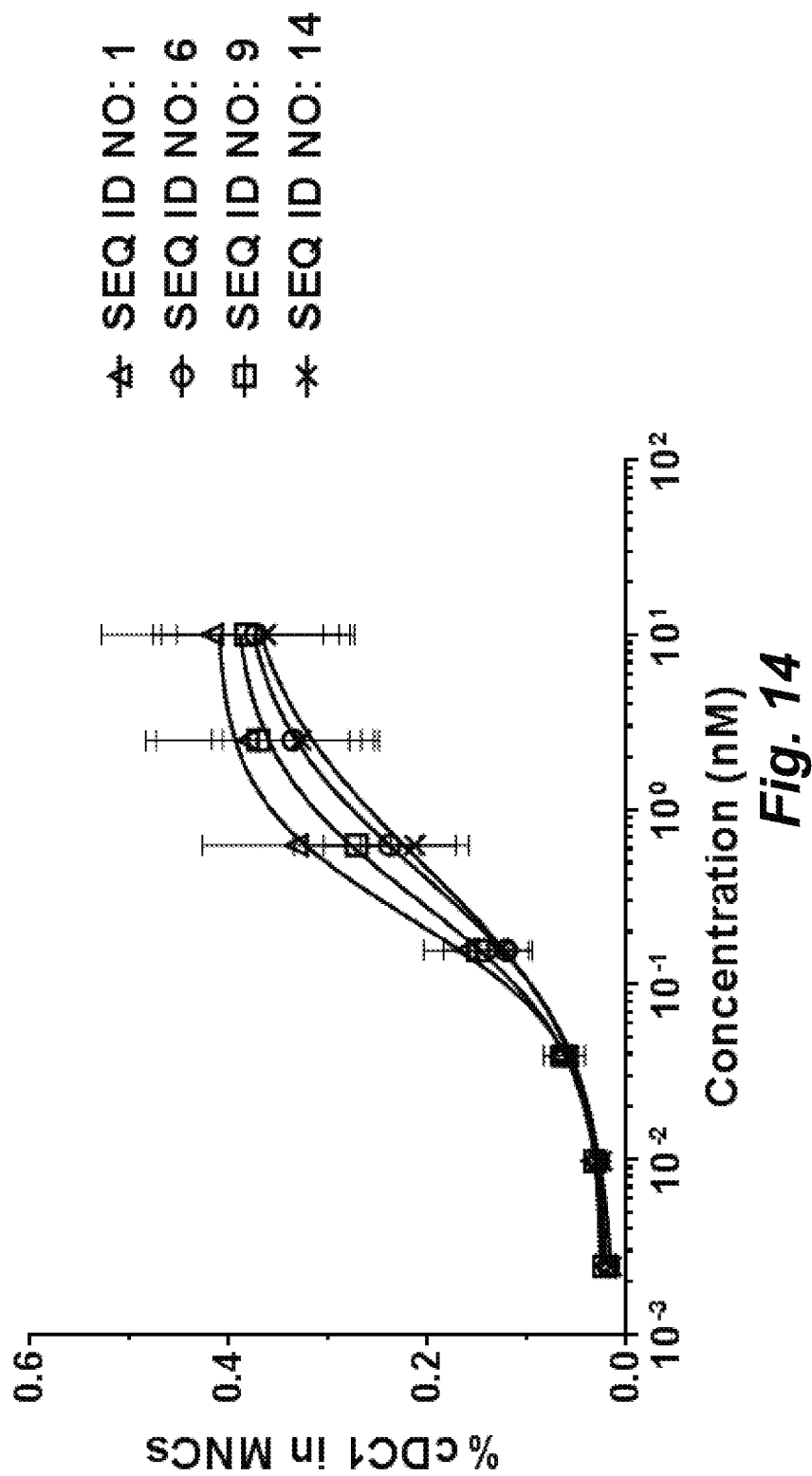
FIG. 14 illustrates differentiation of conventional dendritic cell subtype 1 (cDC1) cells from human bone marrow CD34+ stem cells by a dose titration (10-0.002 nM) of human FLT3-ligand human hingeless IgG1 fusion protein (SEQ ID NO:1, open triangle), human FLT3-ligand (Δ5 amino acid) human IgG4 (S228P/F234A/L235A) fusion protein (SEQ ID NO:6, open circle), human FLT3-ligand human hingeless IgG1 (M252Y/S254T/T256E) fusion protein (SEQ ID NO:9, open square), or human FLT3-ligand (Δ5 amino acid) human IgG4 (S228P/F234A/L235A/M252Y/S254T/T256E) fusion protein (SEQ ID NO:14, cross). The x-axis shows the protein concentration (nM) and the y-axis shows percentage of cDC1 in total mononuclear cells (MNCs). Graph is a summary of 13 bone marrow donors. Error bars represent standard error mean of the mean values. EC50 values are shown in Table 14.

These data demonstrated that the potency of the four human FLT3-ligand Fc fusion proteins with different Fc variants (SEQ ID NOs: 1, 6, 9 and 14) in inducing cDC1 differentiation in vitro from primary human CD34+ bone marrow stem cells was similar, with EC50 values ranging between 0.788-1.252 nM. The results are summarized in Table 14 and depicted in FIG. 14.

TABLE 14

EC50 values for differentiation of human CD34+ stem cells into cDC1 by proteins corresponding to FLT3L-Fc Variant SEQ ID NOs: 1, 6, 9 and 14

| FLT3L-Fc Variant SEQ ID NO: | EC50 (nM) |
|---|---|
| 1 | 1.252 |
| 6 | 1.031 |
| 9 | 0.915 |
| 14 | 0.788 |

Example 15

In Vitro Potency of FLT3L-Fc Variants in Promoting cDC1 Survival

In this example, we compared the in vitro potency of four different human FLT3-ligand human Fc fusion proteins to enhance the survival of human PBMC-derived conventional dendritic cell subtype 1 (cDC1).

Methods

Sixteen fresh human healthy donor PBMCs were obtained from PPA Research Group Inc. Pan-DCs were isolated from the PBMCs following the manufacturer's protocol for Easy-Sep Human Pan-DC Pre-Enrichment Kit (Stemcell Technologies, Inc, 19251). Pan-DCs were then stained with eBioscience Cell Proliferation Dye efluor 450 (Invitrogen, 65-0842-85) for 8 min in a 37° C. water bath. After staining with the cell proliferation dye, cells were washed 2× and resuspended with complete RPMI. 100,000 cells per well were plated into a 96-well round bottom tissue culture plate and titrations of the compounds were added to the cells for a final volume of 200u1 per well. Plates were sealed with a breathable plate sealer (Breathe Easy Sealing Membrane, Millipore Sigma, Z380059-1Pak) and then incubated for 4 days at 37° C. After incubation, cells were washed with FACS staining buffer and Fc blocked (Human TruStain FcX Biolegend, 422302) for at least 10 min at 4° C. Staining antibodies were then directly added to the cells and incubated for 30 min at 4° C. Cells were then washed twice with FACS staining buffer and analyzed LSR Fortessa FACS analyzer (BD Bioscience). Raw data were analyzed by FlowJo X (BD Bioscience).

Results

Figure 15:
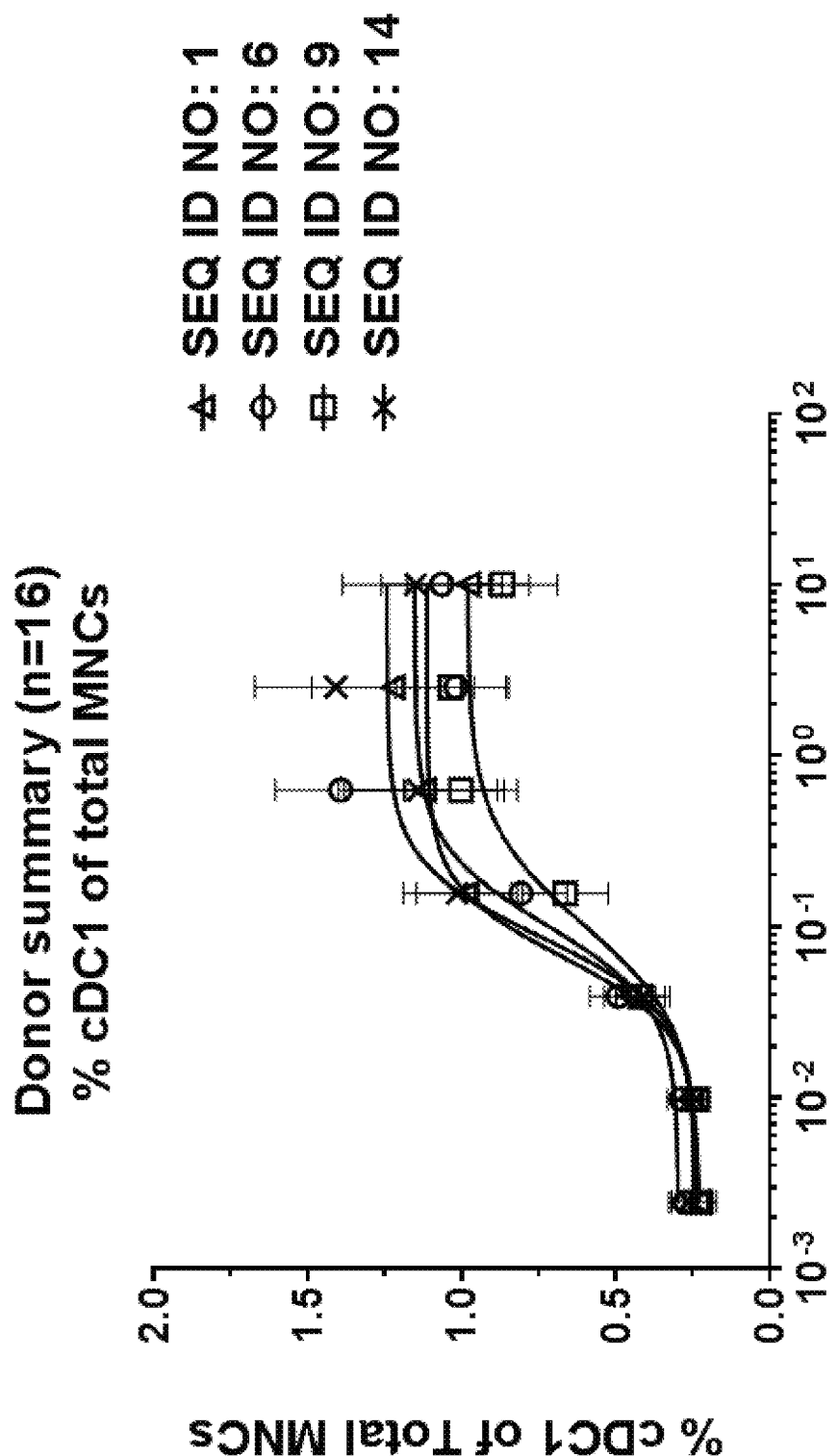
FIG. 15 illustrates a dose titration (10-0.002 nM) potency of enhancing survival of PBMC-derived conventional dendritic cell subtype 1 (cDC1) cells by human FLT3-ligand human hingeless IgG1 fusion protein (SEQ ID NO:1, open triangle), human FLT3-ligand (Δ5 amino acid) human IgG4 (S228P/F234A/L235A) fusion protein (SEQ ID NO:6, open circle), human FLT3-ligand human hingeless IgG1 (M252Y/S254T/T256E) fusion protein (SEQ ID NO:9, open square), or human FLT3-ligand (Δ5 amino acid) human IgG4 (S228P/F234A/L235A/M252Y/S254T/T256E) fusion protein (SEQ ID NO:14, cross). The x-axis shows the protein concentration (nM) and the y-axis shows percentage of cDC1 in total mononuclear cells (MNCs). Graph is a summary of 16 PBMC donors. Error bars represent standard error mean of the mean values. EC50 values are shown in Table 15.

The data demonstrated that the potency of the 4 human FLT3-ligand Fc fusion proteins with different Fc variants (SEQ ID NOs: 1, 6, 9 and 14) in enhancing primary human cDC1 survival in vitro was similar, with EC50 values ranging between 0.067-0.102 nM. The results are summarized in Table 15 and depicted in FIG. 15.

TABLE 15

EC50 values for promoting cDC1 survival by proteins corresponding to FLT3L-Fc Variant SEQ ID NOs: 1, 6, 9 and 14

| FLT3L-Fc Variant SEQ ID NO: | EC50 (nM) |
| --- | --- |
| 1 | 0.067 |
| 6 | 0.102 |
| 9 | 0.102 |
| 14 | 0.087 |

Example 16

In Vitro Binding of FLT3L-Fc Variants to FLT3

In this example, we compared the in vitro binding of four different human FLT3-ligand human Fc fusion proteins to human recombinant FLT3 by ELISA. The methods are as described above in Example 6.

Results

Figure 16:
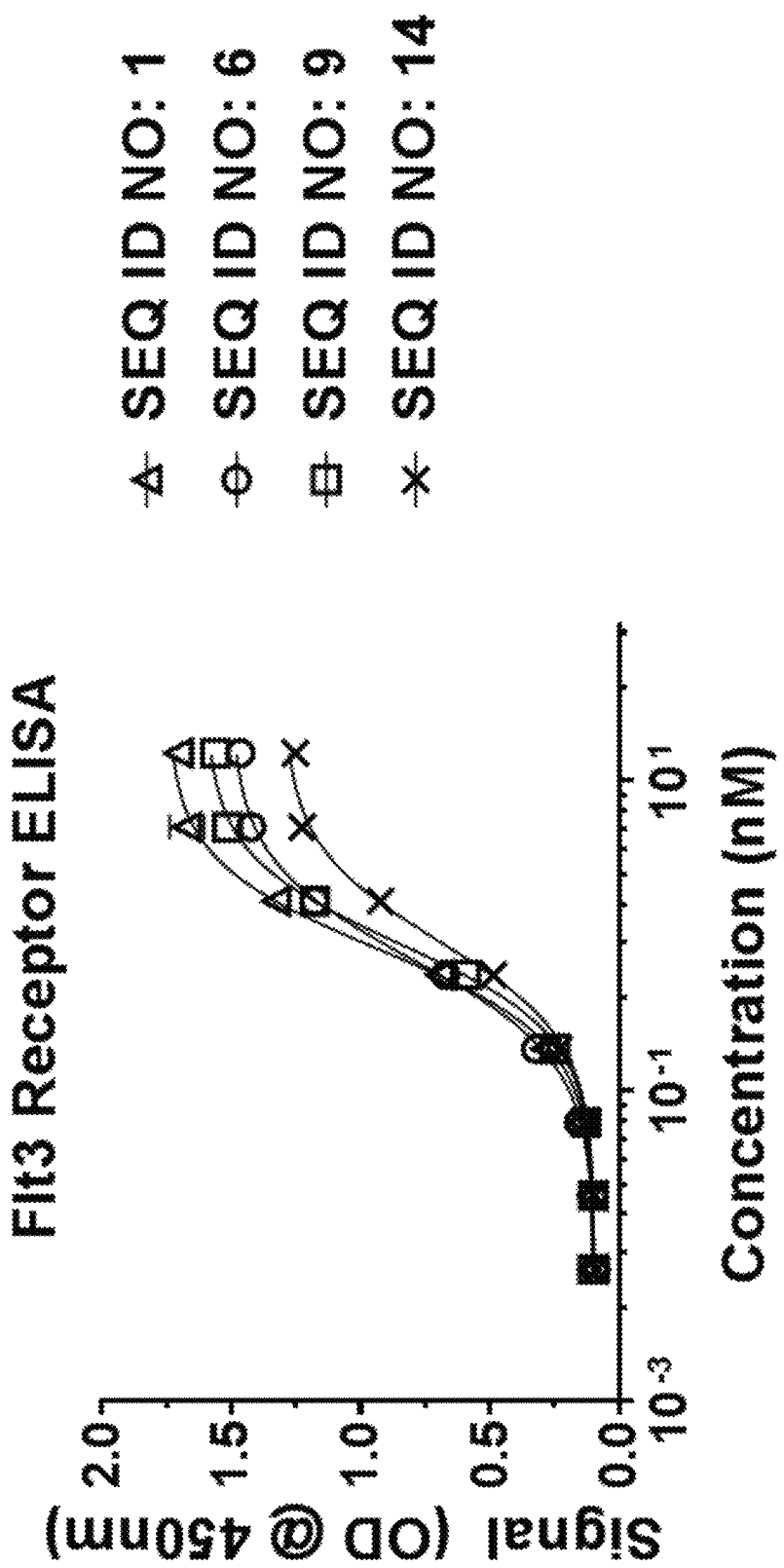
FIG. 16 illustrates binding of recombinant human FLT3 to a titration (15-0.007 nM) of human FLT3-ligand human hingeless IgG1 fusion protein (SEQ ID NO:1, open triangle), human FLT3-ligand (Δ5 amino acid) human IgG4 (S228P/F234A/L235A) fusion protein (SEQ ID NO:6, open circle), human FLT3-ligand human hingeless IgG1 (M252Y/S254T/T256E) fusion protein (SEQ ID NO:9, open square), or human FLT3-ligand (Δ5 amino acid) human IgG4 (S228P/F234A/L235A/M252Y/S254T/T256E) fusion protein (SEQ ID NO:14, cross). The x-axis shows the protein concentration (nM) and the y-axis shows optical density (OD) at 450 nm. Graph is a result of one experiment. Experiment was performed in duplicate. Error bars represent standard deviation of the mean values. EC50 values are shown in Table 16.

These data demonstrated that binding to human FLT3 receptor was similar among the four human FLT3-ligand Fc fusion proteins with different Fc variants (SEQ ID NOs: 1, 6, 9 and 14), with EC50 values ranged between 0.70 to 0.92 nM. The results are summarized in Table 16 and depicted in FIG. 16.

TABLE 16

EC50 values for FLT3L-Fc Variant SEQ ID NOs: 1, 6, 9 and 14 Binding to Human Recombinant FLT3

| FLT3L-Fc Variant SEQ ID NO: | EC50 (nM) |
| --- | --- |
| 1 | 0.81 |
| 6 | 0.70 |
| 9 | 0.88 |
| 14 | 0.92 |

Example 17

In Vitro Binding of FLT3L-Fc Variants to FcRn

In this example, we compared the in vitro binding of four different human FLT3-ligand human Fc fusion proteins to human recombinant FcRn by ELISA. The methods are as described above in Example 7.

Results

Figure 17:
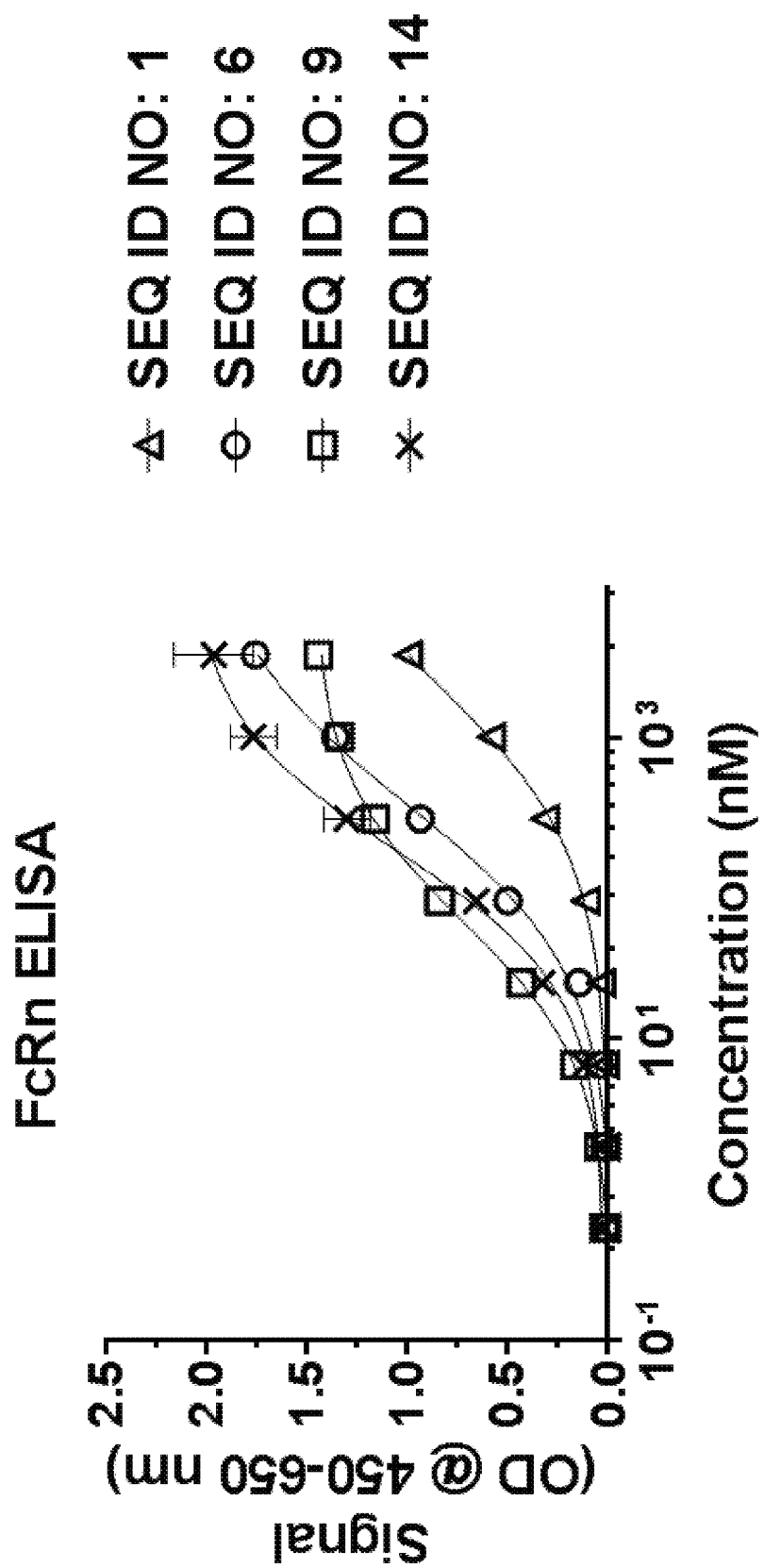
FIG. 17 illustrates binding of recombinant human FcRn to a dose titration (3529-0.55 nM) of human FLT3-ligand human hingeless IgG1 fusion protein (SEQ ID NO:1, open triangle), human FLT3-ligand (Δ5 amino acid) human IgG4 (S228P/F234A/L235A) fusion protein (SEQ ID NO:6, open circle), human FLT3-ligand human hingeless IgG1 (M252Y/S254T/T256E) fusion protein (SEQ ID NO:9, open square), or human FLT3-ligand (45 amino acid) human IgG4 (S228P/F234A/L235A/M252Y/S254T/T256E) fusion protein (SEQ ID NO:14, cross). The x-axis shows the protein concentration (nM) and the y-axis shows optical density (OD) at 450-650 nm. Graph is a result of one experiment. Experiment was performed in duplicate. Error bars represent standard deviation of the mean values. EC50 values are shown in Table 17.

The data demonstrated that M252Y/S254T/T256E mutations in the human IgG Fc region leads to improved FcRn binding for SEQ ID NOs: 9 and 14, compared to their counterparts without these mutations (SEQ ID NOs: 1 and 6). A 38-fold increase in FcRn binding was observed for Flt3L-Fc in the hingeless IgG1 format (SEQ ID NOs: 1 and 9), compared to a 2-fold increase in the IgG4 format (SEQ ID NOs: 6 and 14). The results are summarized in Table 17 and depicted in FIG. 17.

TABLE 17

EC50 Values for FLT3L-Fc Variant SEQ ID NOs: 1, 6, 9 and 14 Binding to Human Recombinant FcRn

| FLT3L-Fc Variant SEQ ID NO: | EC50 (nM) |
| --- | --- |
| 1 | 2332 |
| 6 | 365.00 |
| 9 | 61 |
| 14 | 178 |

Example 18

Ability of FLT3L-Fc Variants to Compete for Binding to Human FcγRI

In this example, we compared the in vitro ability of four different human FLT3-ligand human Fc fusion proteins to compete for binding of human recombinant FcγRI with a human IgG molecule. To evaluate the ability to compete for binding to FcγRI, we employed an amplified luminescent proximity homogeneous assay (AlphaScreen® by Perkin Elmer). The methods are as described above in Example 8.

Results

Figure 18:
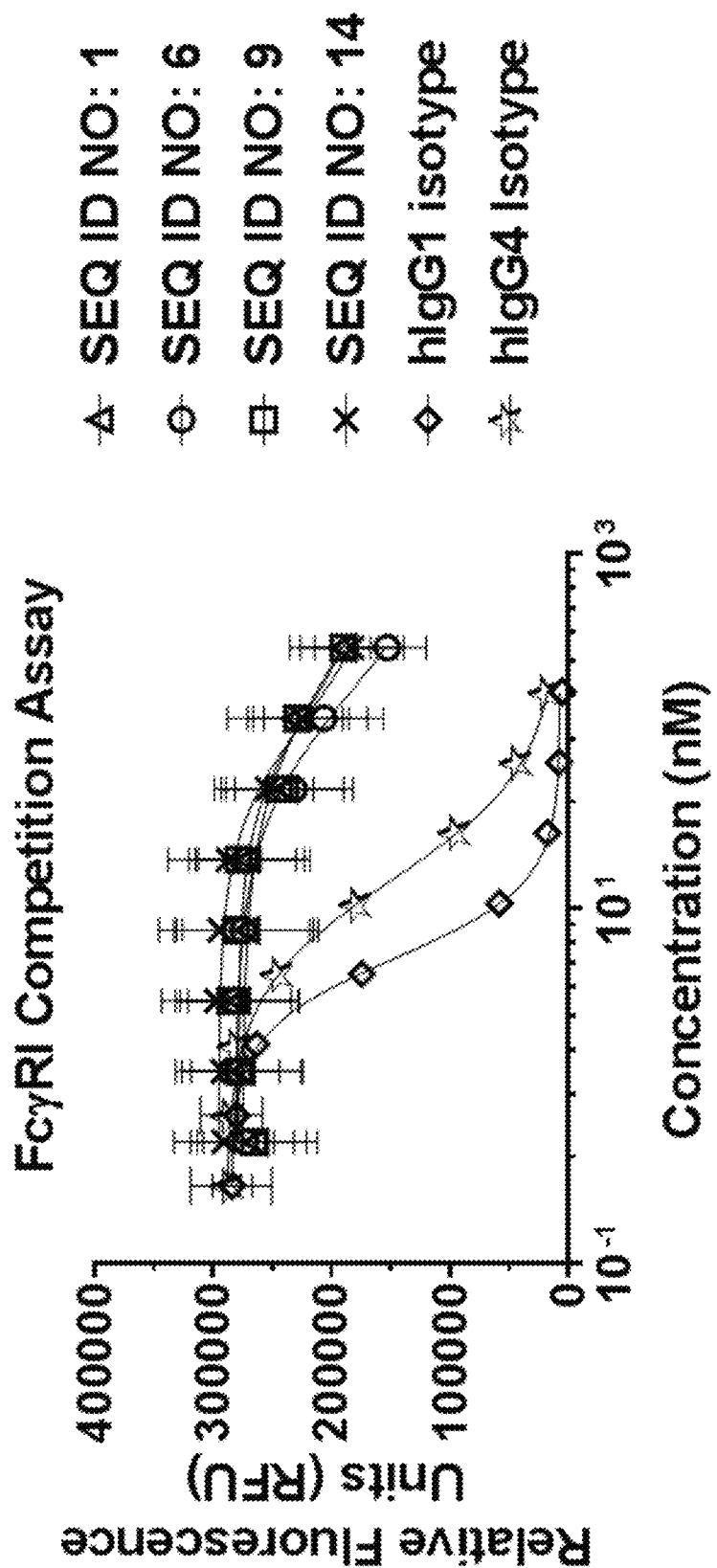
FIG. 18 illustrates binding of human IgG to recombinant human FcγRI competed with a titration (294-0.48 nM) of human FLT3-ligand human hingeless IgG1 fusion protein (SEQ ID NO:1, open triangle), human FLT3-ligand (Δ5 amino acid) human IgG4 (S228P/F234A/L235A) fusion protein (SEQ ID NO:6, open circle), human FLT3-ligand human hingeless IgG1 (M252Y/S254T/T256E) fusion protein (SEQ ID NO:9, open square), human FLT3-ligand (Δ5 amino acid) human IgG4 (S228P/F234A/L235A/M252Y/S254T/T256E) fusion protein (SEQ ID NO:14, cross), human IgG1 isotype antibody (open diamond), or human IgG4 isotype antibody (open star). The x-axis shows the protein concentration (nM) and the y-axis shows the relative fluorescence units (RFU). Graph is a result of one experiment. Experiment was performed in duplicate. Error bars represent standard deviation of the mean values. EC50 values are shown in Table 18.

These data demonstrated that none of the 4 human FLT3-ligand Fc fusion proteins with different Fc variants (SEQ ID NOs: 1, 6, 9 and 14) could fully compete with human IgG for binding to FcγRI at the highest concentrations tested. Both the human IgG1 and IgG4 isotype antibody controls demonstrated complete dose-response curves, with the IgG4 isotype showing reduced competition compared to the IgG1. The results are summarized in Table 18 and depicted in FIG. 18.

TABLE 18

EC50 values for the ability of FLT3L-Fc Variant SEQ ID NOs: 1, 6, 9 and 14 to compete with a human IgG molecule for binding to human recombinant FcγRI

| FLT3L-Fc Variant SEQ ID NO: | EC50 (nM) |
| --- | --- |
| 1 | NA |
| 6 | NA |
| 9 | NA |
| 14 | NA |
| hIgG1 Isotype | 5.25 |
| hIgG4 Isotype | 14.54 |

Example 19

Ability of FLT3L-Fc Variants to Compete for Binding to Human FcγRIIIa

In this example, we compared the in vitro ability of four different human FLT3-ligand human Fc fusion proteins to compete for binding of human recombinant FcγRIIIa (Val176 variant) with a human IgG molecule. To evaluate the ability to compete for binding to FcγRIIIa, we employed an amplified luminescent proximity homogeneous assay (AlphaScreen® by Perkin Elmer). The methods are as described above in Example 9.

Results

Figure 19:
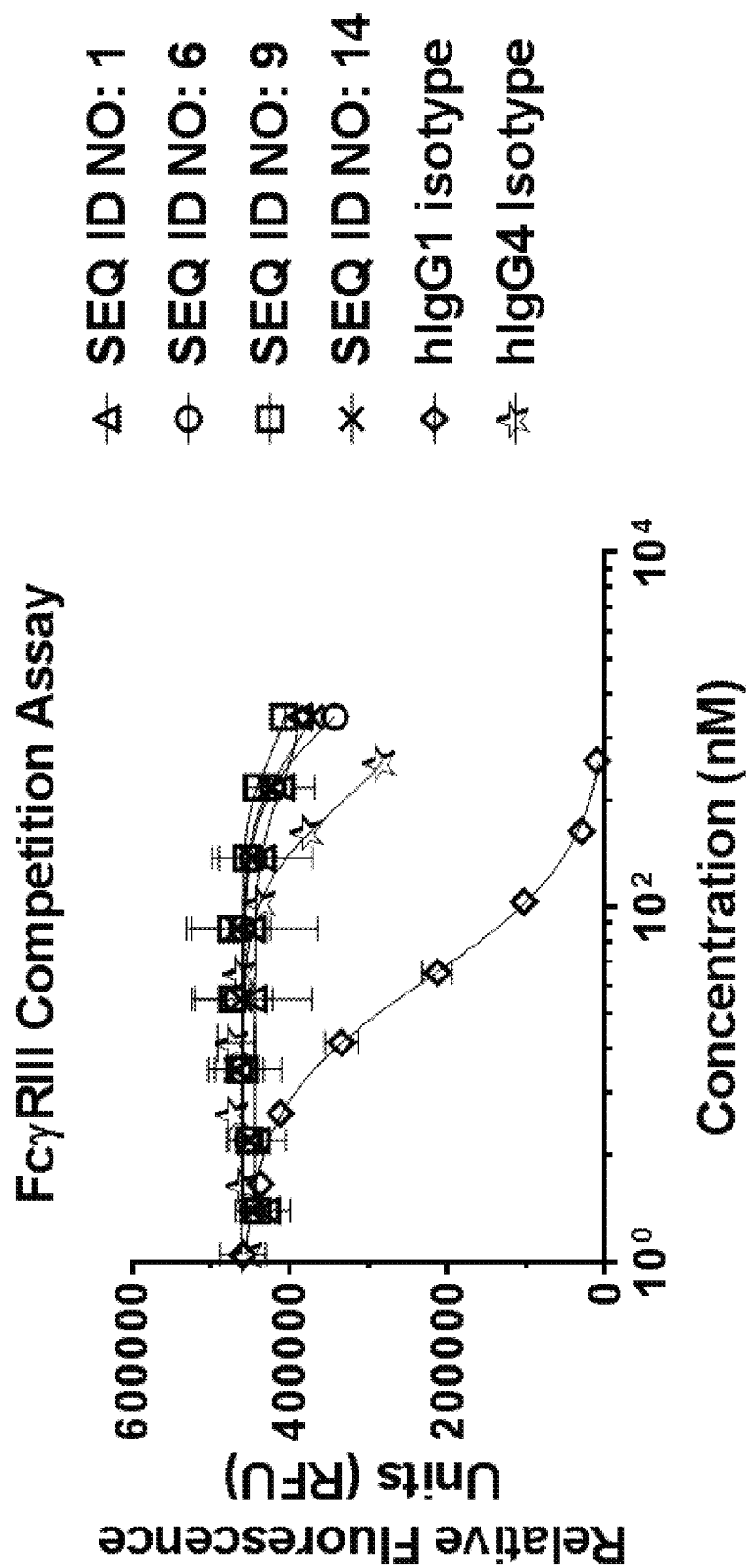
FIG. 19 illustrates binding of human IgG to recombinant human FcγRIIIa (V-variant) competed by a dose titration (1176-1.92 nM) of human FLT3-ligand human hingeless IgG1 fusion protein (SEQ ID NO:1, open triangle), human FLT3-ligand (Δ5 amino acid) human IgG4 (S228P/F234A/L235A) fusion protein (SEQ ID NO:6, open circle), human FLT3-ligand human hingeless IgG1 (M252Y/S254T/T256E) fusion protein (SEQ ID NO:9, open square), human FLT3-ligand (Δ5 amino acid) human IgG4 (S228P/F234A/L235A/M252Y/S254T/T256E) fusion protein (SEQ ID NO:14, cross), human IgG1 isotype antibody (open diamond), or human IgG4 isotype antibody (open star). The x-axis shows the protein concentration (nM) and the y-axis shows the relative fluorescence units (RFU). Graph is a result of one experiment. Experiment was performed in duplicate. Error bars represent standard deviation of the mean values. EC50 values are shown in Table 19.

The results demonstrated that none of the 4 human FLT3-ligand Fc fusion proteins with different Fc variants (SEQ ID NOs: 1, 6, 9 and 14) could fully compete with human IgG for binding to FcγRIIIa (Val176 variant). Only human IgG1 isotype antibody control demonstrated a complete dose-response curve. The results are summarized in Table 19 and depicted in FIG. 19.

TABLE 19

EC50 values for the ability of FLT3L-Fc Variant SEQ ID NOs: 1, 6, 9 and 14 to compete with a human IgG for binding to human recombinant FcγRIIIa (V-variant)

| FLT3L-Fc Variant SEQ ID NO: | EC50 (nM) |
|---|---|
| 1 | NA |
| 6 | NA |
| 9 | NA |
| 14 | NA |
| hIgG1 Isotype | 38.80 |
| hIgG4 Isotype | 368.30 |

Example 20

In Vitro Binding of FLT3L-Fc Variants to Human C1q

In this example, we compared the in vitro binding of four different human FLT3-ligand human Fc fusion proteins to human recombinant C1q. To evaluate the in vitro binding to C1q, we employed an ELISA. The methods are as described above in Example 10.

Results

Figure 20:
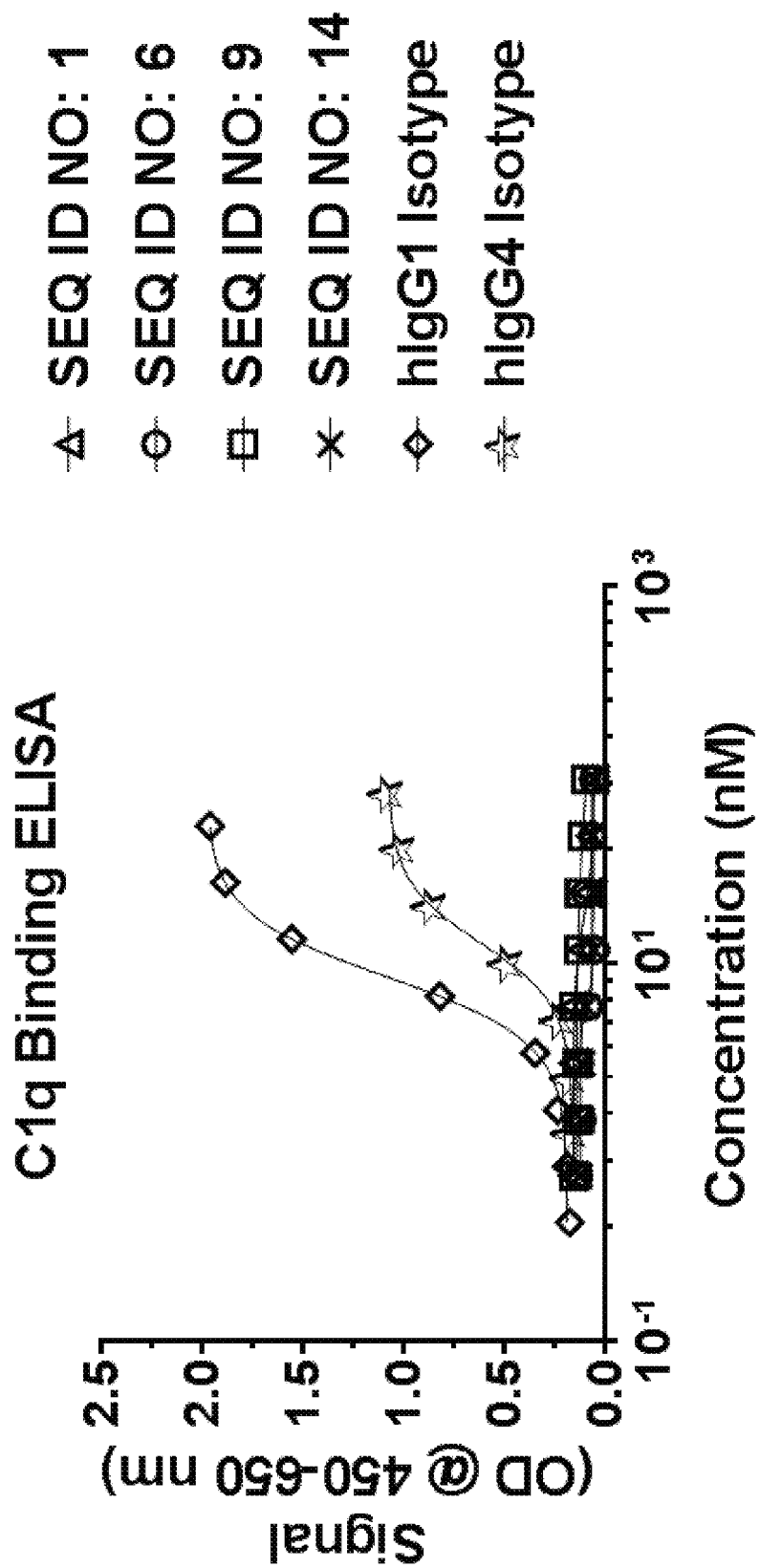
FIG. 20 illustrates binding of recombinant human C1q to a titration (94-0.74 nM) of human FLT3-ligand human hingeless IgG1 fusion protein (SEQ ID NO:1, open triangle), human FLT3-ligand (Δ5 amino acid) human IgG4 (S228P/F234A/L235A) fusion protein (SEQ ID NO:6, open circle), human FLT3-ligand human hingeless IgG1 (M252Y/S254T/T256E) fusion protein (SEQ ID NO:9, open square), human FLT3-ligand (Δ5 amino acid) human IgG4 (S228P/F234A/L235A/M252Y/S254T/T256E) fusion protein (SEQ ID NO:14, cross), human IgG1 isotype antibody (open diamond), or human IgG4 isotype antibody (open star). The x-axis shows the protein concentration (nM) and the y-axis shows optical density (OD) at 450-650 nm. Graph is a result of one experiment. Experiment was performed in duplicate. Error bars represent standard deviation of the mean values. EC50 values are shown in Table 20.

These data demonstrated that the four human FLT3-ligand Fc fusion proteins with different Fc variants (SEQ ID NOs: 1, 6, 9 and 14) are devoid of C1q binding ability. Both the human IgG1 and IgG4 isotype controls demonstrated binding to C1q, with the IgG4 isotype showing reduced binding compared to the IgG1. The results are summarized in Table 20 and depicted in FIG. 20.

TABLE 20

EC50 values for FLT3L-Fc Variants SEQ ID NOs: 1, 6, 9 and 14 Binding to Human Recombinant C1q

| FLT3L-Fc Variant SEQ ID NO: | EC50 (nM) |
|---|---|
| 1 | NA |
| 6 | NA |
| 9 | NA |
| 14 | NA |
| hIgG1 Isotype | 8.44 |
| hIgG4 Isotype | 13.71 |

Example 21

Single Dose Pharmacokinetics of FLT3L-Fc Variants in Cynomolgus Macaque

In this example, we compared the single dose pharmacokinetics of four different human FLT3-ligand human Fc fusion proteins in Cynomolgus macaque.

Methods

Four FLT3L-Fc variants (SEQ ID NOs: 1, 6, 9, and 14) were administered to cynomologus macaques n=3/group (Covance, Tex.) at 0.5 mg/kg via a single intravenous (IV) and subcutaneous (SC) injection to characterize their basic PK profiles. Serial serum samples collected from macaques were analyzed using U-PLEX FLT3L assay (Meso Scale Discovery, MSD) according to the manufacturer's instructions. The calibration curve used the respective individual FLT3-ligand fusion proteins as reference standards in spiked macaque matrix fit to a 4-parameter logistic model with 1/Y2 weighting. Analyte concentrations were determined from the electrochemiluminescence signals back-fitted to the calibration curve. Serum concentration-time profiles were used to calculate the mean±SD serum PK parameters by non-compartmental PK analysis.

Results

Figure 21A:
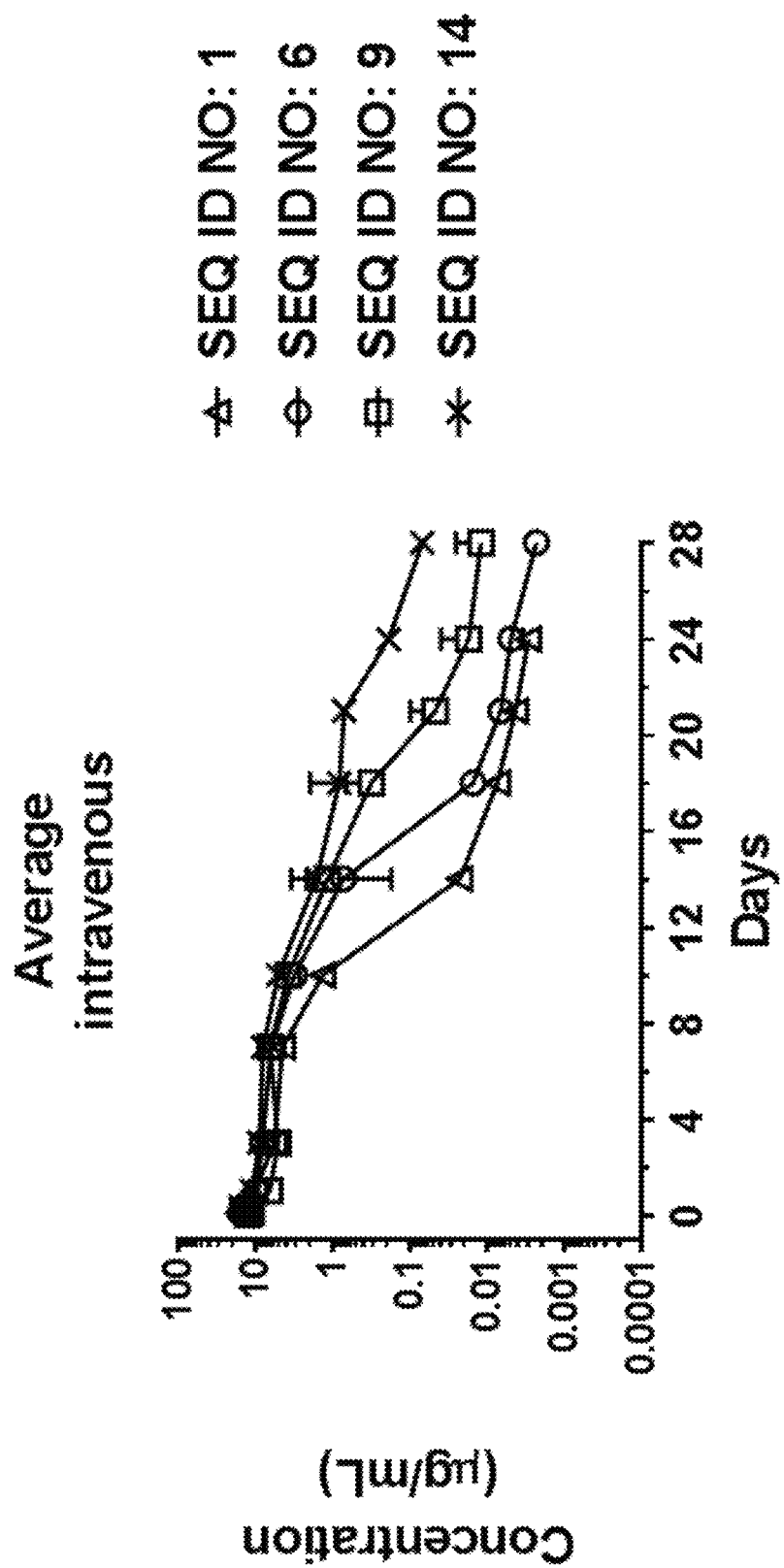
FIGS. 21A-21B illustrate Cynomolgus macaque serum concentration-time profile following 500 µg/kg intravenous and subcutaneous dosing of 4 FLT3-ligand fusion proteins relative to recombinant FLT3-ligand. Average serum concentration-time profiles after intravenous (Panel A) or subcutaneous (Panel B) administration of human FLT3-ligand human hingeless IgG1 fusion protein (SEQ ID NO:1, open triangle), human FLT3-ligand (Δ5 amino acid) human IgG4 (S228P/F234A/L235A) fusion protein (SEQ ID NO:6, open circle), human FLT3-ligand human hingeless IgG1 (M252Y/S254T/T256E) fusion protein (SEQ ID NO:9, open square), human FLT3-ligand (Δ5 amino acid) human IgG4 (S228P/F234A/L235A/M252Y/S254T/T256E) fusion protein (SEQ ID NO:14, cross). The x-axis shows days post injection and the y-axis shows protein concentration in serum (µg/mL). Each data point represents the mean value of 3 animals. Error bars represent standard deviation of the mean values. Mean pharmacokinetic values are shown in Table 21.
Figure 21B:
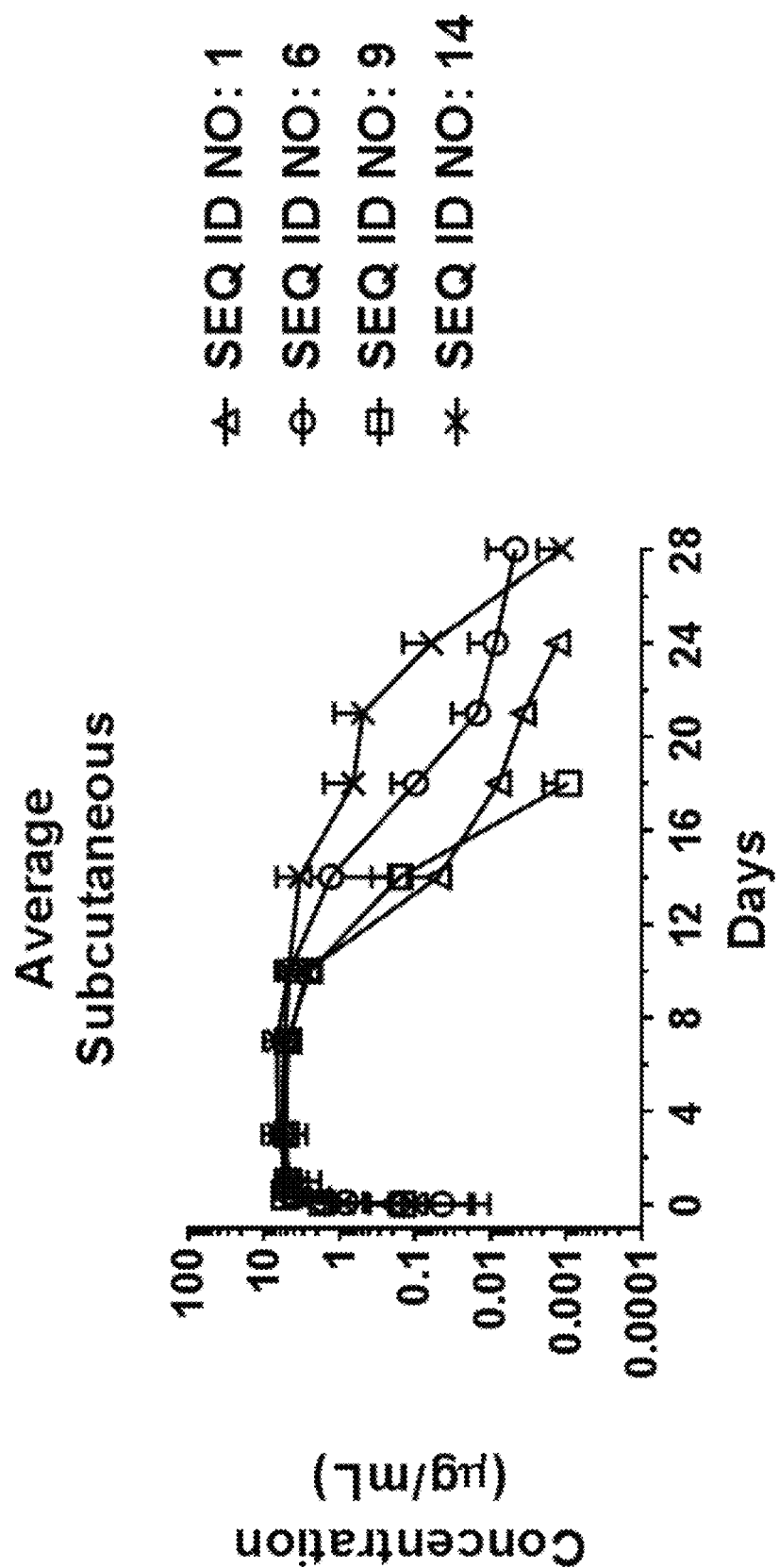

Pharmacokinetic (PK) analysis demonstrated that all 4 Fc-fusions had IgG-like pharmacokinetics with Cl values range from 4.71-7.74 mL/d/kg (Table 21) following IV administration in cynomologus macaques. Similar pharmacokinetics were observed following subcutaneous administration with bioavailability ranging from 66.8-91.4%. SEQ ID NOs: 9 and 14 containing the M252Y/S254T/T256E modifications had reduced clearance relative to unmodified sequence, consistent with improved FcRn binding. The results are summarized in Table 21 and depicted in FIGS. 21A-21B.

TABLE 21

Single dose PK values for FLT3L-Fc Variants SEQ ID NOs: 1, 6, 9 and 14 in Cynomolgus macaques

| FLT3L-Fc Variant SEQ ID NO: | Intravenous | | Subcutaneous | |
|---|---|---|---|---|
| | AUC$_{0-last}$ (μg*d/mL) | Cl (mL/d/kg) | AUC$_{0-last}$ (μg*d/mL) | Cl/F (mL/d/kg) |
| 1 | 59.3 ± 5.29 | 7.74 ± 1.35 | 54.2 ± 5.04 | 9.29 ± 0.91 |
| 6 | 82.4 ± 15.6 | 6.23 ± 1.31 | 66.2 ± 20.1 | 7.98 ± 2.10 |
| 9 | 73.8 ± 12.2 | 6.89 ± 1.08 | 49.3 ± 3.36 | 9.16 ± 1.01 |
| 14 | 107 ± 11.6 | 4.71 ± 0.502 | 79.4 ± 30.4 | 7.04 ± 3.27 |

Example 22

Ability of FLT3L-Fc Variants to Promote cDC1 Proliferation in Cynomolgus Macaque In this example, we compared the ability of four different FLT3L-Fc variants (SEQ ID NOs: 1, 6, 9 and 14) to induce proliferation and expansion of conventional dendritic cell subtype 1 (cDC1) in Cynomolgus macaque.

Methods

Whole blood samples from cynomolgus macaques administered one of SEQ ID NO: 1, 6, 9, or 14 at day 0 were drawn into Sodium Heparin blood collection tubes at indicated time points. One hundred microliters of each sample were transferred to FACS tubes containing FACS antibodies and Fc blocker. Cells were incubated at room temperature for 20 min, then washed twice with 1×DPBS-CMF. Residual red blood cells were then lysed for 8-12 minutes in the dark at room temperature with 1 mL 1×FACS Lyse (BD Biosciences). After incubation, the samples were centrifuged and washed once by adding 1×DPBS-CMF (1 mL). Samples were then resuspended in 125 μL 1×DPBS-CMF and 100 μL CountBright Beads for acquisition on the Canto FACS analyzer (BD Biosciences). Raw data were analyzed by FlowJo X (BD Bioscience).

Results

Figure 22A:
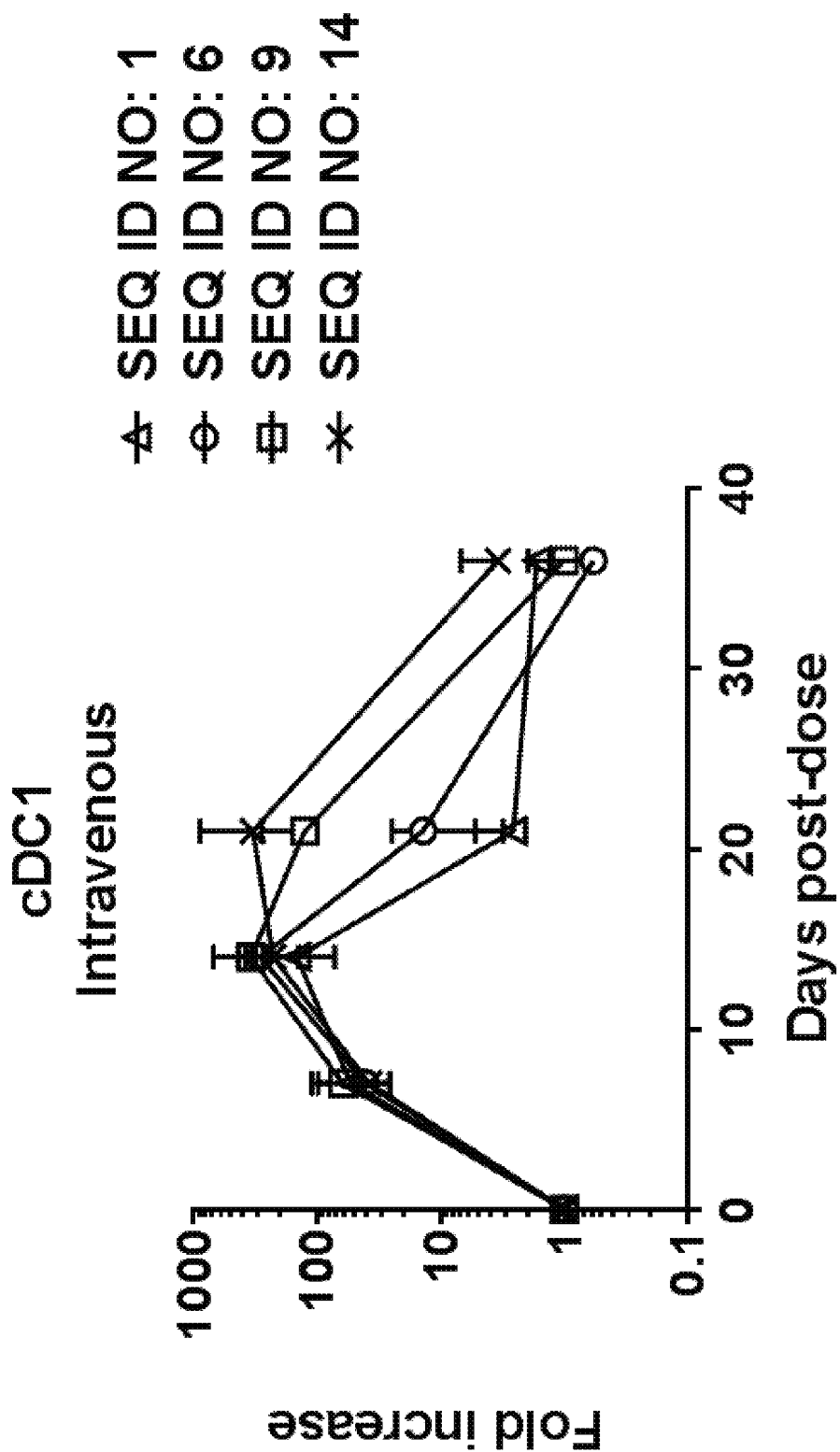
FIGS. 22A-22B illustrate kinetics of conventional dendritic cell subtype 1 (cDC1) fold-change in peripheral blood of Cynomolgus macaque administrated intravenously (Panel A) or subcutaneously (Panel B) with 500 µs/kg of human FLT3-ligand human hingeless IgG1 fusion protein (SEQ ID NO:1, open triangle), human FLT3-ligand (Δ5 amino acid) human IgG4 (S228P/F234A/L235A) fusion protein (SEQ ID NO:6, open circle), human FLT3-ligand human hingeless IgG1 (M252Y/S254T/T256E) fusion protein (SEQ ID NO:9, open square), human FLT3-ligand (Δ5 amino acid) human IgG4 (S228P/F234A/L235A/M252Y/S254T/T256E) fusion protein (SEQ ID NO:14, cross) at day 0. Graph is a result of one experiment. Each data point represents the mean value of 3 animals. Error bars represent standard deviation of the mean values.
Figure 22B:
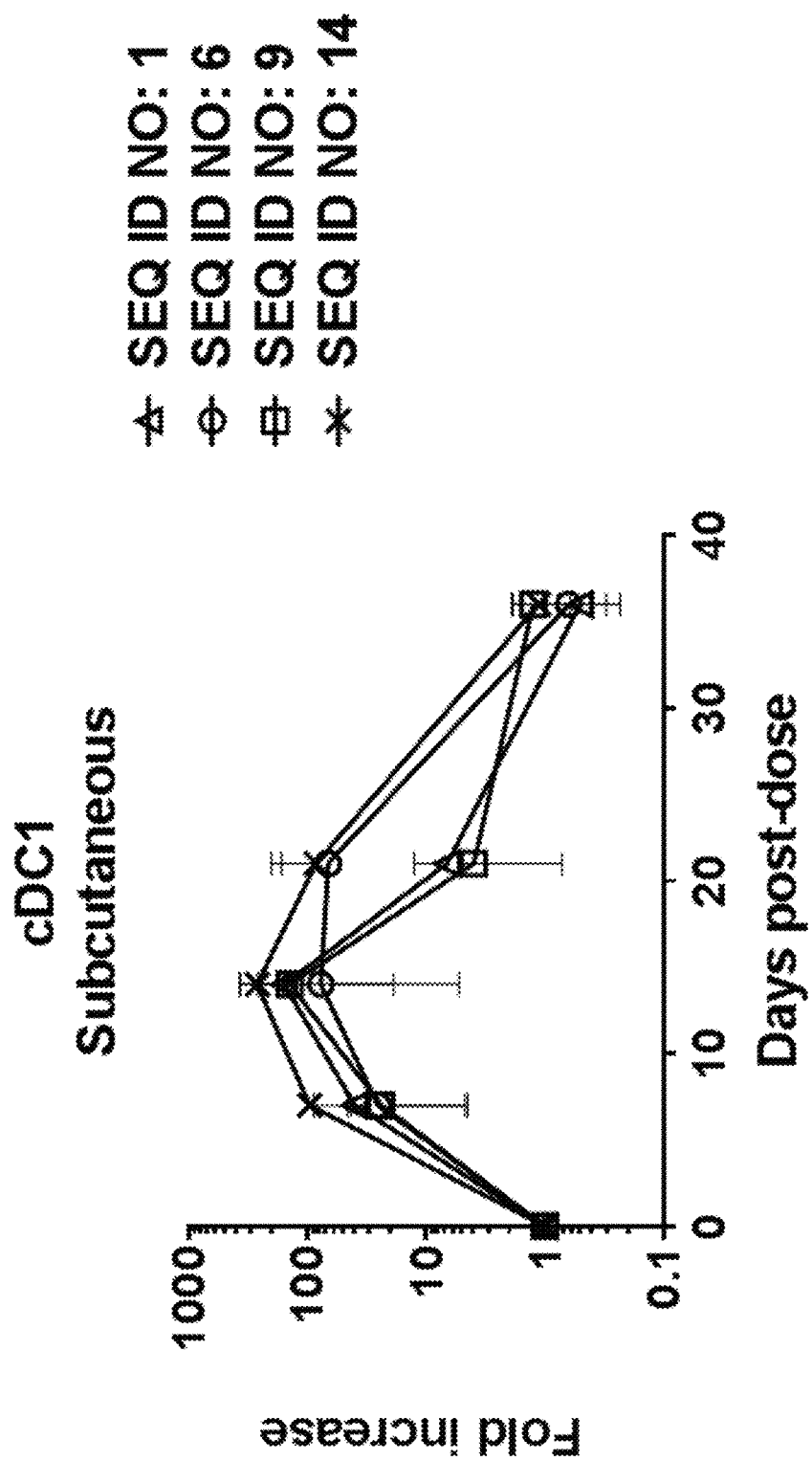

These data demonstrated a similar ability of the four human FLT3-ligand Fc fusion proteins with different Fc variants (SEQ ID: 1, 6, 9, and 14) to expand conventional dendritic cell subtype 1 (cDC1) in peripheral blood of Cynomolgus macaque from day 0 to day 14 after single-dose intravenous or subcutaneous administration. The cDC1 number of each group gradually declined to baseline levels between days 14 to 38 after test article administration, at a rate which paralleled the corresponding decline in serum levels of FLT3-ligand Fc fusion proteins as shown in FIG. 21. These results are depicted in FIGS. 22A-22B.

Example 23

Anti-Tumor Activity of Murine Surrogate FLT3L-Fc Fusion Protein

In this example, we demonstrated the anti-tumor activity of a murine surrogate FLT3L-Fc fusion protein (SEQ ID NO:20) in a mouse tumor model.

Methods

Eight-week old C57Bl/6 mice (Jackson Laboratory) were inoculated with $2.5 \times 10^5$ MC38 cells subcutaneously. Mice were then randomized when tumor volume reached 45-55 $mm^3$ on day 0 and dosed intraperitoneally with SEQ ID NO: 20 or an Fc-silent (N297A) mouse IgG2a isotype control at indicated concentration within the same day. Tumors were measured 3 times a week using calipers. Tumor volumes were calculated using the following equation: (longest diameter*shortest diameter$^2$)/2.

Results

Figure 23:
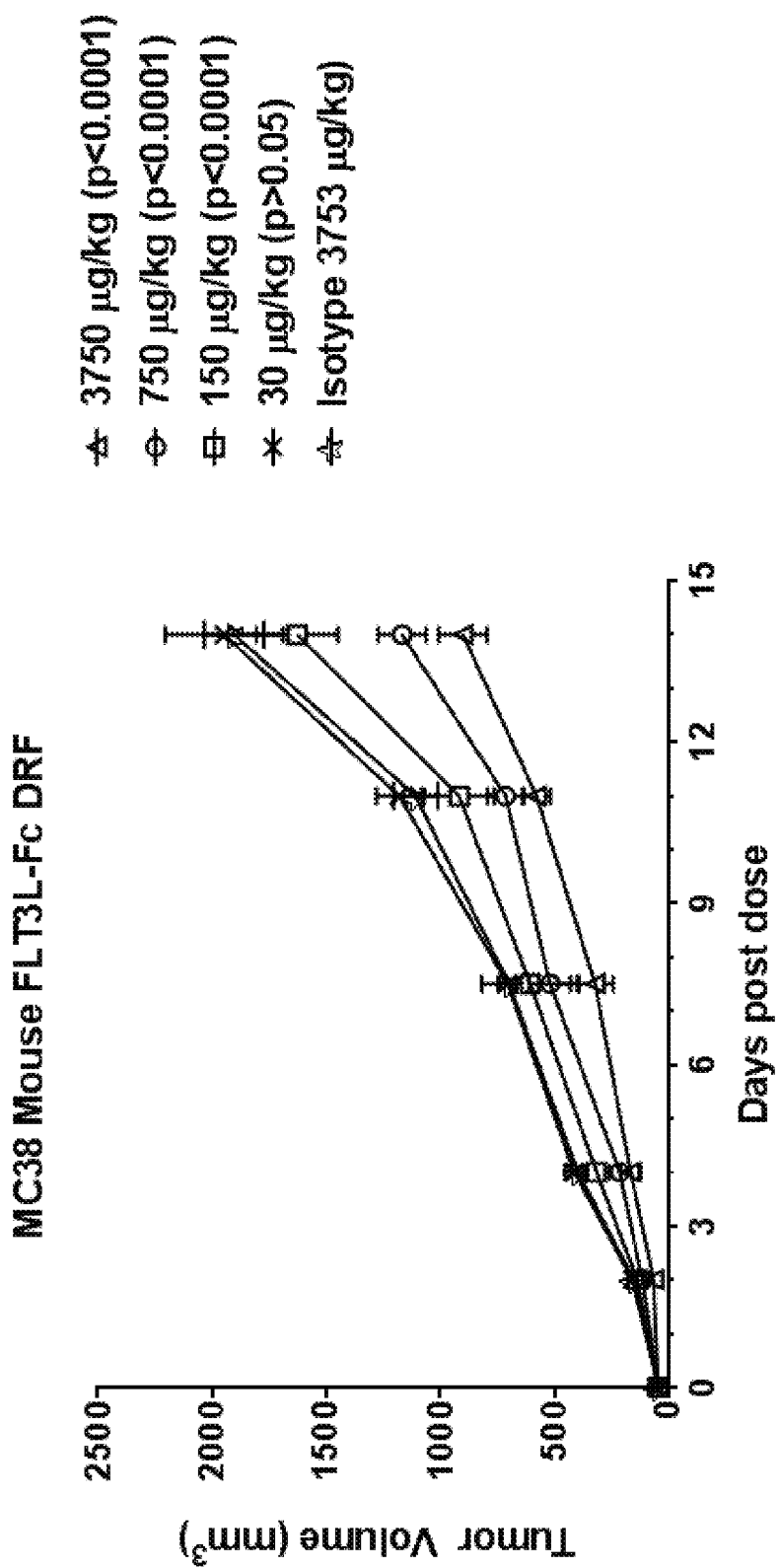
FIG. 23 illustrates tumor growth kinetics of MC38 tumor-bearing C57BL/6 mice administrated intravenously with 3750 µg/kg (open triangle), 750 µg/kg (open circle), 150 µg/kg (open square), 30 µg/kg (cross) mouse FLT3-Ligand mouse IgG2a (C136S, LALA-PG), or 3753 µg/kg mouse IgG2a isotype (open star) at day 0 when tumor volume reached 50 mm³. The x-axis is days post dosing. The y-axis is tumor volume in mm³. Graph is representative of two independent experiments. Each data point represents the mean value of 7 animals. Error bars represent standard deviation of the mean values. Statistical differences in tumor growth rate of each dose group compared to the isotype group were determined by repeated mixed ANOVA mode. Data was fitted with a linear mixed effect model.

The data demonstrated a dose-dependent tumor growth inhibition of MC38 tumors in C57BL/6 mice after a single-dose intraperitoneal administration by the mouse FLT3-ligand Fc-fusion protein (SEQ ID NO:20) at day 0. Groups dosed with 150 μs/kg, 750 μs/kg and 3750 μg/kg of SEQ ID NO:20 show significantly slower tumor growth rates compared to the isotype control group. The results are summarized in Table 22 and depicted in FIG. 23.

TABLE 22

Tumor Growth Inhibition (TGI) at Day 14 Post-Dose for SEQ ID NO: 20 Relative to Isotype Control in MC38 Mouse Tumor Model

| Dose | TGI (%) | p-value |
|---|---|---|
| 3750 μg/kg | 52.67 | <0.0001 |
| 750 μg/kg | 38.68 | <0.0001 |
| 150 μg/kg | 14.51 | <0.0035 |
| 30 μg/kg | −2.35; | not significant |

Example 24

Intratumoral and Peripheral Expansion of cDC1 in Tumor Bearing Mice

In this example, we demonstrated the intratumoral and peripheral expansion of conventional dendritic cell subtype 1 (cDC1) in tumor bearing mice by FLT3L-Fc fusion protein using a murine surrogate (SEQ ID NO:20).

Methods

Tumors and spleens were harvested at Day 7 post administration and shipped O/N at 4° C. in HypoThermosol solution (BioLife Solutions) from the CROs. Tumors and spleens were then dissociated using the gentleMACS Dissociator (Miltenyi Biotec) with heaters, following manufacturer's protocol. After enzymatic digestion, cell suspension was filtered through a 70 μm cell strainer. The remaining tube and strainer were rinsed 1× with 15-20 ml of RPMI and collected with the rest of the sample. Cells were centrifuged at 500×g for 5 min at room temperature. Supernatant was discarded and cells were washed 1× with PBS. Residual red blood cells from spleens were lysed by adding 2 ml of ACK lysis buffer to each sample for 1-2 min at room temperature. FACS staining Buffer (BD Bioscience) was added to the samples to stop the ACK lysis activity. Cells were spun down and washed additionally with PBS. Samples were then stained with Live/Dead Fixable Aqua Dead Cell Stain Kit (ThermoFisher) at 1:750 dilution for 15 min at 4° C. Ten microliters of cells from each sample were taken for count by 123count eBeads (eBiosciences) following manufacturer's protocol. Cells were washed 2× with FACS staining buffer, then Fc blocked for 30 min at 4° C. FACS antibodies (Biolegend) were directly added to the blocked samples and incubated at 4° C. for 30 min without spinning down or washing out the Fc block. Cells were washed 2x, resuspended in Staining Buffer, and analyzed by LSR Fortessa FACS analyzer. Raw data were analyzed by FlowJo X (BD Bioscience).

Results

Figure 24A:
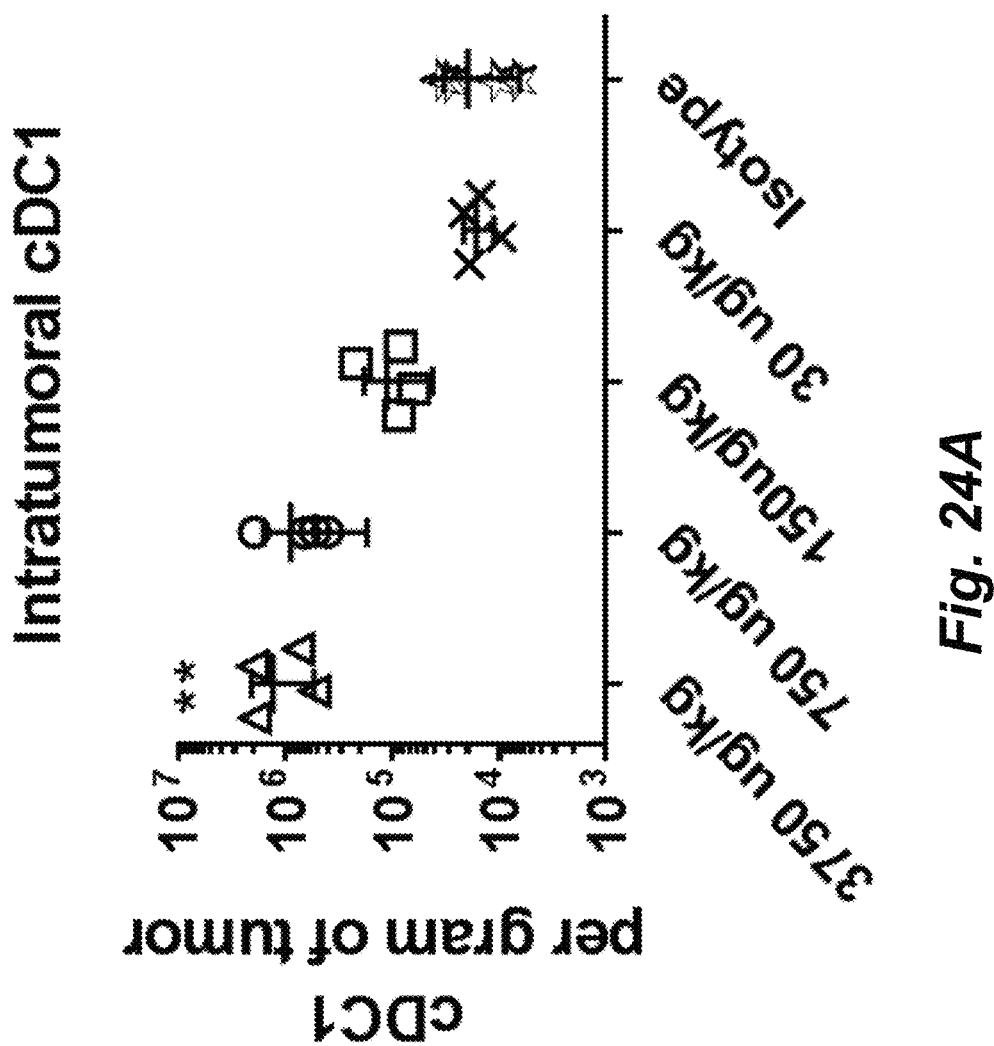
FIGS. 24A-24B illustrate day 7 quantification of conventional dendritic cell subtype 1 (cDC1) numbers in tumors (Panel A) or spleens (Panel B) of MC38 tumor-bearing C57BL/6 mice administrated intravenously with 3750 µg/kg (open triangle), 750 µg/kg (open circle), 150 µg/kg (open square), 30 µg/kg (cross) mouse FLT3-Ligand mouse IgG2a (C136S, LALA-PG), or 3753 µg/kg mouse IgG2a isotype (open star) at day 0 when tumor volume reached 50 mm³. The x-axis indicates dose groups. The y-axis shows the cDC1 number per gram of tumor (Panel A) or cDC1 number per spleen (Panel B). Graph is a result of one experiment. Each individual symbol represents the data point of a single mouse. Horizontal bars represent the mean values and the error bars represent standard deviation of the mean values. Statistical differences were determined one-way ANOVA with Dunnett's post-test. **p-value<0.0001; *p-value<0.001; **p-value<0.01.
Figure 24B:
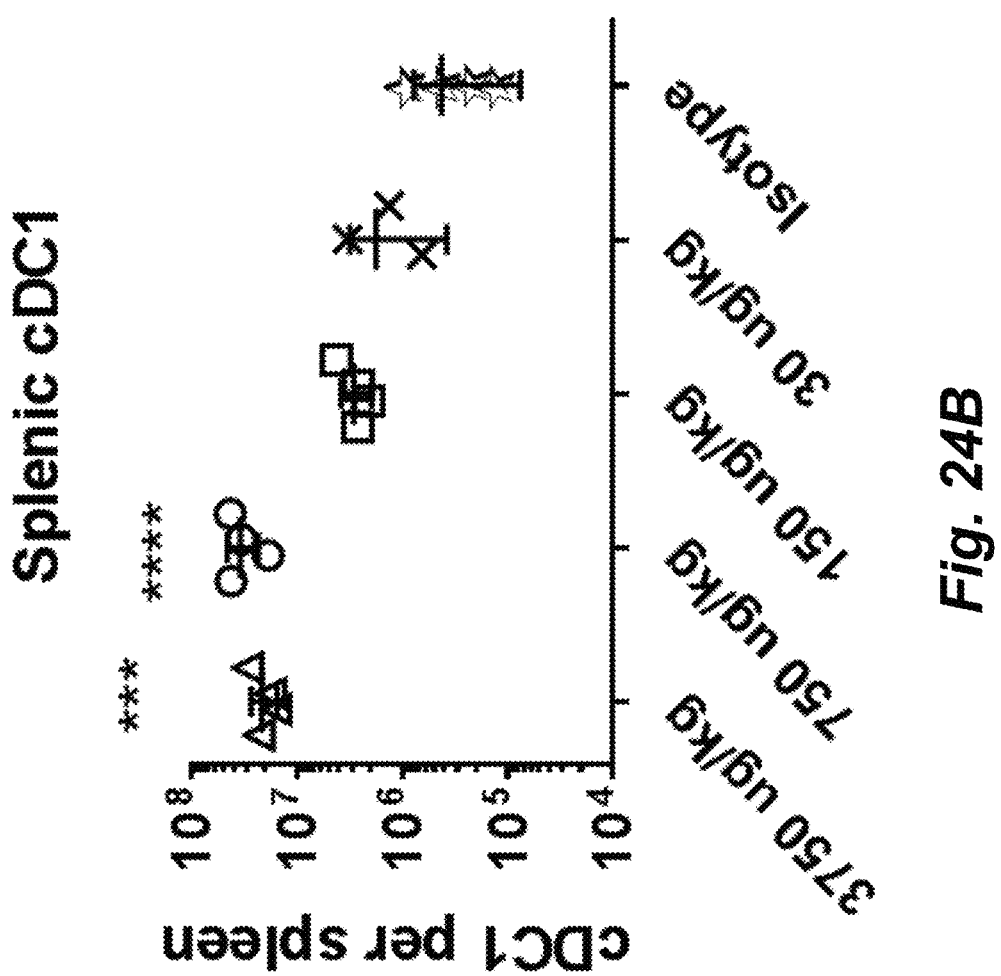

The results demonstrated a dose-dependent increase of conventional dendritic cell subtype 1 (cDC1) number in tumors (FIG. 24A) or in spleens (FIG. 24B) in the MC38 tumor model after a single-dose intraperitoneal administration by the mouse surrogate FLT3-ligand Fc-fusion protein (SEQ ID NO:20) at day 0. Groups dosed 750 μg/kg and 3750 μs/kg of SEQ ID NO:20 showed a significant increase of cDC1 number in tumors compared to the isotype group, while groups dosed 750 μg/kg and 3750 μg/kg of SEQ ID NO:20 show significant increase of cDC1 number in spleens compared to the isotype group. Similar increase of cDC1 number in tumors and spleens was observed in groups dosed with 750 μg/kg and 3750 μg/kg of SEQ ID NO:20. The results are summarized in Table 23 and depicted in FIG. 24.

TABLE 23 cDC1 Fold-Change in Tumor and Spleen at day 7 Post-Dose for SEQ ID NO: 20 Relative to Isotype Control in MC38 Mouse Tumor Model

| Dose | cDC1 fold change in tumor | cDC1 fold change in spleen |
|---|---|---|
| 3750 μg/kg | 65.57 | 50.7 |
| 750 μg/kg | 44.21 | 81.76 |
| 150 μg/kg | 4.72 | 6.84 |
| 30 μg/kg | −0.17 | 4.18 |

Example 25

Sialic Acid Content Evaluation of Eight FLT3L-Fc Variants

In this example, we determined the total sialic acid content of eight Flt3L-Fc constructs. To evaluate sialic acid content, we performed chemical release of sialic acids followed by fluorescence labeling and reversed-phase separation with fluorescence detection.

Methods

Proteins from Flt3L-Fc constructs SEQ ID NOs: 1-8 were diluted to 10 or 50 μg/mL in water. Sialic acids were released by mild acid hydrolysis with acetic acid, separated from the protein by filtration, and fluorescently labeled with 1,2-diamino-4,5-methylenedioxybenzene dihydrochloride (DMB) by a reductive amination reaction. The labeled sialic acid products were then separated by reversed-phase chromatography using a C18 column with fluorescence detection at 373 nm (excitation) and 448 nm (emission). The concentrations of N-acetylneuraminic acid (NANA) and N-Glycolylneuraminic acid (NGNA) present were determined from an identically labeled 6-point standard curve and expressed as a mole to mole ratio of sialic acid to protein content.

Results

The results are summarized in Table 24.

TABLE 24

Sialic Acid Content of SEQ ID NO. 1-8

| FLT3L-Fc Variant SEQ ID NO: | mol/mol NANA | mol/mol NGNA |
|---|---|---|
| 1 | 16.5 | ND* |
| 2 | 13.7 | ND |
| 3 | 15.2 | ND |
| 4 | 17.4 | ND |
| 5 | 14.3 | ND |
| 6 | 15.4 | ND |
| 7 | 8.1 | ND |
| 8 | 13.0 | ND |

*ND = not detected

The data obtained for SEQ ID NOs: 1-8 showed similar amounts of N-acetylneuraminic acid (NANA) in each sample, at an average of 15 mol/mol. One exception was noted, in which SEQ ID NO: 7 contained only 8 mol/mol sialic acid. A subtle trend was also observed in which sialic acid content decreased in constructs containing C-terminal truncations of the Flt3L portion of the fusion proteins (constructs SEQ ID NO: 2 and 7 relative to SEQ ID NO:1; constructs SEQ ID NO: 6 and 8 relative to SEQ ID NO: 4), indicating this region contained the majority of sialic acid. Furthering this idea was the observation that N-glycan removal from the ligand domain did not result in a major loss of sialic acid content, shown by comparison of SEQ ID NO: 5 and SEQ ID NO: 1.

Total sialic acid content was shown to have a positive correlation to PK in mAbs and Fc-fusion proteins, consistent with the reporting of, e.g., Li, et al., *J Pharm Sci* (2015) 104:1866-1884; and Liu, et al., *Protein Cell.* (2018) 9(1): 15-32.

Example 26

Sialic Acid Content Evaluation of Four FLT3L-Fc Variants

In this example, we determined the sialic acid content on the two FLT3L N-glycans at positions 100 and 123 of SEQ ID NOs: 1, 6, 9, and 14 ("Asn100" and "Asn123," respectively).

Methods

Protein digest followed by reversed-phase separation with detection by mass spectrometry was performed.

Following denaturation, reduction and cysteine carboxymethylation, proteins from SEQ ID NOs: 1, 6, 9, and 14 were digested for 6 hours at 37° C. using a 1:10 enzyme: substrate (w:w) ratio of Lys-C and Glu-C Mix. Digestion was then quenched by adding trifluoroacetic acid to 0.1% final concentration. The resulting Lys-C/Glu-C peptides were separated by reverse phase gradient UPLC on a C18 column. The separation of the peptides was monitored at 214 nm prior to elution into the inlet of a Thermo Scientific QE HF Orbitrap mass spectrometer operating in positive, data-dependent acquisition mode. N-glycan peptide assignments were based on matching the observed masses of the intact peptides in the LC/MS analysis to the masses predicted based on a theoretical Lys-C and Glu-C digest of SEQ ID NOs: 1, 6, 9, and 14.

Results

The results are presented in Table 25.

TABLE 25

Sialylalation Analysis of FLT3L-Fc Variants SEQ ID NOs: 1, 6, 9, and 14

| | SEQ ID NO. 1 | | SEQ ID NO. 6 | | SEQ ID NO. 9 | | SEQ ID NO. 14 | |
|---|---|---|---|---|---|---|---|---|
| | Sialylated Peptides[1] (%) | Occupancy[2] (%) | Sialylated Peptides[1] (%) | Occupancy[2] (%) | Sialylated Peptides[1] (%) | Occupancy[2] (%) | Sialylated Peptides[1] (%) | Occupancy[2] (%) |
| Asn 100 | 43 | 66 | 43 | 64 | 33 | 61 | 46 | 63 |
| Asn 123 | 63 | 70 | 57 | 68 | 39 | 63 | 57 | 67 |
| | Relative abundance of sialylated FLT3L N-glycans corrected by occupancy (%) | | | | | | | |
| Asn 100 | 65 | | 68 | | 54 | | 72 | |
| Asn 123 | 90 | | 84 | | 62 | | 94 | |
| | Average across the two sites (%) | | | | | | | |
| | 77 | | 76 | | 58 | | 83 | |

[1]FLT3L N-glycans with one or more sialic acid unit. Percentage determined including asialylated peptides
[2]N-glycan occupancy at the two sites was determined by peptide mapping The molecular masses of the N-glycosylated peptides were consistent with the predicted masses based on the amino acid sequences of the FTL3L-Fc constructs. FTL3L-Fc SEQ ID NOs 1, 6, and 14 contained a consistent level of species with one or more sialic acid unit (43-63%, Table 25). FTL3L-Fc SEQ ID NO: 9 showed a decrease of approximately 10% at Asn 100 and 24% at Asn 123 (Table 25). Ligand N-glycans site occupancy for SEQ ID NOs: 1, 6, 9 and 14 was consistent across all four molecules tested and ranged from 61% to 70% across the two sites (Table 25).

The percent of ligand N-glycans species containing at least one sialic acid unit were corrected by the percent occupancy at each site and averaged across the two sites to allow a direct comparison across the constructs (Table 25). After correction and averaging, FTL3L-Fc SEQ ID NOs: 1, 6, and 14 showed a level of overall ligand sialylated N-glycans ranging from 76 to 83%; while FTL3L-Fc SEQ ID NO: 9 showed a lower overall level at 58%.

Example 27

Conformational Stability of FLT3L-Fc Variants

In this example, we evaluated the conformational stability of FLT3L-Fc variants SEQ ID NOs: 1 to 9 and SEQ ID NO: 14.

Each FLT3L-Fc construct was prepared in a matrix of 20 mM sodium phosphate, 9% sucrose, 0.02% PS80 pH 6.5 and loaded into a capillary. Intrinsic fluorescence was measured by a Nano differential scanning fluorimetry (NanoTemper) instrument as the samples were heated from 25-95° C. The ratio of fluorescence signal at 350/330 nm was plotted versus temperature to compare melting profiles of each sample. Duplicate measurements were performed for each construct.

The data obtained for FLT3L-Fc variants SEQ ID NOs: 1 to 8 show similar conformational stability, with onset temperatures ($T_{on}$) greater than 55° C. for each FLT3L-Fc variant. FLT3L-Fc SEQ ID NO 3 has a lower $T_{ml}$ compared to the three other IgG4 FLT3L-Fc constructs, indicating that the L235E mutation is slightly destabilizing resulting in lower conformational stability. Results of the IgG1 FLT3L-Fc constructs also show that FLT3L-Fc SEQ ID NO 5 has a decreased $T_{on}$ and $T_{ml}$ compared with the three other IgG1 constructs (Table 26).

The half-life enhancing YTE mutation lowers the $T_{ml}$ value of FLT3L-Fc variants SEQ ID NOs: 9 and 14. Onset temperatures remain well above physiological temperature despite this shift (Table 26).

TABLE 26

Conformational Stability by Nano Differential Scanning Fluorimetry

| FLT3L-Fc Variant SEQ ID NO: | $T_{on}$ (° C.) | $T_{ml}$ (° C.) |
|---|---|---|
| 1 | 60.3 | 67.4 |
| 2 | 60.6 | 67.6 |
| 3 | 59.5 | 65.3 |
| 4 | 63.5 | 68.8 |
| 5 | 55.0 | 66.3 |
| 6 | 64.2 | 68.4 |
| 7 | 59.5 | 71.3 |
| 8 | 64.3 | 68.9 |
| 9 | 51.0 | 55.2 |
| 14 | 49.4 | 52.3 |

Example 28

FLT3L-Fc and Anti-PD1 Combination Study

Figure 25:
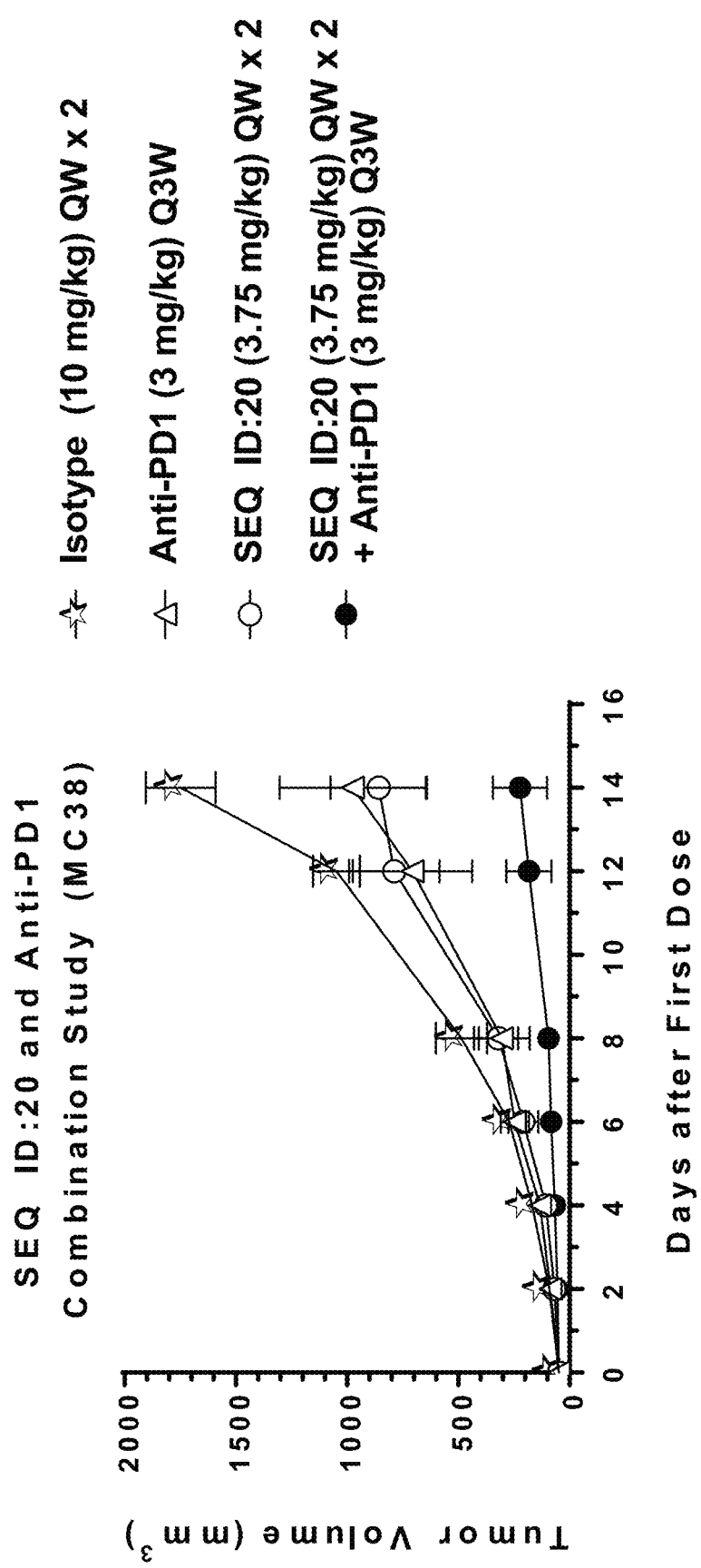
FIG. 25 illustrates tumor growth kinetics of MC38 tumor-bearing C57BL/6 mice administrated intravenously with QWx2 dose of 3.75 µg/kg (open circle) mouse FLT3-Ligand mouse IgG2a (C136S, LALA-PG), Q3W dose of 3 mg/kg (open triangle) anti-mouse PD-1 (clone RMP1-14), combination of the two reagents (closed circle) or QWx2 dose of 10 mg/kg mouse IgG2a isotype control (open star) at day 0 when tumor volume reached 50 mm³. Each data point represents the mean value of 10 animals. Error bars represent standard deviation of the mean values.

In this example, we demonstrated the combined effects of anti-PD1 antibody (clone RMP1-14) and a FLT3L-Fc fusion protein using SEQ ID NO:20 (a murine surrogate) in a syngeneic mouse tumor model.
Methods:
Eight-week old C57BL/6 mice (Jackson Laboratory) were inoculated with 2.5×10⁵ MC38 cells subcutaneously. Mice were then randomized when tumor volume reached 45-55 mm³ on day 0 and dosed intraperitoneally with FTL3L-Fc SEQ ID NO:20, anti-mouse PD-1 (clone RMP1-14) or an isotype control at the indicated concentrations and dosing frequencies. Tumors were measured at least 2 times a week using calipers. Tumor volumes were calculated using the following equation: (longest diameter*shortest diameter²)/2.
Results
The results demonstrated a modest growth inhibition of MC38 tumors in C57BL/6 mice after single agent treatment with either one of the mouse FLT3-ligand Fc-fusion protein (SEQ ID NO:20) or anti-mouse PD-1, while combined treatment with the anti-PD1 antibody (clone RMP1-14) and the FLT3L-Fc fusion protein yielded strong tumor growth inhibition. The results are depicted in FIG. 25.

Example 29

FLT3L-Fc and Anti-CTLA4 Combination Study

Figure 26:
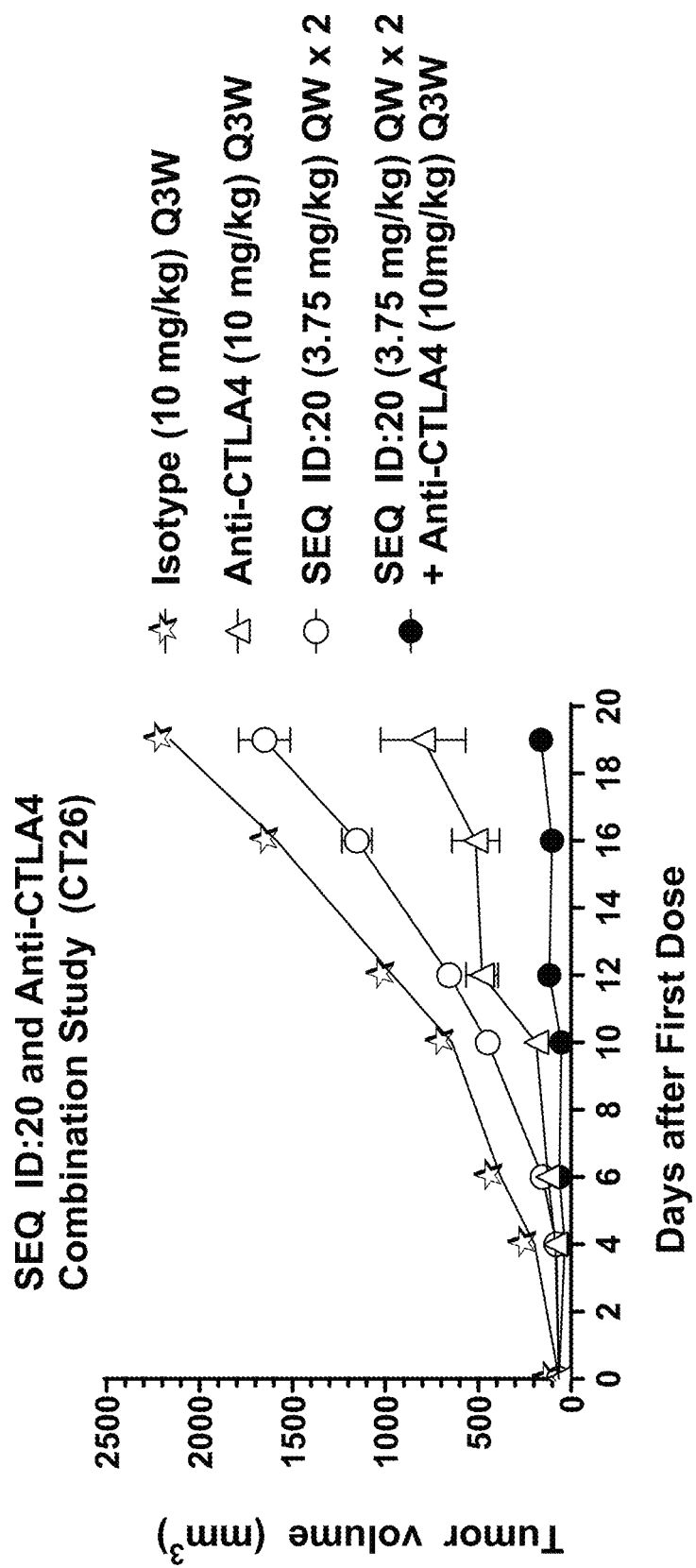
FIG. 26 illustrates tumor growth kinetics of CT26 tumor-bearing BALB/c mice administrated intravenously with QWx2 dose of 3.75 µg/kg (open circle) mouse FLT3-Ligand mouse IgG2a (C136S, LALA-PG), Q3W dose of 3 mg/kg (open triangle) anti-mouse CTLA4 (clone 9D9), combination of the two reagents (closed circle) or Q3W dose of 10 mg/kg mouse IgG2a isotype control (open star) at day 0 when tumor volume reached 65 mm³. Each data point represents the mean value of 10 animals. Error bars represent standard deviation of the mean values.

In this example, we demonstrated the combined effects of anti-CTLA4 antibody (clone 9D9) and a FLT3L-Fc fusion protein using SEQ ID NO:20 (a murine surrogate) in a syngeneic mouse tumor model.
Methods:
Nine-week old BALB/c mice (Taconic) were inoculated with 8×10⁵ CT26 cells subcutaneously. Mice were then randomized when tumor volume reached 60-70 mm³ on day 0 and dosed intraperitoneally with FTL3L-Fc SEQ ID NO:20, anti-mouse CTLA4 (clone 9D9) or an isotype control at the indicated concentrations and dosing frequencies. Tumors were measured at least 2 times a week using calipers. Tumor volumes were calculated using the following equation: (longest diameter*shortest diameter²)/2.
Results:
The results demonstrated a modest growth inhibition of CT26 tumors in BALB/c mice after single agent treatment with either one of the mouse FLT3-ligand Fc-fusion protein (SEQ ID NO:20) or anti-mouse CTLA4, while combined treatment with the anti-CTLA4 antibody (clone 9D9) and the FLT3L-Fc fusion protein yielded strong tumor growth inhibition. The results are depicted in FIG. 26.

Example 30

Figure 27:
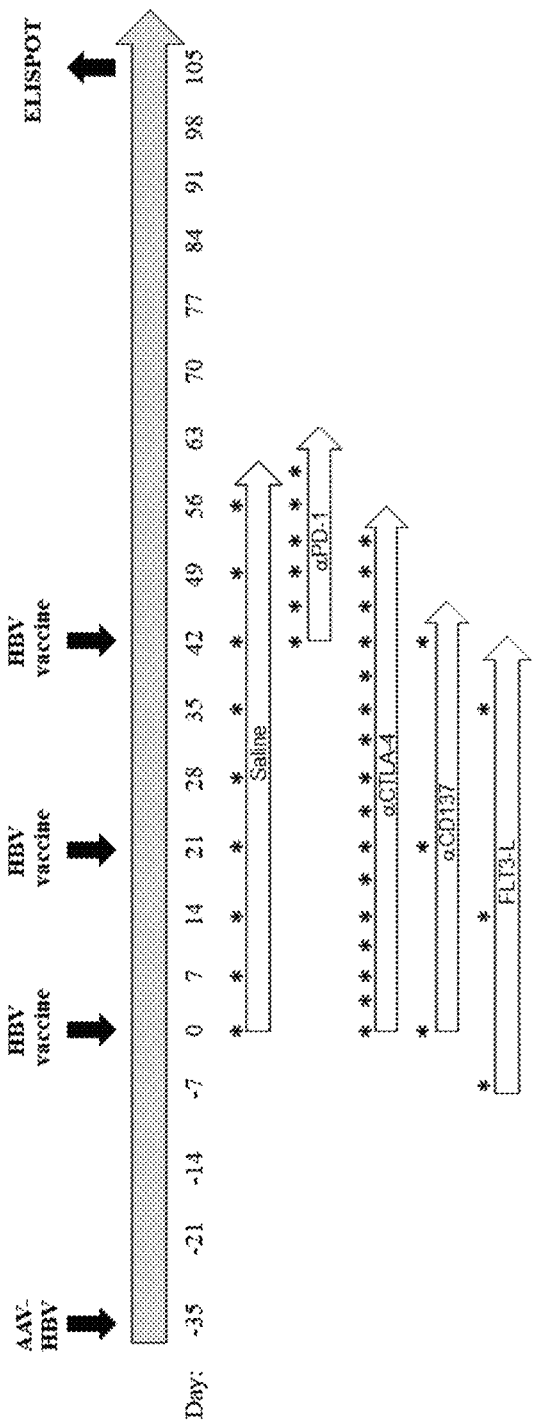
FIG. 27 diagrams an immunogenicity study in C57BL/6 mice that were transduced with an Adeno-Associated Virus (AAV) vector encoding a 1.2× length hepatitis B virus (HBV) genome (AAV-HBV mice). At indicated times (asterisks) AAV-HBV mice were administered 3 doses of an HBV vaccine and treated with saline, mouse FLT3L, anti-mouse inhibitory PD-1, anti-mouse inhibitory CTLA-4 or anti-mouse stimulatory CD137 antibodies. A control group of mice received the HBV vaccine alone but no AAV-HBV. HBV-specific IFN-γ ELISPOT was performed using spleens of all animals at day 105 post first vaccination.

Effect of FLT3L on the Immunogenicity of an HBV Vaccine in a Mouse Model of Chronic HBV We evaluated the potential effect of FLT3L on the immunogenicity of an HBV vaccine in the context of chronic HBV using an Adeno-Associated Virus (AAV)-HBV mouse model (Dion, et al., *J Virol.* (2013) 87(10):5554-63; and Yang, et al., *Cell Mol Immunol.* (2014) 11(1):71-8). Other immunomodulators including antibodies targeting PD-1, CTLA-4 and CD137 were also tested.
Methods
In this model, C57BL/6 mice were transduced with an AAV vector encoding a 1.2× length HBV genome (AAV-HBV mice), resulting in persistent HBV protein and virion production in hepatocytes, accompanied by antigenemia and viremia in serum. AAV-HBV mice were administered 3 doses of an HBV vaccine that is an arenavirus vector expressing HBV antigens including HBsAg, core and polymerase. Mice were treated with saline, mouse FLT3L, anti-mouse inhibitory PD-1, anti-mouse inhibitory CTLA-4 or anti-mouse stimulatory CD137 antibodies. A control group of mice received the HBV vaccine alone but no AAV-HBV to determine how the immunogenicity of the HBV vaccine was affected in the context of chronic HBV. HBV-specific IFN-γ ELISPOT was performed using spleens of all animals at the end of the study (day 105 post first vaccination). A diagram of this AAV-HBV immunogenicity study is shown in FIG. 27 and treatment groups are shown in Table 27. Data are expressed after subtraction of background signal in no-peptide control wells. Statistical analysis was performed using Mann-Whitney non-parametric test.

Results

Figure 28A:
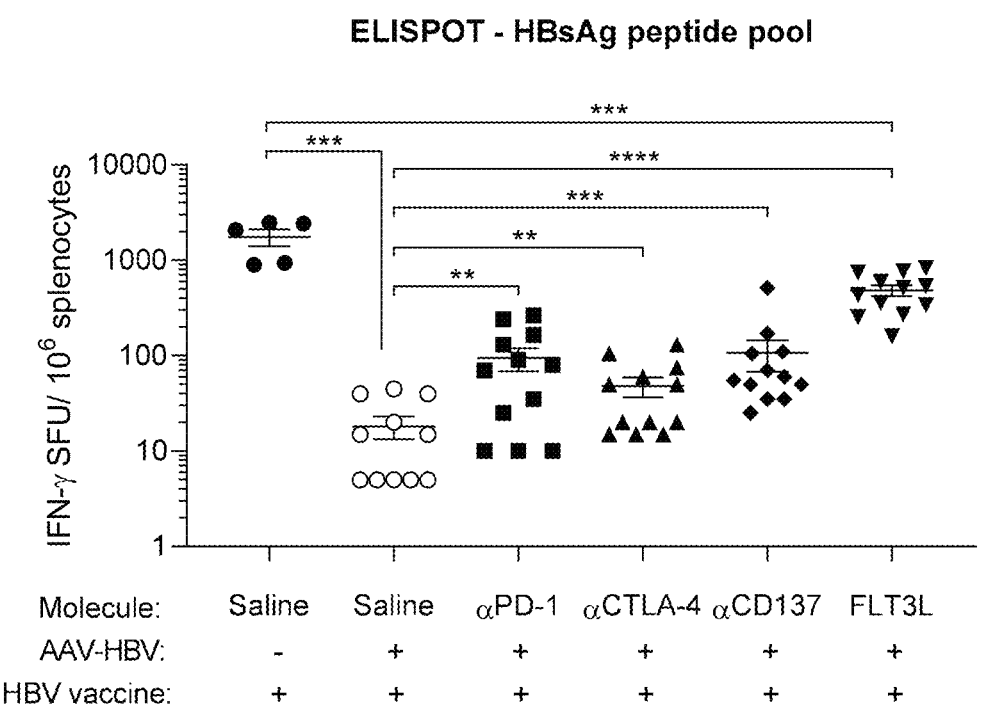
FIGS. 28A-C illustrates IFN-γ ELISPOT responses of AAV-HBV mice specific for HBsAg (FIG. 28A), HBV core (FIG. 28B) and HBV polymerase (FIG. 28C) observed at the end of the immunogenicity study diagrammed in FIG. 27 for indicated treatment and control groups.
Figure 28B:
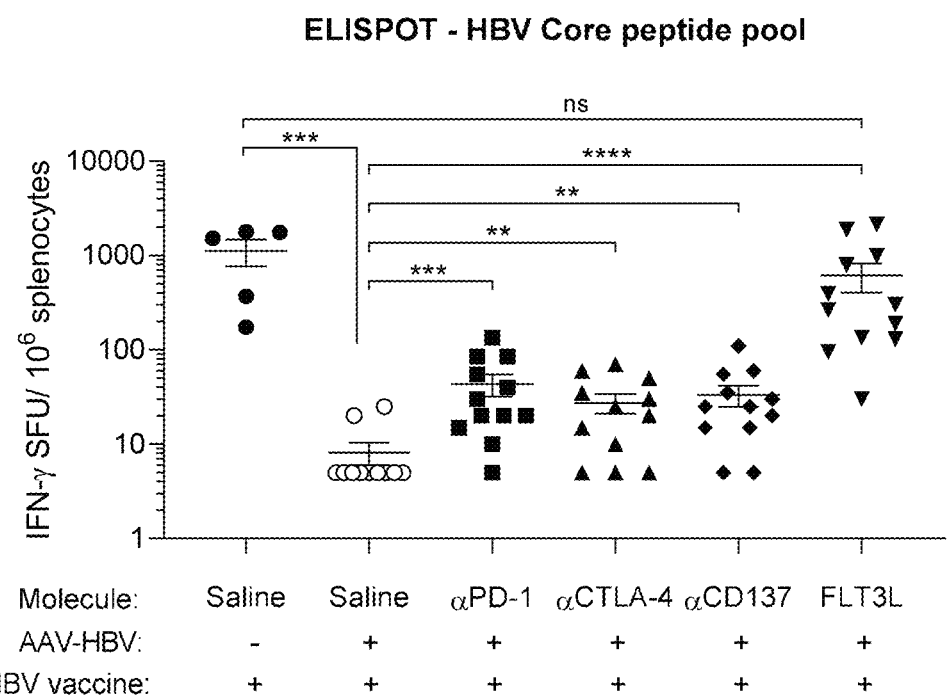
Figure 28C:
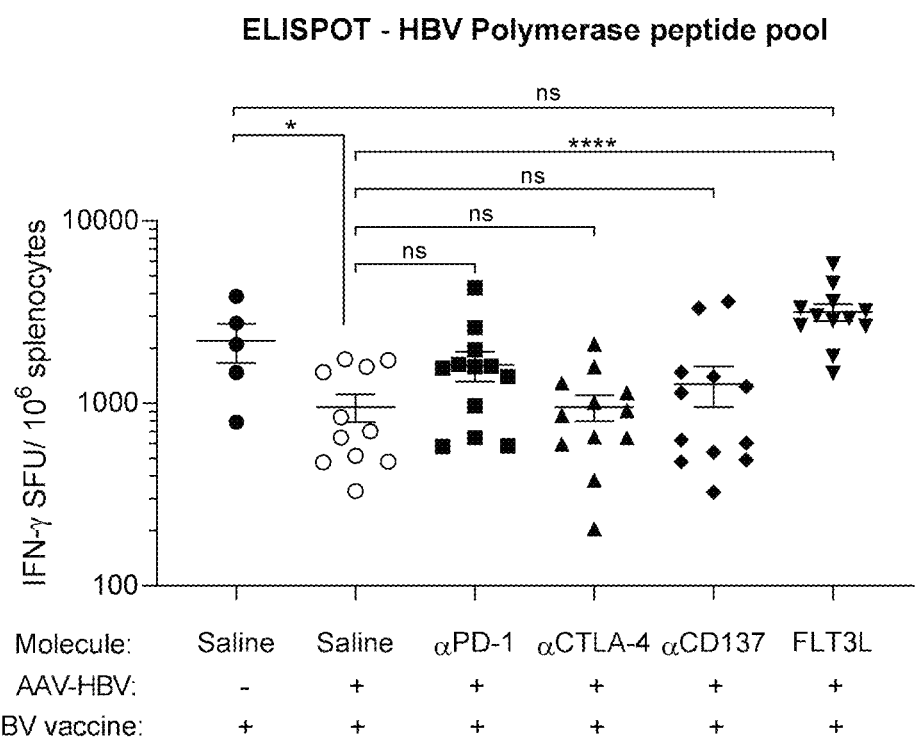

IFN-γ ELISPOT responses specific for HBsAg, HBV core and HBV polymerase are summarized in FIGS. 28A-C. Robust ELISPOT responses were observed for all 3 HBV antigens in mice without persistent HBV. In contrast, the ELISPOT responses obtained from AAV-HBV mice that received the HBV vaccine alone were significantly reduced, demonstrating T cell tolerance against the HBV proteins in AAV-HBV mice. In these mice, combined administration of FLT3L and HBV vaccine significantly increased the HBV-specific IFN-γ ELISPOT responses for all 3 HBV antigens. A comparable effect (except for HBV pol-specific responses) was observed with the other immunomodulators anti PD-1, anti CTLA-4 and anti CD137 antibodies although with lower magnitude.

TABLE 27

Study Groups in AAV-HBV Immunogenicity Study

| Group | N | AAV-HBV | HBV vaccine | Immuno-modulator | Molecule and Dose |
|---|---|---|---|---|---|
| 1 | 11 | Yes | Yes | Vehicle | Saline |
| 2 | 12 | Yes | Yes | α-PD-1 | Clone RMP1-14 8 mg/kg/dose |
| 3 | 12 | Yes | Yes | α-CTLA-4 | Clone 9D9 10 mg/kg/dose |
| 4 | 12 | Yes | Yes | α-CD137 | Clone mAb8 2.5 mg/kg/dose |
| 5 | 12 | Yes | Yes | FLT3L | Mouse surrogate of FLT3L-Fc (SEQ ID NO: 20) 1 mg/kg/dose |
| 6 | 5 | No | Yes | Vehicle | Saline |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A fusion protein comprising: a human fms related tyrosine kinase 3 ligand (FLT3L) extracellular domain operably linked to an immunoglobulin fragment crystallizable region (Fc region), wherein the fusion protein comprises the amino acid sequence of SEQ ID NO: 14.

* * * * *